US012336982B2

(12) United States Patent
Markowitz et al.

(10) Patent No.: US 12,336,982 B2
(45) Date of Patent: Jun. 24, 2025

(54) COMPOSITIONS AND METHODS OF MODULATING SHORT-CHAIN DEHYDROGENASE ACTIVITY

(71) Applicants: RODEO THERAPEUTICS CORPORATION, Thousand Oaks, CA (US); Case Western Reserve University, Cleveland, OH (US); Board of Regents of the University of Texas System, Austin, TX (US)

(72) Inventors: Sanford Markowitz, Pepper Pike, OH (US); Joseph Ready, Carrolton, TX (US); Stephen L. Gwaltney, II, Chapel Hill, NC (US); Monika Antczak, Fort Worth, TX (US)

(73) Assignees: Rodeo Therapeutics Corporation, Thousand Oaks, CA (US); Case Western Reserve University, Cleveland, OH (US); Board of Regents of the University of Texas System, Austin, TX (US)

( * ) Notice: Subject to any disclaimer, the term of this patent is extended or adjusted under 35 U.S.C. 154(b) by 1040 days.

(21) Appl. No.: 17/296,055

(22) PCT Filed: Nov. 21, 2019

(86) PCT No.: PCT/US2019/062686
§ 371 (c)(1),
(2) Date: May 21, 2021

(87) PCT Pub. No.: WO2020/106998
PCT Pub. Date: May 28, 2020

(65) Prior Publication Data
US 2023/0039604 A1    Feb. 9, 2023

Related U.S. Application Data

(60) Provisional application No. 62/770,571, filed on Nov. 21, 2018.

(51) Int. Cl.
| | | |
|---|---|---|
| A61K 31/4365 | (2006.01) | |
| A61K 31/437 | (2006.01) | |
| A61K 31/501 | (2006.01) | |
| A61K 31/506 | (2006.01) | |
| A61K 31/519 | (2006.01) | |
| A61K 31/5377 | (2006.01) | |
| A61K 31/541 | (2006.01) | |
| A61K 45/06 | (2006.01) | |
| C07D 495/04 | (2006.01) | |
| C07D 519/00 | (2006.01) | |

(52) U.S. Cl.
CPC ........ *A61K 31/4365* (2013.01); *A61K 31/437* (2013.01); *A61K 31/501* (2013.01); *A61K 31/506* (2013.01); *A61K 31/519* (2013.01); *A61K 31/5377* (2013.01); *A61K 31/541* (2013.01); *A61K 45/06* (2013.01); *C07D 495/04* (2013.01); *C07D 519/00* (2013.01)

(58) Field of Classification Search
CPC ........................... C07D 495/04; C07D 519/00
See application file for complete search history.

(56) References Cited

U.S. PATENT DOCUMENTS

| | | |
|---|---|---|
| 3,382,247 A | 5/1968 | Anthony et al. |
| 4,043,819 A | 8/1977 | Baumann |
| 4,725,676 A | 2/1988 | Agback et al. |
| 4,767,766 A | 8/1988 | Baker et al. |
| 4,889,846 A | 12/1989 | Crossley |
| 4,910,226 A | 3/1990 | Holt et al. |
| 4,966,974 A | 10/1990 | Klausener et al. |
| 4,973,474 A | 11/1990 | Hocquaux et al. |
| 5,006,532 A | 4/1991 | Baker et al. |
| 5,015,629 A | 5/1991 | diZerega |
| 5,041,157 A | 8/1991 | Seiler et al. |
| 5,217,521 A | 6/1993 | Durr |
| 5,405,842 A | 4/1995 | Silverman |
| 5,411,981 A | 5/1995 | Gaillard-Kelly et al. |
| 5,438,058 A | 8/1995 | Dufetel et al. |
| 5,445,164 A | 8/1995 | Worthen et al. |
| 5,460,964 A | 10/1995 | McGlave et al. |
| 5,466,694 A | 11/1995 | Terranova et al. |
| 5,468,888 A | 11/1995 | Bouboutou et al. |
| 5,480,913 A | 1/1996 | Liao et al. |
| 5,516,779 A | 5/1996 | Von Langen et al. |
| 5,529,769 A | 6/1996 | Cho et al. |
| 5,565,467 A | 10/1996 | Batchelor et al. |
| 5,631,282 A | 5/1997 | Goetz |

(Continued)

FOREIGN PATENT DOCUMENTS

| | | |
|---|---|---|
| AR | 060498 A1 | 6/2008 |
| AU | 2013/249434 B2 | 10/2017 |

(Continued)

OTHER PUBLICATIONS

U.S. Appl. No. 17/296,055, filed May 21, 2021, Docket Central, Pending.
U.S. Appl. No. 15/359,330, US 2017-00165241 A1 U.S. Pat. No. 10,301,320, filed Nov. 22, 2016, Jun. 15, 2017 May 28, 2019, Issued.
U.S. Appl. No. 16/943,932, US 2021-0032265 A1, filed Oct. 12, 2020, Feb. 4, 2021, Pending.
U.S. Appl. No. 14/395,021, US-2015-0072998 A1 U.S. Pat. No. 9,790,233, filed Oct. 16, 2014, Mar. 12, 2015 Oct. 17, 2017, Issued.
U.S. Appl. No. 17/879,379, filed Aug. 2, 2022, Docket Central, Pending.

(Continued)

*Primary Examiner* — James D. Anderson
(74) *Attorney, Agent, or Firm* — BARNES & THORNBURG LLP

(57) ABSTRACT

Compounds and methods of modulating 15-PGDH activity, modulating tissue prostaglandin levels, treating disease, diseases disorders, or conditions in which it is desired to modulate 15-PGDH activity and/or prostaglandin levels include 15-PGDH inhibitors described herein.

83 Claims, No Drawings

(56) References Cited

U.S. PATENT DOCUMENTS

| | | |
|---|---|---|
| 5,635,387 A | 5/1997 | Fei et al. |
| 5,650,145 A | 7/1997 | Saint-Leger |
| 5,677,136 A | 10/1997 | Simmons et al. |
| 5,681,559 A | 10/1997 | DiGuisto et al. |
| 5,716,827 A | 2/1998 | Tsukamoto et al. |
| 5,750,397 A | 5/1998 | Tsukamoto et al. |
| 5,756,092 A | 5/1998 | Michelet et al. |
| 5,772,990 A | 5/1998 | Hocquax et al. |
| 5,759,793 A | 6/1998 | Schwartz et al. |
| 5,760,043 A | 6/1998 | Dufetel et al. |
| 5,807,895 A | 9/1998 | Stratton et al. |
| 6,027,896 A | 2/2000 | Roses et al. |
| 6,121,254 A | 9/2000 | Saint-Leger |
| 6,214,533 B1 | 4/2001 | Ho et al. |
| 6,281,227 B1 | 8/2001 | Choi-Sledeski et al. |
| 6,414,027 B1 | 7/2002 | Neal |
| 6,465,421 B1 | 10/2002 | Duranton et al. |
| 6,468,972 B1 | 10/2002 | Pruche et al. |
| 7,004,913 B1 | 2/2006 | Rutenberg et al. |
| 7,022,675 B2 | 4/2006 | Rodgers et al. |
| 7,091,216 B2 | 8/2006 | Toupence et al. |
| 7,131,958 B2 | 11/2006 | Deverre |
| 7,147,626 B2 | 12/2006 | Goodman et al. |
| 7,189,724 B2 | 3/2007 | An et al. |
| 7,294,641 B2 | 11/2007 | Boulle et al. |
| 7,320,967 B2 | 1/2008 | Michelet et al. |
| 7,396,525 B2 | 7/2008 | Rozot et al. |
| 7,629,112 B1 | 12/2009 | Zengerle et al. |
| 7,705,041 B2 | 4/2010 | Michelet et al. |
| 8,068,897 B1 | 11/2011 | Gazdzinski |
| 8,202,882 B2 | 5/2012 | Hoelzemann et al. |
| 8,637,558 B2 | 1/2014 | Cho et al. |
| 8,642,660 B2 | 2/2014 | Goldfarb |
| 9,649,350 B2 | 5/2017 | Choi et al. |
| 9,789,116 B2 | 10/2017 | Markowitz et al. |
| 9,790,233 B2 | 10/2017 | Markowitz et al. |
| 9,801,863 B2 | 10/2017 | Markowitz et al. |
| 10,301,320 B2 | 5/2019 | Markowitz et al. |
| 10,420,752 B2 | 9/2019 | Markowitz et al. |
| 10,869,871 B2 | 12/2020 | Markowitz et al. |
| 10,945,998 B2 | 3/2021 | Markowitz et al. |
| 11,426,420 B2 | 8/2022 | Markowitz et al. |
| 11,690,847 B2 | 7/2023 | Markowitz et al. |
| 11,718,589 B2 | 8/2023 | Markowitz et al. |
| 2002/0044953 A1 | 4/2002 | Michelet et al. |
| 2002/0045659 A1 | 4/2002 | Michelet et al. |
| 2003/0083381 A1 | 5/2003 | Kumagai et al. |
| 2003/0096823 A1 | 5/2003 | Asp et al. |
| 2004/0052760 A1 | 3/2004 | Michelet et al. |
| 2004/0087593 A1 | 5/2004 | Clark et al. |
| 2004/0241726 A1 | 12/2004 | Liew |
| 2004/0241727 A1 | 12/2004 | Liew |
| 2004/0241729 A1 | 12/2004 | Liew |
| 2005/0026923 A1 | 2/2005 | An et al. |
| 2005/0187221 A1 | 8/2005 | Matsuda et al. |
| 2006/0019976 A1 | 1/2006 | Karp et al. |
| 2006/0034786 A1 | 2/2006 | Michelet et al. |
| 2006/0051540 A1 | 3/2006 | Kagawa |
| 2006/0089349 A1 | 4/2006 | Gundertofte et al. |
| 2006/0233797 A1 | 10/2006 | Gujrathi |
| 2006/0287284 A1 | 12/2006 | Schutze et al. |
| 2007/0049603 A1 | 3/2007 | Miknis et al. |
| 2007/0059265 A1 | 3/2007 | Boulle |
| 2007/0071699 A1 | 3/2007 | Boulle |
| 2007/0078175 A1 | 4/2007 | Boulle et al. |
| 2007/0155884 A1 | 7/2007 | Pellegatti et al. |
| 2007/0219234 A1 | 9/2007 | Oizumi et al. |
| 2007/0293533 A1 | 12/2007 | Ginn et al. |
| 2008/0039459 A1 | 2/2008 | Folkes et al. |
| 2008/0206320 A1 | 8/2008 | Michelet et al. |
| 2008/0249117 A1 | 10/2008 | Michelet et al. |
| 2009/0105210 A1 | 4/2009 | Ashton et al. |
| 2009/0118337 A1 | 5/2009 | Davis |
| 2009/0163545 A1 | 6/2009 | Goldfarb |
| 2010/0022521 A1 | 1/2010 | Nogradi et al. |
| 2010/0076041 A1 | 3/2010 | Kilburn et al. |
| 2010/0099672 A1 | 4/2010 | Karp et al. |
| 2010/0120732 A1 | 5/2010 | Tabunoki |
| 2010/0190853 A1 | 7/2010 | Rethore et al. |
| 2010/0234369 A1 | 9/2010 | Hoelzemann et al. |
| 2011/0009374 A1 | 1/2011 | Keller |
| 2011/0014250 A1 | 1/2011 | Michelet et al. |
| 2011/0034564 A1 | 2/2011 | Parkkinen |
| 2011/0142816 A1 | 6/2011 | Landry et al. |
| 2011/0195031 A1 | 8/2011 | Du |
| 2011/0269954 A1 | 11/2011 | Cho et al. |
| 2012/0065200 A1 | 3/2012 | Barbosa et al. |
| 2012/0302586 A1 | 11/2012 | Rathod et al. |
| 2013/0078632 A1 | 3/2013 | Krishnadath |
| 2013/0190297 A1 | 7/2013 | DeJonghe et al. |
| 2014/0371219 A1 | 12/2014 | Bae et al. |
| 2015/0072998 A1 | 3/2015 | Markowitz et al. |
| 2015/0118744 A1 | 4/2015 | Tanaka et al. |
| 2015/0202241 A1 | 7/2015 | Choi et al. |
| 2016/0136185 A1 | 5/2016 | Shin et al. |
| 2016/0311825 A1 | 10/2016 | Farmer et al. |
| 2016/0376430 A1 | 12/2016 | Kusumoto et al. |
| 2017/0165241 A1 | 6/2017 | Markowitz et al. |
| 2017/0173028 A1 | 6/2017 | Markowitz et al. |
| 2017/0174704 A1 | 6/2017 | Gigstad et al. |
| 2017/0216265 A1 | 8/2017 | Markowitz et al. |
| 2017/0266141 A1 | 9/2017 | Nagy |
| 2018/0064694 A1 | 3/2018 | Markowitz et al. |
| 2018/0118756 A1 | 5/2018 | Markowitz et al. |
| 2018/0125829 A1 | 5/2018 | Markowitz et al. |
| 2019/0126044 A1 | 5/2019 | Lozano |
| 2019/0275014 A1 | 9/2019 | Markowitz et al. |
| 2019/0365769 A1 | 12/2019 | Markowitz et al. |
| 2020/0030348 A1 | 1/2020 | Markowitz et al. |
| 2020/0061073 A1 | 2/2020 | Markowitz et al. |
| 2020/0095206 A1 | 3/2020 | Markowitz et al. |
| 2020/0140453 A1 | 5/2020 | Markowitz et al. |
| 2020/0147063 A1 | 5/2020 | Markowitz et al. |
| 2020/0165249 A1 | 5/2020 | Panarese et al. |
| 2021/0032265 A1 | 2/2021 | Markowitz et al. |
| 2021/0094968 A1 | 4/2021 | Markowitz et al. |
| 2021/0100778 A1 | 4/2021 | Markowitz et al. |
| 2021/0100779 A1 | 4/2021 | Markowitz et al. |
| 2021/0106587 A1 | 4/2021 | Markowitz et al. |
| 2021/0108177 A1 | 4/2021 | Di Santo et al. |
| 2021/0165249 A1 | 6/2021 | Wang et al. |
| 2021/0283113 A1 | 9/2021 | Markowitz et al. |
| 2021/0317132 A1 | 10/2021 | Markowitz et al. |
| 2021/0386070 A1 | 12/2021 | Arlt et al. |
| 2023/0039604 A1 | 2/2023 | Markowitz et al. |
| 2023/0052363 A1 | 2/2023 | Markowitz et al. |
| 2023/0116062 A1 | 4/2023 | Markowitz et al. |
| 2023/0165883 A1 | 6/2023 | Markowitz et al. |
| 2023/0192717 A1 | 6/2023 | Gwaltney et al. |
| 2023/0285402 A1 | 9/2023 | Markowitz et al. |
| 2023/0310390 A1 | 10/2023 | Markowitz et al. |
| 2023/0322684 A1 | 10/2023 | Markowitz et al. |
| 2023/0355636 A1 | 11/2023 | Markowitz et al. |
| 2024/0024297 A1 | 1/2024 | Markowitz et al. |
| 2024/0043440 A1 | 2/2024 | Markowitz et al. |
| 2024/0043443 A1 | 2/2024 | Markowitz et al. |
| 2024/0100026 A1 | 3/2024 | Markowitz et al. |
| 2024/0174688 A1 | 5/2024 | Markowitz et al. |

FOREIGN PATENT DOCUMENTS

| | | |
|---|---|---|
| AU | 2016/248080 A1 | 11/2017 |
| AU | 2014/342811 B2 | 1/2019 |
| AU | 2018/200368 B2 | 7/2019 |
| AU | 2018/215678 A1 | 8/2019 |
| AU | 2018/249956 A1 | 11/2019 |
| AU | 2019/250163 A1 | 11/2019 |
| AU | 2016/229918 B2 | 10/2020 |
| AU | 2019/247838 A1 | 10/2020 |
| AU | 2019/202208 B2 | 12/2020 |
| AU | 2021/201332 A1 | 3/2021 |
| AU | 2019/384821 A1 | 6/2021 |
| AU | 2021/204985 A1 | 8/2021 |
| AU | 2017/300377 B2 | 4/2022 |

(56) References Cited

FOREIGN PATENT DOCUMENTS

| | | |
|---|---|---|
| AU | 2022/201982 A1 | 4/2022 |
| AU | 2022/005248 A1 | 8/2022 |
| AU | 2022/205248 A1 | 8/2022 |
| AU | 2018/272108 B2 | 9/2022 |
| AU | 2021/200610 B2 | 9/2022 |
| AU | 2021/224268 A1 | 9/2022 |
| AU | 2021/201332 B2 | 11/2022 |
| AU | 2021/275122 A1 | 12/2022 |
| CA | 2007351 A1 | 7/1990 |
| CA | 2870666 A1 | 10/2013 |
| CA | 2927730 A1 | 4/2016 |
| CA | 2979203 A1 | 9/2016 |
| CA | 2974266 A1 | 7/2017 |
| CA | 2984594 A1 | 10/2017 |
| CA | 3031091 A1 | 1/2018 |
| CA | 3052466 A1 | 8/2018 |
| CA | 3059255 A1 | 10/2018 |
| CA | 3068445 A1 | 11/2018 |
| CA | 2984588 C | 10/2019 |
| CA | 3095308 A1 | 10/2019 |
| CA | 3120858 A1 | 5/2020 |
| CA | 3168728 A1 | 8/2021 |
| CA | 3183262 A1 | 11/2021 |
| CL | 2007001610 A1 | 1/2008 |
| CL | 2013000682 A1 | 11/2013 |
| CL | 2014001729 A1 | 9/2014 |
| CL | 2020002741 A1 | 1/2021 |
| CL | 2021001288 A1 | 1/2022 |
| CL | 2021001321 A1 | 4/2022 |
| CL | 2021003378 A1 | 8/2022 |
| CN | 1589793 A | 3/2005 |
| CN | 1966500 A | 5/2007 |
| CN | 102888208 B | 2/2015 |
| CN | 107921025 A | 4/2018 |
| CN | 108012528 A | 5/2018 |
| CN | 110573154 A | 12/2019 |
| CN | 110582277 A | 12/2019 |
| CN | 110891568 A | 3/2020 |
| CN | 111132982 A | 5/2020 |
| CN | 11273944 A | 4/2021 |
| CN | 113507931 A | 10/2021 |
| CN | ZL 2017 8 0053063.5 | 11/2023 |
| EA | 202191422 A1 | 10/2021 |
| EP | 0142811 A2 | 5/1985 |
| EP | 0271273 A2 | 6/1988 |
| EP | 0378508 A2 | 7/1990 |
| EP | 0434624 A1 | 6/1991 |
| EP | 0648488 B1 | 11/2000 |
| EP | 1080728 A1 | 3/2001 |
| EP | 1175890 A1 | 1/2002 |
| EP | 1175891 A1 | 1/2002 |
| EP | 0854700 B1 | 5/2002 |
| EP | 0680745 B1 | 11/2002 |
| EP | 2564841 B1 | 5/2015 |
| EP | 2838533 B1 | 10/2017 |
| EP | 3267995 A1 | 1/2018 |
| EP | 3280398 A1 | 2/2018 |
| EP | 3283074 A1 | 2/2018 |
| EP | 3295940 A1 | 3/2018 |
| EP | 3484473 A1 | 5/2019 |
| EP | 3057973 B1 | 9/2019 |
| EP | 3548035 A1 | 10/2019 |
| EP | 3576737 A1 | 12/2019 |
| EP | 3606520 A1 | 2/2020 |
| EP | 3630773 A1 | 4/2020 |
| EP | 3781154 A1 | 2/2021 |
| EP | 3883577 A1 | 9/2021 |
| EP | 4106748 | 12/2022 |
| EP | 4153299 | 3/2023 |
| EP | 4192455 | 6/2023 |
| FR | 2838641 A1 | 10/2003 |
| FR | 2860431 A1 | 4/2005 |
| GB | 1 516 894 | 7/1978 |
| JP | S51-30286 A | 3/1976 |
| JP | S60-172984 A | 9/1985 |
| JP | H02-288810 | 11/1990 |
| JP | H04-234888 A | 8/1992 |
| JP | H09-295921 A | 11/1997 |
| JP | H10-287532 A | 10/1998 |
| JP | 2003/286171 A | 10/2003 |
| JP | 2004-067629 A | 3/2004 |
| JP | 2004/528319 A | 9/2004 |
| JP | 2005/515182 A | 5/2005 |
| JP | 2005/325099 A | 11/2005 |
| JP | 2004/528319 A5 | 1/2006 |
| JP | 2006-522746 A | 10/2006 |
| JP | 2006-522749 A | 10/2006 |
| JP | 2006/522750 A | 10/2006 |
| JP | 2006-522749 A5 | 5/2007 |
| JP | 2006/522750 A5 | 5/2007 |
| JP | 2006-522746 A5 | 6/2007 |
| JP | 2007/527850 A | 10/2007 |
| JP | 2008/507518 A | 3/2008 |
| JP | 2008/527011 A | 7/2008 |
| JP | 2008/536855 A | 9/2008 |
| JP | 2008/536855 A5 | 5/2009 |
| JP | 2009/520016 A | 5/2009 |
| JP | 2009/535335 A | 10/2009 |
| JP | 2009/535335 A5 | 1/2010 |
| JP | 2010/053332 A | 3/2010 |
| JP | 2010/520864 A | 6/2010 |
| JP | 2007/527850 A5 | 7/2010 |
| JP | 2011/500610 A | 1/2011 |
| JP | 2013/506004 A | 2/2013 |
| JP | 2013/506004 A5 | 10/2013 |
| JP | 2015/514770 A | 5/2015 |
| JP | 2016/531864 A | 10/2016 |
| JP | 2016/537328 A | 12/2016 |
| JP | 2017/514809 A | 6/2017 |
| JP | 6203820 B2 | 9/2017 |
| JP | 2018/511581 A | 4/2018 |
| JP | 2018/511616 A | 4/2018 |
| JP | 2018/511616 A5 | 5/2019 |
| JP | 6517197 B2 | 5/2019 |
| JP | 2019/135253 A | 8/2019 |
| JP | 2020/502070 A | 1/2020 |
| JP | 2020/503851 A | 2/2020 |
| JP | 2020/514323 A | 5/2020 |
| JP | 2020/516617 A | 6/2020 |
| JP | 2020/516617 A5 | 7/2020 |
| JP | 6789542 B2 | 11/2020 |
| JP | 2020/502070 A5 | 1/2021 |
| JP | 2021/020942 A | 2/2021 |
| JP | 2020/514323 A5 | 3/2021 |
| JP | 2021/038247 A | 3/2021 |
| JP | 2021/519797 A | 8/2021 |
| JP | 2022/507888 A | 1/2022 |
| JP | 2021/519797 A5 | 4/2022 |
| JP | 2022/141390 A | 9/2022 |
| JP | 2022/141930 A | 9/2022 |
| JP | 7139308 B2 | 9/2022 |
| JP | 2022/163172 A | 10/2022 |
| JP | 2022/174196 A | 11/2022 |
| JP | 2022/191415 A | 12/2022 |
| JP | 2023/527279 A | 6/2023 |
| KR | 2008/0112764 A | 12/2008 |
| KR | 2010/0137090 A | 12/2010 |
| KR | 2012-0025903 A | 3/2012 |
| KR | 2013/0103945 A | 9/2013 |
| RU | 2006/127472 A | 2/2008 |
| WO | WO 1990/006100 A1 | 6/1990 |
| WO | WO 1993/013664 A2 | 7/1993 |
| WO | WO 1995/011003 A1 | 4/1995 |
| WO | WO 97/39750 A1 | 10/1997 |
| WO | WO 1998/027092 A1 | 6/1998 |
| WO | WO 1998/033497 A1 | 8/1998 |
| WO | WO 2001/017480 A2 | 3/2001 |
| WO | WO 2001/072268 A1 | 10/2001 |
| WO | WO 2001/074307 A2 | 10/2001 |
| WO | WO 2001/074313 A2 | 10/2001 |
| WO | WO 2001/074314 A2 | 10/2001 |
| WO | WO 2001/074315 A2 | 10/2001 |
| WO | WO 2004/012671 A2 | 2/2004 |

(56) References Cited

FOREIGN PATENT DOCUMENTS

| | | |
|---|---|---|
| WO | WO 2004/089415 A2 | 10/2004 |
| WO | WO 2004/089416 A2 | 10/2004 |
| WO | WO 2004/089470 A2 | 10/2004 |
| WO | WO 2004/089471 A2 | 10/2004 |
| WO | WO 2004/099204 A1 | 11/2004 |
| WO | WO 2005/002503 A2 | 1/2005 |
| WO | WO 2005/021552 A1 | 3/2005 |
| WO | WO 2005/028676 A2 | 3/2005 |
| WO | WO 2005/030773 A1 | 4/2005 |
| WO | WO 2005/046434 A2 | 5/2005 |
| WO | WO 2005/062735 A2 | 7/2005 |
| WO | WO 2005/090333 A1 | 9/2005 |
| WO | WO 2006/019832 A1 | 2/2006 |
| WO | WO 2006/048264 A2 | 5/2006 |
| WO | WO 2006/048266 A2 | 5/2006 |
| WO | WO 2006/074226 A2 | 7/2006 |
| WO | WO 2006/078676 A2 | 7/2006 |
| WO | WO 2006/096649 A2 | 9/2006 |
| WO | WO 2006/098961 A2 | 9/2006 |
| WO | WO 2006/138275 A2 | 12/2006 |
| WO | WO 2007/013665 A2 | 2/2007 |
| WO | WO 2007/019180 A2 | 2/2007 |
| WO | WO 2007/027855 A2 | 3/2007 |
| WO | WO 2007/038519 A1 | 4/2007 |
| WO | WO 2007/072095 A1 | 6/2007 |
| WO | WO 2007/100775 A2 | 9/2007 |
| WO | WO 2007/101224 A2 | 9/2007 |
| WO | WO 2007/127183 A1 | 11/2007 |
| WO | WO 2007/146602 A1 | 12/2007 |
| WO | WO 2007/146602 A8 | 12/2007 |
| WO | WO 2008/063671 A2 | 5/2008 |
| WO | WO 2008/156614 A2 | 12/2008 |
| WO | WO 2008/157500 A1 | 12/2008 |
| WO | WO 2009/029669 A1 | 3/2009 |
| WO | WO 2009/073460 A2 | 6/2009 |
| WO | WO 2009/082691 A1 | 7/2009 |
| WO | WO 2009/111648 A1 | 9/2009 |
| WO | WO 2009/120877 A2 | 10/2009 |
| WO | WO 2010/023181 A1 | 3/2010 |
| WO | WO 2010/045017 A1 | 4/2010 |
| WO | WO 2010/052569 A2 | 5/2010 |
| WO | WO 2010/077101 A2 | 7/2010 |
| WO | WO 2010/080996 A1 | 7/2010 |
| WO | WO 2010/091808 A1 | 8/2010 |
| WO | WO 2010/111711 A2 | 9/2010 |
| WO | WO 2011/041304 A2 | 4/2011 |
| WO | WO 2011/042860 A2 | 4/2011 |
| WO | WO 2011/094847 A1 | 8/2011 |
| WO | WO 2011/147753 A1 | 12/2011 |
| WO | WO 2012/037141 A1 | 3/2012 |
| WO | WO 2012/058671 A1 | 5/2012 |
| WO | WO 2012/146933 A1 | 11/2012 |
| WO | WO 2013/034927 A1 | 3/2013 |
| WO | WO 2013/100632 A1 | 4/2013 |
| WO | WO 2013/082243 A1 | 6/2013 |
| WO | WO 2013/083991 A1 | 6/2013 |
| WO | WO 2013/112699 A2 | 8/2013 |
| WO | WO 2013/158649 A1 | 10/2013 |
| WO | WO 2013/180336 A1 | 12/2013 |
| WO | WO 2014/081617 A1 | 5/2014 |
| WO | WO 2014/081878 A2 | 5/2014 |
| WO | WO 2014/160183 A1 | 10/2014 |
| WO | WO 2014/160947 A1 | 10/2014 |
| WO | WO 2015/005239 A1 | 1/2015 |
| WO | WO 2015/065716 A1 | 5/2015 |
| WO | WO 2015/077382 A2 | 5/2015 |
| WO | WO 2015/161142 A1 | 10/2015 |
| WO | WO 2016/106340 A2 | 6/2016 |
| WO | WO 2016/124939 A1 | 8/2016 |
| WO | WO 2016/144958 A1 | 9/2016 |
| WO | WO 2016/168472 A1 | 10/2016 |
| WO | WO 2017/152044 A1 | 9/2017 |
| WO | WO 2018/017582 A1 | 1/2018 |
| WO | WO 2018/102552 A1 | 6/2018 |
| WO | WO 2018/145080 A1 | 8/2018 |
| WO | WO 2018/187810 A1 | 10/2018 |
| WO | WO 2018/196870 A1 | 11/2018 |
| WO | WO 2018/218251 A1 | 11/2018 |
| WO | WO 2018/227134 A1 | 12/2018 |
| WO | WO 2019/010482 A1 | 1/2019 |
| WO | WO 2019/195565 A1 | 10/2019 |
| WO | WO 2020/051207 A2 | 3/2020 |
| WO | WO 2020/106998 A1 | 5/2020 |
| WO | WO 2020/160151 | 8/2020 |
| WO | WO 2020/252146 A1 | 12/2020 |
| WO | WO 2021/151014 A1 | 7/2021 |
| WO | WO 2021/168430 A1 | 8/2021 |
| WO | WO 2021/236779 A1 | 11/2021 |
| WO | WO 2021/252936 A1 | 12/2021 |
| WO | WO 2021/236779 A9 | 1/2022 |
| WO | WO 2022/032230 A1 | 2/2022 |
| WO | WO 2022/087631 A1 | 4/2022 |
| WO | WO 2022/126125 A1 | 6/2022 |

OTHER PUBLICATIONS

U.S. Appl. No. 17/898,776, filed Aug. 30, 2022, Docket Central, Pending.
U.S. Appl. No. 15/347,587, US-2017-0216265 U.S. Pat. No. 9,801,863, filed Nov. 9, 2016, Aug. 3, 2017 Oct. 31, 2017, Issued.
U.S. Appl. No. 15/785,259, US 2019-0365769 A1 U.S. Pat. No. 10,869,871, filed Oct. 16, 2017, Dec. 5, 2019 Dec. 22, 2020, Issued.
U.S. Appl. No. 15/799,307, US 2018-0125829 A1 U.S. Pat. No. 10,420,752, filed Oct. 31, 2017, May 10, 2018 Sep. 24, 2019, Issued.
U.S. Appl. No. 15/029,943, US 2017-0173028 A1 U.S. Pat. No. 9,789,116, filed Apr. 15, 2016, Jun. 22, 2017 Oct. 17, 2017, Issued.
U.S. Appl. No. 17/131,911, US-2021-0283113-A1, filed Dec. 23, 2020, Sep. 16, 2021, Pending.
U.S. Appl. No. 16/869,879, US 2021-0094968 A1, filed May 8, 2020, Apr. 1, 2021, Pending.
U.S. Appl. No. 15/566,637, US 2018-0118756 A1, filed Oct. 13, 2017, May 3, 2018, Abandoned.
U.S. Appl. No. 16/995,878, US 2021-0100778 A1, filed Aug. 18, 2020, Apr. 8, 2021, Pending.
U.S. Appl. No. 16/319,159, US 2019-0275014 A1, filed Jan. 18, 2019, Sep. 24, 2019, Abandoned.
U.S. Appl. No. 16/465,500, US 2020-0061073 A1, filed May 30, 2019, Feb. 27, 2020, Pending.
U.S. Appl. No. 16/484,045, US 2020-0095206 A1, filed Aug. 6, 2019, Mar. 26, 2020, Pending.
U.S. Appl. No. 17/893,777, filed Aug. 23, 2022, To Be Assigned, Pending.
U.S. Appl. No. 16/603,544, US 2020-0030348 A1 U.S. Pat. No. 11,246,420, filed Oct. 7, 2019, Jan. 30, 2020 Aug. 20, 2022, Issued.
U.S. Appl. No. 18/057,589, filed Nov. 21, 2022, Pending.
U.S. Appl. No. 17/044,888, US 2021-0100779 A1, filed Apr. 4, 2019, Apr. 8, 2021, Pending.
U.S. Appl. No. 17/892,585, filed Aug. 22, 2022, To Be Assigned, Pending.
International Search Report, Written Opinion, and International Preliminary Report on Patentability issued in PCT International Application No. PCT/US2013/036790, ISA/KR Korean Intellectual Property Office, Daejeon Metropolitan City, Republic of Korea. 13 pages.
International Search Report, Written Opinion, and International Preliminary Report on Patentability issued in PCT/US2014/060761, ISA/US United States Patent and Trademark Office, Alexandria, VA. 14 pages.
International Search Report and Written Opinion and International Preliminary Report on Patentability issued in PCT International Application No. PCT/US2016/021374, ISA/US United States Patent and Trademark Office, Alexandria, VA. 15 pages.
International Search Report, Written Opinion, and International Preliminary Report on Patentability issued in PCT/US2016/027549, ISA/US United States Patent and Trademark Office, Alexandria, VA. 16 pages.
International Search Report, Written Opinion, and International Preliminary Report on Patentability issued in PCT/US2017/042620,

(56) References Cited

OTHER PUBLICATIONS

ISA/US United States Patent and Trademark Office, Alexandria, VA. 24 pages.
International Search Report, Written Opinion, and International Preliminary Report on Patentability issued in PCT/US2017/063959, ISA/US United States Patent and Trademark Office, Alexandria, VA. 31 pages.
International Search Report, Written Opinion, and International Preliminary Report on Patentability issued in PCT/US2018/017044, ISA/US United States Patent and Trademark Office, Alexandria, VA. 15 pages.
International Search Report and Written Opinion and International Preliminary Report on Patentability issued in PCT International Application No. PCT/US2018/026739, ISA/US United States Patent and Trademark Office, Alexandria, VA. 17 pages.
International Search Report, Written Opinion, and International Preliminary Report on Patentability issued in PCT/US2018/034944, ISA/US United States Patent and Trademark Office, Alexandria, VA. 15 pages.
International Search Report, Written Opinion, and International Preliminary Report on Patentability issued in PCT/US2019/025812, ISA/US United States Patent and Trademark Office, Alexandria, VA. 16 pages.
International Search Report and Written Opinion and International Preliminary Report on Patentability issued in PCT/US2019/062686, ISA/RU Federal Institute of Industrial Property, Moscow, RU. 15 pages.
International Search Report, Written Opinion, and International Preliminary Report on Patentability issued in PCT/US2021/019084, ISA/US United States Patent and Trademark Office, Alexandria, VA. 13 pages.
International Search Report and Written Opinion issued in PCT/US2021/033170, ISA/EP European Patent Office, NL. 16 pages.
International Search Report and Written Opinion issued in PCT/US2021/045231, ISA/US United States Patent and Trademark Office, Alexandria, VA. 9 pages.
International Search Report and Written Opinion issued in PCT/US2022/12423, ISA/US United States Patent and Trademark Office, Alexandria, VA. 12 pages.
Abulwerdi, F.A., et al., "Development of Small Molecules with a Non-Canonical Binding Mode to HIV-1 Trans Activation Response (TAR) RNA," *Journal of Medicinal Chemistry*, Dec. 22, 2016, pp. 11148-11160, 59(24), American Chemical Society, Washington, DC, US.
Ahmad, Muzamil, et al., "The $PGE_2EP2$ receptor and its selective actibvation are beneficial against ischemic stroke," *Experimental & Translational Stroke Medicine*, 2010, 8 pages, vol. 2, No. 12, BioMed Central, UK.
"AKos Screening Samples ca. 3.5 million compounds Version Dec. 2007," Web page <www.akosgmbh.de/AKosSamples/index.html>, 3 pages, Dec. 19, 2007, retrieved from the Internet Archive Wayback Machine via Page Vault <http://web.archive.org/web/20071219115313/http://www.akosgmbh.de/AKosSamples/index.html> on Sep. 29, 2022.
Almeida, Camila Bononi, et al., "High Expression of the cGMP-specific Phosphodiesterase, PDE9A, in Sickle Cell Disease (SCD) and the Effects of its Inhibition in Erythroid Cells and SCD Neutrophils," *British Journal of Haematology*, Sep. 2008, pp. 836-844, 142(5), Blackwell Publishing Ltd, Oxford, UK.
Almeida, Camila Bononi, et al., "Hydroxyurea and a cGMP-amplifying Agent Have Immediate Benefits on Acute Vaso-Occlusive Events in Sickle Cell Disease Mice," *Blood*, Oct. 4, 2012, 23 pages, 120(14), American Society of Hematology, Washington, DC, US.
Al-Najjar, Belal O., et al., "Pharmacophore Modeling and 3D-QSAR Studies of 15-Hydroxyprostaglandin Dehydrogenase (15-PGDH) Inhibitors," *Indian Journal of Chemistry*, Nov. 2017, pp. 1200-1207, vol. 56B, Scientific Publishers of India, IN.
Alvarez, F.J., and Slade, R.T., "Kinetics and Mechanism of Degradation of Zileuton, a Potent 5-Lipoxygenase Inhibitor," *Pharmaceutical Research*, 1992, pp. 1465-1473, vol. 9, No. 11, Plenum Publishing Corporation-Springer Science and Business Media, DE.
Antczak, M.I., et al., "Inhibitors of 15-Prostaglandin Dehydrogenase To Potentiate Tissue Repair", *Journal of Medicinal Chemistry*, 2017, pp. 23 pages, vol. 60, No. 9, American Chemical Society, Washington, DC, US.
Archelas, A., et al., "Absolute Configuration of α-Methylstyrene Oxide: The Correct Absolute Configuration/ Optical Rotation Correlation", *The Journal of Organic Chemistry*, Aug. 1, 1999, pp. 6112-6114, vol. 64, No. 16, American Chemical Society, Washington, DC, US.
Asati, V., et al., "Molecular Modeling Studies of Some Thiazolidine-2,4-Dione Derivatives as 15-PGDH Inhibitors," *Medicinal Chemistry Research*, Aug. 29, 2015, pp. 94-108, vol. 25, Springer Science + Business Media, DE.
Astatech, "AstaTech Inc. Catalog Product Search Result," Compound: 6-Bromo-3-Methylpyrimidin-4(3H)-One, 2 pages, Oct. 18, 2022, retrieved via Page Vault https://astatechnic.com/CPSResult.php?CRNO=183100 on Oct. 18, 2022.
Bagshaw, S. M., et al., "A comparison of the Rifle and Akin criteria for acute kidney injury in critically ill patients," *Nephrology Dialysis Transplantation*, May 2008, pp. 1569-1574, vol. 23, Issue 5, Oxford University Press, Oxford, UK, retrieved from https://academic.oup.com/ndt/article/23/5/1569/1809429, on Oct. 18, 2022.
Baker, Michael E. "Licorice and Enzymes Other Than 11β-Hydroxysteroid Dehydrogenase: An Evolutionary Perspective," *Steroids*, Feb. 1994, pp. 136-141, vol. 59, Issue 2, Butterworth-Heinemann, Elsevier, Ltd, Oxford, UK.
Bakhle, Y.S., "Action of Prostaglandin Dehydrogenase Inhibitors on Prostaglandin Uptake in Rat Isolated Lung," *British Journal of Pharmacology*, Apr. 1979, pp. 635-639, 65(4), British Pharmacological Society, Macmillan Journals Ltd, UK.
Baliga, B.S, et al., "Combined Effects of Arginine and Hydroxyurea on BFU-E Derived Colony Growth and HbF Synthesis in Erythroid Progenitors Isolated from Sickle Cell Blood," *Cellular and Molecular Biology*, 2010, pp. OL1290-OL1298, vol. 56, No. 3, Cellular and Molecular Biology Association, Paris, FR.
Bärnthaler, Thomas, et al., "Inhibiting Eicosanoid Degradation Exerts Antifibrotic Effects in a Pulmonary Fibrosis Mouse Model and Human Tissue," *Journal of Allergy and Clinical Immunology*, Mar. 2020, pp. 818-833, vol. 145, No. 3, Elsevier Inc, Amsterdam, NL.
Battistini, Bruno, et al., "COX-1 and COX-2: Toward the Development of More Selective NSAIDS," Advances in prostaglandin research were presented at the 9th International Conference on Prostaglandins and Related Compounds in Florence, Italy, Jun. 6-10, 1994, and the 12th International Congress of Pharmacology in Montreal, Canada, Jul. 24-29, 1994, *Drug News & Perspectives Meeting Report*, Oct. 1994, pp. 501-512, 7(8).
Becker, C., et al., "In Vivo Imaging of Colitis and Colon Cancer Development in Mice Using High-Resolution Chromoendoscopy," *Gut*, 2005, pp. 950-954, vol. 54, BMJ, UK.
Berg, Daniel J., et al. "Rapid Development of Colitis in NSAID-Treated IL-10-Deficient Mice", *Gastroenterology*, 2002, pp. 1527-1542, vol. 123, No. 5, American Gastroenterological Association, W.B. Saunders, Philadelphia, PA.
Berk, L.B., et al., "16,16-Dimethyl Prostaglandin E2 and/or Syngeneic Bone Marrow Transplantation Increase Mouse Survival After Supra-Lethal Total Body Irradiation." *International Journal of Radiation Oncology Biology Physics*, Jun. 1990, pp. 1387-1392, vol. 18, No. 6, Pergamon Press plc, Oxford, UK.
Berry, C.N., et al., "Inhibition of Prostaglandin 15-Hydroxydehydrogenase by Sulphasalazine and a Novel Series of Potent Analogues," *Biochemical Pharmacology*, Oct. 1, 1983, pp. 2863-2871, vol. 32, No. 19, Pergamon Press Ltd., GB.
Bertram, Lars, et al., "Systematic meta-analyses of Alzheimer disease genetic association studies: the AlzGene database," *Nature Genetics*, Jan. 2007, pp. 17-23, vol. 39, No. 1, Nature Publishing Group, UK.
Bertram, Lars, et al., "Is α-T catenin (VR22) an Alzheimer's disease risk gene?", *Journal of Medical Genetics, Electronic Letters*, Jan. 2007, pp. 1-4, vol. 44, No. 1, BMJ Group, UK.

(56) References Cited

OTHER PUBLICATIONS

Blackwell, G.J., and Flower, R.J., "A Rapid Method for the Estimation of Prostaglandin 15-Hydroxydehydrogenase Activity and its Application to Pharmacology," *British Journal of Pharmacology*, 1976, pp. 589-597, vol. 57, Issue 4, British Pharmacological Society, UK.

Blake, Martin I., et al., "Studies with Deuterated Drugs", *Journal of Pharmaceutical Sciences*, Mar. 1975, pp. 367-391, vol. 64, No. 3, Elsevier, Amsterdam, NL.

Borm, Michelle E.A., and Bouma, Gerd, "Animal Models of Inflammatory Bowel Disease," *Drug Discovery Today: Disease Models*, Dec. 2004, pp. 437-443, vol. 1, Issue 4, Elsevier, Amsterdam, NL.

Bray, James E., et al., "The Human Short-Chain Dehydrogenase/Reductase (SPR) Superfamily: A Bioinformatics Summary," *Chemico-Biological Interactions*, Mar. 16, 2009, pp. 99-109, vol. 178, Issues 1-3, Elsevier, Amsterdam, NL.

Breyer, Richard M., et al., "Prostanoid Receptors: Subtypes and Signaling," *Annual Review of Pharmacology and Toxicology*, 2001, 32 pages including pp. 661-690, vol. 41, Annual Reviews, San Mateo, CA, US.

Brown, J.R., et al., "COX-2: A Molecular Target for Colorectal Cancer Prevention," *Journal of Clinical Oncology*, Apr. 20, 2005, pp. 2840-2855, vol. 23, No. 12, American Society of Clinical Oncology, Lippincott Williams and Wilkins, Philadelphia, PA, US.

Cahn, R.S., and Ingold, C.K., "Specification of Configuration about Quadricovalent Asymmetric Atoms,"*Journal of the Chemical Society*, 1951, pp. 612-622, Chemical Society, UK.

Cahn, R.S., et al., "The Specification of Asymmetric Configuration in Organic Chemistry," *Experientia*, 1956, pp. 81-94, vol. 12, No. 3, Springer Science + Business Media, Berlin, DE.

Cahn, R.S., "An Introduction to the Sequence Rule: A System for the Specification of Absolute Configuration," *Journal of Chemical Education*, Mar. 1964, pp. 116-125, vol. 41, No. 3, American Chemical Society, Washington, DC.

Cahn, R.S., et al., "Specification of Molecular Chirality," *Angew. Chem. Inter. Edit.*, 1966, pp. 385-415, vol. 5, No. 4, Wiley-VCH, Weinheim, DE.

Cahn, R.S., et al., Errata "Specification of Molecular Chirality,", *Angew, Chem. Inter. Edit.*, 1966, p. 511, vol. 5, No. 5, Wiley-VCH, Weinheim, DE.

Cancer Genome Atlas Network, "Comprehensive molecular characterization of human colon and rectal cancer," *Nature*, Jul. 19, 2012, pp. 330-337, vol. 487, Macmillan Publishers Limited, UK.

Cancer Genome Atlas Network, "Comprehensive molecular portraits of human breast tumours," *Nature*, Oct. 4, 2012, pp. 61-70, vol. 490, Macmillan Publishers Limited, UK.

Cancer Genome Atlas Network, "Integrated genomic analyses of ovarian carcinoma," *Nature*, Jun. 30, 2011, pp. 609-615, vol. 474, and Erratum, *Nature*, Oct. 11, 2012, p. 292, vol. 490, Macmillan Publishers Limited, UK.

Castellone, M.D., et al., "Prostaglandin $E_2$ Promotes Colon Cancer Cell Growth Through a $G_s$-Axin-β-Catenin Signaling Axis," *Science*, Dec. 2, 2005, pp. 1504-1510, vol. 310, Issue 5753, American Association for the Advancement of Science, Washington, DC, US.

Chang, Kyung Hee., et al., "Vasculopathy-Associated Hyperangiotensinemia Mobilizes Haematopoietic Stem Cells/Progenitors Through Endothelial $AT_2R$ and Cytoskeletal Dysregulation," *Nature Communications*, Jan. 9, 2015, 11 pages, 6, Article 5914, Macmillan Publishers Limited, Nature Research, London, UK.

"ChemBridge | Screening Libraries: Key Facts," Web page <www.chembridge.com/screening_libraries/>, 2 pages, Jan. 22, 2013, retrieved from the Internet Archive Wayback Machine via Page Vault <http://web.archive.org/web/20130122020518/https://www.chembridge.com/screening_libraries/> on Sep. 29, 2022.

Chemtob, Sylvain, et al., "Deficiency in Prostaglandin $E_2$ ($PGE_2$) Receptors, Mainly $EP_2$ Subtype, on Brain Synaptosomes in Early Development: Implications on Cerebral Metabolism," *Seminars in Perinatology*, Feb. 1994, pp. 23-29, vol. 18, No. 1, W.B. Saunders Company, Philadelphia, PA, US.

Chen, H., et al., "Prostaglandin E2 Mediates Sensory Nerve Regulation of Bone Homeostasis," *Nature Communications*, Jan. 14, 2019, pp. 1-13, vol. 10, Issue 1, Article No. 181, Nature Research, London, UK.

Chi, Xiuling, et al., "15-Hydroxyprostaglandin Dehydrogenase (15-PGDH) is Up-Regulated by Flurbiprofen and Other Non-Steroidal Anti-Inflammatory Drugs in Human Colon Cancer HT29 Cells," *Archives of Biochemistry and Biophysics*, Jul. 15, 2009, pp. 139-145, vol. 487, No. 2, Elsevier, Amsterdam, NL.

Childs, April C., et al., "Doxorubicin Treatment in Vivo Causes Cytochrome c Release and Cardiomyocyte Apoptosis, As Well As Increased Mitochondrial Efficiency, Superoxide Dismutase Activity, and Bcl-2:Bax Ratio," *Cancer Research*, Aug. 15, 2002, pp. 4592-4598, vol. 62, American Association for Cancer Research, Philadelphia, PA, US.

Cho, H., Tai, H.-H., "Inhibition of $NAD^+$-dependent 15-hydroxyprostaglandin dehydrogenase (15-PGDH) by cyclooxygenase inhibitors and chemopreventive agents," *Prostaglandins, Leukotrienes, and Essential Fatty Acids*, 2002, p. 461-465, vol. 67(6), Elsevier Science Ltd, Amsterdam, NL.

Cho, Hoon, and Tai, Hsin-Hsiung, "Thiazolidinediones as a Novel Class of NAD+-Dependent 15-Hydroxyprostaglandin Dehydrogenase Inhibitors," *Archives of Biochemistry and Biophysics*, 2002, pp. 247-251, vol. 405, Academic Press, Elsevier Science (USA).

Cho, Hoon, et al., "Role of glutamine 148 of human 15-hydroxyprostaglandin dehydrogenase in catalytic oxidation of prostaglandin E2", *Bioorganic & Medicinal Chemistry*, 2006, pp. 6486-6491, vol. 14, Elsevier Ltd, Amsterdam, NL.

Choi, Dubok, et al., "Control of the Intracellular Levels of Prostaglandin $E_2$ Through Inhibition of the 15-Hydroxyprostaglandin Dehydrogenase for Wound Healing," *Bioorganic and Medicinal Chemistry*, 2013, 8 pages, Elsevier, Amsterdam, NL.

Clifford, P.C., et al., "Treatment of Vasospastic Disease with Prostaglandin $E_1$," *British Medical Journal*, Oct. 18, 1980, pp. 1031-1034, vol. 281, British Medical Association, UK.

Colombe, L., "Prostaglandin Metabolism in Human Hair Follicle," *Experimental Dermatology*, 2007, pp. 762-769, vol. 16, No. 9, Blackwell Munksgaard, Copenhagen, DK.

Combrinck, M., et al. "Levels of CSF Prostaglandin $E_2$, Cognitive Decline, and Survival in Alzheimer's disease," *Journal of Neurology, Neurosurgery, and Psychiatry*, Jun. 8, 2005, pp. 85-88, vol. 77, pp. 85-88, BMJ Group, London, UK.

Cooper, H. S. et al., "Clinicopathologic Study of Dextran Sulfate Sodium Experimental Murine Colitis," *Laboratory Investigation*, (1993), pp. 238-249, vol. 69, No. 2, The United States and Canadian Academy of Pathology, Inc., USA.

Coteron, J.M., et al., "Structure-Guided Lead Optimization of Triazolopyrimidine-Ring Substituents Identifies Potent *Plasmodium falciparum* Dihydroorotate Dehydrogenase Inhibitors with Clinical Candidate Potential", *Journal of Medicinal Chemistry*, Aug. 11, 2011, pp. 5540-5561, vol. 54, No. 15, American Chemical Society, Washington, DC, US.

Croft, D., et al., "The Reactome pathway knowledgebase," *Nucleic acids research*, 2014, pp. D472-D477, vol. 42, Oxford University Press, UK.

Cudaback, Eiron, et al., "Therapeutic Implications of the Prostaglandin Pathway in Alzheimer's Disease," *Biochemical Pharmacology*, Apr. 15, 2014, pp. 565-572, vol. 88, Issue 4, Elsevier Inc., Amsterdam, NL.

Cutler, Corey, et al., "Prostaglandin-Modulated Umbilical Cord Blood Hematopoietic Stem Cell Transplantation," *Blood*, 2013, 30 pages, American Society of Hematology, Washington, DC, US.

Dai, Liying, et al., "Inverse Expression of Prostaglandin $E_2$-Related Enzymes Highlights Differences Between Diverticulitis and Inflammatory Bowel Disease," *Digestive Diseases and Sciences*, 2015, pp. 1236-1246, vol. 60, Springer Science + Business Media, Berlin, DE.

Dalvi, Siddhartha, et al., "Exogenous Arachidonic Acid Mediates Permeability of Human Brain Microvessel Endothelial Cells through Prostaglandin $E_2$ Activation of $EP_3$ and $EP_4$ Receptors," *Journal of*

(56) References Cited

OTHER PUBLICATIONS

*Neurochemistry*, Apr. 27, 2015, pp. 867-879, vol. 135, International Society for Neurochemistry, Wiley-Blackwell, Hoboken, NJ, US.

Deng, Yang, et al., "Lipopolysaccharide Stimulates Bovine Endometrium Explants through Toll-Like Receptor 4 Signaling and $PGE_2$ Synthesis," *Prostaglandins, Leukotrienes, and Essential Fatty Acids*, May 2021, Abstract only-2pages, vol. 168, Elsevier Ltd., Amsterdam, NL.

Desai, A., et al., "A Second-Generation 15-PGDH Inhibitor Promotes Bone Marrow Transplant Recovery Independently of Age, Transplant Dose, and Granulocyte Colony-Stimulating Factor Support," *Haematologica*, 2018, pp. 1054-1064, 103(6), Ferrata Storti Foundation, IT.

Dong, Yuanqiang, et al., "Effects of SW033291 on the Myogenesis of Muscle-Derived Stem Cells and Muscle Regeneration," *Stem Cell Research and Therapy*, 2020, 17 pages, vol. 11, Issue 76, BioMedCentral, London, UK.

Douville, Christopher, et al., "Assessing Aneuploidy with Repetitive Element Sequencing," *Proceedings of the National Academy of Sciences*, Mar. 3, 2020, pp. 4858-4863, vol. 117, No. 9, United States National Academy of Sciences, Washington, DC, US.

Dowd, Noreen P., et al., "Inhibition of Cyclooxygenase-2 Aggravates Doxorubicin-Mediated Cardiac Injury in Vivo," *The Journal of Clinical Investigation*, Aug. 15, 2001, pp. 585-590, vol. 108, No. 4, American Society for Clinical Investigation, US.

Doxorubicin Hydrochloride Package Insert and Package Label Display Panel, Revised: Jan. 2021, 16 pages, Teva Pharmaceuticals USA, Inc., Labeler: Actavis Pharma, Inc.

Duveau, Damien Y., et al., "Discovery of two small molecule inhibitors, ML387 and ML388, of human $NAD^+$-dependent 15-hydroxyprostaglandin dehydrogenase," *Probe Reports from the NIH Molecular Libraries Program*, 2013, 26 pages, National Center for Biotechnology Information, US.

Duveau, Damien Y., et al., "Structure-activity relationship studies and biological characterization of human $NAD^+$-dependent 15 hydroxyprostaglandin dehydrogenase inhibitors", *Bioorganic and Medicinal Chemistry Letters*, Jan. 15, 2014, pp. 630-635, vol. 24, Elsevier, Amsterdam, NL.

Echeverria, Valentina, et al., "Stimulation of $PGE_2$ Receptors $EP_2$ and $EP_4$ Protects Cultured Neurons Against Oxidative Stress and Cell Death Following β-Amyloid Exposure," *European Journal of Neuroscience*, 2005, pp. 2199-2206, vol. 22, Federation of European Neuroscience Societies, Wiley-Blackwell, Hoboken, NJ.

"Enamine—Screening Compounds," Web page <http://www.enamine.net/index.php?option=com_content&taskeview&id=22& menuid=51&PHPSESSID=64a4f248f69d671a413f487bb62c4d90>, 2 pages, Jun. 30, 2007, retrieved from the Internet Archive Wayback Machine via Page Vault <http://web.archive.org/web/20070630171813/http://www.enamine.net/index.php?option=com_content&task=view&id=22&menuid=51&PHPSESSID=64a4f248f69d671a413f487bb62c4d90> on Sep. 29, 2022.

Ensor, C.M, et al., "Site-Directed Mutagenesis of the Conserved Tyrosine 151 of Human Placental $NAD^+$-dependent 15-Hydroxyprostaglandin Dehydrogenase Yields a Catalytically Inactive Enzyme", *Biochemical and Biophysical Research Communications*, Apr. 30, 1991, pp. 840-845, vol. 176, No. 2, Academic Press, Inc., Elsevier, Amsterdam, NL.

Ensor, Charles Mark, et al., "Bacterial expression and site-directed mutagenesis of two critical residues (tyrosine-151 and lysine-155) of human placental $NAD^+$-dependent 15-hydroxyprostaglandin dehydrogenase", *Biochimica et Biophysica Acta*, 1994, pp. 151-156, vol. 1208, Elsevier Science B.B., Amsterdam, NL.

Eridani, S., and Mosca, A., "Fetal hemoglobin reactivation and cell engineering in the treatment of sickle dell anemia," *Journal of Blood Medicine*, Feb. 28, 2011, pp. 23-30, vol. 2, Dove Medical Press, UK.

Esrick, Erica B., et al., "Inactivation of HDAC1 or HDAC2 induces gamma globulin expression without altering cell cycle or proliferation," *American Journal of Hematology*, Jul. 2015, pp. 624-628, vol. 90, No. 7, Wiley Pharmaceuticals, Inc., Hoboken, NJ, US.

European Directorate for the Quality of Medicines & Healthcare, Structure / Nomenclature Guide, "A Guide to the Graphic Representation and Nomenclature of Chemical Formulae in the European Pharmacopoeia," *European Pharmacopoeia*, 2011, 40 pages, $2^{nd}$ Edition, Council of Europe, Strasbourg, FR.

Fauchier, L., et al., "Use of Anticoagulants and Antiplatelet Agents in Stable Outpatients with Coronary Artery Disease and Atrial Fibrillation. International CLARIFY Registry," *PLoS One*, Apr. 27, 2015, 23 pages, 10(4), Public Library of Science, San Francisco, CA, US.

Filippini, A., et al., "Covid-19 Acute Respiratory Distress Syndrome: Can Iloprost Have a Role for This Treatment?"*Respiratory Medicine Case Reports*, 2021, 101358, 4 pages, vol. 32, Elsevier, NL.

Fitzpatrick, F.A., et al., "The Stability of 13,14-Dihydro-15 Keto-$PGE_2$," *Prostaglandins*, Jun. 1980, pp. 917-931, vol. 19, No. 6., Elsevier Inc., NL.

Frias, M.A., et al., "The $PGE_2$-Stat3 Interaction in Doxorubicin-Induced Myocardial Apoptosis," *Cardiovascular Research*, 2008, pp. 69-77, vol. 80, Published on behalf of the European Society of Cardiology, Oxford University Press, Oxford, UK.

Frisch, Benjamin, et al., "In Vivo Prostaglandin $E_2$ Treatment Alters the Bone Marrow Microenvironment and Preferentially Expands Short-Term Hematopoietic Stem Cells," *Blood*, Nov. 5, 2009, 12 pages including pp. 4054-4063, vol. 114, No. 19, American Society of Hematology, Washington, DC, US.

Galiè, Nazzareno, et al., "Guidelines for the diagnosis and treatment of pulmonary hypertension," *European Heart Journal*, 2009, pp. 2493-2537, vol. 30, European Society of Cardiology, Oxford University Press, Oxford, UK.

Gentile, P., et al., "In Vivo Modulation of Murine Myelopoiesis Following Intravenous Administration of Prostaglandin E2", *Blood*, 1983, 8 pages including pp. 1100-1107, vol. 62, No. 5, American Society of Hematology, Washington, DC, US.

Ghiso, Jorge, et al., "Cerebral amyloidosis, amyloid angiopathy, and their relationship to stroke and dementia," *Journal of Alzheimer's Disease*, 2001, pp. 65-73, vol. 3, No. 1, IOS Press, Amsterdam, NL.

Girgis, Adel S., et al., "Synthesis of new 3-pyridinecarboxylates of potential vasodilation properties," *European Journal of Medicinal Chemistry*, 2008, vol. 43, pp. 1818-1827, Elsevier, NL.

Giugliano, Robert P., et al., "Edoxaban versus Warfarin in Patients with Atrial Fibrillation," *The New England Journal of Medicine*, Nov. 28, 2013, pp. 2093-2104, vol. 369, No. 22, Massachusetts Medical Society, Waltham, MA, US.

Goessling, Wolfram, et al., "Genetic Interaction of PGE2 and Wnt Signaling Regulates Developmental Specification of Stem Cells and Regeneration," *Cell*, Mar. 20, 2009, pp. 1136-1147, vol. 136, Issue 6, Cell Press, Elsevier Inc., Cambridge, MA, US.

Goessling, Wolfram, et al., "Prostaglandin E2 Enhances Human Cord Blood Stem Cell Xenotransplants and Shows Long-Term Safety in Preclinical Nonhuman Primate Transplant Models," *Cell Stem Cell*, Apr. 8, 2011, pp. 445-458, vol. 8, Cell Press, Elsevier Inc., Cambridge, MA, US.

Gu, Xiaosong, et al., "Prostaglandin E2 Reduces Cardiac Contractility via EP3 Receptor," *Circulation: Heart Failure*, Aug. 2016, 8 pages, e003291, vol. 9, Issue 8, American Heart Association, Lippincott Williams & Wilkins, Philadelphia, PA, US.

Guo, Jian-You, et al., "Chronic unpredictable mild stress induces parallel reductions of 15-PGDH in the hypothalamus and lungs in rats," *Behavioural Brain Research*, 2015, pp. 278-284, vol. 286, Elsevier B.V., NL.

Hagedorn, E. J., et al., "Getting More for Your Marrow: Boosting Hematopoietic Stem Cell Numbers with PGE2", *Experimental Cell Research*, 2014, 7 pages, Elsevier Inc., Amsterdam, NL.

Hall, P. R. et al., "Small Molecule Inhibitors of Hantavirus Infection", *Bioorganic & Medicinal Chemistry Letters*, Dec. 1, 2010, pp. 1-17, vol. 20, No. 23, Elsevier, Amsterdam, NL.

Hamed, S., et al., "Erythropoietin Improves Myocardial Performance in Doxorubicin-Induced Cardiomyopathy," *European Heart Journal*, 2006, pp. 1876-1883, vol. 27, Oxford University Press, Oxford, UK.

Hamid, N., et al., "A Neural System Dynamics Modeling Platform And Its Applications In Randomized Controlled Trial Data Analy-

(56) References Cited

OTHER PUBLICATIONS sis," *Informatics in Medicine Unlocked*, 2021, 13 pages, 100612, vol. 24, Elsevier Ltd., Amsterdam, NL.

Hamza, Adel, et al., "Understanding human 15-hydroxyprostaglandin dehydrogenase binding with $NAO^+$ and $PGE_2$ by homology modeling, docking and molecular dynamics simulation," *Bioorganic & Medicinal Chemistry*, pp. 4544-4551, vol. 13, Elsevier Ltd., Amsterdam, NL.

Hanai, H., et al., "Curcumin Maintenance Therapy for Ulcerative Colitis: Randomized, Multicenter, Double-Blind, Placebo-Controlled Trial," *Clinical Gastroenterology and Hepatology*, December 2006, pp. 11502-1506, vol. 4, Issue 5, Elsevier, Amsterdam, NL.

Hao, C.M., "Physiological Regulation of Prostaglandins in the Kidney," *Annual Review of Physiology*, 2008, 25 pages including pp. 357-377, vol. 70, Annual Reviews, San Mateo, CA, US.

Hao, G., et al., "Protective Effects of Berberine Against Doxorubicin-Induced Cardiotoxcity in Rats by Inhibiting Metabolism of Doxorubicin," *Xenobiotica*, 2015, pp. 1024-1029, vol. 45, Issue 11, Informa, London, UK.

Harrowven, D. C. "'Cascade' Radical Reactions in Synthesis: Condensed Thiophenes from Ketenethioacetals," *Tetrahedron Letters*, 1993, pp. 5653-5656, vol. 34, No. 35, Elsevier, Amsterdam, NL.

Hassan, M., et al., "Modulatory Effects of Meloxicam on Cardiotoxicity and Antitumor Activity of Doxorubicin in Mice," *Cancer Chemotherapy and Pharmacology*, Jul. 23, 2014, pp. 559-569, vol. 74, Springer Science + Business Media, Berlin, DE.

Heyman, Samuel N., et al., "Animal models of renal dysfunction: acute kidney injury," *Expert Opinon on Drug Discovery*, 2009, pp. 629-641, 4(6), Taylor & Francis, UK.

Heyman, Samuel N. , et al., "Acute Kidney Injury: Lessons from Experimental Models," *Experimental Models for Renal Diseases: Pathogenesis and Diagnosis*, 2011, pp. 286-296, vol. 169, Karger, Basel, CH.

Hoffman, Corey M., et al., "Minireview: Complexity of Hematopoietic Stem Cell Regulation in the Bone Marrow Microenvironment", *Molecular Endocrinology*, 2014, pp. 1-11, vol. 28, The Endocrine Society, Washington, DC, US.

Hoggatt, J., et al., "Prostaglandin $E_2$ Enhances Hematopoietic Stem Cell Homing, Survival, and Proliferation," *Blood*, May 28, 2009, cover page, pp. 5444-5455, vol. 113, No. 22, American Society for Hematology, Washington, DC, US.

Hoggatt, J., et al., "Differential Stem- and Progenitor-Cell Trafficking by Prostaglandin E2", *Nature*, 00 Month 2013, 7 pages, vol. 000, Nature Portfolio, London, UK.

Hoggatt, J., et al., "Prostaglandin $E_2$ Enhances Long-Term Repopulation but Does not Permanently Alter Inherent Stem Cell Competitiveness", *Blood*, Oct. 24, 2013, pp. 2997-3000, vol. 122, No. 17, American Society of Hematology, Washington, DC, US.

Hoggatt, Jonathan, et al., "Recovery from Hematopoietic Injury by Modulating Prostaglandin $E_2$ Signaling Post-Irradiation", *Blood Cells, Molecules and Diseases*, 2013, pp. 147-153, vol. 50, Elsevier Inc., Amsterdam, NL.

Hong, Yu Ah, et al., Paricalcitol Pretreatment Attenuates Renal Ischemia-Reperfusion Injury via Prostaglandin $E_2$ Receptor E4 Pathway, *Oxidative Medicine and Cellular Longevity*, 2017, 17 pages, vol. 2017, Hindawi Publishing Corporation, London, UK.

Hoult, J.R.S., and Moore, P.K., "Sulphasalazine is a Potent Inhibitor of Prostaglandin 15-Hydroxydehydrogenase: Possible Basis for Therapeutic Action in Ulcerative Colitis," *British Journal of Pharmacology*, 1978, pp. 6-8, vol. 64, Macmillan Journals Ltd, UK.

Hoyt, A.L., et al., "On the nature of the chain-extending species in organolithium initiated stereospecific reagent-controlled homologation reactions using α-chloroalkyl aryl sulfoxides," *Tetrahedron Letters*, 2015, vol. 1 56, pp. 2980-2982, Elsevier Ltd., NL.

Huang, X., et al., "Safety and Efficacy of Bivalirudin Monotherapy in Patients with Non-ST-Segment Elevation Acute Coronary Syndromes with Positive Biomarkers Undergoing Percutaneous Coronary Intervention: A Report From The Acute Catheterization and Urgent Intervention Triage Strategy Trial," *Coronary Artery Disease*, Jan. 1, 2020, pp. 59-65, vol. 31, Issue 1, Wolters Kluwer Health, Inc., Lippincott Williams & Wilkins, Philadelphia, PA, US.

Huang, W.J., and Tang, X.X., "Virus Infection Induced Pulmonary Fibrosis," *Journal of Translational Medicine*, 2021, 15 pages, vol. 19, Issue 496, BioMedCentral, UK.

Hughes, P.A., et al., "Experimental Colitis Models," *TRP Channels in Drug Discovery: vol. II*, Chapter 23, Jan. 1, 2012, pp. 379-390, Humana Press, Springer, Munich, DE.

Hunt, T. K., et al., "Coagulation and Macrophage Stimulation of Angiogenesis and Wound Healing," *The Surgical Wound, ed. F. Dineen & G. Hildrick-Smith*, 1981, 21 pages including pp. 1-18, Lea & Febiger, Philadelphia, PA.

"Inflammatory Bowel Disease," Web page <https://www.healthline.com/health/inflammatory-bowel-disease>, 6 pages, Jan. 7, 2015, retrieved from the Internet Archive Wayback Machine via Page Vault <http://web.archive.org/web/20070630171813/http://www.enamine.net/index.php?option=com_content&task=view&id=22&menuid=51&PHPSESSID=64a4f248f69d671a413f487bb62c4d90> on Oct. 25 2022.

Iqubal, A., et al., "Clinical Updates on Drug-Induced Cardiotoxicity," *International Journal of Pharmaceutical Sciences and Research*, 2018, pp. 16-26, vol. 9, Issue 1, Society of Pharmaceutical Sciences and Research, Panchkula, Haryana, IN.

Jadapalli, J.K., et al., "Doxorubicin Triggers Splenic Contraction and Irreversible Dysregulation of COX and LOX That Alters the Inflammation-Resolution Program in the Myocardium," *American Journal of Physiology—Heart and Circulatory Physiology*, 2018, pp. H1091-H1100, vol. 315, American Physiological Society, Rockville, MD, US.

Jadhav, A., et al., "Potent and Selective Inhibitors of $NAD^+$-Dependent 15-Hydroxyprostaglandin Dehydrogenase (HPGD)", *Molecular Libraries, Pathways to Discovery*, Jul. 8, 2011, 36 pages, NIH.

Jain, D., et al., "Cardiac Complications of Cancer Therapy: Pathophysiology, Identification, Prevention, Treatment, and Future Directions," *Current Cardiology Reports*, 2017, 12 pages, vol. 19, Issue 36, Springer Science + Business Media, Berlin, DE.

Johnston, Dudley E., "Wound Healing in Skin," *Plastic and Reconstructive Surgery, Veterinary Clinics of North American: Small Animal Practice*, Jan. 1990, pp. 1-25, vol. 20, No. 1, W.B. Saunders Ltd., US.

Jolly, L., et al. "Influenza Promotes Collagen Deposition via αvβ6 Integrin-Mediated Transforming Growth Factor β activation," *The Journal of Biological Chemistry*, Dec. 19, 2014, pp. 35246-35263, vol. 289, No. 51, pp. 35246-35263, American Society for Biochemistry and Molecular Biology, Rockville, MD, US.

Julkunen, I., et al., "Inflammatory Response to Influenza A Virus Infection," *Vaccine*, 2001, pp. S32-S37, vol. 19, Elsevier Science Ltd., Amsterdam, NL.

Jung, P., et al., "Isolation ard in vitro Expansion of Human Colonic Stem Cells," *Nature Medicine*, Oct. 2011, pp. 1225-1227, vol. 17, No. 10, Nature Publishing Group, London, UK.

Kabashima, K., et al., "The Prostaglandin Receptor EP4 Suppresses Colitis, Mucosal Damage and CD4 Cell Activation in the Gut", *The Journal of Clinical Investigation*, Apr. 2002, pp. 883-893, vol. 109, No. 7, American Society for Clinical Investigation, US.

Kalugin, V.E. et al. "Functionalized Sulfur-Containing Compounds. 13. *Synthesis of Substituted 3-amino-2-(organylsulfinyl)-and-(organylsulfonyl)thieno[2,3-b]pyridines," *Russian Chemical Bulletin, International Edition*, Mar. 2006, pp. 529-534, vol. 55, No. 3, Springer Science + Business Media, Berlin, DE.

Kalugin, V.E., et al., "Utilization of Potassium Carbonate for the Synthesis of 2-(organylsulfonyl) thieno[2,3-b]pyridine Derivatives," *Russian Chemical Bulletin, International Edition*, Feb. 2019, pp. 357-364, vol. 68, No. 2, Springer Science + Business Media, Berlin, DE.

Kang, G.-J., et al., "High-Mobility Group Box 1 Suppresses Resolvin D1-Induced Phagocytosis via Induction of Resolvin D1-Inactivating Enzyme, 15-Hydroxyprostaglandin Dehydrogenase," *Biochimica et Biophysica Acta*, 2015, pp. 1981-1988, vol. 1852, No. 9, Elsevier B.V., Amsterdam, NL.

Karna, Sandeep, et al. "Novel Potent 15-Hydroxyprostaglandin Dehydrogenase Inhibitors," *Journal of Advanced Engineering and Technology*, 2010, pp. 301-304, vol. 3, No. 3.

(56) References Cited

OTHER PUBLICATIONS

Karna, Sandeep, "In-vitro Wound Healing Effect of 15-Hydroxyprostaglandin Dehydrogenase Inhibitor from Plant," *Pharmacognosy Magazine*, Apr. 7, 2017, pp. S122-S126, vol. 13, Issue 49, Supplement 1, Wolters Kluwer—Medkenow Publications, Mumbai, IN.

Katz, J.A., "The Practical Use of Corticosteroids in the Treatment of Inflammatory Bowel Disease," *Practical Gastroenterology*, Jan. 2005, pp. 14, 16, 18, 21, 22, 25, Shugar Publishing, Westhampton Beach, NY, US.

Kawaguchi, H., et al., "The Role of Prostaglandins in the Regulation of Bone Metabolism," *Clinical Orthopaedics and Related Research*, 1995, pp. 36-46, No. 313, J.B. Lippincott and Company, Philadelphia, PA.

Keller, M.D., J., et al., "Short-term Effect of Local Application of $PGE_2$ on Callus in Rabbit Osteotomy," *Eur J Exp Musculoskel Res*, 1992, vol. 1, pp. 86-92.

Kim, M. et al., "Decreased Catalytic Activity of the Insulin-degrading Enzyme in Chromosome 10-Linked Alzheimer Disease Families," *The Journal of Biological Chemistry*, Mar. 16, 2007, pp. 7825-7832, vol. 282, No. 11, The American Society for Biochemistry and Molecular Biology, Inc., USA.

Kim, H.J., et al., "Inhibition of 15-PGDH Prevents Ischemic Renal Injury by the $PGE_2/EP_4$ Signaling Pathway Mediating Vasodilation, Increased Renal Blood Flow, and Increased Adenosine/$A_{2A}$ Receptors," *American Journal of Physiology—Renal Physiology*, 2020, F1054-F1066, vol. 319, American Physiological Society, Rockville, MD.

Kimball, Frances A., et al., "Plasma Concentrations of 9-Deoxo-16,16-Dimethyl-9-methylene-$PGE_2$ In Rhesus Monkeys after Administration by Various Routes," *Prostaglandins*, Sep. 1980, pp. 559-569, vol. 20, No. 3, Elsevier, Amsterdam, NL.

Kishore, A.H., et al., "Prostaglandin Dehydrogenase is a Target for Successful Induction of Cervical Ripening," *Proceedings of the National Academy of Sciences*, Jul. 17, 2017, pp. E6427-E6436, vol. 114, No. 29, United States National Academy of Sciences, Washington, DC, US.

Kishore, B.K, et al., "Ticagrelor Reduces Urinary Concentration and Arginine Vasopressin (AVP) Levels: Potential Use in AVP Excess States," *Kidney Week*, Oct. 23, 2018, Poster SA-PO1018, San Diego, CA, in the Journal of the American Society of Nephrology, 2018, p. 1002, vol. 29, American Society of Nephrology, Washington, DC, US.

Konturek, P.C., et al., "Prostaglandins as Mediators of Cox-2 Derived Carcinogenesis in Gastrointestinal Tract," Journal of Physiology and Pharmacology, Sep. 1, 2005, 12 pages, vol. 56, Suppl. 5.

Konturek, S.J., et al., "Prostaglandins and Ulcer Healing," Journal of Physiology and Pharmacology, 2005, 22 pages, vol. 56, No. 5.

Kurland, J.I., et al., "Role for Monocyte-Macrophage-Derived Colony-Stimulating Factor and Prostaglandin E in the Positive and Negative Feedback Control of Myeloid Stem Cell Proliferation," *Blood*, 1978, 21 pages including pp. 388-407, vol. 52, American Society of Hematology, Washington, DC, US.

Lakatos et al., "The Role of PPARs in Lung Fibrosis," *PPAR Research*, Jul. 2, 2007, pp. 1-10, Hindawi Publishing Corporation, London, UK.

Lam, P.-Y., et al., "Cyp1 Inhibition Prevents Doxorubicin-Induced Cardiomyopathy in a Zebrafish Heart Failure Model," *ChemBioChem*, Jul. 1, 2020, pp. 1905-1910, vol. 21, Issue 13, Wiley-VCH, Weinheim, DE.

Lewis, J.D., et al., "An Open-Label Trial of the PPARγ Ligand Rosiglitazone for Active Ulcerative Colitis," *The American Journal of Gastroenterology*, 2001, pp. 3323-3328, vol. 96, No. 12, Elsevier Science Inc., NL.

Li, J., et al., "Neutrophil AKT2 Regulates Heterotypic Cell-Cell Interactions During Vascular Inflammation," *Journal of Clinical Investigation*, Apr. 2014, 15 pages including pp. 1483-1496, vol. 124, Issue 4, American Society for Clinical Investigation, US.

Li, T., et al., "$PGE_2$ Increases Inflammatory Damage in *Escherichia coli*-infected Bovine Endometrial Tissue in vitro Via the EP4-PKA Signaling Pathway," *Biology of Reproduction*, 2019, pp. 175-186, vol. 100, Issue 1, Oxford University Press, Oxford, UK.

Li, T., et al., "Prostaglandin $E_2$ Promotes Nitric Oxide Synthase 2, Platelet-Activating Factor Receptor, and Matrix Metalloproteinase-2 Expression in *Escherichia coli*-challenged ex vivo Endometrial Explants via the Prostaglandin $E_2$ Receptor 4/Protein Kinase A Signaling Pathway," *Theriogenology*, Aug. 2019, pp. 65-73, vol. 134, Elsevier, Amsterdam, NL.

Li, N., et al., "Ferritinophagy-Mediated Ferroptosis is Involved in Sepsis-Induced Cardiac Injury," *Free Radical Biology and Medicine*, 2020, pp. 303-318, vol. 160, Elsevier, Amsterdam, NL. Submitted in 2 parts.

Lian, W.-S., et al., "The Prostaglandin Agonist Beraprost Aggravates Doxorubicin-Mediated Apoptosis by Increasing iNOS Expression in Cardiomyocytes," *Current Vascular Pharmacology*, Jan. 1, 2015, pp. 54-63, vol. 13, No. 1, Bentham Science Publishers, UK.

Liu, Y.-C. et al., "Triazolopyrimidines as a New Herbicidal Lead for Combating Weed Resistance Associated with Acetohydroxyacid Synthase Mutation", *Journal of Agricultural and Food Chemistry*, 2016, pp. 4845-4857, vol. 64, No. 24, American Chemical Society, Washington, DC, US.

Liu, C., et al., "Development and Stimulation of a Sensitive and Rapid UHPLC-MS/MS Method for the Simultaneous Quantification of the Common Active and Inactive Metabolites of Vicagrel and Clopidogrel in Human Plasma," *Journal of Pharmaceutical and Biomedical Analysis*, Feb. 5, 2018, pp. 394-402, vol. 149, Elsevier, Amsterdam, NL.

Liu, C., et al., "Pharmacokinetics and Pharmacokinetic/Pharmacodynamic Relationship of Vicagrel, a Novel Thineopyridine $P2Y_{12}$ Inhibitor, Compared with Clopidogrel in Healthy Chinese Subjects Following Single Oral Dosing," *European Journal of Pharmaceutical Sciences*, Jan. 15, 2019, pp. 151-160, vol. 127, Elsevier, Amsterdam, NL.

Lopes, J.A., et al., "The Rifle and Akin Classifications for Acute Kidney Injury: A Critical and Comprehensive Review," *Clinical Kidney Journal*, 2013, pp. 8-14, vol. 6, Oxford University Press, Oxford, UK.

Lorente, A., et al., "Synthesis of Heterocyclic Compounds. XXXIX [1]. Synthesis of 5-Cyano-2-Phenyl-4-Thioxo-3,4-Dihydropyrimidines," *Journal of Heterocyclic Chemistry*, 1985, pp. 49-51, vol. 22, Wiley-Blackwell, Hoboken, NJ, US Lovgren, A.K., et al., "COX-2-Derived Prostacyclin Protects Against Bleomycin-Induced Pulmonary Fibrosis," *American Journal of Physiology—Lung Cellular and Molecular Physiology*, pp. L144-L156, Feb. 10, 2006, vol. 291, The American Physiological Society, Rockville, MD, US.

Lu, L., et al., "Animal Models of Gastrointestinal Inflammation and Cancer," *Life Sciences*, 2014, pp. 1-6, vol. 108, Issue 1, Elsevier, Amsterdam, NL.

Luca, G., "The Future of Targeted Therapy: Combining Novel Agents," *Oncology*, 2002, pp. 47-56, vol. 63 (Supplement 1), Karger Publishers, Basel, CH.

Luu, A.Z., "Role of Endothelium in Doxorubicin-Induced Cardiomyopathy," *JACC: Basic to Translational Science*, Dec. 2018, pp. 861-870, vol. 3, No. 6, Elsevier on behalf of American College of Cardiology, Amsterdam, NL.

Ma, F., et al., "Discovery and Structure-Activity Relationships Study of Thieno[2,3-b]pyridine Analogues as Hepatic Gluconeogenesis Inhibitors," *European Journal of Medicinal Chemistry*, May 25, 2018, Abstract, vol. 152, Elsevier, Amsterdam, NL.

Makala, L., et al., "FK228 Analogues Induce Fetal Hemoglobin in Human Erythroid Progenitors," *Anemia*, 2012, Article ID 428137, 13 pages, vol. 2012, Hindawi Publishing Corporation, London, UK.

Mallipeddi, P.L., et al., "Structural Insights into Novel 15-Prostaglandin Dehydrogenase Inhibitors," *Molecules*, 2021, 17 pages, 5903, Multidisciplinary Digital Publishing Institute, Basel, CH.

Markowitz, S., et al., "Aspirin and Colon Cancer—Targeting Prevention", *The New England Journal of Medicine*, May 24, 2007, pp. 2195-2198, vol. 356, No. 21, Massachusetts Medical Society, MA, US.

(56) References Cited

OTHER PUBLICATIONS

Markowitz, S., et al., "Molecular Origins of Cancer—Molecular Basis of Colorectal Cancer," *The New England Journal of Medicine*, Dec. 17, 2009, pp. 2449-2460, vol. 361, No. 25, Massachusetts Medical Society, MA, US.

Mayo Clinic, "Diseases and Conditions—Chronic Kidney Disease," Web page <www.mayoclinic.org/diseases-conditions/kidney-disease/basics/causes/con20026778>, Jan. 7, 2015, retrieved from the Internet Archive Wayback Machine via Page Vault <http://web.archive.org/web/20150107203836/www.mayoclinic.org/diseases-conditions/kidney-disease/basics/causes/con-20026778> on Oct. 25, 2022.

Mayo Clinic, "Diseases and Conditions—Chronic kidney disease", Jan. 30, 2015, http://www.mayoclinic.org/diseases-conditions/kidney disease/basics/causes/con-20026778, accessed Dec. 11, 2015.

Mayo Clinic, "Chronic kidney disease—Care at Mayo Clinic," Oct. 25, 2022, retrieved from Page Vault https://www.mayoclinic.org/diseases-conditions/chronic-kidney-disease/care-at-mayo-clinic/mac-20354531 on Oct. 25, 2022.

Mayo Clinic, "Chronic kidney disease—Diagnosis and treatment," Oct. 25, 2022, retrieved from Page Vault https://www.mayoclinic.org/diseases-conditions/chronic-kidney-disease/diagnosis-treatment/drc-20354527 on Oct. 25, 2022.

Mayo Clinic, "Chronic kidney disease—Doctors and departments," Oct. 25, 2022, retrieved from Page Vault https://www.mayoclinic.org/diseases-conditions/chronic-kidney-disease/doctors-departments/ddc:20354530 on Oct. 25, 2022.

Mayo Clinic, "Chronic kidney disease—Symptoms and causes," Oct. 25, 2022, retrieved from Page Vault https://www.mayoclinic.org/diseases-conditions/chronic-kidney-disease/symptoms-causes/syc-20354521 on Oct. 25, 2022.

McCaffrey, T.A., et al., "Genomic Profiling Reveals the Potential Role of TCLIA and MDRI Deficiency in Chemotherapy-Induced Cardiotoxicity," *International Journal of Biological Sciences*, 2013, pp. 350-360, vol. 9, Issue 4, Ivyspring International Publisher Pty Ltd, AU.

McCullough, Louise, et al., "Neuroprotecive Function of the $PGE_2$ EP2 Receptor in Cerebral Ischemia," *The Journal of Neuroscience*, Jan. 7, 2004, pp. 257-268, vol. 24, No. 1, Society for Neuroscience, Washington, D.C., US.

Michelet, J.F., et al., "Expression of $NAD^+$ Dependent 15-Hydroxyprostaglandin Dehydrogenase and Protection of Prostaglandins in Human Hair Follicle," *Experimental Dermatology*, 2008, pp. 821-828, vol. 17, No. 10, Wiley, Hoboken, NJ, US.

Mitchell, C., and Willenbring, H., "A Reproducible and Well-Tolerated Method for ⅔ Partial Hepalectomy in Mice," *Nature Protocols*, 2008, pp. 1167-1170, vol. 3, No. 7, Nature Publishing Group, London, UK.

Montrose, D.C., et al., "The Role of $PGE_2$ in Intestinal Inflammation and Tumorigenesis," *Prostaglandins and Other Lipid Mediators*, 2015, 23 pages, Elsevier, Amsterdam, NL.

Mordente, A., et al., "Human Heart Cytosolic Reductases and Anthracycline Cardiotoxicity", *IUBMB Life*, 2001, pp. 83-88, vol. 52, John Wiley and Sons, Hoboken, NJ, US.

Morishita, Yoshiyuki, et al., "Establishment of Acute Kidney Injury Mouse Model by 0.75% Adenine Ingestion," *Renal Failure*, 2011, pp. 1013-1018, vol. 33, No. 10, Informa Healthcare USA, Inc., US.

Moustafa, Y.M., et al., "15-PGDH Inhibitors: The Antiulcer Effects of Carbenoxolone, Pioglitazone and Verapamil in Indomethacin Induced Peptic Ulcer Rats," *European Review for Medical and Pharmacological Sciences*, 2013, pp. 2000-2009, vol. 17, Verduci Editore, Rome, IT.

Myung, Seung-Jae, et al., "15-Hydroxyprostaglandin dehydrogenase is an in vivo suppressor of colon tumorigenesis," *Proceedings of the National Academy of Sciences*, Aug. 8, 2006, pp. 12098-12102, vol. 103, No. 32, United States National Academy of Sciences, Washington, DC, US.

Na, H.-K., et al., "15-Hydroxyprostaglandin Dehydrogenase as a Novel Molecular Target for Cancer Chemoprevention and Therapy," *Biochemical Pharmacology*, 2011, pp. 1352-1360, vol. 82, Elsevier, Amsterdam, NL.

Nakanishi, M., and Rosenberg, D.W., "Multifaceted Roles of $PGE_2$ in Inflammation and Cancer," *Seminars in Immunopathology*, 2013, pp. 123-137, vol. 35, Springer, Berlin, DE.

Nasrallah, Rania, et al., "$PGE_2$, Kidney Disease, and Cardiovascular Risk: Beyond Hypertension and Diabetes," *Journal of the American Society of Nephrology*, 2016, pp. 666-676, vol. 27, American Society of Nephrology, US.

Neilan, T.G., et al., "Disruption of COX-2 Modulates Gene Expression and the Cardiac Injury Response to Doxorubicin," *American Journal of Physiology—Heart and Circulatory Physiology*, Apr. 14, 2006, pp. H532-H536, vol. 291, American Physiological Society, Rockville, MD, US.

Niesen., F.H., et al., "High-Affinity Inhibitors of Human $NAD^+$-Dependent 15-Hydroxyprostaglandin Dehydrogenase: Mechanisms of Inhibition and Structure-Activity Relationships", *PLoS One*, Nov. 2010, e13719, 12 pages, vol. 5, issue 11, Public Library of Science, San Francisco, CA, US.

Noe, A., et al., "High Incidence of Severe Cyclosporine Neurotoxicity in Children Affected by Haemoglobinopaties Undergoing Myeloablative Haematopoietic Stem Cell Transplantation: Early Diagnosis and Prompt Intervention Ameliorates Neurological Outcome," *Italian Journal of Pediatrics*, Feb. 6, 2010, Article No. 14, pp. 1-6, vol. 36, BioMedCentral, London, UK.

Nogradi, K., et al., "Thieno[2,3-b]pyridines as Negative Allosteric Modulators of Metabotropic GluR5 Receptors: Hit-To-Lead Optimization," *Bioorganic and Medicinal Chemistry Letters*, 2014, pp. 3845-3849, vol. 24, Elsevier, Amsterdam, NL.

North, T.E., et al., "Prostaglandin E2 Regulates Vertebrate Haematopoietic Stem Cell Homeostasis," *Nature*, Jun. 21, 2007, pp. 1007-1011, vol. 447, Nature Research, London, UK.

North, Trisla E., "PGE2-Regulaled wnl Signaling and N-Acetylcysteine Are Synergistically Hepatoprotective in Zebrafish Acetaminophen Injury", *Proceedings of the National Academy of Sciences*, Oct. 5, 2010, pp. 17315-17320, vol. 107, No. 40, United States National Academy of Sciences, Washington, DC, US.

Obeid, J., et al., "TYR-179 and LYS-183 are Essential for Enzymatic Activity of 11 β-Hydroxysteroid Dehydroxysteroid Dehydrogenase," *Biochemical and Biophysical Research Communications*, Oct. 15, 1992, Abstract, vol. 188, Issue 1, Academic Press, Elsevier, Amsterdam, NL.

Oh, S.Y., et al., "Comparison of Experimental Mouse Models of Inflammatory Bowel Disease," *International Journal of Molecular Medicine*, 2014, pp. 333-340, vol. 33, Issue 2, Spandidos Publications, UK.

Olson, L.E., et al., "Protection from Doxorubicin-Induced Cardiac Toxicity in Mice with a Null Allele of Carbonyl Reductase 1", *Cancer Research*, Oct. 15, 2003, six pages including pp. 6602-6606, vol. 63, American Association for Cancer Research, Philadelphia, PA, US.

Otani, T., et al., "Levels of $NAD^+$-dependent 15-Hydroxyprostaglandin Dehydrogenase are Reduced in Inflammatory Bowel Disease: Evidence for Involvement of TNF-α", *American Journal of Physiology—Gastrointestinal and Liver Physiology*, 2006, G361-G368, vol. 290, American Physiological Society, Rockville, MD, US.

Packer, Milton, et al., "Consensus recommendations for the management of chronic heart failure. On behalf of the membership of the advisory council to improve outcomes nationwide in heart failure," *The American Journal of Cardiology*, Jan. 21, 1999, pp. 1a-38a, vol. 83 (2a), Elsevier Inc., NL.

Park, S.H., et al., "Effect of Thiazolidinedione Phenylacetate Derivatives on Wound-Healing Activity," *Archives of Pharmacal Research*, 2019, pp. 790-814, vol. 42, Springer Science + Business Media, Berlin, DE.

Parveen, H., et al., "Synthesis and Characterization of a New Series of Hydroxy Pyrazolines," *Synthetic Communications*, 2008, pp. 3973-3983, vol. 38, Taylor and Francis, London, UK.

Patani, L., et al., "Bioisosterism: A Rational Approach in Drug Design," *Chemical Reviews*, 1996, pp. 3147-3176, vol. 96, No. 8, American Chemical Society, Washington, DC, US.

Pelus, L.M., et al., "Pleiotropic Effects of Prostaglandin $E_2$ in Hematopoiesis; Prostaglandin $E_2$ and Other Eicosanoids Regulate

(56) References Cited

OTHER PUBLICATIONS

Hematopoietic Stem and Progenitor Cell Function," *Prostaglandins and Other Lipid Mediators*, 2011, pp. 3-9, vol. 96, Elsevier, Amsterdam, NL.

Pelus, L.M., et al., "Pulse Exposure of Haematopoietic Grafts to Prostaglandin $E_2$ in vitro Facilitates Engraftment and Recovery," *Cell Proliferation*, 2011, pp. 22-29, vol. 44, Suppl. 1, Wiley, Hoboken, NJ, US.

Perse, M., and Cerar, A., "Dextran Sodium Sulphate Colitis Mouse Model: Traps and Tricks," *Journal of Biomedicine and Biotechnology*, 2012, Article ID 718617, 13 pages, vol. 2012, Hindawi Publishing Corporation, London, UK.

Piao, Y.L., et al., "Wound Healing Effects of New 15-Hydroxyprostaglandin Dehydrogenase Inhibitors," *Prostaglandins, Leukotrienes and Essential Fatty Acids*, 2014, pp. 325-332, vol. 91, Elsevier, Amsterdam, NL Piao, Y.L., et al., "Cell-based Biological Evaluations of 5-(3-bromo-4-phenethoxybenzylidene)thiazolidine-2,4-dione As Promising Wound Healing Agent," *Bioorganic and Medicinal Chemistry*, May 1, 2015, pp. 2098-2103, vol. 23, Issue 9, Elsevier, Amsterdam, NL.

Piska, K., et al., "Metabolic Carbonyl Reduction of Anthracyclines—Role in Cardiotoxicity and Cancer Resistance: Reducing Enzymes as Putative Targets for Novel Cardioprotective and Chemosensitizing Agents", *Investigational New Drugs*, 2017, pp. 375-385, vol. 35, Springer, Berlin, DE.

Porter, G.A., "Contrast-Associated Nephropathy," *The American Journal of Cardiology*, Sep. 5, 1989, pp. 22E-26E, vol. 64, Issue 9, Elsevier, Amsterdam, NL.

Porter, R.L., et al., "Prostaglandin E2 Increases Hematopoietic Stem Cell Survival and Accelerates Hematopoietic Recovery After Radiation Injury," *Stem Cells*, 2013, pp. 372-383, vol. 31, AlphaMed Press, Hoboken, NJ, US.

Randhawa, P.K., et al., "A Review on Chemical-Induced Inflammatory Bowel Disease Models in Rodents," *Korean Journal of Physiology and Pharmacology*, Aug. 2014, pp. 279-288, vol. 18, Issue 4, The Korean Journal of Physiology and Pharmacology, KR.

Renneville, A., et al., "EHMT1 and EHMT2 Inhibition Induces Fetal Hemoglobin Expression," *Blood*, Oct. 15, 2015, pp. 1930-1939, vol. 126, No. 16, American Society of Hematology, Washington, DC, US.

Rieder, F., et al., "Animal Models of Intestinal Fibrosis: New Tools for the Understandig of Pathogenesis and Therapy of Human Disease," *American Journal of Physiology—Gastrointestinal and Liver Physiology*, Aug. 9, 2012, G786-G801, 303(4, Pt. 1), American Physiological Society, Rockville, MD, US.

Roberts, C.R., "Is Asthma a Fibrotic Disease," *Chest*, Mar. 1995, vol. 107, pp. 111S-117S, American College of Chest Physicians, Glenview, IL, US.

Robison, T.W., and Giri, S.N., "Effects of Chronic Administration of Doxorubicin on Plasma Levels of Prostaglandins, Thromboxane $B_2$, and Fatty Acids in Rats," *Cancer Chemotherapy and Pharmacology*, May 1987, pp. 213-220, vol. 19, Springer Science + Business Media, Berlin, DE.

Rocchiccioli, F., et al., "Quantitative Gas Chromatography-Chemical Ionization Mass Spectrometry of 2-Ketoglutarate from Urine as its O-trimethylsilyl-quinoxalinol Derivative", *Journal of Chromatography*, Dec. 11, 1981, pp. 325-332, vol. 226, No. 2, Elsevier, Amsterdam, NL.

Rogaeva, Ekaterina, et al., "The neuronal sortilin-related receptor SORL1 is genetically associated with Alzheimer disease," *Nature Genetics*, Feb. 2007, pp. 168-177, vol. 39, No. 2, Nature Publishing Group, UK.

Ronzoni, L., et al., "Modulation of Gamma Globulin Genes Expression by Histone Deacetylase Inhibitors: An in vitro Study," Mar. 7, 2014, pp. 714-721, vol. 165, *British Journal of Hematology*, John Wiley & Sons, UK.

Rossi, F., et al., "Cardiotoxicity of Doxorubicin: Effects of Drugs Inhibiting the Release of Vasoactive Substances," *Pharmacology & Toxicology*, Aug. 1994, Abstract, vol. 75, Issue 2, Pharmacology & Toxicology, DK.

Sasaki, S., et al., "Prostaglandin $E_2$ Inhibits Lesion Formation in Dextran Sodium Sulphate-Induced Colitis in Rats and Reduces the Levels of Mucosal Inflammatory Cytokines", *Scandinavian Journal of Immunology*, 2000, pp. 23-28, vol. 51, Wiley, UK.

Schaefer, C.F., et al., "PID: The Pathway Interaction Database," *Nucleic Acids Research*, 2009, pp. D674-D679, vol. 37, Oxford University Press, Oxford, UK.

Seo, S.Y., et al., "Effect of 15-Hydroxyprostaglandin Dehydrogenase Inhibitor on Wound Healing," *Prostaglandins, Leukotrienes, and Essential Fatty Acids*, 2015, pp. 35-41, vol. 97, Elsevier, Amsterdam, NL.

Seto, M., et al., "Orally Active CCR5 Antagonists as Anti-HIV-1 Agents. Part 3: Synthesis and Biological Activities of 1-Benzazepine Derivatives Containing a Sulfoxide Moiety," *Bioorganic and Medicinal Chemistry*, 2005, pp. 363-386, vol. 13, Elsevier, Amsterdam, NL.

Shannon, P., et al., "Cytoscape: A Software Environment for Integrated Models of Biomolecular Interaction Networks," *Genome Researc*, 2003, 8 pages including pp. 2498-2504, vol. 13, Cold Spring Harbor Laboratory Press, Cold Spring Harbor, NY, US.

Sharkey, L.C., et al., "Differential Cardiotoxicity in Response to Chronic Doxorubicin Treatment in Male Spontaneous Hypertension-Heart Failure (SHHF), Spontaneously Hypertensive (SHR), and Wistar Kyoto (WKY) Rats," *Toxicology and Applied Pharmacology*, 2013, pp. 47-57, vol. 273, Issue 1, Elsevier, Amsterdam, NL.

Smith, J.N.P., et al., "Inhibition of 15-PGDH Protects Mice from Immune-Mediated Bone Marrow Failure," *Biology of Blood and Marrow Transplantation*, 2020, pp. 1552-1556, vol. 26, Elsevier, Amsterdam, NL.

Smith, J.N.P., "Therapeutic Targeting of 15-PGDH in Murine Pulmonary Fibrosis," *Scientific Reports*, 2020, 11657, 10 pages, vol. 10, Nature Research, London, UK.

Smusz, S., et al., "Fingerprint-based Consensus Virtual Screening Towards Structurally New 5-HT$_6$R Ligands," *Bioorganic and Medicinal Chemistry Letters*, 2015, pp. 1827-1830, vol. 25, Issue 9, Elsevier, Amsterdam, NL.

Solomon, L., et al., "The Dextran Sulphate Sodium (DSS) Model of Colitis: An Overview," *Comparative Clinical Pathology*, Mar. 4, 2010, pp. 235-239, vol. 19, Springer, Munich, DE.

Somasundaram, S., et al., "The DNMT1-Associated lincRNA DACOR1 Reprograms Genome-Wide DNA Methylation in Colon Cancer," *Clinical Epigenetics*, 2018, 15 pages, 10:127, BioMedCentral, London, UK.

Sood, A., et al., "A Prospective, Open-Label Trial Assessing Dexamethasone Pulse Therapy in Moderate to Sever Ulcerative Colitis," *Journal of Clinical Gastroenterology*, Oct. 2002, pp. 328-331, vol. 35, Issue 4, Lippincott Williams & Wilkins, Philadelphia, PA, US.

"Specs," Web page <www.specs.net/>, 2 pages, Dec. 25, 2003, retrieved from the Internet Archive Wayback Machine without Page Vault <http://web.archive.org/web/20031225052253/http://www.specs.net/> on Oct. 26, 2022.

"Specs," Web page <www.specs.net/>, 2 pages, Dec. 25, 2003, retrieved from the Internet Archive Wayback Machine via Page Vault <http://web.archive.org/web/20031225052253/http://www.specs.net/> on Sep. 29, 2022.

Speth, J. M., et al., "Pharmacologic Increase in HIF1α Enhances Hematopoietic Stem and Progenitor Homing and Engraftment," *Blood*, Jan. 9, 2014, six pages including pp. 203-207, vol. 123, No. 2, American Society of Hematology, Washington, DC, US.

St George-Hyslop, P.H., et al., "The Genetic Defect Causing Familial Alzheimer's Disease Maps on Chromosome 21" *Science*, Feb. 20, 1987, pp. 885-890, vol. 235, Issue 4791, American Association for the Advancement of Science, Washington, DC, US.

Tai, H.-H., et al., "Prostaglandin Catabolizing Enzymes", *Prostaglandins and Other Lipid Mediators*, 2002, pp. 483-493, Elsevier Science Inc., Amsterdam, NL.

Tanaka, N., et al., "Crystal Structures of the Binary and Ternary Complexes of 7α-Hydroxysteroid Dehydrogenase from *Escherichia coli*," *Biochemistry*, Jun. 18, 1996, pp. 7715-7730, vol. 35, Issue 24, American Chemical Society, Washington, DC, US.

Tanaka, Y., et al., "Systems Analysis of ATF3 in Stress Response and Cancer Reveals Opposing Effects on Pro-Apoptotic Genes in

(56) References Cited

OTHER PUBLICATIONS p53 Pathway," *PLoS One*, Oct. 2011, e26848, 12 pages, vol. 6, Issue 10, Public Library of Science, San Francisco, CA, US.

Tatsuwaki, H., et al., "Reduction of 15-Hydroxyprostaglandin Dehydrogenase Expression Is An Independent Predictor of Poor Survival Associated with Enhanced Cell Proliferation in Gastric Adenocarcinoma," *Cancer Science*, Feb. 2010, pp. 550-558, vol. 101, No. 2, Wiley-Blackwell, Hoboken, NJ, US.

Tessner, T.G., et al., "Prostaglandins Prevent Decreased Epithelial Cell Proliferation Associated With Dextran Sodium Sulfate Injury in Mice", *Gastroenterology*, Oct. 1998, pp. 874-882, vol. 115, No. 4, Elsevier, Amsterdam, NL.

Tong, M., et al., "15-Hydroxyprostaglandin Dehydrogenase Can Be Induced by Dexamethasone and Other Glucocorticoids at the Therapeutic Level in A549 Human Lung Adenocarcinoma Cells," *Archives of Biochemistry and Biophysics*, Mar. 1, 2005, pp. 50-55, vol. 435, issue 1, Elsevier, Amsterdam, NL.

Valatas, V., et al., "Experimental Colitis Models: Insights into the Pathogenesis of Inflammatory Bowel Disease and Translational Issues," *European Journal of Pharmacology*, 2015, pp. 253-264, vol. 759, Elsevier, Amsterdam, NL.

Varadan, V., et al., "The Integration of Biological Pathway Knowledge in Cancer Genomics," *IEEE Signal Processing Magazine*, Jan. 2012, 20 pages, vol. 29, Issue 1, IEEE Signal Processing Society, Piscataway, NJ, US.

Vaske, C.J., et al, "Inference of patient-specific pathway activities from multi-dimensional cancer genomics data using Paradigm," *Bioinformatics*, 2010, pp. i237-i245, vol. 26, Oxford University Press, Oxford, UK.

Vukicevic, S., et al., "Role of EP2 and EP4 Receptor-Selective Agonists of Prostaglandin $E_2$ in Acute and Chronic Kidney Failure," *Kidney International*, 2006, pp. 1099-1106, vol. 70, Elsevier on behalf of the International Society of Nephrology, Amsterdam, NL.

Wallace, J.L., "Prostaglandins, NSAIDs, and Gastric Mucosal Protection: Why Doesn't the Stomach Digest Itself?" *Physiol Reviews*, 2008, pp. 1547-1565, vol. 88, No. 4, The American Physiological Society, Rockville, MD, US.

Wang, Y.F., et al., "Meta-Analysis of Drug-Eluting Versus Bare Mtal Stents in Patients with Indications for Oral Anticoagulation Undergoing Coronary Stenting," *Acta Cardiologica*, 2014, pp. 237-244, vol. 69, Issue 3, Belgian Society of Cardiology, BE, Springer.

Wang, Q., et al., "Discovery of Novel Allosteric Effectors Based on the Predicted Allosteric Sites for *Escherichia coli* D-3-Phosphoglycerate Dehydrogenase", *PLoS One*, Apr. 14, 2014, p. e94829, vol. 9, issue 4, Public Library of Science, San Francisco, CA, US.

Wang, J., et al., "Design, Synthesis, and Pharmacological Evaluation of Novel Piperlongumine Derivatives as Potential Antiplatelet Aggregation Candidate," *Chemical Biology and Drug Design*, 2016, pp. 883-840, vol. 87, Issue 6, John Wiley & Sonse A/S, Hoboken, NJ.

Wang, J., et al., "Chemopreventive Efficacy of the Cyclooxygenase-2 (Cox-2) Inhibitor, Celecoxib, is Predicted By Adenoma Expression of Cox-2 and 15-PGDH," *Cancer Epidemiology, Biomarkers, and Prevention*, Jul. 2018, 20 pages, vol. 27, Issue 7, American Association for Cancer Research, Philadelphia, PA, US.

Wei, Q., and Dong, Z., "Mouse Model of Ischemic Acute Kidney Injury: Technical Notes and Tricks," *American Journal of Physiology—Renal Physiology*, Sep. 19, 2012, F1487-F1494, vol. 303, American Physiological Society, Rockville, MD, US.

Westbrook, A.M., et al., "Mouse Models of Intestinal Inflammation and Cancer," *Archives of Toxicology*, 2016, 22 pages, vol. 90, Issue 9, Springer-Verlag, DE.

Wirtz, S., and Neurath, M.F., "Mouse Models of Inflammatory Bowel Disease," *Advanced Drug Delivery Reviews*, 2007, pp. 1073-1083, vol. 59, Issue 11, Elsevier B.V., Amsterdam, NL.

Wu, Y., et al., "Synthesis and SAR of Thiazolidinedione Derivatives as 15-PGDH Inhibitors," *Bioorganic and Medicinal Chemistry*, Feb. 15, 2010, Abstract, vol. 18, Issue 4, Elsevier Ltd., Amsterdam, NL.

Wu, Y., et al. "Synthesis and Biological Evaluation of Novel Thiazolidinedione Analogues as 15-Hydroxyprostaglandin Dehydrogenase Inhibitors," *Journal of Medicinal Chemistry*, 2011, pp. 5260-5264, vol. 54, American Chemical Society, Washington, DC, US.

Yan, M., et al., "15-Hydroxyprostaglandin dehydrogenase, a COX-2 oncogene antagonist, is a TGF-β-induced suppressor of human gastrointestinal cancers", *Proceedings of the National Academy of Sciences*, Dec. 14, 2004, pp. 17468-17473, vol. 101, No. 50, United States National Academy of Sciences, Washington, DC, US.

Yan, C., et al., "Cyclooxygenases, Microsomal Prostaglandin E Synthase-1, and Cardiovascular Function," *The Journal of Clinical Investigation*, 2006, pp. 1391-1399, vol. 116, Issue 5, American Society for Clinical Investigation, US.

Yan, Min, et al, "15-Hydroxyprostaglandin dehydrogenase inactivation as a mechanism of resistance to celecoxib chemoprevention of colon tumors", Proceedings of the National Academy of Sciences, Jun. 9, 2009, pp. 9409-9413, vol. 106, No. 23, United States National Academy of Sciences, Washington, DC, US.

Yang, H., et al., "Altered Hippocampal Long-Term Synaptic Plasticity in Mice Deficient in the PGE2 EP2 Receptor," *Journal of Neurochemistry*, 2009, pp. 295-304, vol. 108, Wiley-Blackwell, Hoboken, NJ, US.

Yao, R., et al., "Comparison of Clinical Efficacy of Different Statins on Cardiovascular Events Following Percutaneous Coronary Intervention," *International Journal of Clinical and Experimental Medicine*, 2017, 11286, vol. 10, Issue 7, e-Century Publishing Corporation, Madison, WI, US, Article Retracted.

Yeh, F.-L., et al., "Keloid-Derived Fibroblasts Have a Diminished Capacity to Produce Prostaglandin $E_2$," *Burns*, 2006, pp. 299-304, vol. 32, Elsevier Ltd., Amsterdam, NL.

Zhang, Y., "Inhibition of the Prostaglandin Degrading Enzyme 15-PGDH Potentiates Tissue Regeneration," *Science*, Jun. 12, 2015, p. 1223, pp. aaa2340-1 to aaa2340-8, vol. 348, Issue 6240, American Association for the Advancement of Science, Washington, DC, US.

Zhang, Y., et al., "Prasugrel Suppresses Development of Lithium-Induced Nephrogenic Diabetes Insipidus in Mice," *Purinergic Signalling*, 2017, pp. 239-248, vol. 13, Springer Science + Business Media, Berlin, DE.

Zhang, Y., et al., "Impacts of CYP2C19 Genetic Polymorphisms on Bioavailability and Effect on Platelet Adhesion of Vicagrel, a Novel Thienopyridine P2Y12 Inhibitor," *British Journal of Clinical Pharmacology*, 2020, pp. 1860-1874, vol. 86, The British Pharmacological Society, Wiley-Blackwell, Hoboken, NJ, US.

Zhao, L., et al., "Design, Synthesis and SAR of Thienopyridines as Potent CHK1 Inhibitors," *Bioorganic and Medicinal Chemistry Letters*, Dec. 15, 2010, pp. 7216-7221, vol. 20, Issue 24, Elsevier Ltd., Amsterdam, NL.

Zhou, Y., and Gong, Y., "Asymmetric Copper(II)-Catalysed Nitroaldol (Henry) Reactions Utilizing a Chiral $C_1$-Symmetric Dinitrogen Ligand," *European Journal of Organic Chemistry*, 2011, pp. 6092-6099, vol. 2011, Issue 30, Wiley-VCH Verlag GmbH & Co. KGaA, Weinheim, DE.

CAS Registry No. 296798-64-6 [online database], STN Entry Date Oct. 18, 2000 [retrieved on Oct. 21, 2022], Retrieved from SciFinder <https://scifinder-n.cas.org/>, substance detail downloaded to PDF.

CAS Registry No. 299406-22-7 [online database], STN Entry Date Oct. 26, 2000 [retrieved on Oct. 24, 2022], Retrieved from SciFinder <https://scifinder-n.cas.org/>, substance detail downloaded to pdf.

CAS Registry No. 299920-58-4 [online database], STN Entry Date Oct. 27, 2000 [retrieved on Sep. 21, 2022], Retrieved from SciFinder <https://scifinder-n.cas.org/>, substance detail downloaded to PDF.

CAS Registry No. 299920-59-5 [online database], STN Entry Date Oct. 27, 2000 [retrieved on Sep. 21, 2022], Retrieved from SciFinder <https://scifinder-n.cas.org/>, substance detail downloaded to PDF.

CAS Registry No. 299920-61-9 [online database], STN Entry Date Oct. 27, 2000 [retrieved on Sep. 16, 2022], Retrieved from SciFinder <https://scifinder-n.cas.org/>, substance detail downloaded to PDF.

CAS Registry No. 299920-78-8 [online database], STN Entry Date Oct. 27, 2000 [retrieved on Sep. 21, 2022], Retrieved from SciFinder <https://scifinder-n.cas.org/>, substance detail downloaded to PDF.

(56) References Cited

OTHER PUBLICATIONS

CAS Registry No. 306766-39-2 [online database], STN Entry Date Dec. 5, 2000 [retrieved on Oct. 24, 2022], Retrieved from SciFinder <https://scifinder-n.cas.org/>, substance detail downloaded to pdf.
CAS Registry No. 313245-69-1 [online database], STN Entry Date Jan. 9, 2001 [retrieved on Oct. 24, 2022], Retrieved from SciFinder <https://scifinder-n.cas.org/>, substance detail downloaded to pdf.
CAS Registry No. 313245-70-4 [online database], STN Entry Date Jan. 9, 2001 [retrieved on Sep. 16, 2022], Retrieved from SciFinder <https://scifinder-n.cas.org/>, substance detail downloaded to PDF.
CAS Registry No. 331447-76-8 [online database], STN Entry Date Apr. 16, 2001 [retrieved on Sep. 16, 2022], Retrieved from SciFinder <https://scifinder-n.cas.org/>, substance detail downloaded to PDF.
CAS Registry No. 331655-85-7 [online database], STN Entry Date Apr. 17, 2001 [retrieved on Sep. 16, 2022], Retrieved from SciFinder <https://scifinder-n.cas.org/>, substance detail downloaded to PDF.
CAS Registry No. 331655-86-8 [online database], STN Entry Date Apr. 17, 2001 [retrieved on Sep. 16, 2022], Retrieved from SciFinder <https://scifinder-n.cas.org/>, substance detail downloaded to PDF.
CAS Registry No. 332945-05-8 [online database], STN Entry Date Apr. 26, 2001 [retrieved on Oct. 24, 2022], Retrieved from SciFinder <https://scifinder-n.cas.org/>, substance detail downloaded to pdf.
CAS Registry No. 348151-19-9 [online database], STN Entry Date Jul. 25, 2001 [retrieved on Sep. 21, 2022], Retrieved from SciFinder <https://scifinder-n.cas.org/>, substance detail downloaded to PDF.
CAS Registry No. 350511-89-6 [online database], STN Entry Date Aug. 6, 2001 [retrieved on Sep. 16, 2022], Retrieved from SciFinder <https://scifinder-n.cas.org/>, substance detail downloaded to PDF.
CAS Registry No. 369400-43-1 [online database], STN Entry Date Nov. 13, 2001 [retrieved on Sep. 16, 2022], Retrieved from SciFinder <https://scifinder-n.cas.org/>, substance detail downloaded to PDF.
CAS Registry No. 369402-41-5 [online database], STN Entry Date Nov. 13, 2001 [retrieved on Sep. 16, 2022], Retrieved from SciFinder <https://scifinder-n.cas.org/>, substance detail downloaded to PDF.
CAS Registry No. 370572-70-6 [online database], STN Entry Date Nov. 16, 2001 [retrieved on Sep. 21, 2022], Retrieved from SciFinder <https://scifinder-n.cas.org/>, substance detail downloaded to PDF.
CAS Registry No. 370870-44-3 [online database], STN Entry Date Nov. 19, 2001 [retrieved on Sep. 21, 2022], Retrieved from SciFinder <https://scifinder-n.cas.org/>, substance detail downloaded to PDF.
CAS Registry No. 371116-23-3 [online database], STN Entry Date Nov. 20, 2001 [retrieved on Sep. 16, 2022], Retrieved from SciFinder <https://scifinder-n.cas.org/>, substance detail downloaded to PDF.
CAS Registry No. 371117-75-8 [online database], STN Entry Date Nov. 20, 2001 [retrieved on Sep. 21, 2022], Retrieved from SciFinder <https://scifinder-n.cas.org/>, substance detail downloaded to PDF.
CAS Registry No. 371118-22-8 [online database], STN Entry Date Nov. 20, 2001 [retrieved on Sep. 21, 2022], Retrieved from SciFinder <https://scifinder-n.cas.org/>, substance detail downloaded to PDF.
CAS Registry No. 371144-00-2 [online database], STN Entry Date Nov. 20, 2001 [retrieved on Sep. 16, 2022], Retrieved from SciFinder <https://scifinder-n.cas.org/>, substance detail downloaded to PDF.
CAS Registry No. 371208-33-2 [online database], STN Entry Date Nov. 21, 2001 [retrieved on Sep. 16, 2022], Retrieved from SciFinder <https://scifinder-n.cas.org/>, substance detail downloaded to PDF.
CAS Registry No. 371213-13-7 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371222-38-7 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371232-15-4 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371926-65-7 [online database], STN Entry Date Nov. 27, 2001 [retrieved on Sep. 16, 2022], Retrieved from SciFinder <https://scifinder-n.cas.org/>, substance detail downloaded to PDF.
CAS Registry No. 384861-16-9 [online database], STN Entry Date Jan. 20, 2002 [retrieved on Sep. 21, 2022], Retrieved from SciFinder <https://scifinder-n.cas.org/>, substance detail downloaded to PDF.
CAS Registry No. 420824-06-2 [online database], STN Entry Date May 23, 2002 [retrieved on Sep. 16, 2022], Retrieved from SciFinder <https://scifinder-n.cas.org/>, substance detail downloaded to PDF.
CAS Registry No. 420825-11-2 [online database], STN Entry Date May 23, 2002 [retrieved on Sep. 21, 2022], Retrieved from SciFinder <https://scifinder-n.cas.org/>, substance detail downloaded to PDF.
CAS Registry No. 420825-38-3 [online database], STN Entry Date May 23, 2002 [retrieved on Sep. 21, 2022], Retrieved from SciFinder <https://scifinder-n.cas.org/>, substance detail downloaded to PDF.
CAS Registry No. 442152-75-2 [online database], STN Entry Date Aug. 2, 2002 [retrieved on Sep. 21, 2022], Retrieved from SciFinder <https://scifinder-n.cas.org/>, substance detail downloaded to PDF.
CAS Registry No. 442152-82-1 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442152-88-7 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442152-94-5 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442153-01-7 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442153-03-9 [online database], STN Entry Date Aug. 2, 2002 [retrieved on Sep. 21, 2022], Retrieved from SciFinder <https://scifinder-n.cas.org/>, substance detail downloaded to PDF.
CAS Registry No. 448191-85-3 [online database], STN Entry Date Sep. 9, 2002 [retrieved on Sep. 21, 2022], Retrieved from SciFinder <https://scifinder-n.cas.org/>, substance detail downloaded to PDF.
CAS Registry No. 448191-89-7 [online database], STN Entry Date Sep. 9, 2002 [retrieved on Sep. 21, 2022], Retrieved from SciFinder <https://scifinder-n.cas.org/>, substance detail downloaded to PDF.
CAS Registry No. 452922-28-0 [online database], STN Entry Date Sep. 19, 2002 [retrieved on Sep. 16, 2022], Retrieved from SciFinder <https://scifinder-n.cas.org/>, substance detail downloaded to PDF.
CAS Registry No. 457958-02-0 [online database], STN Entry Date Oct. 2, 2002 [retrieved on Sep. 16, 2022 ], Retrieved from SciFinder <https://scifinder-n.cas.org/>, substance detail downloaded to PDF.
CAS Registry No. 457958-03-1 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-04-2 [online database], STN Entry Date Oct. 2, 2002 [retrieved on Sep. 19, 2022], Retrieved from SciFinder <https://scifinder-n.cas.org/>, substance detail downloaded to PDF.
CAS Registry No. 457958-05-3 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-06-4 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-16-6 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-17-7 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-18-8 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-30-4 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-31-5 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-32-6 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-38-2 [online database], STN Entry Date Oct. 2, 2002 [retrieved on Sep. 16, 2022], Retrieved from SciFinder <https://scifinder-n.cas.org/>, substance detail downloaded to PDF.

(56) References Cited

OTHER PUBLICATIONS

CAS Registry No. 457958-39-3 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-40-6 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 457958-41-7 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-49-5 [online database], STN Entry Date Oct. 2, 2002 [retrieved on Sep. 16, 2022], Retrieved from SciFinder <https://scifinder-n.cas.org/>, substance detail downloaded to PDF.
CAS Registry No. 457958-50-8 [online database], STN Entry Date Oct. 2, 2002 [retrieved on Sep. 21, 2022], Retrieved from SciFinder <https://scifinder-n.cas.org/>, substance detail downloaded to PDF.
CAS Registry No. 459147-27-4 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459147-39-8 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459147-74-1 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459150-70-0 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459150-74-4 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459150-94-8 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459151-05-4 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459152-84-2 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459153-20-9 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459153-24-3 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459153-30-1 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459153-75-4 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 459154-25-7 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459154-76-8 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459154-80-4 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459155-72-7 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459155-77-2 [online database], STN Entry Date Oct. 4, 2002 [retrieved on Sep. 16, 2022], Retrieved from SciFinder <https://scifinder-n.cas.org/>, substance detail downloaded to PDF.
CAS Registry No. 459155-84-1 [online database], STN Entry Date Oct. 4, 2002 [retrieved on Sep. 21, 2022], Retrieved from SciFinder <https://scifinder-n.cas.org/>, substance detail downloaded to PDF.
CAS Registry No. 693820-48-3 [online database], STN Entry Date Jun. 16, 2004 [retrieved on Sep. 16, 2022], Retrieved from SciFinder <https://scifinder-n.cas.org/>, substance detail downloaded to PDF.
CAS Registry No. 924846-44-6 [online database], STN Entry Date Mar. 5, 2007 [retrieved on Sep. 16, 2022], Retrieved from SciFinder <https://scifinder-n.cas.org/>, substance detail downloaded to PDF.
CAS Registry No. 957625-42-2 [online database], STN Entry Date Dec. 11, 2007 [retrieved on Sep. 21, 2022], Retrieved from SciFinder <https://scifinder-n.cas.org/>, substance detail downloaded to PDF.
CAS Registry No. 957939-31-0 [online database], STN Entry Date Dec. 13, 2007 [retrieved on Sep. 16, 2022], Retrieved from SciFinder <https://scifinder-n.cas.org/>, substance detail downloaded to PDF.
CAS Registry No. 957948-58-2 [online database], STN Entry Date Dec. 13, 2007 [retrieved on Sep. 16, 2022], Retrieved from SciFinder <https://scifinder-n.cas.org/>, substance detail downloaded to PDF.
CAS Registry No. 957957-90-3 [online database], STN Entry Date Dec. 13, 2007 [retrieved on Sep. 21, 2022], Retrieved from SciFinder <https://scifinder-n.cas.org/>, substance detail downloaded to PDF.
CAS Registry No. 1015864-36-4 [online database], STN Entry Date Apr. 20, 2008 [retrieved on Sep. 16, 2022], Retrieved from SciFinder <https://scifinder-n.cas.org/>, substance detail downloaded to PDF.
CAS Registry No. 1015864-38-6 [online database], STN Entry Date Apr. 20, 2008 [retrieved on Sep. 21, 2022], Retrieved from SciFinder <https://scifinder-n.cas.org/>, substance detail downloaded to PDF.
CAS Registry No. 1020685-61-3 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020685-65-7 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-01-4 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-06-9 [online database], STN Entry Date May 14, 2008 [retrieved on Sep. 21, 2022], Retrieved from SciFinder <https://scifinder-n.cas.org/>, substance detail downloaded to PDF.
CAS Registry No. 1020686-10-5 [online database], STN Entry Date May 14, 2008 [retrieved on Sep. 21, 2022], Retrieved from SciFinder <https://scifinder-n.cas.org/>, substance detail downloaded to PDF.
CAS Registry No. 1020686-49-0 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-53-6 [online database], STN Entry Date May 14, 2008 [retrieved on Sep. 21, 20221], Retrieved from SciFinder <https://scifinder-n.cas.org/>, substance detail downloaded to PDF.
CAS Registry No. 1020686-57-0 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-77-4 [online database], STN Entry Date May 14, 2008 [retrieved on Sep. 16, 2022], Retrieved from SciFinder <https://scifinder-n.cas.org/>, substance detail downloaded to PDF.
CAS Registry No. 1020686-81-0 [online database], STN Entry Date May 14, 2008 [retrieved on Sep. 21, 2022], Retrieved from SciFinder <https://scifinder-n.cas.org/>, substance detail downloaded to PDF.
CAS Registry No. 1020687-17-5 [online database], STN Entry Date May 14, 2008 [retrieved on Sep. 16, 2022], Retrieved from SciFinder <https://scifinder-n.cas.org/>, substance detail downloaded to PDF.
CAS Registry No. 1112019-47-2 [online database], STN Entry Date Feb. 26, 2009 [retrieved on Sep. 16, 2022], Retrieved from SciFinder <https://scifinder-n.cas.org/>, substance detail downloaded to PDF.
CAS Registry No. 1115479-64-5 [online database], STN Entry Date Mar. 4, 2009 [retrieved on Sep. 16, 2022], Retrieved from SciFinder <https://scifinder-n.cas.org/>, substance detail downloaded to PDF.
CAS Registry No. 1221411-67-1 [online database], STN Entry Date May 5, 2010 [retrieved on Sep. 16, 2022], Retrieved from SciFinder <https://scifinder-n.cas.org/>, substance detail downloaded to PDF.
CAS Registry No. 1221411-70-6 [online database], STN Entry Date May 5, 2010 [retrieved on Sep. 16, 2022], Retrieved from SciFinder <https://scifinder-n.cas.org/>, substance detail downloaded to PDF.
CAS Registry No. 1347499-81-3 [online database], STN Entry Date Dec. 2, 2011 [retrieved on Sep. 21, 2022], Retrieved from SciFinder <https://scifinder-n.cas.org/>, substance detail downloaded to PDF.

(56) References Cited

OTHER PUBLICATIONS

CAS Registry No. 1348234-90-1 [online database], STN Entry Date Dec. 4, 2011 [retrieved on Sep. 21, 2022], Retrieved from SciFinder <https://scifinder-n.cas.org/>, substance detail downloaded to PDF.
CAS Registry No. 1348857-03-3 [online database], STN Entry Date Dec. 5, 2011 [retrieved on Sep. 21, 2022], Retrieved from SciFinder <https://scifinder-n.cas.org/>, substance detail downloaded to PDF.
CAS Registry No. 1349215-63-9 [online database], STN Entry Date Dec. 5, 2011 [retrieved on Sep. 21, 2022], Retrieved from SciFinder <https://scifinder-n.cas.org/>, substance detail downloaded to PDF.
CAS Registry No. 1421694-45-2 [online database], STN Entry Date Feb. 22, 2013 [retrieved on Sep. 16, 2022], Retrieved from SciFinder <https://scifinder-n.cas.org/>, substance detail downloaded to PDF.
CAS Registry No. 1471306-25-8 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-27-0 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-29-2 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-31-6 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-33-8 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-35-0 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-37-2 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1471306-39-4 [online database], STN Entry Date Nov. 11, 2013 [retrieved on Sep. 16, 2022], Retrieved from SciFinder <https://scifinder-n.cas.org/>, substance detail downloaded to PDF.
CAS Registry No. 1611464-74-4 [online database], STN Entry Date Jun. 20, 2014 [retrieved on Oct. 25, 2022], Retrieved from SciFinder <https://scifinder-n.cas.org/>, substance detail downloaded to PDF.
CAS Registry No. 1714959-81-5 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-82-6 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-83-7 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-86-0 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-92-8 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-93-9 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-95-1 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714959-96-2 [online database], STN Entry Date May 28, 2015 [retrieved on Sep. 16, 2022], Retrieved from SciFinder <https://scifinder-n.cas.org/>, substance detail downloaded to PDF.
CAS Registry No. 1714961-85-9 [online database], STN Entry Date May 28, 2015 [retrieved on Sep. 16, 2022], Retrieved from SciFinder <https://scifinder-n.cas.org/>, substance detail downloaded to PDF.
CAS SciFinder Search Result on Jan. 27, 2022, at 5:14 pm (2 results)—1-Preparation of thienopyridines and related compounds, their compositions and methods of modulating short-chain dehydrogenase activity (WO 2018/218251);—2-Compositions and methods of modulating short-chain dehydrogenase activity (WO 2016/168472).
CAS SciFinder Search Result on Jan. 27, 2022, at 11:52 am (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:02 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 3:25 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:30 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 4:08 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 4:11 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 4:14 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 4:16 pm (2 results)—1-Preparation of thienopyridines and similar bicyclic heterocyclic compounds as modulators of 15-hydroxyprostaglandin dehydrogenase type I for therapy (2015/065716);—2-Preparation of thienopyridines and related compounds, their compositions and methods of modulating short-chain dehydrogenase activity (WO 2018/218251).
CAS SciFinder Search Result on Jan. 27, 2022, at 4:50 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 5:09 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 5:52 pm (2 results)—1-Preparation of thienopyridines and related compounds, their compositions and methods of modulating short-chain dehydrogenase activity (WO 2018/218251);—2-Compositions and methods of modulating short-chain dehydrogenase activity (WO 2016/168472).

(56) References Cited

OTHER PUBLICATIONS

CAS SciFinder Search Result on Jan. 27, 2022, at 5:58 pm (2 results)—1-Preparation of thienopyridines and related compounds, their compositions and methods of modulating short-chain dehydrogenase activity (WO 2018/218251);—2-Compositions and methods of modulating short-chain dehydrogenase activity (WO 2016/168472).
CAS SciFinder Search Result on Jan. 27, 2022, at 6:03 pm (6 results)—1-Preparation of thienopyridines and similar bicyclic heterocyclic compounds as modulators of 15-hydroxyprostaglandin dehydrogenase type I for therapy (WO 2015/065716);—2-Inhibitors of 15-Prostaglandin Dehydrogenase To Potentiate Tissue Repair (Antczak et al.);—3-Compositions and methods of modulating short-chain dehydrogenase activity (WO 2016/168472);—4-Preparation of thienopyridines and related compounds, their compositions and methods of modulating short-chain dehydrogenase activity (WO 2018/218251);—5-Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:17 pm (6 results)—1-Compositions and methods of modulating short-chain dehydrogenase activity (WO 2016/168472);—2-Preparation of thienopyridines and similar bicyclic heterocyclic compounds as modulators of 15-hydroxyprostaglandin dehydrogenase type I for therapy (WO 2015/065716);—3-Inhibitors of 15-Prostaglandin Dehydrogenase To Potentiate Tissue Repair (Antczak et al.);—4-Preparation of thienopyridines and related compounds, their compositions and methods of modulating short-chain dehydrogenase activity (WO 2018/218251);—5-Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6-Preparation of thienopyridine compounds having sulfur-containing substituent as Inhibitors of short-chain dehydrogenase activity for treating fibrosis (WO 2016/144958).
CAS SciFinder Search Result on Jan. 27, 2022, at 7:21 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 7:30 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:31 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:32 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:39 pm (6 results)—1-Preparation of thienopyridines and similar bicyclic heterocyclic compounds as modulators of 15-hydroxyprostaglandin dehydrogenase type I for therapy (WO 2015/065716);—2-Inhibitors of 15-Prostaglandin Dehydrogenase To Potentiate Tissue Repair (Antczak et al.);—3-Compositions and methods of modulating short-chain dehydrogenase activity (WO 2016/168472);—4-Preparation of thienopyridines and related compounds, their compositions and methods of modulating short-chain dehydrogenase activity (WO 2018/218251);—5-Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:47 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 7:50 pm (2 results)—1-Preparation of thienopyridines and similar bicyclic heterocyclic compounds as modulators of 15-hydroxyprostaglandin dehydrogenase type I for therapy;—2-Preparation of thienopyridines and related compounds, their compositions and methods of modulating short-chain dehydrogenase activity.
CAS SciFinder Search Result on Jan. 27, 2022, at 7:52 pm (2 results)—1-Preparation of thienopyridines and related compounds, their compositions and methods of modulating short-chain dehydrogenase Activity (WO 2015/065716);—2-Preparation of thienopyridines and similar bicyclic heterocyclic compounds as modulators of 15-hydroxyprostaglandin dehydrogenase type I for therapy (WO 2018/218251).
CAS SciFinder Search Result on Jan. 27, 2022, at 7:55 pm (2 results)—1-Preparation of thienopyridines and related compounds, their compositions and methods of modulating short-chain dehydrogenase activity (WO 2018/218251);—2-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:28 pm (0 results).
NCBI Database Accession No. CID 654955 [online database], create date Jun. 4, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 1826991 [online database], create date Jul. 12, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337838 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337839 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337991 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337992 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337993 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337994 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337995 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337996 [online database], create date Sep. 7, 2005, modify date Sep. 10, 2022, [retrieved on Sep. 16, 2022], Retrieved from PubChem <https://pubchem.ncbi.nlm.nih.gov>, compound summary printed to pdf.

(56) References Cited

OTHER PUBLICATIONS

NCBI Database Accession No. CID 3337997 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337998 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 46864148 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 52943190 [online database], create date Jun. 16, 2011, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188203 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188204 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272562 [online database], create date Dec. 10, 2015, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272564 [online database], create date Dec. 10, 2015, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 118050369 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050655 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050656 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050707 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050770 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050833 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050838 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118050952 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118051074 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118051078 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059027 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059055 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059089 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059090 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 118059098 [online database], create date Feb. 23, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 122624302 [online database], create date Dec. 8, 2016, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 123677271 [online database], create date Jan. 25, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 129266585 [online database], create date Aug. 4, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 129266602 [online database], create date Aug. 4, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 130296193 [online database], create date Oct. 7, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 130296194 [online database], create date Oct. 7, 2017, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 132012504 [online database], create date Jan. 29, 2018, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 134314069 [online database], create date Jun. 23, 2018, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 134474501 [online database], create date Jun. 23, 2018, modify date Sep. 10, 2022, [retrieved Sep. 15, 2022], Retrieved from PubChem <https://pubchem.ncbi.nlm.nih.gov>, compound summary printed to pdf.
NCBI Database Accession No. CID 134576829 [online database], create date Jun. 23, 2018, modify date Sep. 10, 2022, [retrieved Sep. 16, 2022], Retrieved from PubChem <https://pubchem.ncbi.nlm.nih.gov>, compound summary printed to pdf.
NCBI Database Accession No. CID 135387726 [online database], create date Dec. 15, 2018, modify date Sep. 10, 2022, [retrieved Sep. 16, 2022], Retrieved from PubChem <https://pubchem.ncbi.nlm.nih.gov>, compound summary printed to pdf.
NCBI Database Accession No. CID 135387830 [online database], create date Dec. 15, 2018, modify date Sep. 10, 2022, [retrieved Sep. 16, 2022], Retrieved from PubChem <https://pubchem.ncbi.nlm.nih.gov>, compound summary printed to pdf.

(56) References Cited

OTHER PUBLICATIONS

NCBI Database Accession No. CID 139476465 [online database], create date Nov. 2, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142484843 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485754 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485836 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485845 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485847 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485863 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485864 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485868 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485879 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485896 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485929 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485938 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485953 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 142485954 [online database], create date Dec. 6, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 144839639 [online database], create date Dec. 7, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 145656773 [online database], create date Dec. 12, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 145656809 [online database], create date Dec. 12, 2019, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146410683 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146580152 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146580711[online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146602898 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146602900 [online database], create date Jun. 27, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146731064 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 146835156 [online database], create date Aug. 12, 2020, modify date Sep. 17, 2022, [retrieved Sep. 19, 2022], Retrieved from PubChem <https://pubchem.ncbi.nlm.nih.g>, compound summary printed to pdf.
NCBI Database Accession No. CID 147432252 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 147594754 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 148490795 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 149178699 [online database], create date Aug. 12, 2020, modify date Sep. 17, 2022, [retrieved Sep. 19, 2022], Retrieved from PubChem <https://pubchem.ncbi.nlm.nih.gov>, compound summary printed to pdf.
NCBI Database Accession No. CID 152798992 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596863 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596870 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596898 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596904 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596919 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.

(56) References Cited

OTHER PUBLICATIONS

NCBI Database Accession No. CID 153596924 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596928 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596948 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596953 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596968 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153596975 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597016 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597047 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597069 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597090 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597104 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597123 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597128 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597141 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597150 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597177 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597180 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597205 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597208 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597214 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 153597233 [online database], create date Aug. 13, 2020, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 155786794 [online database], create date Feb. 22, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156156400 [online database], create date Aug. 21, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837702 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837721 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837722 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837731 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837741 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 156837742 [online database], create date Nov. 10, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157158417 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157167058 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157167059 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157167060 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157213480 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157216800 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.

(56) References Cited

OTHER PUBLICATIONS

NCBI Database Accession No. CID 157257517 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157294602 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157302941 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157386272 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157400808 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157440570 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157440572 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157456496 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157498212 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157526683 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157600443 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157604959 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157688874 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157717185 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157767490 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157848053 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157864542 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157864543 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157872044 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157901254 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157944805 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157949758 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 157955983 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158049978 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158088730 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158134580 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158145130 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158221946 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158221947 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158258231 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158329834 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158370045 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158404656 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158415066 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158432471 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.

(56) References Cited

OTHER PUBLICATIONS

NCBI Database Accession No. CID 158531185 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158540614 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158568511 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158628602 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158653266 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158660366 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158784514 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158829687 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 158910891 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159056851 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159130668 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159144809 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159154352 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159191585 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159215478 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159233281 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159233282 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159474011 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159590113 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159820000 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 159891397 [online databas], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160071422 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160071423 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160155004 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 160156242 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 161100344 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 162062070 [online database], create date Dec. 3, 2021, modify date Sep. 17, 2022, [retrieved Sep. 22, 2022], Retrieved from PubChem <https://pubchem.ncbi.nlm.nih.gov>, compound summary printed to pdf.
NCBI Database Accession No. CID 162728470 [online database], create date Apr. 5, 2022, modify date Sep. 17, 2022, [retrieved Sep. 22, 2022], Retrieved from PubChem <https://pubchem.ncbi.nlm.nih.gov>, compound summary printed to pdf.
Notification of Reexamination issued in Chinese Application No. 201680026631.8, China National Intellectual Property Administration, Beijing, CN. May 25, 2023. 16 pages. Translation included.
Office Action issued in U.S. Appl. No. 14/395,021, Jun. 1, 2015, United States Patent and Trademark Office, Alexandria, VA, US.
Office Action issued in U.S. Appl. No. 14/395,021, Oct. 19, 2015, United States Patent and Trademark Office, Alexandria, VA, US.
Office Action issued in U.S. Appl. No. 14/395,021, Jun. 22, 2016, United States Patent and Trademark Office, Alexandria, VA, US.
Office Action issued in U.S. Appl. No. 14/395,021, Mar. 31, 2017, United States Patent and Trademark Office, Alexandria, VA, US.
Office Action issued in U.S. Appl. No. 15/359,330, Aug. 17, 2017, United States Patent and Trademark Office, Alexandria, VA, US.
Office Action issued in U.S. Appl. No. 15/359,330, Feb. 2, 2018, United States Patent and Trademark Office, Alexandria, VA, US.
Office Action issued in U.S. Appl. No. 15/556,972, Mar. 7, 2018, United States Patent and Trademark Office, Alexandria, VA, US.
Office Action issued in U.S. Appl. No. 15/556,972, Sep. 13, 2018, United States Patent and Trademark Office, Alexandria, VA, US.
Office Action issued in U.S. Appl. No. 15/556,972, Feb. 14, 2019, United States Patent and Trademark Office, Alexandria, VA, US.
Office Action issued in U.S. Appl. No. 15/556,972, Jul. 8, 2019, United States Patent and Trademark Office, Alexandria, VA, US.
Office Action issued in U.S. Appl. No. 15/556,972, Sep. 5, 2019, United States Patent and Trademark Office, Alexandria, VA, US.
Office Action issued in U.S. Appl. No. 15/556,972, Apr. 9, 2020, United States Patent and Trademark Office, Alexandria, VA, US.
Office Action issued in U.S. Appl. No. 15/556,972, Sep. 3, 2020, United States Patent and Trademark Office, Alexandria, VA, US.

(56) References Cited

OTHER PUBLICATIONS

Office Action issued in U.S. Appl. No. 15/566,637, Dec. 20, 2018, United States Patent and Trademark Office, Alexandria, VA, US.
Office Action issued in U.S. Appl. No. 15/566,637, Jun. 28, 2019, United States Patent and Trademark Office, Alexandria, VA, US.
Office Action issued in U.S. Appl. No. 15/566,637, Jan. 8, 2020, United States Patent and Trademark Office, Alexandria, VA, US.
Office Action issued in U.S. Appl. No. 15/566,637, Apr. 10, 2020, United States Patent and Trademark Office, Alexandria, VA, US.
Office Action issued in U.S. Appl. No. 15/785,259, Sep. 27, 2019, United States Patent and Trademark Office, Alexandria, VA, US.
Office Action issued in U.S. Appl. No. 15/785,259, Apr. 17, 2020, United States Patent and Trademark Office, Alexandria, VA, US.
Office Action issued in U.S. Appl. No. 15/799,307, May 23, 2018, United States Patent and Trademark Office, Alexandria, VA, US.
Office Action issued in U.S. Appl. No. 16/319,159, Sep. 9, 2019, United States Patent and Trademark Office, Alexandria, VA, US.
Office Action issued in U.S. Appl. No. 16/319,159, Feb. 18, 2020, United States Patent and Trademark Office, Alexandria, VA.
Office Action issued in U.S. Appl. No. 16/421,867, Feb. 12, 2020, United States Patent and Trademark Office, Alexandria, VA, US.
Office Action issued in U.S. Appl. No. 16/421,867, Jul. 2, 2020, United States Patent and Trademark Office, Alexandria, VA, US.
Office Action issued in U.S. Appl. No. 16/421,867, Jul. 26, 2021, United States Patent and Trademark Office, Alexandria, VA, US.
Office Action issued in U.S. Appl. No. 16/465,500, Sep. 21, 2021, United States Patent and Trademark Office, Alexandria, VA, US.
Office Action issued in U.S. Appl. No. 16/465,500, Feb. 7, 2022, United States Patent and Trademark Office, Alexandria, VA, US.
Office Action issued in U.S. Appl. No. 16/465,500, Sep. 23, 2022, United States Patent and Trademark Office, Alexandria, VA, US.
Office Action issued in U.S. Appl. No. 16/484,045, Jun. 8, 2020, United States Patent and Trademark Office, Alexandria, VA, US.
Office Action issued in U.S. Appl. No. 16/484,045, Oct. 2, 2020, United States Patent and Trademark Office, Alexandria, VA, US.
Office Action issued in U.S. Appl. No. 16/484,045, Jun. 7, 2021, United States Patent and Trademark Office, Alexandria, VA, US.
Office Action issued in U.S. Appl. No. 16/484,045, Dec. 20, 2021, United States Patent and Trademark Office, Alexandria, VA, US.
Office Action issued in U.S. Appl. No. 16/581,024, Jun. 29, 2020, United States Patent and Trademark Office, Alexandria, VA, US.
Office Action issued in U.S. Appl. No. 16/581,024, Oct. 16, 2020, United States Patent and Trademark Office, Alexandria, VA, US.
Office Action issued in U.S. Appl. No. 16/581,024, Apr. 30, 2021, United States Patent and Trademark Office, Alexandria, VA, US.
Office Action issued in U.S. Appl. No. 16/581,024, Nov. 12, 2021, United States Patent and Trademark Office, Alexandria, VA, US.
Office Action issued in U.S. Appl. No. 16/603,544, Feb. 5, 2021, United States Patent and Trademark Office, Alexandria, VA, US.
Office Action issued in U.S. Appl. No. 16/603,544, Aug. 31, 2021, United States Patent and Trademark Office, Alexandria, VA, US.
Office Action issued in U.S. Appl. No. 16/617,137, Jul. 20, 2021, United States Patent and Trademark Office, Alexandria, VA, US.
Office Action issued in U.S. Appl. No. 16/617,137, Dec. 17, 2021, United States Patent and Trademark Office, Alexandria, VA, US.
Office Action issued in U.S. Appl. No. 16/617,137, Jul. 21, 2022, United States Patent and Trademark Office, Alexandria, VA, US.
Office Action issued in U.S. Appl. No. 16/869,879, Mar. 29, 2022, United States Patent and Trademark Office, Alexandria, VA, US.
Office Action issued in U.S. Appl. No. 16/869,879, Nov. 3, 2022, United States Patent and Trademark Office, Alexandria, VA, US.
Office Action issued in U.S. Appl. No. 16/869,879, Jul. 5, 2023, United States Patent and Trademark Office, Alexandria, VA, US.
Office Action issued in U.S. Appl. No. 16/943,932, Feb. 4, 2022, United States Patent and Trademark Office, Alexandria, VA, US.
Office Action issued in U.S. Appl. No. 16/943,932, Sep. 15, 2022, United States Patent and Trademark Office, Alexandria, VA, US.
Office Action issued in U.S. Appl. No. 16/943,932, May 3, 2023, United States Patent and Trademark Office, Alexandria, VA, US.
Office Action issued in U.S. Appl. No. 16/995,878, Jun. 24, 2021, United States Patent and Trademark Office, Alexandria, VA, US.
Office Action issued in U.S. Appl. No. 16/995,878, Sep. 28, 2021, United States Patent and Trademark Office, Alexandria, VA, US.
Office Action issued in U.S. Appl. No. 16/997,273, Feb. 3, 2022, United States Patent and Trademark Office, Alexandria, VA, US.
Office Action issued in U.S. Appl. No. 17/044,888, Dec. 8, 2021, United States Patent and Trademark Office, Alexandria, VA, US.
Office Action issued in U.S. Appl. No. 17/044,888, Mar. 22, 2022, United States Patent and Trademark Office, Alexandria, VA, US.
Office Action issued in U.S. Appl. No. 17/044,888, Nov. 30, 2022, United States Patent and Trademark Office, Alexandria, VA, US.
Office Action issued in U.S. Appl. No. 17/044,888, Apr. 7, 2023, United States Patent and Trademark Office, Alexandria, VA, US.
Office Action issued in U.S. Appl. No. 17131,911, Aug. 18, 2022, United States Patent and Trademark Office, Alexandria, VA, US.
Office Action issued in U.S. Appl. No. 17/131,911, Jan. 12, 2023, United States Patent and Trademark Office, Alexandria, VA, US.
Office Action issued in U.S. Appl. No. 17/131,911, Aug. 24, 2023, United States Patent and Trademark Office, Alexandria, VA, US.
Office Action issued in U.S. Appl. No. 17/296,055, Apr. 22, 2024, United States Patent and Trademark Office, Alexandria, VA, US.
Office Action issued in U.S. Appl. No. 17/893,777, Jun. 2, 2023, United States Patent and Trademark Office, Alexandria, VA, US.
Office Action issued in U.S. Appl. No. 17/893,777, Nov. 13, 2023, United States Patent and Trademark Office, Alexandria, VA, US.
Office Action issued in U.S. Appl. No. 17/898,776, Nov. 9, 2023, United States Patent and Trademark Office, Alexandria, VA, US.
Office Action issued in U.S. Appl. No. 17/898,776, Feb. 23, 2024, United States Patent and Trademark Office, Alexandria, VA, US.
Office Action issued in U.S. Appl. No. 17/898,776, Jul. 5, 2024, United States Patent and Trademark Office, Alexandria, VA, US.
Office Action issued in U.S. Appl. No. 18/057,589, Apr. 18, 2024, United States Patent and Trademark Office, Alexandria, VA, US.
Office Action issued in U.S. Appl. No. 18/117,257, May 9, 2024, United States Patent and Trademark Office, Alexandria, VA, US.
Office Action issued in U.S. Appl. No. 18/128,075, Nov. 13, 2023, United States Patent and Trademark Office, Alexandria, VA, US.
Office Action issued in U.S. Appl. No. 18/128,075, Jun. 12, 2024, United States Patent and Trademark Office, Alexandria, VA, US.
Office Action issued in U.S. Appl. No. 18/144,065, Jul. 11, 2024, United States Patent and Trademark Office, Alexandria, VA, US.
Office Action issued in U.S. Appl. No. 18/228,452, Jun. 21, 2024, United States Patent and Trademark Office, Alexandria, VA, US.
Office Action issued in U.S. Appl. No. 18/481,787, Apr. 25, 2024, United States Patent and Trademark Office, Alexandria, VA, US.
Huang, S., "New Developments in Pulmonary Medicine", Version 1, pp. 268-275, Nov. 2000, People's Medical Publishing House, CN, with machine translation.
Iran-Nejad, Akram, et al., "Preventive Role of Estradiol on Kidney Injury Induced by Renal Ischemia-Reperfusion in Male and Female Rats," *International Journal of Preventive Medicine*, 2015, 5 pages, vol. 6(1), Lippincott, Wolters-Kluwer.
Kim, Byeong Woo, et al., P0522 "Inhibiting 15-PGDH Prevents Ischemic Renal Injury by a PGE2/EP4 Signaling Pathway Mediating Vasodilation, Increased Renal Blood Flow, and Increased Adenosine/A2A Receptor," *Nephrology Dialysis Transplantation*, Jun. 6, 2020, 4 pages, XP093121187, retrieved from the internet Jan. 18, 2024.
Kim, Byeong Woo, et al., P0544 "Inhibition of 15-Hydroxyprostaglandin Dehydrogenase (15-PGDH) Protects Mice Against Contrast-Induced Acute Kidney Injury," *Nephrology Dialysis Transplantation*, Jun. 6, 2020, 3 pages, XP093121183, retrieved from the internet Jan. 18, 2024.
Lucas, S.D, et al., "Structure based virtual screening for discovery of novel human neutrophil elastaseinhibitors," *Med. Chem, Commun.*, 2012, vol. 3, No. 10, 7 pages, including pp. 1299-1304, The Royal Society of Chemistry, UK, Retrieved from ResearchGate Feb. 9, 2024, https://www.researchgate.net/publication/234169520_Structure_based_virtual_screening_for_discovery_of_novel_human_neutrophil_elastase_inhibitors.
McCullough, Peter A., M.D., "Contrast-Induced Acute Kidney Injury," *Journal of the American College of Cardiology*, Apr. 15,

(56) References Cited

OTHER PUBLICATIONS 2008, pp. 1419-1428, vol. 51, No. 15, American College of Cardiology Foundation, Elsevier Inc., CA, US.
Miao, Shuying, et al., "Pharmacologic Blockade of 15-PGDH Protects Against Acute Renal Injury Induced by LPS in Mice," *Frontiers in Physiology*, Mar. 13, 2020, pp. 1-14, vol. 11, Open Access, XP055883549.
Nogradi, K., et al., "Thieno[2,3-b]pyridines as Negative Allosteric Modulators of Metabotropic GluR5 Receptors: Lead Optimization," *Bioorganic and Medicinal Chemistry Letter*, 2015, pp. 1724-1729, vol. 25(8), Elsevier, Amsterdam, NL.
Nurse Key, "IV Bolus Injection," Retrieved from the Internet on Apr. 29, 2024, https://nursekey.com/iv-bolus-injection/, published 2016, 2 pages.
Paller, Mark S., et al., "Prostaglandins protect kidneys againstischemic and toxic injury by a cellular effect," *Kidney International*, 1992, pp. 1345-1354, vol. 42, International Society of Nephrology, Elsevier Inc.
Saat, T.C., et al., "Improving the outcome of kidney transplantation by ameliorating renal ischemia reperfusion injury: lost in translation?" *Jounal of Translation Medicine*, 2016, 9 pages, vol. 14, No. 20, https://doi.org/10.1186/s12967-016-0767-2.
Sawicki, E., et al. "Ultraviolet-Visible Absorption Spectra of Quinoxaline Derivatives," Electronic Spectra of Quinoxalines, *Journal of Organic Chemistry*, Jun. 1957, pp. 625-629, American Chemical Society, US.
Shin, Min-Kyoo., et al., "Inhibition of 15-hydroxyprostaglandin dehydrogenase protects a mouse model of Alzheimer's disease without affecting amyloid pathology," *Alzheimer's & Dementia*, 2021:17(Suppl. 3), The Alzheimer's Association, US (Abstract only).
Story, Colleen, M., et al., (Kohl, Paval, M.D., Medically reviewed), "What is Cardiomyopathy?", Healthline, Updated Jan. 2, 2023, 18 pages. 222.healthline.com/health/heart-disease/cardiomyopathy (Downloaded on Nov. 1, 2023, referred as Cardiomyopathy).
Yao, Bing, et al., "Renal localization and regulation of 15-hydroxyprostaglandin dehydrogenase," *American Journal of Physiology-Renal Physiology*, Feb. 2008, pp. F433-F439, vol. 294, Issue 2, American Physiological Society, US.
Zhao, Z., et al., "Development of potent, allosteric dual Akt1 and Akt2 inhibitors with improved physical properties and cell activity," *Biorganic and Medicinal Chemistry Letters*, 2007, pp. 49-53, vol. 18, Elsevier Ltd., Amsterdam, NL.
CAS Registry No. 296242-98-3 [online database], STN Entry Date Oct. 17, 2000 [retrieved Oct. 23, 2023], Retrieved from SciFinder <https://scifinder-n.cas.org/>, substance detail downloaded to PDF.
CAS Registry No. 311777-19-2 [online database], STN Entry Date Dec. 28, 2000 [retrieved Oct. 11, 2023], Retrieved from SciFinder <https://scifinder-n.cas.org/>, substance detail downloaded to PDF.
CAS Registry No. 312952-25-3 [online database], STN Entry Date Jan. 5, 2001 [retrieved May 30, 2024], Retrieved from Retrieved from SciFinder <https://scifinder-n.cas.org/>, substance detail downloaded to PDF.
CAS Registry No. 331431-80-2 [online database], STN Entry Date Apr. 16, 2001 [retrieved Oct. 11, 2023], Retrieved from SciFinder <https://scifinder-n.cas.org/>, substance detail downloaded to PDF.
CAS Registry No. 331431-88-0 [online database], STN Entry Date Apr. 16, 2001 [retrieved Oct. 11, 2023], Retrieved from SciFinder <https://scifinder-n.cas.org/>, substance detail downloaded to PDF.
CAS Registry No. 332404-52-1 [online database], STN Entry Date Apr. 25, 2001 [retrieved Oct. 11, 2023], Retrieved from SciFinder <https://scifinder-n.cas.org/>, substance detail downloaded to PDF.
CAS Registry No. 332404-53-2 [online database], STN Entry Date Apr. 25, 2001 [retrieved Oct. 11, 2023], Retrieved from SciFinder <https://scifinder-n.cas.org/>, substance detail downloaded to PDF.
CAS Registry No. 332404-54-3 [online database], STN Entry Date Apr. 25, 2001 [retrieved Oct. 11, 2023], Retrieved from SciFinder <https://scifinder-n.cas.org/>, substance detail downloaded to PDF.
CAS Registry No. 332404-55-4 [online database], STN Entry Date Apr. 25, 2001 [retrieved Oct. 11, 2023], Retrieved from SciFinder <https://scifinder-n.cas.org/>, substance detail downloaded to PDF.
CAS Registry No. 508185-74-8 [online database], STN Entry Date May 1, 2003 [retrieved Feb. 9, 2024], Retrieved from SciFinder <https://scifinder-n.cas.org/>, substance detail downloaded to PDF.
CAS Registry No. 622806-06-8 [online database], STN Entry Date Dec. 2, 2003 [retrieved Oct. 11, 2023], Retrieved from SciFinder <https://scifinder-n.cas.org/>, substance detail downloaded to PDF.
CAS Registry No. 622806-14-8 [online database], STN Entry Date Dec. 2, 2003 [retrieved Oct. 11, 2023], Retrieved from SciFinder <https://scifinder-n.cas.org/>, substance detail downloaded to PDF.
CAS Registry No. 622806-22-8 [online database], STN Entry Date Dec. 2, 2003 [retrieved Oct. 11, 2023], Retrieved from SciFinder <https://scifinder-n.cas.org/>, substance detail downloaded to PDF.
CAS Registry No. 622806-54-6 [online database], STN Entry Date Dec. 2, 2003 [retrieved Oct. 11, 2023], Retrieved from SciFinder <https://scifinder-n.cas.org/>, substance detail downloaded to PDF.
CAS Registry No. 622807-31-2 [online database], STN Entry Date Dec. 2, 2003 [retrieved Feb. 9, 2024], Retrieved from SciFinder <https://scifinder-n.cas.org/>, substance detail downloaded to PDF.
CAS Registry No. 865097-40-1 [online database], STN Entry Date Oct. 12, 2005 [retrieved Feb. 9, 2024], Retrieved from SciFinder <https://scifinder-n.cas.org/>, substance detail downloaded to PDF.
CAS Registry No. 896364-40-2 [online database], STN Entry Date Jul. 27, 2006 [retrieved Feb. 9, 2024], Retrieved from SciFinder <https://scifinder-n.cas.org/>, substance detail downloaded to PDF.
CAS Registry No. 896367-61-6 [online database], STN Entry Date Jul. 27, 2006 [retrieved Feb. 9, 2024], Retrieved from SciFinder <https://scifinder-n.cas.org/>, substance detail downloaded to PDF.
CAS Registry No. 896367-68-3 [online database], STN Entry Date Jul. 27, 2006 [retrieved Feb. 9, 2024], Retrieved from SciFinder <https://scifinder-n.cas.org/>, substance detail downloaded to PDF.
CAS Registry No. 896380-79-3 [online database], STN Entry Date Jul. 27, 2006 [retrieved Feb. 9, 2024], Retrieved from SciFinder <https://scifinder-n.cas.org/>, substance detail downloaded to PDF.
CAS Registry No. 913494-73-2 [online database], STN Entry Date Nov. 17, 2006 [retrieved Oct. 11, 2023], Retrieved from SciFinder <https://scifinder-n.cas.org/>, substance detail downloaded to PDF.
CAS Registry No. 958612-61-8 [online database], STN Entry Date Dec. 18, 2007 [retrieved Feb. 9, 2024], Retrieved from SciFinder <https://scifinder-n.cas.org/>, substance detail downloaded to PDF.
CAS Registry No. 1023573-77-4 [online database], STN Entry Date May 29, 2008 [retrieved Feb. 9, 2024], Retrieved from SciFinder <https://scifinder-n.cas.org/>, substance detail downloaded to PDF.
CAS Registry No. 1024264-64-9 [online database], STN Entry Date Jun. 1, 2008 [retrieved Feb. 9, 2024], Retrieved from SciFinder <https://scifinder-n.cas.org/>, substance detail downloaded to PDF.
CAS Registry No. 1052069-68-7 [online database], STN Entry Date Sep. 24, 2008 [retrieved Oct. 11, 2023], Retrieved from SciFinder <https://scifinder-n.cas.org/>, substance detail downloaded to PDF.
CAS Registry No. 1798165-36-2 [online database], STN Entry Date Jul. 9, 2015 [retrieved Oct. 11, 2023], Retrieved from SciFinder <https://scifinder-n.cas.org/>, substance detail downloaded to PDF.
CAS Registry No. 2096475-10-2 [online database], STN Entry Date May 22, 2017 [retrieved Jun. 17, 2024], Retrieved from SciFinder, <https://scifinder-n.cas.org/>, substance detail downloaded to PDF.
CAS Registry No. 2096475-11-3 [online database], STN Entry Date May 22, 2017 [retrieved Jun. 17, 2024], Retrieved from SciFinder, <https://scifinder-n.cas.org/>, substance detail downloaded to PDF.
CAS Registry No. 2096475-12-4 [online database], STN Entry Date May 22, 2017 [retrieved Jun. 17, 2024], Retrieved from SciFinder, <https://scifinder-n.cas.org/>, substance detail downloaded to PDF.
U.S. Appl. No. 17/296,055, US 2023-0039604 A1, filed May 21, 2021, Feb. 9, 2023, Docket Central, Pending.
U.S. Appl. No. 17/898,776, US 2023-0116062 A1, filed Aug. 30, 2022, Apr. 13, 2023, Docket Central, Pending.
U.S. Appl. No. 18/481,787, US 2024-0174688 A1, filed Oct. 5, 2023, May 30, 2024.
U.S. Appl. No. 18/144,065, US 2023-0355636 A1, filed May 5, 2023, Nov. 2023.
U.S. Appl. No. 16/465,500, US 2020-0061073 A1 U.S. Pat. No. 11,690,847, filed May 30, 2019, Feb. 27, 2020 Jul. 4, 2023, Issued.

(56) References Cited

OTHER PUBLICATIONS

U.S. Appl. No. 16/484,045, US 2020-0095206 A1 U.S. Pat. No. 11,718,589, filed Aug. 6, 2019, Mar. 26, 2020 Aug. 8, 2023, Issued.
U.S. Appl. No. 18/128,075, US-2024-0024297 A1, filed Mar. 29, 2023, Jan. 25, 2024, Pending.
U.S. Appl. No. 18/020,202, US 2023-0310390 A1, filed Feb. 7, 2023, Oct. 5, 2023, Pending.
Chassaing, B. et al., "Dextran Sulfate Sodium (DSS)-Induced Colitis in Mice." Current Protocals in Immunology; (Feb. 4, 20154), 16 pages, vol. 104:Unit—15.25, John Wiley & Sons, Inc, US. NIH-PA Author Manuscript Submitted.
Hu, B., et al., "Orally Bioavailable Quinoxaline Inhibitors of 15-Prostaglandin Dehydrogenase (15-PGDH) Promote Tissue Repair and Regeneration." *Journal of Medicinal Chemistry*, (Nov. 2022), pp. 15327-15343, 65, ACS Publications, Washington, DC.
Johansson, J.U., et al., "Prostaglandin signaling suppresses beneficial microglial function in Alzheimer's disease models." *The Journal of Clinical Investigation*, (Jan. 2015), pp. 350-364, vol. 125, No. 1, American Society for Clinical Investigation, US.
Shi, J., et al., "Inflammatory Prostaglandin E2 Signaling in a Mouse Model of Alzheimer Disease," *Annals of Neurology*, (Nov. 2012), pp. 1-11, vol. 72, Iss. 5, John Wiley and Sons, Hoboken, NJ, US.
Xie, M., et al., "Effects of small molecule inhibitor SW033291 on hepatic ischemia-reperfusion injury in mice." *Biochemical and Biophysical Research Communications*, (Jul. 2022), pp. 70-74, vol. 615, Elsevier, Amsterdam, NL.
Zhan, C., et al., "A dopamine-precursor-based nanoprodrug for in-situ drug release and treatment of acute liver failure by inhibiting NLRP3 inflammasome and facilitating liver regeneration." *Biomaterials*, (Jan. 2021), pp. 1-13, vol. 268, Elsevier, Amsterdam, NL.
CAS Registry No. 299920-60-8 [online database], STN Entry Date Oct. 27, 2000 [retrieved on Feb. 8, 2023], Retrieved from SciFinder <https://scifinder-n.cas.org/>, substance detail downloaded to PDF.
U.S. Appl. No. 17/926,214, filed Nov. 18, 2022, Pending.
U.S. Appl. No. 18/117,257, filed Mar. 3, 2023, Pending.
U.S. Appl. No. 15/566,637, US 2018-0118756 A1, filed Oct. 13, 2017, May 3, 3018, Abandoned.
U.S. Appl. No. 17/044,888, US 2021-0100779 A1, filed Oct. 2, 2020, Apr. 8, 2021, Pending.
U.S. Appl. No. 18/128,075, filed Mar. 29, 2023, Pending.
U.S. Appl. No. 18/020,202, filed Feb. 7, 2023, Pending.
International Search Report, Written Opinion, and International Preliminary Report on Patentability issued in PCT/US2021/033170, ISA/EP European Patent Office, NL. 28 pages.
Office Action issued in U.S. Appl. No. 17/296,055, Sep. 16, 2024, United States Patent and Trademark Office, Alexandria, VA, US, 21 pages.
Office Action issued in U.S. Appl. No. 17/893,777, Aug. 1, 2024, United States Patent and Trademark Office, Alexandria, VA, US, 25 pages.
Office Action issued in U.S. Appl. No. 18/117,257, Oct. 11, 2024, United States Patent and Trademark Office, Alexandria, VA, US, 53 pages.
Office Action issued in U.S. Appl. No. 18/207,777, Sep. 29, 2024, United States Patent and Trademark Office, Alexandria, VA, US, 7 pages.
Final Office Action issued in U.S. Appl. No. 18/228,452, Dec. 4, 2024, United States Patent and Trademark Office, Alexandria, VA, US, 10 pages.
Malik, Kashif, et al., "Prostaglandins," *NCBI Bookshelf. A service of the National Library of MedicneZ National Institutes of Health*, Last Update Nov. 21, 2022, Copyright 2024, 5 pages, StatPearls Publishing LLC, (www.ncbi.nlm.nih.gov/books/NBK553155/#:~:text=Prostaglandins%20can20cause%20vasodilation%20or%20vasoconstriction%20in%20vascular,system%20to%20cause%20fever%20and%20influence%20pain%20perception); downloaded Jul. 25, 2024 ).
Mitry, Maria A., et al., "Doxorubicin induced heart failure: Phenotype and molecular mechanisms," *IJC Heart & Vasculature*, 2016, pp. 17-24, vol. 10, Elsevier Ireland Ltd., IE.
CAS Registry No. 420823-48-9 [online database], STN Entry Date May 22, 2002 [retrieved on Oct. 17, 2024], Retrieved from SciFinder <https://scifinder-n.cas.org/>, substance detail downloaded to PDF.
U.S. Appl. No. 17/926,214 US 2023/0192717 A1, filed Nov. 18, 2022, Jun. 22, 2023, Pending.
U.S. Appl. No. 17/296,055, US 2023-0039604 A1, filed May 21, 2021, Feb. 9, 2023, Pending.
U.S. Appl. No. 15/359,330, US 2017-0165241 A1 U.S. Pat. No. 10,301,320, filed Nov. 22, 2016, Jun. 15, 2017 May 28, 2019, Issued.
U.S. Appl. No. 16/421,867, US 2020-0140453 A1, filed May 24, 2019, May 7, 2020, Abandoned.
U.S. Appl. No. 16/943,932, US-2021-0032265 A1, filed Oct. 12, 2020, Feb. 4, 2021, Abandoned.
U.S. Appl. No. 18/228,452, US 2024-0043443 A1, filed Jul. 31, 2023, Feb. 8, 2024, Pending.
U.S. Appl. No. 14/395,021, US-2015-0072998 A1 U.S. Pat. No. 9,790,233, filed Oct. 16, 2014, Mar. 12, 2015 Oct. 17, 2018, Issued.
U.S. Appl. No. 17/898,776, US 2023/0116062 A1, filed Aug. 30, 2022, Apr. 13, 2023, Pending.
U.S. Appl. No. 18/905,874, filed Oct. 3, 2024, Pending.
U.S. Appl. No. 18/117,257, US 2023-0285402 A1, filed Mar. 3, 2023, Sep. 14, 2023, Pending.
U.S. Appl. No. 15/347,587 US 2017-0216265 A1, U.S. Pat. No. 9,801,863, filed Nov. 9, 2016, Aug. 3, 2017 Oct. 31, 2017, Issued.
U.S. Appl. No. 15/785,259, US 2019-0365769 A1, filed Oct. 16, 2017, Dec. 5, 2019 Dec. 22, 2020, Issued.
U.S. Appl. No. 15/799,307, US 2018-0125829 A1, filed Oct. 31, 2017, May 10, 2018 Sep. 24, 2019, Issued.
U.S. Appl. No. 16/581,024, US 2020-0147063 A1, filed Sep. 24, 2019, May 14, 2020, Abandoned.
U.S. Appl. No. 16/997,273, US 2021-0106587 A1, filed Aug. 19, 2020, Apr. 15, 2021, Abandoned.
U.S. Appl. No. 15/029,943, US 2017-0173028 A1, filed Apr. 15, 2016, Jun. 22, 2017 Oct. 17, 2017, Issued.
U.S. Appl. No. 17/131,911, US 2021-0283113 A1, filed Dec. 23, 2020, Sep. 6, 2021, Pending
U.S. Appl. No. 15/556,972, US 2018-0064694 A1 U.S. Pat. No. 10,945,998, filed Sep. 8, 2017, Mar. 8, 2018 Mar. 16, 2021, Issued.
U.S. Appl. No. 18/481,787, US 2024-0174688 A1, filed Oct. 5, 2023, May 30, 2024, Abandoned.
U.S. Appl. No. 18/924,696, filed Oct. 23, 2024, Pending.
U.S. Appl. No. 16/869,879, US 2021-0094968 A1, filed May 8, 2020, Apr. 1, 2021, Abandoned.
U.S. Appl. No. 15/566,637, US 2018-0118756 A1 , filed Oct. 13, 2017, May 30, 2018, Abandoned.
U.S. Appl. No. 16/995,878, US 2021-0100778 A1, filed Aug. 18, 2020, Apr. 8, 2021, Abandoned.
U.S. Appl. No. 16/319,159, US 2019-0275014 A1 , filed Jan. 18, 2019, Sep. 12, 2019, Abandoned.
U.S. Appl. No. 18/196,106, US 2024-0100026 A1 , filed May 11, 2023, Mar. 28, 2024, Pending.
U.S. Appl. No. 18/144,065, US 2023-0355636 A1, filed May 5, 2023, Nov. 9, 2023, Pending.
U.S. Appl. No. 16/465,500, US 2020-0061073 A1 U.S. Pat. No. 11,690,847, filed May 30, 2019, Feb. 27, 2020 Jul. 4, 2023, Pending.
U.S. Appl. No. 16/484,045, US 2020-0095206 A1 U.S. Pat. No. 11,718,589, filed Aug. 6, 2019, Mar. 26, 2020 Aug. 8, 2023, Pending.
U.S. Appl. No. 18/207,777, US 2023-0322684 A1, filed Jun. 9, 2023, Oct. 12, 2023, Pending.
U.S. Appl. No. 17/893,777, US 2023-0165883 A1, filed Aug. 23, 2022, Jun. 1, 2023, Pending.
U.S. Appl. No. 16/603,544, US 2020-0030348 A1 U.S. Pat. No. 11,426,420, filed Oct. 7, 2019, Jan. 30, 2020 Aug. 30, 2022, Issued.
U.S. Appl. No. 16/617,137, US 2021-0317132 A1, filed Nov. 26, 2019, Oct. 14, 2021, Abandoned.
U.S. Appl. No. 18/057,589, US 2024-0043440 A1, filed Nov. 21, 2022, Feb. 8, 2024, Pending.
U.S. Appl. No. 18/910,653, filed Oct. 9, 2023, Pending.
U.S. Appl. No. 17/044,888, US 2021-0100779 A1, filed Oct, 2, 2020, Apr. 8, 2021, Abandoned.

(56) References Cited

OTHER PUBLICATIONS

U.S. Appl. No. 18/128,075, US-2024-0024297 A1, filed Mar. 29, 2023, Jan. 5, 2024, Pending.
U.S. Appl. No. 18/976,590, filed Dec. 11, 2024, Pending.
U.S. Appl. No. 17/892,585, US 2023-0052363 A1, filed Aug. 22, 2022, Feb. 16, 2023, Docket Central, Pending.
U.S. Appl. No. 18/020,202, US 2023-0310390 A1, filed Feb. 7, 2023, Oct. 5, 2023, Docket Central, Pending.

COMPOSITIONS AND METHODS OF MODULATING SHORT-CHAIN DEHYDROGENASE ACTIVITY

CROSS-REFERENCE TO RELATED APPLICATIONS

This application claims the benefit of U.S. Provisional Application No. 62/770,571, filed Nov. 21, 2018, the disclosure of which is incorporated by reference herein in its entirety.

BACKGROUND

Short-chain dehydrogenases (SCDs) are a family of dehydrogenases that share only 15% to 30% sequence identity, with similarity predominantly in the coenzyme binding domain and the substrate binding domain. In addition to their role in detoxification of ethanol, SCDs are involved in synthesis and degradation of fatty acids, steroids, and some prostaglandins, and are therefore implicated in a variety of disorders such as lipid storage disease, myopathy, SCD deficiency, and certain genetic disorders.

The SCD, 15-hydroxy-prostaglandin dehydrogenase (15-PGDH), (hydroxyprostaglandin dehydrogenase 15-(nicotinamide adeninedinucleotide); 15-PGDH; Enzyme Commission number 1.1.1.141; encoded by the HPGD gene), represents the key enzyme in the inactivation of a number of active prostaglandins, leukotrienes and hydroxyeicosatetraenoic acids (HETEs) (e.g., by catalyzing oxidation of $PGE_2$ to 15-keto-prostaglandin E2, 15k-PGE). The human enzyme is encoded by the HPGD gene and consists of a homodimer with subunits of a size of 29 kDa. The enzyme belongs to the evolutionarily conserved superfamily of short-chain dehydrogenase/reductase enzymes (SDRs), and according to the recently approved nomenclature for human enzymes, it is named SDR36C1. Thus far, two forms of 15-PGDH enzyme activity have been identified, NAD+-dependent type 115-PGDH that is encoded by the HPGD gene, and the type II NADP-dependent 15-PGDH, also known as carbonyl reductase 1 (CBR1, SDR21C1). However, the preference of CBR1 for NADP and the high Km values of CBR1 for most prostaglandin suggest that the majority of the in vivo activity can be attributed to type 115-PGDH encoded by the HPGD gene, that hereafter, and throughout all following text, simply denoted as 15-PGDH.

Recent studies suggest that inhibitors of 15-PGDH and activators of 15-PGDH could be therapeutically valuable. It has been shown that there is an increase in the incidence of colon tumors in 15-PGDH knockout mouse models. A more recent study implicates increased 15-PGDH expression in the protection of thrombin-mediated cell death. It is well known that 15-PGDH is responsible for the inactivation of prostaglandin E2 ($PGE_2$), which is a downstream product of COX-2 metabolism. $PGE_2$ has been shown to be beneficial in a variety of biological processes, such as hair density, dermal wound healing, and bone formation.

SUMMARY

Embodiments described herein relate to compounds and methods of modulating short chain dehydrogenase (SCD) (e.g., 15-PGDH) activities, modulating tissue prostaglandin levels, and/or treating diseases, disorders, or conditions in which it is desired to modulate SCD (e.g., 15-PGDH) activity and/or prostaglandin levels.

In some embodiments, the modulator of SCD can be an SCD inhibitor that can be administered to tissue or blood of a subject at an amount effective to inhibit the activity of a short chain dehydrogenase enzyme. The SCD inhibitor can be a 15-PGDH inhibitor that can be administered to tissue or blood of a subject at an amount effective to increase prostaglandin levels in the tissue or blood. The 15-PGDH inhibitor can include a compound having a structure of formula (IA):

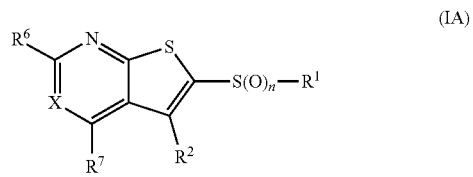

(IA)

or a pharmaceutically acceptable salt, tautomer, or solvate thereof, wherein:

$R^1$ is alkyl, haloalkyl, cycloalkyl, alkylene-cycloalkyl, alkylene-alkoxy, heterocyclyl, or alkylene-heterocyclyl;

$R^2$ is —$NH_2$, CN, or —NHC(O)alkyl;

$R^6$ is heterocyclyl or heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;

$R^3$ is oxo, —OH, —O-alkylene-OH, —O-alkylene-N$(R^5)_2$, —N$(R^5)_2$, —N($R^5$)(alkylene-OH), —N($R^5$)(alkylene-O-alkyl), alkyl, -alkylene-OH, haloalkyl, cycloalkyl, heterocyclyl, —C(O)N$(R^5)_2$, —C(O)N($R^5$)(alkylene-OH), —C(O)-alkyl, —C(O)O-alkyl, or —S(O)$_m$-alkyl, wherein the cycloalkyl and the heterocyclyl is each optionally substituted with $R^{10}$;

$R^4$ is oxo, halogen, —CN, —N$(R^5)_2$, —OH, —O-alkylene-OH, —S(O)$_m$-alkyl, —C(O)— alkyl, —C(O)-cycloalkyl, alkyl, -alkylene-O-alkyl, alkoxy, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-$NH_2$, -alkylene-N$(R^9)_2$, -alkylene-O-alkylene-OH, -alkylene-O-alkylene-$NH_2$, —C(O)-alkyl, —C(O)O-alkyl, -alkylene-COOH, or —S(O)$_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, S(O)$_t$, or N;

$R^{10}$ is —OH, halogen, alkyl, or alkoxy;

X is N or CH;

m is 0, 1, or 2;

n is 0, 1, or 2; and t is 0, 1, or 2.

In some embodiments, $R^1$ is $C_1$-$C_6$ alkyl, $C_1$-$C_6$ haloalkyl, 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).

In other embodiments, $R^1$ is cyclopropyl, cyclobutyl, cyclopentyl, cyclohexyl, —($CH_2$)$_p$-cyclopropyl, —($CH_2$)$_p$-cyclobutyl, —($CH_2$)$_p$-cyclopentyl, or —($CH_2$)$_p$-cyclohexyl; wherein p is 1, 2, or 3.

In still other embodiments, $R^2$ is —$NH_2$.

In some embodiments, $R^6$ is 5- to 6-membered heterocyclyl or 5- to 10-membered heteroaryl, each of which is optionally substituted with one or more $R^3$.

In other embodiments, $R^6$ is 5- to 6-membered heteroaryl optionally substituted with one or more $R^3$.

In still other embodiments, $R^6$ is 8- to 10-membered bicyclic heteroaryl optionally substituted with one or more $R^3$.

In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)NR$^5$($C_1$-$C_6$ alkyl), each of which is optionally substituted with one or more $R^4$.

In other embodiments, $R^7$ is $C_1$-$C_6$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.

In still other embodiments, $R^7$ is $C_1$-$C_6$ haloalkyl, 3- to 6-membered cycloalkyl, phenyl, 5- to 10-membered heteroaryl each of which is optionally substituted with one or more $R^4$.

In some embodiments, $R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In other embodiments, $R^3$ is —($C_1$-$C_3$ alkyl)OH, —$NH_2$, —N($C_1$-$C_3$ alkyl)$_2$, —NHCH$_2$CH$_2$OH, —N($C_1$-$C_3$ alkyl)CH$_2$CH$_2$OH, N(CH$_2$CH$_2$OH)$_2$, —NHCH$_2$CH(CH$_2$OH)$_2$, —N($C_1$-$C_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N($C_1$-$C_3$ alkyl)CH$_2$CH$_2$NH$_2$, —NHCH$_2$CH$_2$NH($C_1$-$C_3$ alkyl), —NHCH$_2$CH$_2$N($C_1$-$C_3$ alkyl)$_2$, —N($C_1$-$C_3$ alkyl)CH$_2$CH$_2$NH($C_1$-$C_3$ alkyl), —N($C_1$-$C_3$ alkyl)CH$_2$CH$_2$N($C_1$-$C_3$ alkyl)$_2$, —NHSO$_2$CH$_3$, —N($C_1$-$C_3$ alkyl)SO$_2$CH$_3$, —OCH$_2$CH$_2$OH, —OCH$_2$CH$_2$NH$_2$, —OCH$_2$CH$_2$NH($C_1$-$C_3$ alkyl), or —OCH$_2$CH$_2$N($C_1$-$C_3$ alkyl)$_2$.

In still other embodiments, $R^3$ is —NHCH$_2$CH$_2$OH or —N(CH$_3$)CH$_2$CH$_2$OH.

In some embodiments, $R^4$ is halogen, —CN, —N($R^5$)$_2$, —OH, —O—($C_1$-$C_6$ alkylene)-OH, —S(O)$_m$($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.

In some embodiments, n is 1.

In other embodiments, the compound has the structure of formula (II):

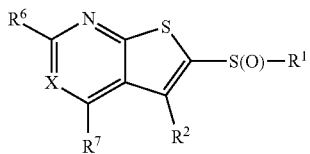

(II)

or a pharmaceutically acceptable salt, tautomer, or solvate thereof, wherein:

$R^1$ is 3- to 6-membered cycloalkyl, —($C_1$-$C_6$ alkylene)-(3- to 6-membered cycloalkyl), 3- to 6-membered heterocyclyl, or —($C_1$-$C_6$ alkylene)-(3- to 6-membered heterocyclyl);

$R^2$ is —$NH_2$, CN, or —NHC(O)alkyl;

$R^6$ is heterocyclyl or heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)NR$^5$-alkyl, each of which is optionally substituted with one or more $R^4$;

$R^3$ is oxo, —OH, —O-alkylene-N($R^5$)$_2$, —N($R^5$)$_2$, —N($R^5$)(alkylene-OH), alkyl, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl;

$R^4$ is oxo, halogen, —CN, —N($R^5$)$_2$, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-NH$_2$, -alkylene-N($R^9$)$_2$, -alkylene-O-alkylene-OH, -alkylene-O-alkylene-NH$_2$, —C(O)-alkyl, —C(O)O-alkyl, -alkylene-COOH, or —S(O)$_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, S(O)$_t$, or N;

X is N or CH;

m is 0, 1, or 2; and t is 0, 1, or 2.

In some embodiments, $R^1$ is 3- to 5-membered cycloalkyl or —($C_1$-$C_6$ alkylene)-(3- to 5-membered cycloalkyl).

In other embodiments, $R^1$ is cyclobutyl.

In still other embodiments, $R^1$ is a bicyclic 4- to 6-membered cycloalkyl.

In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)NR$^5$($C_1$-$C_6$ alkyl), each of which is optionally substituted with one or more $R^4$.

In other embodiments, $R^7$ is $C_1$-$C_4$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$. In other embodiments, $R^7$ is $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.

In other embodiments, $R^7$ is $C_1$-$C_3$ alkyl, $C_1$-$C_3$ haloalkyl, 3-membered cycloalkyl, phenyl, 4-membered heterocyclyl, or 5- to 6-membered heteroaryl, each of which is optionally substituted with one or more $R^4$. In other embodiments, $R^7$ is $C_1$-$C_3$ haloalkyl, 3-membered cycloalkyl, phenyl, 4-membered heterocyclyl, or 5- to 6-membered heteroaryl, each of which is optionally substituted with one or more $R^4$.

In other embodiments, $R^7$ is —CF$_3$, isopropyl, cyclopropyl, phenyl, pyridyl, or triazole, each of which is optionally substituted with one or more $R^4$. In other embodiments, $R^7$ is —CF₃, isopropyl, cyclopropyl, phenyl, pyridyl, or triazole, each of which is optionally substituted with one or more R⁴.

In some embodiments, R⁷ is —CF₃, isopropyl,

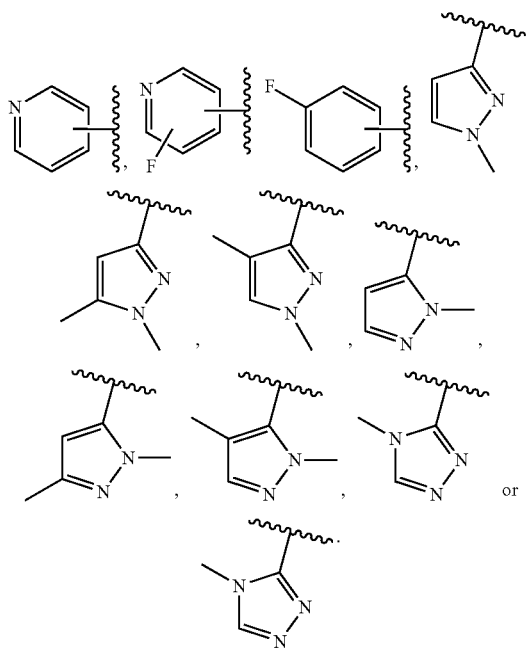

In other embodiments, R⁷ is —CF₃, isopropyl,

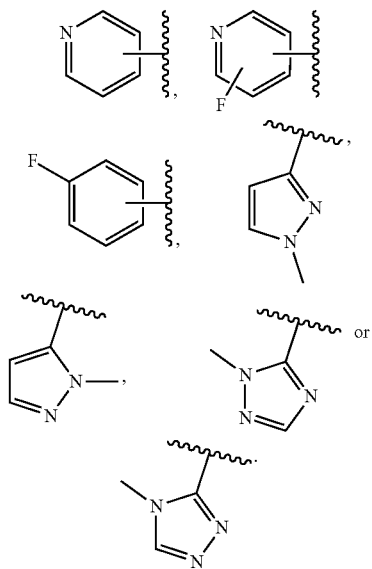

In still other embodiments, R⁷ is —CF₃,

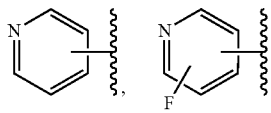

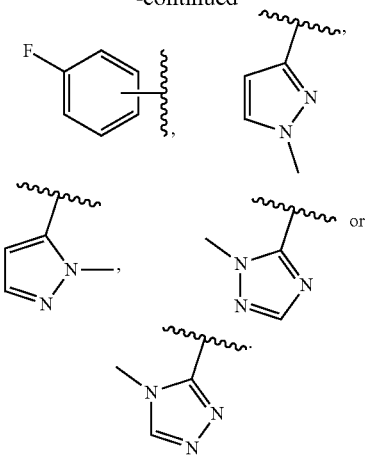

In some embodiments, R³ is —O—(C₁-C₆ alkylene)-N(R⁵)₂, —N(R⁵)₂, —N(R⁵)(C₁-C₆ alkylene-OH), —C(O)N(R⁵)₂, —C(O)N(R⁵)(C₁-C₆ alkylene-OH), —C(O)(C₁-C₆ alkyl), —C(O)O(C₁-C₆ alkyl), or —S(O)$_m$(C₁-C₆ alkyl).

In other embodiments, R³ is —NH₂, —N(C₁-C₃ alkyl)₂, —NHCH₂CH₂OH, —N(C₁-C₃ alkyl)CH₂CH₂OH, N(CH₂CH₂OH)₂, —NHCH₂CH(CH₂OH)₂, —N(C₁-C₃ alkyl)CH₂CH(CH₂OH)₂, —NHCH₂CH₂OCH₂CH₂OH, —NHCH₂CH₂OCH₂CH₂NH₂, —NHCH₂CH₂NH₂, —N(C₁-C₃ alkyl)CH₂CH₂NH₂, —NHCH₂CH₂NH(C₁-C₃ alkyl), —NHCH₂CH₂N(C₁-C₃ alkyl)₂, —N(C₁-C₃ alkyl) CH₂CH₂NH(C₁-C₃ alkyl), —N(C₁-C₃ alkyl)CH₂CH₂N(C₁-C₃ alkyl)₂, —NHSO₂CH₃, —N(C₁-C₃ alkyl)SO₂CH₃, —OCH₂CH₂OH, —OCH₂CH₂NH₂, —OCH₂CH₂NH(C₁-C₃ alkyl), or —OCH₂CH₂N(C₁-C₃ alkyl)₂.

In still other embodiments, R³ is —NHCH₂CH₂OH or —N(CH₃)CH₂CH₂OH.

In other embodiments, the compound has the structure of formula (III):

(III)

or a pharmaceutically acceptable salt, tautomer, or solvate thereof, wherein:
R¹ is cycloalkyl, alkylene-cycloalkyl, alkylene-alkoxy, heterocyclyl, or alkylene-heterocyclyl;
R² is —NH₂, CN, or —NHC(O)alkyl;
R⁶ is heterocyclyl or heteroaryl, each of which is optionally substituted with one or more R³;
R⁷ is C₁-C₆ haloalkyl, aryl or heteroaryl, each of which is optionally substituted with one or more R⁴;
R³ is oxo, —OH, —O-alkylene-N(R⁵)₂, —N(R⁵)₂, —N(R⁵)(alkylene-OH), alkyl, haloalkyl, cycloalkyl, heterocyclyl, —C(O)N(R⁵)₂, —C(O)N(R⁵)(alkylene-OH), —C(O)-alkyl, —C(O)O-alkyl, or —S(O)$_m$-alkyl;
each R⁵ is independently, H, alkyl, -alkylene-OH optionally substituted with —OH, -alkylene-NH₂, -alkylene-N(R⁹)₂, -alkylene-O-alkylene-OH, -alkylene-O-alkylene-NH₂, —C(O)-alkyl, -alkylene-COOH, —C(O)O-alkyl, or —S(O)$_m$-alkyl;

or alternative, two R⁵ together with the N atom to which they are attached can form a 4- to 7-membered heterocycle, optionally containing an additional heteroatom selected from O, S, or N, and wherein the heterocycle is optionally substituted with R⁸;
R⁴ is halogen, alkyl, or alkoxy;
X is N or CH; and
m is 0, 1, or 2.

In some embodiments, R¹ is cyclobutyl. In some embodiments, R¹ is —(C₁-C₄ alkylene)-(C₁-C₃ alkoxy).

In some embodiments, R⁷ is —CF₃, pyridyl, pyrazole, phenyl, or triazole, each of which is optionally substituted with one or more R⁴.

In other embodiments, R⁷ is —CF₃, pyridyl, fluorophenyl, or a triazole optionally substituted with one or more halogen or methyl.

In still other embodiments, R⁷ is —CF₃,

In still other embodiments, R⁷ is —CF₃.
In still other embodiments, R⁷ is

In some embodiments, R⁷ is

In other embodiments, R⁶ is 8- to 10-membered bicyclic heteroaryl optionally substituted with one or more R³.

In other embodiments, the compound has the structure of formula (IV):

(IV)

or a pharmaceutically acceptable salt, tautomer, or solvate thereof, wherein:
R¹ is cycloalkyl, -alkylene-cycloalkyl, -alkylene-alkoxy, heterocyclyl, or -alkylene-heterocyclyl;
R² is —NH₂, CN, or —NHC(O)alkyl;
R⁶ is heterocyclyl or heteroaryl, each of which is optionally substituted with one or more R³;
R⁷ is 3- to 6-membered cycloalkyl, optionally substituted with one or more R⁴;
R³ is oxo, —OH, —O-alkylene-N(R⁵)₂, —N(R⁵)₂, —N(R⁵)(alkylene-OH), alkyl, haloalkyl, cycloalkyl, heterocyclyl, —C(O)N(R⁵)₂, —C(O)N(R⁵)(alkylene-OH), —C(O)-alkyl, —C(O)O-alkyl, or —S(O)ₘ-alkyl;
R⁴ is halogen, —CN, —NH₂, —OH, or C₁-C₃ alkyl;
each R⁵ is independently, H, alkyl, -alkylene-OH optionally substituted with —OH, -alkylene-NH₂, -alkylene-N(R⁹)₂, -alkylene-O-alkylene-OH, -alkylene-O-alkylene-NH₂, —C(O)-alkyl, -alkylene-COOH, —C(O)O-alkyl, or —S(O)ₘ-alkyl;
or alternative, two R⁵ together with the N atom to which they are attached can form a 4- to 7-membered heterocycle, optionally containing an additional heteroatom selected from O, S, or N, and wherein the heterocycle is optionally substituted with R⁸;
R⁸ is halogen, alkyl, or alkoxy;
X is N or CH;
m is 0, 1, or 2.

In some embodiments, R⁷ is cyclopropyl.
In other embodiments, R¹ is 3- to 6-membered cycloalkyl, —(C₁-C₆ alkylene)-(3- to 6-membered cycloalkyl), —(C₁-C₆ alkylene)-(C₁-C₆ alkoxy), 3- to 6-membered heterocyclyl, or —(C₁-C₆ alkylene)-(3- to 6-membered heterocyclyl).

In some embodiments, R¹ is cyclopropyl, cyclobutyl, cyclopentyl, cyclohexyl, —(CH₂)ₚ-cyclopropyl, —(CH₂)ₚ-cyclobutyl, —(CH₂)ₚ-cyclopentyl, or —(CH₂)ₚ-cyclohexyl; wherein p is 1, 2, or 3.

In some embodiments, R¹ is cyclobutyl. In some embodiments, R¹ is —(C₁-C₄ alkylene)-(C₁-C₃ alkoxy).

In some embodiments, R³ is —O—(C₁-C₆ alkylene)-N(R⁵)₂, —N(R⁵)₂, —N(R⁵)(C₁-C₆ alkylene-OH), —C(O)N(R⁵)₂, —C(O)N(R⁵)(C₁-C₆ alkylene-OH), —C(O)(C₁-C₆ alkyl), —C(O)O(C₁-C₆ alkyl), or —S(O)ₘ(C₁-C₆ alkyl).

In some embodiments, R³ is —NH₂, —N(C₁-C₃ alkyl)₂, —NHCH₂CH₂OH, —N(C₁-C₃ alkyl)CH₂CH₂OH, N(CH$_2$CH$_2$OH)$_2$, —NHCH$_2$CH(CH$_2$OH)$_2$, —N(C$_1$-C$_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N(C$_1$-C$_3$ alkyl)CH$_2$CH$_2$NH$_2$, —NHCH$_2$CH$_2$NH(C$_1$-C$_3$ alkyl), —NHCH$_2$CH$_2$N(C$_1$-C$_3$ alkyl)$_2$, —N(C$_1$-C$_3$ alkyl) CH$_2$CH$_2$NH(C$_1$-C$_3$ alkyl), —N(C$_1$-C$_3$ alkyl)CH$_2$CH$_2$N(C$_1$-C$_3$ alkyl)$_2$, —NHSO$_2$CH$_3$, —N(C$_1$-C$_3$ alkyl)SO$_2$CH$_3$, —OCH$_2$CH$_2$OH, —OCH$_2$CH$_2$NH$_2$, —OCH$_2$CH$_2$NH(C$_1$-C$_3$ alkyl), or —OCH$_2$CH$_2$N(C$_1$-C$_3$ alkyl)$_2$.

In other embodiments, R$^3$ is —NHCH$_2$CH$_2$OH or —N(CH$_3$)CH$_2$CH$_2$OH.

In other embodiments, the compound has the structure of formula (V):

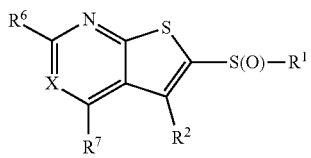

(V)

or a pharmaceutically acceptable salt, tautomer, or solvate thereof, wherein:
R$^1$ is cycloalkyl, -alkylene-cycloalkyl, -alkylene-alkoxy, heterocyclyl, or -alkylene-heterocyclyl;
R$^2$ is —NH$_2$, CN, or —NHC(O)alkyl;
R$^6$ is heterocyclyl or heteroaryl, each of which is substituted with one or more R$^3$;
R$^7$ is haloalkyl, cycloalkyl, aryl, heterocyclyl, heteroaryl, —C(O)-alkyl, —C(O)O-alkyl, or —C(O)NR$^5$-alkyl, each of which is optionally substituted with one or more R$^4$;
R$^3$ is —O—(C$_1$-C$_6$ alkylene)-N(R$^5$)$_2$, —N(R$^5$)$_2$, —N(R$^5$) (C$_1$-C$_6$ alkylene-OH), —C(O)N(R$^5$)$_2$, —C(O)N(R$^5$) (C$_1$-C$_6$ alkylene-OH), —C(O)(C$_1$-C$_6$ alkyl), —C(O)O (C$_1$-C$_6$ alkyl), or —S(O)$_m$(C$_1$-C$_6$ alkyl);
R$^4$ is oxo, halogen, —CN, —N(R$^5$)$_2$, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with R$^8$;
each R$^5$ is independently H, C$_1$-C$_6$ alkyl, —(C$_1$-C$_6$ alkylene)-OH optionally substituted with —OH, -alkylene-NH$_2$, -alkylene-N(R$^9$)$_2$, -alkylene-O-alkylene-OH, -alkylene-O-alkylene-NH$_2$, —C(O)(C$_1$-C$_6$ alkyl), —C(O)O(C$_1$-C$_6$ alkyl), alkylene-COOH, or —S(O)$_m$ (C$_1$-C$_6$ alkyl);
or alternative, two R$^5$ together with the N atom to which they are attached can form a 4- to 7-membered heterocycle, optionally containing an additional heteroatom selected from O, S, or N, and wherein the heterocycle is optionally substituted with R$^8$;
R$^8$ is halogen, alkyl, or alkoxy;
X is N or CH;
m is 0, 1, or 2.

In some embodiments, R$^1$ is cyclobutyl. In some embodiments, —(C$_1$-C$_4$ alkylene)-(C$_1$-C$_3$ alkoxy).

In some embodiments, R$^3$ is —O—(C$_1$-C$_6$ alkylene)-N (R$^5$)$_2$, —N(R$^5$)$_2$ or —N(R$^5$)(C$_1$-C$_6$ alkylene-OH).

In other embodiments, R$^5$ is H, C$_1$-C$_6$ alkyl, —(C$_1$-C$_6$ alkylene)-OH, or —S(O)$_2$(C$_1$-C$_3$ alkyl).

In some embodiments, R$^3$ is —NH$_2$, —N(C$_1$-C$_3$ alkyl)$_2$, —NHCH$_2$CH$_2$OH, —N(C$_1$-C$_3$ alkyl)CH$_2$CH$_2$OH, N(CH$_2$CH$_2$OH)$_2$, —NHCH$_2$CH(CH$_2$OH)$_2$, —N(C$_1$-C$_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N(C$_1$-C$_3$ alkyl)CH$_2$CH$_2$NH$_2$, —NHCH$_2$CH$_2$NH(C$_1$-C$_3$ alkyl), —NHCH$_2$CH$_2$N(C$_1$-C$_3$ alkyl)$_2$, —N(C$_1$-C$_3$ alkyl) CH$_2$CH$_2$NH(C$_1$-C$_3$ alkyl), —N(C$_1$-C$_3$ alkyl)CH$_2$CH$_2$N(C$_1$-C$_3$ alkyl)$_2$, —NHSO$_2$CH$_3$, —N(C$_1$-C$_3$ alkyl)SO$_2$CH$_3$, —OCH$_2$CH$_2$OH, —OCH$_2$CH$_2$NH$_2$, —OCH$_2$CH$_2$NH(C$_1$-C$_3$ alkyl), or —OCH$_2$CH$_2$N(C$_1$-C$_3$ alkyl)$_2$.

In other embodiments, R$^3$ is —NHCH$_2$CH$_2$OH or —N(CH$_3$)CH$_2$CH$_2$OH.

In still other embodiments, R$^3$ is —NHCH$_2$CH$_2$OH.

In some embodiments, R$^6$ is 5- to 6-membered heterocyclyl or 5- to 10-membered heteroaryl, each of which is optionally substituted with one or more R$^3$.

In other embodiments, R$^6$ is 5- to 6-membered heteroaryl optionally substituted with one or more R$^3$.

In some embodiments, R$^6$ is furan, thiophene, pyrrole, thiazole, isothiazole, oxazole, isooxazole, pyrazole, imidazole, triazole, pyridine, pyrimidine, pyridazine, or pyrazine, each optionally substituted with one or more R$^3$.

In other embodiments, R$^6$ is thiazole, imidazole, oxazole, pyridine, or pyrimidine.

In some embodiments, R$^6$ is 8- to 10-membered bicyclic heteroaryl optionally substituted with one or more R$^3$.

In other embodiments, R$^6$ is 5- to 6-membered heterocyclyl, optionally substituted with one or more R$^3$, selected from morpholine, pyridine-one, or piperidine.

In some embodiments, R$^7$ is C$_1$-C$_3$ haloalkyl, 3-membered cycloalkyl, phenyl, 4-membered heterocyclyl, or 5- to 6-membered heteroaryl, each of which is optionally substituted with one or more R$^4$.

In other embodiments, R$^7$ is —CF$_3$, cyclopropyl, phenyl, pyrzole, pyridyl, or triazole, each of which is optionally substituted with one or more R$^4$. In still other embodiments, R$^7$ is —CF$_3$,

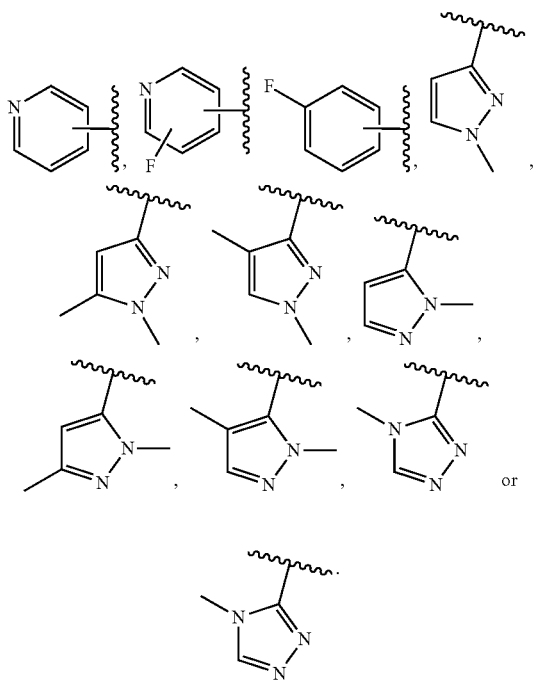

In some embodiments, the compound has the structure of formula (VI):

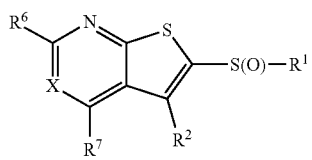

(VI)

or a pharmaceutically acceptable salt, tautomer, or solvate thereof, wherein:
$R^1$ is cycloalkyl, alkylene-cycloalkyl, alkylene-alkoxy, heterocyclyl, or alkylene-heterocyclyl;
$R^2$ is —$NH_2$, CN, or —NHC(O)alkyl;
$R^6$ is fused bicyclic heterocyclyl or fused bicyclic heteroaryl, each of which is optionally substituted with one or more $R^3$;
$R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;
$R^3$ is oxo, —OH, —O-alkylene-$N(R^5)_2$, —$N(R^5)_2$, —$N(R^5)$(alkylene-OH), alkyl, haloalkyl, cycloalkyl, heterocyclyl, —C(O)$N(R^5)_2$, —C(O)-alkyl, —C(O)O-alkyl, or —$S(O)_m$-alkyl;
$R^4$ is oxo, halogen, —CN, —$N(R^5)_2$, —OH, —O-alkylene-OH, —$S(O)_m$-alkyl, —C(O)— alkyl, —C(O)-cycloalkyl, alkyl, haloalkyl, cycloalkyl, heterocyclyl, or -alkylene-aryl optionally substituted with $R^8$;
each $R^5$ is independently, H, alkyl, -alkylene-OH optionally substituted with —OH, -alkylene-O-alkylene-OH, -alkylene-O-alkylene-$NH_2$, —C(O)-alkyl, —C(O)O-alkyl, or —$S(O)_m$-alkyl;
or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;
$R^8$ is halogen, alkyl, or alkoxy;
X is N or CH; and
m is 0, 1, or 2.
In some embodiments, $R^6$ is 8- to 10-membered fused bicyclic heteroaryl, each of which is optionally substituted with one or more $R^3$.
In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)$NR^5$($C_1$-$C_6$ alkyl), each of which is optionally substituted with one or more $R^4$.
In other embodiments, $R^7$ is $C_1$-$C_4$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$. In other embodiments, $R^7$ is $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.
In still other embodiments, $R^7$ is $C_1$-$C_3$ alkyl, $C_1$-$C_6$ haloalkyl, 3- to 6-membered cycloalkyl, phenyl, 3- to 6-membered heterocyclyl, or 5- to 6-membered heteroaryl, each of which is optionally substituted with one or more $R^4$.
In other embodiments, $R^7$ is $C_1$-$C_3$ alkyl, $C_1$-$C_6$ haloalkyl, 3- to 6-membered cycloalkyl, phenyl, pyrazole, pyridyl, or triazole, each of which is optionally substituted with one or more $R^4$. In other embodiments, $R^7$ is $C_1$-$C_6$ haloalkyl, 3- to 6-membered cycloalkyl, phenyl, pyrazole, pyridyl, or triazole, each of which is optionally substituted with one or more $R^4$.

In other embodiments, $R^7$ is —$CF_3$, isopropyl, cyclopropyl, phenyl, pyridyl, or triazole, each of which is optionally substituted with one or more $R^4$. In other embodiments, $R^7$ is —$CF_3$, cyclopropyl, phenyl, pyridyl, or triazole, each of which is optionally substituted with one or more $R^4$. In further embodiments, $R^7$ is isopropyl,

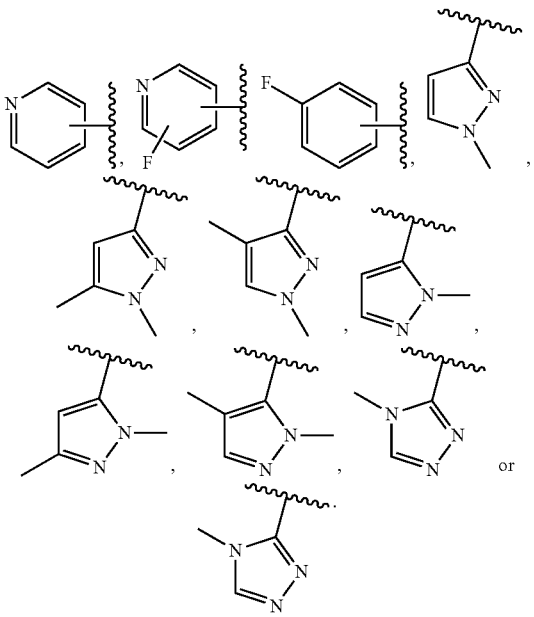

In further embodiments, $R^7$ is

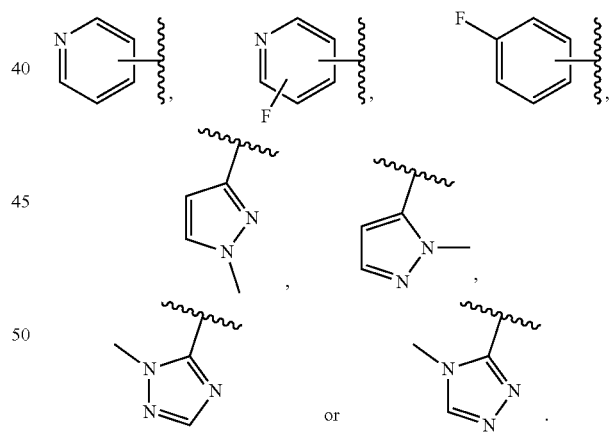

In some embodiments, $R^1$ is $C_1$-$C_6$ alkyl, $C_1$-$C_6$ haloalkyl, 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).
In other embodiments, $R^1$ is cyclopropyl, cyclobutyl, cyclopentyl, cyclohexyl, —$(CH_2)_p$-cyclopropyl, —$(CH_2)_p$-cyclobutyl, —$(CH_2)_p$-cyclopentyl, or —$(CH_2)_p$-cyclohexyl; wherein p is 1, 2, or 3. In some embodiments, $R^1$ is cyclobutyl. In some embodiments, —($C_1$-$C_4$ alkylene)-($C_1$-$C_3$ alkoxy).

In some embodiments, $R^3$ is —O—($C_1$-$C_6$ alkylene)-N$(R^5)_2$, —N$(R^5)_2$, —N$(R^5)$($C_1$-$C_6$ alkylene-OH), —C(O)N$(R^5)_2$, —C(O)N$(R^5)$($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In other embodiments, $R^3$ is —NH$_2$, —N($C_1$-$C_3$ alkyl)$_2$, —NHCH$_2$CH$_2$OH, —N($C_1$-$C_3$ alkyl)CH$_2$CH$_2$OH, N(CH$_2$CH$_2$OH)$_2$, —NHCH$_2$CH(CH$_2$OH)$_2$, —N($C_1$-$C_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N($C_1$-$C_3$ alkyl)CH$_2$CH$_2$NH$_2$, —NHCH$_2$CH$_2$NH($C_1$-$C_3$ alkyl), —NHCH$_2$CH$_2$N($C_1$-$C_3$ alkyl)$_2$, —N($C_1$-$C_3$ alkyl)CH$_2$CH$_2$NH($C_1$-$C_3$ alkyl), —N($C_1$-$C_3$ alkyl)CH$_2$CH$_2$N($C_1$-$C_3$ alkyl)$_2$, —NHSO$_2$CH$_3$, —N($C_1$-$C_3$ alkyl)SO$_2$CH$_3$, —OCH$_2$CH$_2$OH, —OCH$_2$CH$_2$NH$_2$, —OCH$_2$CH$_2$NH($C_1$-$C_3$ alkyl), or —OCH$_2$CH$_2$N($C_1$-$C_3$ alkyl)$_2$.

In some embodiments, $R^3$ is —NHCH$_2$CH$_2$OH or —N(CH$_3$)CH$_2$CH$_2$OH.

In other embodiments, $R^4$ is halogen, —CN, —N$(R^5)_2$, —OH, —O—($C_1$-$C_6$ alkylene)-OH, —S(O)$_m$($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.

In some embodiments, the compound has the structure of formula (VII):

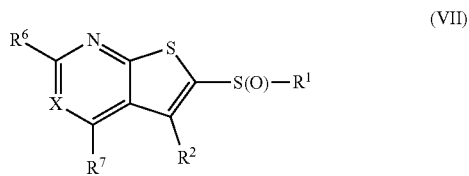

(VII)

or a pharmaceutically acceptable salt, tautomer, or solvate thereof, wherein:
$R^1$ is cyclobutyl or —($C_1$-$C_4$ alkylene)-($C_1$-$C_3$ alkoxy);
$R^2$ is —NH$_2$, CN, or —NHC(O)alkyl;
$R^6$ is heterocyclyl or heteroaryl, each of which is optionally substituted with one or more $R^3$;
$R^7$ is —CF$_3$, isopropyl,

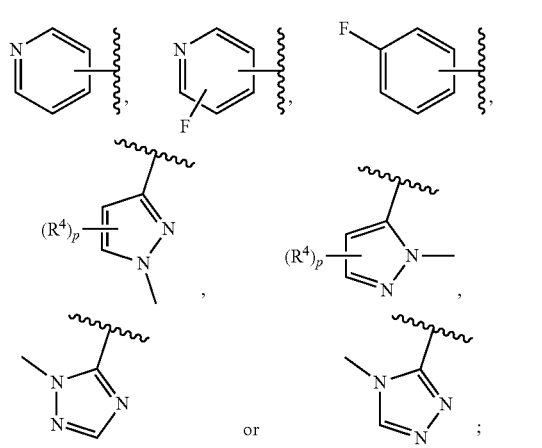

$R^3$ is oxo, —OH, —O-alkylene-OH, —O-alkylene-N$(R^5)_2$, —N$(R^5)_2$, —N$(R^5)$(alkylene-OH), —N$(R^5)$(alkylene-O-alkyl), alkyl, -alkylene-OH, haloalkyl, cycloalkyl, heterocyclyl, —C(O)N$(R^5)_2$, —C(O)N$(R^5)$(alkylene-OH), —C(O)-alkyl, —C(O)O-alkyl, or —S(O)$_m$-alkyl, wherein the cycloalkyl and the heterocyclyl is each optionally substituted with $R^{10}$;

$R^4$ is $C_1$-$C_3$ alkyl;
each $R^5$ is independently, H, alkyl, -alkylene-OH optionally substituted with —OH, -alkylene-NH$_2$, -alkylene-N$(R^9)_2$, -alkylene-O-alkylene-OH, -alkylene-O-alkylene-NH$_2$, —C(O)-alkyl, —C(O)O-alkyl, -alkylene-COOH, or —S(O)$_m$-alkyl;
or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;
$R^8$ is halogen, alkyl, or alkoxy;
$R^9$ is H or alkyl, or two $R^9$ together with the N atom to which they are attached can form a 4- to 7-membered heterocycle, optionally containing an additional heteroatom selected from O, S(O)$_t$, or N;
$R^{10}$ is —OH, halogen, alkyl, or alkoxy;
X is N or CH;
m is 0, 1, or 2;
p is 0 or 1; and
t is 0, 1, or 2.

In some embodiments, the compound has the structure of formula (VIII):

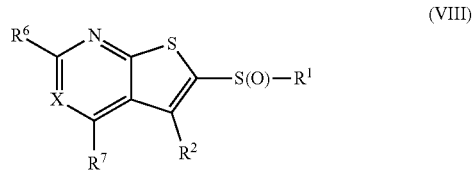

(VIII)

or a pharmaceutically acceptable salt, tautomer, or solvate thereof, wherein:
$R^1$ is cyclobutyl or —($C_1$-$C_4$ alkylene)-($C_1$-$C_3$ alkoxy);
$R^2$ is —NH$_2$, CN, or —NHC(O)alkyl;
$R^6$ is

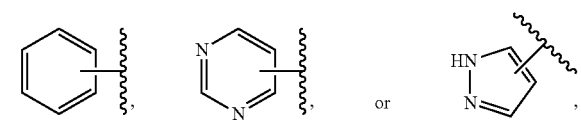

each of which is optionally substituted with one or more $R^3$;
$R^7$ is —CF$_3$, isopropyl, cyclopropyl, cyclobutyl, each of which is optionally substituted with one or more $R^4$;

$R^3$ is —$NH_2$, —$NH(C_1-C_3$ alkyl), —$NH(C_1-C_4$ alkylene)-OH, or $C_1-C_3$ alkyl;

$R^4$ is $C_1-C_3$ alkyl; and

X is N or CH.

In some embodiments, the compound or 15-PGDH inhibitor can inhibit the enzymatic activity of recombinant 15-PGDH at an $IC_{50}$ of less than 1 µM, at an $IC_{50}$ of less than 250 nM, at an $IC_{50}$ of less than 50 nM, at an $IC_{50}$ of less than 10 nM, at an $IC_{50}$ of less than 5 nM at a recombinant, at an $IC_{50}$ of about 2.5 nM to about 10 nM, or less than about 2.5 nM at a 15-PGDH concentration of about 5 nM to about 10 nM.

The 15-PGDH inhibitor can be provided in a topical composition that can be applied to skin of a subject to promote and/or stimulate pigmentation of the skin and/or hair growth and/or inhibiting hair loss, and/or treat skin damage or inflammation.

The 15-PGDH inhibitor can also be administered to a subject to promote wound healing, tissue repair, and/or tissue regeneration and/or engraftment or regeneration of a tissue graft.

In one embodiment, the 15-PGDH inhibitor can be administered to a subject to treat at least one of oral ulcers, gum disease, colitis, ulcerative colitis, gastrointestinal ulcers, inflammatory bowel disease, vascular insufficiency, Raynaud's disease, Buerger's disease, diabetic neuropathy, pulmonary artery hypertension, cardiovascular disease, and renal disease.

In another embodiment, the 15-PGDH inhibitor can be administered to a subject in combination with a prostanoid agonist for the purpose of enhancing the therapeutic effect of the agonist in prostaglandin responsive conditions.

In other embodiments, the 15-PGDH inhibitor can be administered to a subject and/or tissue of the subject to increase tissue stem cells. For example, the 15-PGDH inhibitor can be administered to bone marrow of a subject to increase stem cells in the subject.

In still other embodiments, the 15-PGDH inhibitor can be administered to a tissue graft donor, bone marrow graft donor, and/or a hematopoietic stem cell donor, and/or a tissue graft, and/or a bone marrow graft, and/or a hematopoietic stem cell graft, to increase the fitness of a donor tissue graft, a donor bone marrow graft, and/or a donor hematopoietic stem cell graft. In one embodiment, the 15-PGDH inhibitor is administered ex vivo to a tissue graft, and/or a bone marrow graft, and/or a hematopoietic stem cell graft. For example, the 15-PGDH inhibitor can be administered to a subject, and/or bone marrow of a subject to increase the fitness of the marrow as a donor graft, and/or to a preparation of hematopoietic stem cells of a subject to increase the fitness of the stem cell preparation as a donor graft, and/or to a preparation of peripheral blood hematopoietic stem cells of a subject to increase the fitness of the stem cell preparation as a donor graft, and/or to a preparation of umbilical cord blood stem cells to increase the fitness of the stem cell preparation as a donor graft, and/or to a preparation of umbilical cord blood stem cells to decrease the number of units of umbilical cord blood required for transplantation.

In other embodiments, the 15-PGDH inhibitor can be administered to a subject to mitigate tissue graft rejection, to enhance tissue and/or bone marrow graft engraftment, to enhance bone marrow graft engraftment, following treatment of the subject or the marrow of the subject with radiation therapy, chemotherapy, or immunosuppressive therapy, to enhance engraftment of a progenitor stem cell graft, hematopoietic stem cell graft, or an umbilical cord blood stem cell graft, to enhance engraftment of a hematopoietic stem cell graft, or an umbilical cord stem cell graft, following treatment of the subject or the marrow of the subject with radiation therapy, chemotherapy, or immunosuppressive therapy, and/or in order to decrease the number of units of umbilical cord blood required for transplantation into the subject.

In other embodiments, the 15-PGDH inhibitor can be administered to a recipient of a tissue graft transplant, bone marrow transplant, and/or hematopoietic stem cell transplant, or of an umbilical cord stem cell transplant, in order to decrease the administration of other treatments or growth factors.

In some embodiments, the 15-PGDH inhibitor can be administered to a subject or to a tissue graft of a subject to mitigate graft rejection, to enhance graft engraftment, and/or to enhance graft engraftment following treatment of the subject or the marrow of the subject with radiation therapy, chemotherapy, or immunosuppressive therapy.

In other embodiments, the 15-PGDH inhibitor can be administered to a subject or to the bone marrow of a subject to confer resistance to toxic or lethal effects of exposure to radiation, to confer resistance to the toxic effect of Cytoxan, the toxic effect of fludarabine, the toxic effect of chemotherapy, or the toxic effect of immunosuppressive therapy, to decrease pulmonary toxicity from radiation, and/or to decrease infection.

In still other embodiments, the 15-PGDH inhibitor can be administered to a subject to increase neutrophil counts following a hematopoetic cell transplant with bone marrow, hematopoetic stem cells, or umbilical cord blood, to increase neutrophil counts in a subject with neutropia following chemotherapy administration or radiation therapy, to increase neutrophil counts in a subject with aplastic anemia, myelodysplasia, myelofibrosis, neutropenia due to other bone marrow diseases, drug induced neutropenia, autoimmune neutropenia, idiopathic neutropenia, or neutropenia following viral infections, to increase neutrophil counts in a subject with neutropia, to increase platelet counts following a hematopoetic cell transplant with bone marrow, hematopoetic stem cells, or umbilical cord blood, to increase platelet counts in a subject with thrombocytopenia following chemotherapy administration or radiation therapy, to increase platelet counts in a subject with aplastic anemia, myelodysplasia, myelofibrosis, thrombocytopenia due to other bone marrow diseases, drug induced thrombocytopenia, autoimmune thrombocytopenia, idiopathic thrombocytopenic purpura, idiopathic thrombocytopenia, or thrombocytopenia following viral infections, to increase platelet counts in a subject with thrombocytopenia, to increase red blood cell counts, or hematocrit, or hemoglobin level, following a hematopoetic cell transplant with bone marrow, hematopoetic stem cells, or umbilical cord blood, to increase red blood cell counts, or hematocrit, or hemoglobin level in a subject with anemia following chemotherapy administration or radiation therapy, to increase red blood cell counts, or hematocrit, or hemoglobin level counts in a subject with aplastic anemia, myelodysplasia, myelofibrosis, anemia due to other disorder of bone marrow, drug induced anemia, immune mediated anemias, anemia of chronic disease, anemia following viral infections, or anemia of unknown cause, to increase red blood cell counts, or hematocrit, or hemoglobin level in a subject with anemia, to increase bone marrow stem cells, following a hematopoetic cell transplant with bone marrow, hematopoetic stem cells, or umbilical cord blood, to increase bone marrow stem cells in a subject following chemotherapy administration or radiation therapy, and/or to increase bone marrow stem cells in a subject with aplastic anemia, myelodysplasia, myelofibrosis, other disorder of bone marrow, drug induced cytopenias, immune cytopenias, cytopenias following viral infections, or cytopenias.

In other embodiments, the administration of a 15-PGDH inhibitor can be used to modulate hematopoietic stem cells and hematopoiesis. For example, a 15-PGDH inhibitor can be administered alone or in combination with a cytokine to a subject in need thereof to increase and/or mobilize hematopoiectic stem cells and/or neutrophils in the blood, marrow, and/or tissue of the subject.

In some embodiments, the administration of a 15-PGDH inhibitor can be in combination with G-CSF for the purpose of increasing neutrophils.

In other embodiments, the administration of a 15-PGDH inhibitor can be in combination with a hematopoietic cytokine for the purpose of increasing neutrophils.

In still other embodiments, the administration of a 15-PGDH inhibitor can be in combination with G-CSF for the purpose of increasing numbers of and/or of mobilizing peripheral blood hematopoietic stem cells.

In other embodiments, the administration of a 15-PGDH inhibitor can be in combination with a hemopoietic cytokine for the purpose of increasing numbers of and/or of mobilizing peripheral blood hematopoietic stem cells.

In some embodiments, the administration of a 15-PGDH inhibitor can be in combination with a second agent, including, for example, Plerixafor, for the purpose of increasing numbers of and/or of mobilizing peripheral blood hematopoietic stem cells.

In other embodiments, the administration of a 15-PGDH inhibitor can be in combination with G-CSF for the purpose of increasing numbers of and/or of mobilizing peripheral blood hematopoietic stem cells for use in hematopoietic stem cell transplantation.

In still other embodiments, the administration of a 15-PGDH inhibitor can be in combination with a hemopoietic cytokine for the purpose of increasing numbers of and/or of mobilizing peripheral blood hematopoietic stem cells for use in hematopoietic stem cell transplantation.

In other embodiments, the administration of a 15-PGDH inhibitor can be in combination with a second agent, including Plerixafor, for the purpose of increasing numbers of and/or of mobilizing peripheral blood hematopoietic stem cells for use in hematopoietic stem cell transplantation.

In still other embodiments, the administration of a 15-PGDH inhibitor can be in combination with G-CSF for the purpose of increasing numbers of hematopoietic stem cells in blood or bone marrow.

In other embodiments, the administration of a 15-PGDH inhibitor can be in combination with a hemopoietic cytokine for the purpose of increasing numbers of hematopoietic stem cells in blood or bone marrow.

In other embodiments, the 15-PGDH inhibitor can be administered to a subject and/or tissue of the subject to increase tissue stem cells. For example, the 15-PGDH inhibitor can be administered to bone marrow of a subject to increase stem cells in the subject.

In other embodiments, the 15-PGDH inhibitor can be administered to a recipient of a tissue graft transplant, bone marrow transplant, and/or hematopoietic stem cell transplant, or of an umbilical cord stem cell transplant, in order to decrease the administration of other treatments or growth factors.

In still other embodiments, the 15-PGDH inhibitor can be administered to a subject to increase neutrophil counts following a hematopoetic cell transplant with bone marrow, hematopoetic stem cells, or umbilical cord blood, to increase neutropil counts in a subject with neutropia following chemotherapy administration or radiation therapy, to increase neutrophil counts in a subject with aplastic anemia, myelodysplasia, myelofibrosis, neutropenia due to other bone marrow diseases, drug induced neutropenia, autoimmune neutropenia, idiopathic neutropenia, or neutropenia following viral infections, to increase neutrophil counts in a subject with neutropia, to increase platelet counts following a hematopoetic cell transplant with bone marrow, hematopoetic stem cells, or umbilical cord blood, to increase platelet counts in a subject with thrombocytopenia following chemotherapy administration or radiation therapy, to increase platelet counts in a subject with aplastic anemia, myelodysplasia, myelofibrosis, thrombocytopenia due to other bone marrow diseases, drug induced thrombocytopenia, autoimmune thrombocytopenia, idiopathic thrombocytopenic purpura, idiopathic thrombocytopenia, or thrombocytopenia following viral infections, to increase platelet counts in a subject with thrombocytopenia, to increase red blood cell counts, or hematocrit, or hemoglobin level, following a hematopoetic cell transplant with bone marrow, hematopoetic stem cells, or umbilical cord blood, to increase red blood cell counts, or hematocrit, or hemoglobin level in a subject with anemia following chemotherapy administration or radiation therapy, to increase red blood cell counts, or hematocrit, or hemoglobin level counts in a subject with aplastic anemia, myelodysplasia, myelofibrosis, anemia due to other disorder of bone marrow, drug induced anemia, immune mediated anemias, anemia of chronic disease, anemia following viral infections, or anemia of unknown cause, to increase red blood cell counts, or hematocrit, or hemoglobin level in a subject with anemia, to increase bone marrow stem cells, following a hematopoetic cell transplant with bone marrow, hematopoetic stem cells, or umbilical cord blood, to increase bone marrow stem cells in a subject following chemotherapy administration or radiation therapy, and/or to increase bone marrow stem cells in a subject with aplastic anemia, myelodysplasia, myelofibrosis, other disorder of bone marrow, drug induced cytopenias, immune cytopenias, cytopenias following viral infections, or cytopenias.

In other embodiments, the 15-PGDH inhibitor can be administered to a subject to increase responsiveness to cytokines in the presence of cytopenias, with cytopenias including any of: neutropenia, thrombocytopenia, lymphocytopenia and anemia; and with cytokines having increased responsiveness potentiated by the 15-PGDH inhibitor including any of: G-CSF, GM-CSF, EPO, IL-3, IL-6, TPO, TPO-RA (thrombopoietin receptor agonist), and SCF.

In some embodiments, the 15-PGDH inhibitor can be administered to a subject to increase bone density, treat osteoporosis, promote healing of fractures, or promote healing after bone surgery or joint replacement and/or to promote healing of bone to bone implants, bone to artificial implants, dental implants, and bone grafts.

In other embodiments, the 15-PGDH inhibitor can be administered to a subject or to the intestine of a subject to increase stem cells or cell proliferation in the intestine and/or and confer resistance to toxic or lethal effects of exposure to radiation or the toxic, lethal, or mucositis effects resultant from treatment with chemotherapy.

In some embodiments, the 15-PGDH inhibitor can be administered to a subject or to intestine of a subject as a treatment for colitis, ulcerative colitis, or inflammatory bowel disease.

In other embodiments, the 15-PGDH inhibitor can be administered to a subject to increase liver regeneration following liver surgery, following live liver donation, following liver transplantation, or following liver injury by toxins and/or to promote recovery from or resistance to liver toxins, including acetaminophen and related compounds.

In still other embodiments, the 15-PGDH inhibitor can be administered to a subject to treat erectile dysfunction.

In yet other embodiments, the 15-PGDH inhibitor can be administered to inhibit at least one of the growth, proliferation, or metastasis of 15-PGDH expressing cancers.

Still other embodiments described herein relate to a method of treating a subject in need of cell therapy. The method includes administering to the subject a therapeutically effective amount of a preparation comprising human hematopoietic stem cell administered a 15-PGDH inhibitor described herein and/or a therapeutic composition comprising human hematopoietic stem cells and a 15-PGDH inhibitor described herein.

In some embodiments, the subject has received human hematopoietic stem cells and/or has received the preparation and/or the therapeutic composition.

In other embodiments, the subject has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, solid tumors, chronic granulomatous disease, mucopolysaccharidoses, or Diamond Blackfan anemia.

Other embodiments relate to a method of treating a subject having at least one symptom associated with an ischemic tissue or a tissue damaged by ischemia. The method includes administering to the subject a therapeutically effective amount of a preparation comprising human hematopoietic stem cells administered a 15-PGDH inhibitor described herein and/or a therapeutic composition comprising human hematopoietic stem cells and a 15-PGDH inhibitor described herein.

In some embodiments, the ischemia can be associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient isc hemic attack (TIA), traumatic brain injury, ulcerative colitis, vascular disease of the kidney, vascular inflammatory conditions, von Hippel-Lindau syndrome, and wounds to tissues or organs.

Other embodiments relate to methods for treating and/or preventing fibrosis and various fibrotic diseases, disorders or conditions by administration of 15-PGDH inhibitors. In some embodiments, a 15-PGDH inhibitor described herein can be administered to a subject in need thereof to decrease fibrotic symptoms, such as collagen deposition, inflammatory cytokine expression, and inflammatory cell infiltration, and treat and/or prevent various fibrotic diseases, disorders, and conditions characterized, in whole or in part, by the excess production of fibrous material, including excess production of fibrotic material within the extracellular matrix, or the replacement of normal tissue elements by abnormal, non-functional, and/or excessive accumulation of matrix-associated components.

Fibrotic diseases, disorders and conditions characterized, in whole or in part, by excess production of fibrotic material can include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulomanry fibrosis (e.g., glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis, acute fibrosis, organ specific fibrosis, and the like.

In some embodiments, a method of treating or preventing a fibrotic disease, disorder or condition includes administering to a subject in need thereof a therapeutically effect amount of a 15-PGDH inhibitor.

In some embodiments, the 15-PGDH inhibitors can be used to treat or prevent lung fibrosis. Lung fibrosis, which can be treated, can be selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

In other embodiments, the 15-PGDH inhibitors can be used to treat or prevent kidney fibrosis. The kidney fibrosis can result from dialysis following kidney failure, catheter placement, a nephropathy, glomerulosclerosis, glomerulonephritis, chronic renal insufficiency, acute kidney injury, end stage renal disease or renal failure, or combinations thereof.

In other embodiments, the 15-PGDH inhibitors can be used to treat or prevent liver fibrosis. The liver fibrosis can result from a chronic liver disease, viral induced hepatic cirrhosis, hepatitis B vims infection, hepatitis C vims infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, autoimmune hepatitis, cystic fibrosis, alpha-1-antitrypsin deficiency, primary biliary cirrhosis, drug reaction and exposure to toxins, or combinations thereof.

In some embodiments, the 15-PGDH inhibitors can be used to treat or prevent heart fibrosis, for example, cardiac fibrosis and endomyocardial fibrosis.

In some embodiments, the 15-PGDH inhibitors can be used to treat or prevent systemic sclerosis.

In some embodiments, the 15-PGDH inhibitors can be used to treat or prevent fibrotic diseases, disorders or conditions caused by post-surgical adhesion formation.

In some embodiments, the 15-PGDH inhibitors can be used for reducing or preventing scar formation in a subject.

In other embodiments, the 15-PGDH inhibitors can be used to reduce or prevent scar formation on skin or scleroderma.

In various embodiments, the 15-PGDH inhibitors can be administered at a therapeutically effective amount such that at least one symptom or feature of a fibrotic disease, disorder or condition, or other related diseases, disorders or conditions, is reduced in intensity, severity, or frequency, or has delayed onset.

In other embodiments, the 15-PGDH inhibitors can be used in a method for decreasing or reducing collagen secretion or collagen deposition in a tissue or organ, such as the lung, the liver, the intestines, the colon, the skin or the heart, of a subject. The method can include administering a therapeutically effective amount of the 15-PGDH inhibitors to the subject in need thereof. The subject can have or be at risk of an excessive collagen secretion or collagen deposition in the tissue or organ, such as the kidney, the lung, the liver, the intestines, the colon, the skin or the heart. Usually, the excessive collagen secretion or collagen deposition in an organ results from an injury or an insult. Such injury and insult can be organ-specific. The 15-PGDH inhibitors can be administered over a sufficient period of time to decrease or reduce the level of collagen deposition in the tissue or organ, completely or partially. A sufficient period of time can be during one week, or between 1 week to 1 month, or between 1 to 2 months, or 2 months or more. For chronic condition, the 15-PGDH inhibitors can be advantageously administered for life time period.

Other embodiments described herein relate to the use of 15-PGDH inhibitors in combination with corticosteroids or TNF inhibitors to treat inflammation, reduce aberrant activity of the immune system, and/or promote wound healing in a subject in need thereof. It was found that corticosteroids administered to a subject can induce 15-PGDH expression in tissue of the subject. Administration of a 15-PGDH inhibitor in combination with a corticosteroid was found to enhance anti-inflammatory and/or immunosuppressive effects of the corticosteroid while attenuating corticosteroid induced adverse and/or cytotoxic effects. Treatment of inflammatory, disorders, immune disorders, and/or wounds by administration of 15-PGDH inhibitors in combination with corticosteroids can increase therapeutic efficacy and can allow the corticosteroids to be administered, in some instances, at lower dosages to achieve similar effects, and, in other instances, at higher dosages and for prolonged periods of times with attenuated and/or reduced adverse or cytotoxic effects.

In some embodiments, the inflammatory and/or immune disease or disorder treated with the combination of 15-PGDH inhibitor and a corticosteroid or TNF inhibitor can include intestinal, gastrointestinal, or bowel disorders. As described below, it was found that inhibitors of short-chain dehydrogenase activity, such as 15-PGDH inhibitors, can be administered to a subject in need thereof alone or in combination with corticosteroids and tumor necrosis factor (TNF)-alpha antagonists to treat intestinal, gastrointestinal, or bowel disorders, such as oral ulcers, gum disease, gastritis, colitis, ulcerative colitis, gastric ulcers, inflammatory bowel disease, and Crohn's disease.

In other embodiments, the 15-PGDH inhibitor can be used as a glucocorticoid sensitizer to treat glucocorticoid insensitivity, restore corticosteroid sensitivity, enhance glucocorticoid sensitivity, and/or reverse the glucocorticoid insensitivity in a subject experiencing corticosteroid dependence or corticoid resistance or unresponsiveness or intolerance to corticosteroids. For example, the 15-PGDH inhibitor can be administered to a subject in combination with the corticosteroid to treat glucocorticoid insensitivity, restore corticosteroid sensitivity, enhance glucocorticoid sensitivity, and/or reverse the glucocorticoid insensitivity in a subject experiencing corticosteroid dependence or corticoid resistance or unresponsiveness or intolerance to corticosteroids.

The 15-PGDH inhibitor can also be administered in combination with a corticosteroid or TNF inhibitor to a subject to promote wound healing, tissue repair, and/or tissue regeneration and/or engraftment or regeneration of a tissue graft.

In some embodiments, the 15-PGDH inhibitor can be administered to a subject at an amount effective to increase prostaglandin levels in the subject and attenuate corticosteroid induced adverse and/or cytotoxic effects.

DETAILED DESCRIPTION

While the following terms are believed to be well understood by one of ordinary skill in the art, the following definitions are set forth to facilitate explanation of the presently disclosed subject matter.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non limiting examples of inorganic or metal salts include lithium, sodium, calcium, potassium, magnesium salts and the like.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds and salts described herein can exist in several tautomeric forms, including the enol and inline form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The terms below, as used herein, have the following meanings, unless indicated otherwise:

"Amino" refers to the —$NH_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes Cn and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes Cn and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes Cn and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_2$-$C_{10}$ alkenyl, or $C_2$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from phenyl (benzene), aceanthrylene, acenaphthylene, acephenanthrylene, anthracene, azulene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$-$R_c$ where $R_b$ is an alkylene group as defined above and $R_c$ is one or more aryl radicals as defined above. Aralkyl radicals include, but are not limited to, benzyl, diphenylmethyl and the like. Unless stated otherwise specifically in the specification, an aralkyl group can be optionally substituted.

"Aralkenyl" or "arylalkenyl" refers to a radical of the formula —$R_b$-$R_c$ where $R_b$ is an alkenylene group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$-$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused, bridged, or spiral ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiral ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused, bridged, or spiral ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$-$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclyl or heterocyclic rings include heteroaryls as defined below. Unless stated otherwise specifically in the specification, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, aziridinyl, oextanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, pyridine-one, and the like. The point of attachment of the heterocyclyl, heterocyclic ring, or heterocycle to the rest of the molecule by a single bond is through a ring member atom, which can be carbon or nitrogen. Unless stated otherwise specifically in the specification, a heterocyclyl group can be optionally substituted.

"Heterocyclylalkyl" refers to a radical of the formula —$R_b$-$R_e$ where $R_b$ is an alkylene group as defined above and $R_e$ is a heterocyclyl radical as defined above. Unless stated otherwise specifically in the specification, a heterocyclylalkyl group can be optionally substituted.

"Heterocyclylalkenyl" refers to a radical of the formula —$R_b$-$R_e$ where $R_b$ is an alkenylene group as defined above and $R_e$ is a heterocyclyl radical as defined above. Unless stated otherwise specifically in the specification, a heterocyclylalkenyl group can be optionally substituted.

"Heterocyclylalkynyl" refers to a radical of the formula —$R_b$-$R_e$ where $R_b$ is an alkynylene group as defined above and $R_e$ is a heterocyclyl radical as defined above. Unless stated otherwise specifically in the specification, a heterocyclylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical one to thirteen carbon atoms and one to six heteroatoms selected from the group consisting of nitrogen, oxygen and sulfur, as the ring member. For purposes of this invention, the heteroaryl radical can be a monocyclic, bicyclic, tricyclic or tetracyclic ring system, which can include fused or bridged ring systems, wherein at least one ring containing a heteroatom ring member is aromatic. The nitrogen, carbon or sulfur atoms in the heteroaryl radical can be optionally oxidized and the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrazolopyridine, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$-$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$-$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$-$R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (e.g., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl, heteroarylalkyl, heteroarylalkenyl, heteroarylalkynyl, etc.) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom, such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "⊢" (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, "A⊢" indicates that the chemical entity "A" is bonded to another chemical entity via the point of attachment bond. Furthermore, the specific point of attachment to the non-depicted chemical entity can be specified by inference. For example, the compound

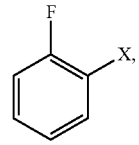

wherein X is "A⊢" infers that the point of attachment bond is the bond by which X is depicted as being attached to the phenyl ring at the ortho position relative to fluorine.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "adenoma", "colon adenoma" and "polyp" are used herein to describe any precancerous neoplasm of the colon.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compounds and methods of modulating SCD activity (e.g., 15-PGDH activity), modulating tissue prostaglandin levels, and/or treating diseases, disorders, or conditions in which it is desired to modulate 15-PGDH activity and/or prostaglandin levels.

"Inhibitors," "activators," and "modulators" of 15-PGDH expression or of 15-PGDH activity are used to refer to inhibitory, activating, or modulating molecules, respectively, identified using in vitro and in vivo assays for 15-PGDH expression or 15-PGDH activity, e.g., ligands, agonists, antagonists, and their homologs and mimetics. The term "modulator" includes inhibitors and activators. Inhibitors are agents that, e.g., inhibit expression of 15-PGDH or bind to, partially or totally block stimulation, decrease, prevent, delay activation, inactivate, desensitize, or down regulate the activity of 15-PGDH, e.g., antagonists. Activators are agents that, e.g., induce or activate the expression of a 15-PGDH or bind to, stimulate, stabilize, increase, open, activate, facilitate, or enhance activation, sensitize or up regulate the activity of 15-PGDH, e.g., agonists. Modulators include naturally occurring and synthetic ligands, small chemical molecules, and the like.

15-PGDH inhibitors described herein can provide a pharmacologic method for elevating prostaglandin levels in tissue. Known activities of prostaglandins include promoting hair growth, promoting skin pigmentation, and promoting skin darkening or the appearance of skin tanning. Known activities of prostaglandins also include ameliorating pulmonary artery hypertension. 15-PGDH inhibitors described herein may also be utilized to increase tissue stem cell numbers for purposes that would include increasing resistance to tissue damage by radiation, increasing resistance to environmental exposures to radiation, increasing stem cell numbers to increase fitness of bone marrow or other types of transplantation (through either in vivo exposure to 15-PGDH inhibitors described herein to increase stem cell numbers prior to harvest of a transplanted tissue, or through ex vivo exposure of a harvested tissue prior to transplant into a recipient host, or through treatment of the graft recipient). 15-PGDH inhibitors described herein may also be utilized for purposes that would include promoting liver regeneration, including liver regeneration after liver resection, and liver regeneration after toxic insults, which for example may be the toxic insult of acetaminophen overdose. Prostaglandin signaling is also known to promote wound healing, protect the stomach from ulceration, and promote healing of ulcers of stomach and intestines. Additionally, 15-PGDH inhibitors described herein can promote activity of human keratinocytes in "healing" scratches across cultures of keratinocyte cells. Hence, 15-PGDH inhibitors described herein may be utilized to also heal ulcers of other tissues, including, but not limited to skin, and including but not limited to diabetic ulcers. Further, 15-PGDH inhibitors described herein may be utilized for the treatment of erectile dysfunction.

15-PGDH inhibitors described herein can be identified using assays in which putative modulator compounds are applied to cells expressing 15-PGDH and then the functional effects on 15-PGDH activity are determined. Samples or assays comprising 15-PGDH that are treated with a potential activator, inhibitor, or modulator are compared to control samples without the inhibitor, activator, or modulator to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Agents tested as modulators of SCD (e.g., 15-PGDH) can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays). Modulators also include agents designed to increase the level of 15-PGDH mRNA or the level of translation from an mRNA.

In some embodiments, the modulator of SCD can be an SCD inhibitor that can be administered to tissue or blood of a subject at an amount effective to inhibit the activity of a short chain dehydrogenase enzyme. The SCD inhibitor can be a 15-PGDH inhibitor that can be administered to tissue or blood of a subject at an amount effective to increase prostaglandin levels in the tissue or blood. The 15-PGDH inhibitor can include a compound having a structure of formula (IA):

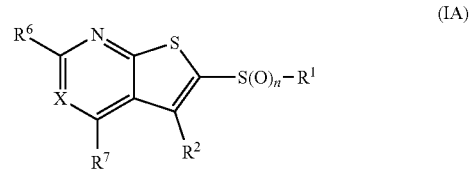

(IA)

or a pharmaceutically acceptable salt, tautomer, or solvate thereof, wherein:

$R^1$ is alkyl, haloalkyl, cycloalkyl, alkylene-cycloalkyl, alkylene-alkoxy, heterocyclyl, or alkylene-heterocyclyl;

$R^2$ is —$NH_2$, CN, or —NHC(O)alkyl;

$R^6$ is heterocyclyl or heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;

$R^3$ is oxo, —OH, —O-alkylene-OH, —O-alkylene-N$(R^5)_2$, —$N(R^5)_2$, —$N(R^5)$(alkylene-OH), —$N(R^5)$(alkylene-O-alkyl), alkyl, -alkylene-OH, haloalkyl, cycloalkyl, heterocyclyl, —C(O)$N(R^5)_2$, —C(O)$N(R^5)$(alkylene-OH), —C(O)-alkyl, —C(O)O-alkyl, or —S(O)$_m$-alkyl, wherein the cycloalkyl and the heterocyclyl is each optionally substituted with $R^{10}$;

$R^4$ is oxo, halogen, —CN, —$N(R^5)_2$, —OH, —O-alkylene-OH, —S(O)$_m$-alkyl, —C(O)— alkyl, —C(O)-cycloalkyl, alkyl, -alkylene-O-alkyl, alkoxy, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-NH$_2$, -alkylene- N(R$^9$)$_2$, -alkylene-O-alkylene-OH, -alkylene-O-alkylene-NH$_2$, —C(O)-alkyl, —C(O)O-alkyl, -alkylene-COOH, or —S(O)$_m$-alkyl;

or alternatively, two R$^5$ together with the N atom to which they are attached can form a 4- to 7-membered heterocycle, optionally containing an additional heteroatom selected from O, S, or N, and wherein the heterocycle is optionally substituted with R$^8$;

R$^8$ is halogen, alkyl, or alkoxy;

R$^9$ is H or alkyl, or two R$^9$ together with the N atom to which they are attached can form a 4- to 7-membered heterocycle, optionally containing an additional heteroatom selected from O, S(O)$_t$, or N;

R$^{10}$ is —OH, halogen, alkyl, or alkoxy;

X is N or CH;

m is 0, 1, or 2;

n is 0, 1, or 2; and t is 0, 1, or 2.

In some embodiment, the 15-PGDH inhibitor can include a compound having a structure of formula (I):

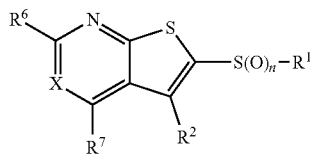

(I)

or a pharmaceutically acceptable salt, tautomer, or solvate thereof, wherein:

R$^1$ is alkyl, haloalkyl, cycloalkyl, alkylene-cycloalkyl, alkylene-alkoxy, heterocyclyl, or alkylene-heterocyclyl;

R$^2$ is —NH$_2$, CN, or —NHC(O)alkyl;

R$^6$ is heterocyclcl or heteroaryl, each of which is optionally substituted with one or more R$^3$; R$^7$ is alkyl, haloalkyl, cycloalkyl, aryl, heterocyclyl, heteroaryl, —C(O)-alkyl, —C(O)O-alkyl, or —C(O)NR$^5$-alkyl, each of which is optionally substituted with one or more R$^4$;

R$^3$ is oxo, —OH, —O-alkylene-N(R$^5$)$_2$, —N(R$^5$)$_2$, —N(R$^5$)(alkylene-OH), alkyl, haloalkyl, cycloalkyl, heterocyclyl, —C(O)N(R$^5$)$_2$, —C(O)N(R$^5$)(alkylene-OH), —C(O)-alkyl, —C(O)O-alkyl, or —S(O)$_m$-alkyl;

R$^4$ is oxo, halogen, —CN, —N(R$^5$)$_2$, —OH, —O-alkylene-OH, —S(O)$_m$-alkyl, —C(O)— alkyl, —C(O)-cycloalkyl, alkyl, alkoxy, haloalkyl, cycloalkyl, heterocyclyl, or -alkylene-aryl optionally substituted with R$^8$;

each R$^5$ is independently, H, alkyl, -alkylene-OH optionally substituted with —OH, -alkylene-NH$_2$, -alkylene-N(R$^9$)$_2$, -alkylene-O-alkylene-OH, -alkylene-O-alkylene-NH$_2$, —C(O)-alkyl, —C(O)O-alkyl, -alkylene-COOH, or —S(O)$_m$-alkyl;

or alternatively, two R$^5$ together with the N atom to which they are attached can form a 4- to 7-membered heterocycle, optionally containing an additional heteroatom selected from O, S, or N, and wherein the heterocycle is optionally substituted with R$^8$;

R$^8$ is halogen, alkyl, or alkoxy;

R$^9$ is H or alkyl, or two R$^9$ together with the N atom to which they are attached can form a 4- to 7-membered heterocycle, optionally containing an additional heteroatom selected from O, S(O)$_t$, or N;

X is N or CH;

m is 0, 1, or 2;

n is 0, 1, or 2; and t is 0, 1, or 2.

In some embodiments, R$^1$ is C$_1$-C$_6$ alkyl, C$_1$-C$_6$ haloalkyl, 3- to 6-membered cycloalkyl, —(C$_1$-C$_6$ alkylene)-(3- to 6-membered cycloalkyl), —(C$_1$-C$_6$ alkylene)-(C$_1$-C$_6$ alkoxy), 3- to 6-membered heterocyclyl, or —(C$_1$-C$_6$ alkylene)-(3- to 6-membered heterocyclyl).

In other embodiments, R$^1$ is cyclopropyl, cyclobutyl, cyclopentyl, cyclohexyl, —(CH$_2$)$_p$-cyclopropyl, —(CH$_2$)$_p$-cyclobutyl, —(CH$_2$)$_p$-cyclopentyl, or —(CH$_2$)$_p$-cyclohexyl; wherein p is 1, 2, or 3.

In still other embodiments, R$^2$ is —NH$_2$.

In some embodiments, R$^6$ is 5- to 6-membered heterocyclcl or 5- to 10-membered heteroaryl, each of which is optionally substituted with one or more R$^3$.

In other embodiments, R$^6$ is 5- to 6-membered heteroaryl optionally substituted with one or more R$^3$.

In still other embodiments, R$^6$ is 8- to 10-membered bicyclic heteroaryl optionally substituted with one or more R$^3$.

In some embodiments, R$^7$ is C$_1$-C$_6$ alkyl, C$_1$-C$_6$ haloalkyl, 3- to 6-membered cycloalkyl, 6- to 10-membered aryl, 3- to 6-membered heterocyclyl, 5- to 10-membered heteroaryl, —C(O)(C$_1$-C$_6$ alkyl), —C(O)O(C$_1$-C$_6$ alkyl), or —C(O)NR$^5$(C$_1$-C$_6$ alkyl), each of which is optionally substituted with one or more R$^4$.

In other embodiments, R$^7$ is C$_1$-C$_6$ alkyl, C$_1$-C$_6$ haloalkyl, 3- to 6-membered cycloalkyl, phenyl, 3- to 6-membered heterocyclyl, or 5- to 10-membered heteroaryl, each of which is optionally substituted with one or more R$^4$.

In still other embodiments, R$^7$ is C$_1$-C$_6$ haloalkyl, 3- to 6-membered cycloalkyl, phenyl, 5- to 10-membered heteroaryl each of which is optionally substituted with one or more R$^4$.

In some embodiments, R$^3$ is —O—(C$_1$-C$_6$ alkylene)-N(R$^5$)$_2$, —N(R$^5$)$_2$, —N(R$^5$)(C$_1$-C$_6$ alkylene-OH), —C(O)N(R$^5$)$_2$, —C(O)N(R$^5$)(C$_1$-C$_6$ alkylene-OH), —C(O)(C$_1$-C$_6$ alkyl), —C(O)O(C$_1$-C$_6$ alkyl), or —S(O)$_m$(C$_1$-C$_6$ alkyl).

In other embodiments, R$^3$ is —(C$_1$-C$_3$ alkyl)OH, —NH$_2$, —N(C$_1$-C$_3$ alkyl)$_2$, —NHCH$_2$CH$_2$OH, —N(C$_1$-C$_3$ alkyl)CH$_2$CH$_2$OH, N(CH$_2$CH$_2$OH)$_2$, —NHCH$_2$CH(CH$_2$OH)$_2$, —N(C$_1$-C$_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N(C$_1$-C$_3$ alkyl)CH$_2$CH$_2$NH$_2$, —NHCH$_2$CH$_2$NH(C$_1$-C$_3$ alkyl), —NHCH$_2$CH$_2$N(C$_1$-C$_3$ alkyl)$_2$, —N(C$_1$-C$_3$ alkyl)CH$_2$CH$_2$NH(C$_1$-C$_3$ alkyl), —N(C$_1$-C$_3$ alkyl)CH$_2$CH$_2$N(C$_1$-C$_3$ alkyl)$_2$, —NHSO$_2$CH$_3$, —N(C$_1$-C$_3$ alkyl)SO$_2$CH$_3$, —OCH$_2$CH$_2$OH, —OCH$_2$CH$_2$NH$_2$, —OCH$_2$CH$_2$NH(C$_1$-C$_3$ alkyl), or —OCH$_2$CH$_2$N(C$_1$-C$_3$ alkyl)$_2$.

In other embodiments, R$^3$ is —NH$_2$, —N(C$_1$-C$_3$ alkyl)$_2$, —NHCH$_2$CH$_2$OH, —N(C$_1$-C$_3$ alkyl)CH$_2$CH$_2$OH, N(CH$_2$CH$_2$OH)$_2$, —NHCH$_2$CH(CH$_2$OH)$_2$, —N(C$_1$-C$_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N(C$_1$-C$_3$ alkyl)CH$_2$CH$_2$NH$_2$, —NHCH$_2$CH$_2$NH(C$_1$-C$_3$ alkyl), —NHCH$_2$CH$_2$N(C$_1$-C$_3$ alkyl)$_2$, —N(C$_1$-C$_3$ alkyl)CH$_2$CH$_2$NH(C$_1$-C$_3$ alkyl), —N(C$_1$-C$_3$ alkyl)CH$_2$CH$_2$N(C$_1$-C$_3$ alkyl)$_2$, —NHSO$_2$CH$_3$, —N(C$_1$-C$_3$ alkyl)SO$_2$CH$_3$, —OCH$_2$CH$_2$OH, —OCH$_2$CH$_2$NH$_2$, —OCH$_2$CH$_2$NH(C$_1$-C$_3$ alkyl), or —OCH$_2$CH$_2$N(C$_1$-C$_3$ alkyl)$_2$.

In still other embodiments, R$^3$ is —NHCH$_2$CH$_2$OH or —N(CH$_3$)CH$_2$CH$_2$OH.

In some embodiments, R$^4$ is halogen, —CN, —N(R$^5$)$_2$, —OH, —O—(C$_1$-C$_6$ alkylene)-OH, —S(O)$_m$(C$_1$-C$_6$ alkyl), —C(O)(C$_1$-C$_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.
In some embodiments, n is 1.
In other embodiments, the 15-PGDH inhibitor can include a compound selected from the group consisting of:
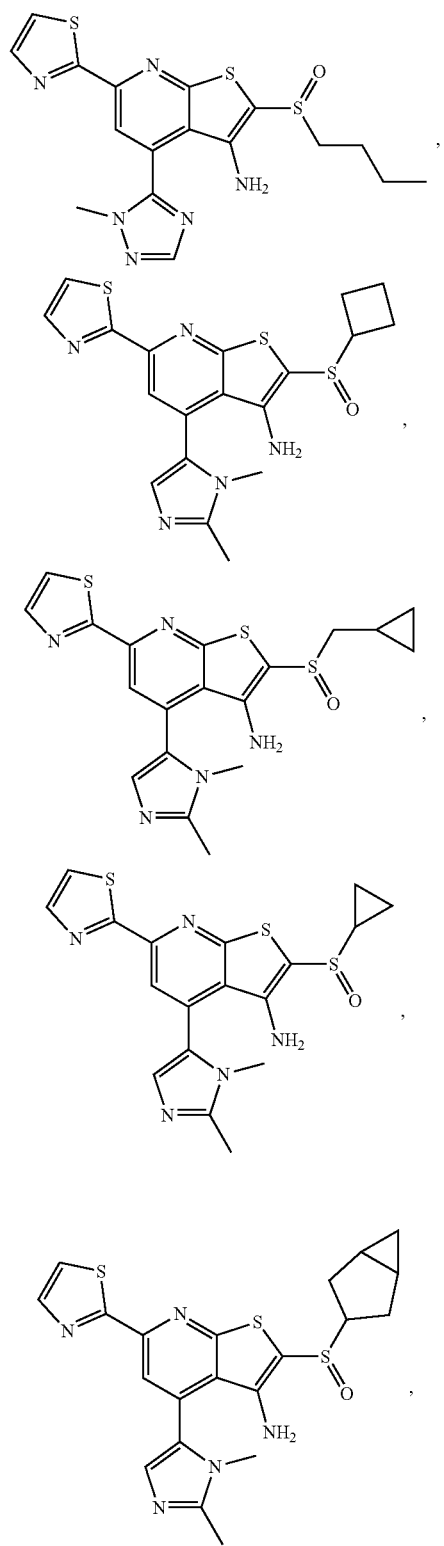
-continued
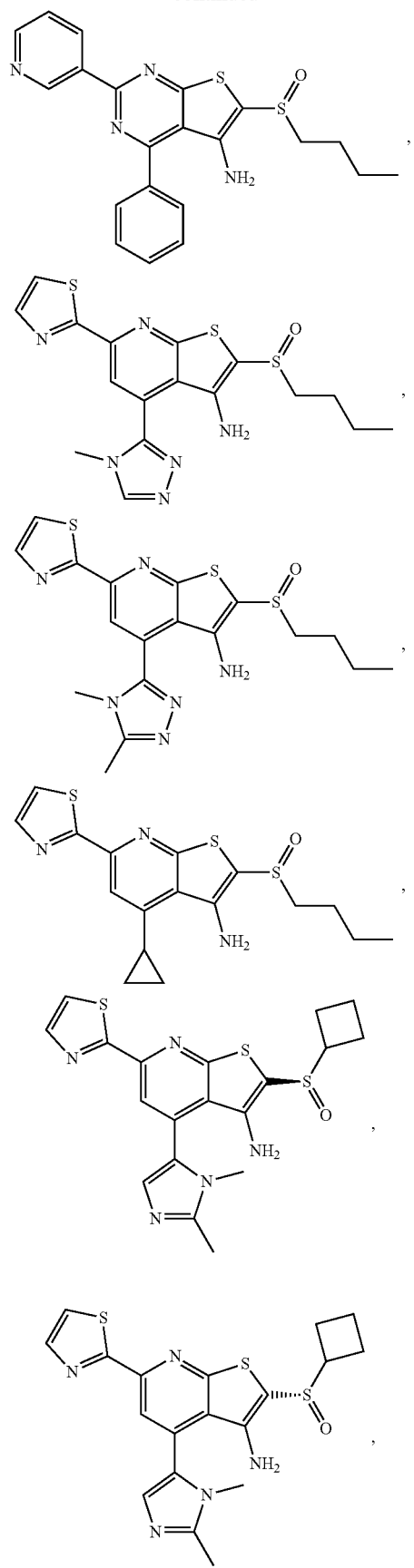

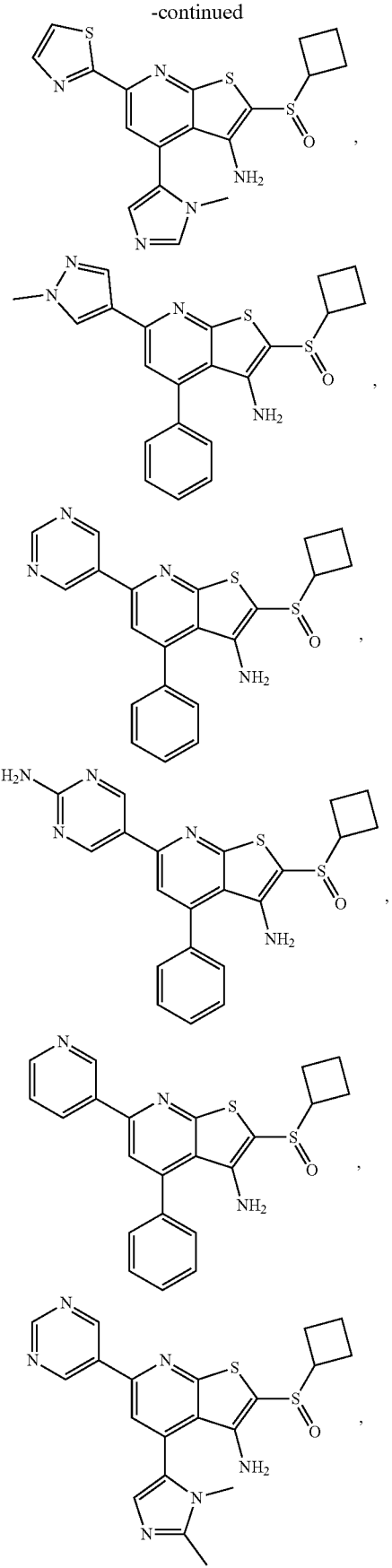
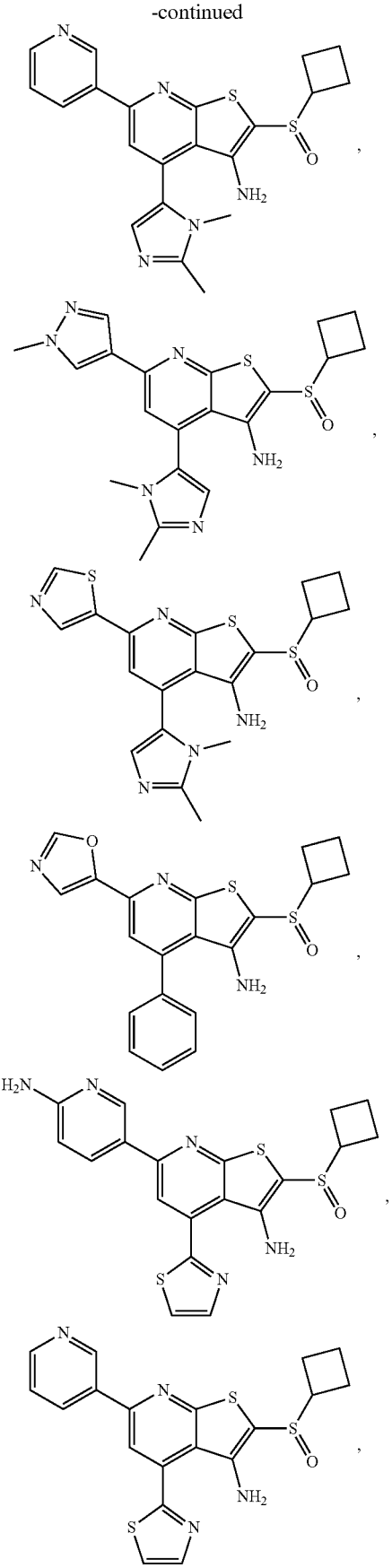

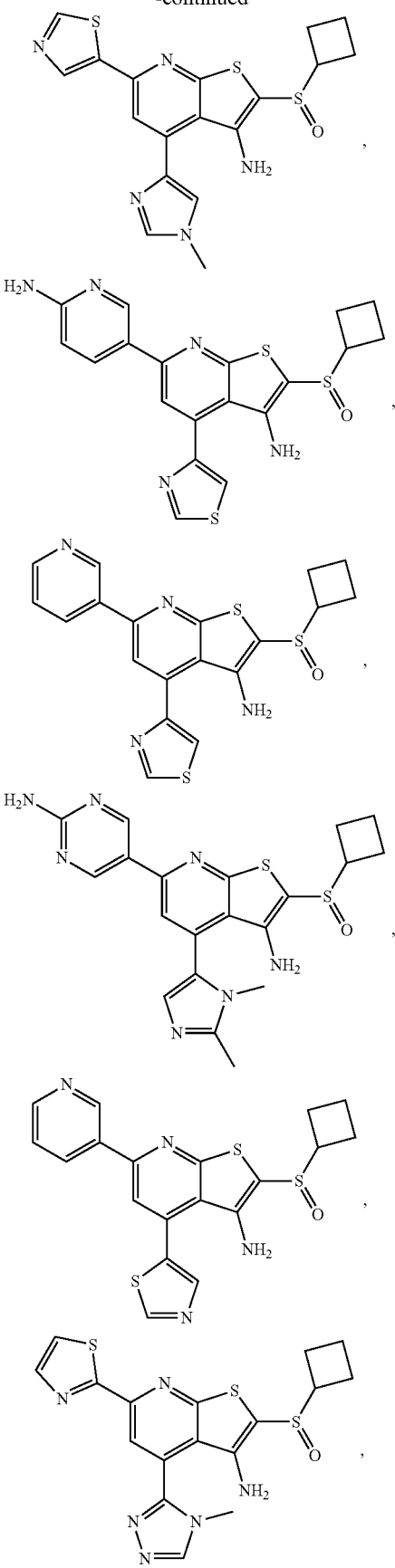
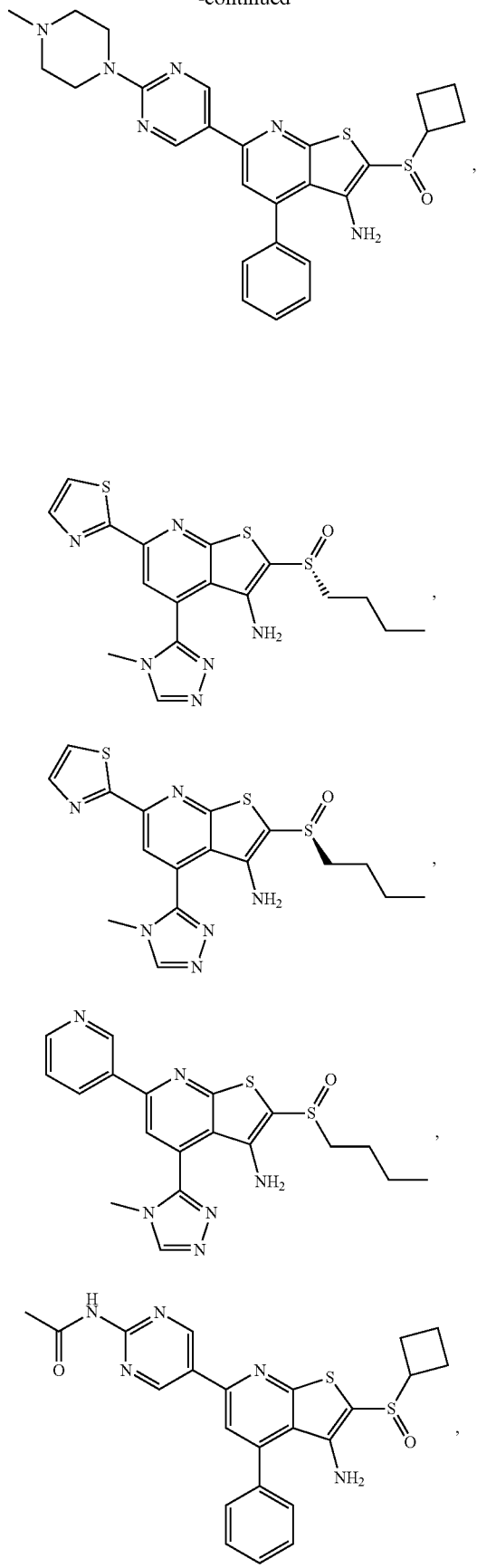

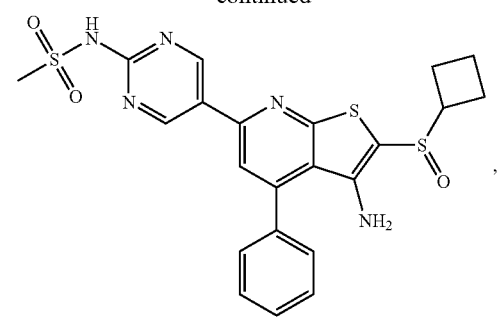
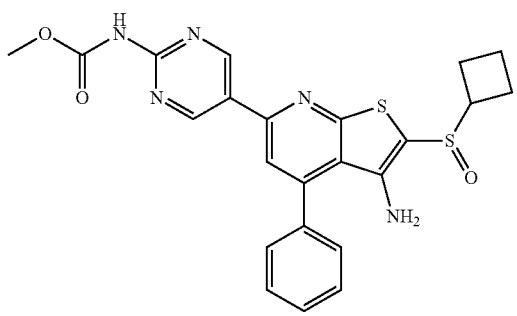
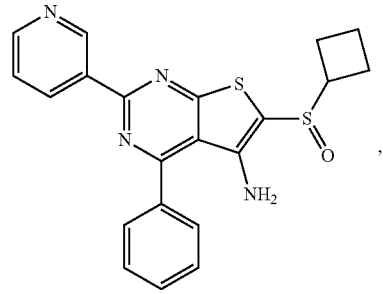
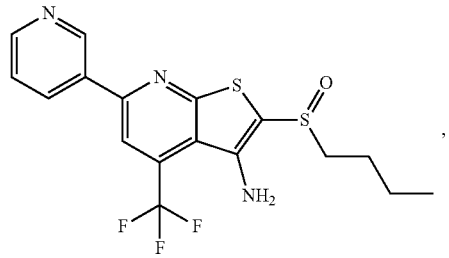
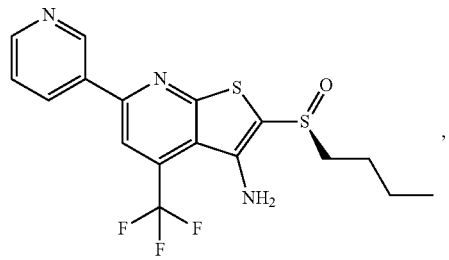
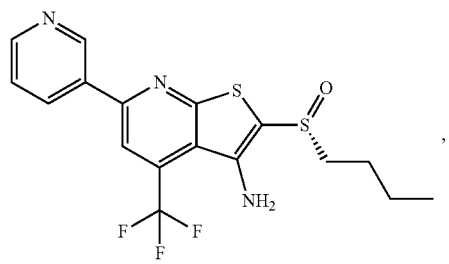
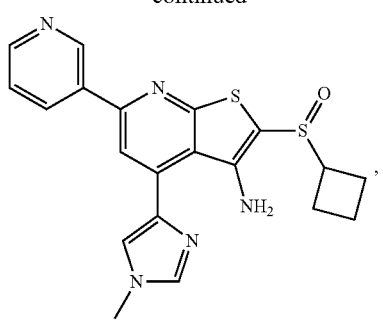
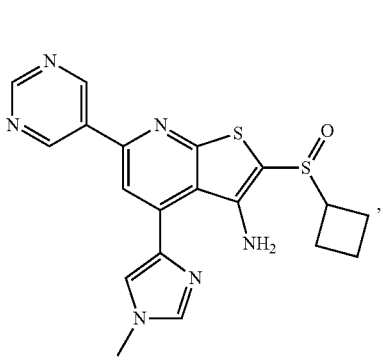
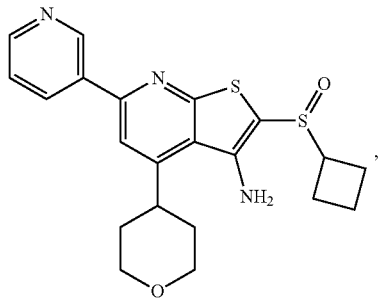
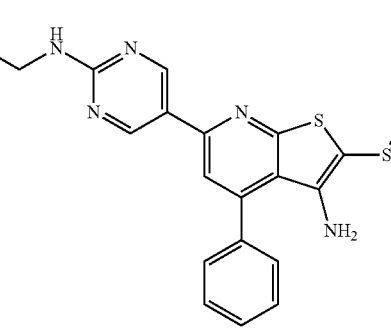
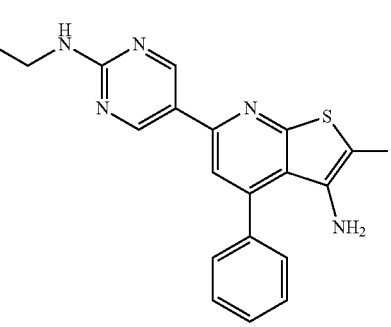

45
-continued
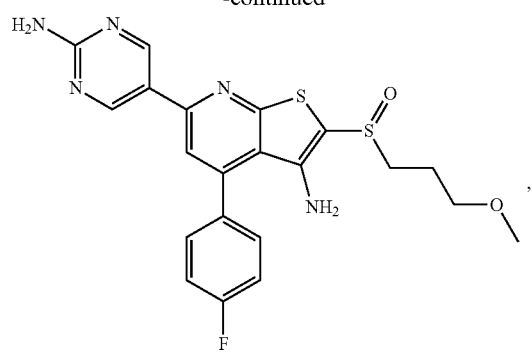
,
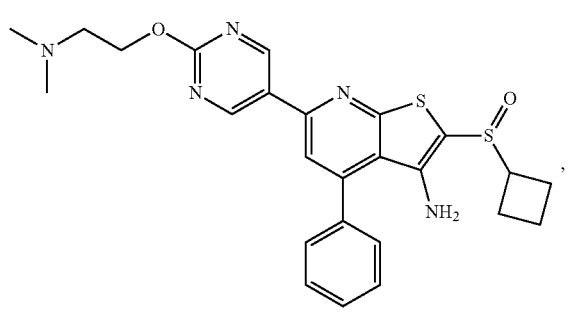
,
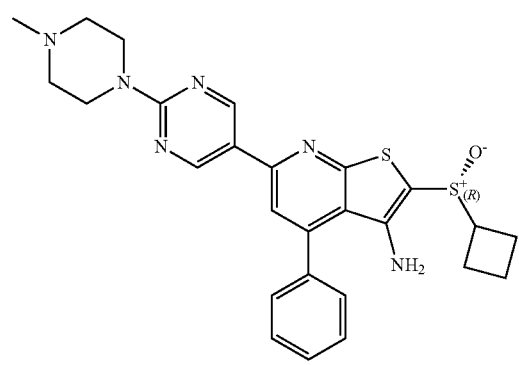
,
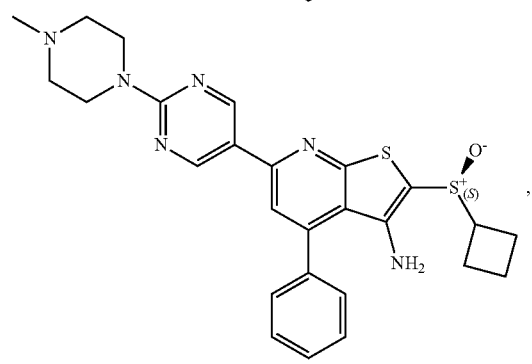
,
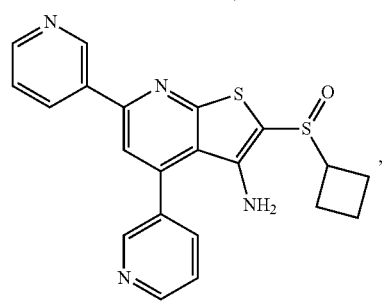
,
46
-continued
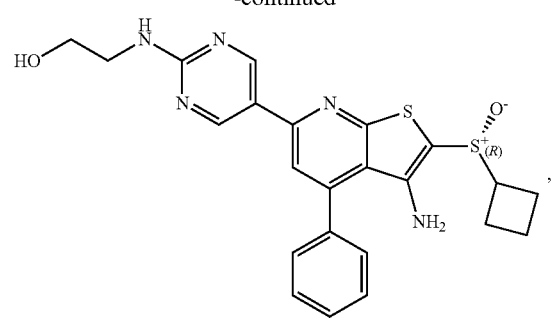
,
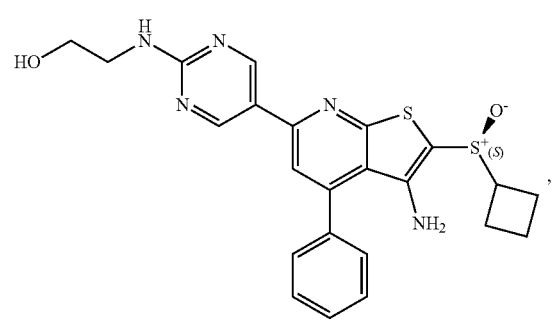
,
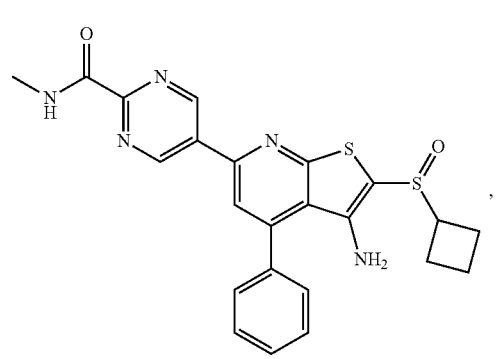
,
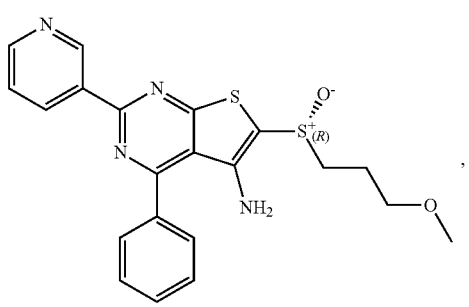
,
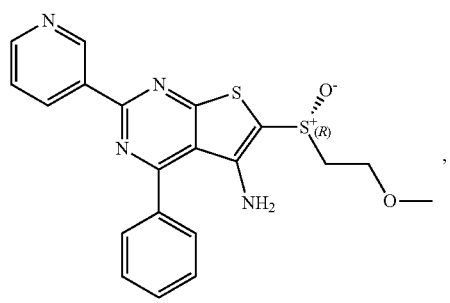
, -continued
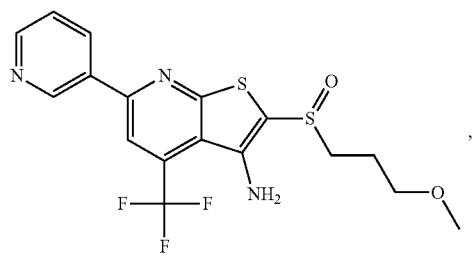
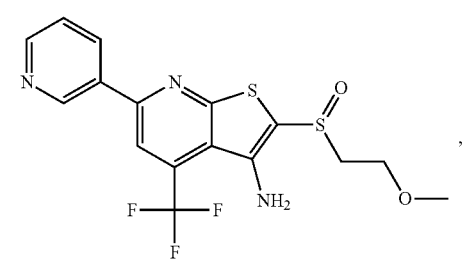
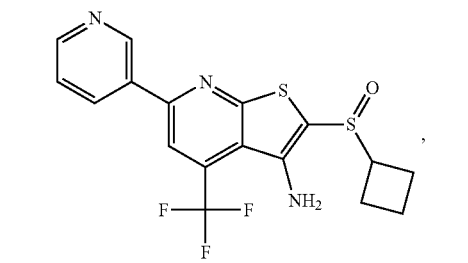
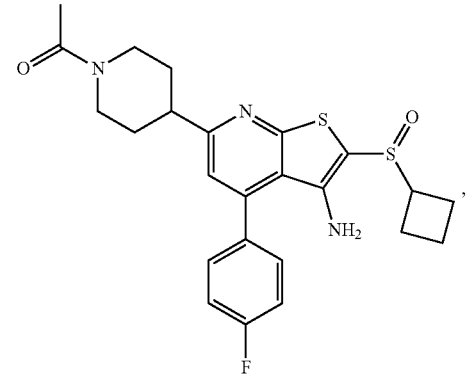
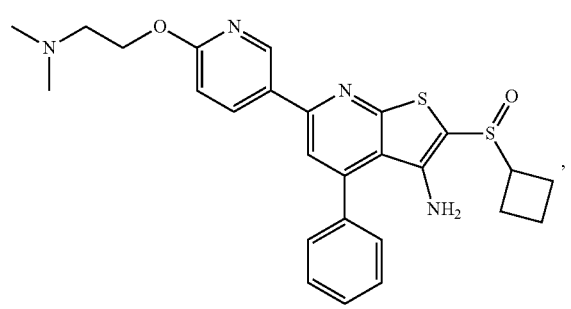
-continued
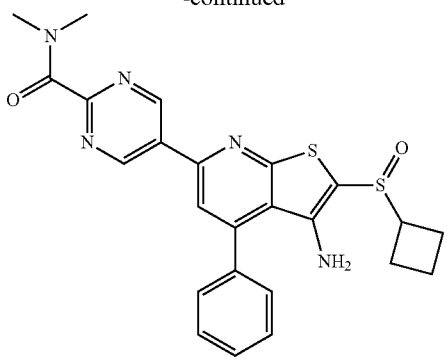
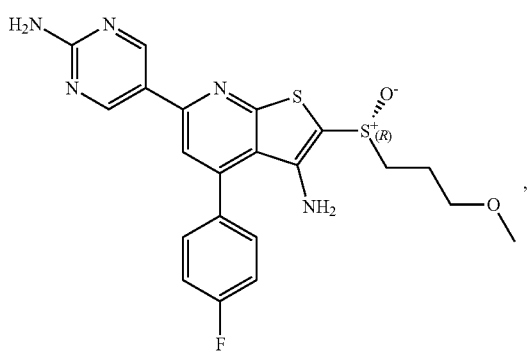
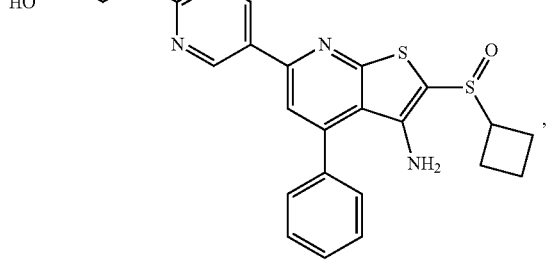
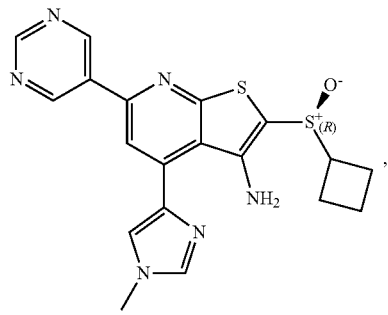
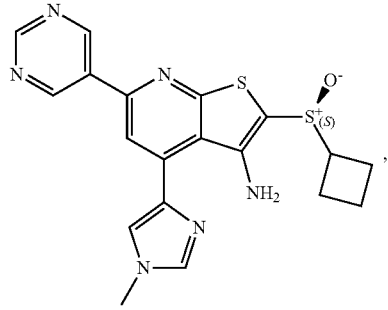

49
-continued
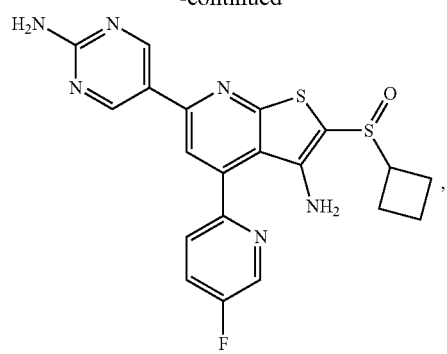
,
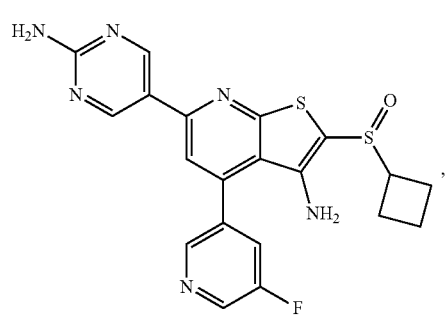
,
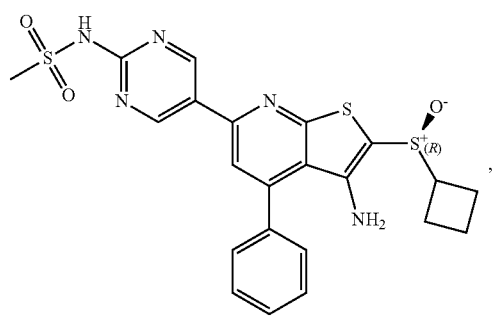
,
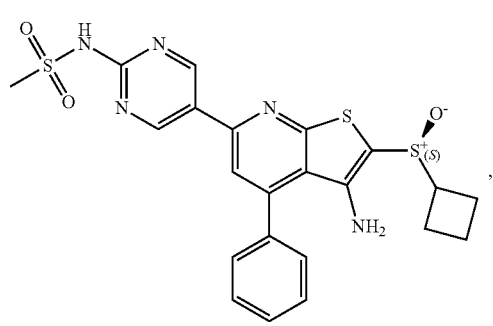
,
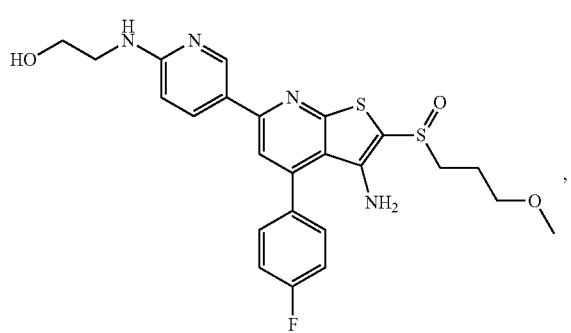
,
50
-continued
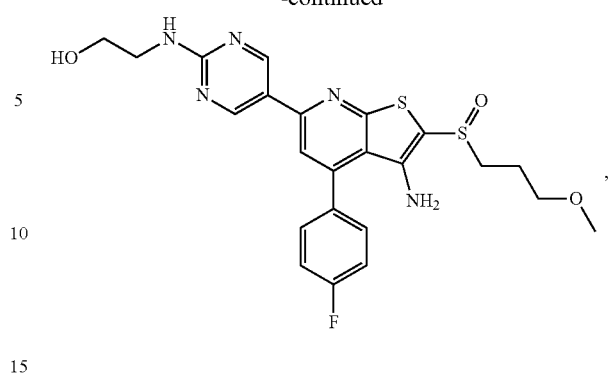
,
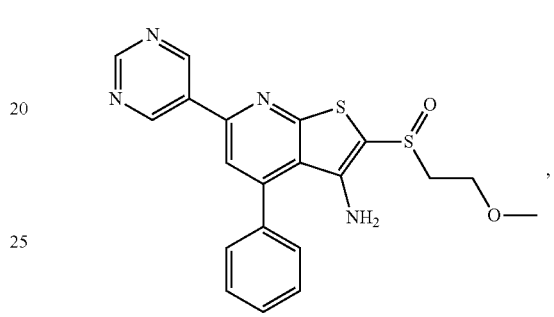
,
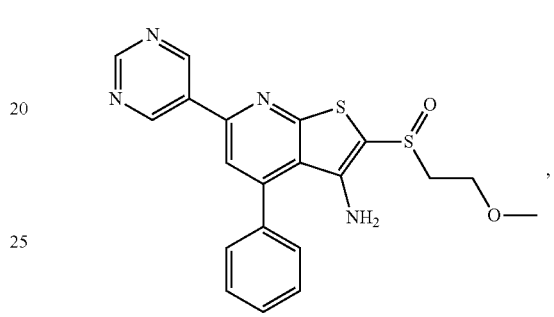
,
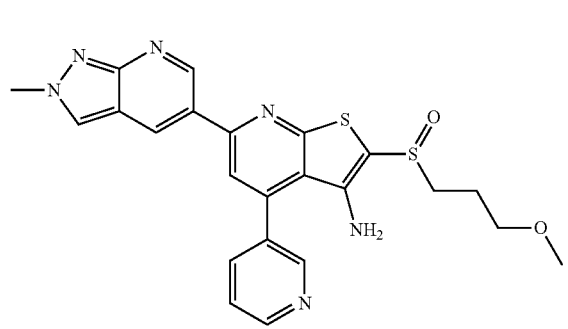
,
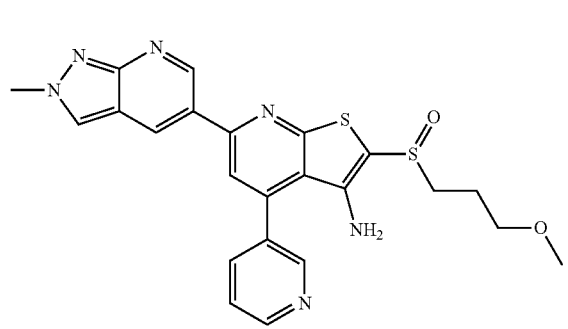
, 51
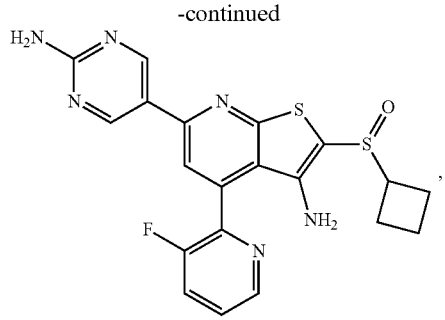
,
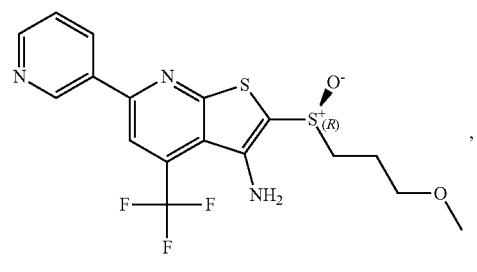
,
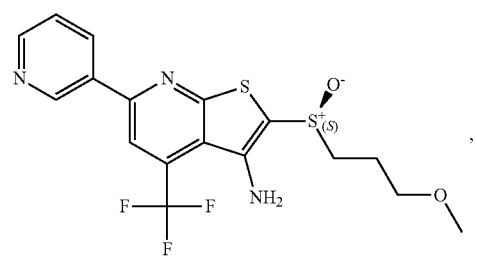
,
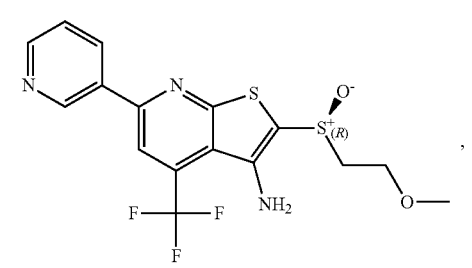
,
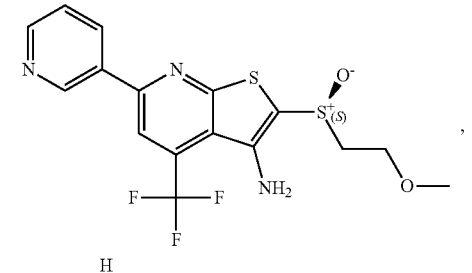
,
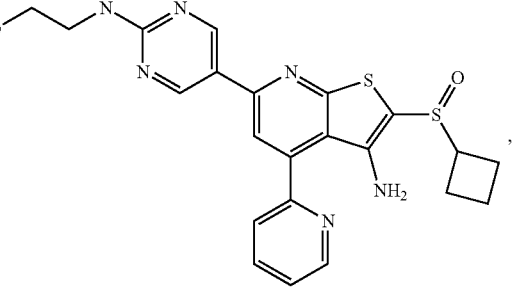
,
52
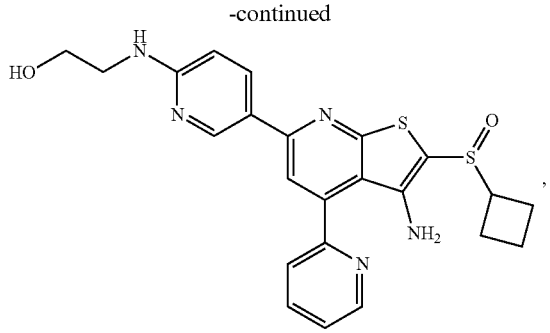
,
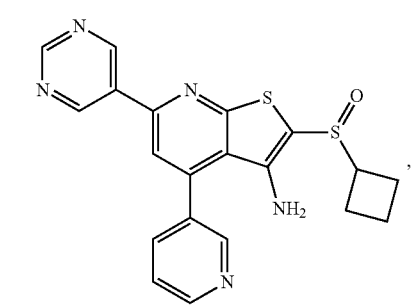
,
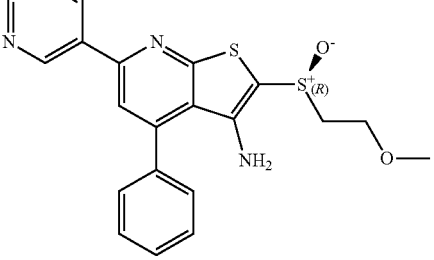
,
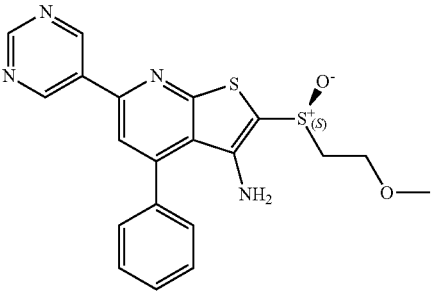
,
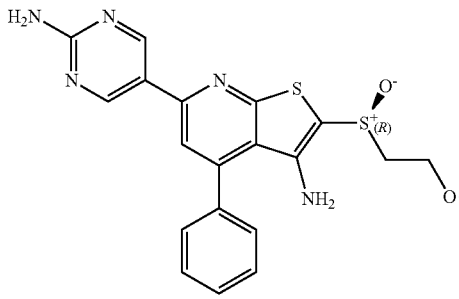
,

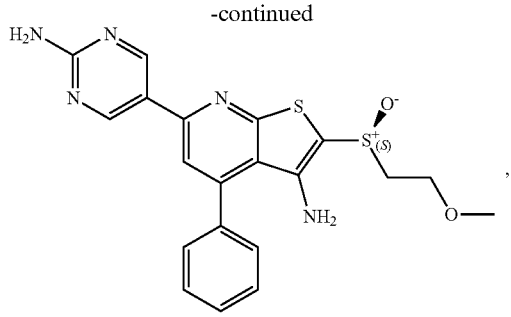
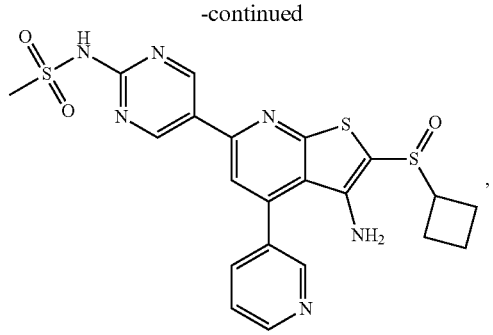
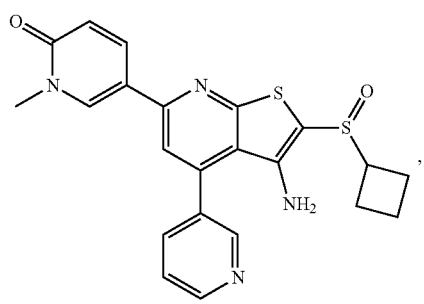
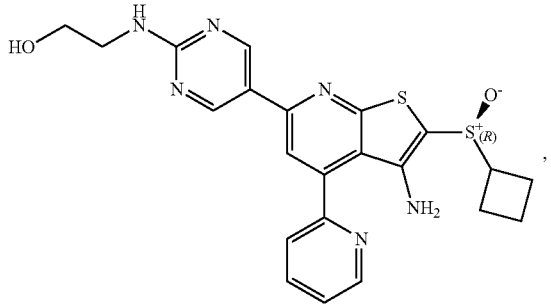
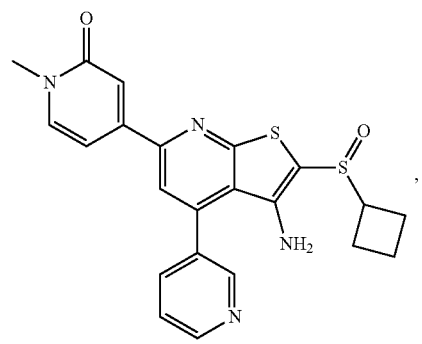
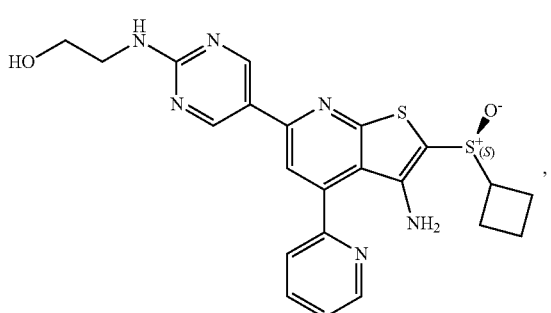
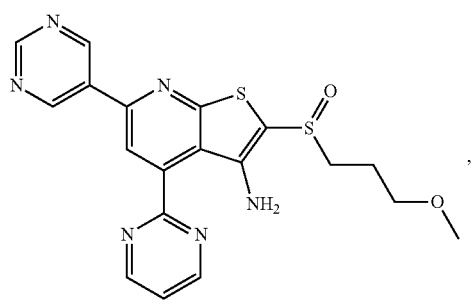
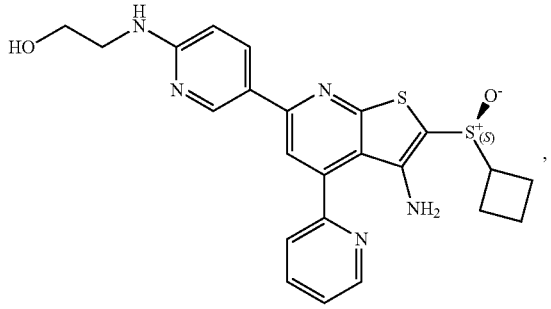
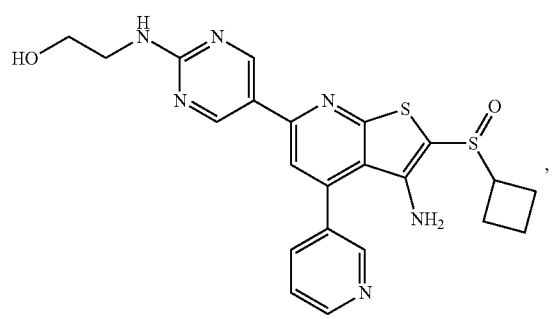
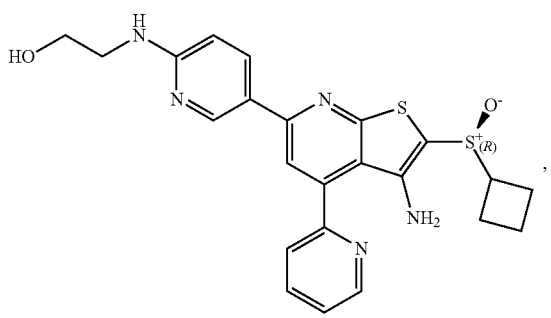

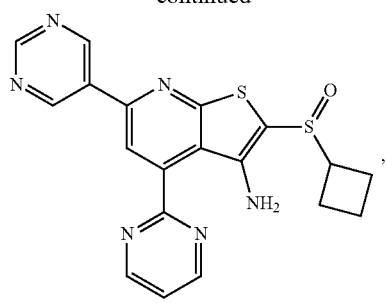
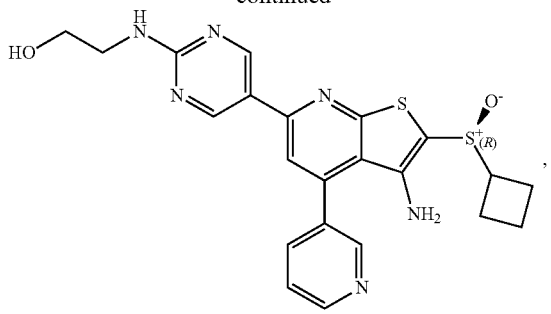
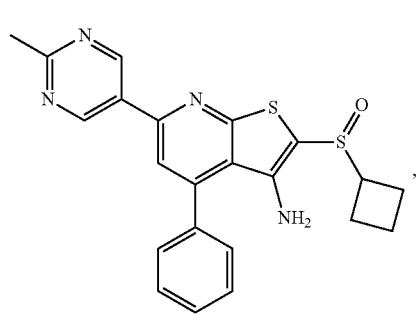
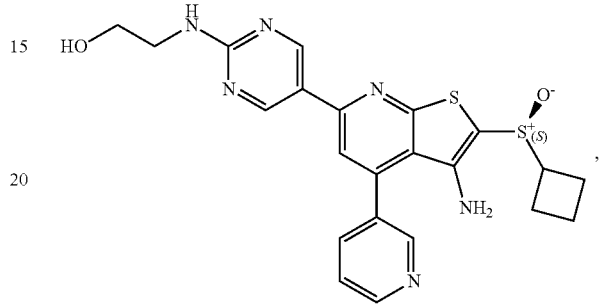
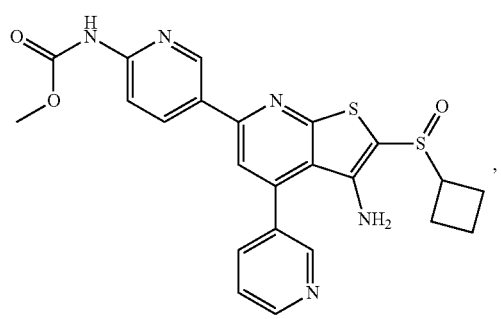
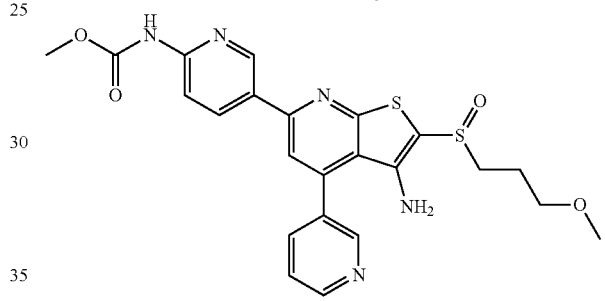
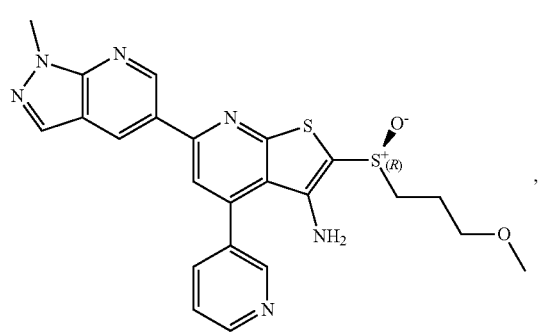
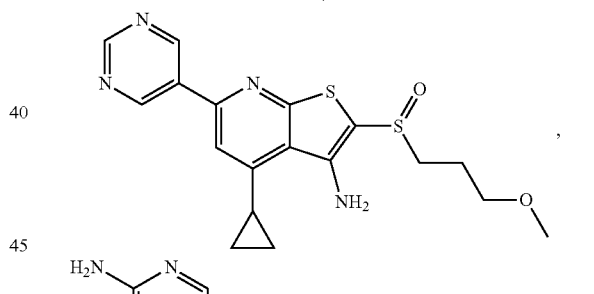
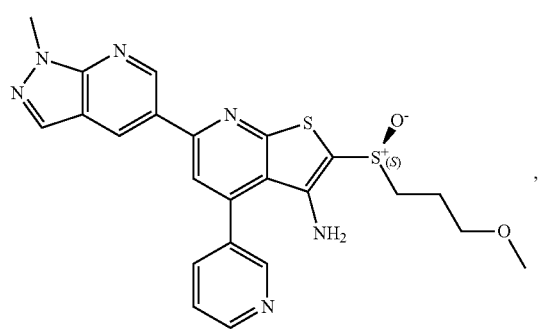
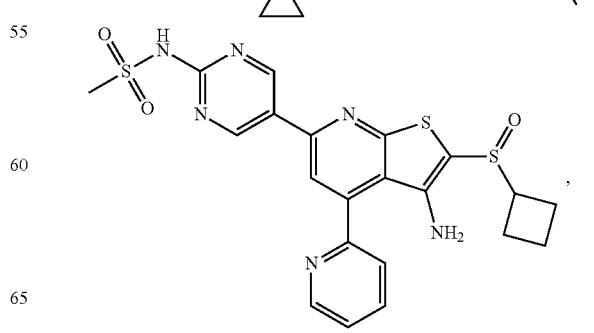

57
-continued
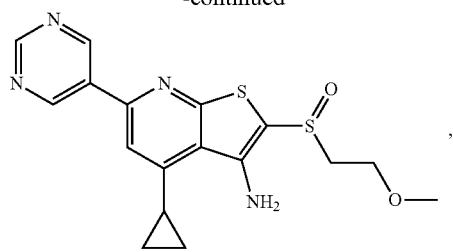
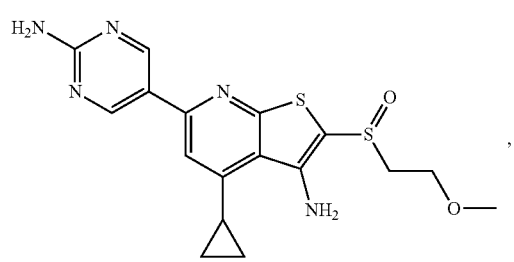
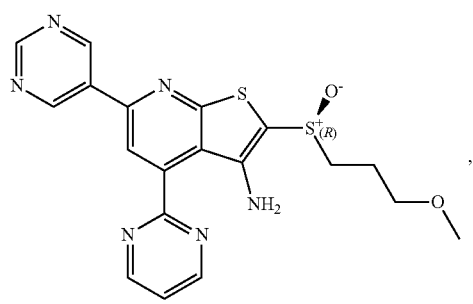
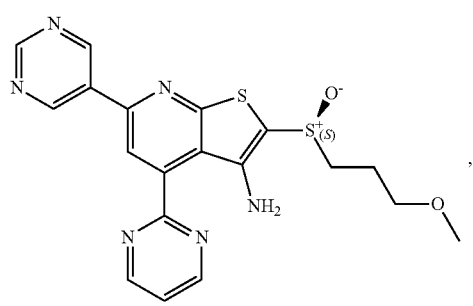
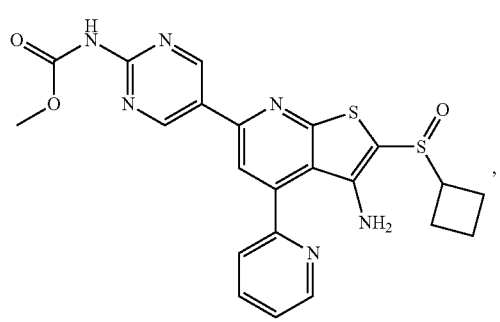
58
-continued
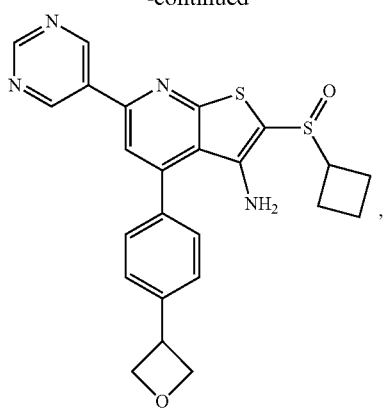
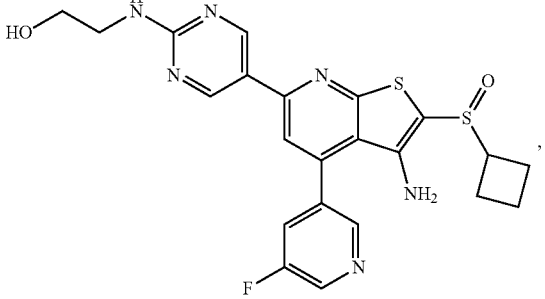
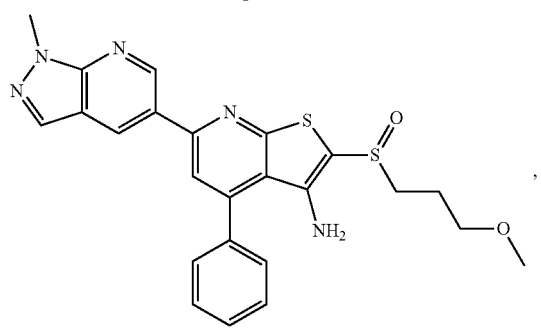
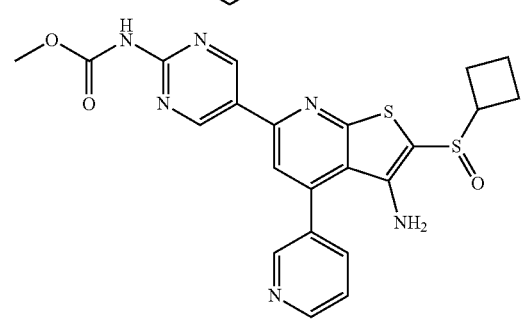
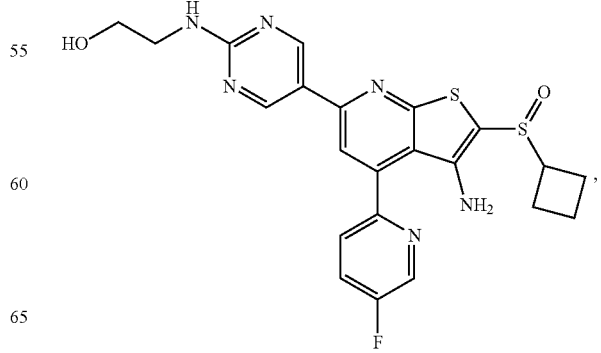

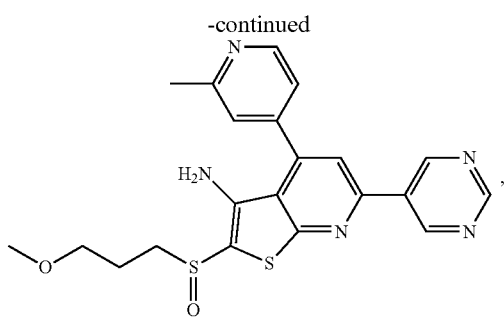
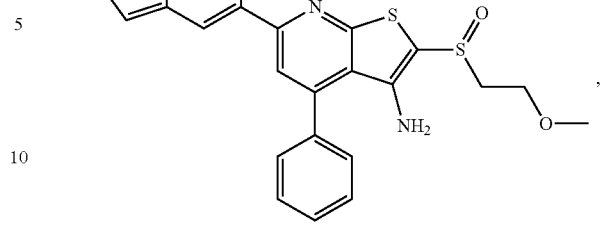
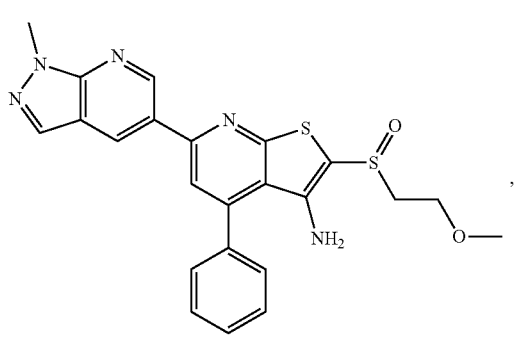
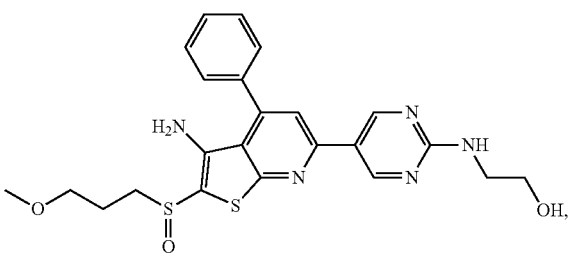
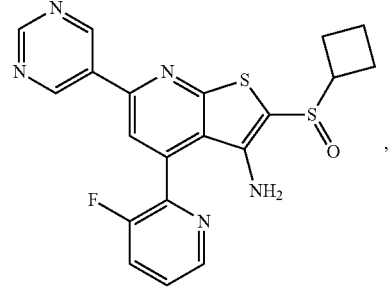
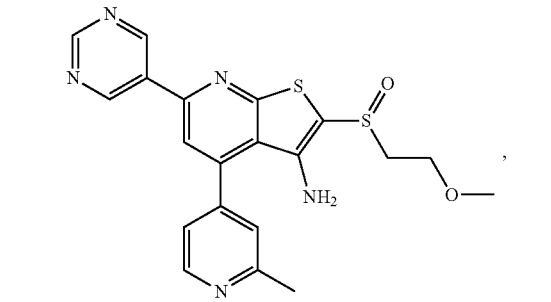
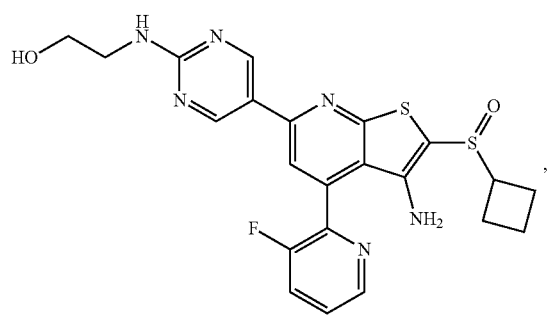
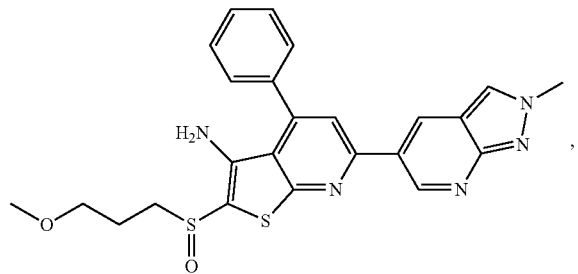
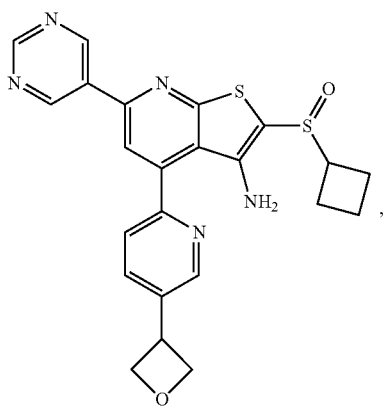

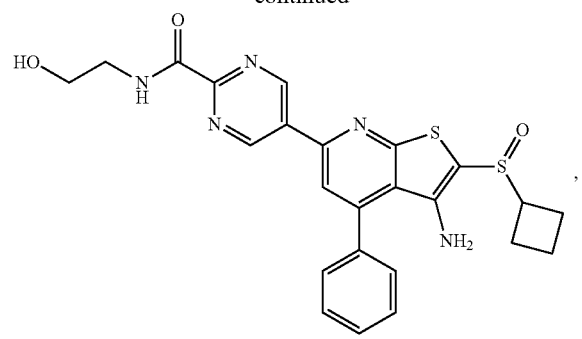
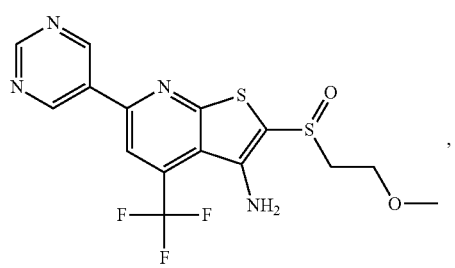
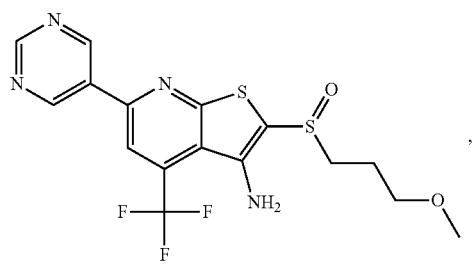
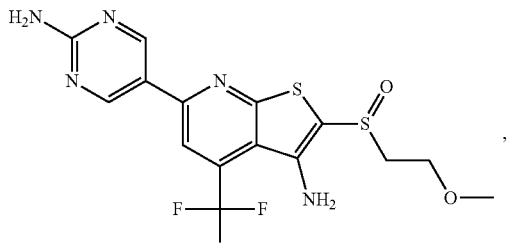
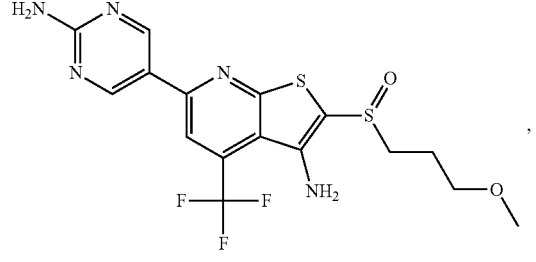
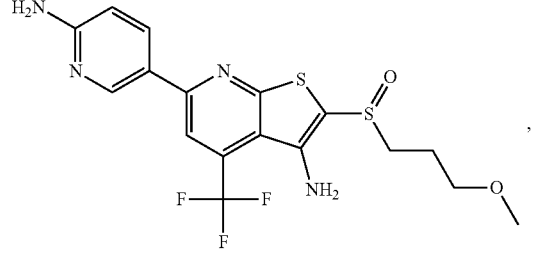
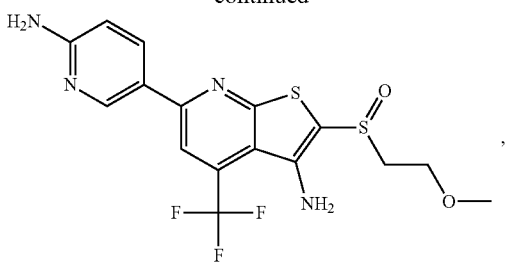
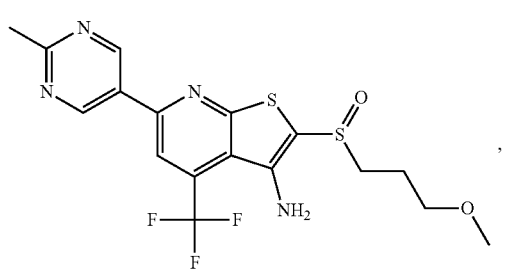
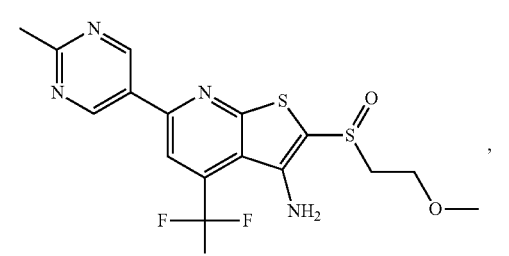
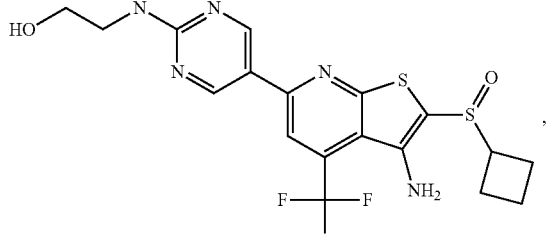
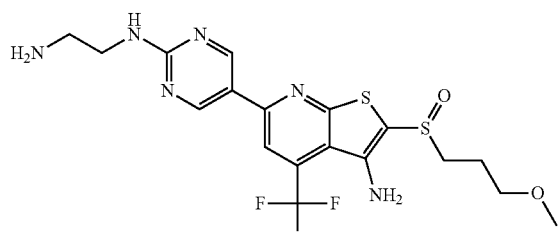
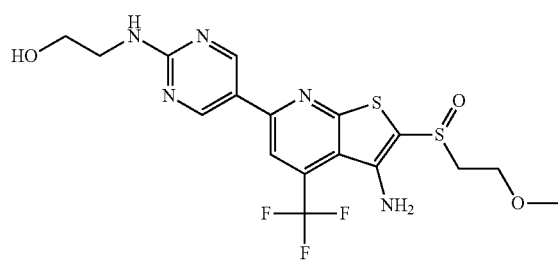

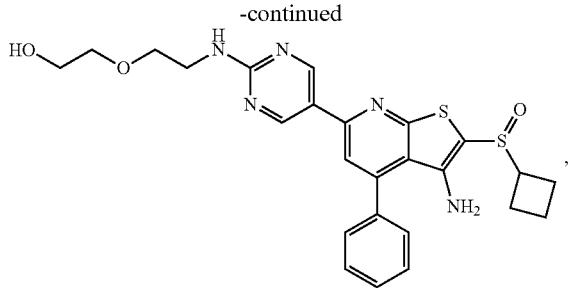
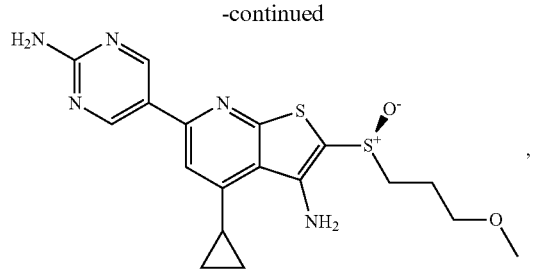
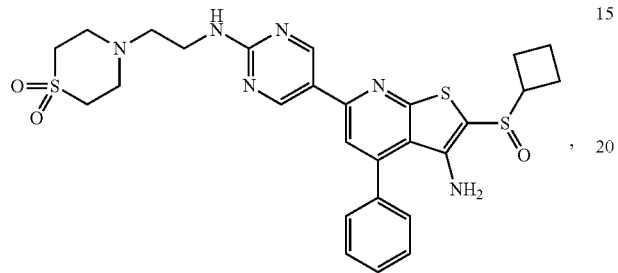
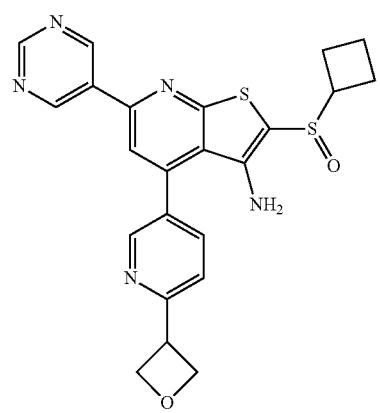
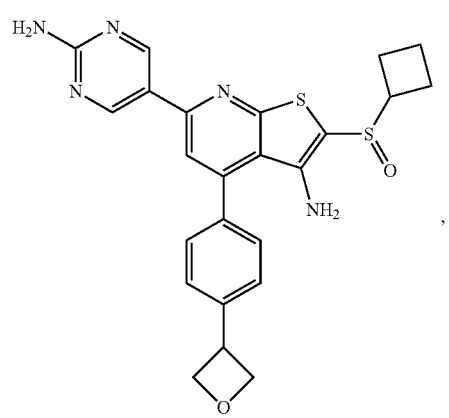
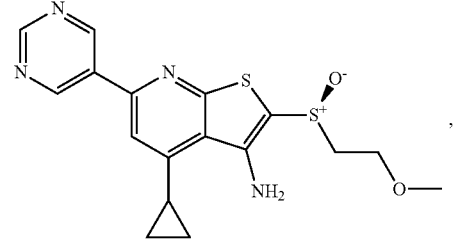
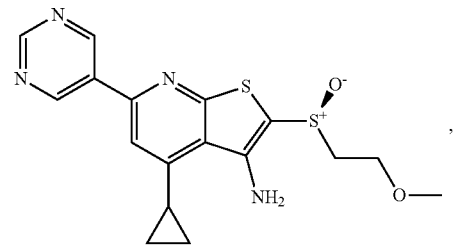
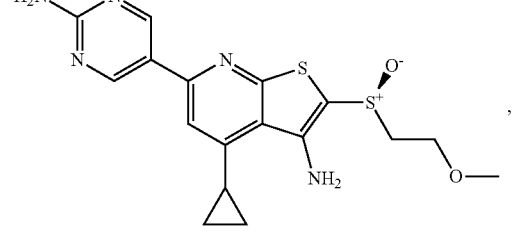
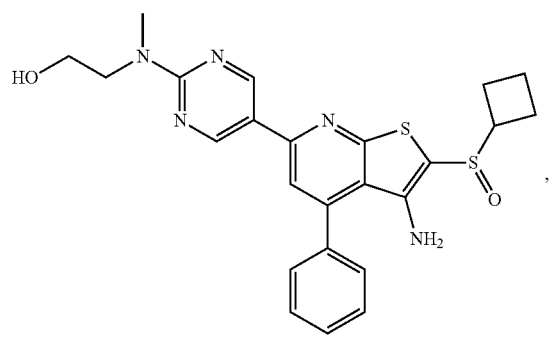
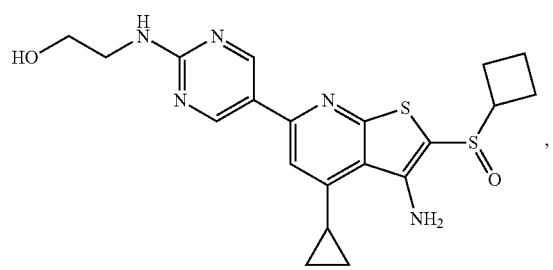
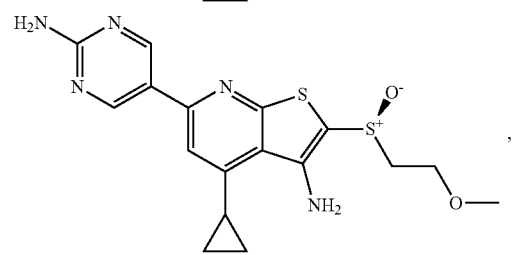

65
-continued
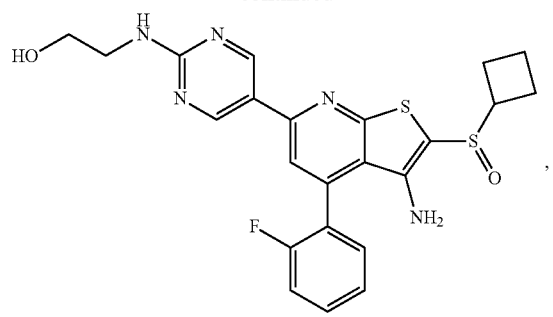
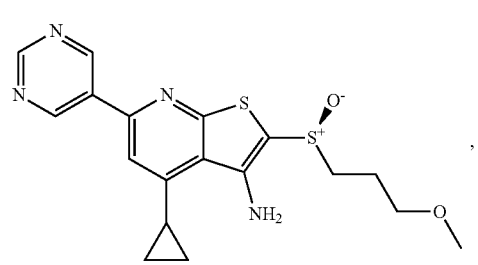
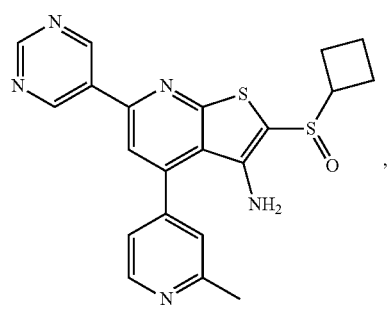
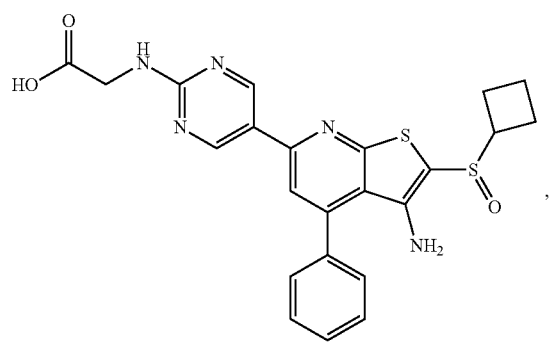
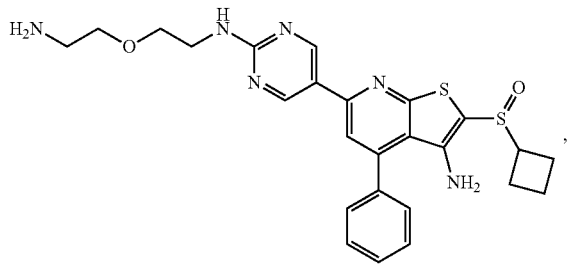
66
-continued
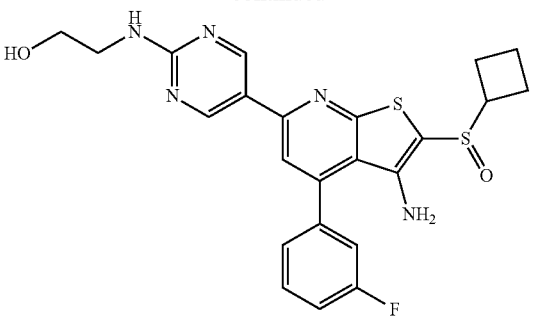
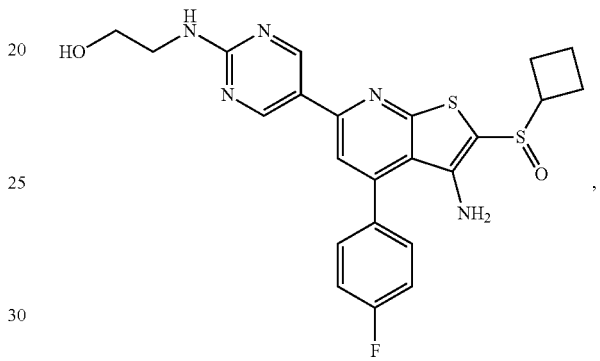
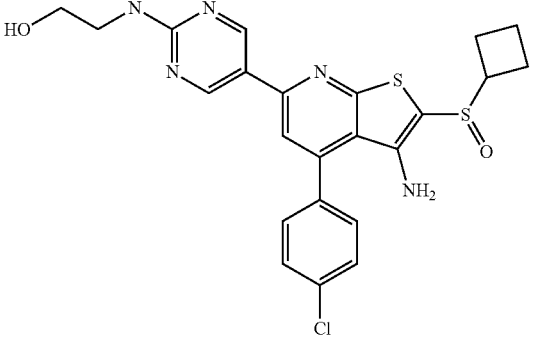
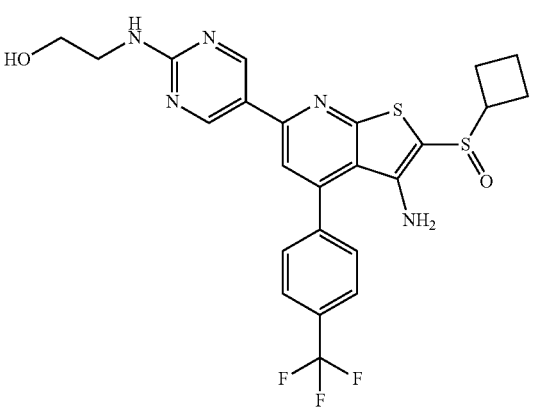

67
-continued
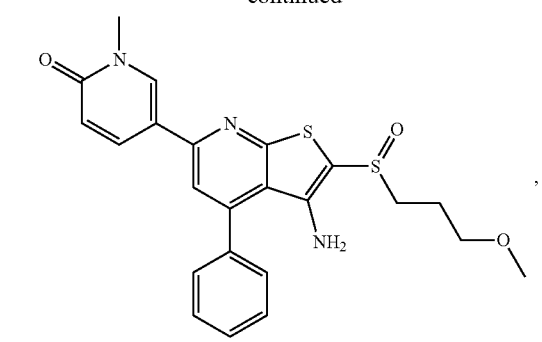
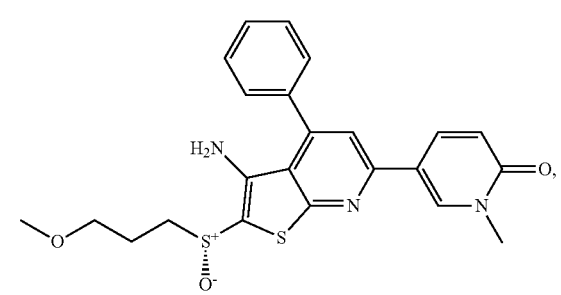
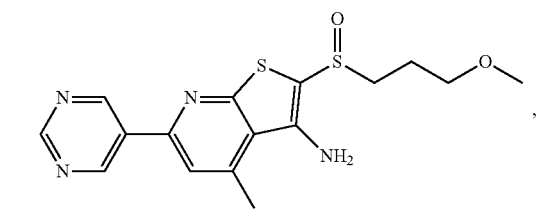
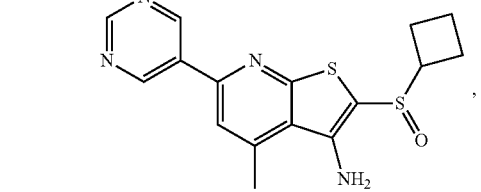
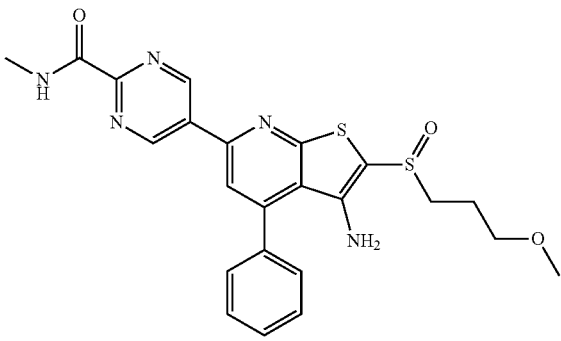
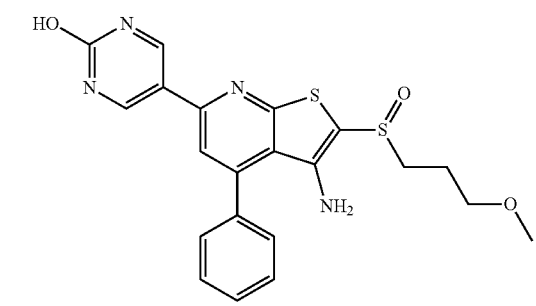
68
-continued
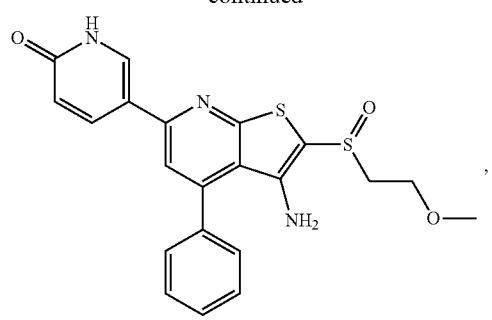
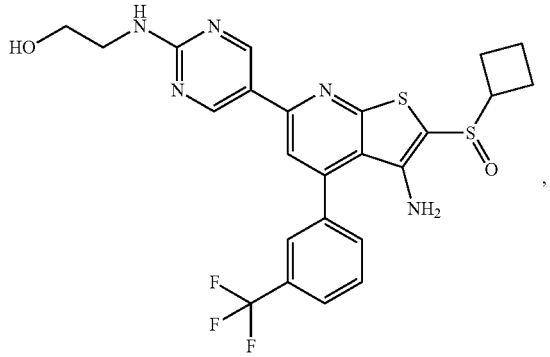
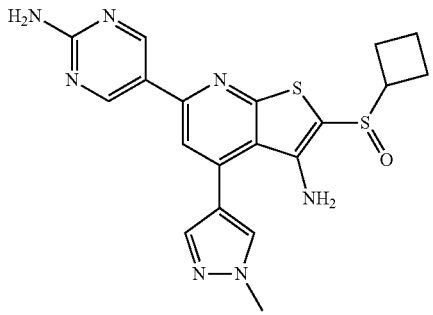
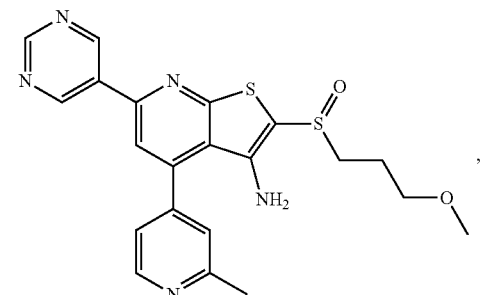
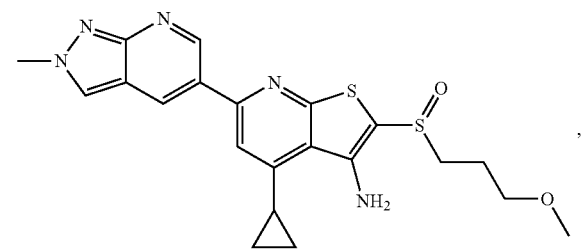

69
-continued
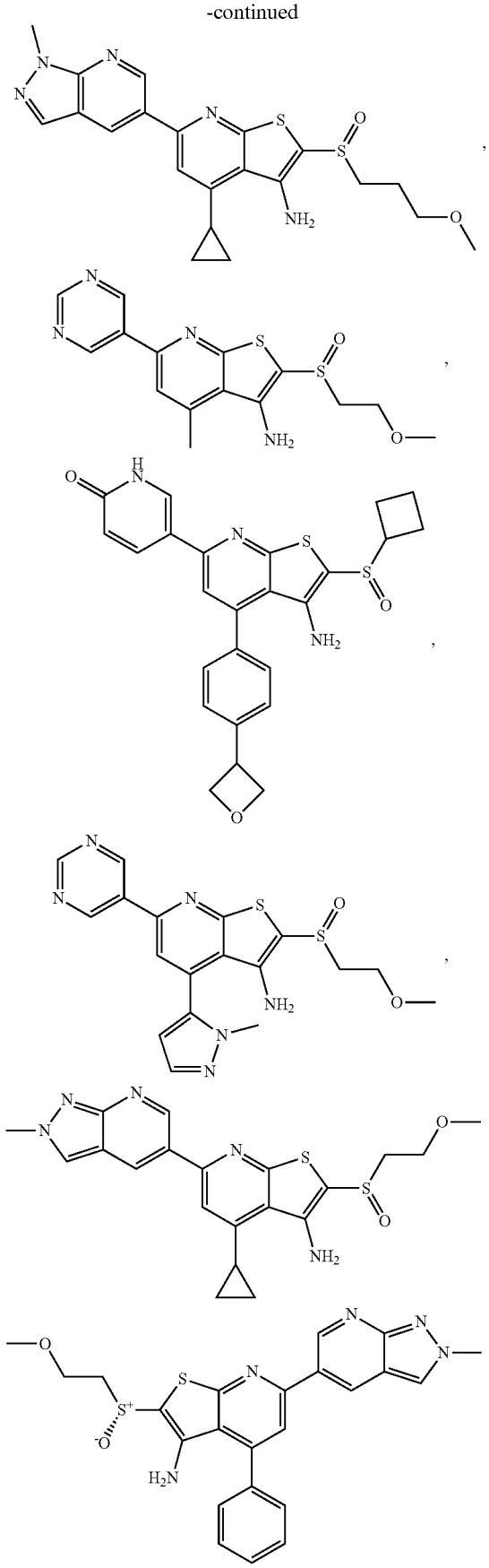
70
-continued
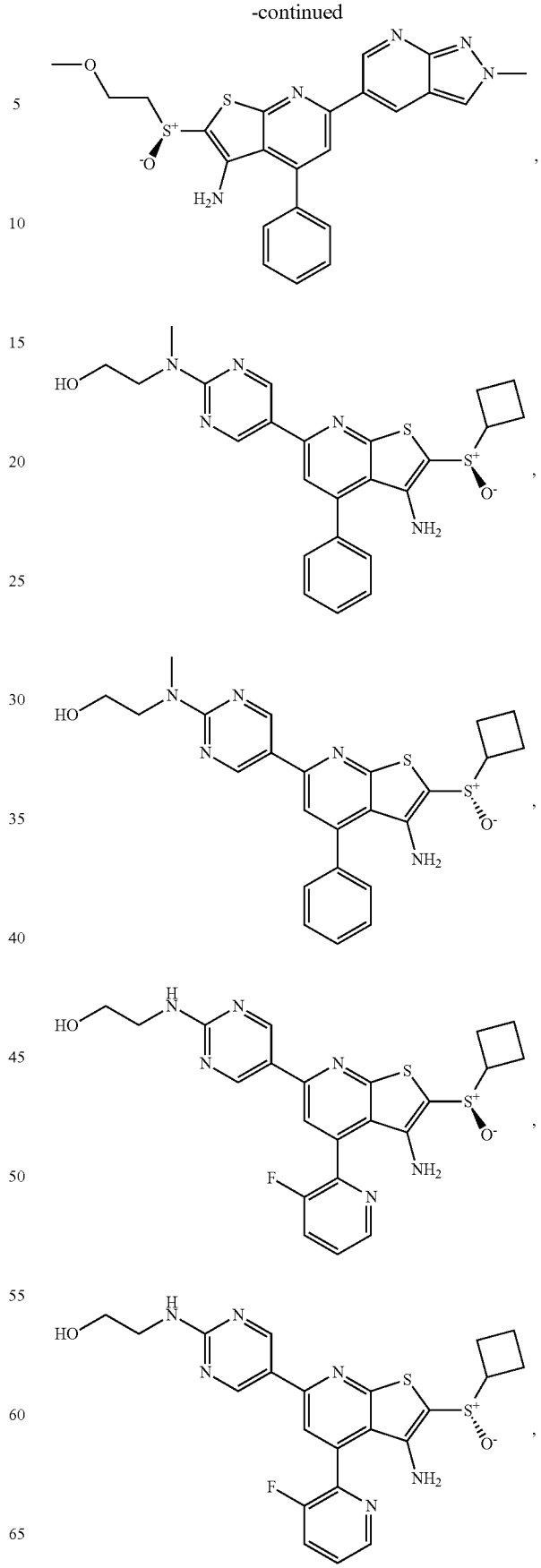

71
-continued
72
-continued
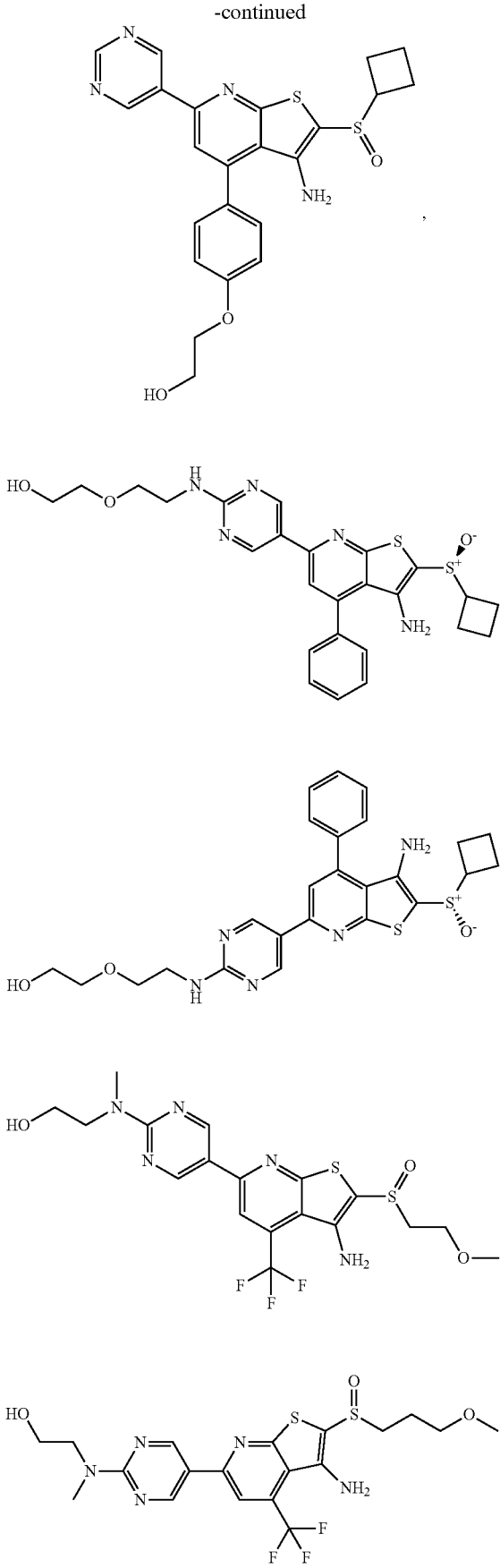
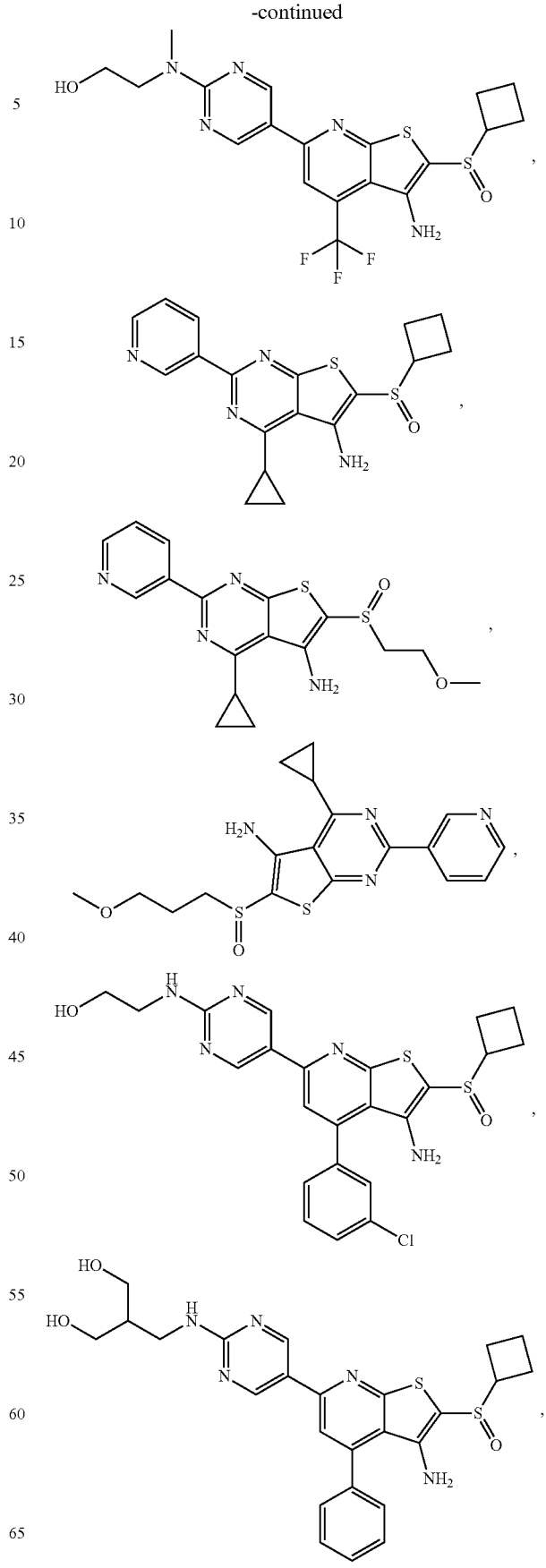

73
-continued
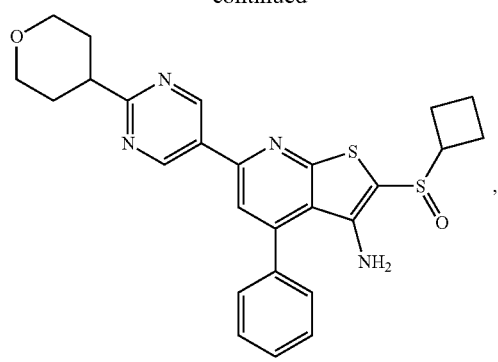,
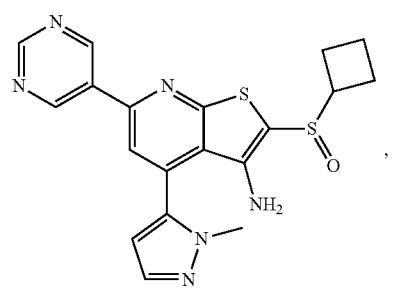,
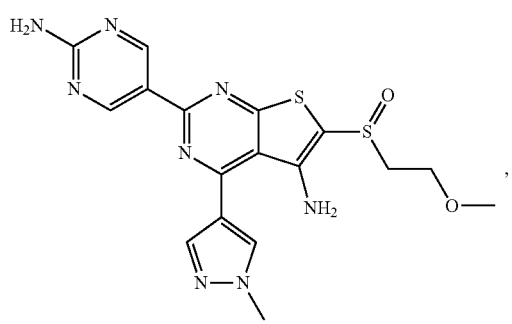,
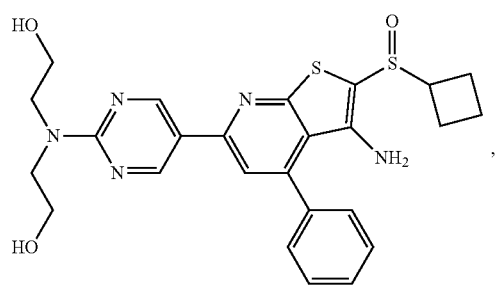,
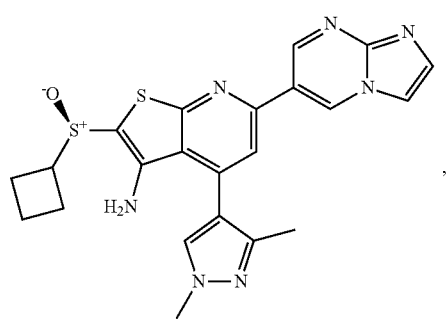,
74
-continued
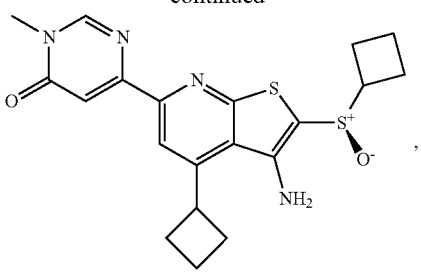,
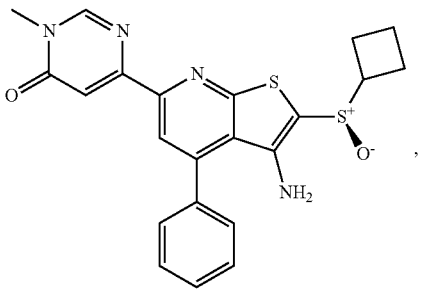,
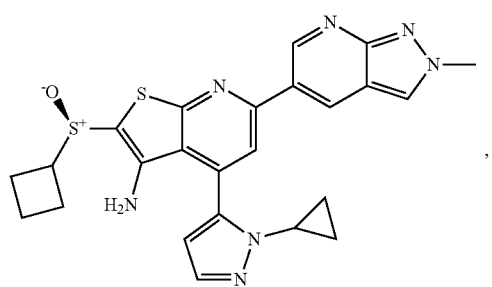,
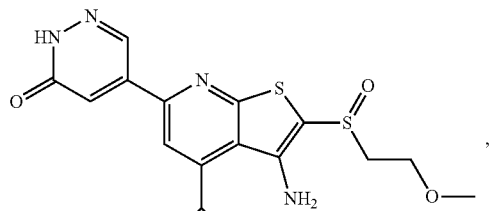,
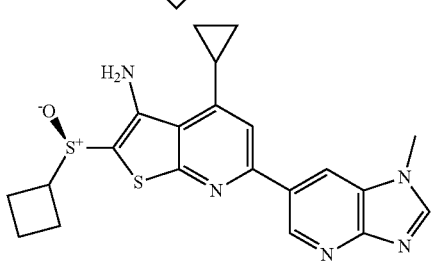,
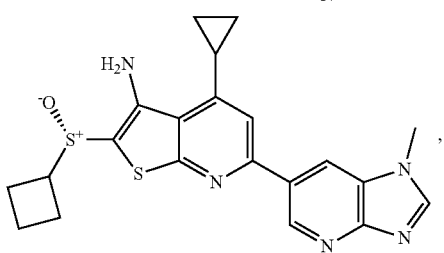, 75
-continued
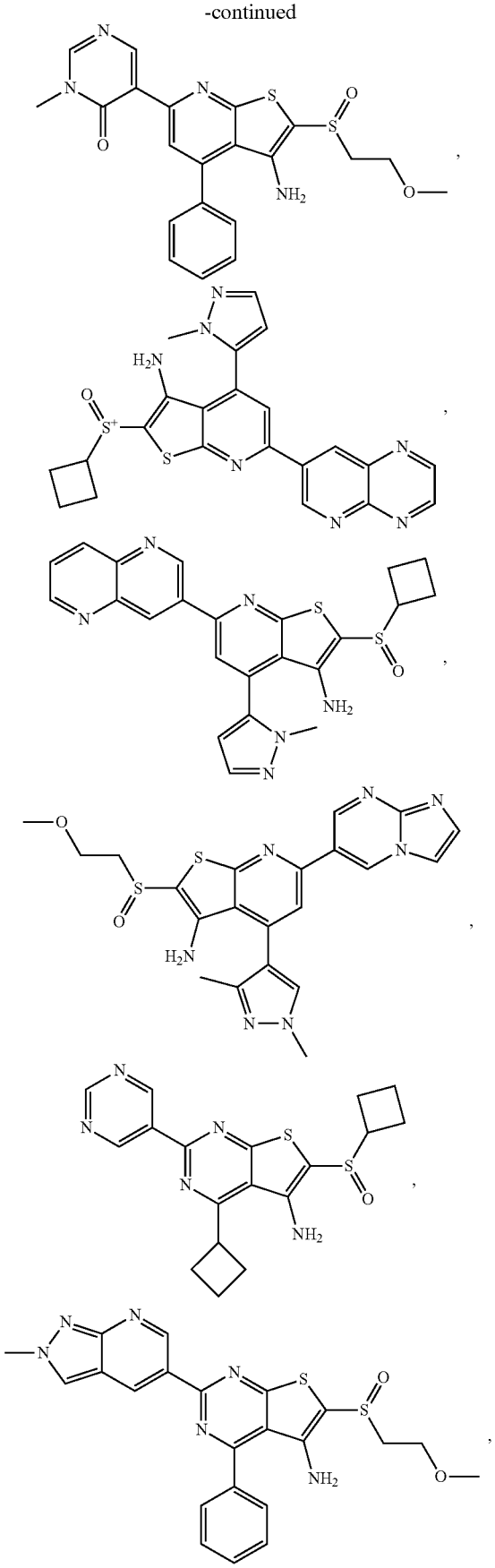
76
-continued
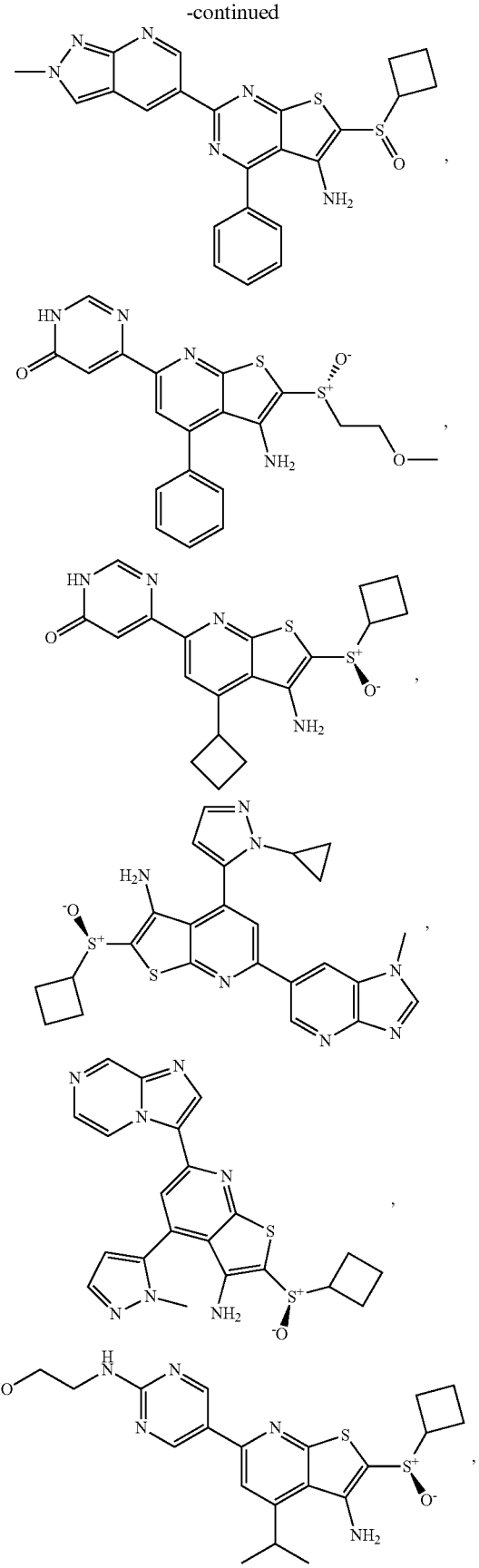

and molecules numbers 198-434 in Table 1, or pharmaceutically acceptable salts thereof, a tautomoers thereof, and a solvates thereof.

In other embodiments, the 15-PGDH inhibitor is selected from compounds disclosed in any one of Examples 1-323, or pharmaceutically acceptable salts thereof, a tautomoers thereof, and a solvates thereof.

In some embodiments, the 15-PGDH inhibitor having formula I, IA, II, III, IV, V, VI, VII, or VIII (i.e., formula I-VIII) is not a compound having the following formula:

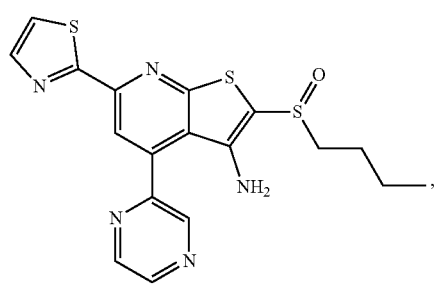

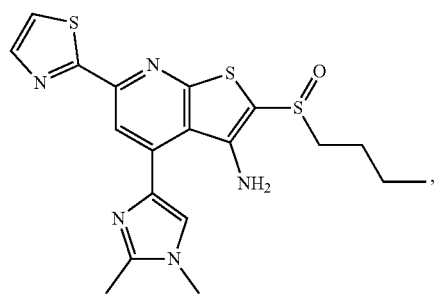

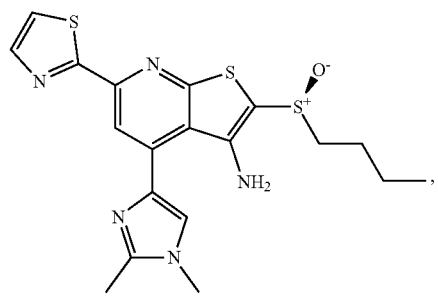

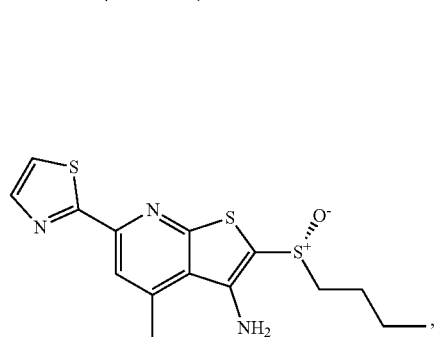

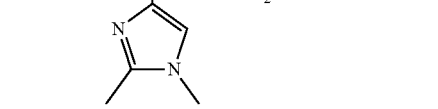

-continued

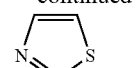

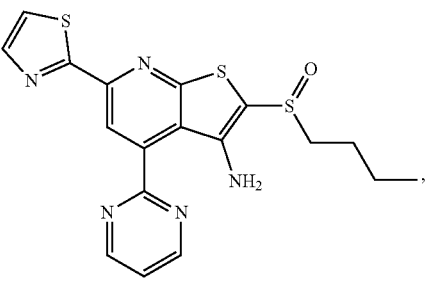

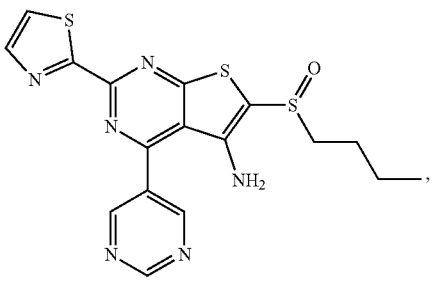

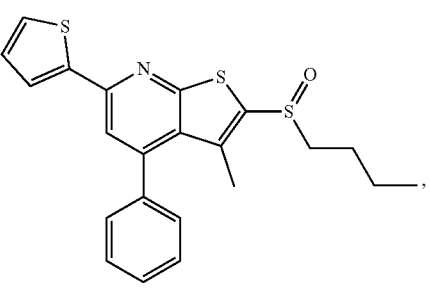

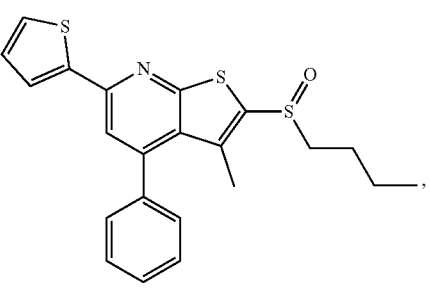

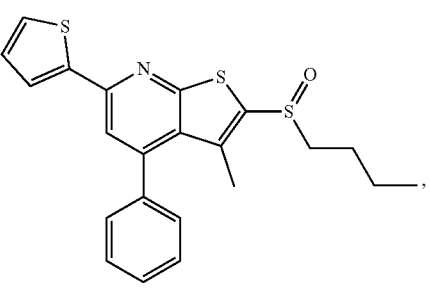

79
-continued
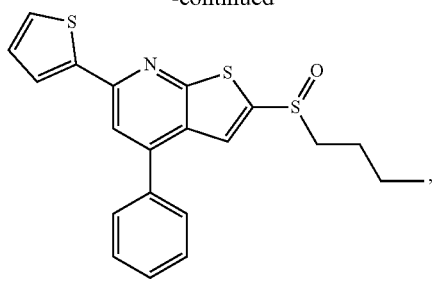
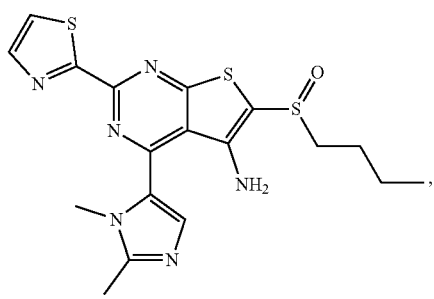
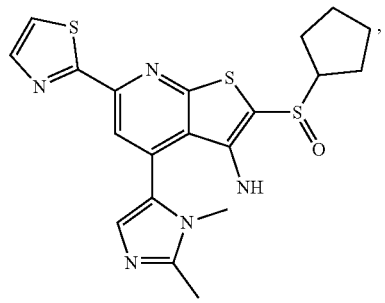
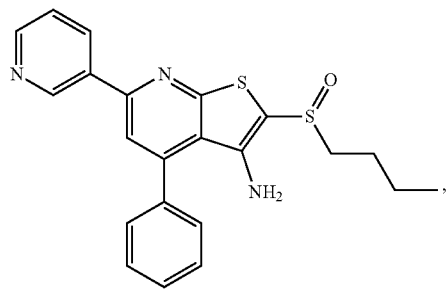
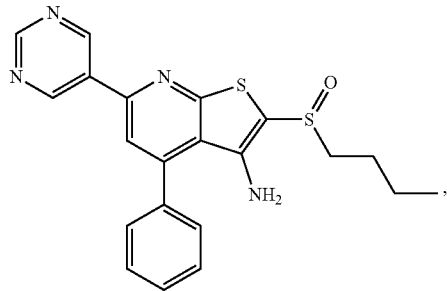
80
-continued
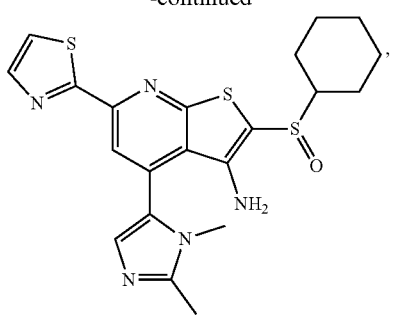
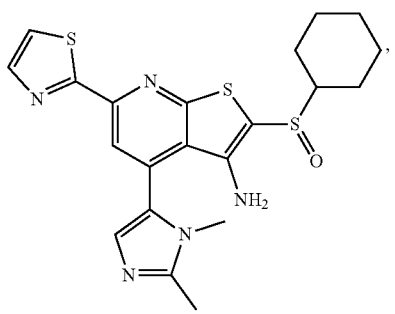
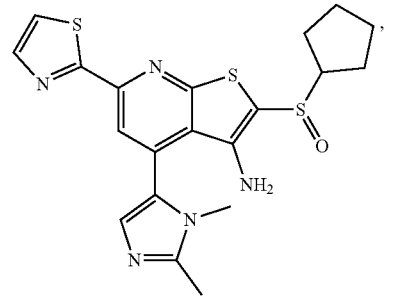
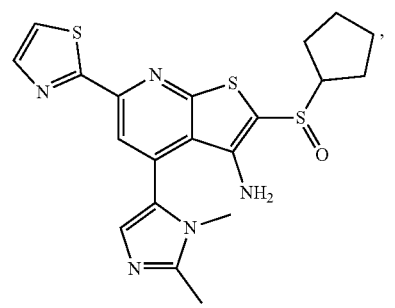
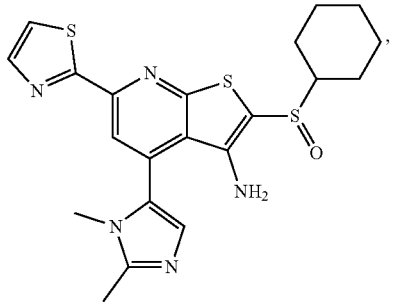

81
-continued
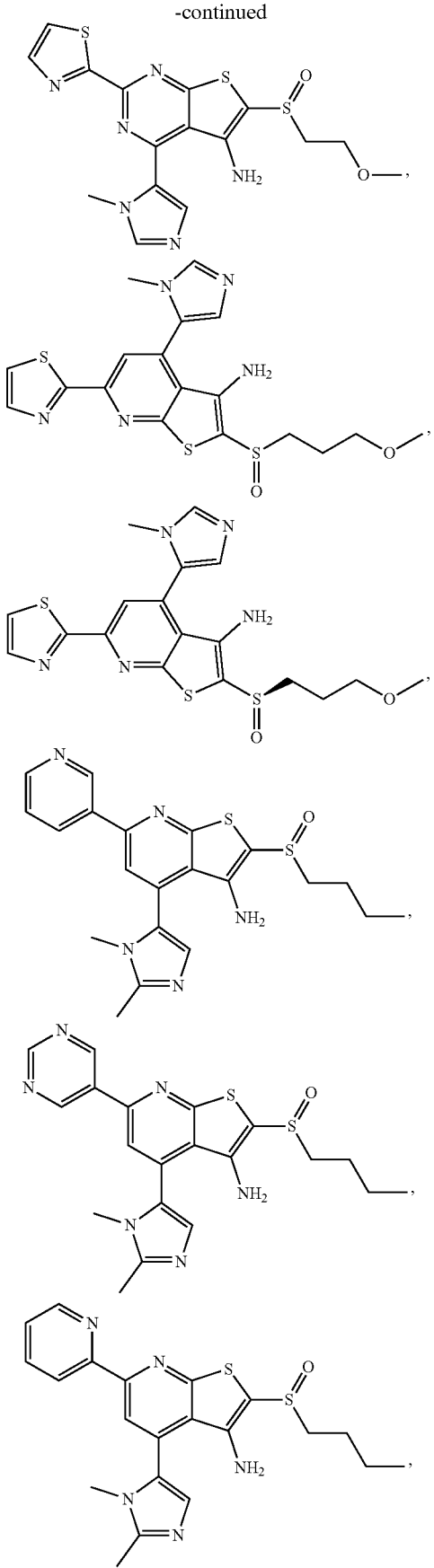
82
-continued
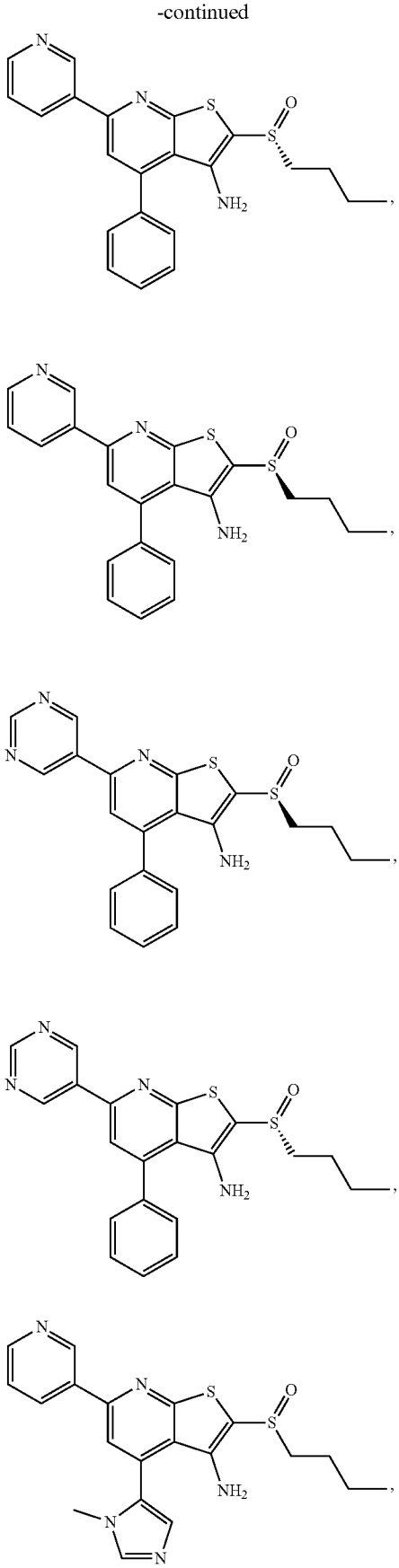

83
-continued
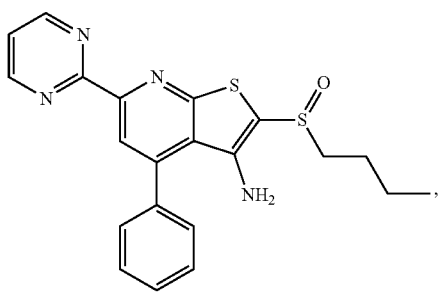
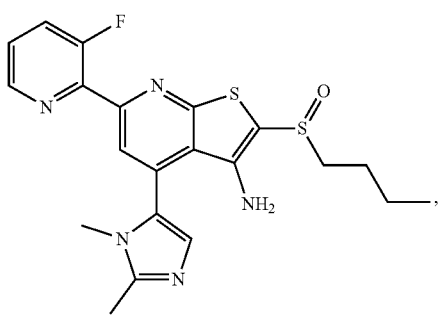
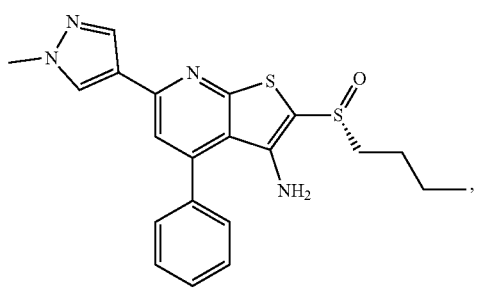
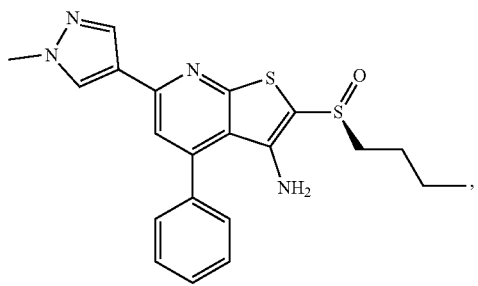
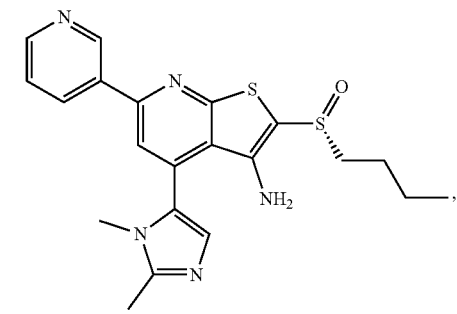
84
-continued
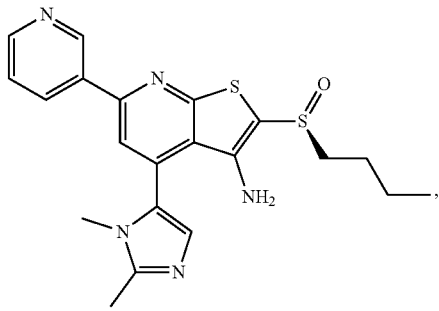
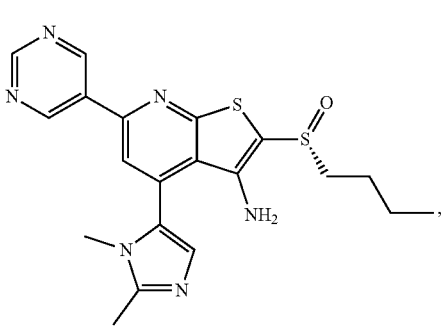
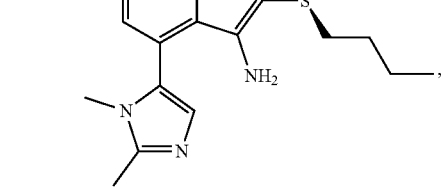
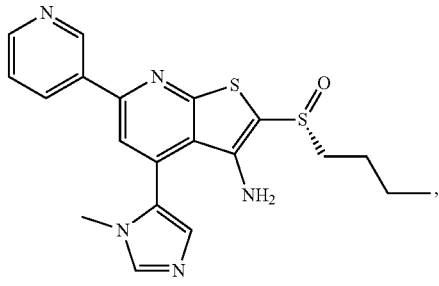
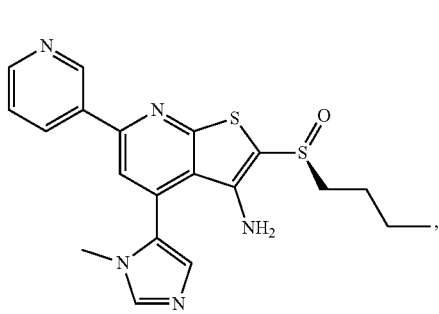

85
-continued
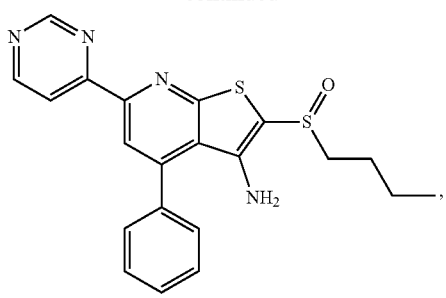
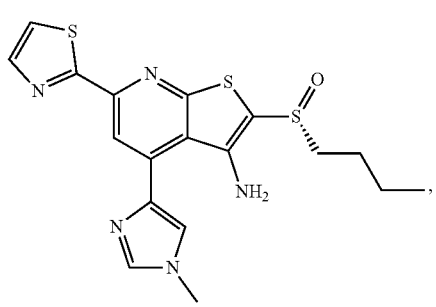
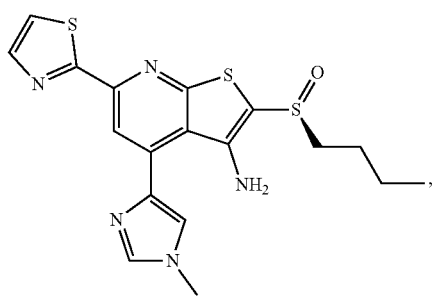
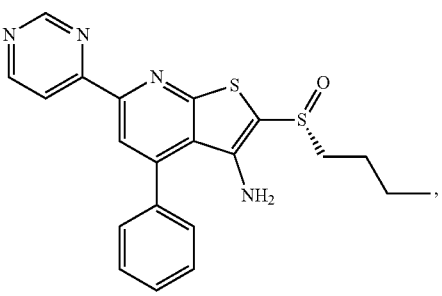
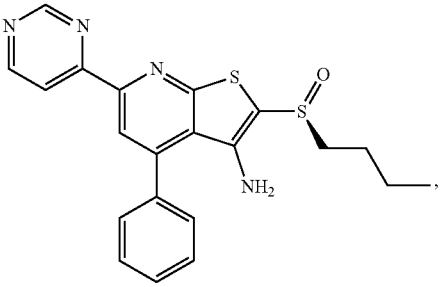
86
-continued
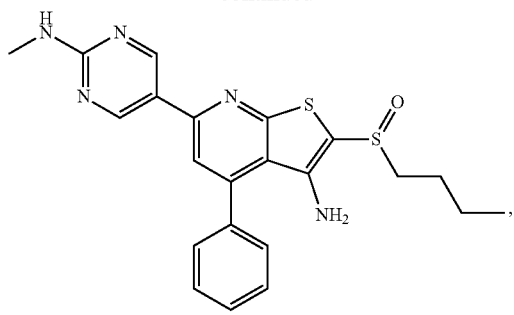
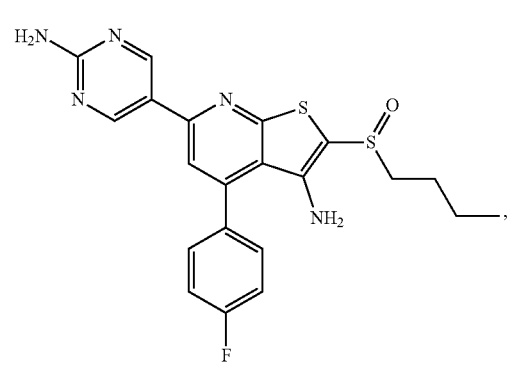
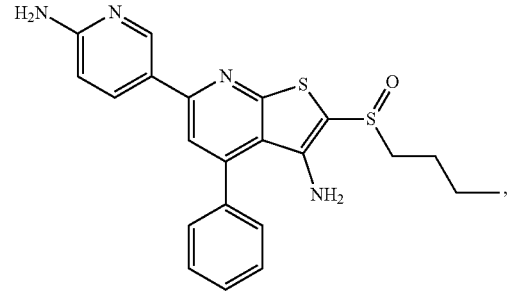
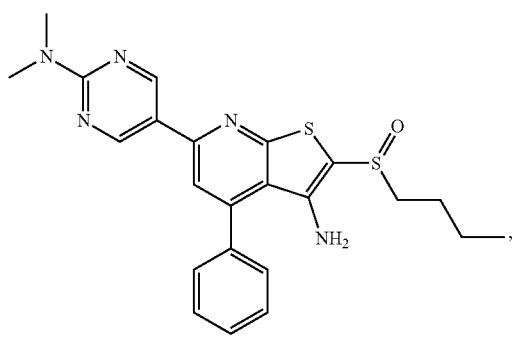
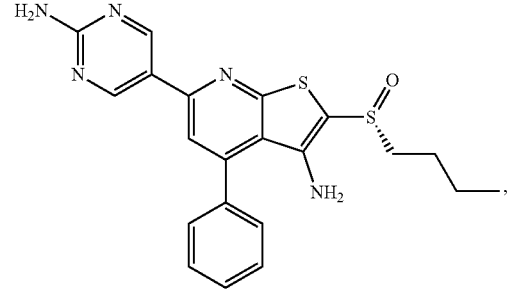

87
-continued
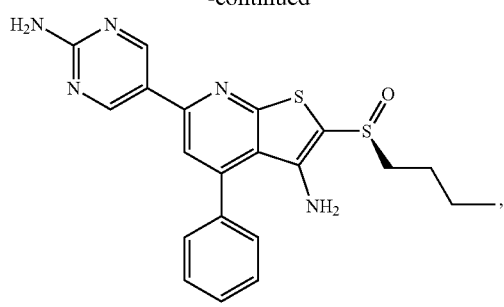
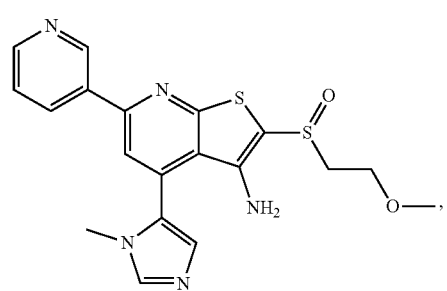
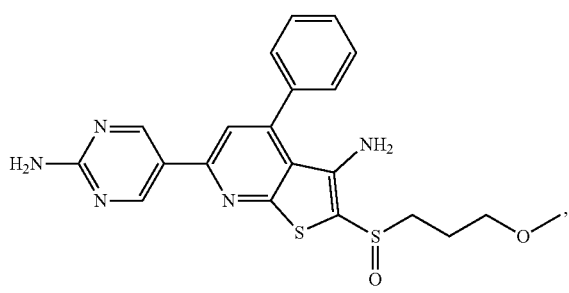
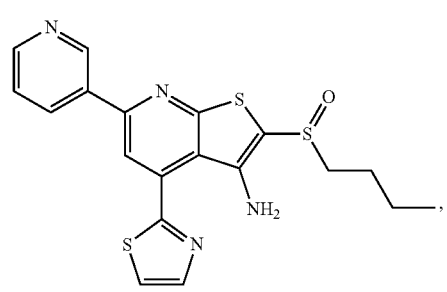
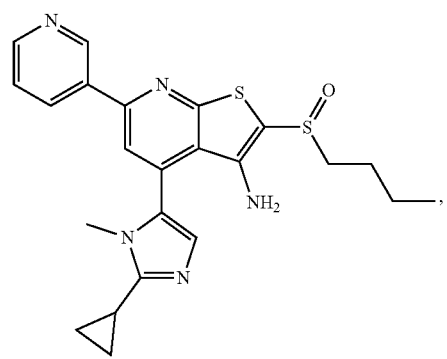
88
-continued
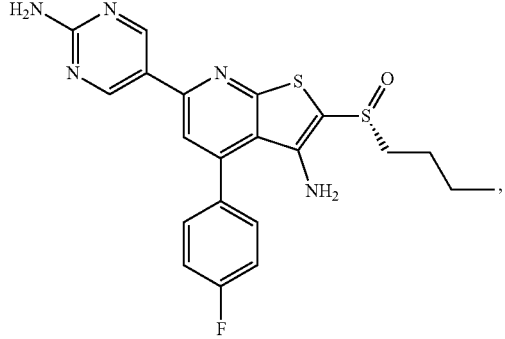
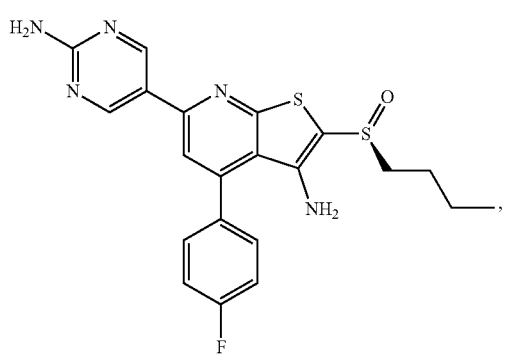
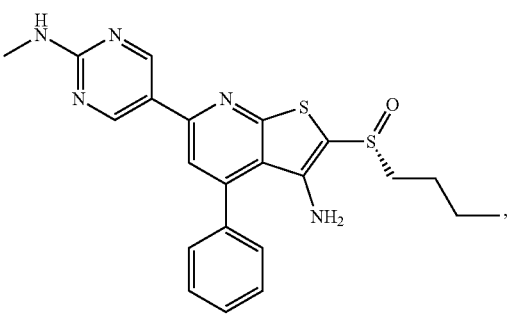
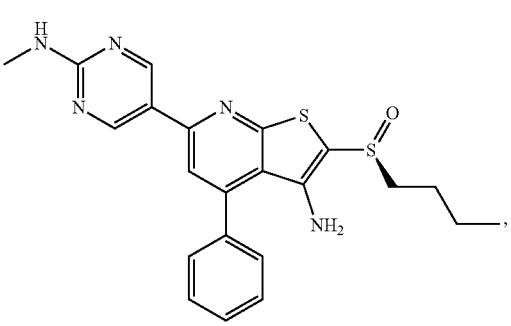
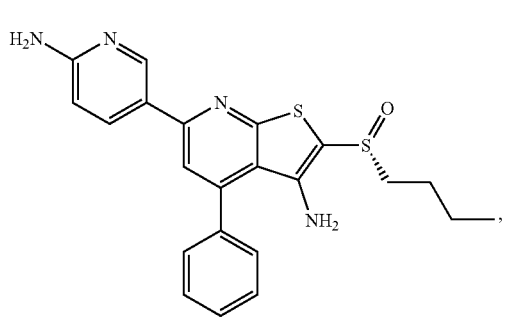

89
-continued
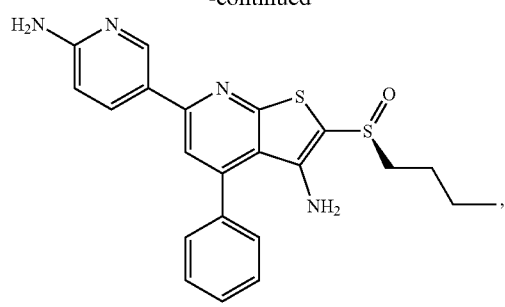
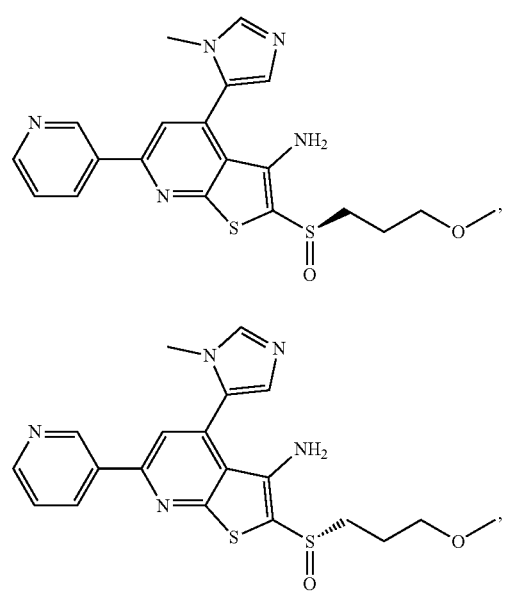
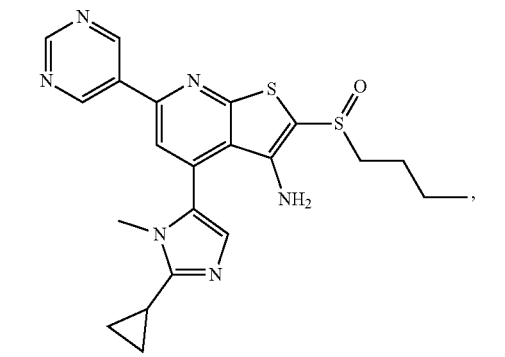
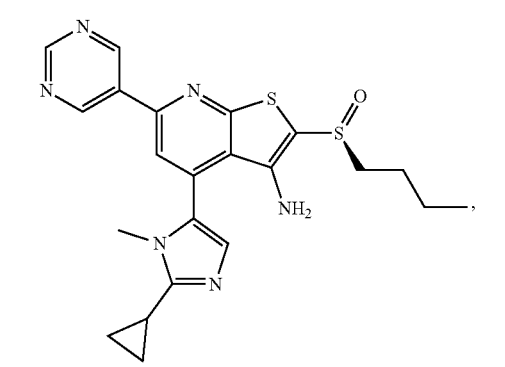
90
-continued
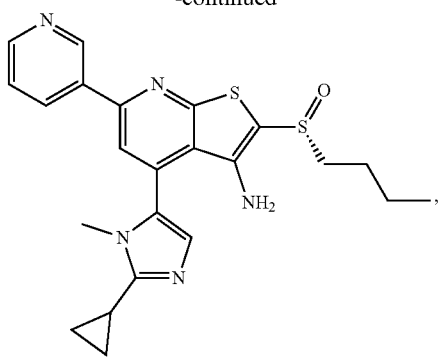
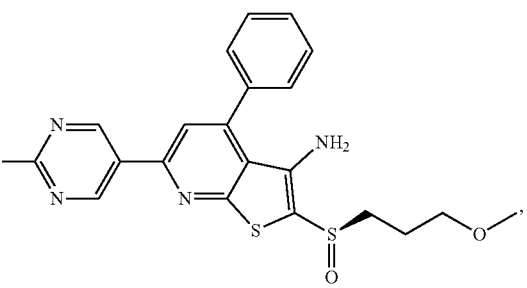
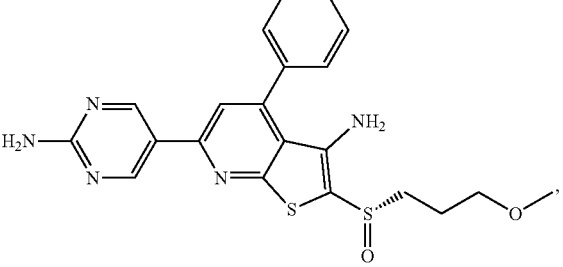
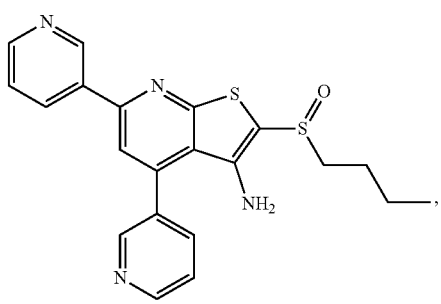
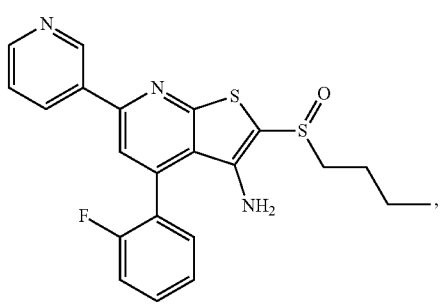

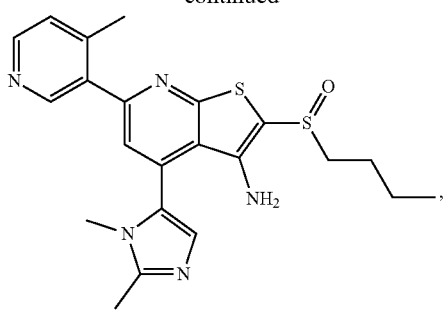
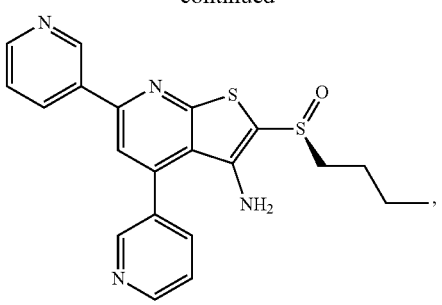
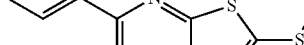
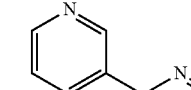

93
-continued
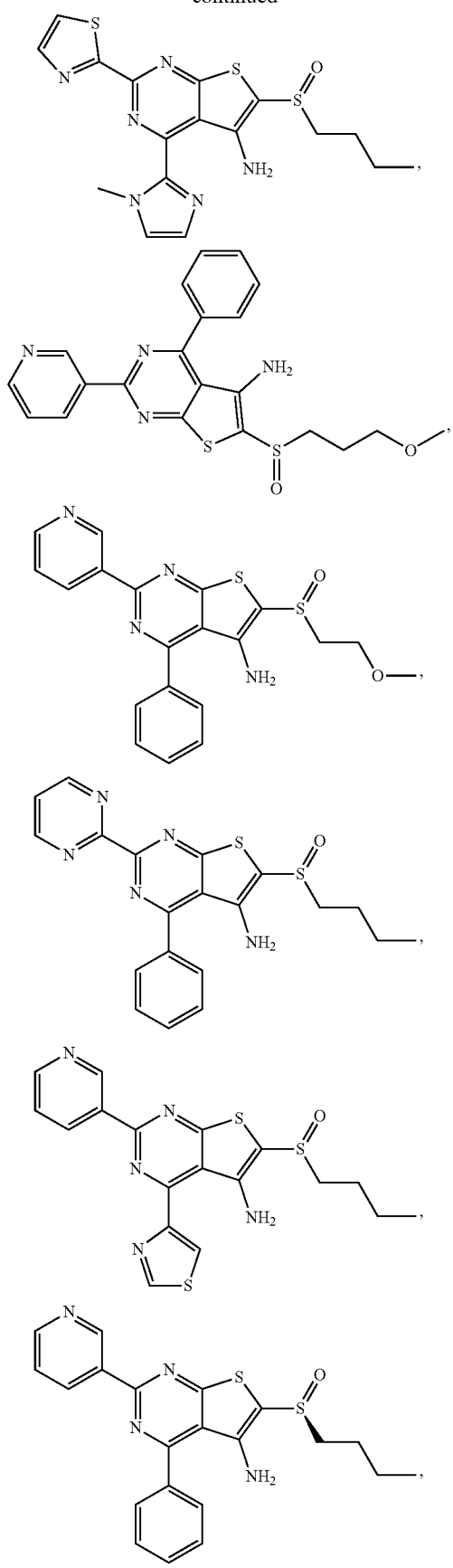
94
-continued
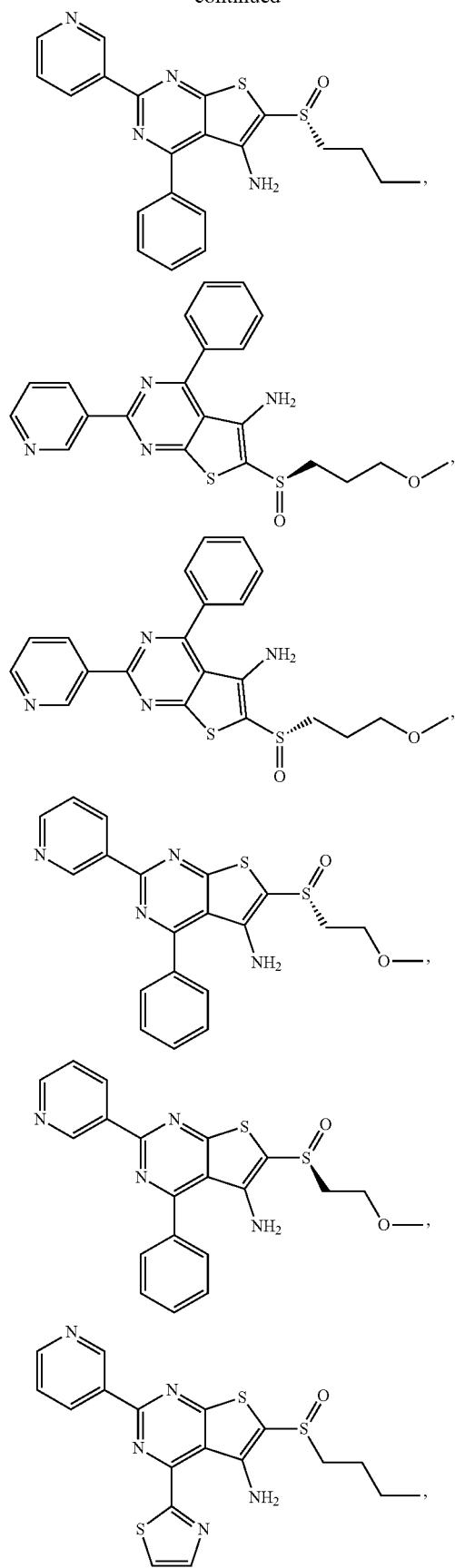

95
-continued
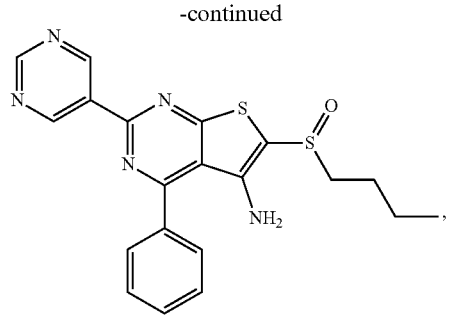
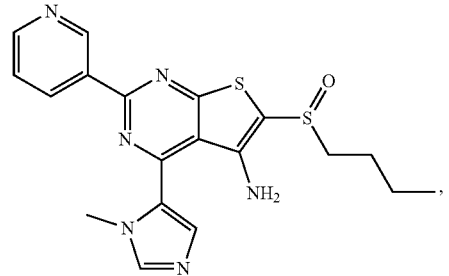
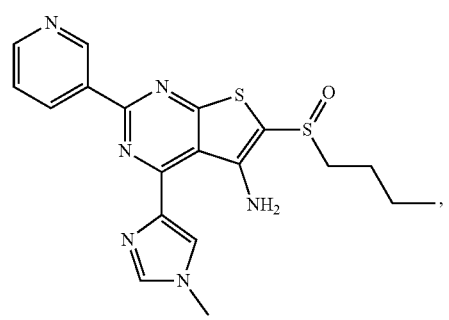
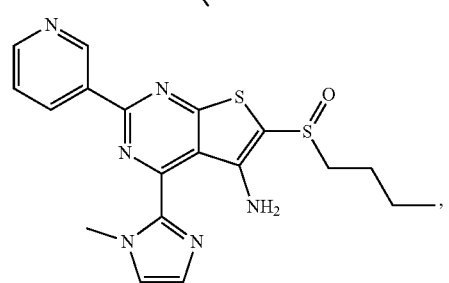
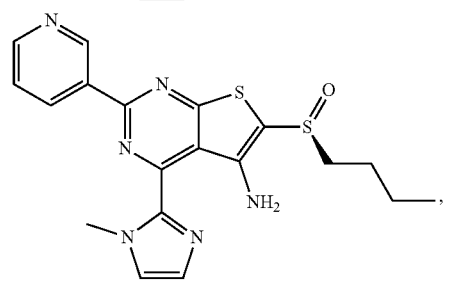
96
-continued
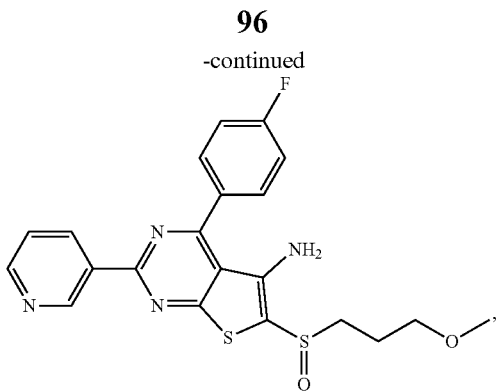
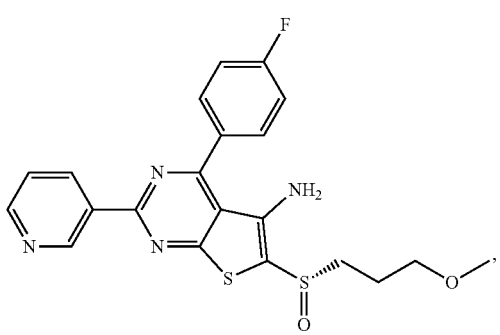
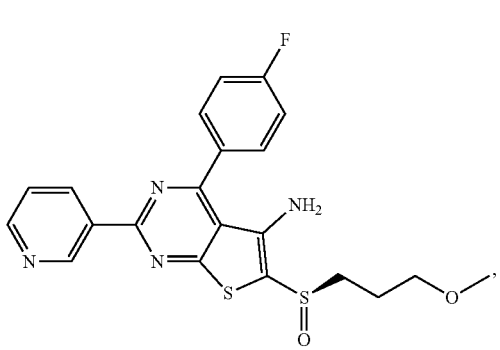
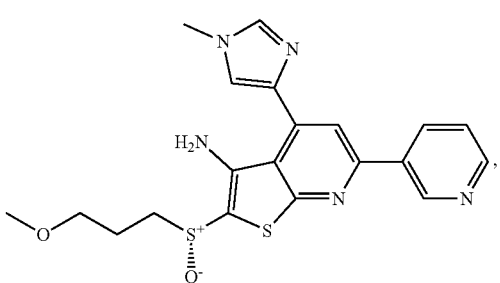
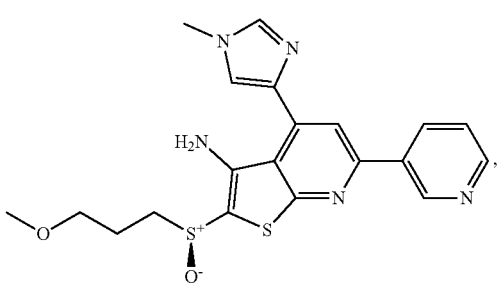

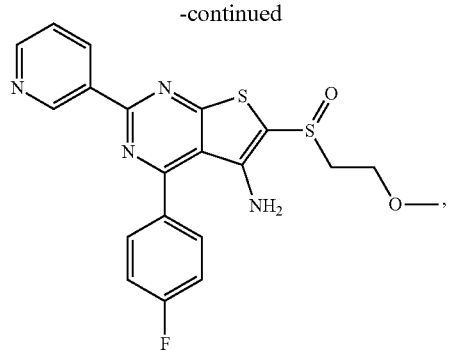
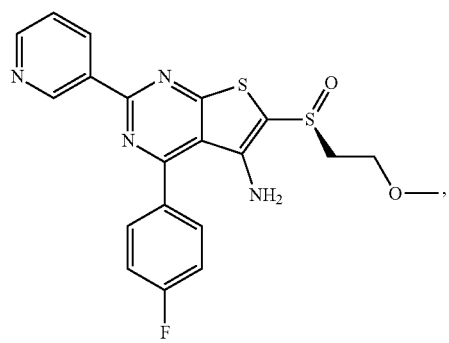
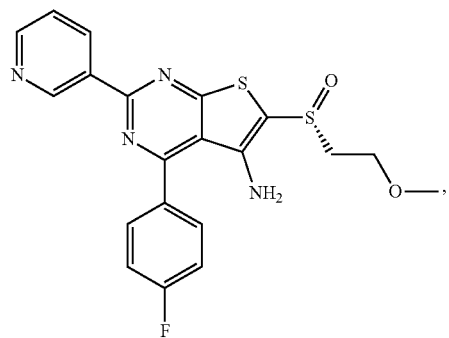
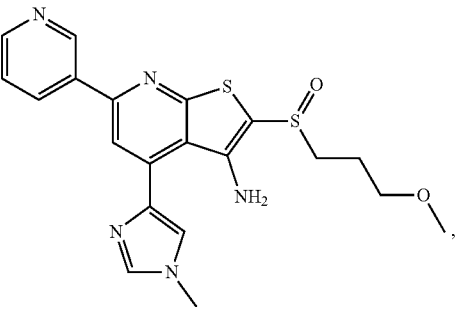
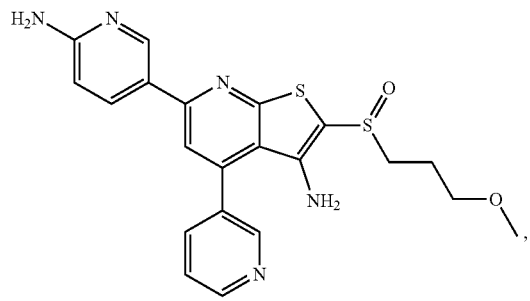
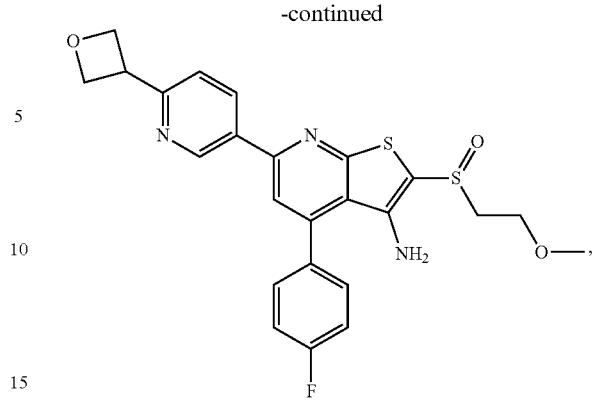
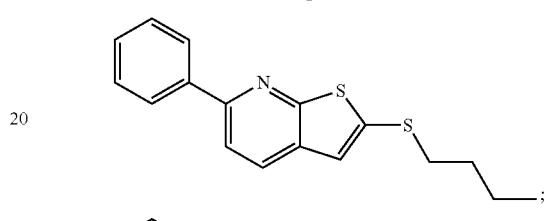
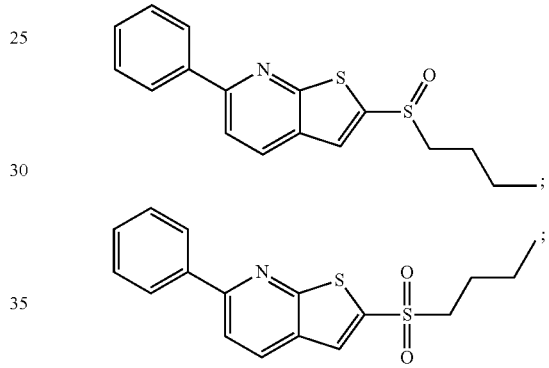
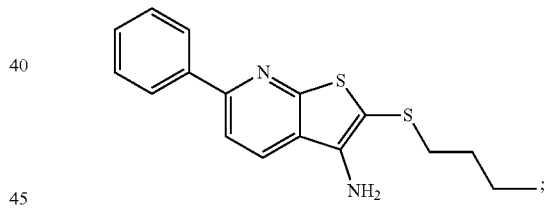
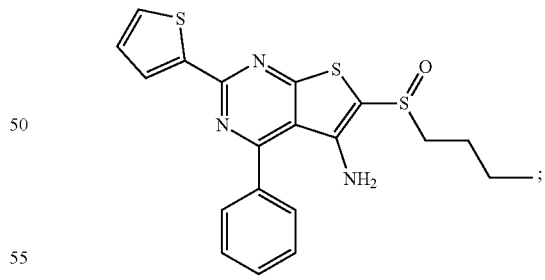
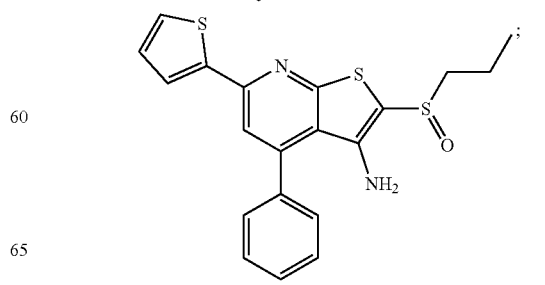

99
-continued
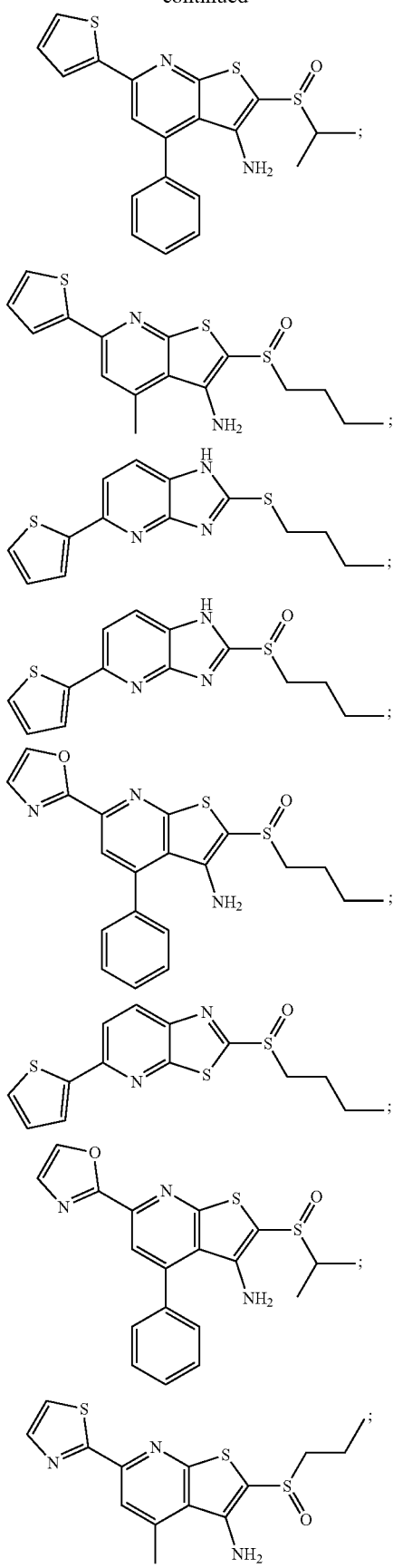
100
-continued
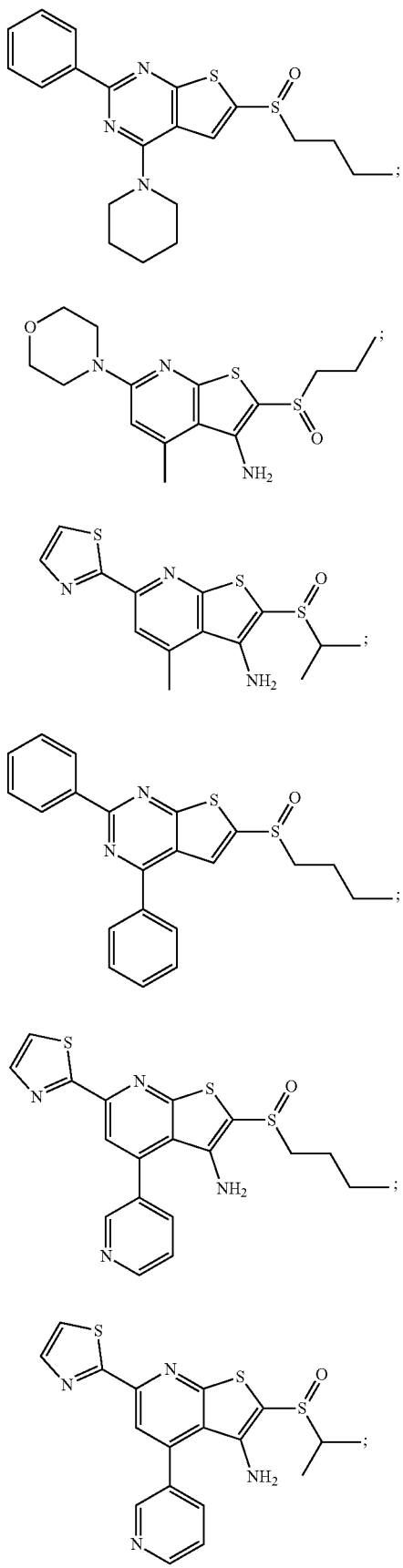

101
-continued
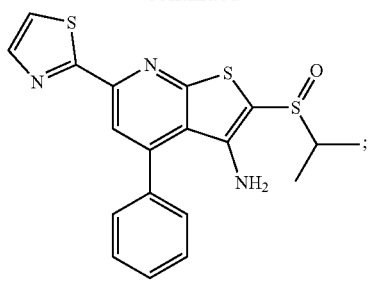
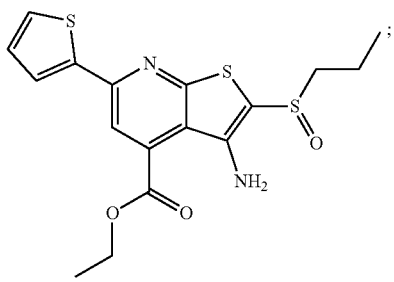
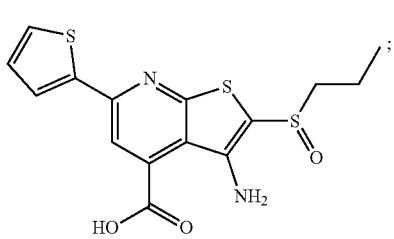
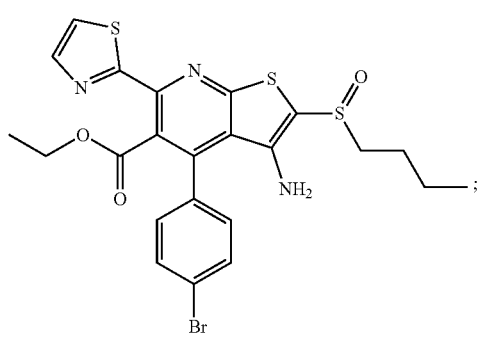
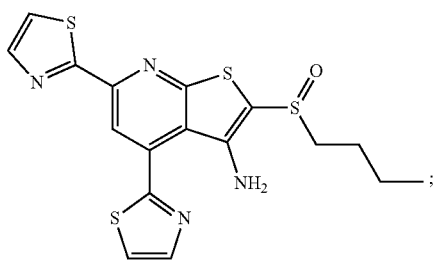
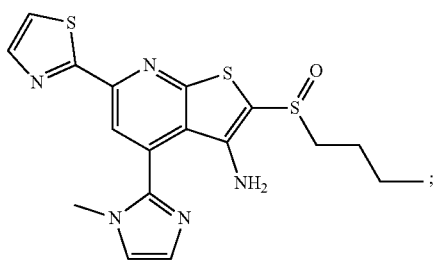
102
-continued
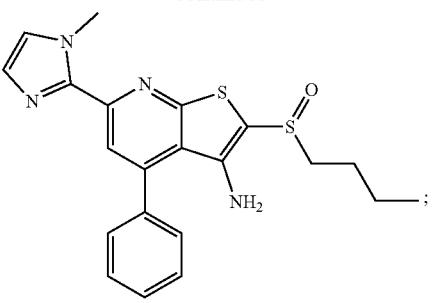
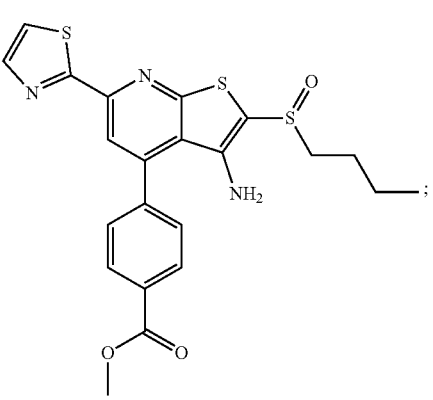
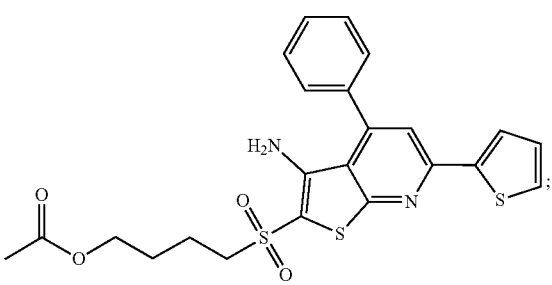
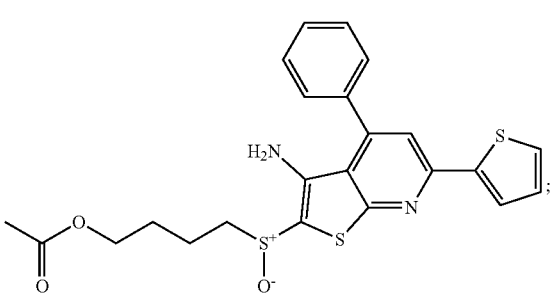
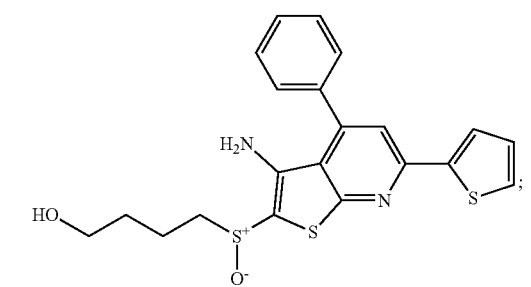

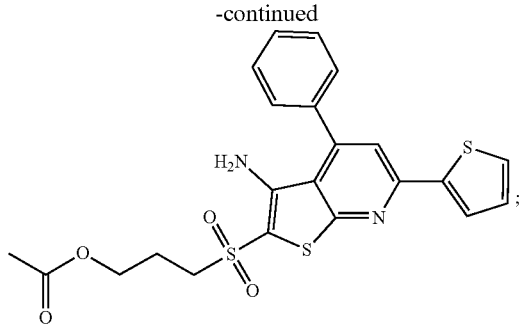
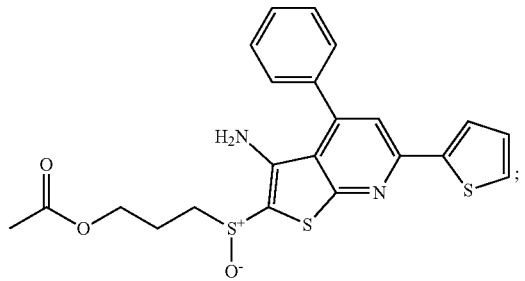
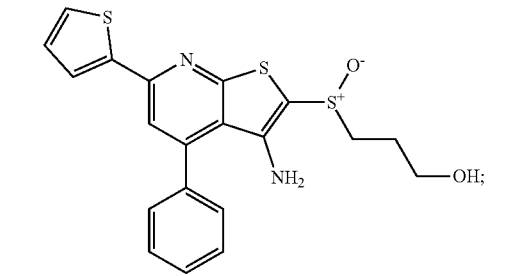
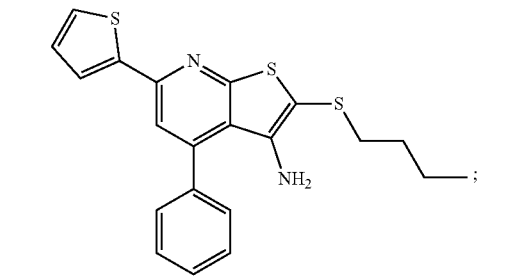
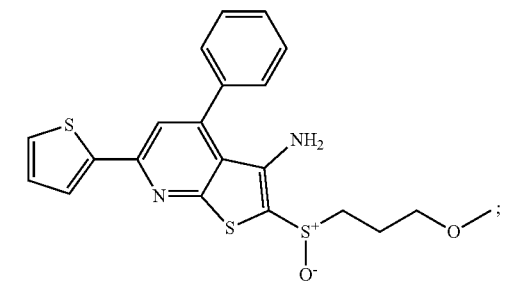
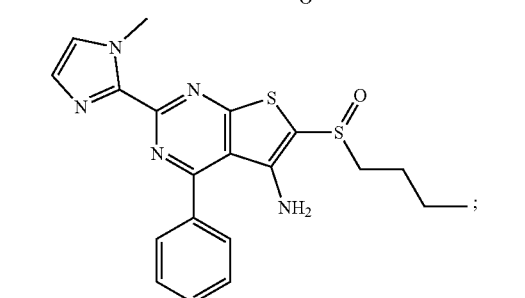
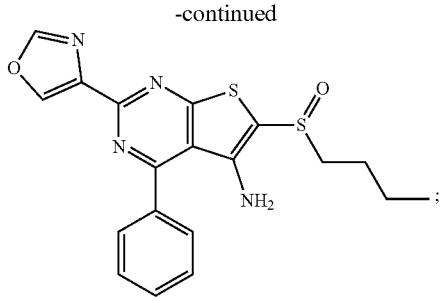
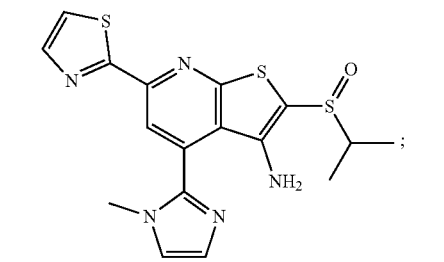
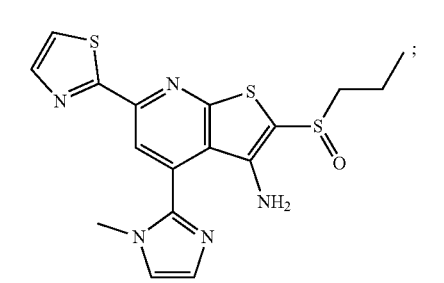
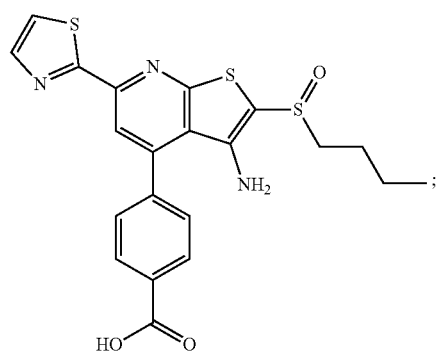
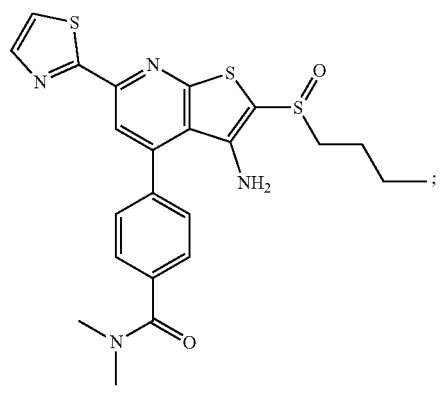

105
-continued
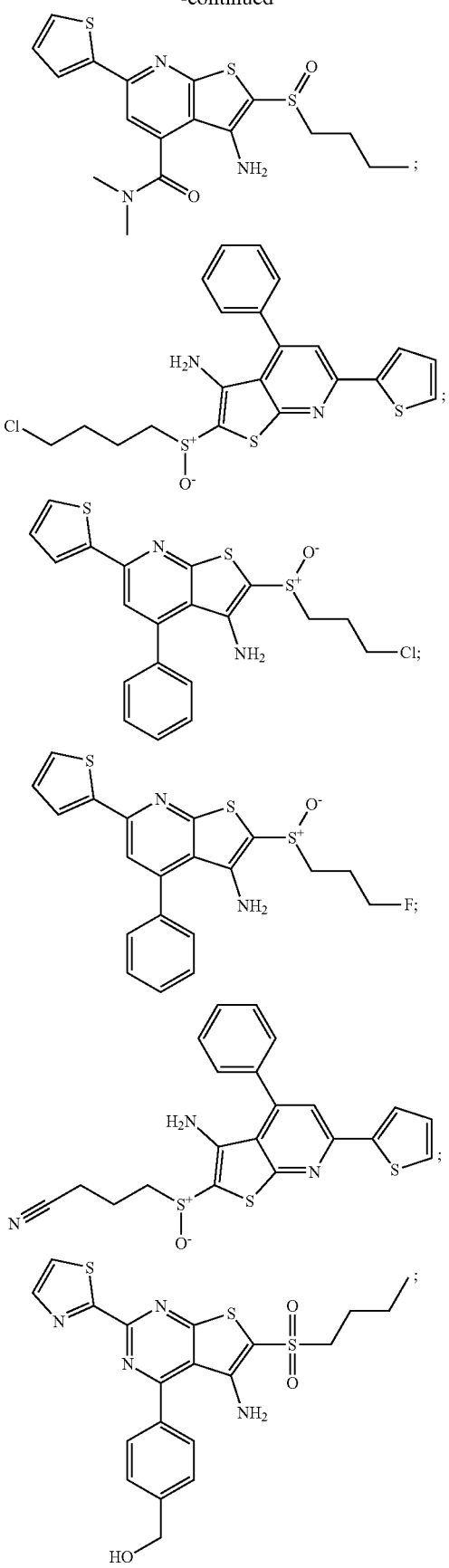
106
-continued
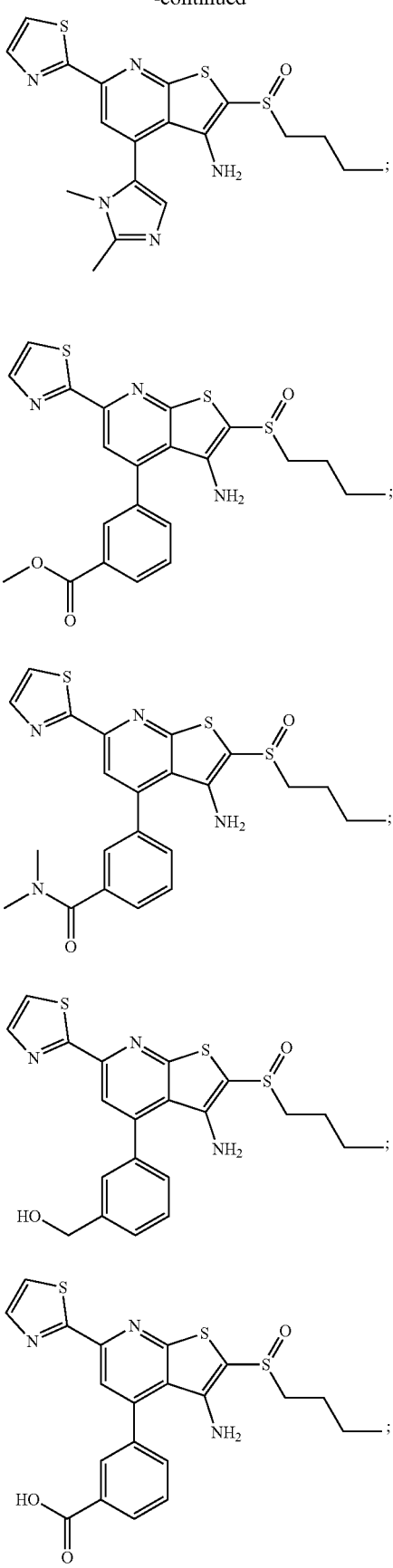

107
-continued
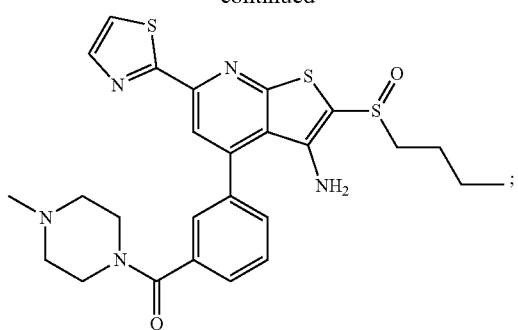
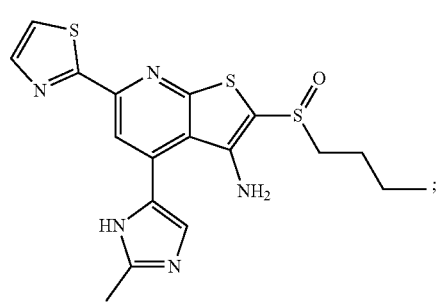
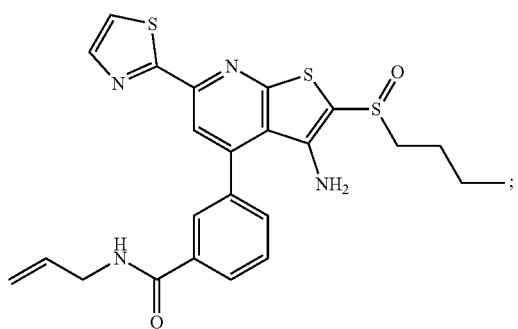
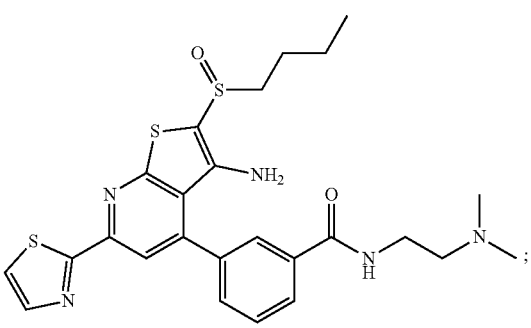
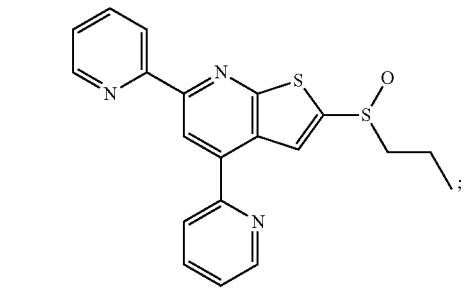
108
-continued
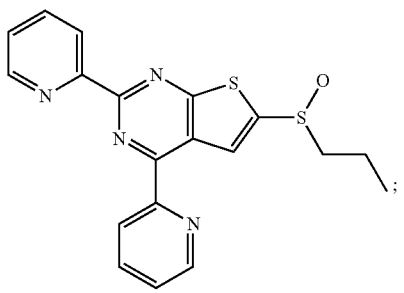
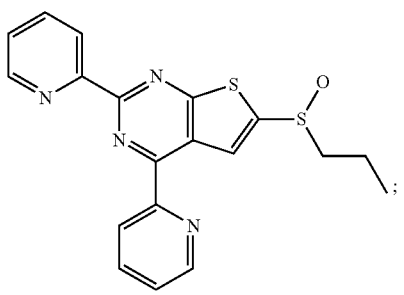
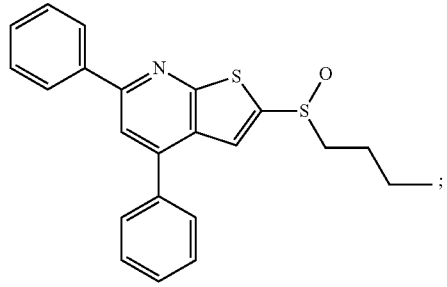
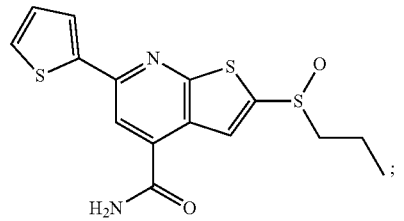
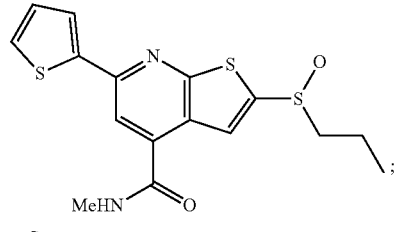
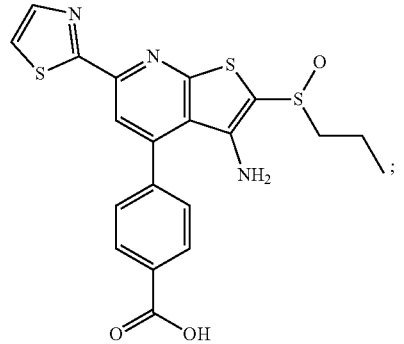

-continued
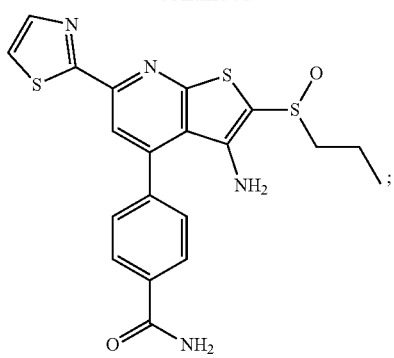
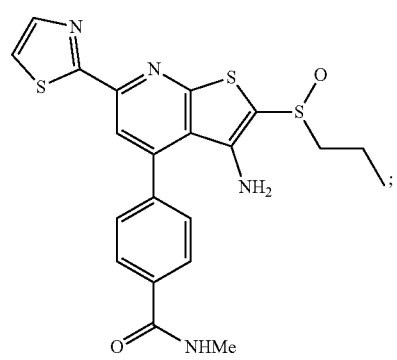
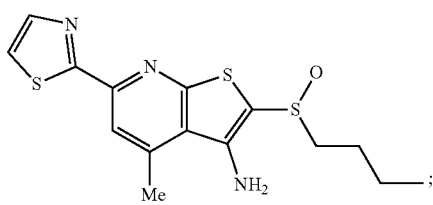
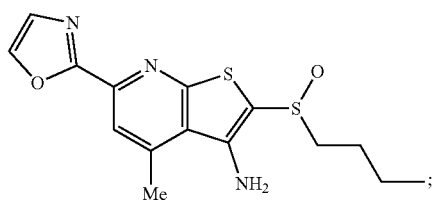
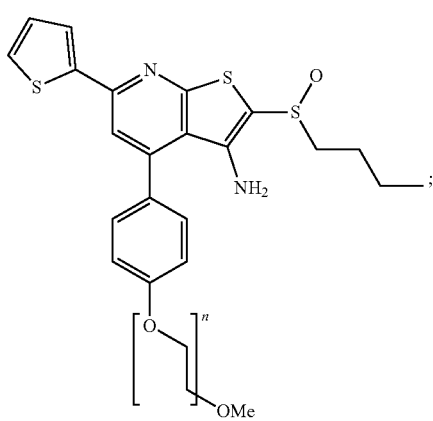
-continued
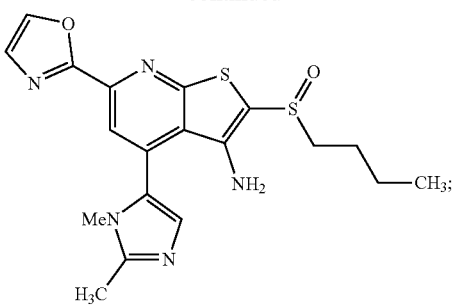
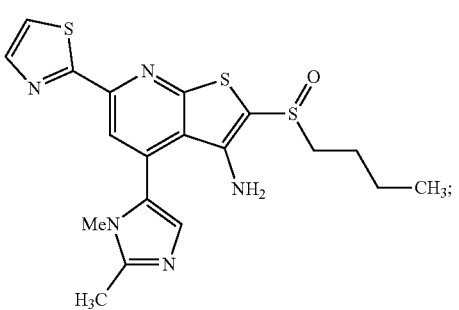
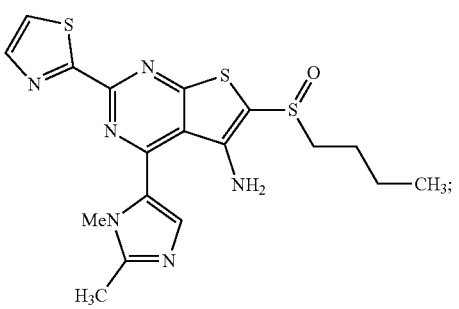
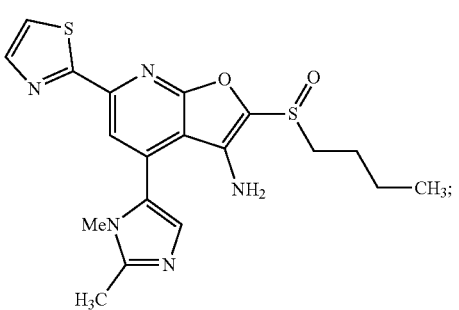
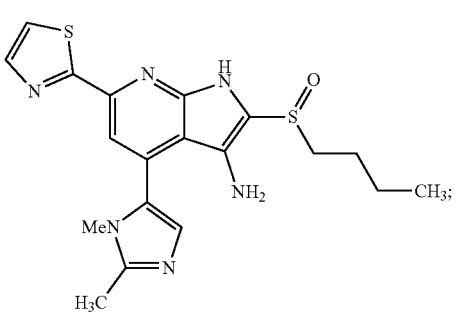

111
-continued
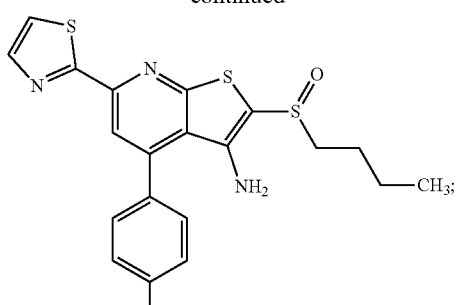

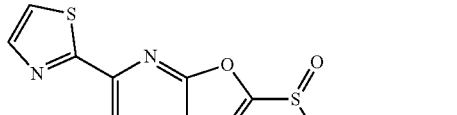
112
-continued
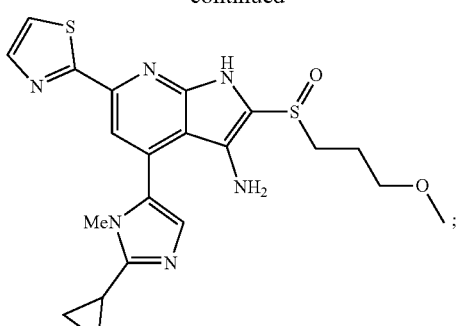
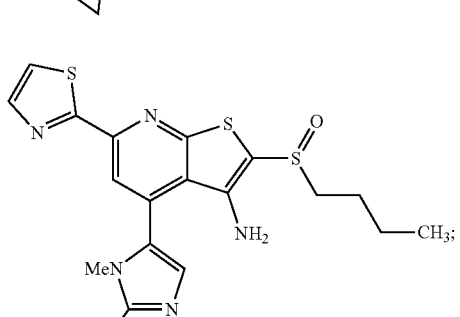
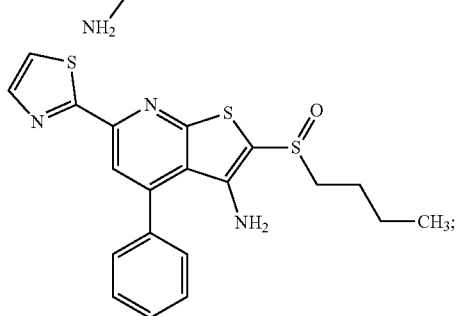
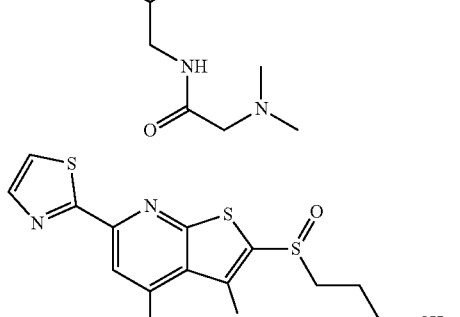
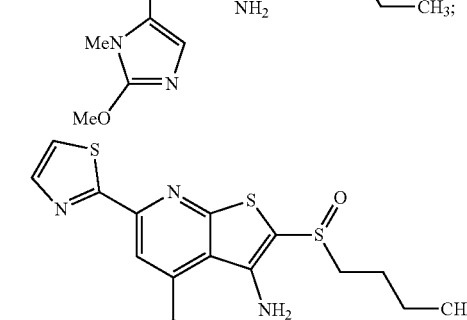
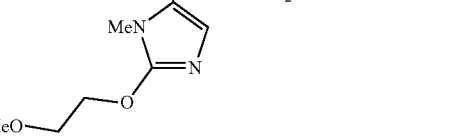

-continued
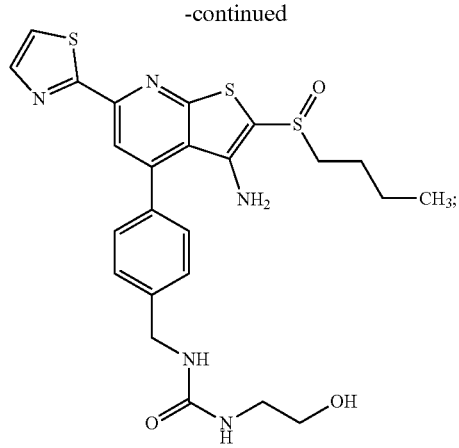
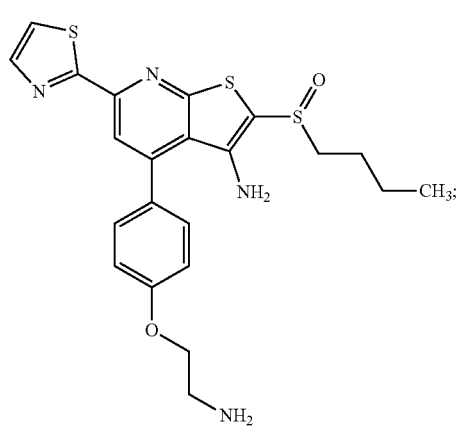
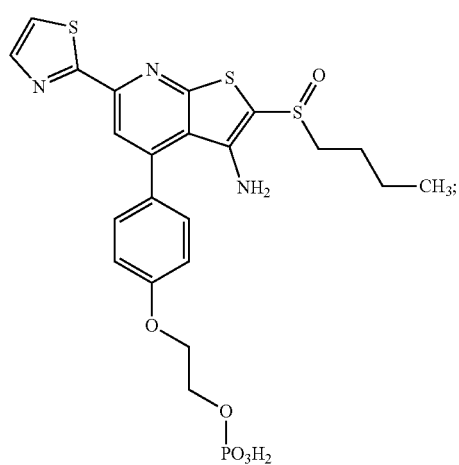
-continued
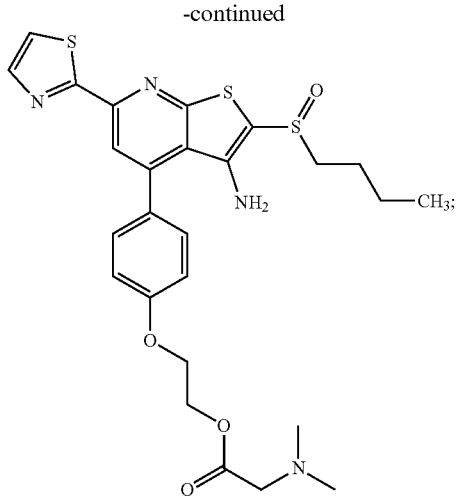
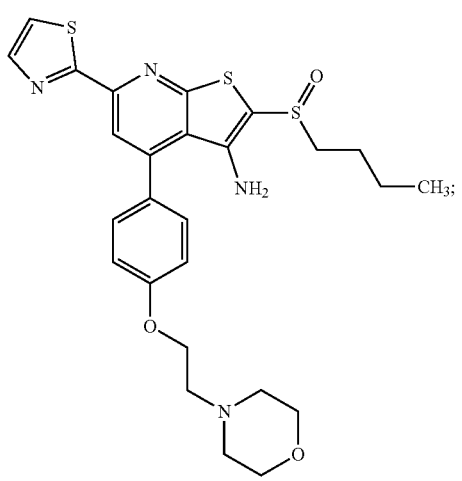
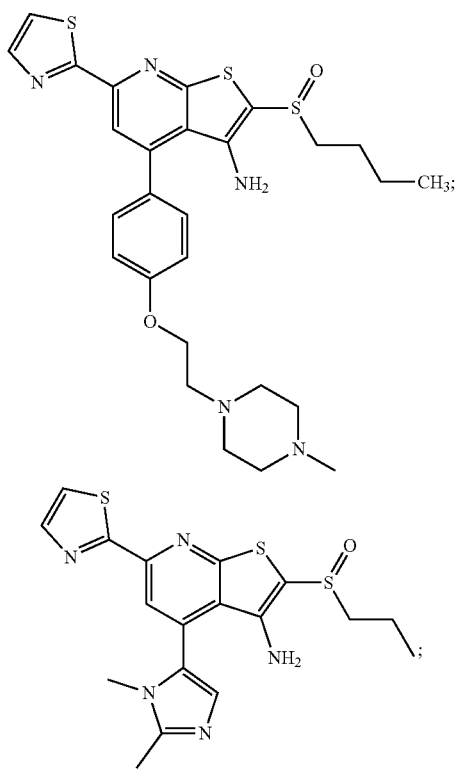

115
-continued
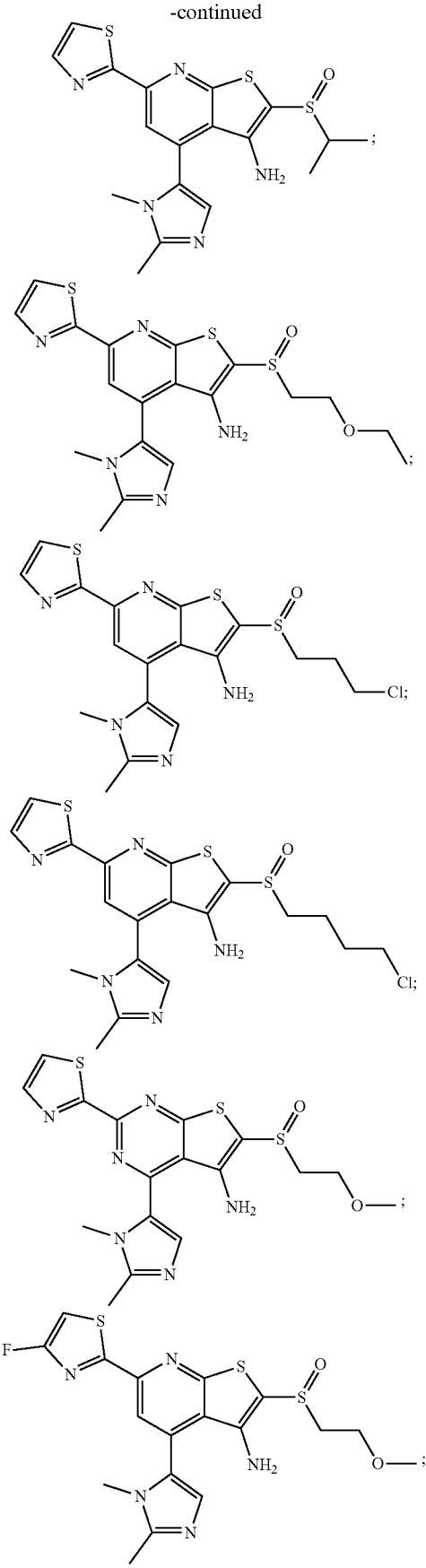
116
-continued
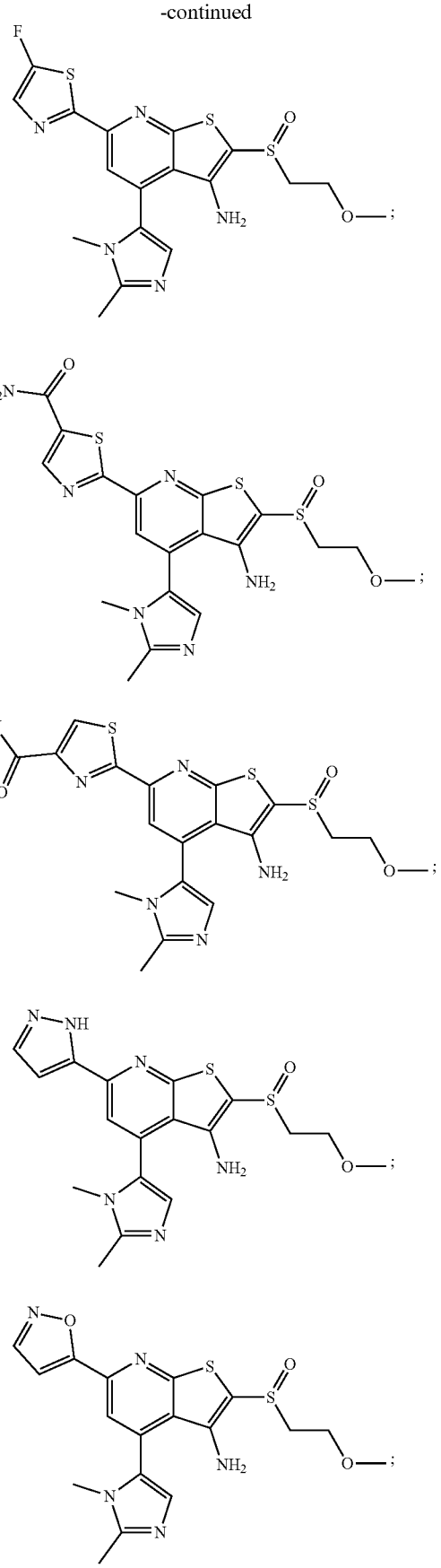

117
-continued
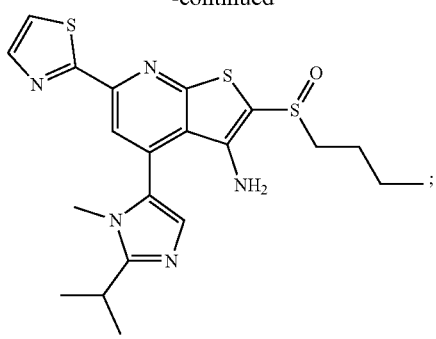
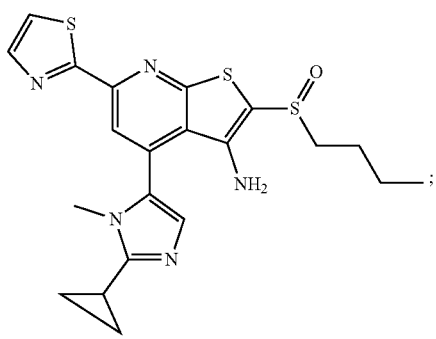
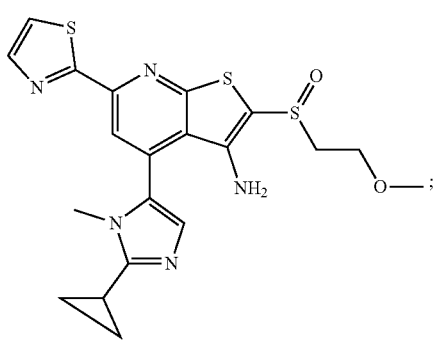
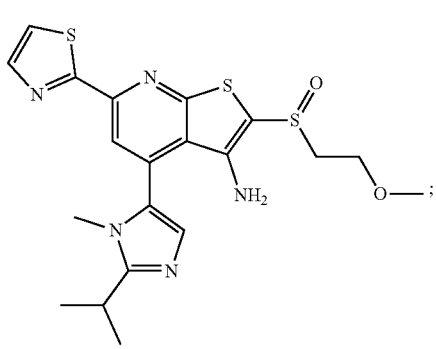
118
-continued
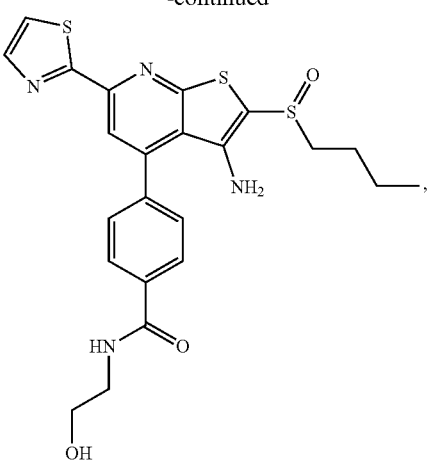
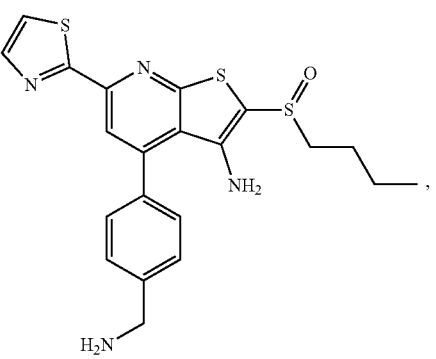
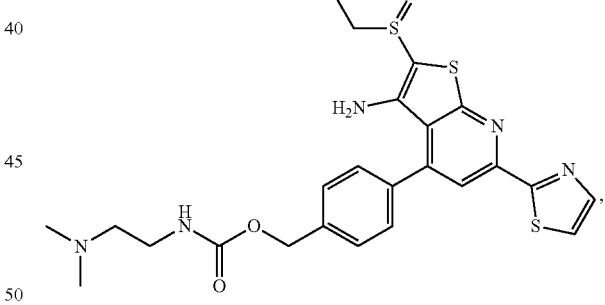
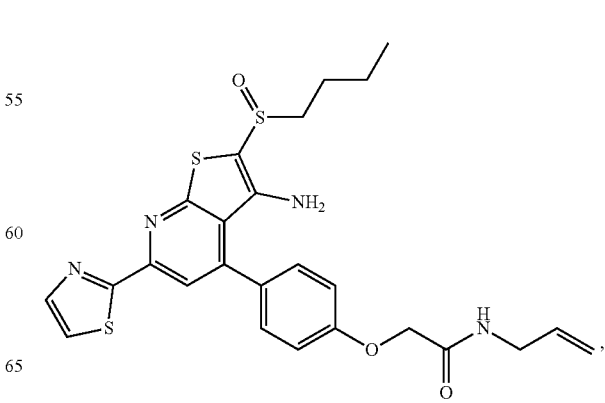

119
-continued
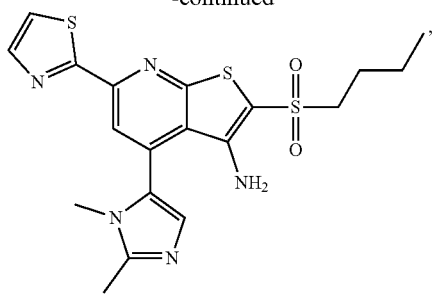
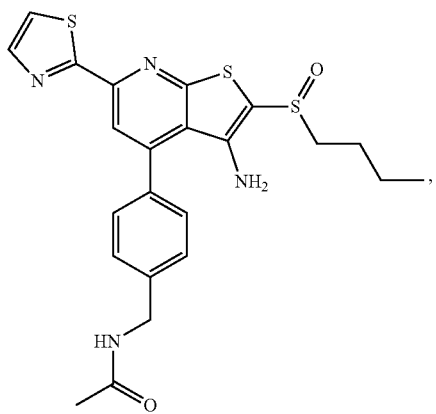
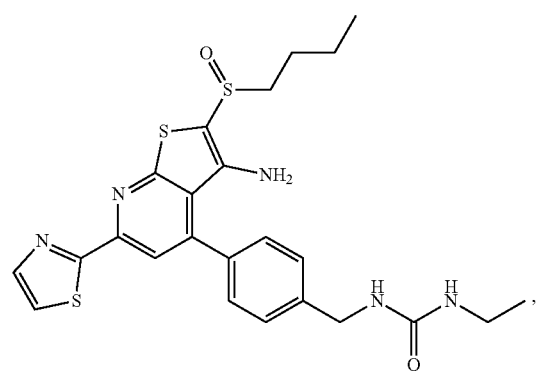
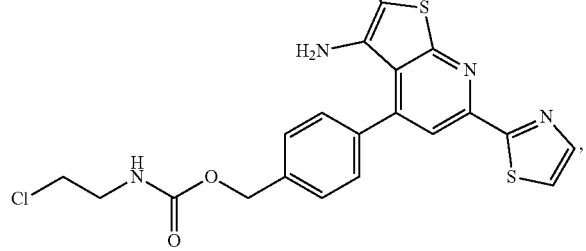
120
-continued
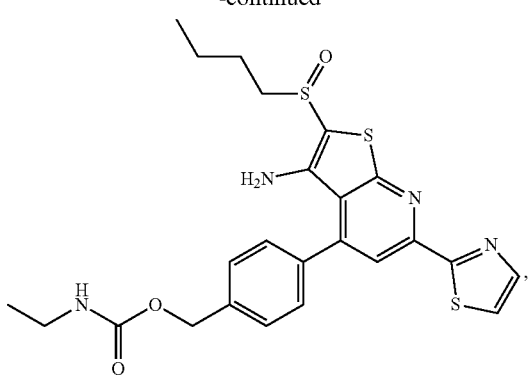
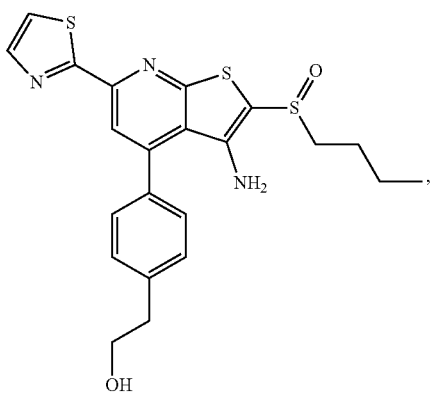
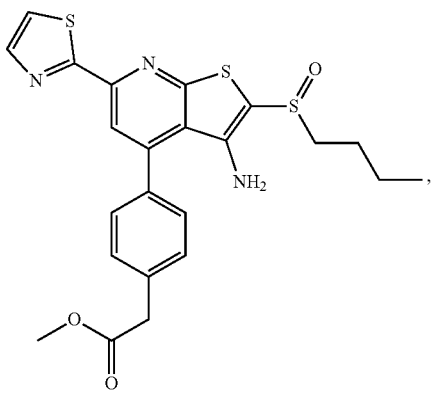
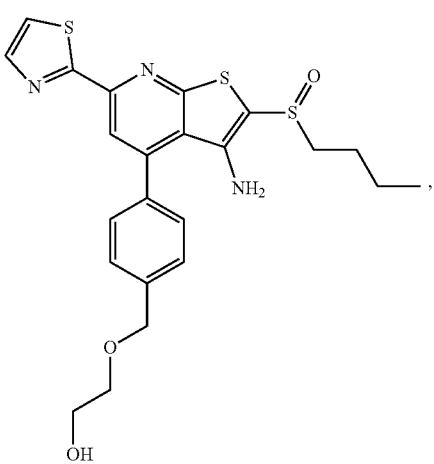

121
-continued
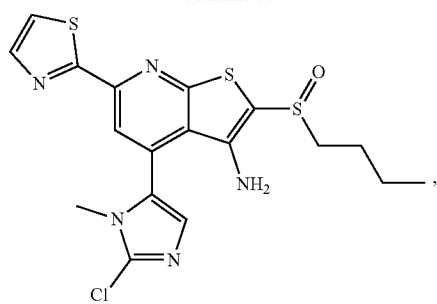
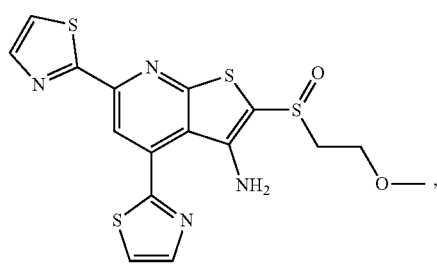
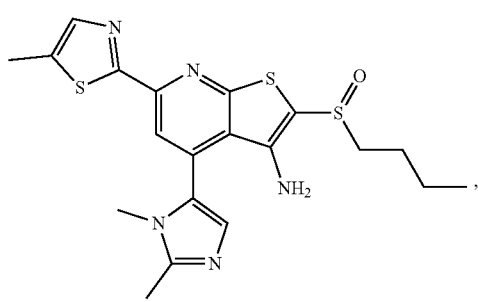
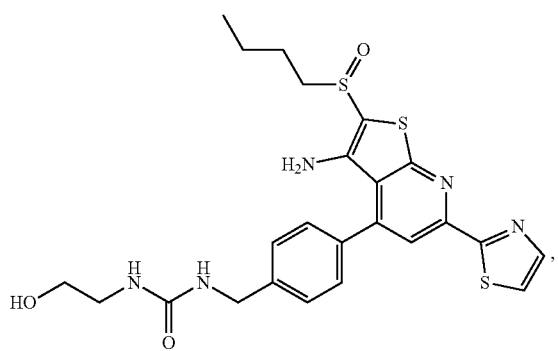
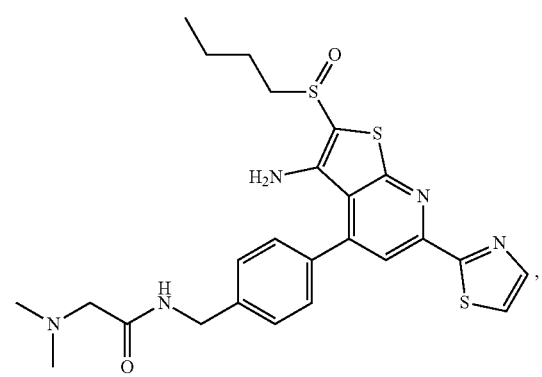
122
-continued
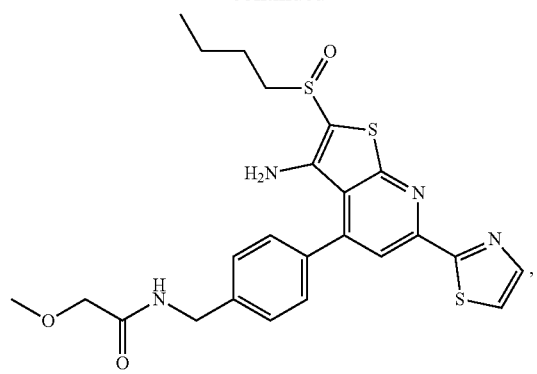
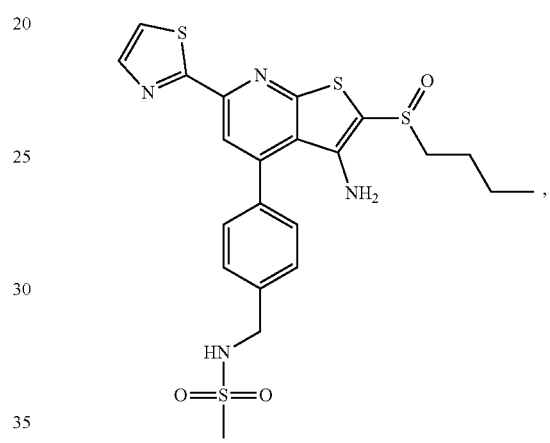
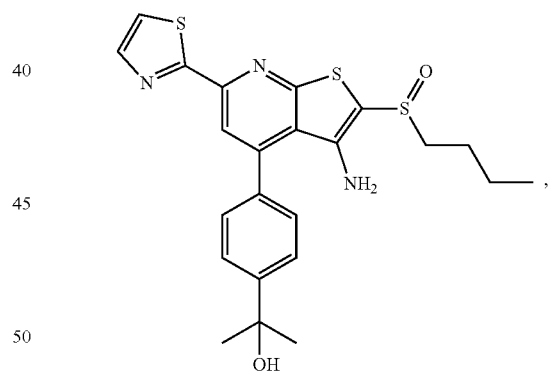
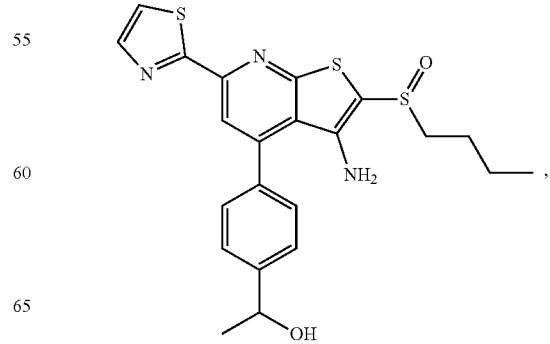

123
-continued
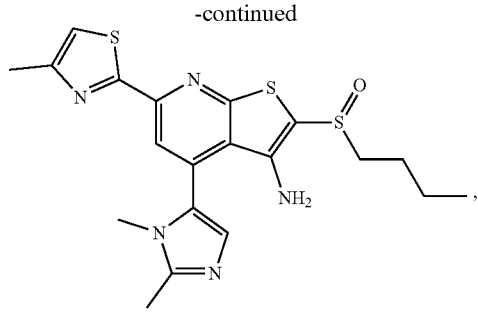
,
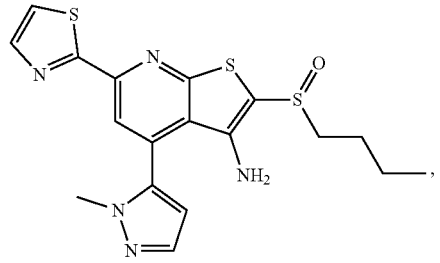
,
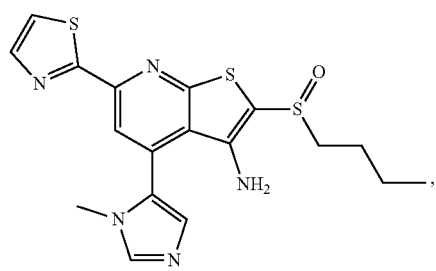
,
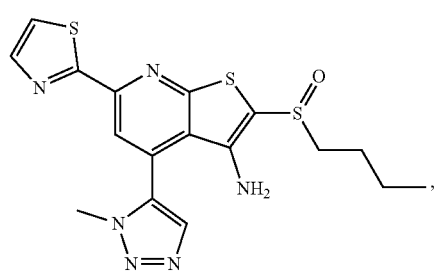
,
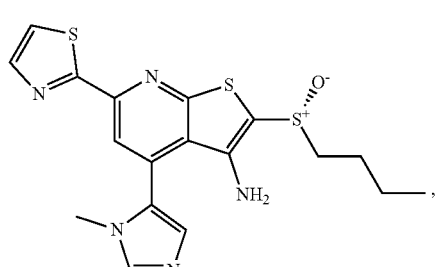
,
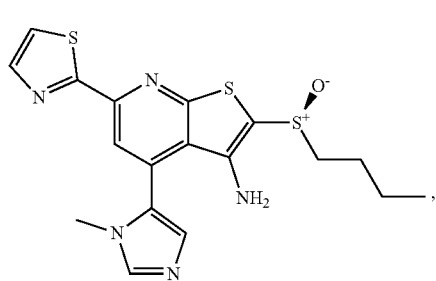
,
124
-continued
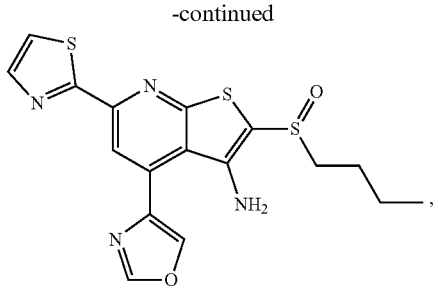
,
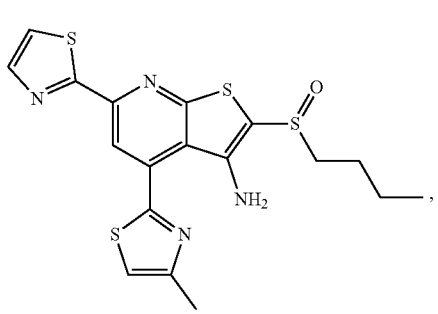
,
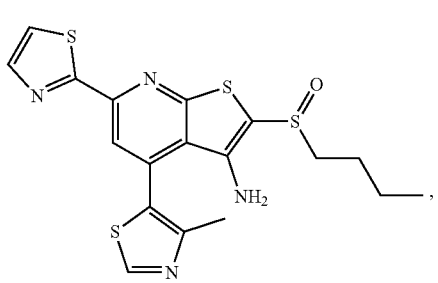
,
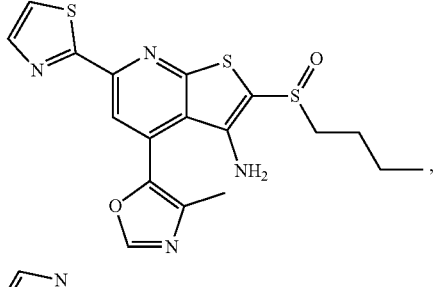
,
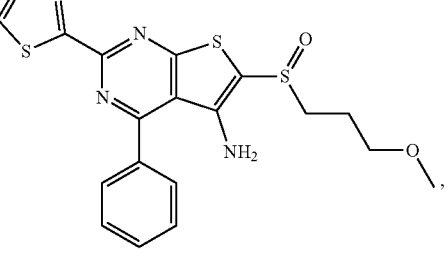
,
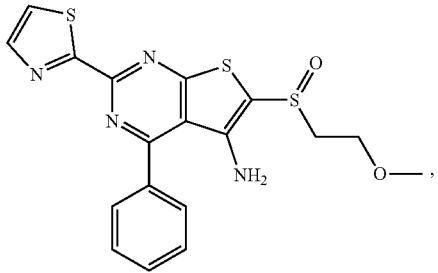
,

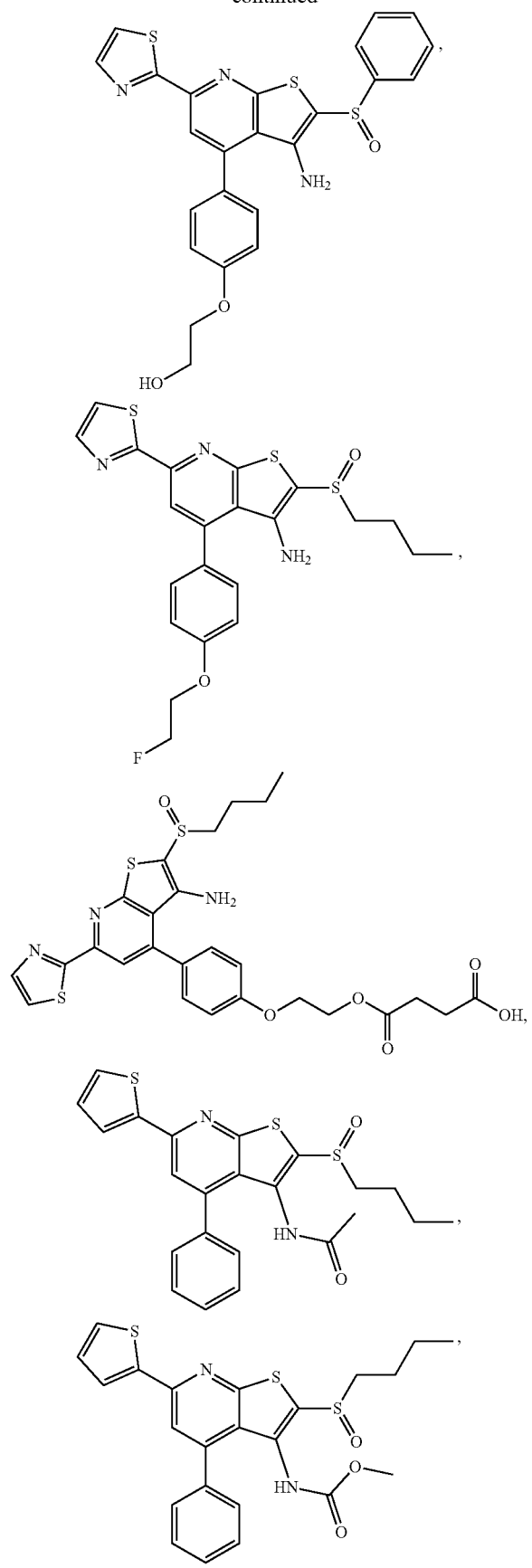
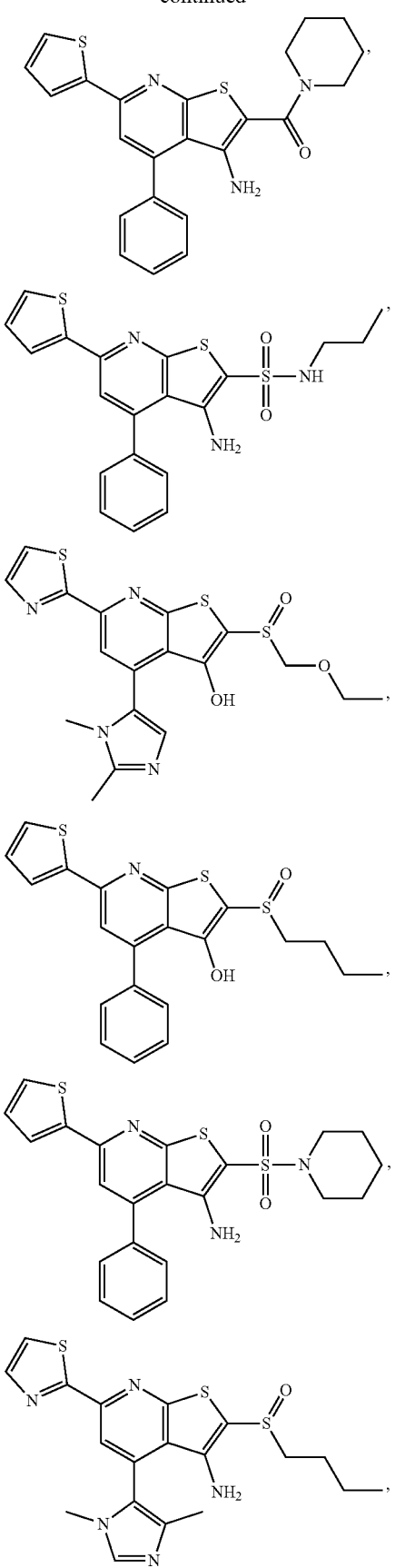

-continued

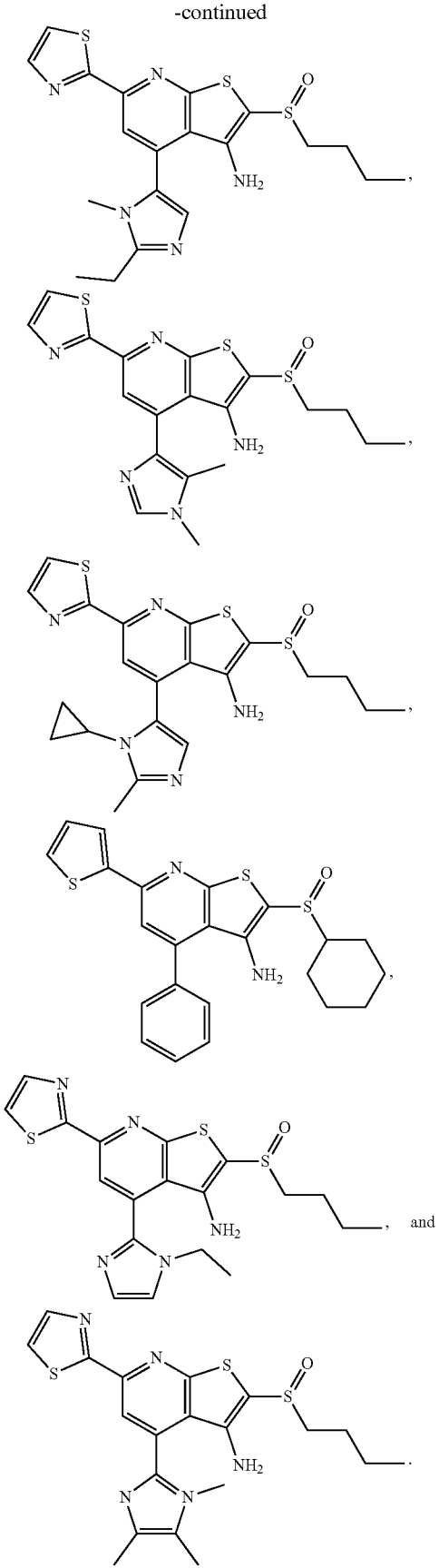

In some embodiments and without being limited by theory, Applicants unexpectedly and surprisingly discovered that carbocyclyl groups at the $R^1$ position increase the half-life of the compound. Half-life is an important parameter of a therapeutic agent because it determines that duration of action of the agent—the longer the half-life, the longer the agent is able to exert a therapeutic effect in the subject. In some embodiments, 3- to 6-membered cycloalkyls, particularly 3- to 5-membered cycloalkyls such as cyclobutyl, were observed to have desirable half-lives.

In other embodiments, the compound has the structure of formula (II):

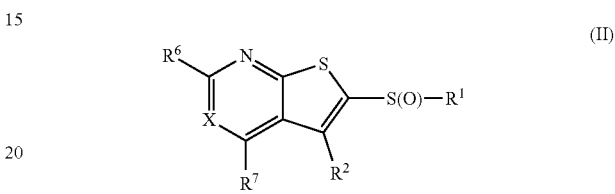

(II)

or a pharmaceutically acceptable salt, tautomer, or solvate thereof, wherein:

$R^1$ is 3- to 6-membered cycloalkyl, —($C_1$-$C_6$ alkylene)-(3- to 6-membered cycloalkyl), 3- to 6-membered heterocyclyl, or —($C_1$-$C_6$ alkylene)-(3- to 6-membered heterocyclyl);

$R^2$ is —$NH_2$, CN, or —NHC(O)alkyl;

$R^6$ is heterocyclyl or heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;

$R^3$ is oxo, —OH, —O-alkylene-N($R^5$)$_2$, —N($R^5$)$_2$, —N($R^5$)(alkylene-OH), alkyl, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl, $R^4$ is oxo, halogen, —CN, —N($R^5$)$_2$, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-$NH_2$, -alkylene-N($R^9$)$_2$, -alkylene-O-alkylene-OH, -alkylene-O-alkylene-$NH_2$, —C(O)-alkyl, —C(O)O-alkyl, -alkylene-COOH, or —S(O)$_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, S(O)$_t$, or N;

X is N or CH;

m is 0, 1, or 2; and t is 0, 1, or 2.

In some embodiments, $R^1$ is 3- to 5-membered cycloalkyl or —($C_1$-$C_6$ alkylene)-(3- to 5-membered cycloalkyl).

In other embodiments, $R^1$ is cyclobutyl.

In still other embodiments, $R^1$ is a bicyclic 4- to 6-membered cycloalkyl.

In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)NR$^5$($C_1$-$C_6$ alkyl), each of which is optionally substituted with one or more $R^4$.

In other embodiments, $R^7$ is $C_1$-$C_4$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$. In other embodiments, $R^7$ is $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.

In other embodiments, $R^7$ is $C_1$-$C_3$ alkyl, $C_1$-$C_3$ haloalkyl, 3-membered cycloalkyl, phenyl, 4-membered heterocyclyl, or 5- to 6-membered heteroaryl, each of which is optionally substituted with one or more $R^4$. In other embodiments, $R^7$ is $C_1$-$C_3$ haloalkyl, 3-membered cycloalkyl, phenyl, 4-membered heterocyclyl, or 5- to 6-membered heteroaryl, each of which is optionally substituted with one or more $R^4$.

In other embodiments, $R^7$ is —$CF_3$, isopropyl, cyclopropyl, phenyl, pyridyl, pyrazole, or triazole, each of which is optionally substituted with one or more $R^4$. In other embodiments, $R^7$ is —$CF_3$, cyclopropyl, phenyl, pyridyl, pyrazole, or triazole, each of which is optionally substituted with one or more $R^4$.

In some embodiments, $R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In other embodiments, $R^3$ is —$NH_2$, —N($C_1$-$C_3$ alkyl)$_2$, —$NHCH_2CH_2OH$, —N($C_1$-$C_3$ alkyl)$CH_2CH_2OH$, N($CH_2CH_2OH$)$_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH(C_1$-$C_3$ alkyl), —$NHCH_2CH_2N(C_1$-$C_3$ alkyl)$_2$, —N($C_1$-$C_3$ alkyl)$CH_2CH_2NH(C_1$-$C_3$ alkyl), —N($C_1$-$C_3$ alkyl)$CH_2CH_2N(C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH(C_1$-$C_3$ alkyl), or —$OCH_2CH_2N(C_1$-$C_3$ alkyl)$_2$.

In still other embodiments, $R^3$ is —$NHCH_2CH_2OH$ or —N($CH_3$)$CH_2CH_2OH$.

In some embodiments and without being limited by theory, Applicants surprisingly and unexpectedly discovered that substituents at the $R^7$ position could be modified to improve hERG activity, including hERG inhibition ($IC_{50}$), blockade, and efflux ratio. For example, in some embodiments, certain 6- to 10-membered aryls (e.g., optionally substituted phenyl) and 5- to 10-membered heteroaryls (e.g., optionally substituted pyridyls, pyrazoles, and triazoles) were observed to have beneficial hERG properties. In some embodiments, certain $C_1$-$C_6$ haloalkyls (e.g., —$CF_3$) exhibited improved hERG inhibition (IC50), while also improving half-life and solubility.

In other embodiments, the compound has the structure of formula (III):

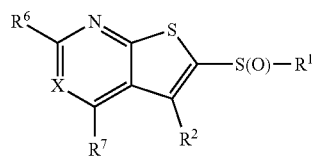

(III)

or a pharmaceutically acceptable salt, tautomer, or solvate thereof, wherein:
$R^1$ is cycloalkyl, alkylene-cycloalkyl, alkylene-alkoxy, heterocyclyl, or alkylene-heterocyclyl;
$R^2$ is —$NH_2$, CN, or —NHC(O)alkyl;
$R^6$ is heterocyclyl or heteroaryl, each of which is optionally substituted with one or more $R^3$;
$R^7$ is $C_1$-$C_6$ haloalkyl, aryl or heteroaryl, each of which is optionally substituted with one or more $R^4$;
$R^3$ is oxo, —OH, —O-alkylene-N($R^5$)$_2$, —N($R^5$)$_2$, —N($R^5$)(alkylene-OH), alkyl, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl;
each $R^5$ is independently, H, alkyl, -alkylene-OH optionally substituted with —OH, -alkylene-$NH_2$, -alkylene-N($R^9$)$_2$, -alkylene-O-alkylene-OH, -alkylene-O-alkylene-$NH_2$, —C(O)-alkyl, -alkylene-COOH, —C(O)O-alkyl, or —S(O)$_m$-alkyl;
or alternative, two $R^5$ together with the N atom to which they are attached can form a 4- to 7-membered heterocycle, optionally containing an additional heteroatom selected from O, S, or N, and wherein the heterocycle is optionally substituted with $R^8$;
$R^4$ is halogen, alkyl, or alkoxy;
X is N or CH; and
m is 0, 1, or 2.

In some embodiments, $R^7$ is —$CF_3$, pyridyl, pyrazole, phenyl, or triazole, each of which is optionally substituted with $R^4$.

In other embodiments, $R^7$ is —$CF_3$, pyridyl, fluorophenyl, or a triazole optionally substituted with halogen or methyl.

In other embodiments, $R^7$ is —$CF_3$,

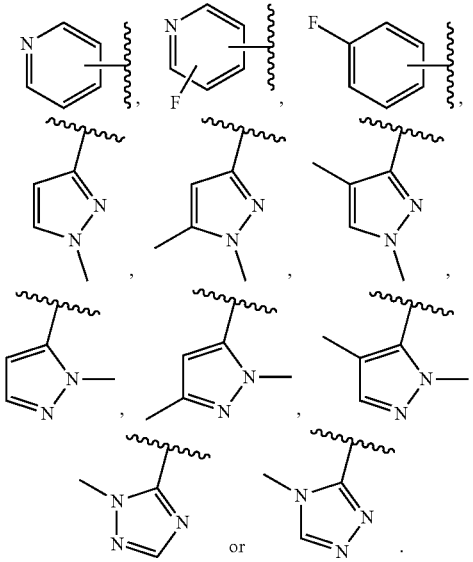

In still other embodiments, $R^7$ is —$CF_3$.
In still other embodiments, $R^7$ is

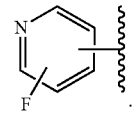

In some embodiments, $R^7$ is

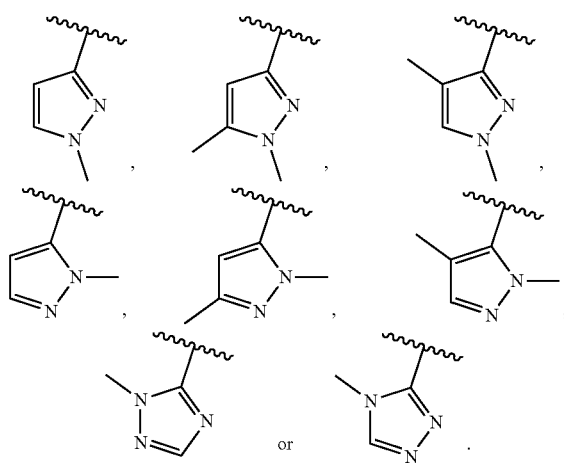

In some embodiments, $R^7$ is

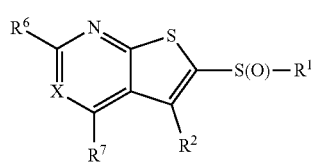

In other embodiments, $R^6$ is 8- to 10-membered bicyclic heteroaryl optionally substituted with one or more $R^3$.

In some embodiments and without being limited by theory, Applicants surprisingly and unexpectedly discovered that 3- to 6-membered cycloalkyls at the $R^7$ position can improve solublity while maintaining PDGH activity.

In other embodiments, the compound has the structure of formula (IV):

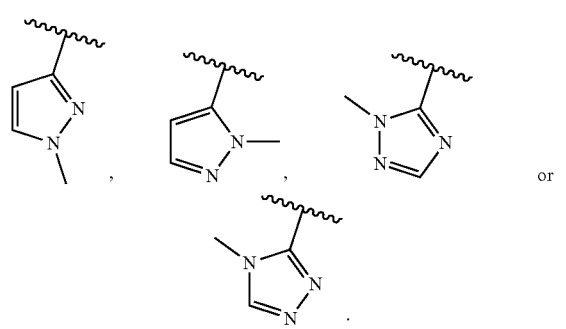

or a pharmaceutically acceptable salt, tautomer, or solvate thereof, wherein:
$R^1$ is cycloalkyl, -alkylene-cycloalkyl, -alkylene-alkoxy, heterocyclyl, or -alkylene-heterocyclyl;
$R^2$ is —$NH_2$, CN, or —NHC(O)alkyl;
$R^6$ is heterocyclyl or heteroaryl, each of which is optionally substituted with one or more $R^3$;
$R^7$ is 3- to 6-membered cycloalkyl, optionally substituted with one or more $R^4$;
$R^3$ is oxo, —OH, —O-alkylene-N($R^5$)$_2$, —N($R^5$)$_2$, —N($R^5$)(alkylene-OH), alkyl, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl;
$R^4$ is halogen, —CN, —$NH_2$, —OH, or $C_1$-$C_3$ alkyl;
each $R^5$ is independently, H, alkyl, -alkylene-OH optionally substituted with —OH, -alkylene-$NH_2$, -alkylene-N($R^9$)$_2$, -alkylene-O-alkylene-OH, -alkylene-O-alkylene-$NH_2$, —C(O)-alkyl, -alkylene-COOH, —C(O)O-alkyl, or —S(O)$_m$-alkyl;
or alternative, two $R^5$ together with the N atom to which they are attached can form a 4- to 7-membered heterocycle, optionally containing an additional heteroatom selected from O, S, or N, and wherein the heterocycle is optionally substituted with $R^8$;
$R^8$ is halogen, alkyl, or alkoxy;
X is N or CH;
m is 0, 1, or 2.

In some embodiments, $R^7$ is cyclopropyl.

In other embodiments, $R^1$ is 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).

In some embodiments, $R^1$ is cyclopropyl, cyclobutyl, cyclopentyl, cyclohexyl, —($CH_2$)$_p$-cyclopropyl, —($CH_2$)$_p$-cyclobutyl, —($CH_2$)$_p$-cyclopentyl, or —($CH_2$)$_p$-cyclohexyl; wherein p is 1, 2, or 3.

In some embodiments, $R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In some embodiments, $R^3$ is —$NH_2$, —N($C_1$-$C_3$ alkyl)$_2$, —NHCH$_2$CH$_2$OH, —N($C_1$-$C_3$ alkyl)CH$_2$CH$_2$OH, N(CH$_2$CH$_2$OH)$_2$, —NHCH$_2$CH(CH$_2$OH)$_2$, —N($C_1$-$C_3$ alkyl)CH$_2$CH(CH$_2$OH)$_2$, —NHCH$_2$CH$_2$OCH$_2$CH$_2$OH, —NHCH$_2$CH$_2$OCH$_2$CH$_2$NH$_2$, —NHCH$_2$CH$_2$NH$_2$, —N($C_1$-$C_3$ alkyl)CH$_2$CH$_2$NH$_2$, —NHCH$_2$CH$_2$NH($C_1$-$C_3$ alkyl), —NHCH$_2$CH$_2$N($C_1$-$C_3$ alkyl)$_2$, —N($C_1$-$C_3$ alkyl)CH$_2$CH$_2$NH($C_1$-$C_3$ alkyl), —N($C_1$-$C_3$ alkyl)CH$_2$CH$_2$N($C_1$-$C_3$ alkyl)$_2$, —NHSO$_2$CH$_3$, —N($C_1$-$C_3$ alkyl)SO$_2$CH$_3$, —OCH$_2$CH$_2$OH, —OCH$_2$CH$_2$NH$_2$, —OCH$_2$CH$_2$NH($C_1$-$C_3$ alkyl), or —OCH$_2$CH$_2$N($C_1$-$C_3$ alkyl)$_2$.

In other embodiments, $R^3$ is —NHCH$_2$CH$_2$OH or —N(CH$_3$)CH$_2$CH$_2$OH.

In some embodiments and without being limited by theory, Applicants surprisingly and unexpectedly discovered that the $R^6$ position can be substituted with certain $R^3$ groups to improve solubility and activity.

In other embodiments, the compound has the structure of formula (V):

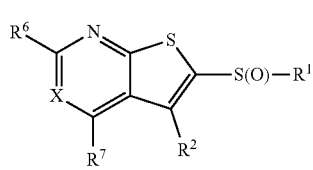

or a pharmaceutically acceptable salt, tautomer, or solvate thereof, wherein:
$R^1$ is cycloalkyl, -alkylene-cycloalkyl, -alkylene-alkoxy, heterocyclyl, or -alkylene-heterocyclyl;
$R^2$ is —$NH_2$, CN, or —NHC(O)alkyl;
$R^6$ is heterocyclyl or heteroaryl, each of which is substituted with one or more $R^3$;

R⁷ is haloalkyl, cycloalkyl, aryl, heterocyclyl, heteroaryl, —C(O)-alkyl, —C(O)O-alkyl, or —C(O)NR⁵-alkyl, each of which is optionally substituted with one or more R⁴;

R³ is —O—(C₁-C₆ alkylene)-N(R⁵)₂, —N(R⁵)₂, —N(R⁵)(C₁-C₆ alkylene-OH), —C(O)N(R⁵)₂, —C(O)N(R⁵)(C₁-C₆ alkylene-OH), —C(O)(C₁-C₆ alkyl), —C(O)O(C₁-C₆ alkyl), or —S(O)$_m$(C₁-C₆ alkyl);

R⁴ is oxo, halogen, —CN, —N(R⁵)₂, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with R⁸;

each R⁵ is independently H, C₁-C₆ alkyl, —(C₁-C₆ alkylene)-OH optionally substituted with —OH, -alkylene-NH₂, -alkylene-N(R⁹)₂, -alkylene-O-alkylene-OH, -alkylene-O-alkylene-NH₂, —C(O)(C₁-C₆ alkyl), —C(O)O(C₁-C₆ alkyl), alkylene-COOH, or —S(O)$_m$ (C₁-C₆ alkyl);

or alternative, two R⁵ together with the N atom to which they are attached can form a 4- to 7-membered heterocycle, optionally containing an additional heteroatom selected from O, S, or N, and wherein the heterocycle is optionally substituted with R⁸;

R⁸ is halogen, alkyl, or alkoxy;

X is N or CH;

m is 0, 1, or 2.

In some embodiments, R³ is —O—(C₁-C₆ alkylene)-N(R⁵)₂, —N(R⁵)₂ or —N(R⁵)(C₁-C₆ alkylene-OH).

In other embodiments, R⁵ is H, C₁-C₆ alkyl, —(C₁-C₆ alkylene)-OH, or —S(O)₂(C₁-C₃ alkyl).

In some embodiments, R³ is —NH₂, —N(C₁-C₃ alkyl)₂, —NHCH₂CH₂OH, —N(C₁-C₃ alkyl)CH₂CH₂OH, N(CH₂CH₂OH)₂, —NHCH₂CH(CH₂OH)₂, —N(C₁-C₃ alkyl)CH₂CH(CH₂OH)₂, —NHCH₂CH₂OCH₂CH₂OH, —NHCH₂CH₂OCH₂CH₂NH₂, —NHCH₂CH₂NH₂, —N(C₁-C₃ alkyl)CH₂CH₂NH₂, —NHCH₂CH₂NH(C₁-C₃ alkyl), —NHCH₂CH₂N(C₁-C₃ alkyl)₂, —N(C₁-C₃ alkyl)CH₂CH₂NH(C₁-C₃ alkyl), —N(C₁-C₃ alkyl)CH₂CH₂N(C₁-C₃ alkyl)₂, —NHSO₂CH₃, —N(C₁-C₃ alkyl)SO₂CH₃, —OCH₂CH₂OH, —OCH₂CH₂NH₂, —OCH₂CH₂NH(C₁-C₃ alkyl), or —OCH₂CH₂N(C₁-C₃ alkyl)₂.

In other embodiments, R³ is —NHCH₂CH₂OH or —N(CH₃)CH₂CH₂OH.

In still other embodiments, R³ is —NHCH₂CH₂OH.

In some embodiments, R⁶ is 5- to 6-membered heterocyclyl or 5- to 10-membered heteroaryl, each of which is optionally substituted with one or more R³.

In other embodiments, R⁶ is 5- to 6-membered heteroaryl optionally substituted with one or more R³.

In some embodiments, R⁶ is furan, thiophene, pyrrole, thiazole, isothiazole, oxazole, isooxazole, pyrazole, imidazole, triazole, pyridine, pyrimidine, pyridazine, or pyrazine, each optionally substituted with one or more R³.

In other embodiments, R⁶ is thiazole, imidazole, oxazole, pyridine, or pyrimidine.

In some embodiments, R⁶ is 8- to 10-membered bicyclic heteroaryl optionally substituted with one or more R³.

In other embodiments, R⁶ is 5- to 6-membered heterocyclyl, optionally substituted with one or more R³, selected from morpholine, pyridine-one, or piperidine.

In some embodiments, R⁷ is C₁-C₃ haloalkyl, 3-membered cycloalkyl, phenyl, 4-membered heterocyclyl, or 5- to 6-membered heteroaryl, each of which is optionally substituted with one or more R⁴.

In other embodiments, R⁷ is —CF₃, cyclopropyl, phenyl, pyrzole, pyridyl, or triazole, each of which is optionally substituted with one or more R⁴.

In some embodiments, the compound has the structure of formula (VI):

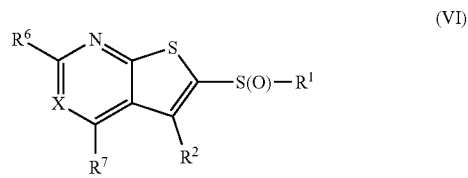

(VI)

or a pharmaceutically acceptable salt, tautomer, or solvate thereof, wherein:

R¹ is cycloalkyl, alkylene-cycloalkyl, alkylene-alkoxy, heterocyclyl, or alkylene-heterocyclyl;

R² is —NH₂, CN, or —NHC(O)alkyl;

R⁶ is fused bicyclic heterocyclyl or fused bicyclic heteroaryl, each of which is optionally substituted with one or more R³;

R⁷ is alkyl, haloalkyl, cycloalkyl, aryl, heterocyclyl, heteroaryl, —C(O)-alkyl, —C(O)O-alkyl, or —C(O)NR⁵-alkyl, each of which is optionally substituted with one or more R⁴;

R³ is oxo, —OH, —O-alkylene-N(R⁵)₂, —N(R⁵)₂, —N(R⁵)(alkylene-OH), alkyl, haloalkyl, cycloalkyl, heterocyclyl, —C(O)N(R⁵)₂, —C(O)-alkyl, —C(O)O-alkyl, or —S(O)$_m$-alkyl;

R⁴ is oxo, halogen, —CN, —N(R⁵)₂, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with R⁸;

each R⁵ is independently, H, alkyl, -alkylene-OH optionally substituted with —OH, -alkylene-O-alkylene-OH, -alkylene-O-alkylene-NH₂, —C(O)-alkyl, —C(O)O-alkyl, or —S(O)$_m$-alkyl;

or alternatively, two R⁵ together with the N atom to which they are attached can form a 4- to 7-membered heterocycle, optionally containing an additional heteroatom selected from O, S, or N, and wherein the heterocycle is optionally substituted with R⁸;

R⁸ is halogen, alkyl, or alkoxy;

X is N or CH; and m is 0, 1, or 2.

In some embodiments, R⁶ is 8- to 10-membered fused bicyclic heteroaryl, each of which is optionally substituted with one or more R³.

In some embodiments, R⁷ is C₁-C₆ alkyl, C₁-C₆ haloalkyl, 3- to 6-membered cycloalkyl, 6- to 10-membered aryl, 3- to 6-membered heterocyclyl, 5- to 10-membered heteroaryl, —C(O)(C₁-C₆ alkyl), —C(O)O(C₁-C₆ alkyl), or —C(O)NR⁵(C₁-C₆ alkyl), each of which is optionally substituted with one or more R⁴.

In other embodiments, R⁷ is C₁-C₄ alkyl, C₁-C₆ haloalkyl, 3- to 6-membered cycloalkyl, phenyl, 3- to 6-membered heterocyclyl, or 5- to 10-membered heteroaryl, each of which is optionally substituted with one or more R⁴. In other embodiments, R⁷ is C₁-C₆ haloalkyl, 3- to 6-membered cycloalkyl, phenyl, 3- to 6-membered heterocyclyl, or 5- to 10-membered heteroaryl, each of which is optionally substituted with one or more R⁴.

In still other embodiments, R⁷ is C₁-C₃ alkyl, C₁-C₆ haloalkyl, 3- to 6-membered cycloalkyl, phenyl, 3- to 6-membered heterocyclyl, or 5- to 6-membered heteroaryl, each of which is optionally substituted with one or more R⁴.

In other embodiments, R⁷ is C₁-C₃ alkyl, C₁-C₆ haloalkyl, 3- to 6-membered cycloalkyl, phenyl, pyrazole, pyridyl, or triazole, each of which is optionally substituted with one or more $R^4$. In other embodiments, $R^7$ is $C_1$-$C_6$ haloalkyl, 3- to 6-membered cycloalkyl, phenyl, pyrazole, pyridyl, or triazole, each of which is optionally substituted with one or more $R^4$.

In other embodiments, $R^7$ is —$CF_3$, isopropyl, cyclopropyl, phenyl, pyridyl, or triazole, each of which is optionally substituted with one or more $R^4$. In other embodiments, $R^7$ is —$CF_3$, cyclopropyl, phenyl, pyridyl, or triazole, each of which is optionally substituted with one or more $R^4$.

In some embodiments, $R^1$ is $C_1$-$C_6$ alkyl, $C_1$-$C_6$ haloalkyl, 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).

In other embodiments, $R^1$ is cyclopropyl, cyclobutyl, cyclopentyl, cyclohexyl, —$(CH_2)_p$-cyclopropyl, —$(CH_2)_p$-cyclobutyl, —$(CH_2)_p$-cyclopentyl, or —$(CH_2)_p$-cyclohexyl; wherein p is 1, 2, or 3.

In some embodiments, $R^3$ is —O—($C_1$-$C_6$ alkylene)-N$(R^5)_2$, —$N(R^5)_2$, —$N(R^5)$($C_1$-$C_6$ alkylene-OH), —C(O)N$(R^5)_2$, —C(O)N$(R^5)$($C_1$-$C_6$ alkylene-OH), —C(O)($C_1$-$C_6$ alkyl), —C(O)O($C_1$-$C_6$ alkyl), or —$S(O)_m$($C_1$-$C_6$ alkyl).

In other embodiments, $R^3$ is —$NH_2$, —$N(C_1$-$C_3$ alkyl$)_2$, —$NHCH_2CH_2OH$, —$N(C_1$-$C_3$ alkyl$)CH_2CH_2OH$, $N(CH_2CH_2OH)_2$, —$NHCH_2CH(CH_2OH)_2$, —$N(C_1$-$C_3$ alkyl$)CH_2CH(CH_2OH)_2$, —$NHCH_2CH_2OCH_2CH_2OH$, —$NHCH_2CH_2OCH_2CH_2NH_2$, —$NHCH_2CH_2NH_2$, —$N(C_1$-$C_3$ alkyl$)CH_2CH_2NH_2$, —$NHCH_2CH_2NH(C_1$-$C_3$ alkyl), —$NHCH_2CH_2N(C_1$-$C_3$ alkyl$)_2$, —$N(C_1$-$C_3$ alkyl$)CH_2CH_2NH(C_1$-$C_3$ alkyl), —$N(C_1$-$C_3$ alkyl$)CH_2CH_2N(C_1$-$C_3$ alkyl$)_2$, —$NHSO_2CH_3$, —$N(C_1$-$C_3$ alkyl$)SO_2CH_3$, —$OCH_2CH_2OH$, —$OCH_2CH_2NH_2$, —$OCH_2CH_2NH(C_1$-$C_3$ alkyl), or —$OCH_2CH_2N(C_1$-$C_3$ alkyl$)_2$.

In some embodiments, $R^3$ is —$NHCH_2CH_2OH$ or —$N(CH_3)CH_2CH_2OH$.

In other embodiments, $R^4$ is halogen, —CN, —$N(R^5)_2$, —OH, —O—($C_1$-$C_6$ alkylene)-OH, —$S(O)_m$($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.

In some embodiments, the compound has the structure of formula (VII):

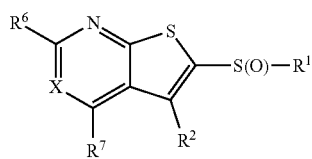

(VII)

or a pharmaceutically acceptable salt, tautomer, or solvate thereof, wherein:
$R^1$ is cyclobutyl or —($C_1$-$C_4$ alkylene)-($C_1$-$C_3$ alkoxy);
$R^2$ is —$NH_2$, CN, or —NHC(O)alkyl;
$R^6$ is heterocyclyl or heteroaryl, each of which is optionally substituted with one or more $R^3$;
$R^7$ is —$CF_3$, isopropyl,

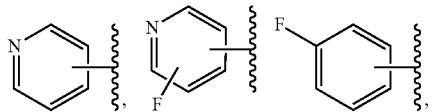

-continued

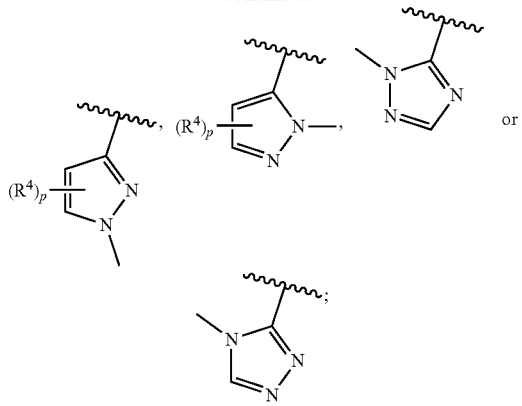

$R^3$ is oxo, —OH, —O-alkylene-OH, —O-alkylene-N$(R^5)_2$, —$N(R^5)_2$, —$N(R^5)$(alkylene-OH), —$N(R^5)$(alkylene-O-alkyl), alkyl, -alkylene-OH, haloalkyl, cycloalkyl, heterocyclyl, —C(O)N$(R^5)_2$, —C(O)N$(R^5)$(alkylene-OH), —C(O)-alkyl, —C(O)O-alkyl, or —$S(O)_m$-alkyl, wherein the cycloalkyl and the heterocyclyl is each optionally substituted with $R^{10}$;
$R^4$ is $C_1$-$C_3$ alkyl;
each $R^5$ is independently, H, alkyl, -alkylene-OH optionally substituted with —OH, -alkylene-$NH_2$, -alkylene-$N(R^9)_2$, -alkylene-O-alkylene-OH, -alkylene-O-alkylene-$NH_2$, —C(O)-alkyl, —C(O)O-alkyl, -alkylene-COOH, or —$S(O)_m$-alkyl;
or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;
$R^8$ is halogen, alkyl, or alkoxy;
$R^9$ is H or alkyl, or two $R^9$ together with the N atom to which they are attached can form a 4- to 7-membered heterocycle, optionally containing an additional heteroatom selected from O, $S(O)_t$, or N;
$R^{10}$ is —OH, halogen, alkyl, or alkoxy;
X is N or CH;
m is 0, 1, or 2;
p is 0 or 1; and
t is 0, 1, or 2.

In still other embodiments, $R^2$ is —$NH_2$.

In some embodiments, $R^6$ is 5- to 6-membered heterocyclcyl or 5- to 10-membered heteroaryl, each of which is optionally substituted with one or more $R^3$.

In other embodiments, $R^6$ is 5- to 6-membered heteroaryl optionally substituted with one or more $R^3$.

In still other embodiments, $R^6$ is 8- to 10-membered bicyclic heteroaryl optionally substituted with one or more $R^3$.

In some embodiments, $R^3$ is —O—($C_1$-$C_6$ alkylene)-N$(R^5)_2$, —$N(R^5)_2$, —$N(R^5)$($C_1$-$C_6$ alkylene-OH), —C(O)N$(R^5)_2$, —C(O)N$(R^5)$($C_1$-$C_6$ alkylene-OH), —C(O)($C_1$-$C_6$ alkyl), —C(O)O($C_1$-$C_6$ alkyl), or —$S(O)_m$($C_1$-$C_6$ alkyl).

In other embodiments, $R^3$ is —($C_1$-$C_3$ alkyl)OH, —$NH_2$, —$N(C_1$-$C_3$ alkyl$)_2$, —$NHCH_2CH_2OH$, —$N(C_1$-$C_3$ alkyl$)CH_2CH_2OH$, $N(CH_2CH_2OH)_2$, —$NHCH_2CH(CH_2OH)_2$, —$N(C_1$-$C_3$ alkyl$)CH_2CH(CH_2OH)_2$, —$NHCH_2CH_2OCH_2CH_2OH$, —$NHCH_2CH_2OCH_2CH_2NH_2$, —$NHCH_2CH_2NH_2$, —$N(C_1$-$C_3$ alkyl$)CH_2CH_2NH_2$, —$NHCH_2CH_2NH(C_1$-$C_3$ alkyl), —$NHCH_2CH_2N(C_1$-$C_3$ alkyl$)_2$, —$N(C_1$-$C_3$ alkyl$)CH_2CH_2NH(C_1$-$C_3$ alkyl), —N(C$_1$-C$_3$ alkyl)CH$_2$CH$_2$N(C$_1$-C$_3$ alkyl)$_2$, —NHSO$_2$CH$_3$, —N(C$_1$-C$_3$ alkyl)SO$_2$CH$_3$, —OCH$_2$CH$_2$OH, —OCH$_2$CH$_2$NH$_2$, —OCH$_2$CH$_2$NH(C$_1$-C$_3$ alkyl), or —OCH$_2$CH$_2$N(C$_1$-C$_3$ alkyl)$_2$.

In still other embodiments, R$^3$ is —NHCH$_2$CH$_2$OH or —N(CH$_3$)CH$_2$CH$_2$OH.

In some embodiments, R$^4$ is halogen, —CN, —N(R$^5$)$_2$, —OH, —O—(C$_1$-C$_6$ alkylene)-OH, —S(O)$_m$(C$_1$-C$_6$ alkyl), —C(O)(C$_1$-C$_6$ alkyl), —C(O)-(3- to 6-membered cycloalkyl), C$_1$-C$_6$ alkyl, C$_1$-C$_6$ haloalkyl, 3- to 6-membered cycloalkyl, or 3- to 6-membered heterocyclyl.

In some embodiments, n is 1.

In some embodiments, the compound has the structure of formula (VIII):

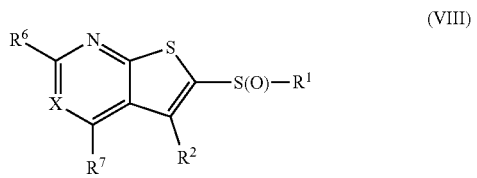

(VIII)

or a pharmaceutically acceptable salt, tautomer, or solvate thereof, wherein:
R$^1$ is cyclobutyl or —(C$_1$-C$_4$ alkylene)-(C$_1$-C$_3$ alkoxy);
R$^2$ is —NH$_2$, CN, or —NHC(O)alkyl;
R$^6$ is

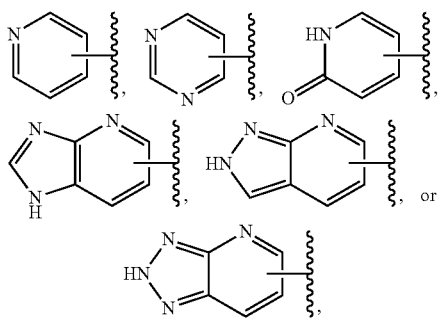

each of which is optionally substituted with one or more R$^3$;
R$^7$ is —CF$_3$, isopropyl, cyclopropyl, cyclobutyl,

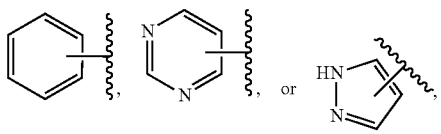

each of which is optionally substituted with one or more R$^4$;
R$^3$ is —NH$_2$, —NH(C$_1$-C$_3$ alkyl), —NH(C$_1$-C$_4$ alkylene)-OH, or C$_1$-C$_3$ alkyl;
R$^4$ is C$_1$-C$_3$ alkyl; and
X is N or CH.

In some embodiments of Formula (VIII), R$^1$ is cyclobutyl. In some embodiments of Formula (VIII), R$^1$—(C$_1$-C$_4$ alkylene)-(C$_1$-C$_3$ alkoxy). In some embodiments of Formula (VIII), the R$^1$—(C$_1$-C$_4$ alkylene)-(C$_1$-C$_3$ alkoxy) is —(C$_2$-C$_3$ alkylene)-(C$_1$ alkoxy).

In some embodiments of Formula (VIII), R$^2$ is —NH$_2$.

In some embodiments of Formula (VIII), R$^6$ is

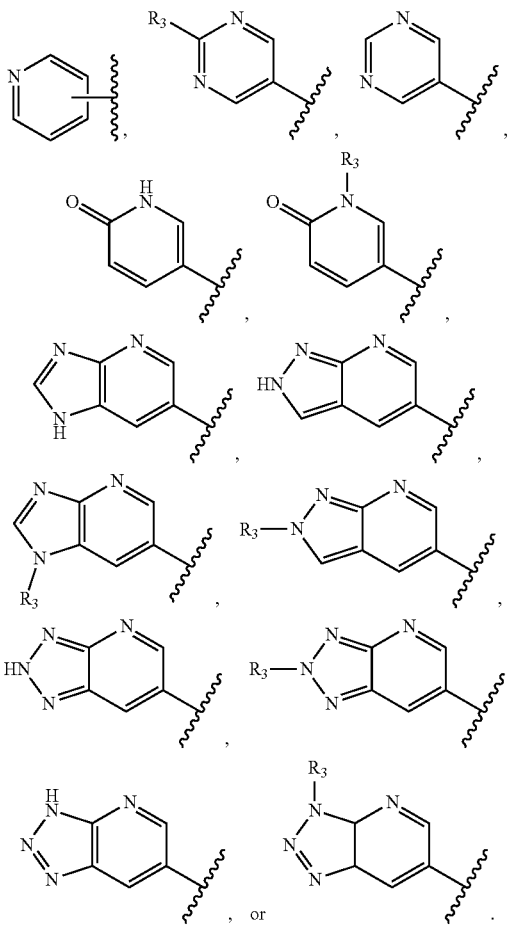

In some embodiments of Formula (VIII), R$^3$ is —NH$_2$. In some embodiments of Formula (VIII), R$^3$ is —NH(C$_1$-C$_3$ alkyl). In some embodiments of Formula (VIII), R$^3$ is —NH(C$_1$-C$_4$ alkylene)-OH (e.g., —NH(C$_2$-C$_4$ alkylene)-OH). In some embodiments of Formula (VIII), R$^3$ is C$_1$-C$_3$ alkyl (e.g., methyl or ethyl).

In some embodiments, of Formula (VIII), R$^7$ is —CF$_3$, isopropyl, cyclopropyl, or cyclobutyl. In some embodiments, of Formula (VIII), R$^7$ is isopropyl. In some embodiments of Formula (VII), R$^7$ is

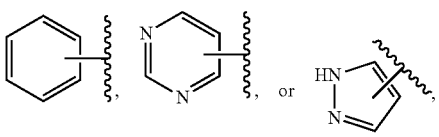

each of which is optionally substituted with one or more R$^4$. In some embodiments, each R$^4$ is independently selected from methyl or ethyl.

In some embodiments of Formula (VIII), X is —CH.

In some embodiments, the compounds of Formula (VIII) are provided in Table 2.

In one embodiment, the compounds of Formula (VIII) excludes:

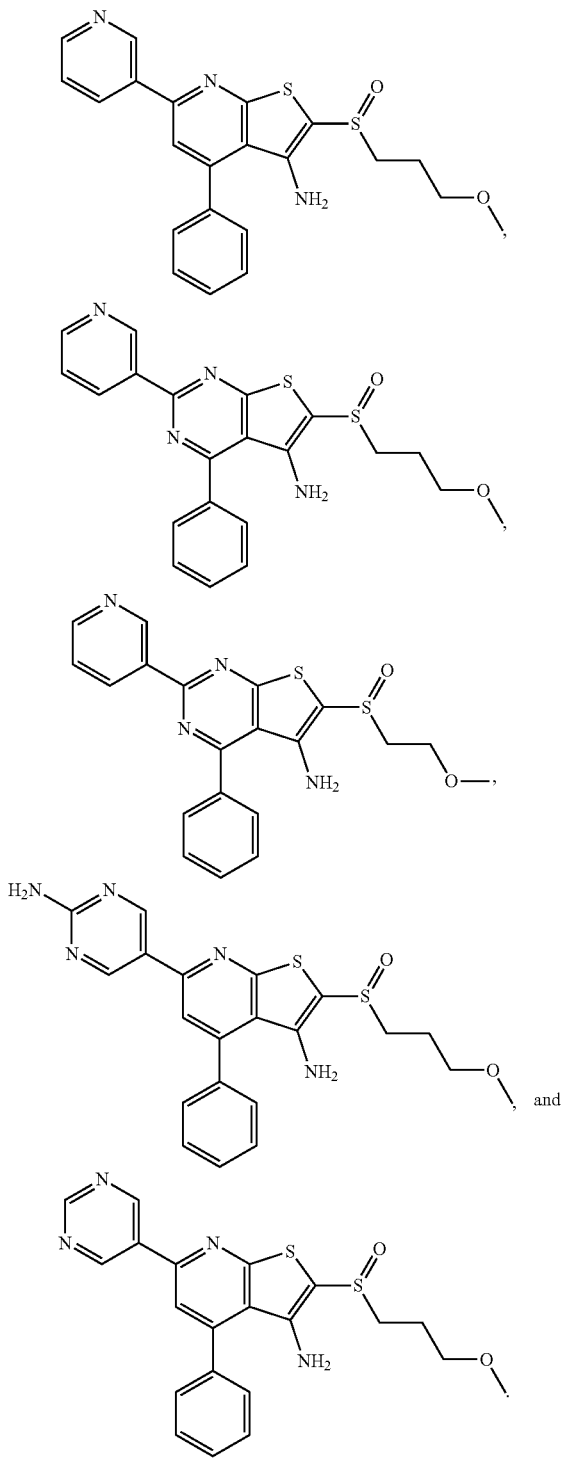

In some embodiments, the 15-PGDH inhibitor of the present disclosure inhibit colon 15-PGDH activity in a range of from about 25% to 100%, e.g., about 25%, about 30%, about 35%, about 40%, about 45%, about 50%, about 55%, about 60%, about 65%, about 70%, about 75%, about 80%, about 85%, about 90%, about 95%, or about 100%, and any subranges therein. Colon 15-PGDH inhibition can be measured (e.g., with the assay described in this present examples) using an appropriate dose of the compounds of the present disclosure, at 30 min, 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 15 hours, 20 hours, 24 hours, 48 hours, 72 hours, or more hours after administration, including all times between these values. In some embodiments, colon 15-PGDH inhibition is measured at 30 minutes after admin strati on. In particular embodiments, colon 15-PGDH inhibition is measured at 4 hours. In some embodiments, the appropate dose is 1 2, 3, 4, 5, 6, 7, 8, 9, 0 15, 20, 30, 40, 50, or more mg/kg, including all values and ranges in between these values.

In one embodiment, lung, liver, intestines, the skin, heart (or any other organ disclosed herein) 15-PGDH inhibition can be measured using an appropriate dose of the compounds of the present disclosure, at 30 min, 1 hour, 1.5 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 15 hours, 20 hours, 24 hours, 48 hours, 72 hours, or more, including all times and ranges in between these values. In some embodiments, lung 15-PGDH inhibition is measured at 30 minutes. In particular embodiments, lung 15-PGDH inhibition is measured at 4 hours. In some embodiments, the appropriate dose is 1 2, 3, 4, 5, 6, 7, 8, 9, 0 15, 20, 30, 40, 50, or more mg/kg, including all values and ranges in between these values. In some embodiments, the 15-PGDH inhibitor of the present disclosure inhibit lung 15-PGDH activity in a range of from about 25% to 100%, e.g., about 25%, about 30%, about 35%, about 40%, about 45%, about 50%, about 55%, about 60%, about 65%, about 70%, about 75%, about 80%, about 85%, about 90%, about 95%, or about 100%, and any subranges therein.

In some embodiments, the 15-PGDH inhibitor of the present disclosure (e.g., having formula I-VIII), is administered at 10 mg/kg in a mammal and inhibits colon 15-PGDH activity at 30 minutes in a range of about 25% to 100%, e.g., about 25%, about 30%, about 35%, about 40%, about 45%, about 50%, about 55%, about 60%, about 65%, about 70%, about 75%, about 80%, about 85%, about 90%, about 95%, or about 100%, and any subranges therein. In some embodiments, the compounds of the present disclosure, when administered at 10 mg/kg in a mammal, inhibit colon 15-PGDH activity at 30 minutes in a range of about 65% to 100% (e.g., about 65%, about 70%, about 75%, about 80%, about 85%, about 90%, about 95%, or about 100%), and any subranges therein. In some embodiments, the compounds of the present disclosure when administered at 10 mg/kg in a mammal can inhibit colon 15-PGDH activity at 30 minutes in a range of about 70% to 100% (e.g., about 70%, about 75%, about 80%, about 85%, about 90%, about 95%, or about 100%), and any subranges therein. In some embodiments, the compounds of the present disclosure, when administered at 10 mg/kg in a mammal, inhibit colon 15-PGDH activity at 30 minutes in a range of about 80% to 100%, and any subranges therein. In some embodiments, the compounds of the present disclosure, when administered at 10 mg/kg in a mammal, inhibit colon 15-PGDH activity at 30 minutes in a range of about 90% to 100%, and any subranges therein. In some embodiments, the compounds of the present disclosure, when administered at 10 mg/kg in a mammal, inhibit colon 15-PGDH activity at 30 minutes in a range of about 95% to 100%, and any subranges therein. This is a unexpected and surprising result, as previously synthesized 15-PGDH inhibitors, such as Reference Compound C (Example B), when given orally at 10 mpk was not sufficiently potent to inhibit colon 15-PGDH activity at 30 minutes. In fact, Reference Compound C actually increased activity colon 15-PGDH activity, as indicated by the −55.2% inhibition.

In some embodiments, the 15-PGDH inhibitor of the present disclosure (e.g., having formula I-VIII), is administered at 10 mg/kg in a mammal and inhibits colon 15-PGDH activity at 4 hours in a range of about 25% to 100%, e.g., about 25%, about 30%, about 35%, about 40%, about 45%, about 50%, about 55%, about 60%, about 65%, about 70%, about 75%, about 80%, about 85%, about 90%, about 95%, or about 100%, and any subranges therein. In some embodiments, the compounds of the present disclosure, when administered at 10 mg/kg in a mammal, inhibit colon 15-PGDH activity at 4 hours in a range of about 65% to 100% (e.g., about 65%, about 70%, about 75%, about 80%, about 85%, about 90%, about 95%, or about 100%), and any subranges therein. In some embodiments, the compounds of the present disclosure when administered at 10 mg/kg in a mammal can inhibit colon 15-PGDH activity at 4 hours in a range of about 70% to 100% (e.g., about 70%, about 75%, about 80%, about 85%, about 90%, about 95%, or about 100%), and any subranges therein. In some embodiments, the compounds of the present disclosure, when administered at 10 mg/kg in a mammal, inhibit colon 15-PGDH activity at 4 hours in a range of about 80% to 100%, and any subranges therein. In some embodiments, the compounds of the present disclosure, when administered at 10 mg/kg in a mammal, inhibit colon 15-PGDH activity at 4 hours in a range of about 80% to 98%, and any subranges therein.

In some embodiments, the 15-PGDH inhibitor of the present disclosure (e.g., having formula I-VIII), is administered at 10 mg/kg in a mammal and inhibits lung, liver, intestines, the skin, heart (or any other organ disclosed herein) 15-PGDH activity at 30 minutes in a range of about 25% to 100%, e.g., about 25%, about 30%, about 35%, about 40%, about 45%, about 50%, about 55%, about 60%, about 65%, about 70%, about 75%, about 80%, about 85%, about 90%, about 95%, or about 100%, and any subranges therein. In some embodiments, the compounds of the present disclosure, when administered at 10 mg/kg in a mammal, inhibit lung 15-PGDH activity at 30 minutes in a range of about 65% to 100% (e.g., about 65%, about 70%, about 75%, about 80%, about 85%, about 90%, about 95%, or about 100%), and any subranges therein. In some embodiments, the compounds of the present disclosure when administered at 10 mg/kg in a mammal can inhibit lung 15-PGDH activity at 30 minutes in a range of about 70% to 100% (e.g., about 70%, about 75%, about 80%, about 85%, about 90%, about 95%, or about 100%), and any subranges therein. In some embodiments, the compounds of the present disclosure, when administered at 10 mg/kg in a mammal, inhibit lung 15-PGDH activity at 30 minutes in a range of about 80% to 100%, and any subranges therein.

In some embodiments, the 15-PGDH inhibitor of the present disclosure (e.g., having formula I-VIII), is administered at 10 mg/kg in a mammal and inhibits lung, liver, intestines, the skin, heart (or any other organ disclosed herein) 15-PGDH activity at 4 hours in a range of about 25% to 100%, e.g., about 25%, about 30%, about 35%, about 40%, about 45%, about 50%, about 55%, about 60%, about 65%, about 70%, about 75%, about 80%, about 85%, about 90%, about 95%, or about 100%, and any subranges therein. In some embodiments, the compounds of the present disclosure, when administered at 10 mg/kg in a mammal, inhibit lung 15-PGDH activity at 4 hours in a range of about 65% to 100% (e.g., about 65%, about 70%, about 75%, about 80%, about 85%, about 90%, about 95%, or about 100%), and any subranges therein. In some embodiments, the compounds of the present disclosure when administered at 10 mg/kg in a mammal can inhibit lung 15-PGDH activity at 4 hours in a range of about 70% to 100% (e.g., about 70%, about 75%, about 80%, about 85%, about 90%, about 95%, or about 100%), and any subranges therein. In some embodiments, the compounds of the present disclosure, when administered at 10 mg/kg in a mammal, inhibit lung 15-PGDH activity at 4 hours in a range of about 80% to 100%, and any subranges therein.

In some embodiments, the 15-PGDH inhibitors of the present disclosure (e.g., formula I-VIII) have a human microsome stability $T_{1/2}$ of greater than 50 minutes. In some embodiments, the compounds of the present disclosure has a human microsome stability $T_{1/2}$ of greater than 60 minutes. In some embodiments, the 15-PGDH inhibitors of the present disclosure have a human microsome stability $T_{1/2}$ of greater than 70 minutes. In some embodiments, the 15-PGDH inhibitors of the present disclosure have a human microsome stability $T_{1/2}$ of greater than 80 minutes. In some embodiments, the 15-PGDH inhibitors of the present disclosure have a human microsome stability $T_{1/2}$ of greater than 90 minutes. In some embodiments, the 15-PGDH inhibitors of the present disclosure have a human microsome stability $T_{1/2}$ of greater than 100 minutes. In some embodiments, the compounds of the present disclosure has a human microsome stability $T_{1/2}$ of greater than 110 minutes. In some embodiments, the 15-PGDH inhibitors of the present disclosure have a human microsome stability $T_{1/2}$ of greater than 120 minutes. In some embodiments, the 15-PGDH inhibitors of the present disclosure have a human microsome stability $T_{1/2}$ of greater than 130 minutes. In some embodiments, the 15-PGDH inhibitors of the present disclosure have a human microsome stability $T_{1/2}$ of greater than 145 minutes. In some embodiments, the 15-PGDH inhibitors of the present disclosure have a human microsome stability $T_{1/2}$ ranging from 65 to at least 145 (e.g., 65, 70, 80, 90, 100, 110, 120, 130, 140, 150, 160, 170, 180, 190, 200, or more, including all values and ranges therebetween).

In some embodiments, the 15-PGDH inhibitors of the present disclosure (e.g., formula I-VIII) have better human microsome stability compared to previously disclosed 15-PGDH inhibitors. See WO 2013/158649, WO 2015/065716, WO 2016/144958, WO 2016/168472, WO 2018/017582, WO 2018/102552, WO 2018/145080, WO 2018/187810, and WO 2018/218251, the disclosures of each are hereby incorporated by reference in their entireties for all purposes. In some embodiments, the 15-PGDH inhibitors of the present disclosure have a human microsome stability $T_{1/2}$ which is at least 15 minutes longer than previously disclosed 15-PGDH inhibitors. In some embodiments, the 15-PGDH inhibitors of the present disclosure have a human microsome stability $T_{1/2}$ which is at least 25 minutes longer than previously disclosed 15-PGDH inhibitors. In some embodiments, the 15-PGDH inhibitors of the present disclosure have a human microsome stability $T_{1/2}$ which is at least 35 minutes longer than previously disclosed 15-PGDH inhibitors. In some embodiments, the 15-PGDH inhibitors of the present disclosure have a human microsome stability $T_{1/2}$ which is at least 45 minutes longer than previously disclosed 15-PGDH inhibitors. In some embodiments, the 15-PGDH inhibitors of the present disclosure have a human microsome stability $T_{1/2}$ which is at least 55 minutes longer than previously disclosed 15-PGDH inhibitors. In some embodiments, the 15-PGDH inhibitors of the present disclosure have a human microsome stability $T_{1/2}$ which is at least 65 minutes longer than previously disclosed 15-PGDH inhibitors. In some embodiments, the 15-PGDH inhibitors of the present disclosure have a human microsome stability $T_{1/2}$ which is at least 75 minutes longer than previously disclosed 15-PGDH inhibitors. In some embodiments, the 15-PGDH inhibitors of the present disclosure have a human microsome stability $T_{1/2}$ which is at least 85 minutes longer than previously disclosed 15-PGDH inhibitors. In some embodiments, the 15-PGDH inhibitors of the present disclosure have human microsome stability $T_{1/2}$ which is at least 95 minutes longer than previously disclosed 15-PGDH inhibitors. In some embodiments, the 15-PGDH inhibitors of the present disclosure have a human microsome stability $T_{1/2}$ which is at least 100 minutes longer than previously disclosed 15-PGDH inhibitors. In some embodiments, the 15-PGDH inhibitors of the present disclosure have a human microsome stability $T_{1/2}$ which is at least 110 minutes longer than previously disclosed 15-PGDH inhibitors. In some embodiments, the 15-PGDH inhibitors of the present disclosure have a human microsome stability $T_{1/2}$ which is at least 120 minutes longer than previously disclosed 15-PGDH inhibitors. In some embodiments, the 15-PGDH inhibitors of the present disclosure have a human microsome stability $T_{1/2}$ ranging that is from 15 minutes to about 120 minutes longer than the microsome stability $T_{1/2}$ of previously disclosed 15-PGDH inhibitors.

In some embodiments, the 15-PGDH inhibitors of the present disclosure (e.g., formula I-VIII) have a human microsome stability $T_{1/2}$ which is at least 40 minutes longer than Reference Compound C (Example B). In some embodiments, the 15-PGDH inhibitors of the present disclosure have a human microsome stability $T_{1/2}$ which is at least 70 minutes longer than Reference Compound C. In some embodiments, the 15-PGDH inhibitors of the present disclosure have a human microsome stability $T_{1/2}$ which is at least 80 minutes longer than Reference Compound C. In some embodiments, the 15-PGDH inhibitors of the present disclosure have a human microsome stability $T_{1/2}$ which is at least 90 minutes longer than Reference Compound C. In some embodiments, the 15-PGDH inhibitors of the present disclosure have a human microsome stability $T_{1/2}$ which is at least 100 minutes longer than Reference Compound C. In some embodiments, the 15-PGDH inhibitors of the present disclosure have a human microsome stability $T_{1/2}$ which is at least 110 minutes longer than Reference Compound C. In some embodiments, the 15-PGDH inhibitors of the present disclosure have a human microsome stability $T_{1/2}$ which is at least 120 minutes longer than Reference Compound C. In some embodiments, the 15-PGDH inhibitors of the present disclosure have a human microsome stability $T_{1/2}$ ranging that is from 70 minutes to about 120 minutes longer than Reference Compound C.

In some embodiments, the 15-PGDH inhibitors of the present disclosure (e.g., formula I-VIII) have a mouse microsome stability $T_{1/2}$ of greater than 10 minutes. In some embodiments, the 15-PGDH inhibitors of the present disclosure have a mouse microsome stability $T_{1/2}$ of greater than 50 minutes. In some embodiments, the 15-PGDH inhibitors of the present disclosure have mouse microsome stability $T_{1/2}$ of greater than 60 minutes. In some embodiments, the 15-PGDH inhibitors of the present disclosure have a mouse microsome stability $T_{1/2}$ of greater than 70 minutes. In some embodiments, the 15-PGDH inhibitors of the present disclosure have a mouse microsome stability $T_{1/2}$ of greater than 80 minutes. In some embodiments, the 15-PGDH inhibitors of the present disclosure have a mouse microsome stability $T_{1/2}$ of greater than 90 minutes. In some embodiments, the 15-PGDH inhibitors of the present disclosure have a mouse microsome stability $T_{1/2}$ of greater than 100 minutes. In some embodiments, the 15-PGDH inhibitors of the present disclosure have a mouse microsome stability $T_{1/2}$ of greater than 110 minutes. In some embodiments, the 15-PGDH inhibitors of the present disclosure have a mouse microsome stability $T_{1/2}$ of greater than 120 minutes. In some embodiments, the 15-PGDH inhibitors of the present disclosure have a mouse microsome stability $T_{1/2}$ of greater than 130 minutes. In some embodiments, the 15-PGDH inhibitors of the present disclosure have a mouse microsome stability $T_{1/2}$ of greater than 140 minutes. In some embodiments, the 15-PGDH inhibitors of the present disclosure have a mouse microsome stability $T_{1/2}$ of greater than 145 minutes. In some embodiments, the 15-PGDH inhibitors of the present disclosure have a mouse microsome stability $T_{1/2}$ ranging from 65 to at least 145 (e.g., 65, 70, 80, 90, 100, 110, 120, 130, 140, 150, 160, 170, 180, 190, 200, or more, including all values and ranges therebetween).

In some embodiments, the 15-PGDH inhibitors of the present disclosure (e.g., formula I-VIII) have a mouse microsome stability $T_{1/2}$ which is at least 10 minutes longer than Reference Compound C (Example B). In some embodiments, the 15-PGDH inhibitors of the present disclosure have a mouse microsome stability $T_{1/2}$ which is at least 20 minutes longer than Reference Compound C. In some embodiments, the 15-PGDH inhibitors of the present disclosure have a mouse microsome stability $T_{1/2}$ which is at least 30 minutes longer than Reference Compound C. In some embodiments, the 15-PGDH inhibitors of the present disclosure have a mouse microsome stability $T_{1/2}$ which is at least 40 minutes longer than Reference Compound C. In some embodiments, the 15-PGDH inhibitors of the present disclosure have a mouse microsome stability $T_{1/2}$ which is at least 50 minutes longer than Reference Compound C. In some embodiments, the 15-PGDH inhibitors of the present disclosure have a mouse microsome stability $T_{1/2}$ which is at least 60 minutes longer than Reference Compound C. In some embodiments, the 15-PGDH inhibitors of the present disclosure have a mouse microsome stability $T_{1/2}$ which is at least 70 minutes longer than Reference Compound C. In some embodiments, the 15-PGDH inhibitors of the present disclosure have a mouse microsome stability $T_{1/2}$ which is at least 80 minutes longer than Reference Compound C. In some embodiments, the 15-PGDH inhibitors of the present disclosure have a mouse microsome stability $T_{1/2}$ which is at least 90 minutes longer than Reference Compound C. In some embodiments, the 15-PGDH inhibitors of the present disclosure have a mouse microsome stability $T_{1/2}$ which is at least 100 minutes longer than Reference Compound C. In some embodiments, the 15-PGDH inhibitors of the present disclosure have a mouse microsome stability $T_{1/2}$ which is at least 110 minutes longer than Reference Compound C. In some embodiments, the 15-PGDH inhibitors of the present disclosure have a mouse microsome stability $T_{1/2}$ which is at least 120 minutes longer than Reference Compound C. In some embodiments, the 15-PGDH inhibitors of the present disclosure have a mouse microsome stability $T_{1/2}$ which is at least 130 minutes longer than Reference Compound C. In some embodiments, the 15-PGDH inhibitors of the present disclosure have a mouse microsome stability $T_{1/2}$ which is at least 140 minutes longer than Reference Compound C. In some embodiments, the 15-PGDH inhibitors of the present disclosure have a mouse microsome stability $T_{1/2}$ that is from 65 to at least 145 longer than Reference Compound C (e.g., 65, 70, 80, 90, 100, 110, 120, 130, 140, 150, 160, 170, 180, 190, 200, or more, including all values and ranges therebetween).

The $EC_{50}$ for induction of PGE2 is determined using A549 cells that have been treated with IL1-β 24 hours. In some embodiments, the 15-PGDH inhibitors of the present disclosure (e.g., formula I-VIII) have an $EC_{50}$ for induction of PGE2 that is less than or equal to 10 nM. In some embodiments, the $EC_{50}$ is less than or equal to 5 nM. In some embodiments, the $EC_{50}$ is less than or equal to 4 nM. In some embodiments, the $EC_{50}$ is less than or equal to 3 nM. In some embodiments, the $EC_{50}$ is less than or equal to 2 nM. In some embodiments, the $EC_{50}$ is less than or equal to 1 nM. In some embodiments, the $EC_{50}$ is from 10 nM to about 0.01 nM including all values and subranges in between these values). In some embodiments, the $EC_{50}$ is at least 4 times less than the previously disclosed 15-PGDH inhibitors, such as those disclosed in the publications referenced above. In some embodiments, the $EC_{50}$ is at least 8 times less than the previously disclosed 15-PGDH inhibitors. In some embodiments, the $EC_{50}$ is at least 10 times less than the previously disclosed 15-PGDH inhibitors. In some embodiments, the $EC_{50}$ is at least 15 times less than the previously disclosed 15-PGDH inhibitors. In some embodiments, the $EC_{50}$ is at least 20 times less than the previously disclosed 15-PGDH inhibitors. In some embodiments, the $EC_{50}$ is at least 30 times less than the previously disclosed 15-PGDH inhibitors. In some embodiments, the $EC_{50}$ is at least 40 times less than the previously disclosed 15-PGDH inhibitors. In some embodiments, the $EC_{50}$ is at least 50 times less than the previously disclosed 15-PGDH inhibitors. In some embodiments, the $EC_{50}$ is 10 times to 50 times less than the previously disclosed 15-PGDH inhibitors.

In some embodiments, the $EC_{50}$ of the 15-PGDH inhibitors of the present disclosure (e.g., formula I-VIII) is at least 5 times less than Reference Compound C (Example B). In some embodiments, the $EC_{50}$ is at least 10 times less than Reference Compound C. In some embodiments, the $EC_{50}$ is at least 15 times less than Reference Compound C. In some embodiments, the $EC_{50}$ is at least 20 times less than Reference Compound C. In some embodiments, the $EC_{50}$ is at least 25 times less than Reference Compound C. In some embodiments, the $EC_{50}$ is at least 30 times less than Reference Compound C. In some embodiments, the $EC_{50}$ is at least 35 times less than Reference Compound C. In some embodiments, the $EC_{50}$ is at least 40 times less than Reference Compound C. In some embodiments, the $EC_{50}$ is at least 45 times less than Reference Compound C. In some embodiments, the $EC_{50}$ is at least 50 times less than Reference Compound C. In some embodiments, the $EC_{50}$ is 5 times to 50 times less than Reference Compound C.

In certain embodiments, the 15-PGDH inhibitor having formula (I-VIII), can be selected that can ia) at 2.5 μM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 μM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-renilla luciferase reporter to a level greater than 20; and va) inhibits the enzymatic activity of recombinant 15-PGDH protein at an $IC_{50}$ of less than 1 μM.

In other embodiments, the 15-PGDH inhibitor can ib) at 2.5 μM concentration, stimulate a Vaco503 reporter cell line expressing a 15-PGDH luciferase fusion construct to increase luciferase output; iib) at 2.5 μM concentration stimulate a V9m reporter cell line expressing a 15-PGDH luciferase fusion construct to increase luciferase output; iiib) at 7.5 μM concentration stimulate a LS174T reporter cell line expressing a 15-PGDH luciferase fusion construct to increase luciferase output; ivb) at 7.5 μM concentration, does not activate a negative control V9m cell line expressing TK-renilla luciferase reporter to a luciferase level greater than 20% above background; and vb) inhibits the enzymatic activity of recombinant 15-PGDH protein at an $IC_{50}$ of less than 1 μM.

In some embodiments, the compound or 15-PGDH inhibitor can inhibit the enzymatic activity of recombinant 15-PGDH at an $IC_{50}$ of less than 1 μM, at an $IC_{50}$ of less than 250 nM, at an $IC_{50}$ of less than 50 nM, at an $IC_{50}$ of less than 10 nM, at an $IC_{50}$ of less than 5 nM at a recombinant, at an $IC_{50}$ of about 2.5 nM to about 10 nM, or less than about 2.5 nM at a 15-PGDH concentration of about 5 nM to about 10 nM.

The 15-PGDH inhibitors described herein can be used for the prevention or the treatment of diseases that are associated with 15-PGDH and/or decreased prostaglandin levels and/or where it desirable to increase prostaglandin levels in the subject. For example, as discussed above, it is known that prostaglandins play an important role in hair growth. Specifically, internal storage of various types ($A_2$, $F_{2a}$, $E_2$) of prostaglandins in the various compartments of hair follicles or their adjacent skin environments has been shown to be essential in maintaining and increasing hair density (Colombe L et. al, 2007, Exp. Dermatol, 16(9), 762-9). It has been reported that 15-PGDH, which is involved in the degradation of prostaglandins is present in the hair follicle dermal papillae, inactivates prostaglandins, especially, $PGF_{2a}$ and $PGE_2$, to cause scalp damage and alopecia (Michelet J F et. al., 2008, Exp. Dermatol, 17(10), 821-8). Thus, the compounds described herein, which have a suppressive or inhibitory activity against 15-PGDH that degrades prostaglandins, can improve scalp damage, prevent alopecia and promote hair growth and be used in a pharmaceutical composition for the prevention of alopecia and the promotion of hair growth.

In other embodiments, the 15-PGDH inhibitors described herein can be used in a pharmaceutical composition for promoting and/or inducing and/or stimulating pigmentation of the skin and/or skin appendages, and/or as an agent for preventing and/or limiting depigmentation and/or whitening of the skin and/or skin appendages, in particular as an agent for preventing and/or limiting canities.

In some embodiments, the 15-PGDH inhibitor can be applied to skin of a subject, e.g., in a topical application, to promote and/or stimulate pigmentation of the skin and/or hair growth, inhibit hair loss, and/or treat skin damage or inflammation, such as skin damage caused by physical or chemical irritants and/or UV-exposure.

In still other embodiments, the 15-PGDH inhibitors described herein can be used in a pharmaceutical composition for the prevention or the treatment of cardiovascular disease and/or diseases of vascular insufficiency, such as Raynaud's disease, Buerger's disease, diabetic neuropathy, and pulmonary artery hypertension. Prostaglandins including prostaglandin homologues produced in the body have been known to maintain the proper action of the blood vessel wall, especially to contribute to vasodilation for blood flow, preventing platelet aggregation and modulating the proliferation of smooth muscle that surrounds blood vessel walls (Yan. Cheng et. al., 2006, J. Clin., Invest). In addition, the inhibition of prostaglandins production or the loss of their activity causes the degeneration of the endothelium in the blood vessel walls, platelet aggregation and the dysfunction of cellular mechanism in the smooth muscle. Among others, the production of prostaglandins in blood vessels was shown to be decreased in hypertension patients, including pulmonary artery hypertension.

In other embodiments, the 15-PGDH inhibitors described herein can be used in a pharmaceutical composition for the prevention or the treatment of oral, intestinal, and/or gastrointestinal injury or diseases, or inflammatory bowel disease, such as oral ulcers, gum disease, gastritis, colitis, ulcerative colitis, and gastric ulcers. Gastritis and gastric ulcer, representatives of the gastrointestinal diseases, are defined as the conditions where gastrointestinal mucus membrane is digested by gastric acid to form ulcer. In stomach walls generally consisting of mucosa, submucosa, muscle layer and serosa, gastric ulcer even damages submucosa and muscle layer, while gastritis damages mucosa only. Although the morbidity rates of gastritis and gastric ulcer are relatively high, the causes thereof have not been clarified yet. Until now, they are known to be caused by an imbalance between aggressive factors and defensive factors, i.e., the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect, gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). In view of the above, since the 15-PGDH inhibitors described herein show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

Moreover, 15-PGDH inhibitors would also be expected to protect from other forms of intestinal injury, such as toxicity from radiation, toxicity from chemotherapy, and chemotherapy induced mucositis.

In the kidney, prostaglandins modulate renal blood flow and may serve to regulate urine formation by both renovascular and tubular effects. In clinical studies, $PGE_1$ has been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy (see Porter, Am., 1989, J. Cardiol., 64: 22E-26E). In addition, U.S. Pat. No. 5,807,895 discloses a method of preventing renal dysfunction by intravenous administration of prostaglandins such as $PGE_1$, $PGE_2$ and $PGI_2$. Furthermore, it has been reported that prostaglandins serve as vasodilators in the kidney, and, thus, the inhibition of prostaglandin production in the kidney results in renal dysfunction (Hao. C M, 2008, Annu Rev Physiol, 70, 357.about.77).

Thus, the 15-PGDH inhibitors described herein, which have a suppressive or inhibitory activity against 15-PGDH that degrades prostaglandins, may be effective in the prevention or the treatment of renal diseases that are associated with renal dysfunction.

The term "renal dysfunction" as used herein includes such manifestations as follows: lower than normal creatinine clearance, lower than normal free water clearance, higher than normal blood urea, nitrogen, potassium and/or creatinine levels, altered activity of kidney enzymes such as gamma glutamyl synthetase, alanine phosphatidase, N-acetyl-O-D-glucosaminidase, or β-w-microglobulin; and increase over normal levels of macroalbuminuria.

Prostaglandins including $PGE_1$, $PGE_2$ and $PGF_{2a}$ have also been shown to stimulate bone resorption and bone formation to increase the volume and the strength of the bone (H. Kawaguchi et. al., Clinical Orthop. Rel. Res., 313, 1995; J. Keller et al., Eur. Jr. Exp. Musculoskeletal Res., 1, 1992, 8692). Considering that 15-PGDH inhibits the activities of prostaglandins as mentioned above, the inhibition of 15-PGDH activity may lead to the promotion of bone resorption and bone formation that are inhibited by 15-PGDH. Thus, 15-PGDH inhibitors described herein can be effective for the promotion of bone resorption and bone formation by inhibiting 15-PGDH activity. 15-PGDH inhibitors can also be used to increase bone density, treat osteoporosis, promote healing of fractures, or promote healing after bone surgery or joint replacement, or to promote healing of bone to bone implants, bone to artificial implants, dental implants, and bone grafts.

In yet other embodiments, the 15-PGDH inhibitors described herein can be effective for treating 15-PGDH expressing cancers. Inhibition of 15-PGDH can inhibit the growth, proliferation, and metastasis of 15-PGDH expressing cancers.

In still other embodiments, the 15-PGDH inhibitors described herein can be effective for wound healing. Among various prostaglandins, $PGE_2$ is known to serve as a mediator for wound healing. Therefore, when skin is injured by wounds or burns, the inhibition of 15-PGDH activity can produce the treatment effect of the wounds or the burns by $PGE_2$.

Additionally, as discussed above, increased prostaglandin levels have been shown to stimulate signaling through the Wnt signaling pathway via increased beta-catenin mediated transcriptional activity. Wnt signaling is known to be a key pathway employed by tissue stem cells. Hence, 15-PGDH inhibitors described herein may be utilized to increase tissue stem cell numbers for purposes that would include promoting tissue regeneration or repair in organs that would include liver, colon, and bone marrow. In addition, 15-PGDH inhibitors described herein may be utilized to promote tissue regeneration or repair in additional organs that would include but are not limited to brain, eye, cornea, retina, lung, heart, stomach, small intestine, pancreas, beta-cells of the pancreas, kidney, bone, cartilage, peripheral nerve.

Syndromic conditions, traumatic injuries, chronic conditions, medical interventions, or other conditions that cause or are associated with tissue damage and a need tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the methods of the present disclosure, include, ischemia resulting from surgery, chemotherapy, radiation therapy, or cell, tissue, or organ transplant or graft.

In various embodiments, the methods described herein are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In some embodiments, the ischemia is associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In some embodiments, the 15-PGDH inhibitor can be administered to a preparation of hematopoietic stem cells, such as peripheral blood hematopoietic stem cells or umbilical cord stem cells of the subject, to increase the fitness of the stem cell preparation as a donor graft or to decrease the number of units of umbilical cord blood required for transplantation.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al, U.S. Pat. No. 5,635,387; McGlave, et al, U.S. Pat. No. 5,460,964; Simmons, P., et al, U.S. Pat. No. 5,677,136; Tsukamoto, et al, U.S. Pat. No. 5,750,397; Schwartz, et al, U.S. Pat. No. 5,759,793; DiGuisto, et al, U.S. Pat. No. 5,681,599; Tsukamoto, et al, U.S. Pat. No. 5,716,827). Hematopoietic stem cells (HSCs) give rise to committed hematopoietic progenitor cells (HPCs) that are capable of generating the entire repertoire of mature blood cells over the lifetime of an organism.

Hematopoietic stem cells and hematopoietic progenitor cells are described herein generally as hematopoietic stem cells or hematopoietic stem and progenitor cells (HSPCs) unless noted otherwise and can refer to cells or populations identified by the presence of the antigenic marker CD34 (CD34$^+$). In some embodiments, the hematopoietic stem cells can be identified by the presence of the antigenic marker CD34 and the absence of lineage (lin) markers and are therefore characterized as CD34$^+$/lin$^-$ cells.

The hematopoietic stem cells used in the methods described herein may be obtained from any suitable source of hematopoietic stem and progenitor cells and can be provided as a high purified population of hematopoietic stem cells or as composition that includes about 0.01% to about 100% of hematopoietic stem cells. For example, hematopoietic stem cells may be provided in compositions, such as unfractionated bone marrow (where the hematopoiectic stem cells comprise less than about 1% of the bone marrow cell population), umbilical cord blood, placental blood, placenta, fetal blood, fetal liver, fetal spleen, Wharton's jelly, or mobilized peripheral blood.

Sources of hematopoietic stem cells can be isolated or obtained from an organ of the body containing cells of hematopoietic origin. The isolated cells can include cells that are removed from their original environment. For example, a cell is isolated if it is separated from some or all of the components that normally accompany it in its native state. For example, an "isolated population of cells," an "isolated source of cells," or "isolated hematopoietic stem cells" and the like, as used herein, refer to in vitro or ex vivo separation of one or more cells from their natural cellular environment, and from association with other components of the tissue or organ, i.e., it is not significantly associated with in vivo substances.

Hematopoiectic stem cells can be obtained or isolated from bone marrow of adults, which includes femurs, hip, ribs, sternum, and other bones. Bone marrow aspirates containing hematopoiectic stem cells can be obtained or isolated directly from the hip using a needle and syringe. Other sources of hematopoietic stem cells include umbilical cord blood, placental blood, mobilized peripheral blood, Wharton's jelly, placenta, fetal blood, fetal liver, or fetal spleen. In particular embodiments, harvesting a sufficient quantity of hematopoietic stem cells for use in therapeutic applications may require mobilizing the stem and progenitor cells in the donor.

"Hematopoietic stem cell mobilization" refers to the release of stem cells from the bone marrow into the peripheral blood circulation for the purpose of leukapheresis, prior to stem cell transplantation. By increasing the number of stem cells harvested from the donor, the number of stem cells available for therapeutic applications can be significantly improved. Hematopoietic growth factors, e.g., granulocyte colony stimulating factor (G-CSF) or chemotherapeutic agents often are used to stimulate the mobilization. Commercial stem cell mobilization drugs exist and can be used in combination with G-CSF to mobilize sufficient quantities of hematopoietic stem and progenitor cells for transplantation into a subject. For example, G-CSF and Mozobil (Genzyme Corporation) can be administered to a donor in order to harvest a sufficient number of hematopoietic cells for transplantation. Other methods of mobilizing hematopoietic stem cells would be apparent to one having skill in the art.

In some embodiments, hematopoietic stem cells are obtained from umbilical cord blood. Cord blood can be harvested according to techniques known in the art {see, e.g., U.S. Pat. Nos. 7,147,626 and 7,131,958, herein incorporated by reference for such methodologies).

In one embodiment, hematopoietic stem cells can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

In some embodiments, the hematopoietic stem cells can be administered or contacted ex vivo with one or more 15-PGDH inhibitors described herein to provide a therapeutic composition. In one embodiment, the therapeutic compositions can include a population of hematopoietic stem cells treated ex vivo with a one or more 15-PGDH inhibitor. In certain embodiments, the therapeutic composition comprising the enhanced hematopoietic stem cells is whole bone marrow, umbilical cord blood, or mobilized peripheral blood.

In particular embodiments, the therapeutic composition includes a population of cells, wherein the population of cells is about 95% to about 100% hematopoietic stem cells. The present disclosure contemplates, in part, that using therapeutic compositions of highly purified hematopoietic stem cells, e.g., a composition comprising a population of cells wherein the cells comprise about 95% hematopoietic stem cells, may improve the efficiency of stem cell therapies. Currently practiced methods of transplantations typically use unfractionated mixtures of cells where hematopoietic stem cells comprise less than 1% of the total cell population.

In some embodiments, the therapeutic composition comprises a population of cells, wherein the population of cells comprises less than about 0.1%, 0.5%, 1%, 2%, 5%, 10%, 15%, 20%, 25%, or 30% hematopoietic stem cells. The population of cells in some embodiments comprises less than about 0.1%, 0.5%, 1%, 2%, 5%, 10%, 15%, 20%, 25%, or 30% hematopoietic stem cells. In other embodiments, the population of cells is about 0.1% to about 1%, about 1% to about 3%, about 3% to about 5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% hematopoietic stem cells.

Hematopoietic stem cells in the therapeutic compositions of the present disclosure can be autologous/autogeneic ("self") or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison.

Hematopoietic stem cells for use in the methods of the present disclosure may be depleted of mature hematopoietic cells such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD79, CD56, CD123, and CD235a. A subsequent step can be performed to further purify the population of cells, in which a substrate labeled with antibodies that bind to the $CD34^+$ antigen are used to isolate primitive hematopoietic stem cells. Kits are commercially available for purifying stem and progenitor cells from various cell sources and in particular embodiments, these kits are suitable for use with the methods described herein.

In one embodiment, the amount of hematopoietic stem cells in the therapeutic composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In one embodiment, the amount of hematopoietic stem cells in the therapeutic composition is the amount of hematopoietic stem cells in a partial or single cord of blood, or is at least $0.1\times10^5$ cells/kg of bodyweight, at least $0.5\times10^5$ cells/kg of bodyweight, at least $1\times10^5$ cells/kg of bodyweight, at least $5\times10^5$ cells/kg of bodyweight, at least $10\times10^5$ cells/kg of bodyweight, at least $0.5\times10^6$ cells/kg of bodyweight, at least $0.75\times10^6$ cells/kg of bodyweight, at least $1\times10^6$ cells/kg of bodyweight, at least $1.25\times10^6$ cells/kg of bodyweight, at least $1.5\times10^6$ cells/kg of bodyweight, at least $1.75\times10^6$ cells/kg of bodyweight, at least $2\times10^6$ cells/kg of bodyweight, at least $2.5\times10^6$ cells/kg of bodyweight, at least $3\times10^6$ cells/kg of bodyweight, at least $4\times10^6$ cells/kg of bodyweight, at least $5\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, or at least $30\times10^6$ cells/kg of bodyweight.

Preparations of hematopoietic stem cells administered one or more 15-PGDH inhibitors and/or therapeutic compositions that include hematopoietic stem cells and one or more 15-PGDH inhibitor can be used for improving hematopoietic stem cell transplants and in treating ischemia or ischemia-damaged tissue, and in reducing further damage to ischemic tissue and/or repairing damage to ischemic tissue through cell recruitment, improving vascularization in ischemic tissue, improving tissue regeneration at sites of ischemia, decreasing ischemic tissue necrosis or apoptosis, and/or increasing cell survival at sites of ischemia. In particular embodiments, the preparations of 15-PGDH inhibitor treated hematopoietic stem cells and/or therapeutic compositions of 15-PGDH inhibitors and hematopoietic stem cells are useful to subjects in need of hematopoietic reconstitution, such as subjects that have undergone or are scheduled to undergo myeloablative therapy.

Subjects, which can be treated with the preparations of 15-PGDH inhibitor treated hematopoietic stem cells and/or therapeutic compositions of 15-PGDH inhibitors and hematopoietic stem cells, can include subjects that have or that have been diagnosed with various types of leukemias, anemias, lymphomas, myelomas, immune deficiency disorders, and solid tumors. A subject also includes a human who is a candidate for stem cell transplant or bone marrow transplantation, such as during the course of treatment for a malignant disease or a component of gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects, which can be treated with the preparations of 15-PGDH inhibitor treated hematopoietic stem cells and/or therapeutic compositions of 15-PGDH inhibitors and hematopoietic stem cells, can also include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects may also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction. Other subjects may have disorders caused by an infection (e.g., viral infection, bacterial infection or fungal infection) which causes damage to stem or progenitor cells of the bone marrow.

In addition, subjects suffering from the following conditions can also benefit from treatment using the preparations of 15-PGDH inhibitor treated hematopoietic stem cells and/or therapeutic compositions of 15-PGDH inhibitors and hematopoietic stem cells: lymphocytopenia, lymphorrhea, lymphostasis, erythrocytopenia, erthrodegenerative disorders, erythroblastopenia, leukoerythroblastosis; erythroclasis, thalassemia, myelodysplasia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan Anemia; Sickle cell disease; or Beta thalassemia major.

In other embodiments, the preparations of 15-PGDH inhibitor treated hematopoietic stem cells and/or therapeutic compositions or 15-PGDH inhibitors and hematopoietic stem cells can be used in cell-based therapy for treating ischemic tissue or treating or ameliorating one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene.

In one embodiment, the subject exhibits at least one symptom of an ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present disclosure, include, ischemia resulting from surgery, chemotherapy, radiation therapy, or cell, tissue, or organ transplant or graft.

In various embodiments, the methods described herein are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, the present disclosure contemplates that the therapeutic cell compositions disclosed herein can be used to treat an ischemic tissue in which it is desirable to increase the blood flow, oxygen supply, glucose supply, or supply of nutrients to the tissue.

In some embodiments, the 15-PGDH inhibitor can be administered to a preparation of tissue stem cells, such as neural stem stems, mesenchymal stem cells, or stem cells that can generate other tissues, and/or a preparation of pluripotent stem cells.

In one embodiment, tissue stems cells can be obtained from pluripotent stem cell sources, e.g., iPSCs and ESCs.

In some embodiments, the tissue stem cells and/or pluripotent stem cells can be administered or contacted ex vivo with one or more 15-PGDH inhibitors described herein to provide a therapeutic composition. In one embodiment, the therapeutic compositions of the can include a population of tissue stem cells treated ex vivo with a one or more 15-PGDH inhibitor.

In particular embodiments, the therapeutic composition includes a population of cells, wherein the population of cells is about 95% to about 100% tissue stem cells. The present disclosure contemplates, in part, that using therapeutic compositions of highly purified tissue stem cells, e.g., a composition comprising a population of cells wherein the cells comprise about 95% tissue stem cells, may improve the efficiency of stem cell therapies.

In some embodiments, the therapeutic composition comprises a population of cells, wherein the population of cells comprises less than about 0.1%, 0.5%, 1%, 2%, 5%, 10%, 15%, 20%, 25%, or 30% tissue stem cells. The population of cells in some embodiments comprises less than about 0.1%, 0.5%, 1%, 2%, 5%, 10%, 15%, 20%, 25%, or 30% tissue stem cells. In other embodiments, the population of cells is about 0.1% to about 1%, about 1% to about 3%, about 3% to about 5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% tissue stem cells.

Tissue stem cells in the therapeutic compositions described herein can be autologous/autogeneic or non-autologous relative to a subject to which the therapeutic composition is to be administered.

Preparations of tissue stem cells administered one or more 15-PGDH inhibitors and/or therapeutic compositions that include tissue stem cells and one or more 15-PGDH inhibitor can be used for improving tissue stem cell transplants and in treating damaged tissue, and in reducing further tissue damage tissue and/or potentiating repair to damaged tissue through stem cell recruitment and/or increasing cell survival at sites of tissue damage.

Genetic disorders, syndromic conditions, traumatic injuries, chronic conditions, medical interventions, or other conditions that cause or are associated with tissue damage and a need for tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the methods of the present invention, include, ischemia resulting from surgery, chemotherapy, radiation therapy, or cell, tissue, or organ transplant or graft.

In other embodiments, the 15-PGDH inhibitor can be administered to a bone marrow graft donor or a hematopoietic stem cell donor to increase the fitness of a donor bone marrow graft or a donor hematopoietic stem cell graft.

In other embodiments, the 15-PGDH inhibitor can also be administered to bone marrow of a subject to increase stem cells in the subject or to increase the fitness of the marrow as a donor graft.

In yet other embodiments, the 15-PGDH inhibitor can be administered to a subject to mitigate bone marrow graft rejection, to enhance bone marrow graft engraftment, to enhance engraftment of a hematopoietic stem cell graft, or an umbilical cord blood stem cell graft, to enhance engraftment of a hematopoietic stem cell graft, or an umbilical cord stem cell graft, and/or to decrease the number of units of umbilical cord blood required for transplantation into the subject. The administration can be, for example, following treatment of the subject or the marrow of the subject with radiation therapy, chemotherapy, or immunosuppressive therapy.

In other embodiments, the 15-PGDH inhibitor can be administered to a recipient of a bone marrow transplant, of a hematopoietic stem cell transplant, or of an umbilical cord blood stem cell transplant, in order to decrease the administration of other treatments or growth factors.

In some embodiments, the 15-PGDH inhibitor can be administered to a subject to enhance recovery of neutrophils following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, neutropenias from other bone marrow diseases, drug induced neutropenia, immune neutropenias, idiopathic neutropenia, and following infections with viruses that include, but are not limited to, HIV, CMV, and parvovirus.

In other embodiments, the 15-PGDH inhibitor can be administered to a subject to enhance recovery of platelets following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, thrombocytopenias from other bone marrow diseases, drug induced thrombocytopenia, immune thrombocytopenia, idiopathic thrombocytopenic purpura, idiopathic thrombocytopenia, and following infections with viruses that include, but are not limited to, HIV, CMV, and parvovirus.

In still other embodiments, the 15-PGDH inhibitor can be administered to a subject to enhance recovery of hemoglobin following bone marrow transplantation, following umbilical cord blood transplantation, following transplantation with hematopoietic stem cells, following conventional chemotherapy, following radiation treatment, and in individuals with anemias from diseases that include but are not limited to aplastic anemia, myelodysplasia, myelofibrosis, anemia from other bone marrow diseases, drug induced anemia, immune mediated anemias, anemia of chronic disease, idiopathic anemia, and following infections with viruses that include, but are not limited to, HIV, CMV, and parvovirus.

In some embodiments, the 15-PGDH inhibitor can be administered to a subject to enhance numbers of bone marrow stem cell numbers following bone marrow transplantation, following umbilical cord blood transplantation, following transplantation with hematopoietic stem cells, following conventional chemotherapy, following radiation treatment, in individuals with other bone marrow diseases, in individuals with cytopenias following viral infections, and in individuals with cytopenias.

In other embodiments, the 15-PGDH inhibitor can be administered to a subject to enhance response to cytokines administered to individuals with cytopenias that include but are not limited to neutropenia, thrombocytopenia, lymphocytopenia, and anemia. Cytokines whose responses may be enhanced by 15-PGDH inhibitors described herein include, but are not limited to: G-CSF, GM-CSF, EPO, IL-3, IL-6, TPO, SCF, and TPO-RA (thrombopoietin receptor agonist).

In further embodiments, the 15-PGDH inhibitor can be administered to a subject or to a tissue graft of a subject to mitigate graft rejection, to enhance graft engraftment, to enhance graft engraftment following treatment of the subject or the marrow of the subject with radiation therapy, chemotherapy, or immunosuppressive therapy, to confer resistance to toxic or lethal effects of exposure to radiation, confer resistance to the toxic effect of Cytoxan, the toxic effect of fludarabine, the toxic effect of chemotherapy, or the toxic effect of immunosuppressive therapy, to decrease infection, and/or to decrease pulmonary toxicity from radiation.

In other embodiments, the 15-PGDH inhibitor can be administered to a recipient of a tissue stem cell transplant, including but not limited to a transplant with hematopoietic stem cells, neural stem stems, mesenchymal stem cells, or stem cells for other tissues, so as to accelerate tissue regeneration and repair following the transplant.

In some embodiments, the administration of a 15-PGDH inhibitor can be in combination with G-CSF for the purpose of increasing neutrophils.

In other embodiments, the administration of a 15-PGDH inhibitor can be in combination with a hematopoietic cytokine for the purpose of increasing neutrophils.

In still other embodiments, the administration of a 15-PGDH inhibitor can be in combination with G-CSF for the purpose of increasing numbers of and/or of mobilizing peripheral blood hematopoietic stem cells.

In other embodiments, the administration of a 15-PGDH inhibitor can be in combination with a hemopoietic cytokine for the purpose of increasing numbers of and/or of mobilizing peripheral blood hematopoietic stem cells.

In some embodiments, the administration of a 15-PGDH inhibitor can be in combination with a second agent, including Plerixafor, for the purpose of increasing numbers of and/or of mobilizing peripheral blood hematopoietic stem cells.

In other embodiments, the administration of a 15-PGDH inhibitor can be in combination with G-CSF for the purpose of increasing numbers of and/or of mobilizing peripheral blood hematopoietic stem cells for use in hematopoietic stem cell transplantation.

In still other embodiments, the administration of a 15-PGDH inhibitor can be in combination with a hemopoietic cytokine for the purpose of increasing numbers of and/or of mobilizing peripheral blood hematopoietic stem cells for use in hematopoietic stem cell transplantation.

In other embodiments, the administration of a 15-PGDH inhibitor can be in combination with a second agent, including Plerixafor, for the purpose of increasing numbers of and/or of mobilizing peripheral blood hematopoietic stem cells for use in hematopoietic stem cell transplantation.

In still other embodiments, the administration of a 15-PGDH inhibitor can be in combination with G-CSF for the purpose of increasing numbers of hematopoietic stem cells in blood or bone marrow.

In other embodiments, the administration of a 15-PGDH inhibitor can be in combination with a hemopoietic cytokine for the purpose of increasing numbers of hematopoietic stem cells in blood or bone marrow.

In other embodiments, the 15-PGDH inhibitors can be used to treat and/or prevent fibrosis and various fibrotic diseases, disorders or conditions, and decrease fibrotic symptoms, such as collagen deposition, inflammatory cytokine expression, and inflammatory cell infiltration.

In some embodiments, a method of treating or preventing a fibrotic disease, disorder or condition includes administering to a subject in need thereof a therapeutically effect amount of a 15-PGDH inhibitor such that at least one symptom or feature of a fibrotic disease, disorder or condition, or other related diseases, disorders or conditions, is reduced in intensity, severity, or frequency, or has delayed onset.

As used herein, the term "fibrotic" diseases, disorders, or conditions include diseases, disorders, or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. The fibriotic disesases, disorders, or conditions, can include acute and chronic, clinical or subclinical presentation, in which fibrogenic associated biology or pathology is evident.

Examples of fibrotic diseases, disorders and conditions include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulomanry fibrosis (e.g., glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fascilitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, glioblastoma in Li-Fraumeni syndrome, sporadic glioblastoma, myleoid leukemia, acute myelogenous leukemia, myelodysplastic syndrome, myeloproferative syndrome, gynecological cancer, Kaposi's sarcoma, Hansen's disease, collagenous colitis, acute fibrosis, organ specific fibrosis, and the like.

Illustrative organ specific fibrotic disorders include, but are not limited to, pulmonary fibrosis, pulmonary hypertension, cystic fibrosis, asthma, chronic obstructive pulmonary disease, liver fibrosis, kidney fibrosis, NASH, and the like. Many fibrotic diseases, disorders or conditions have disordered and/or exaggerated deposition of extracellular matrix in affected tissues. Fibrosis may be associated with inflammation, occur as a symptom of underlying disease, and/or caused by surgical procedure or wound healing process. Unchecked fibrosis can result in destruction of the architecture of the underlying organ or tissue, commonly referred to as scarring.

In some embodiments, the 15-PGDH inhibitors can be used to treat or prevent lung fibrosis. The lung fibrosis can be selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

Pulmonary fibrosis is characterized by progressive scarring of lung tissue accompanied by fibroblast proliferation, excessive accumulation of extracellular matrix proteins, and abnormal alveolar structure. The thickened and stiff tissue makes it difficult for lungs to work properly, leading to breathing problems such as shortness of breath, and can ultimately be fatal. Pulmonary fibrosis may be caused by acute lung injury, viral infection, exposure to toxins, radiation, chronic disease, medications, or may be idiopathic (i.e., an undiscovered underlying cause).

The classic findings in idiopathic pulmonary fibrosis show diffuse peripheral scarring of the lungs with small bubbles (known as bullae) adjacent to the outer lining of the surface of the lung, often at the bases of the lungs. Idiopathic pulmonary fibrosis often has a slow and relentless progression. Early on, patients often complain of a dry unexplained cough. Next, shortness of breath (dyspnea) sets in and worsens over time triggered by less and less activity. Eventually, the shortness of breath becomes disabling, limiting all activity and even occurring while sitting still. In rarer cases, the fibrosis can be rapidly progressive, with dyspnea and disability occurring in weeks to months of onset of the disease. This form of pulmonary fibrosis has been referred to as Hamman-Rich syndrome.

Pulmonary hypertension is marked by an increase in the blood pressure of the lung vasculature, including the pulmonary artery, pulmonary vein, and/or pulmonary capillaries. Abnormally high pressure strains the right ventricle of the heart, causing it to expand. Over time, the right ventricle can weaken and lose its ability to pump enough blood to the lungs, leading to the development of heart failure. Pulmonary hypertension can occur as a result of other medical conditions, such as chronic liver disease and liver cirrhosis; rheumatic disorders such as scleroderma or systemic lupus erythematosus (lupus); and lung conditions including tumors, emphysema, chronic obstructive pulmonary disease (COPD), and pulmonary fibrosis. Pulmonary fibrosis may lead to narrowing of pulmonary vasculature resulting in pulmonary hypertension.

Chronic Obstructive Pulmonary Disease (COPD) is a common lung disease that is often associated with chronic bronchitis or emphysema. Symptoms can often include cough, mucus build up, fatigue, wheezing, and respiratory infection.

Chronic bronchitis and emphysema are diseases of the lungs in which the airways become narrowed. This leads to a limitation of the flow of air to and from the lungs, causing shortness of breath (dyspnea). In clinical practice, COPD is defined by its characteristically low airflow on lung function tests.

Lung damage and inflammation in the large airways results in chronic bronchitis. In the airways of the lung, the hallmark of chronic bronchitis is an increased number (hyperplasia) and increased size (hypertrophy) of the goblet cells and mucous glands of the airway. As a result, there is more mucus than usual in the airways, contributing to narrowing of the airways and causing a cough with sputum. Microscopically there is infiltration of the airway walls with inflammatory cells. Inflammation is followed by scarring and remodeling that thickens the walls and also results in narrowing of the airways. As chronic bronchitis progresses, there is squamous metaplasia (an abnormal change in the tissue lining the inside of the airway) and fibrosis (further thickening and scarring of the airway wall). The consequence of these changes is a limitation of airflow and difficulty breathing.

Asthma is a chronic lung disease characterized by inflammation and constriction of the airways. Asthma causes recurring periods of wheezing, tightness of the chest, shortness of breath, and coughing. Swelling and overproduction of mucus can cause further airway constriction and worsening of symptoms. There is evidence that increased matrix degradation may occur in asthma, and this may contribute to mechanical changes in the airways in asthma (Roberts et al (1995) Chest 107:111 S-117S, incorporated herein by reference in its entirety. Treatment of extracellular matrix degradation may ameliorate symptoms of asthma.

Cystic fibrosis is a recessive multi-system genetic disease characterized by abnormal transport of chloride and sodium across epithelium, leading to thick, viscous secretions in the lungs, pancreas, liver, intestine and reproductive tract. Cystic fibrosis is caused by a mutation in the gene for the protein cystic fibrosis transmembrane conductance regulator (CFTR). Lung disease results from clogging of the airways due to mucus build-up, decreased mucociliary clearance, and resulting inflammation, which can cause fibrotic injury and structural changes to the lungs. The fibrotic lung damage progresses over time leading some cystic fibrosis patients to require lung transplant.

Common symptoms of subjects suffering from cystic fibrosis include, but are not limited to, accumulation of thick mucus, copious phlegm production, frequent chest infections, frequent coughing, frequent shortness of breath, inflammation, decreased ability to exercise, opportunistic infections of the lung and sinus (including but not limited to *Staphylococcus aureus, Haemophilus influenzae, Mycobacterium aviium,* and *Pseudomonas aeruginosa*), pneumonia, tuberculosis, bronchiectasis, hemoptysis, pulmonary hypertension (and resulting heart failure), hypoxia, respiratory failure, allergic bronchopulmonary aspergillosis, mucus in the paranasal sinuses, sinus infection, facial pain, fever, excessive nasal drainage, development of nasal polyps, cardiorespiratory complications, CF-related diabetes, rectal prolapse, pancreatitis, malabsorption, intestinal blockage, exocrine pancreatic insufficiency, bile duct blockage, and liver cirrhosis.

In other embodiments, the 15-PGDH inhibitors can be used to treat or prevent fibrotic diseases, disorders or conditions caused by post-surgical adhesion formation. Post-surgical adhesion formation is a common complication of surgery. The formation of adhesions, from mechanical damage, ischemia, and infections, can increase morbidity and mortality following surgery. Although refined surgical procedures can reduce the magnitude of adhesion formation, adhesions are rarely eviscerated and an effective adjunctive therapy is needed. Reducing the fibrosis associated with this process could reduce pain, obstruction and other complications of surgery and promote healing and recovery.

Wounds (e.g., lacerations, openings) in mammalian tissue result in tissue disruption and coagulation of the microvasculature at the wound face. Repair of such tissue represents an orderly, controlled cellular response to injury. Soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in detail and have in some instances been quantified (see e.g., Hunt, T. K., et al., "Coagulation and macrophage stimulation of angiogenesis and wound healing," in The Surgical Wound, pp. 1-18, ed. F. Dineen & G. Hildrick-Smith (Lea & Febiger, Philadelphia: 1981)). The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). U.S. Pat. Nos. 5,015,629 and 7,022,675 (each incorporated by reference herein) disclose methods and compositions for increasing the rate of wound repair.

In some embodiments, the 15-PGDH inhibitors can used for reducing or preventing scar formation in a subject by administering to a subject in need of treatment. Scar formation is a natural part of the healing process. Disorderly collagen synthesis and deposition in a wound can result in excessive, thick, or raised scar formation. Generally, the larger the wound, the longer it takes to heal and the greater the chance of a problematic scar.

In other embodiments, the 15-PGDH inhibitors can be used to reduce or prevent scar formation on skin or scleroderma. There are several types of scars on skin. Hypertropic scars are raised, pinkish-red areas located inside the borders of the original injury. They are often described as itchy. In some cases, hypertropic scars shrink and fade on their own. Keloids are raised, deep-red areas that tend to cover much more area than that of the original injury. Even when surgically removed, keloids tend to recur. Atrophic scars are skin depressions, like those that sometimes form from severe acne. They are caused by inflammation that destroys the collagen during the rebuilding process, leaving an area of indentation.

In some embodiments, the 15-PGDH inhibitors can be used to treat or prevent systemic sclerosis. Systemic sclerosis is a systemic connective tissue disease characterized by alterations of the microvasculature, disturbances of the immune system and by massive deposition of collagen and other matrix substances in the connective tissue. Systemic sclerosis is a clinically heterogeneous generalized disorder which affects the connective tissue of the skin and internal organs such as gastrointestinal tract, lungs, heart and kidneys. Reduction of fibrosis resulting from systemic sclerosis may ameliorate symptoms and/or prevent further complications in affected tissues.

In other embodiments, the 15-PGDH inhibitors can be used to treat or prevent liver fibrosis. Liver fibrosis can result from a chronic liver disease, viral induced hepatic cirrhosis, hepatitis B virus infection, hepatitis C virus infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, auto-immune hepatitis, cystic fibrosis, α-1-antitrypsin deficiency, primary biliary cirrhosis, drug reaction and exposure to toxins.

Nonalcoholic steatohepatitis (NASH) is a common liver disease. It resembles alcoholic liver disease but occurs in people who drink little or no alcohol. The major feature in NASH is fat in the liver, along with inflammation and damage. Nevertheless, NASH can be severe and can lead to cirrhosis, in which the liver is permanently damaged and scarred and no longer able to work properly.

NASH is usually a silent disease with few or no symptoms. Patients generally feel well in the early stages and only begin to have symptoms—such as fatigue, weight loss, and weakness-once the disease is more advanced or cirrhosis develops. The progression of NASH can take years, even decades. The process can stop and, in some cases may even begin to reverse on its own without specific therapy. Or NASH can slowly worsen, causing scarring or fibrosis to appear and accumulate in the liver. As fibrosis worsens, cirrhosis develops in which the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease.

In some embodiments, the 15-PGDH inhibitors can be used to treat or prevent kidney fibrosis. Kidney fibrosis can result from dialysis following kidney failure, catheter placement, a nephropathy, glomerulosclerosis, glomerulonephritis, chronic renal insufficiency, acute kidney injury, end stage renal disease or renal failure.

Kidney (renal) fibrosis results from excessive formation of fibrous connective tissue in the kidney. Kidney fibrosis causes significant morbidity and mortality and leads to a need for dialysis or kidney transplantation. Fibrosis can occur in either the filtering or reabsorptive component of the nephron, the functional unit of the kidney. A number of factors may contribute to kidney scarring, particularly derangements of physiology involved in the autoregulation of glomerular filtration. This in turn leads to replacement of normal structures with accumulated extracellular matrix. A spectrum of changes in the physiology of individual cells leads to the production of numerous peptide and non-peptide fibrogens that stimulate alterations in the balance between extracellular matrix synthesis and degradation to favor scarring.

In some embodiments, the symptoms of fibrosis of a tissue organ can comprise inflammation. In these embodiments, a therapeutically effective amount of the 15-PGDH inhibitor administered to the subject in need thereof can be an amount effective to decrease or reduce inflammatory cell count in the tissue or organ. A relevant sample can be obtained from the subject to determine the decrease or reduction in inflammatory cell count. In a non-limiting embodiment, the beneficial effect may be assessed by demonstrating a reduction in neutrophil count in BAL fluid from the subject with cystic fibrosis. The excessive recruitment of neutrophils into the airways of patients with CF is a significant predictor of lung disease severity in CF and therefore is an important therapeutic target. Methods for measuring such cell counts are well known in the art, including but not limited to FACS techniques. In some embodiments, the method may comprise reducing neutrophil cell count in BAL fluid from the subject compared to control. Any suitable control can be used for comparison, such as cystic fibrosis subjects not treated the 15-PGDH inhibitors. In some embodiments, a decrease in inflammatory cell count, such as neutrophil count, provides a clinical benefit to the subject. In various embodiments, the reduction in inflammatory cell count is at least 5%, 10%, 15%, 20%, 25%, 50%, or more compared to control.

In another embodiment, the beneficial effect of the 15-PGDH inhibitors may be assessed by a reduction in one or more inflammatory biomarkers in a relevant sample from the subject. In various non-limiting embodiments, the inflammatory biomarker may comprise or consist of one or more of cytokines or inflammatory cytokines associated with fibrosis. Such cytokines can include, for example, IL1β, MIP2 (e.g., CCL3 or CCL4), IFNδ, TGFβ, TNFα, IL-6, MCP-1, IL2, and IL-10 in BAL fluid. Methods for measuring the amount of such biomarkers are well known in the art, including but not limited to ELISAs. Thus, in this embodiment, the methods may further comprise the reducing an amount of one or more inflammatory biomarkers in a sample from the subject compared to control.

In other embodiments, the 15-PGDH inhibitors can be used in a method for decreasing or reducing collagen secretion or collagen deposition in a tissue or organ, such as the lung, the liver, the skin or the heart, of a subject. The method can include administering a therapeutically effective amount of the 15-PGDH inhibitors to the subject in need thereof. The subject can have or be at risk of an excessive collagen secretion or collagen deposition in the tissue or organ, such as the kidney, the lung, the liver, the intestines, the colon, the skin or the heart. Usually, the excessive collagen secretion or collagen deposition in an organ results from an injury or an insult. Such injury and insult are organ-specific. The 15-PGDH inhibitors can be administered over a sufficient period of time to decrease or reduce the level of collagen deposition in the tissue or organ, completely or partially. A sufficient period of time can be during one week, or between 1 week to 1 month, or between 1 to 2 months, or 2 months or more. For chronic condition, the 15-PGDH inhibitors can be advantageously administered for life time period.

15-PGDH inhibitors used to treat the fibrotic disease, disorder or condition and/or reduce collagen deposition can be identified using assays in which putative inhibitor compounds are applied to cells expressing 15-PGDH and then the functional effects on 15-PGDH activity are determined.

Samples or assays comprising 15-PGDH that are treated with a potential inhibitor are compared to control samples without the inhibitor to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%. Additionally, in a model organism, $PGE_2$ signaling stimulates liver regeneration and increase survival after exposure to hepatoxic agents, such as acetaminophen. Hence, 15-PGDH inhibitors described herein may be utilized to increase liver regeneration after liver resection, in other settings that include after liver surgery, after live liver donation, or after receiving a liver transplant or to increase liver regeneration and increase survival after exposures to hepatoxic agents, including but not limited to acetaminophen and similar compounds.

PGE1 analogues have also been used in the treatment of erectile dysfunction. Accordingly, in some embodiments, 15-PGDH inhibitors described herein can used either alone or combination with a prostaglandin for the treatment of erectile dysfunction.

Other embodiments described herein relate to the use of 15-PGDH inhibitors in combination with corticosteroids to treat inflammation and/or reduce aberrant activity of the immune system in a subject in need thereof. It was found that corticosteroids administered to a subject can induce 15-PGDH expression in tissue of the subject. Administration of a 15-PGDH inhibitor in combination with a corticosteroid was found to enhance anti-inflammatory and/or immunosuppressive effects of the corticosteroid while attenuating corticosteroid induced adverse and/or cytotoxic effects. Treatment of inflammatory and/or immune disorders by administration of 15-PGDH inhibitors in combination with corticosteroids can increase therapeutic efficacy and can allow the corticosteroids to be administered, in some instances, at lower dosages to achieve similar effects, and, in other instances, at higher dosages and for prolonged periods of times with attenuated and/or reduced adverse or cytotoxic effects. Additional embodiments herein relate to the use of 15-PGDH inhibitors in combination with TNF alpha inhibitors to treat inflammation and/or reduce aberrant activity of the immune system in a subject in need thereof.

In some embodiments, the 15-PGDH inhibitors can be administered in combination with corticosteroids and/or TNF inhibitors to treat intestinal, gastrointestinal, or bowel disorders. The intestinal, gastrointestinal, or bowel disorders treated can include oral ulcers, gum disease, gastritis, colitis, ulcerative colitis, gastric ulcers, inflammatory bowel disease, and Crohn's disease. As described below, it was found that that inhibitors of short-chain dehydrogenase activity, such as 15-PGDH inhibitors, can be administered to a subject in need thereof alone or in combination with corticosteroids to treat intestinal, gastrointestinal, or bowel disorders, such as oral ulcers, gum disease, gastritis, colitis, ulcerative colitis, gastric ulcers, inflammatory bowel disease, and Crohn's disease.

The 15-PGDH inhibitors described herein can be used in a pharmaceutical composition for the prevention or the treatment of oral, intestinal, and/or gastrointestinal injury or diseases, or inflammatory bowel disease (IBD), such as Crohn's disease, oral ulcers, gum disease, gastritis, colitis, ulcerative colitis, and gastric ulcers. Gastritis and gastric ulcer, representatives of the gastrointestinal diseases, are defined as the conditions where gastrointestinal mucus membrane is digested by gastric acid to form ulcer. In the stomach walls generally consisting of mucosa, submucosa, muscle layer and serosa, gastric ulcer even damages submucosa and muscle layer, while gastritis damages mucosa only. Although the morbidity rates of gastritis and gastric ulcer are relatively high, the causes thereof have not been clarified yet. Until now, they are known to be caused by an imbalance between aggressive factors and defensive factors, that is, the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect, gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). In view of the above, since the 15-PGDH inhibitors described herein show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

Additionally, corticosteroids and TNF alpha antagonists are both used in the treatment of ulcerative colitis and IBD patients. In mouse models, 15-PGDH inhibitors speed healing of ulcerative colitis. We have found that administering corticosteroids to mice elevates levels of colon 15-PGDH, an effect that should reduce the therapeutic effectiveness of corticosteroids in colitis treatment. This suggests that combining a corticosteroid with a 15-PGDH inhibitor should be more effective in colitis (and IBD) treatment than using either agent alone.

Similarly, we have shown that TNF-alpha suppresses colon 15-PGDH expression. This suggests that TNF-alpha antagonists will increase colon 15-PGDH expression, an effect that should reduce the therapeutic effectiveness of corticosteroids in colitis treatment. This suggests that combining a TNF-alpha antagonist, e.g., the chimeric antibody REMICADE (infliximab), with a 15-PGDH inhibitor should be more effective in colitis (and IBD) treatment than using either agent alone.

In other embodiments, the 15-PGDH inhibitors and corticosteroids or 15-PGDH inhibitors and TNF inhibitors can be provided in a topical composition or formulation that is used to treat inflammation and/or aberrant immune system activity associated with medical conditions, such as atopic dermatitis, psoriasis, eczematous dermatitis, nummular dermatitis, irritant contact dermatitis, allergic contact dermatitis (such as poison ivy exposure, poison oak exposure, and poison sumac exposure), seborrheic dermatitis, stasis dermatitis, and other steroid responsive dermatoses.

In other embodiments, the 15-PGDH inhibitors and corticosteroids or 15-PGDH inhibitors and TNF inhibitors provided in a topical composition can be used to treat, for example, acne vulgaris, alopecia, alopecia greata, vitiligo, eczema, xerotic eczema, keratosis pilaris, lichen planus, lichen sclerosus, lichen striatus, lichen simplex chronicus, prurigo nodularis, discoid lupus erythematosus, lymphocytic infiltrate of Jessner/Kanof, lymphacytoma cutis, pyoderma gangrenosum, pruritis ani, sarcoidosis, chondrodermatitis nodularis helices, and other inflammatory dermatological disorders.

Medical conditions treated by the 15-PGDH inhibitors and corticosteroids or 15-PGDH inhibitors and TNF inhibitors can also include, for example, keloids, hypertrophic scars, pretibial myxedema and other infiltrative dermatological disorders. Additional medical conditions include, for example, granuloma annulare, necrobiosis lipoidica diabeticorum, sarcoidosis, and other noninfectious granulomas.

In still other embodiments, the 15-PGDH inhibitors described herein can be administered in combination with corticosteroids or TNF inhibitors for wound healing, tissue regeneration, and/or tissue repair. Among various prostaglandins, $PGE_2$ is known to serve as a mediator for wound healing. Therefore, subjects who are receiving steroids, including those healing of wounds from undergoing surgery, can be admnisistered a 15-PGDH inhibitor to enhance $PGE_2$ and promote would healing.

Additionally, increased prostaglandin levels have been shown to stimulate signaling through the Wnt signaling pathway via increased beta-catenin mediated transcriptional activity. Wnt signaling is known to be a key pathway employed by tissue stem cells. Hence, 15-PGDH inhibitors described herein may be utilized to increase tissue stem cell numbers for purposes that would include promoting tissue regeneration or repair in subjects receiving corticosteroid treatment. In addition, 15-PGDH inhibitors described herein may be utilized to promote tissue regeneration or repair in additional organs that would include but are not limited to brain, eye, cornea, retina, lung, heart, stomach, small intestine, pancreas, beta-cells of the pancreas, kidney, bone, cartilage, and peripheral nerve.

In other embodiments, the 15-PGDH inhibitor can be used as a glucocorticoid sensitizer to treat glucocorticoid insensitivity, restore corticosteroid sensitivity, enhance glucocorticoid sensitivity, and/or reverse the glucocorticoid insensitivity in a subject experiencing corticosteroid dependence or corticoid resistance or unresponsiveness or intolerance to corticosteroids. Therapeutic effects of the 15-PGDH inhibitors when used as a glucocorticoid sensitizer include any, but are not limited to, steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune functions, easier responses for the subject or patient when steroid administration is tapered or withdrawn, or after prolonged administration of corticosteroids, decreased risks for developing corticosteroid-related adverse events such as opportunistic infections, bone loss, pathologic fracture, diabetes, cataract, and combinations thereof.

In some embodiments, the 15-PGDH inhibitor can be administered to a subject in combination with the corticosteroid to treat glucocorticoid insensitivity, restore corticosteroid sensitivity, enhance glucocorticoid sensitivity, and/or reverse the glucocorticoid insensitivity in a subject experiencing corticosteroid dependence or corticoid resistance or unresponsiveness or intolerance to corticosteroids. The glucocorticoid insensitivity related conditions can include a range of immune-inflammatory disorders/diseases treated with steroids when the therapy fails to achieve disease control or is not effective or intolerant or dependent to corticosteroids, and combinations thereof.

In other embodiments, the 15-PGDH inhibitor and corticosteroid or the 15-PGDH inhibitor and TNF inhibitor can be administered to a subject that exhibits one or more glucocorticoid insensitivity related diseases, disorders, or conditions selected from the group consisting of glucocorticoid resistant asthma, refractory rheumatoid arthritis, refractory inflammatory bowel disease, chronic obstructive pulmonary disease, acute respiratory distress syndrome, interstitial pulmonary fibrosis, cystic fibrosis, refractory ulcerative colitis, children with severe Crohn's disease, corticosteroid refractory asthma, desquamative interstitial pneumonia refractory to corticosteroid, refractory inflammatory myopathies, refractory myasthenia gravis, refractory pemphigus vulgaris, methotrexate-refractory RA patients, refractory nephrotic syndrome, refractory multiple sclerosis, refractory sprue-like disease, steroid-resistant sarcoidosis, refractory mucosal lesions of pemphigus vulgaris, refractory Schnitzler syndrome, resistant dermatitis of the head and neck, severe refractory atopic dermatitis, refractory Idiopathic thrombocytopenia purpura, refractory orbital myositis, refractory or recurrent lymphomas, critically ill patients with sepsis or acute respiratory distress syndrome (ARDS) and relative adrenal insufficiency, rosacea, polymyalgia rheumatic, giant cell arteritis, polymyositis, dermatomyositis, Kawasaki syndrome, Guillain-Barre syndrome, chronic inflammatory demyelinating polyneuropathy, multifocal motor neuropathy, Stiff man syndrome, corticosteroid dependent systemic lupus erythematosus, corticosteroid dependent multiple sclerosis, symptomatic corticosteroid dependent asthma, primary Sjogren's syndrome, systemic vasculitis, polymyositis, organ transplants, graft-versus-host disease, inflammatory diseases, autoimmune diseases, hyperproliferative diseases, lupus, osteoarthritis, rhinosinusitis, polyarteritis nodosa, Wegener's granulomatosis, giant cell arteritis, allergic rhinitis, urticaria, hereditary angioedema, tendonitis, bursitis, autoimmune chronic active hepatitis, cirrhosis, transplant rejection, psoriasis, dermatitus, malignancies, leukemia, myelomas, lymphomas, acute adrenal insufficiency, rheumatic fever, granulomatous disease, immune proliferation/apoptosis, hypothalamic-pituitary-adrenal (HPA) axis suppression and regulation, hypercortisolemia, modulation of the Th1/Th2 cytokine balance, chronic kidney disease, spinal cord injury, cerebral edema, thrombocytopenia, Little's syndrome, Addison's disease, autoimmune hemolytic anemia, uveitis, pemphigus vulgaris, nasal polyps, sepsis, bacterial infections, viral infections, rickettsial infections, parasitic infections, type II diabetes, obesity, metabolic syndrome, depression, schizophrenia, mood disorders, Cushing's syndrome, anxiety, sleep disorders, memory and learning enhancement, glucocorticoid-induced glaucoma, atopic dermatitis, drug hypersensitivity reactions, serum sickness, bullous dermatitis herpetiformis, contact dermatitis, exfoliative erythroderma, mycosis fungoides, pemphigus, nonsuppurative thyroiditis, sympathetic ophthalmia, uveitis, ocular inflammatory conditions unresponsive to topical steroids, allergic bronchopulmonary aspergillosis, fulminating or disseminated pulmonary tuberculosis when used concurrently with appropriate chemotherapy, hypersensitivity pneumonitis, idiopathic bronchiolitis obliterans with organizing pneumonia, idiopathic eosinophilic pneumonias, idiopathic pulmonary fibrosis, *Pneumocystis carinii* pneumonia (PCP) associated with hypoxemia occurring in an HIV(+) individual who is also under treatment with appropriate anti-PCP antibiotics, a diuresis or remission of proteinuria in nephrotic syndrome, without uremia, of the idiopathic type or that due to lupus erythematosus, ankylosing spondylitis, polymyalgia rheumatic, psoriatic arthritis, relapsing polychondritis, trichinosis with neurologic or myocardial involvement, and tuberculous meningitis.

It will be appreciated that other 15-PGDH inhibitors can be used in the methods described described herein. These other 15-PGDH inhibitors can include known 15-PGDH inhibitors including, for example, tetrazole compounds of formulas (I) and (II), 2-alkylideneaminooxyacetamide compounds of formula (I), heterocyclic compounds of fourmulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I) described in U.S. Patent Application Publication No. 2007/0071699; phenylfurylmethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenylfuran, phenylthiophene, or phenylpyrrazole compounds described in U.S. Pat. No. 7,294,641; 5-(3,5-disubstituted phenylazo)-2-hydroxybenzene-acetic acids and salts; and lactones described in U.S. Pat. No. 4,725,676; azo compounds described in U.S. Pat. No. 4,889,846; and 15-PGHD inhibitors described in PCT/US2014/060761 and US Patent Application Publication No. 2015/0072998A1, all of which are herein incorporated by reference in their entirety.

The 15-PGDH inhibitors described herein can be provided in a pharmaceutical composition or cosmetic composition depending on the pathological or cosmetic condition or disorder being treated. A pharmaceutical composition containing the 15-PGDH inhibitors described herein as an active ingredient may be manufactured by mixing the derivative with a pharmaceutically acceptable carrier(s) or an excipient(s) or diluting the 15-PGDH inhibitors with a diluent in accordance with conventional methods. The pharmaceutical composition may further contain fillers, anticohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. In some embodiments, the 15-PGDH inhibitors described herein can be administered orally, intravenously, or intraperitoneally. The dosage can be a pharmaceutically effective amount. The pharmaceutically effective amount can be, for example, an amount of the 15-PGDH inhibitor to treat or improve alopecia, cardiovascular disease, gastrointestinal disease, wounds, and renal disease. The pharmaceutically effective amount of the compound will be appropriately determined depending on the kind and the severity of the disease to be treated, age, sex, body weight and the physical condition of the patients to be treated, administration route, duration of therapy and the like. Generally, the effective amount of the compound may be in the range of about 1 to 1,000 mg in the oral administration, about 0.1 to 500 mg in the intravenous administration, about 5 to 1,000 mg in the rectal administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose.

Cosmetic compositions containing the 15-PGDH inhibitor can include any substance or preparation intended to be brought into contact with the various superficial parts of the human body (epidermis, body hair and hair system, nails, lips and external genital organs) or with the teeth or the buccal mucous membranes for the purpose, exclusively or mainly, of cleansing them, of giving them a fragrance, of modifying their appearance and/or of correcting body odors and/or protecting them or of maintaining them in good condition.

The cosmetic composition can comprise a cosmetically acceptable medium that may be water or a mixture of water and at least one solvent selected from among hydrophilic organic solvents, lipophilic organic solvents, amphiphilic organic solvents, and mixtures thereof.

For topical application, the cosmetic composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

The cosmetic compositions may in particular comprise a hair care composition, and in particular a shampoo, a setting lotion, a treating lotion, a styling cream or gel, restructuring lotions for the hair, a mask, etc. The cosmetic compositions can be a cream, a hair lotion, a shampoo or a conditioner. These can be used in particular in treatments using an application that may or may not be followed by rinsing, or else in the form of a shampoo. A composition in the form of a foam, or else in the form of spray or an aerosol, then comprising propellant under pressure, is also intended. It can thus be in the form of a lotion, serum, milk, cream, gel, salve, ointment, powder, balm, patch, impregnated pad, cake or foam.

In particular, the compositions for application to the scalp or the hair can be in the form of a hair care lotion, for example for daily or twice-weekly application, of a shampoo or of a hair conditioner, in particular for twice-weekly or weekly application, of a liquid or solid soap for cleansing the scalp, for daily application, of a hairstyle shaping product (lacquer, hair setting product or styling gel), of a treatment mask, or of a foaming gel or cream for cleansing the hair. These may also be in the form of a hair dye or mascara to be applied with a brush or a comb.

Moreover, for topical application to the eyelashes or body hair, the compositions may be in the form of a pigmented or unpigmented mascara, to be applied with a brush to the eyelashes or alternatively to beard or moustache hair. For a composition administration by injection, the composition may be in the form of an aqueous lotion or an oily suspension. For oral use, the composition may be in the form of capsules, granules, oral syrups or tablets. According to a particular embodiment, the composition is in the form of a hair cream or hair lotion, a shampoo, a hair conditioner or a mascara for the hair or for the eyelashes.

In a known manner, the cosmetic compositions may also contain adjuvants that are normal in the cosmetics field, such as hydrophilic or lipophilic gelling agents, hydrophilic or lipophilic additives, preservatives, antioxidants, solvents, fragrances, fillers, UV-screening agents, odor absorbers and dyestuffs. The amounts of these various adjuvants are those conventionally used in the cosmetics field, and are for example from 0.1% to 20%, in particular less than or equal to 10%, of the total weight of the composition. According to their nature, these adjuvants can be introduced into the fatty phase, into the aqueous phase and/or into the lipid spherules.

In some embodiments, the 15-PGDH inhibitor can be administered in a combinatorial therapy or combination therapy that includes administration of a 15-PGDH inhibitor with one or more additional active agents. The phrase "combinatorial therapy" or "combination therapy" embraces the administration of the 15-PGDH inhibitor, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the additional active agent can be chosen in particular from lipoxygenase inhibitors as described in EP 648488, the bradykinin inhibitors described in particular in EP 845700, prostaglandins and their derivatives, in particular those described in WO 98/33497, WO 95/11003, JP 97-100091, JP 96-134242, the agonists or antagonists of the receptors for prostaglandins, and the nonprostanoic analogues of prostaglandins as described in EP 1175891 and EP 1175890, WO 01/74307, WO 01/74313, WO 01/74314, WO 01/74315 or WO 01/72268.

In other embodiments, the 15-PGDH inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5.alpha.-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11):1465-1473).

Other active compounds, which can be present in pharmaceutical and/or cosmetic compositions can include aminexil and its derivatives, 60-[(9Z,12Z)octadec-9,12-dienoyl] hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium pantothenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

Pharmaceutical and/or cosmetic compositions including the 15-PGDH inhibitor described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_{2a}$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy $PGE_1$, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-(3-[(3R,S)-3-cyclohexyl-3-isopropyl]-2,5-dioxo)-4-imidazolidinehept-anoic acid), BW246C ((4R)-(3-[(3R,S)-3-cyclohexyl-3-isopropyl]-2,5-dioxo)-4-imidazolidinehept-anoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodophenoxy)-1-butenyl]-7-oxabicyclo-[2.2.1]hept-2-yl]-5-heptenoic acid).

Advantageously, the composition can include at least one 15-PGDH inhibitor as defined above and at least one prostaglandin or one prostaglandin derivative such as for example the prostaglandins of series 2 including in particular $PGF_{2a}$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl $PGF_{2a}$ 17-phenyl $PGF_{2a}$, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

The invention is further illustrated by the following examples, which is not intended to limit the scope of the claims.

EXAMPLES

Example A. Analysis of 15-PGDH Inhibitors of the Present Invention

This Example provides data on 15-PGDH inhibitors using an assay described in U.S. Pat. No. 9,790,233, which is herein incorporated by reference in its entirety. The data categorizes the $IC_{50}$ of each compound for inhibiting enzymatic activity of recombinant 15-PGDH in an in vitro assay: <2.5 nM (*), ≥2.5 nM and ≤10 nM (), or ≥10 nM (*). The Recombinant 15-PGDH is human unless otherwise specified.

TABLE 1

| Molecule Name | Structure | PDGH Assay-$IC_{50}$ |
|---|---|---|
| 1 | 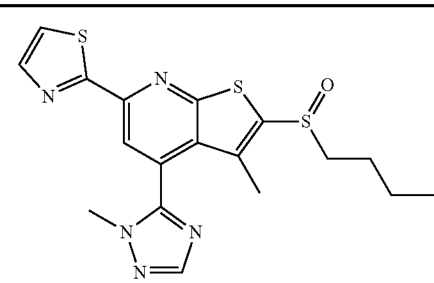 | *** |

TABLE 1-continued

| Molecule Name | Structure | PDGH Assay-IC$_{50}$ |
|---|---|---|
| 2 | 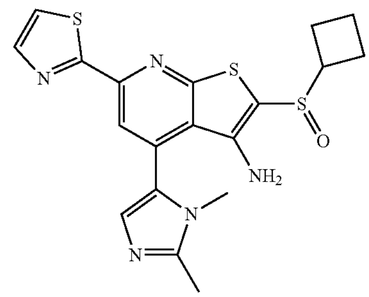 [SMILES: Cc1ncc(-c2cc(-c3nccs3)nc3sc(S(=O)C4CCC4)c(N)c23)n1C] | *** |
| 3 | 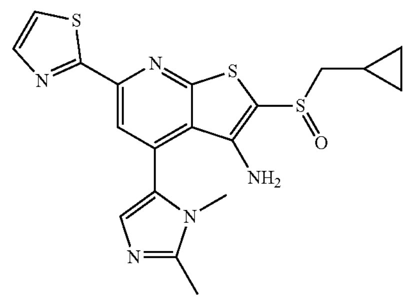 [SMILES: Cc1ncc(-c2cc(-c3nccs3)nc3sc(S(=O)CC4CC4)c(N)c23)n1C] | ** |
| 4 | 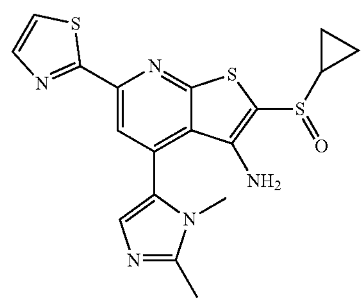 [SMILES: Cc1ncc(-c2cc(-c3nccs3)nc3sc(S(=O)C4CC4)c(N)c23)n1C] | ** |
| 5 | 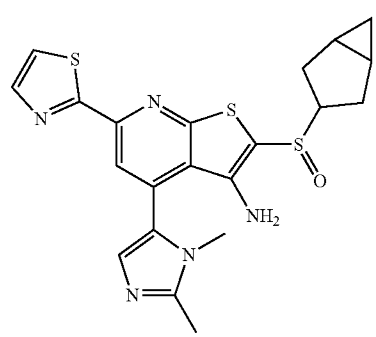 [SMILES: Cc1ncc(-c2cc(-c3nccs3)nc3sc(S(=O)C4CC5CC5C4)c(N)c23)n1C] | *** |
| 6 | 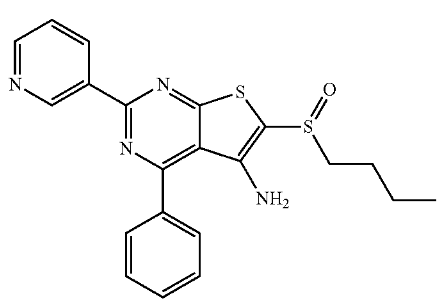 [SMILES: CCCCS(=O)c1sc2nc(-c3cccnc3)nc(-c3ccccc3)c2c1N] | *** |

TABLE 1-continued

| Molecule Name | Structure | PDGH Assay-IC$_{50}$ |
|---|---|---|
| 7 | 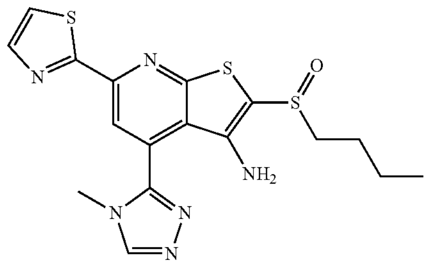 [SMILES: CCCCS(=O)c1sc2nc(-c3nccs3)cc(-c3nncn3C)c2c1N] | *** |
| 8 | 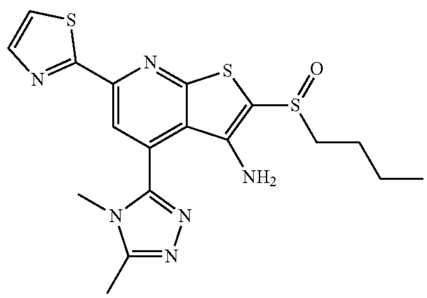 [SMILES: CCCCS(=O)c1sc2nc(-c3nccs3)cc(-c3nnc(C)n3C)c2c1N] | *** |
| 9 | 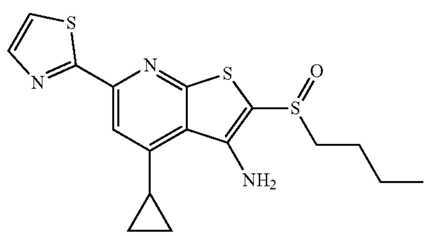 [SMILES: CCCCS(=O)c1sc2nc(-c3nccs3)cc(C3CC3)c2c1N] | *** |
| 10 | 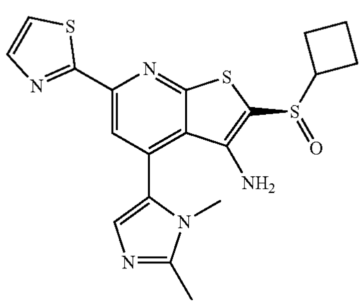 [SMILES: Cc1ncc(-c2cc(-c3nccs3)nc3sc([S@](=O)C4CCC4)c(N)c23)n1C] | *** |
| 11 | 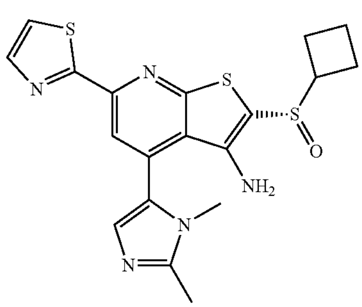 [SMILES: Cc1ncc(-c2cc(-c3nccs3)nc3sc([S@@](=O)C4CCC4)c(N)c23)n1C] | * |

TABLE 1-continued

| Molecule Name | Structure | PDGH Assay-IC$_{50}$ |
|---|---|---|
| 12 | 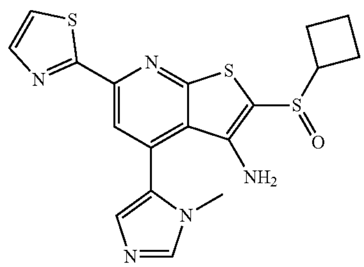 [SMILES: Cn1cncc1-c1cc(-c2nccs2)nc2sc(S(=O)C3CCC3)c(N)c12] | *** |
| 13 | 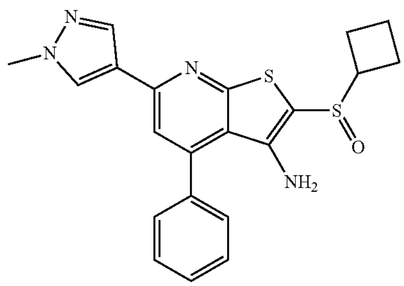 [SMILES: Cn1cc(-c2cc(-c3ccccc3)c3c(N)c(S(=O)C4CCC4)sc3n2)cn1] | *** |
| 14 | 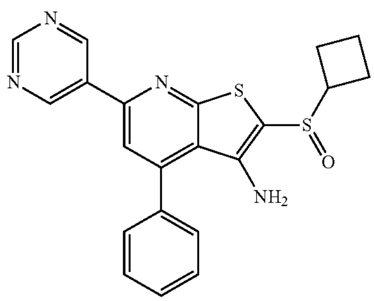 [SMILES: Nc1c(S(=O)C2CCC2)sc2nc(-c3cncnc3)cc(-c3ccccc3)c12] | *** |
| 15 | 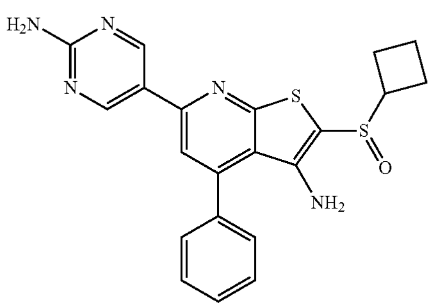 [SMILES: Nc1ncc(-c2cc(-c3ccccc3)c3c(N)c(S(=O)C4CCC4)sc3n2)cn1] | *** |
| 16 | 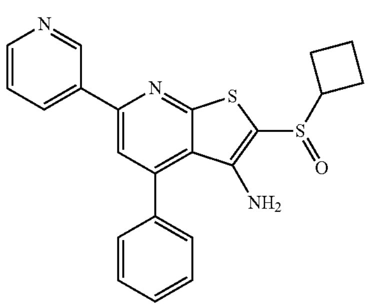 [SMILES: Nc1c(S(=O)C2CCC2)sc2nc(-c3cccnc3)cc(-c3ccccc3)c12] | *** |

TABLE 1-continued

| Molecule Name | Structure | PDGH Assay-IC$_{50}$ |
|---|---|---|
| 17 | 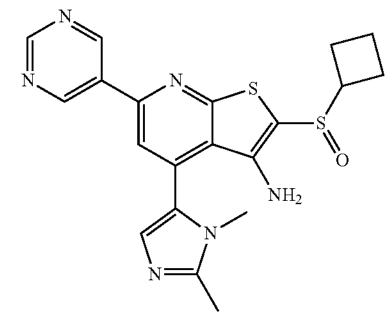 [SMILES: Cc1ncc(-c2cc(-c3cncnc3)nc3sc(S(=O)C4CCC4)c(N)c23)n1C] | *** |
| 18 | 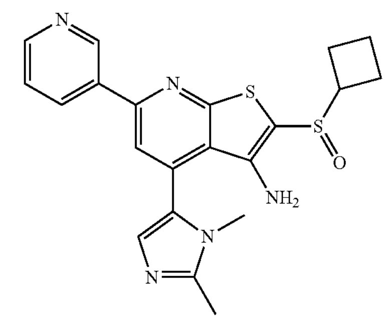 [SMILES: Cc1ncc(-c2cc(-c3cccnc3)nc3sc(S(=O)C4CCC4)c(N)c23)n1C] | *** |
| 19 | 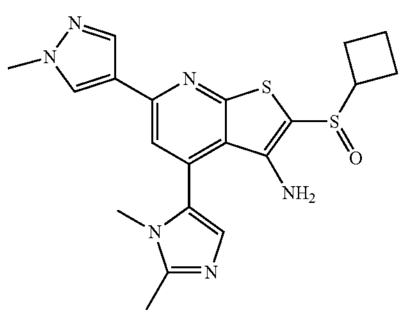 [SMILES: Cc1ncc(-c2cc(-c3cnn(C)c3)nc3sc(S(=O)C4CCC4)c(N)c23)n1C] | *** |
| 20 | 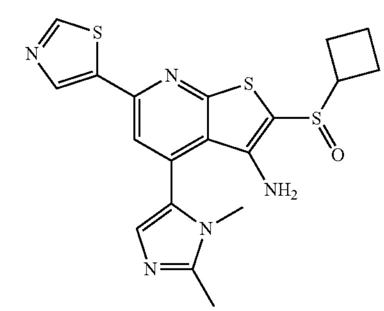 [SMILES: Cc1ncc(-c2cc(-c3cncs3)nc3sc(S(=O)C4CCC4)c(N)c23)n1C] | *** |
| 21 | 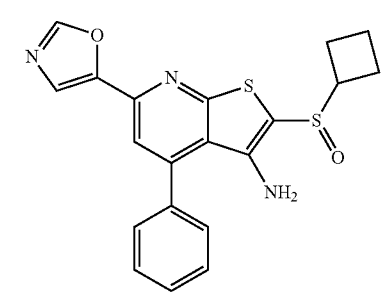 [SMILES: Nc1c(S(=O)C2CCC2)sc2nc(-c3cnco3)cc(-c3ccccc3)c12] | *** |

TABLE 1-continued
| Molecule Name | Structure | PDGH Assay-IC$_{50}$ |
|---|---|---|
| 22 | 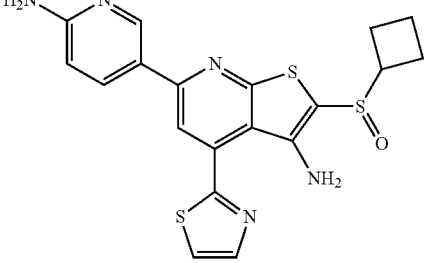 | *** |
| 23 | 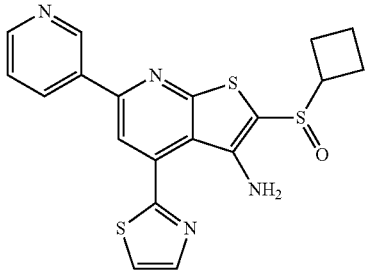 [SMILES: Nc1c(S(=O)C2CCC2)sc2nc(-c3cccnc3)cc(-c3nccs3)c12] | *** |
| 24 | 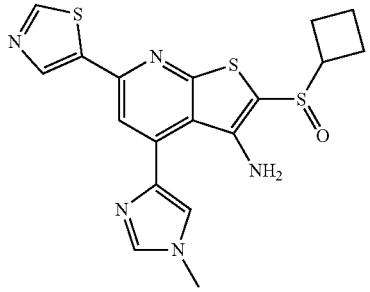 [SMILES: Cn1cnc(-c2cc(-c3cncs3)nc3sc(S(=O)C4CCC4)c(N)c23)c1] | *** |
| 25 | 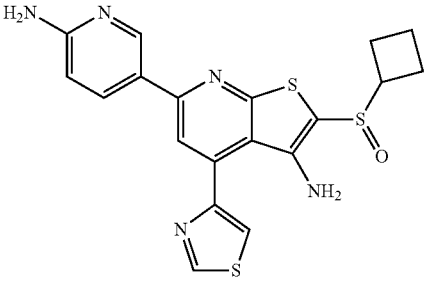 [SMILES: Nc1ccc(-c2cc(-c3cscn3)c3c(N)c(S(=O)C4CCC4)sc3n2)cn1] | *** |
| 26 | 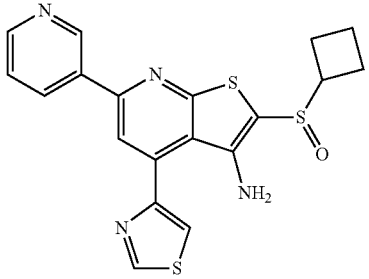 [SMILES: Nc1c(S(=O)C2CCC2)sc2nc(-c3cccnc3)cc(-c3cscn3)c12] | *** |

TABLE 1-continued
| Molecule Name | Structure | PDGH Assay-IC$_{50}$ |
|---|---|---|
| 27 | 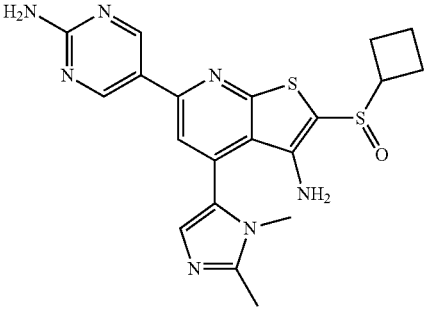 [SMILES: Cc1ncc(-c2cc(-c3cnc(N)nc3)nc3sc(S(=O)C4CCC4)c(N)c23)n1C] | *** |
| 28 | 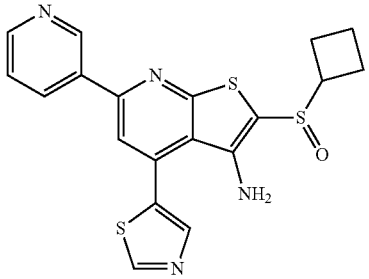 [SMILES: Nc1c(S(=O)C2CCC2)sc2nc(-c3cccnc3)cc(-c3cncs3)c12] | *** |
| 29 | 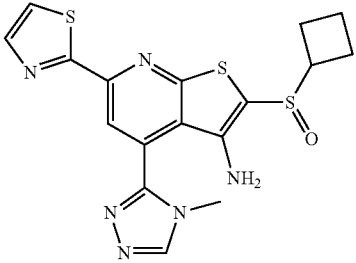 [SMILES: Cn1cnnc1-c1cc(-c2nccs2)nc2sc(S(=O)C3CCC3)c(N)c12] | *** |
| 30 | 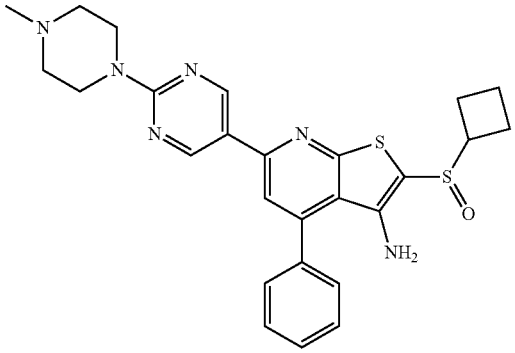 [SMILES: CN1CCN(c2ncc(-c3cc(-c4ccccc4)c4c(N)c(S(=O)C5CCC5)sc4n3)cn2)CC1] | *** |
| 31 | 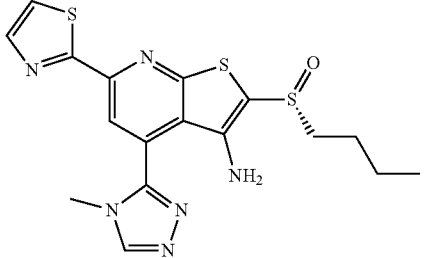 [SMILES: CCCC[S@@](=O)c1sc2nc(-c3nccs3)cc(-c3nncn3C)c2c1N] | *** |

TABLE 1-continued

| Molecule Name | Structure | PDGH Assay-IC$_{50}$ |
|---|---|---|
| 32 | 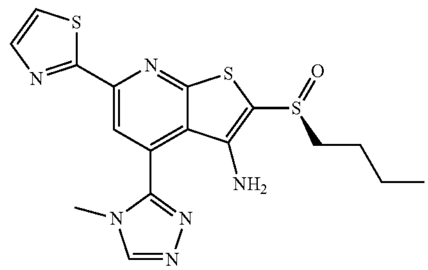 [SMILES: CCCC[S@](=O)c1sc2nc(-c3nccs3)cc(-c3nncn3C)c2c1N] | * |
| 33 | 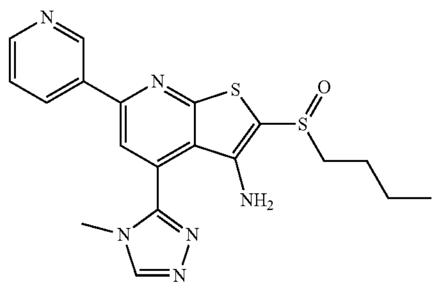 [SMILES: CCCCS(=O)c1sc2nc(-c3cccnc3)cc(-c3nncn3C)c2c1N] | *** |
| 34 | 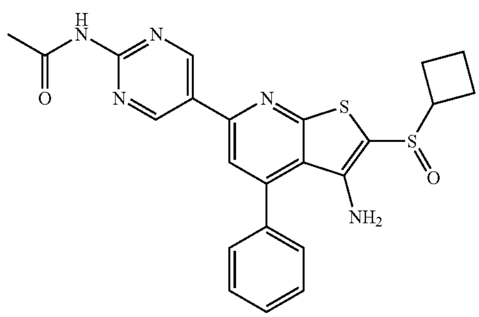 [SMILES: CC(=O)Nc1ncc(-c2cc(-c3ccccc3)c3c(N)c(S(=O)C4CCC4)sc3n2)cn1] | *** |
| 35 | 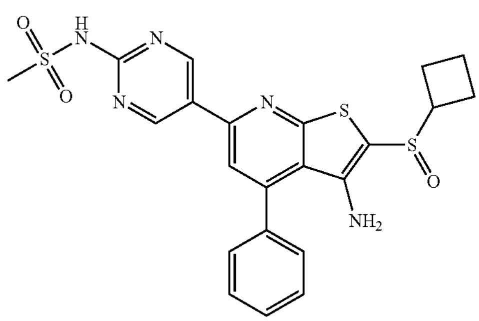 [SMILES: CS(=O)(=O)Nc1ncc(-c2cc(-c3ccccc3)c3c(N)c(S(=O)C4CCC4)sc3n2)cn1] | *** |
| 36 | 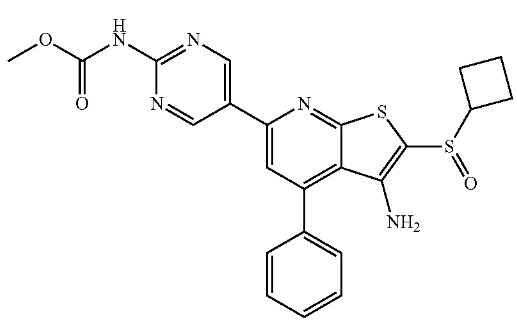 [SMILES: COC(=O)Nc1ncc(-c2cc(-c3ccccc3)c3c(N)c(S(=O)C4CCC4)sc3n2)cn1] | *** |

TABLE 1-continued
| Molecule Name | Structure | PDGH Assay-IC$_{50}$ |
|---|---|---|
| 37 | 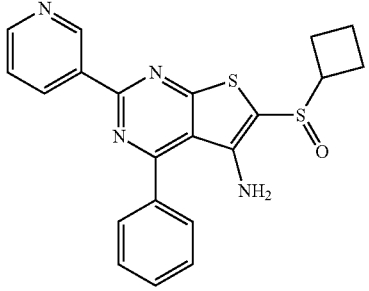 [SMILES: Nc1c(S(=O)C2CCC2)sc2nc(-c3cccnc3)nc(-c3ccccc3)c12] | *** |
| 38 | 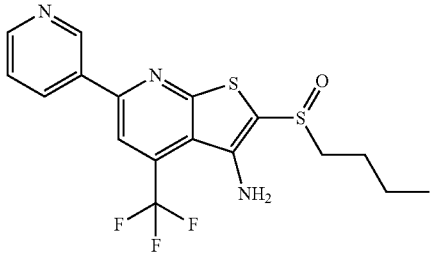 [SMILES: CCCCS(=O)c1sc2nc(-c3cccnc3)cc(C(F)(F)F)c2c1N] | *** |
| 39 | 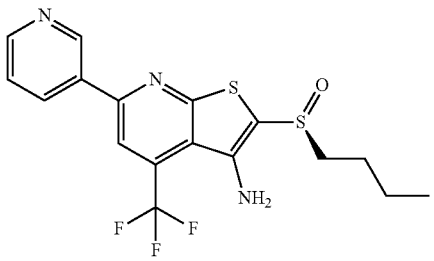 [SMILES: CCCC[S@](=O)c1sc2nc(-c3cccnc3)cc(C(F)(F)F)c2c1N] | *** |
| 40 | 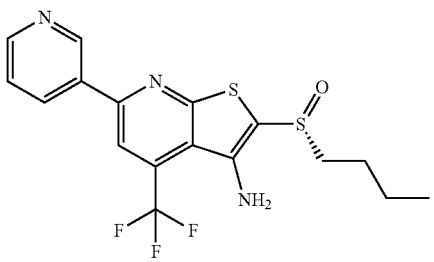 | *** |
| 41 | 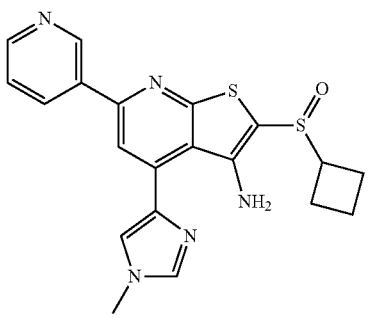 [SMILES: Cn1cnc(-c2cc(-c3cccnc3)nc3sc(S(=O)C4CCC4)c(N)c23)c1] | *** |

TABLE 1-continued

| Molecule Name | Structure | PDGH Assay-IC$_{50}$ |
|---|---|---|
| 42 | 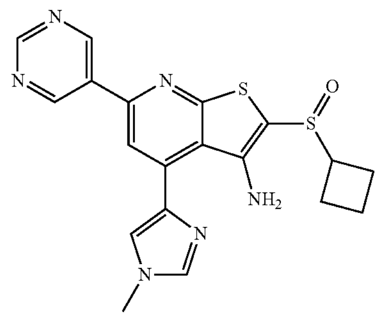 [SMILES: Cn1cnc(-c2cc(-c3cncnc3)nc3sc(S(=O)C4CCC4)c(N)c23)c1] | *** |
| 43 | 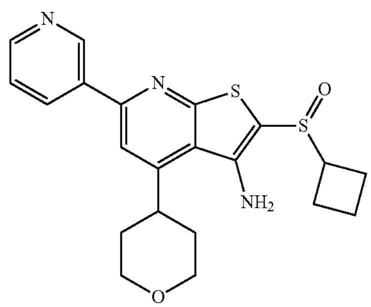 [SMILES: Nc1c(S(=O)C2CCC2)sc2nc(-c3cccnc3)cc(C3CCOCC3)c12] | *** |
| 44 | 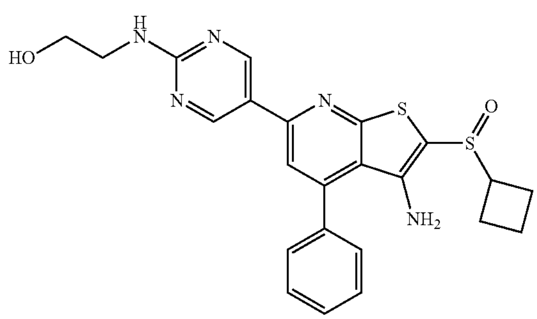 [SMILES: Nc1c(S(=O)C2CCC2)sc2nc(-c3cnc(NCCO)nc3)cc(-c3ccccc3)c12] | *** |
| 45 | 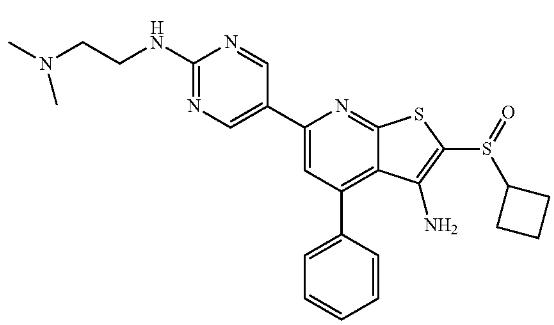 [SMILES: CN(C)CCNc1ncc(-c2cc(-c3ccccc3)c3c(N)c(S(=O)C4CCC4)sc3n2)cn1] | * |

TABLE 1-continued

| Molecule Name | Structure | PDGH Assay-IC$_{50}$ |
|---|---|---|
| 46 | 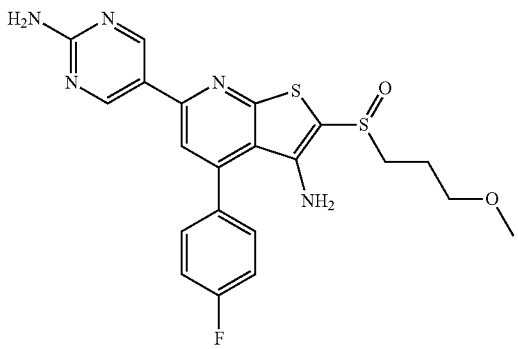 [SMILES: COCCCS(=O)c1sc2nc(-c3cnc(N)nc3)cc(-c3ccc(F)cc3)c2c1N] | *** |
| 47 | 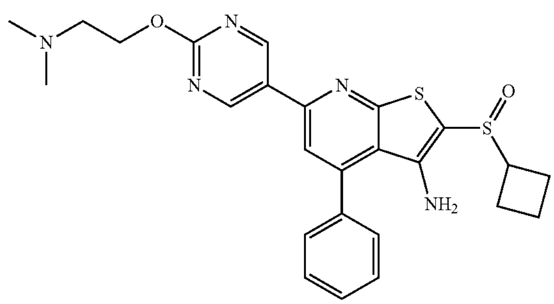 [SMILES: CN(C)CCOc1ncc(-c2cc(-c3ccccc3)c3c(N)c(S(=O)C4CCC4)sc3n2)cn1] | ** |
| 48 | 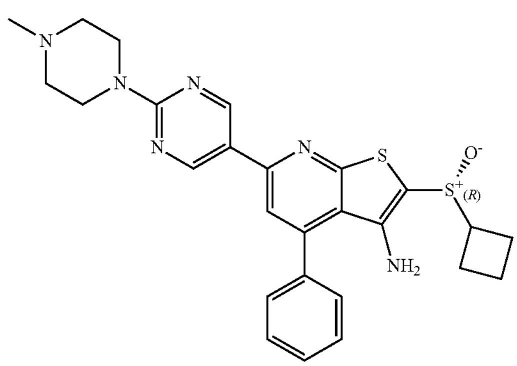 | *** |
| 49 | 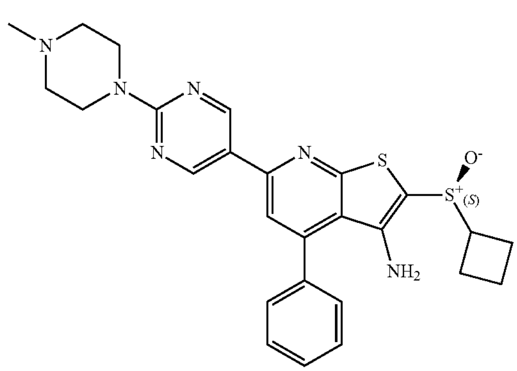 | * |

TABLE 1-continued

| Molecule Name | Structure | PDGH Assay-IC$_{50}$ |
|---|---|---|
| 50 | 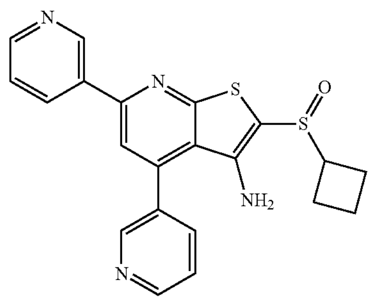 [SMILES: Nc1c(S(=O)C2CCC2)sc2nc(-c3cccnc3)cc(-c3cccnc3)c12] | *** |
| 51 | 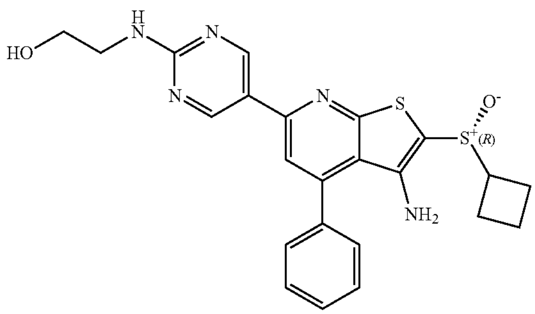 | *** |
| 52 | 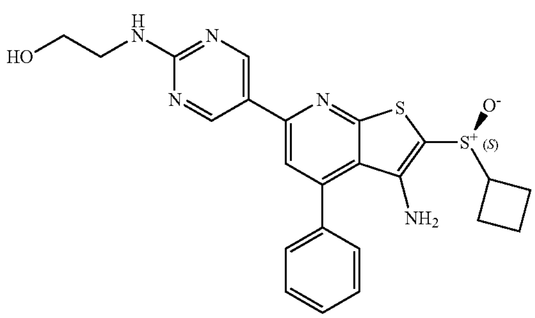 | * |
| 53 | 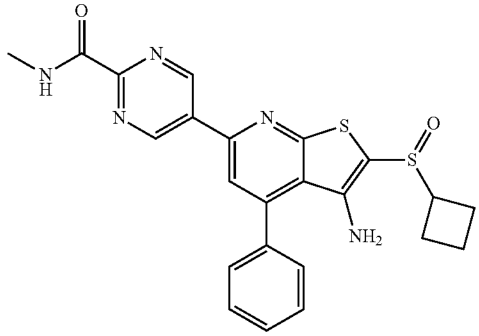 [SMILES: CNC(=O)c1ncc(-c2cc(-c3ccccc3)c3c(N)c(S(=O)C4CCC4)sc3n2)cn1] | *** |

TABLE 1-continued

| Molecule Name | Structure | PDGH Assay-IC$_{50}$ |
|---|---|---|
| 54 | 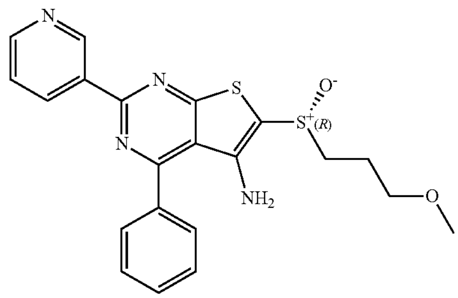 | *** |
| 55 | 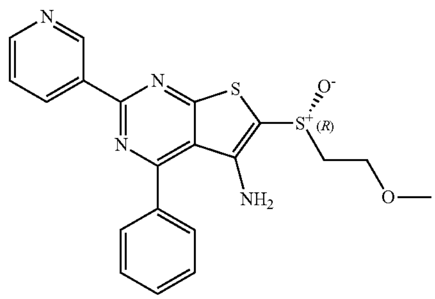 | *** |
| 56 | 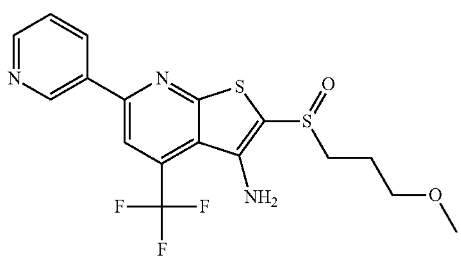 [SMILES: COCCCS(=O)c1sc2nc(-c3cccnc3)cc(C(F)(F)F)c2c1N] | *** |
| 57 | 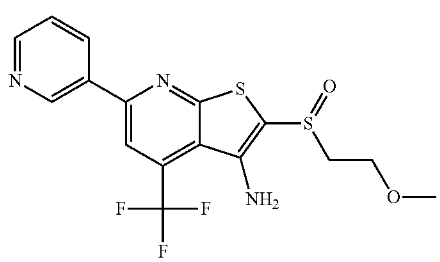 [SMILES: COCCS(=O)c1sc2nc(-c3cccnc3)cc(C(F)(F)F)c2c1N] | *** |
| 58 | 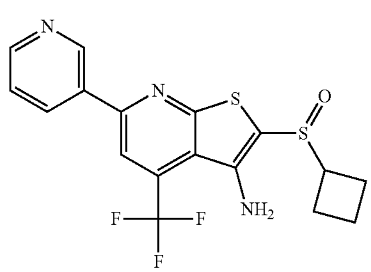 [SMILES: Nc1c(S(=O)C2CCC2)sc2nc(-c3cccnc3)cc(C(F)(F)F)c12] | *** |

TABLE 1-continued

| Molecule Name | Structure | PDGH Assay-IC$_{50}$ |
|---|---|---|
| 59 | 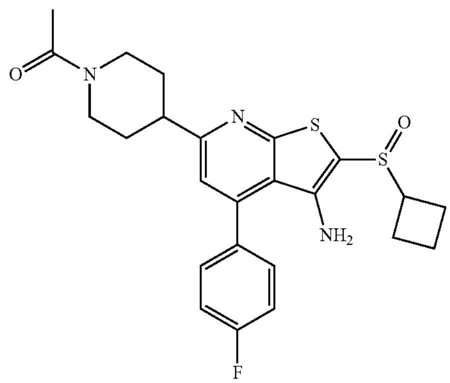 [SMILES: CC(=O)N1CCC(c2cc(-c3ccc(F)cc3)c3c(N)c(S(=O)C4CCC4)sc3n2)CC1] | * |
| 60 | 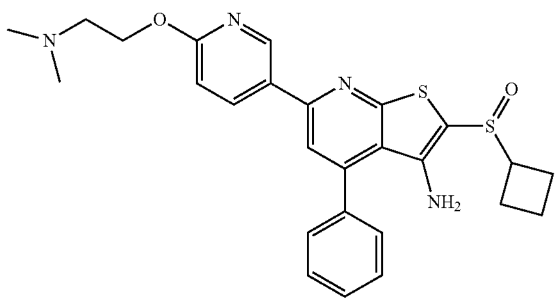 [SMILES: CN(C)CCOc1ccc(-c2cc(-c3ccccc3)c3c(N)c(S(=O)C4CCC4)sc3n2)cn1] | ** |
| 61 | 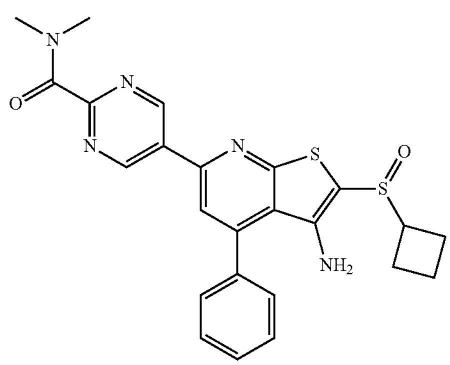 [SMILES: CN(C)C(=O)c1ncc(-c2cc(-c3ccccc3)c3c(N)c(S(=O)C4CCC4)sc3n2)cn1] | ** |
| 62 | 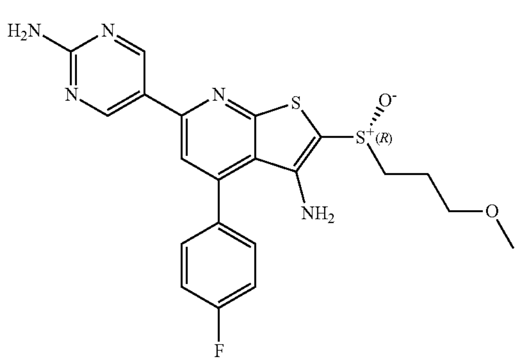 | *** |

TABLE 1-continued

| Molecule Name | Structure | PDGH Assay- IC$_{50}$ |
|---|---|---|
| 63 | 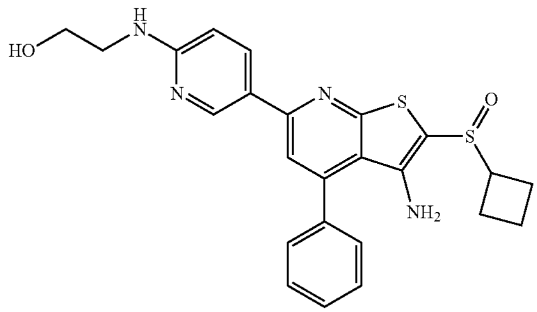 [SMILES: Nc1c(S(=O)C2CCC2)sc2nc(-c3ccc(NCCO)nc3)cc(-c3ccccc3)c12] | *** |
| 64 | 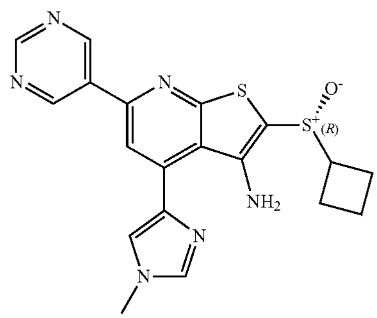 | *** |
| 65 | 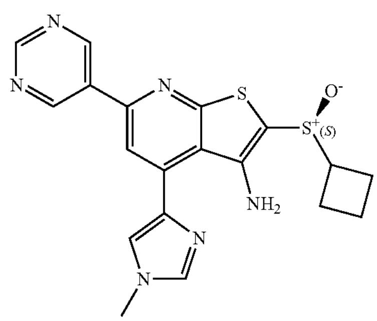 | * |
| 66 | 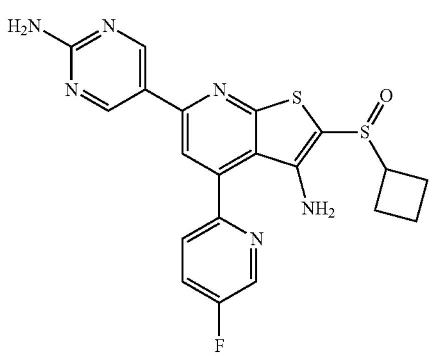 [SMILES: Nc1ncc(-c2cc(-c3ccc(F)cn3)c3c(N)c(S(=O)C4CCC4)sc3n2)cn1] | *** |

TABLE 1-continued
| Molecule Name | Structure | PDGH Assay-IC$_{50}$ |
|---|---|---|
| 67 | 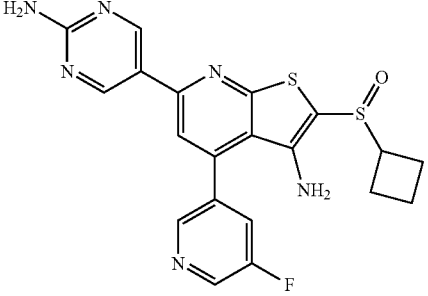 [SMILES: Nc1ncc(-c2cc(-c3cncc(F)c3)c3c(N)c(S(=O)C4CCC4)sc3n2)cn1] | *** |
| 68 | 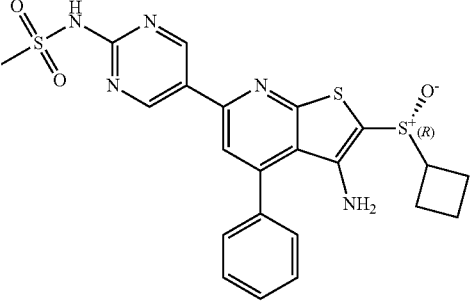 | *** |
| 69 | 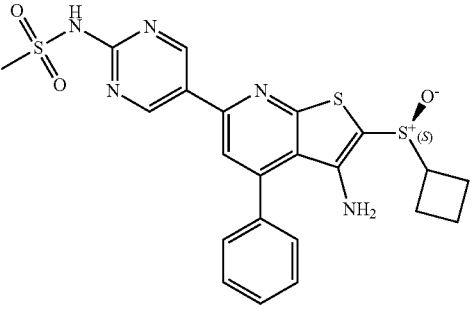 | * |
| 70 | 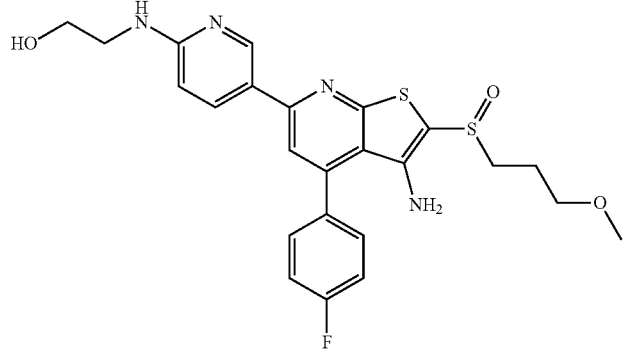 [SMILES: COCCCS(=O)c1sc2nc(-c3ccc(NCCO)nc3)cc(-c3ccc(F)cc3)c2c1N] | ** |

TABLE 1-continued

| Molecule Name | Structure | PDGH Assay-IC$_{50}$ |
|---|---|---|
| 71 | 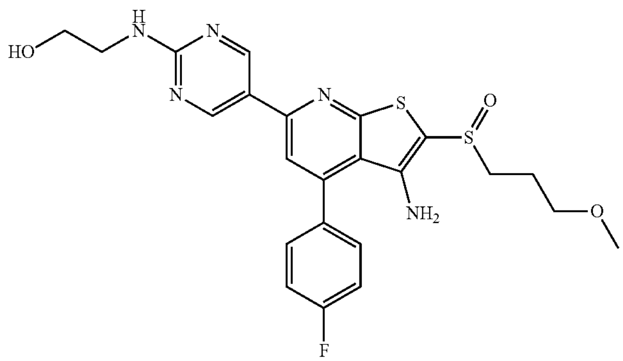 [SMILES: COCCCS(=O)c1sc2nc(-c3cnc(NCCO)nc3)cc(-c3ccc(F)cc3)c2c1N] | ** |
| 72 | 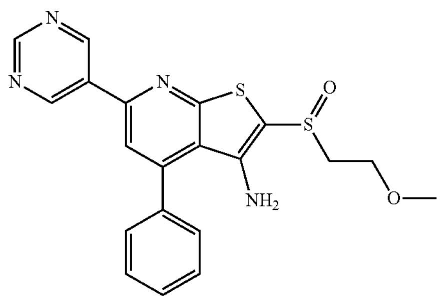 [SMILES: COCCS(=O)c1sc2nc(-c3cncnc3)cc(-c3ccccc3)c2c1N] | *** |
| 73 | 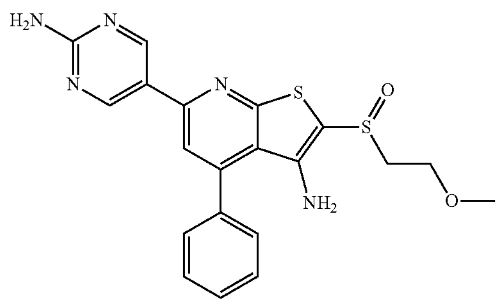 [SMILES: COCCS(=O)c1sc2nc(-c3cnc(N)nc3)cc(-c3ccccc3)c2c1N] | *** |
| 74 | 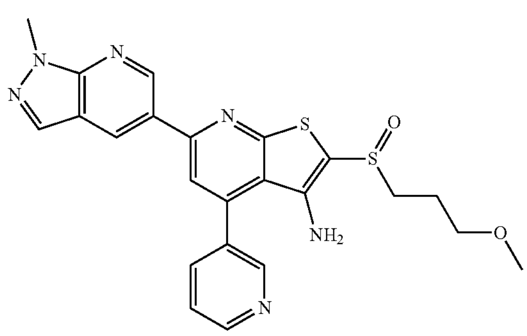 [SMILES: COCCCS(=O)c1sc2nc(-c3cnc4c(cnn4C)c3)cc(-c3cccnc3)c2c1N] | *** |

TABLE 1-continued

| Molecule Name | Structure | PDGH Assay-IC$_{50}$ |
|---|---|---|
| 75 | 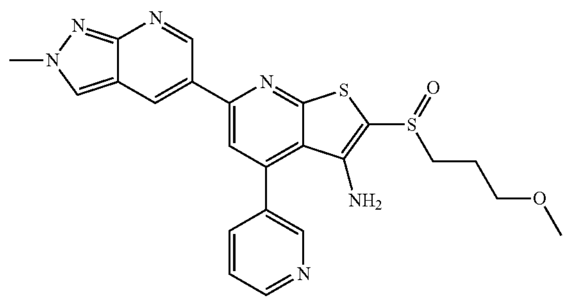 | *** |
| 76 | 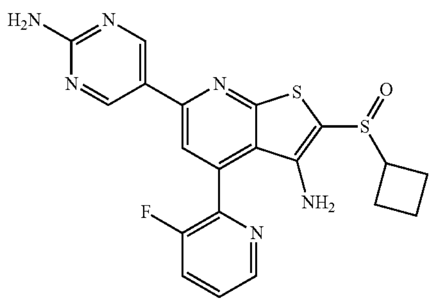 [SMILES: Nc1ncc(-c2cc(-c3ncccc3F)c3c(N)c(S(=O)C4CCC4)sc3n2)cn1] | *** |
| 77 | 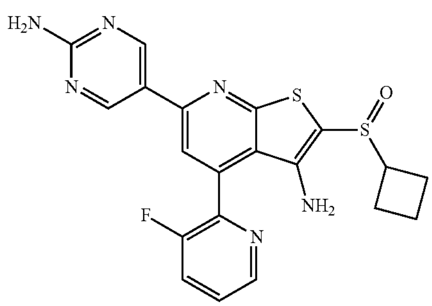 [SMILES: Nc1ncc(-c2cc(-c3ncccc3F)c3c(N)c(S(=O)C4CCC4)sc3n2)cn1] | *** |
| 78 | 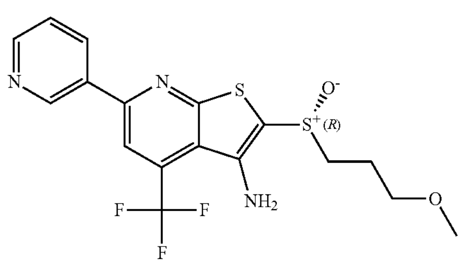 | *** |
| 79 | 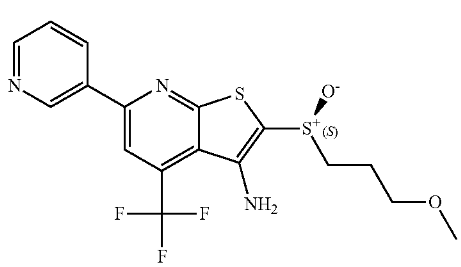 | * |

TABLE 1-continued

| Molecule Name | Structure | PDGH Assay-IC$_{50}$ |
|---|---|---|
| 80 | 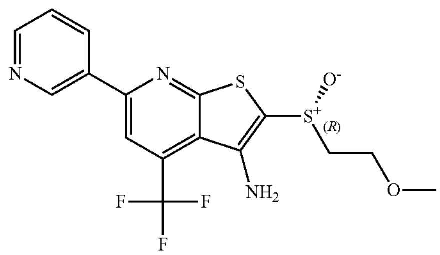 | *** |
| 81 | 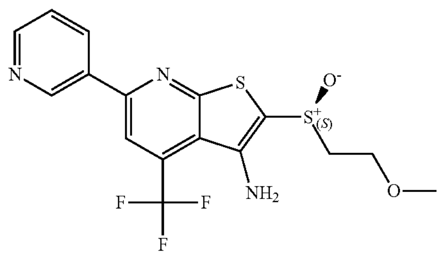 | * |
| 82 | 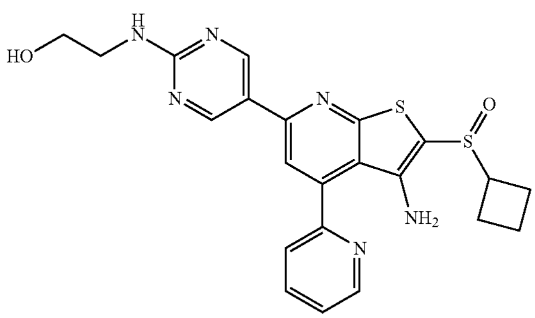 | *** |
| 83 | 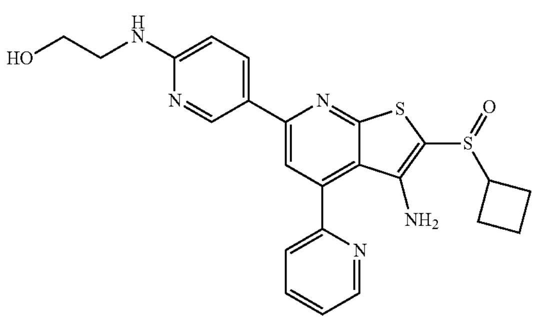 [SMILES: Nc1c(S(=O)C2CCC2)sc2nc(-c3ccc(NCCO)nc3)cc(-c3ccccn3)c12] | *** |
| 84 | 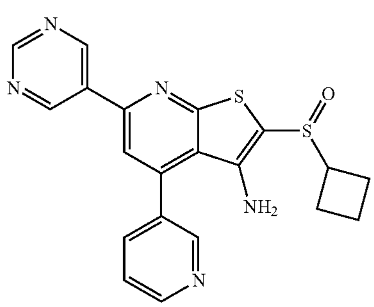 [SMILES: Nc1c(S(=O)C2CCC2)sc2nc(-c3cncnc3)cc(-c3cccnc3)c12] | *** |

TABLE 1-continued

| Molecule Name | Structure | PDGH Assay-IC$_{50}$ |
|---|---|---|
| 85 | 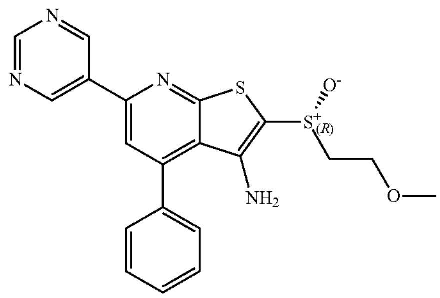 | *** |
| 86 | 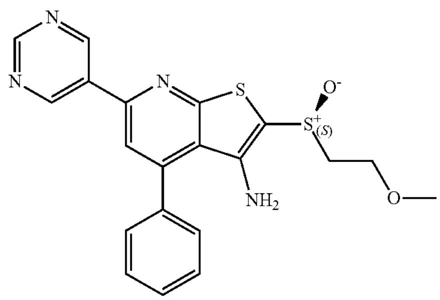 | * |
| 87 | 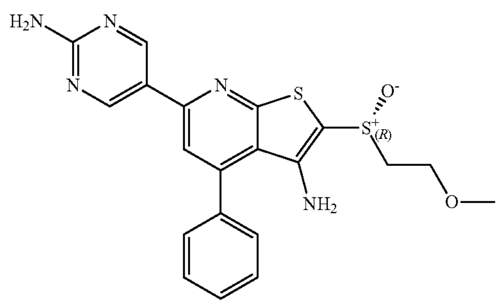 | *** |
| 88 | 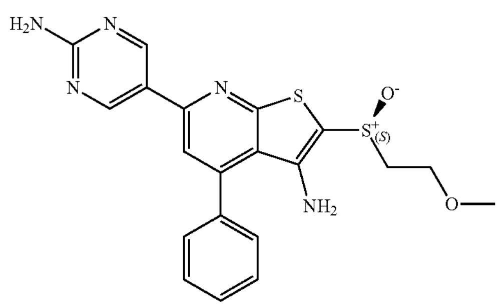 | * |
| 89 | 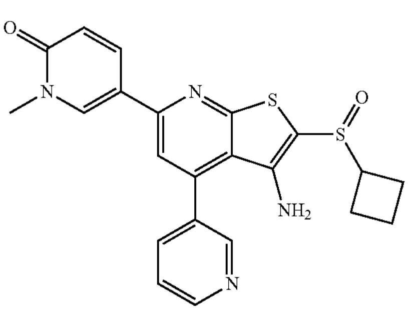 [SMILES: Cn1cc(-c2cc(-c3cccnc3)c3c(N)c(S(=O)C4CCC4)sc3n2)ccc1=O] | *** |

TABLE 1-continued

| Molecule Name | Structure | PDGH Assay-IC$_{50}$ |
|---|---|---|
| 90 | 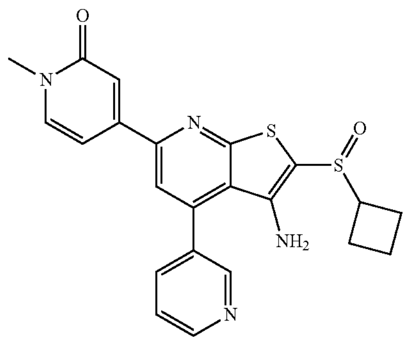 [SMILES: Cn1ccc(-c2cc(-c3cccnc3)c3c(N)c(S(=O)C4CCC4)sc3n2)cc1=O] | ** |
| 91 | 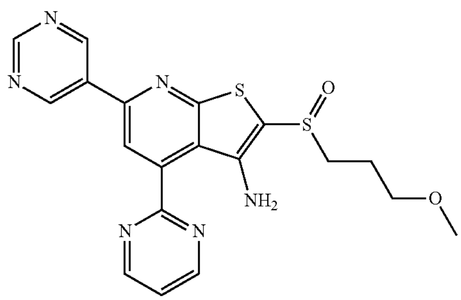 [SMILES: COCCCS(=O)c1sc2nc(-c3cncnc3)cc(-c3ncccn3)c2c1N] | *** |
| 92 | 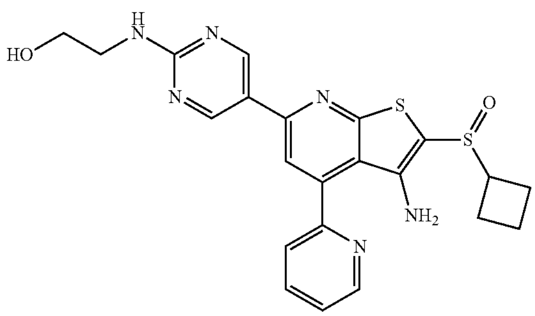 [SMILES: Nc1c(S(=O)C2CCC2)sc2nc(-c3cnc(NCCO)nc3)cc(-c3ccccn3)c12] | *** |
| 93 | 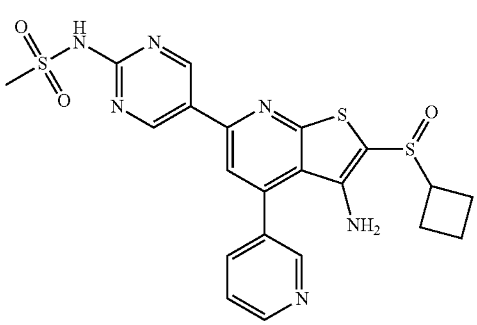 [SMILES: CS(=O)(=O)Nc1ncc(-c2cc(-c3cccnc3)c3c(N)c(S(=O)C4CCC4)sc3n2)cn1] | *** |

TABLE 1-continued

| Molecule Name | Structure | PDGH Assay-IC$_{50}$ |
|---|---|---|
| 94 | 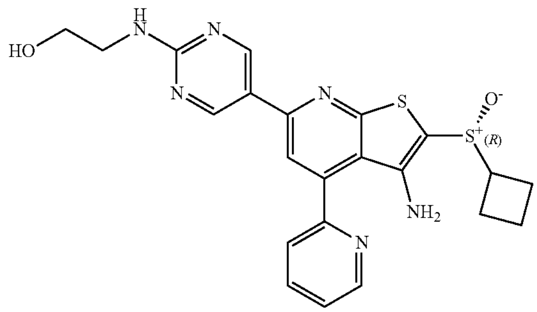 | *** |
| 95 | 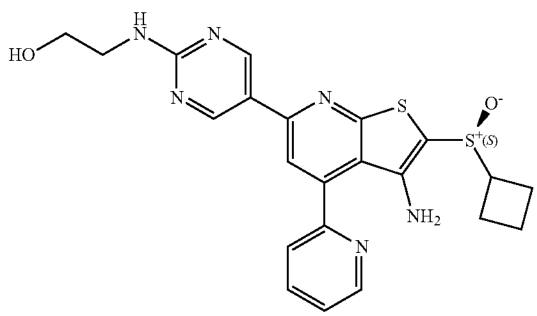 | * |
| 96 | 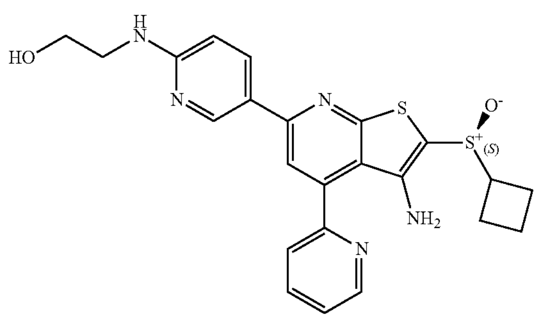 | *** |
| 97 | 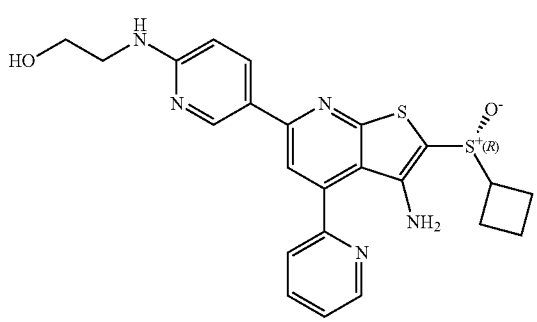 | *** |

TABLE 1-continued

| Molecule Name | Structure | PDGH Assay-IC$_{50}$ |
|---|---|---|
| 98 | 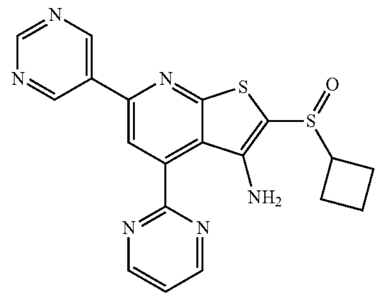 [SMILES: Nc1c(S(=O)C2CCC2)sc2nc(-c3cncnc3)cc(-c3ncccn3)c12] | *** |
| 99 | 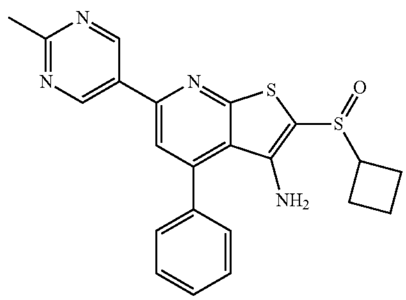 [SMILES: Cc1ncc(-c2cc(-c3ccccc3)c3c(N)c(S(=O)C4CCC4)sc3n2)cn1] | *** |
| 100 | 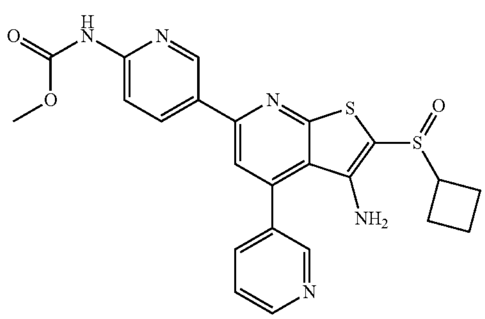 [SMILES: COC(=O)Nc1ccc(-c2cc(-c3cccnc3)c3c(N)c(S(=O)C4CCC4)sc3n2)cn1] | *** |
| 101 | 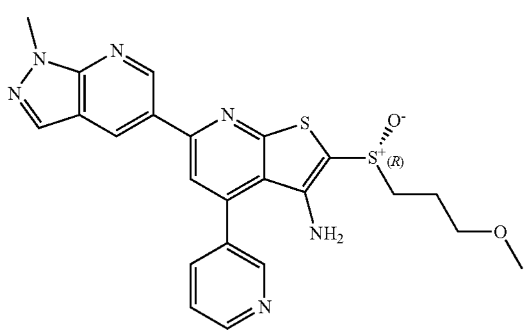 | *** |

TABLE 1-continued

| Molecule Name | Structure | PDGH Assay-IC$_{50}$ |
|---|---|---|
| 102 | 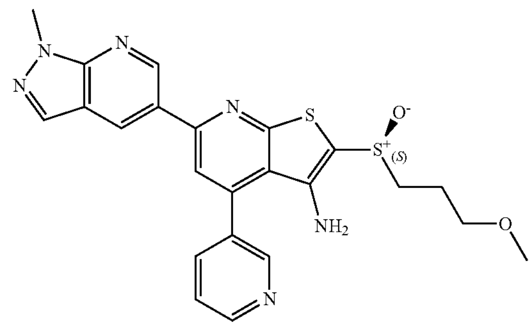 | * |
| 103 | 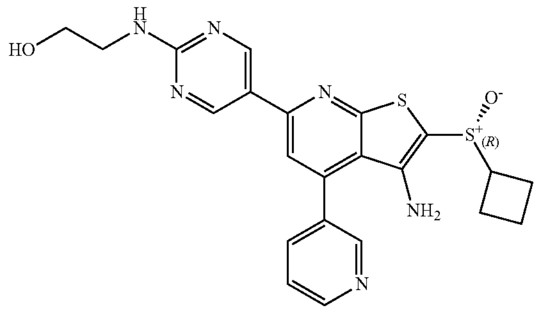 | *** |
| 104 | 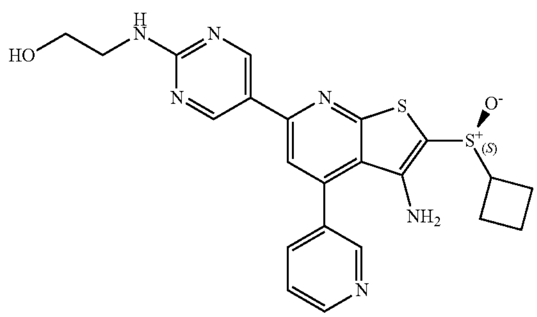 | * |
| 105 | 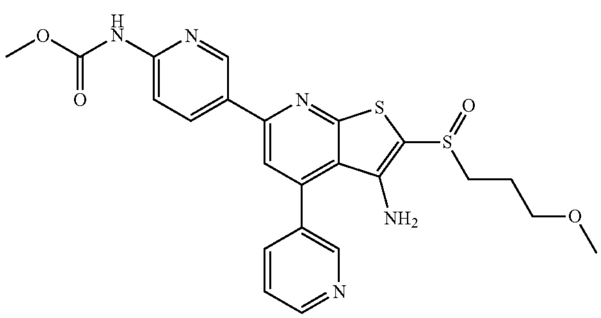 | ** |
| 106 | 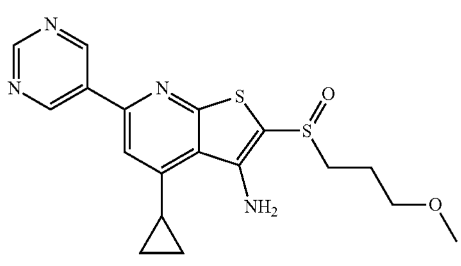 [SMILES: COCCCS(=O)c1sc2nc(-c3cncnc3)cc(C3CC3)c2c1N] | *** |

TABLE 1-continued

| Molecule Name | Structure | PDGH Assay-IC$_{50}$ |
|---|---|---|
| 107 | 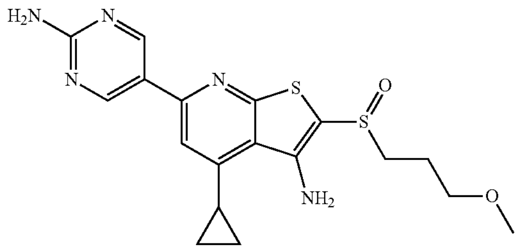 [SMILES: COCCCS(=O)c1sc2nc(-c3cnc(N)nc3)cc(C3CC3)c2c1N] | *** |
| 108 | 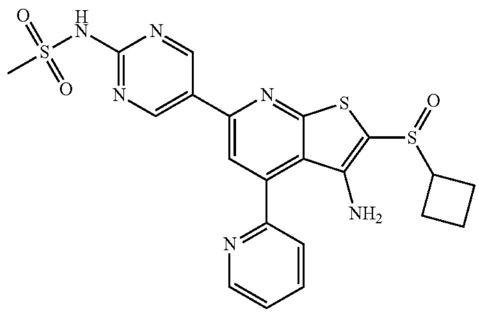 [SMILES: CS(=O)(=O)Nc1ncc(-c2cc(-c3ccccn3)c3c(N)c(S(=O)C4CCC4)sc3n2)cn1] | *** |
| 109 | 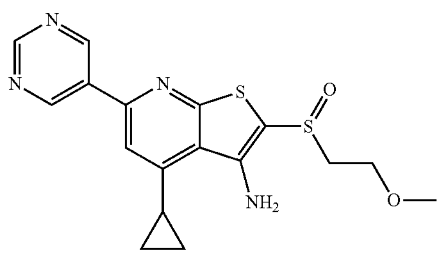 [SMILES: COCCS(=O)c1sc2nc(-c3cncnc3)cc(C3CC3)c2c1N] | *** |
| 110 | 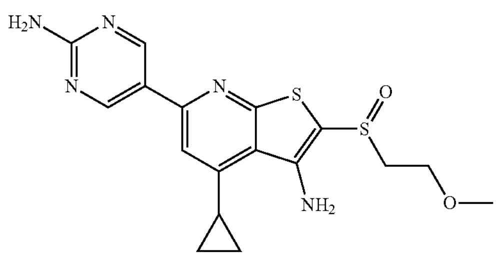 [SMILES: COCCS(=O)c1sc2nc(-c3cnc(N)nc3)cc(C3CC3)c2c1N] | *** |
| 111 | 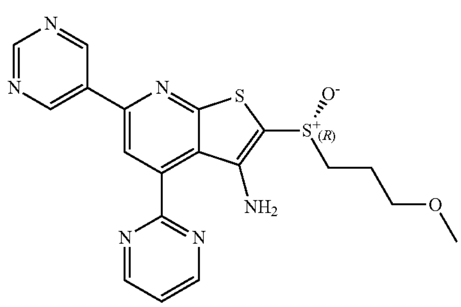 | *** |

TABLE 1-continued

| Molecule Name | Structure | PDGH Assay-IC$_{50}$ |
|---|---|---|
| 112 | 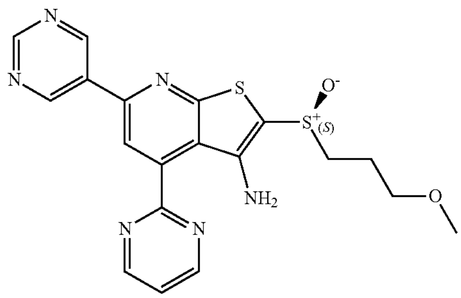 | * |
| 113 | 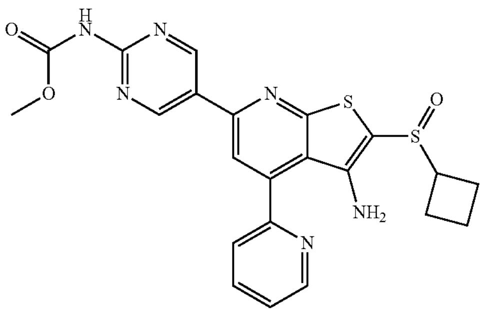 [SMILES: COC(=O)Nc1ncc(-c2cc(-c3ccccn3)c3c(N)c(S(=O)C4CCC4)sc3n2)cn1] | ** |
| 114 | 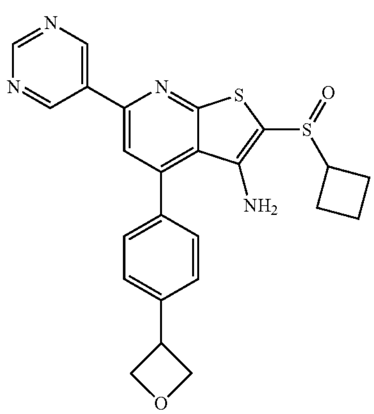 [SMILES: Nc1c(S(=O)C2CCC2)sc2nc(-c3cncnc3)cc(-c3ccc(C4COC4)cc3)c12] | *** |
| 115 | 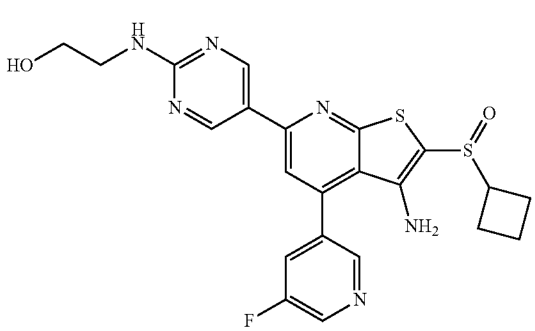 [SMILES: Nc1c(S(=O)C2CCC2)sc2nc(-c3cnc(NCCO)nc3)cc(-c3cncc(F)c3)c12] | *** |

TABLE 1-continued

| Molecule Name | Structure | PDGH Assay-IC$_{50}$ |
|---|---|---|
| 116 | 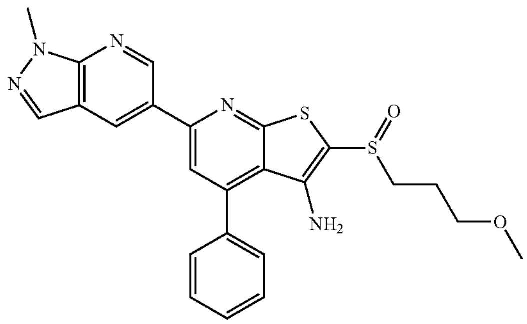 [SMILES: COCCCS(=O)c1sc2nc(-c3cnc4c(cnn4C)c3)cc(-c3ccccc3)c2c1N] | ** |
| 117 | 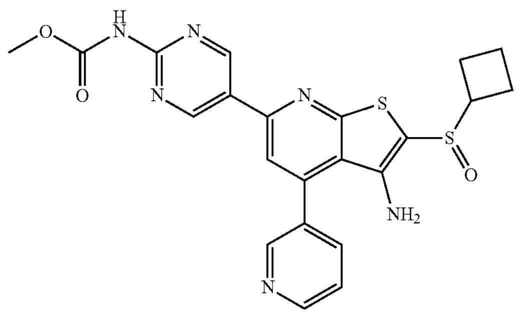 [SMILES: COC(=O)Nc1ncc(-c2cc(-c3cccnc3)c3c(N)c(S(=O)C4CCC4)sc3n2)cn1] | ** |
| 118 | 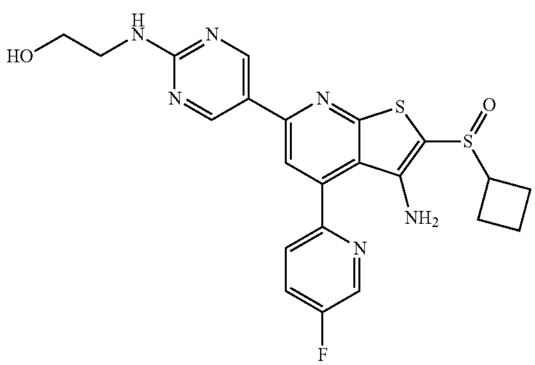 [SMILES: Nc1c(S(=O)C2CCC2)sc2nc(-c3cnc(NCCO)nc3)cc(-c3ccc(F)cn3)c12] | ** |
| 119 | 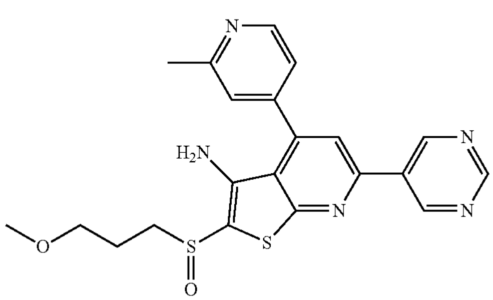 [SMILES: COCCCS(=O)c1sc2nc(-c3cncnc3)cc(-c3ccnc(C)c3)c2c1N] | *** |

TABLE 1-continued

| Molecule Name | Structure | PDGH Assay-IC$_{50}$ |
|---|---|---|
| 120 | 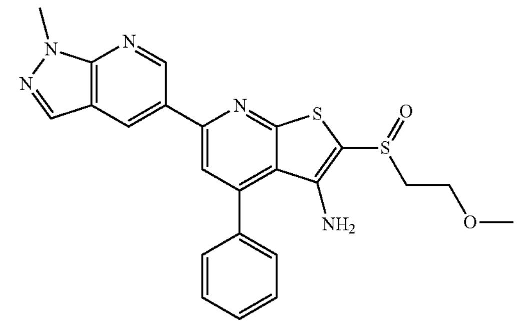 [SMILES: COCCS(=O)c1sc2nc(-c3cnc4c(cnn4C)c3)cc(-c3ccccc3)c2c1N] | *** |
| 121 | 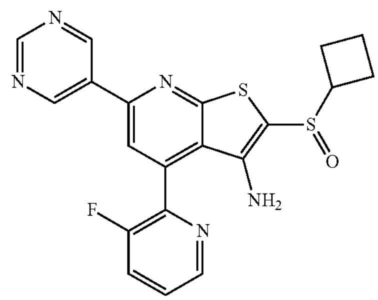 [SMILES: Nc1c(S(=O)C2CCC2)sc2nc(-c3cncnc3)cc(-c3ncccc3F)c12] | *** |
| 122 | 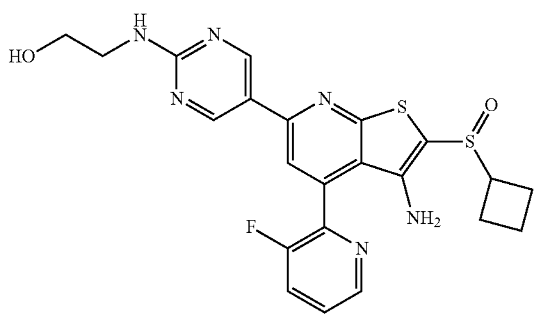 [SMILES: Nc1c(S(=O)C2CCC2)sc2nc(-c3cnc(NCCO)nc3)cc(-c3ncccc3F)c12] | *** |
| 123 | 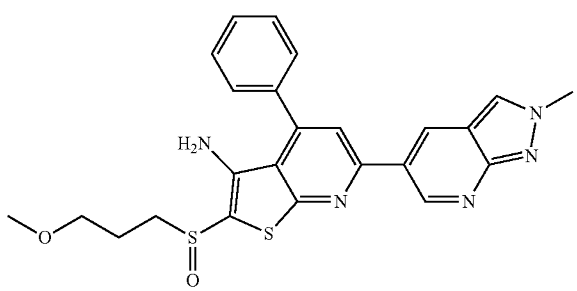 | *** |
| 124 | 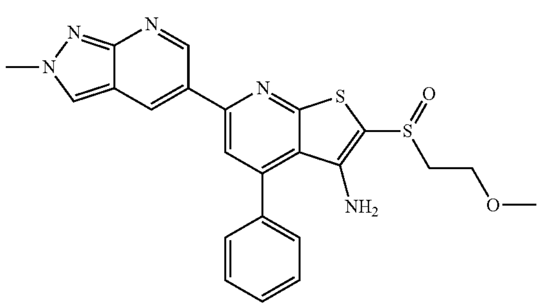 | *** |

TABLE 1-continued
| Molecule Name | Structure | PDGH Assay-IC$_{50}$ |
|---|---|---|
| 125 | 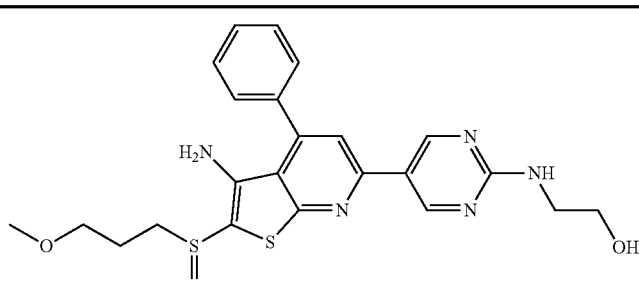 | *** |
| 126 | 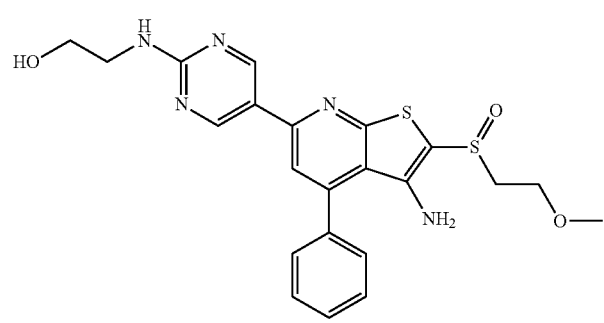 | *** |
| 127 | 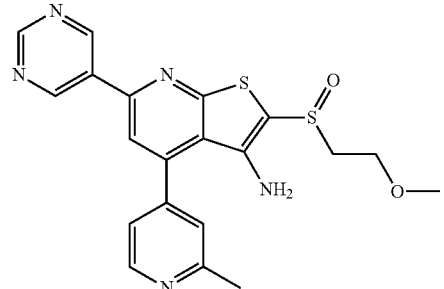 | *** |
| 128 | 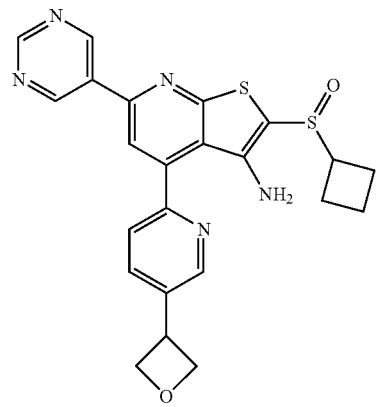 [SMILES: Nc1c(S(=O)C2CCC2)sc2nc(-c3cncnc3)cc(-c3ccc(C4COC4)cn3)c12] | *** |

TABLE 1-continued

| Molecule Name | Structure | PDGH Assay-IC$_{50}$ |
|---|---|---|
| 129 | 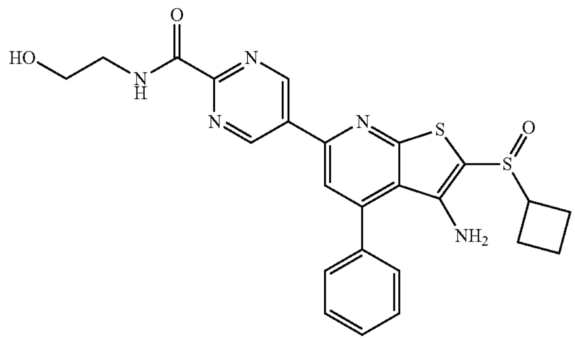 [SMILES: Nc1c(S(=O)C2CCC2)sc2nc(-c3cnc(C(=O)NCCO)nc3)cc(-c3ccccc3)c12] | *** |
| 130 | 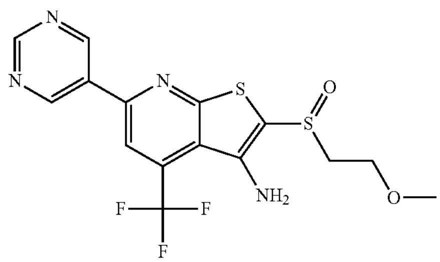 [SMILES: COCCS(=O)c1sc2nc(-c3cncnc3)cc(C(F)(F)F)c2c1N] | *** |
| 131 | 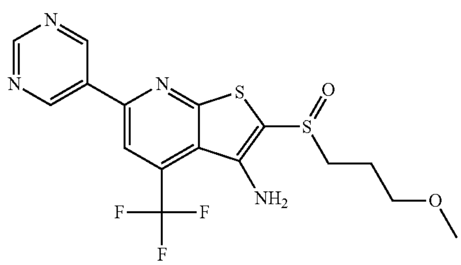 [SMILES: COCCCS(=O)c1sc2nc(-c3cncnc3)cc(C(F)(F)F)c2c1N] | *** |
| 132 | 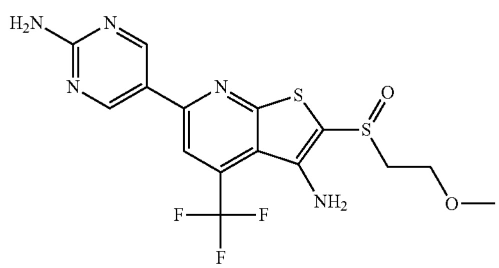 | *** |
| 133 | 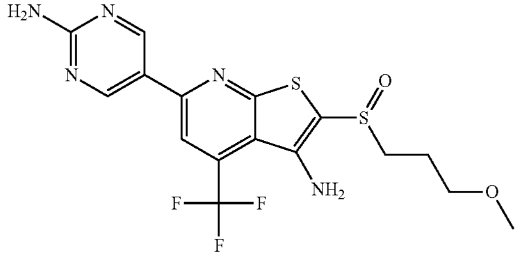 [SMILES: COCCCS(=O)c1sc2nc(-c3cnc(N)nc3)cc(C(F)(F)F)c2c1N] | *** |

| Molecule Name | Structure | PDGH Assay-IC$_{50}$ |
|---|---|---|
| 134 | 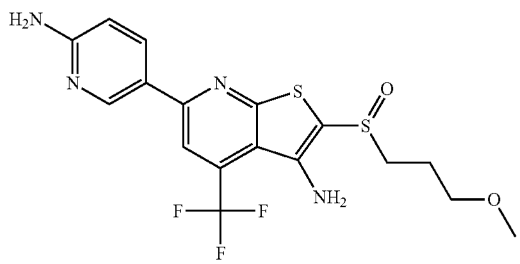 [SMILES: COCCCS(=O)c1sc2nc(-c3ccc(N)nc3)cc(C(F)(F)F)c2c1N] | ** |
| 135 | 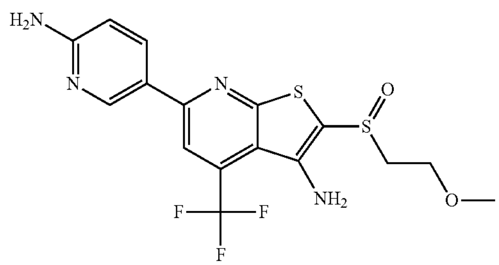 [SMILES: COCCS(=O)c1sc2nc(-c3ccc(N)nc3)cc(C(F)(F)F)c2c1N] | ** |
| 136 | 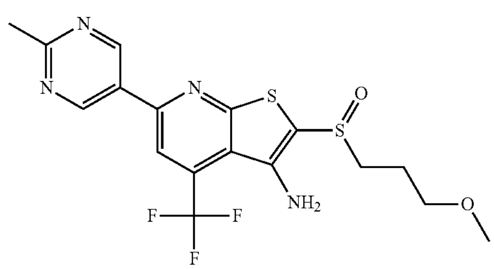 | ** |
| 137 | 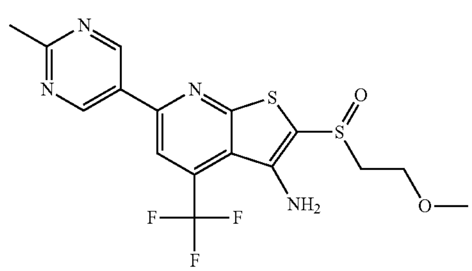 | *** |
| 138 | 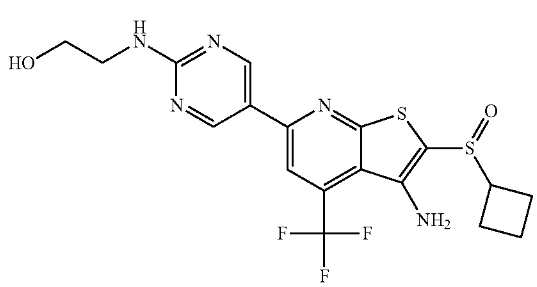 [SMILES: Nc1c(S(=O)C2CCC2)sc2nc(-c3cnc(NCCO)nc3)cc(C(F)(F)F)c12] | ** |

TABLE 1-continued

| Molecule Name | Structure | PDGH Assay-IC$_{50}$ |
|---|---|---|
| 139 | 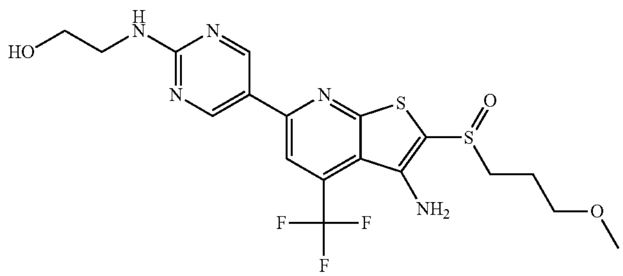 [SMILES: COCCCS(=O)c1sc2nc(-c3cnc(NCCO)nc3)cc(C(F)(F)F)c2c1N] | ** |
| 140 | 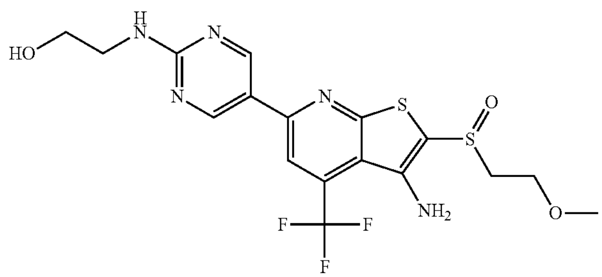 [SMILES: COCCS(=O)c1sc2nc(-c3cnc(NCCO)nc3)cc(C(F)(F)F)c2c1N] | ** |
| 141 | 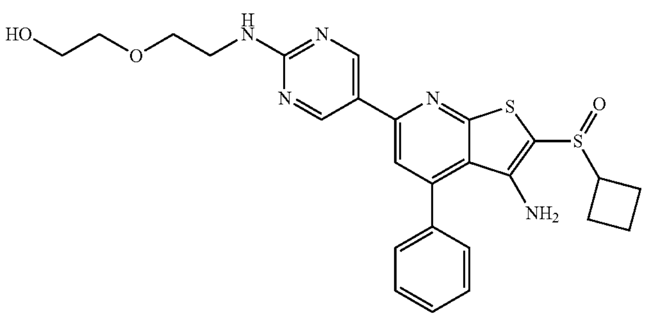 [SMILES: Nc1c(S(=O)C2CCC2)sc2nc(-c3cnc(NCCOCCO)nc3)cc(-c3ccccc3)c12] | *** |
| 142 | 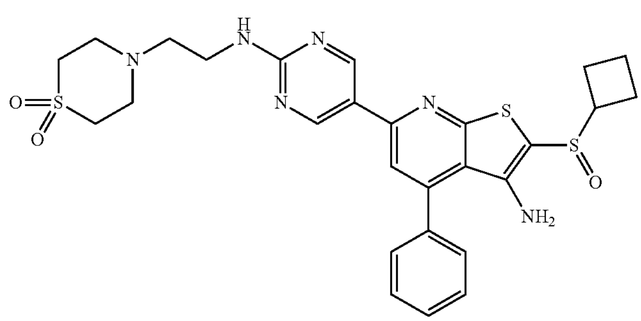 [SMILES: Nc1c(S(=O)C2CCC2)sc2nc(-c3cnc(NCCN4CCS(=O)(=O)CC4)nc3)cc(-c3ccccc3)c12] | *** |

TABLE 1-continued

| Molecule Name | Structure | PDGH Assay-IC$_{50}$ |
|---|---|---|
| 143 | 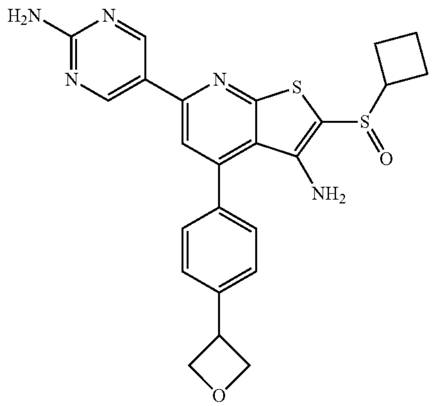 [SMILES: Nc1ncc(-c2cc(-c3ccc(C4COC4)cc3)c3c(N)c(S(=O)C4CCC4)sc3n2)cn1] | *** |
| 144 | 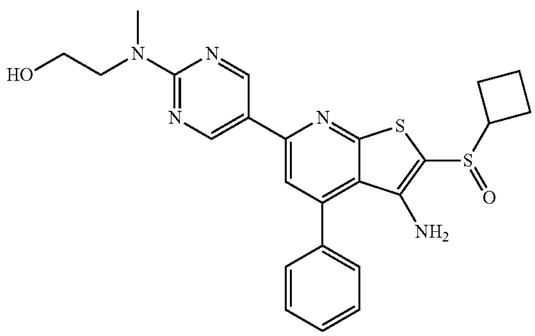 [SMILES: CN(CCO)c1ncc(-c2cc(-c3ccccc3)c3c(N)c(S(=O)C4CCC4)sc3n2)cn1] | *** |
| 145 | 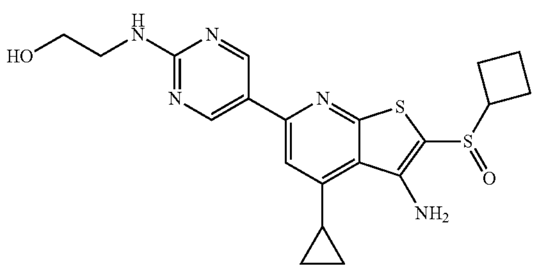 [SMILES: Nc1c(S(=O)C2CCC2)sc2nc(-c3cnc(NCCO)nc3)cc(C3CC3)c12] | *** |
| 146 | 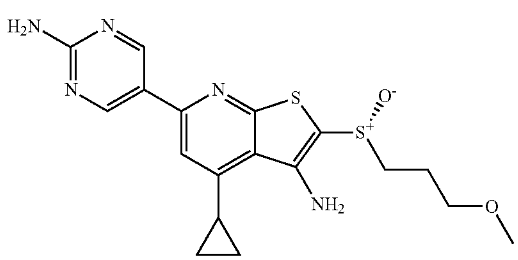 [SMILES: COCCC[S@@+]([O-])c1sc2nc(-c3cnc(N)nc3)cc(C3CC3)c2c1N] | *** |

TABLE 1-continued

| Molecule Name | Structure | PDGH Assay-IC$_{50}$ |
|---|---|---|
| 147 | 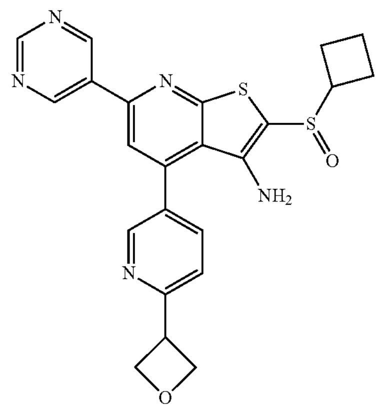 [SMILES: Nc1c(S(=O)C2CCC2)sc2nc(-c3cncnc3)cc(-c3ccc(C4COC4)nc3)c12] | *** |
| 148 | 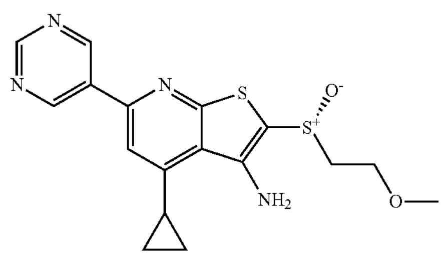 | *** |
| 149 | 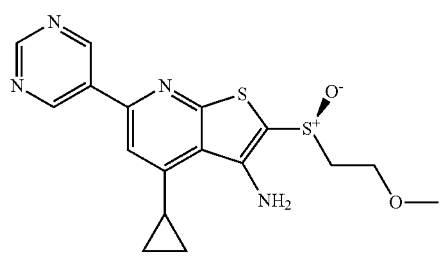 [SMILES: COCC[S@+]([O-])c1sc2nc(-c3cncnc3)cc(C3CC3)c2c1N] | * |
| 150 | 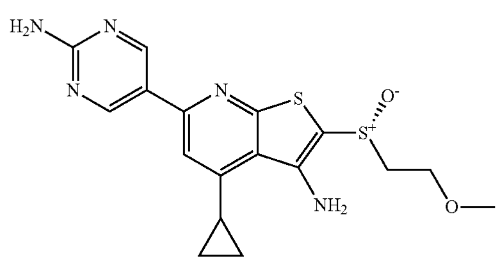 [SMILES: COCC[S@@+]([O-])c1sc2nc(-c3cnc(N)nc3)cc(C3CC3)c2c1N] | *** |
| 151 | 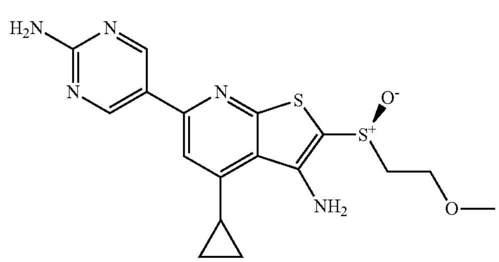 [SMILES: COCC[S@+]([O-])c1sc2nc(-c3cnc(N)nc3)cc(C3CC3)c2c1N] | * |

TABLE 1-continued

| Molecule Name | Structure | PDGH Assay- IC$_{50}$ |
|---|---|---|
| 152 | 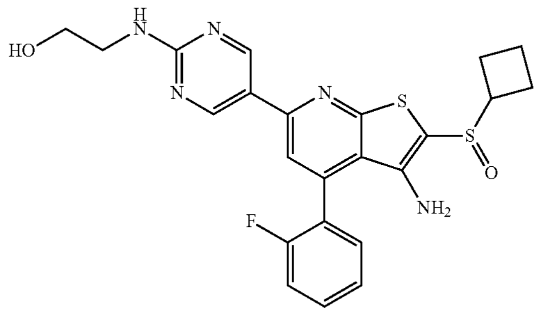 [SMILES: Nc1c(S(=O)C2CCC2)sc2nc(-c3cnc(NCCO)nc3)cc(-c3ccccc3F)c12] | *** |
| 153 | 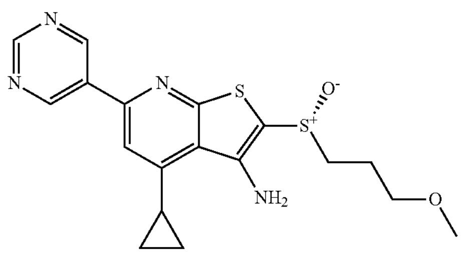 | *** |
| 154 | 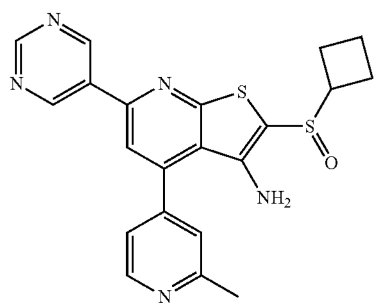 [SMILES: Cc1cc(-c2cc(-c3cncnc3)nc3sc(S(=O)C4CCC4)c(N)c23)ccn1] | *** |
| 155 | 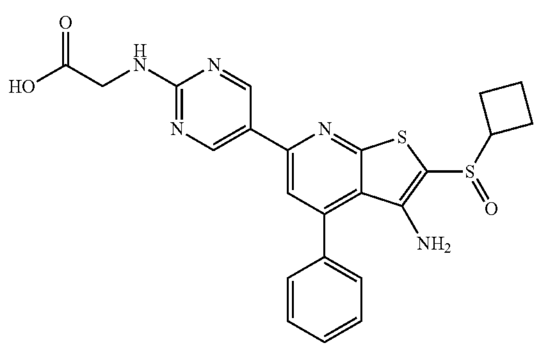 [SMILES: Nc1c(S(=O)C2CCC2)sc2nc(-c3cnc(NCC(=O)O)nc3)cc(-c3ccccc3)c12] | *** |
| 156 | 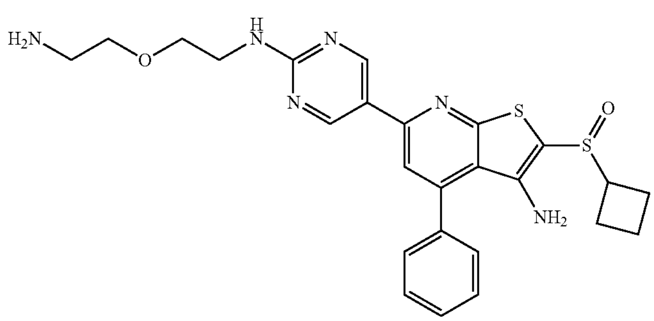 [SMILES: NCCOCCNc1ncc(-c2cc(-c3ccccc3)c3c(N)c(S(=O)C4CCC4)sc3n2)cn1] | *** |

TABLE 1-continued

| Molecule Name | Structure | PDGH Assay-IC$_{50}$ |
|---|---|---|
| 157 | 2-((5-(3-amino-2-(cyclobutylsulfinyl)-4-(3-fluorophenyl)thieno[2,3-b]pyridin-6-yl)pyrimidin-2-yl)amino)ethanol | *** |
| 158 | 2-((5-(3-amino-2-(cyclobutylsulfinyl)-4-(4-fluorophenyl)thieno[2,3-b]pyridin-6-yl)pyrimidin-2-yl)amino)ethanol | ** |
| 159 | 2-((5-(3-amino-4-(4-chlorophenyl)-2-(cyclobutylsulfinyl)thieno[2,3-b]pyridin-6-yl)pyrimidin-2-yl)amino)ethanol | *** |
| 160 | 2-((5-(3-amino-2-(cyclobutylsulfinyl)-4-(4-(trifluoromethyl)phenyl)thieno[2,3-b]pyridin-6-yl)pyrimidin-2-yl)amino)ethanol | ** |

TABLE 1-continued

| Molecule Name | Structure | PDGH Assay-IC$_{50}$ |
|---|---|---|
| 161 | 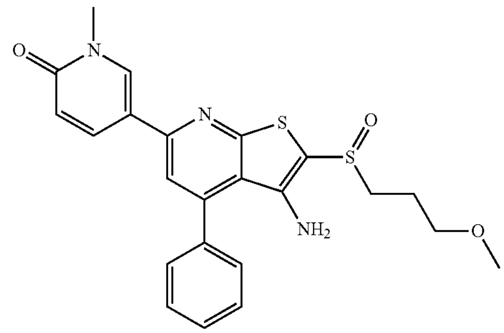 [SMILES: COCCCS(=O)c1sc2nc(-c3ccc(=O)n(C)c3)cc(-c3ccccc3)c2c1N] | *** |
| 162 | 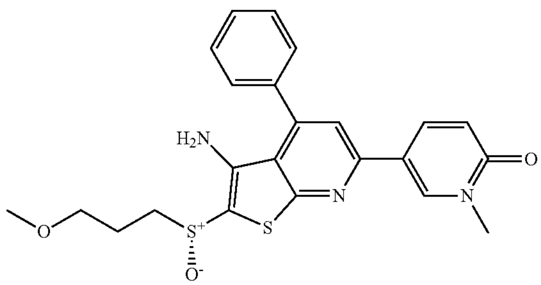 | *** |
| 163 | 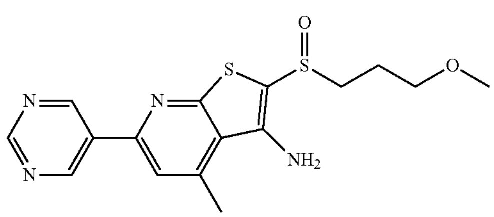 [SMILES: COCCCS(=O)c1sc2nc(-c3cncnc3)cc(C)c2c1N] | *** |
| 164 | 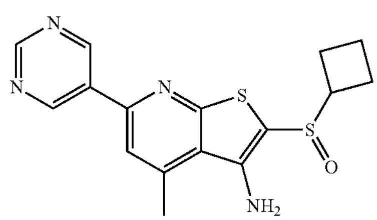 [SMILES: Cc1cc(-c2cncnc2)nc2sc(S(=O)C3CCC3)c(N)c12] | *** |
| 165 | 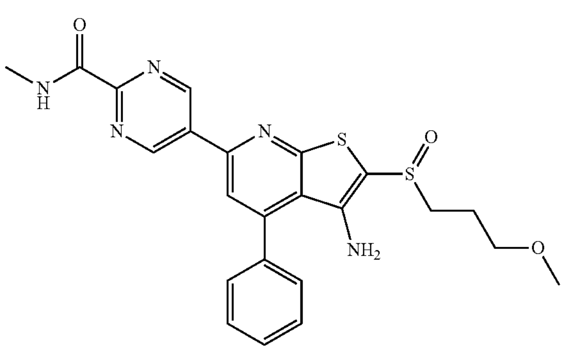 | ** |

TABLE 1-continued

| Molecule Name | Structure | PDGH Assay-IC$_{50}$ |
|---|---|---|
| 166 | 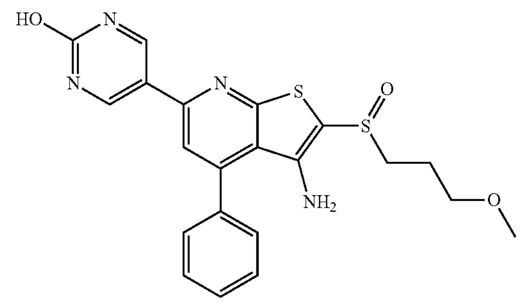 [SMILES: COCCCS(=O)c1sc2nc(-c3cnc(O)nc3)cc(-c3ccccc3)c2c1N] | ** |
| 167 | 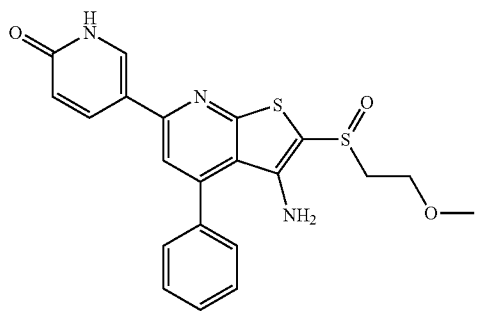 [SMILES: COCCS(=O)c1sc2nc(-c3ccc(=O)[nH]c3)cc(-c3ccccc3)c2c1N] | *** |
| 168 | 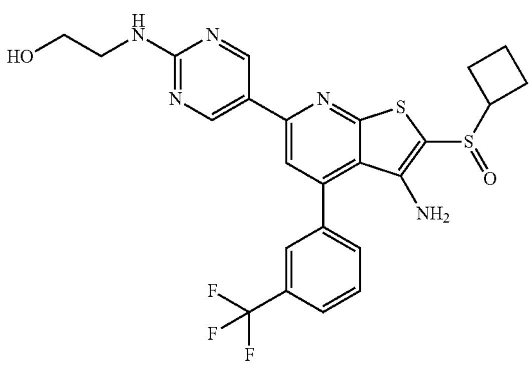 [SMILES: Nc1c(S(=O)C2CCC2)sc2nc(-c3cnc(NCCO)nc3)cc(-c3cccc(C(F)(F)F)c3)c12] | ** |
| 169 | 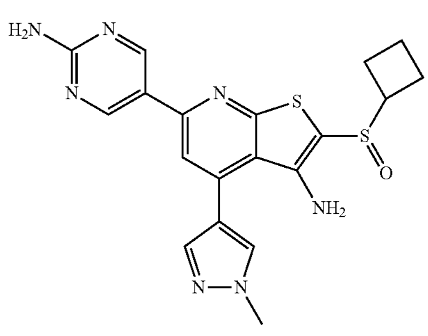 [SMILES: Cn1cc(-c2cc(-c3cnc(N)nc3)nc3sc(S(=O)C4CCC4)c(N)c23)cn1] | *** |

TABLE 1-continued

| Molecule Name | Structure | PDGH Assay-IC$_{50}$ |
|---|---|---|
| 170 | 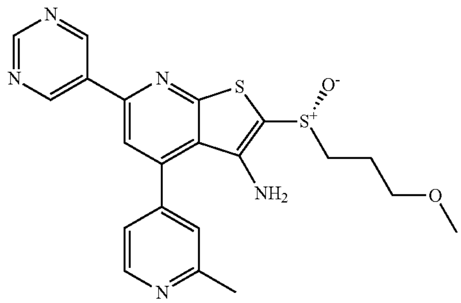 [SMILES: COCCC[S@@+]([O-])c1sc2nc(-c3cncnc3)cc(-c3ccnc(C)c3)c2c1N] | *** |
| 171 | 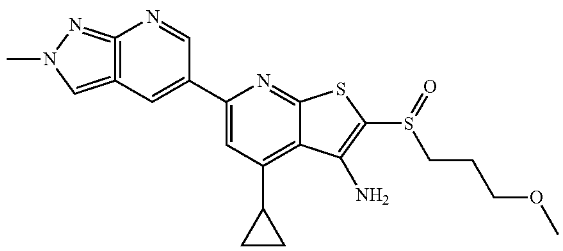 | *** |
| 172 | 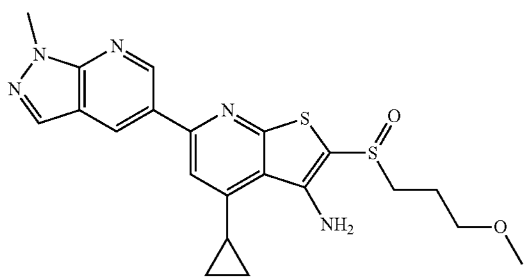 [SMILES: COCCCS(=O)c1sc2nc(-c3cnc4c(cnn4C)c3)cc(C3CC3)c2c1N] | ** |
| 173 | 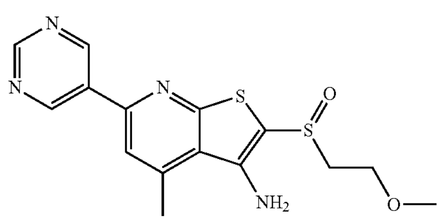 [SMILES: COCCS(=O)c1sc2nc(-c3cncnc3)cc(C)c2c1N] | *** |
| 174 | 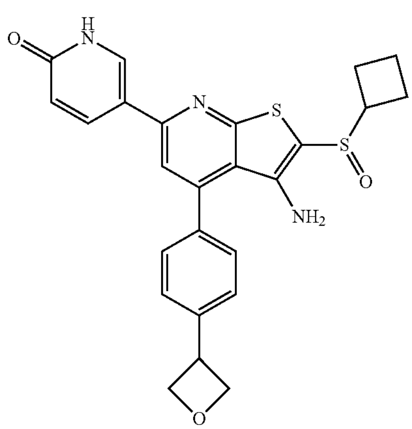 [SMILES: Nc1c(S(=O)C2CCC2)sc2nc(-c3ccc(=O)[nH]c3)cc(-c3ccc(C4COC4)cc3)c12] | ** |

TABLE 1-continued

| Molecule Name | Structure | PDGH Assay-IC$_{50}$ |
|---|---|---|
| 175 | 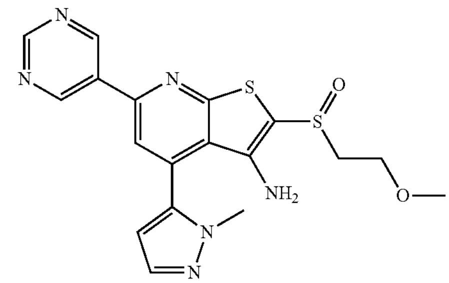 [SMILES: COCCS(=O)c1sc2nc(-c3cncnc3)cc(-c3ccnn3C)c2c1N] | ** |
| 176 | 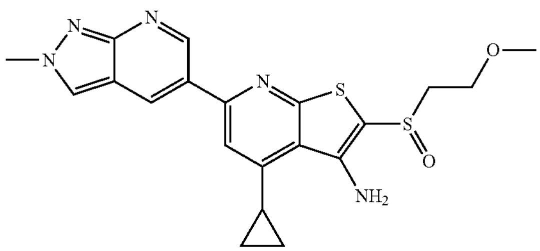 | *** |
| 177 | 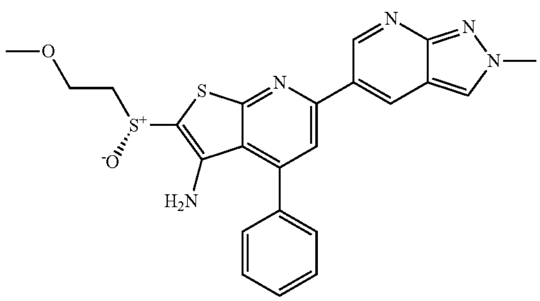 | ** |
| 178 | 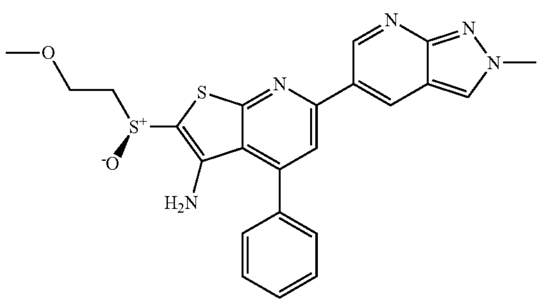 | * |
| 179 | 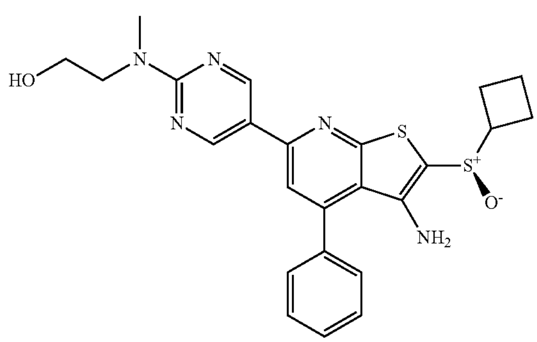 [SMILES: CN(CCO)c1ncc(-c2cc(-c3ccccc3)c3c(N)c([S@+]([O-])C4CCC4)sc3n2)cn1] | *** |

TABLE 1-continued

| Molecule Name | Structure | PDGH Assay-IC$_{50}$ |
|---|---|---|
| 180 | 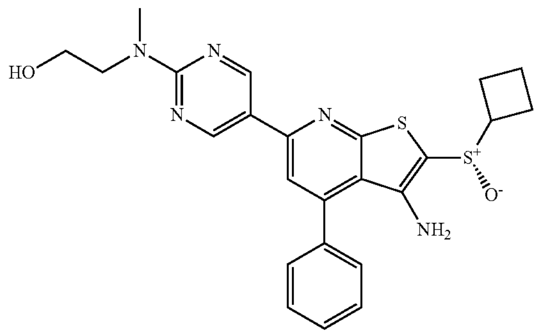 [SMILES: CN(CCO)c1ncc(-c2cc(-c3ccccc3)c3c(N)c([S@@+]([O-])C4CCC4)sc3n2)cn1] | * |
| 181 | 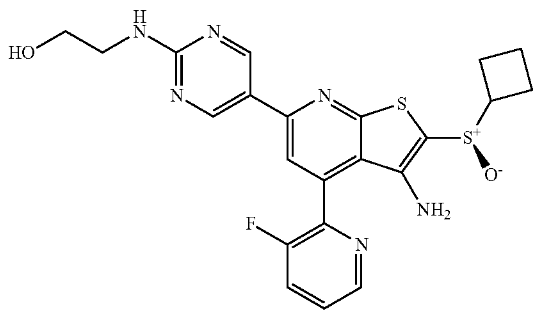 [SMILES: Nc1c([S@+]([O-])C2CCC2)sc2nc(-c3cnc(NCCO)nc3)cc(-c3ncccc3F)c12] | *** |
| 182 | 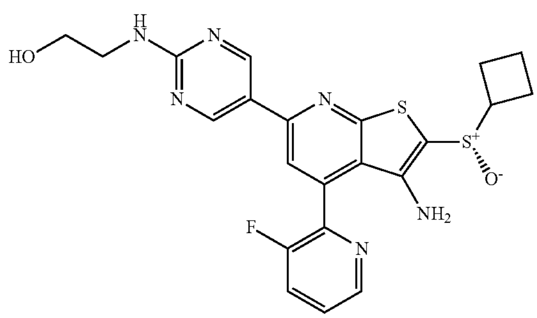 [SMILES: Nc1c([S@@+]([O-])C2CCC2)sc2nc(-c3cnc(NCCO)nc3)cc(-c3ncccc3F)c12] | * |
| 183 | 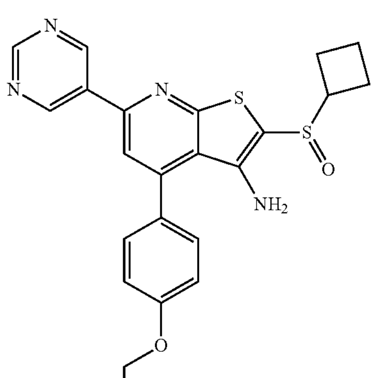 | *** |

TABLE 1-continued

| Molecule Name | Structure | PDGH Assay-IC$_{50}$ |
|---|---|---|
| 184 | 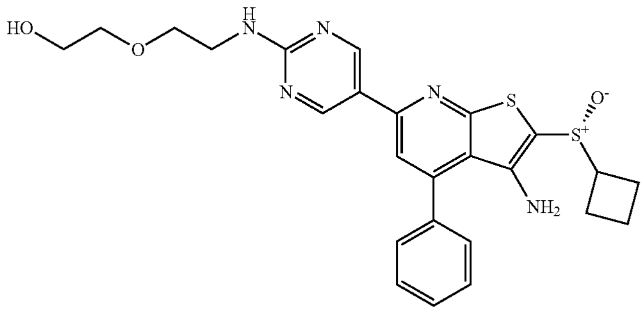 [SMILES: Nc1c([S@+]([O-])C2CCC2)sc2nc(-c3cnc(NCCOCCO)nc3)cc(-c3ccccc3)c12] | *** |
| 185 | 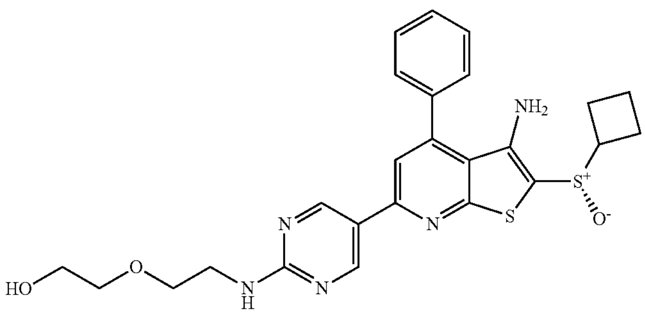 [SMILES: Nc1c([S@@+]([O-])C2CCC2)sc2nc(-c3cnc(NCCOCCO)nc3)cc(-c3ccccc3)c12] | * |
| 186 | 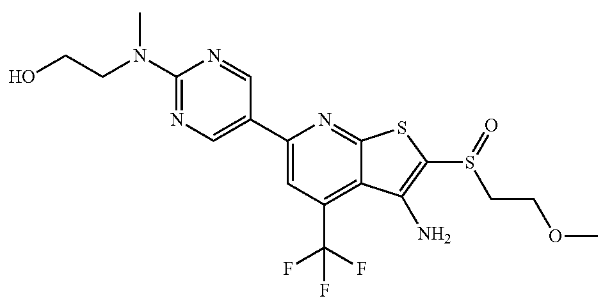 [SMILES: COCCS(=O)c1sc2nc(-c3cnc(N(C)CCO)nc3)cc(C(F)(F)F)c2c1N] | ** |
| 187 | 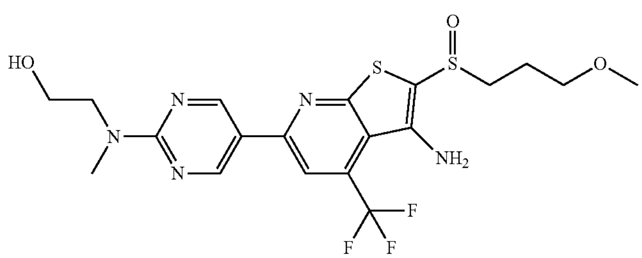 [SMILES: COCCCS(=O)c1sc2nc(-c3cnc(N(C)CCO)nc3)cc(C(F)(F)F)c2c1N] | ** |
| 188 | 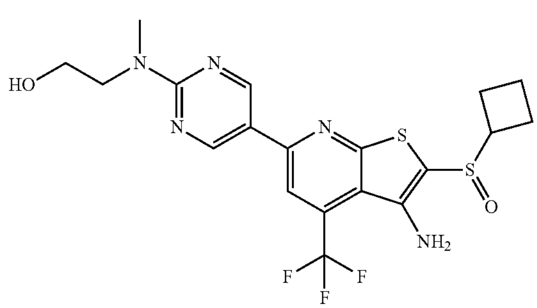 [SMILES: CN(CCO)c1ncc(-c2cc(C(F)(F)F)c3c(N)c(S(=O)C4CCC4)sc3n2)cn1] | ** |

TABLE 1-continued

| Molecule Name | Structure | PDGH Assay- IC$_{50}$ |
|---|---|---|
| 189 | 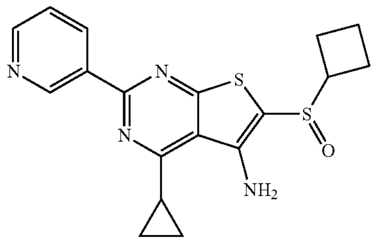 [SMILES: Nc1c(S(=O)C2CCC2)sc2nc(-c3cccnc3)nc(C3CC3)c12] | *** |
| 190 | 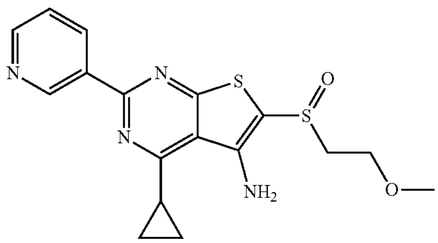 [SMILES: COCCS(=O)c1sc2nc(-c3cccnc3)nc(C3CC3)c2c1N] | *** |
| 191 | 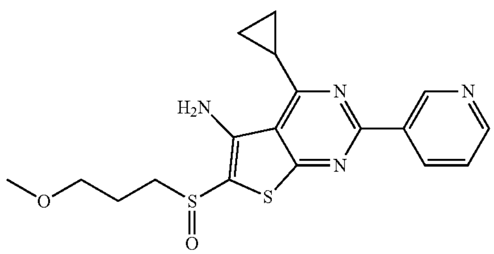 [SMILES: COCCCS(=O)c1sc2nc(-c3cccnc3)nc(C3CC3)c2c1N] | ** |
| 192 | 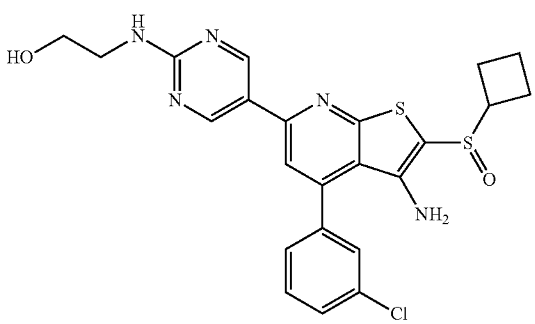 | *** |
| 193 | 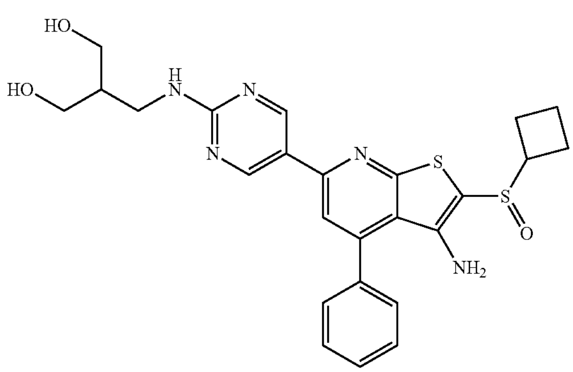 [SMILES: Nc1c(S(=O)C2CCC2)sc2nc(-c3cnc(NCC(CO)CO)nc3)cc(-c3ccccc3)c12] | *** |

TABLE 1-continued

| Molecule Name | Structure | PDGH Assay-IC$_{50}$ |
|---|---|---|
| 194 | 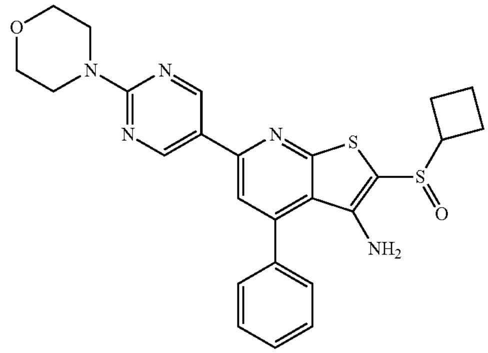 [SMILES: Nc1c(S(=O)C2CCC2)sc2nc(-c3cnc(N4CCOCC4)nc3)cc(-c3ccccc3)c12] | ** |
| 195 | 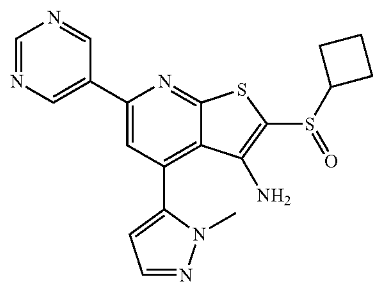 [SMILES: Cn1nccc1-c1cc(-c2cncnc2)nc2sc(S(=O)C3CCC3)c(N)c12] | *** |
| 196 | 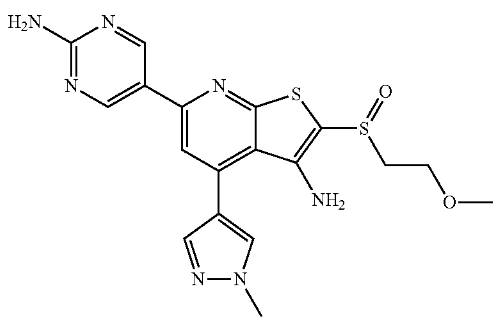 [SMILES: COCCS(=O)c1sc2nc(-c3cnc(N)nc3)cc(-c3cnn(C)c3)c2c1N] | *** |
| 197 | 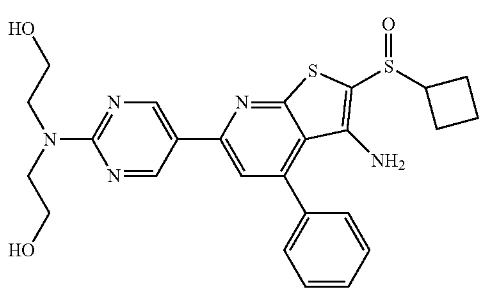 [SMILES: Nc1c(S(=O)C2CCC2)sc2nc(-c3cnc(N(CCO)CCO)nc3)cc(-c3ccccc3)c12] | *** |
| 198 | 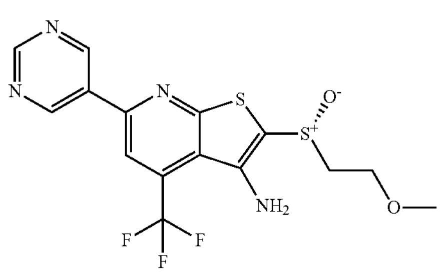 [SMILES: COCC[S@@+]([O-])c1sc2nc(-c3cncnc3)cc(C(F)(F)F)c2c1N] | *** |

| Molecule Name | Structure | PDGH Assay-IC$_{50}$ |
|---|---|---|
| 199 | 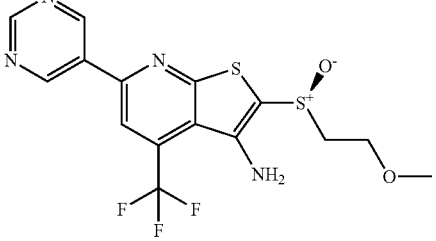 | * |
| 200 | 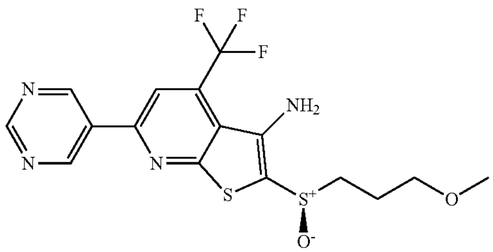 [SMILES: COCCC[S@@+]([O-])c1sc2nc(-c3cncnc3)cc(C(F)(F)F)c2c1N] | *** |
| 201 | 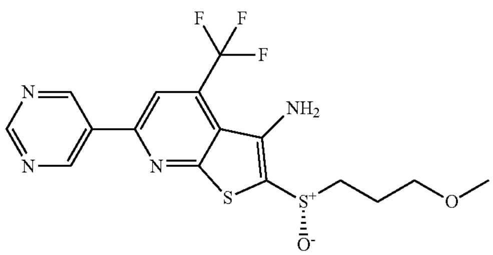 [SMILES: COCCC[S@+]([O-])c1sc2nc(-c3cncnc3)cc(C(F)(F)F)c2c1N] | * |
| 202 | 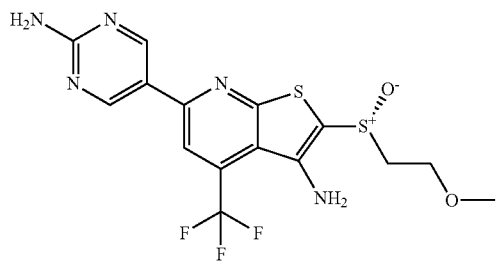 [SMILES: COCC[S@@+]([O-])c1sc2nc(-c3cnc(N)nc3)cc(C(F)(F)F)c2c1N] | *** |
| 203 | 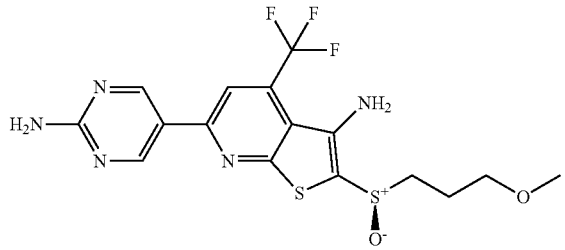 [SMILES: COCCC[S@@+]([O-])c1sc2nc(-c3cnc(N)nc3)cc(C(F)(F)F)c2c1N] | *** |
| 204 | 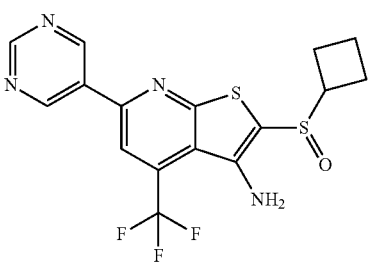 [SMILES: Nc1c(S(=O)C2CCC2)sc2nc(-c3cncnc3)cc(C(F)(F)F)c12] | *** |

TABLE 1-continued

| Molecule Name | Structure | PDGH Assay-IC$_{50}$ |
|---|---|---|
| 205 | 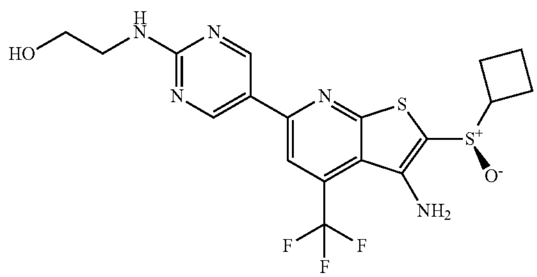 [SMILES: Nc1c([S@+]([O-])C2CCC2)sc2nc(-c3cnc(NCCO)nc3)cc(C(F)(F)F)c12] | *** |
| 206 | 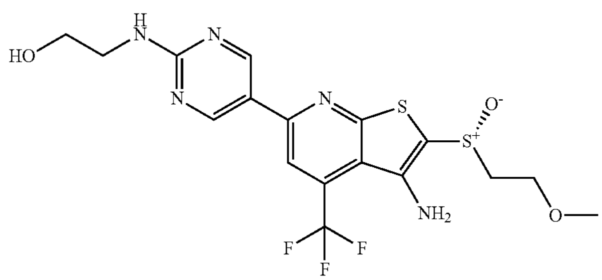 [SMILES: COCC[S@@+]([O-])c1sc2nc(-c3cnc(NCCO)nc3)cc(C(F)(F)F)c2c1N] | *** |
| 207 | 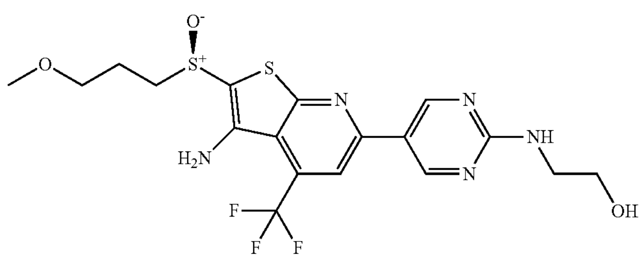 [SMILES: COCCC[S@@+]([O-])c1sc2nc(-c3cnc(NCCO)nc3)cc(C(F)(F)F)c2c1N] | *** |
| 208 | 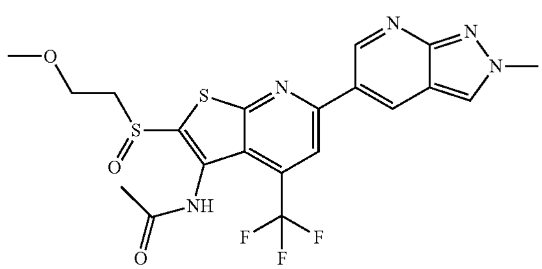 | * |
| 209 | 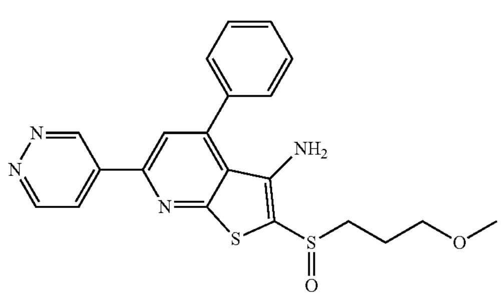 [SMILES: COCCCS(=O)c1sc2nc(-c3ccnnc3)cc(-c3ccccc3)c2c1N] | *** |

TABLE 1-continued

| Molecule Name | Structure | PDGH Assay-IC$_{50}$ |
|---|---|---|
| 210 | 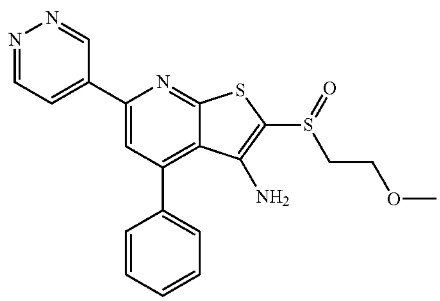 [SMILES: COCCS(=O)c1sc2nc(-c3ccnnc3)cc(-c3ccccc3)c2c1N] | *** |
| 211 | 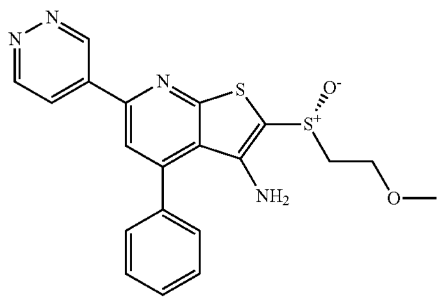 [SMILES: COCC[S@@+]([O-])c1sc2nc(-c3ccnnc3)cc(-c3ccccc3)c2c1N] | *** |
| 212 | 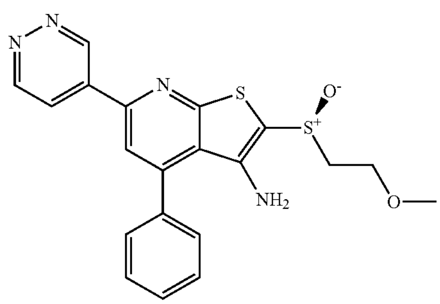 [SMILES: COCC[S@+]([O-])c1sc2nc(-c3ccnnc3)cc(-c3ccccc3)c2c1N] | * |
| 213 | 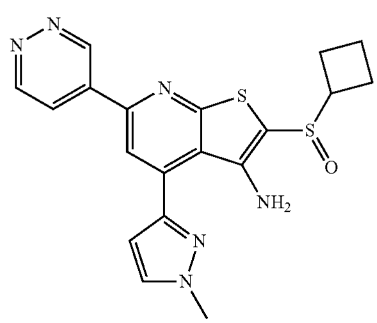 [SMILES: Cn1ccc(-c2cc(-c3ccnnc3)nc3sc(S(=O)C4CCC4)c(N)c23)n1] | *** |
| 214 | 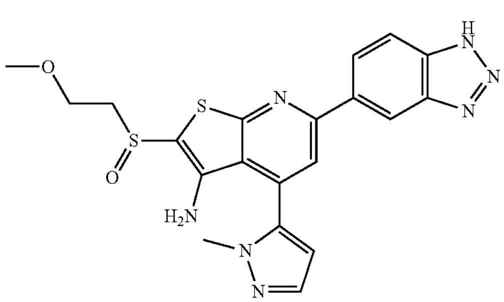 [SMILES: COCCS(=O)c1sc2nc(-c3ccc4[nH]nnc4c3)cc(-c3ccnn3C)c2c1N] | *** |

| Molecule Name | Structure | PDGH Assay-IC$_{50}$ |
|---|---|---|
| 215 | 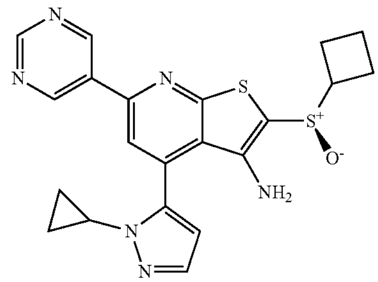 [SMILES: Nc1c([S@+]([O-])C2CCC2)sc2nc(-c3cncnc3)cc(-c3ccnn3C3CC3)c12] | *** |
| 216 | 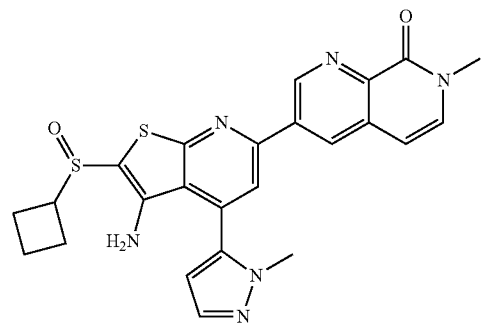 [SMILES: Cn1nccc1-c1cc(-c2cnc3c(=O)n(C)ccc3c2)nc2sc(S(=O)C3CCC3)c(N)c12] | *** |
| 217 | 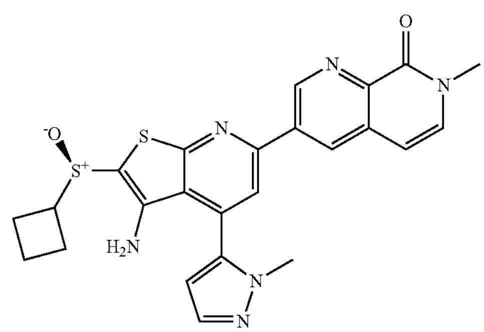 | *** |
| 218 | 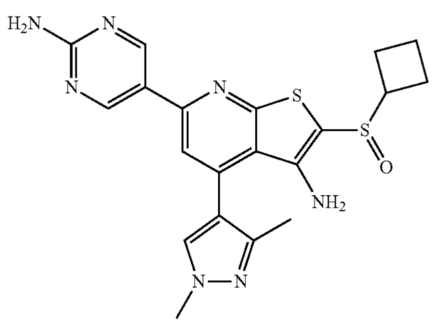 [SMILES: Cc1nn(C)cc1-c1cc(-c2cnc(N)nc2)nc2sc(S(=O)C3CCC3)c(N)c12] | *** |
| 219 | 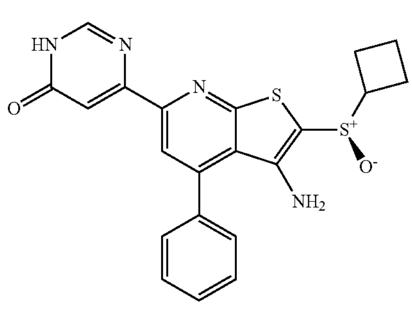 [SMILES: Nc1c([S@+]([O-])C2CCC2)sc2nc(-c3cc(=O)[nH]cn3)cc(-c3ccccc3)c12] | *** |

TABLE 1-continued

| Molecule Name | Structure | PDGH Assay-IC$_{50}$ |
|---|---|---|
| 220 | 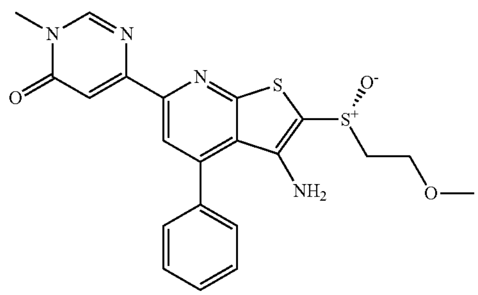 [SMILES: COCC[S@@+]([O-])c1sc2nc(-c3cc(=O)n(C)cn3)cc(-c3ccccc3)c2c1N] | *** |
| 221 | 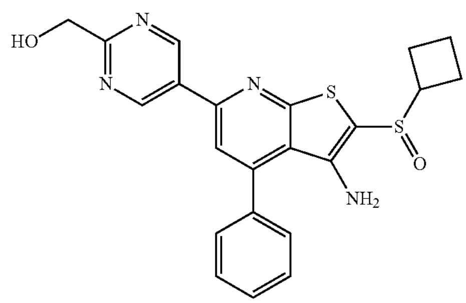 [SMILES: Nc1c(S(=O)C2CCC2)sc2nc(-c3cnc(CO)nc3)cc(-c3ccccc3)c12] | *** |
| 222 | 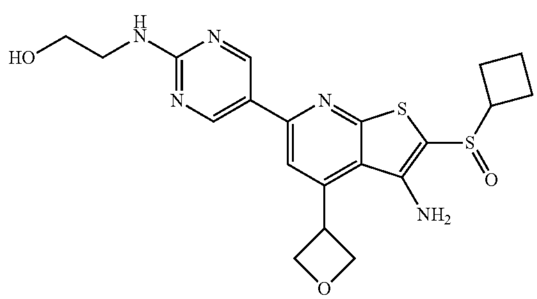 [SMILES: Nc1c(S(=O)C2CCC2)sc2nc(-c3cnc(NCCO)nc3)cc(C3COC3)c12] | *** |
| 223 | 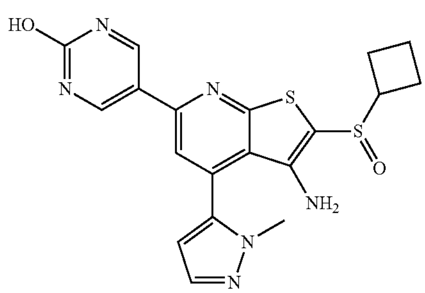 [SMILES: Cn1nccc1-c1cc(-c2cnc(O)nc2)nc2sc(S(=O)C3CCC3)c(N)c12] | *** |
| 224 | 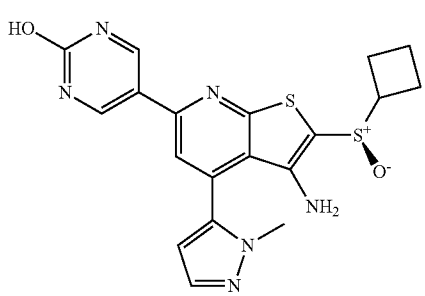 [SMILES: Cn1nccc1-c1cc(-c2cnc(O)nc2)nc2sc([S@+]([O-])C3CCC3)c(N)c12] | *** |

TABLE 1-continued

| Molecule Name | Structure | PDGH Assay-IC$_{50}$ |
|---|---|---|
| 225 | 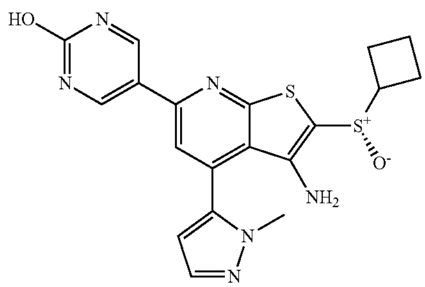 [SMILES: Cn1nccc1-c1cc(-c2cnc(O)nc2)nc2sc([S@@+]([O-])C3CCC3)c(N)c12] | * |
| 226 | 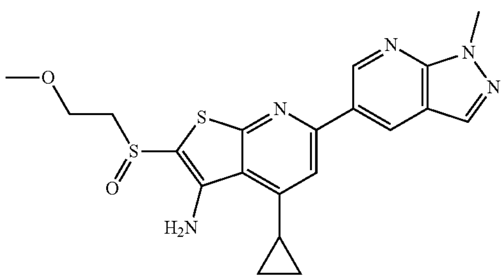 [SMILES: COCCS(=O)c1sc2nc(-c3cnc4c(cnn4C)c3)cc(C3CC3)c2c1N] | *** |
| 227 | 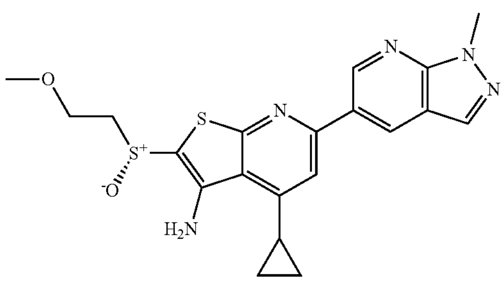 | *** |
| 228 | 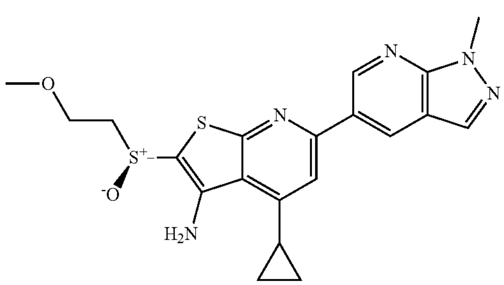 | * |
| 229 | 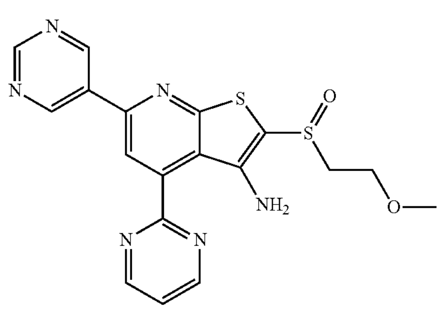 [SMILES: COCCS(=O)c1sc2nc(-c3cncnc3)cc(-c3ncccn3)c2c1N] | *** |

TABLE 1-continued

| Molecule Name | Structure | PDGH Assay-IC$_{50}$ |
|---|---|---|
| 230 | 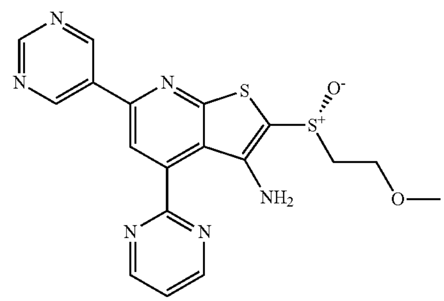 [SMILES: COCC[S@@+]([O-])c1sc2nc(-c3cncnc3)cc(-c3ncccn3)c2c1N] | *** |
| 231 | 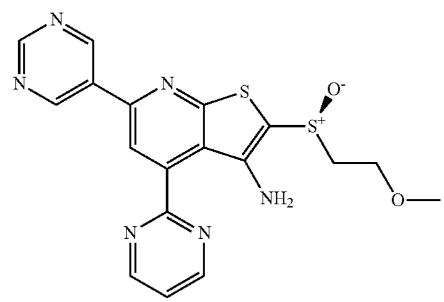 [SMILES: COCC[S@+]([O-])c1sc2nc(-c3cncnc3)cc(-c3ncccn3)c2c1N] | * |
| 232 | 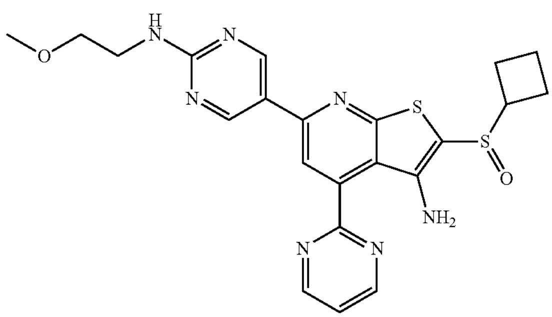 [SMILES: COCCNc1ncc(-c2cc(-c3ncccn3)c3c(N)c(S(=O)C4CCC4)sc3n2)cn1] | *** |
| 233 | 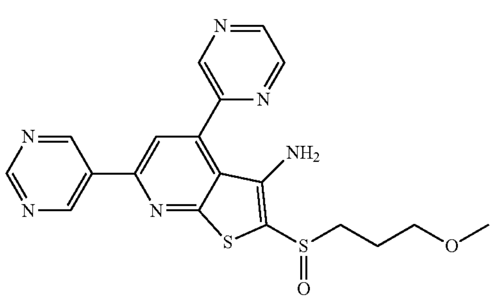 [SMILES: COCCCS(=O)c1sc2nc(-c3cncnc3)cc(-c3cnccn3)c2c1N] | *** |
| 234 | 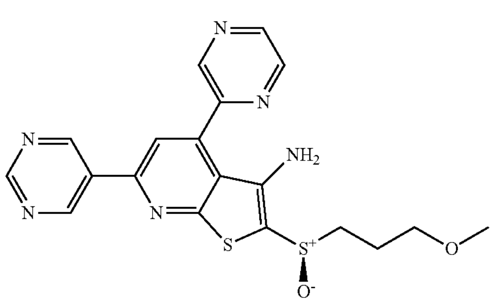 [SMILES: COCCC[S@@+]([O-])c1sc2nc(-c3cncnc3)cc(-c3cnccn3)c2c1N] | * |

TABLE 1-continued

| Molecule Name | Structure | PDGH Assay-IC$_{50}$ |
|---|---|---|
| 235 | 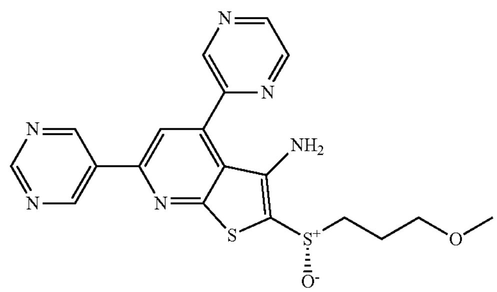 [SMILES: COCCC[S@+]([O-])c1sc2nc(-c3cncnc3)cc(-c3cnccn3)c2c1N] | *** |
| 236 | 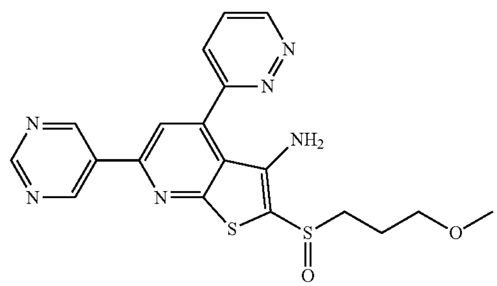 [SMILES: COCCCS(=O)c1sc2nc(-c3cncnc3)cc(-c3cccnn3)c2c1N] | *** |
| 237 | 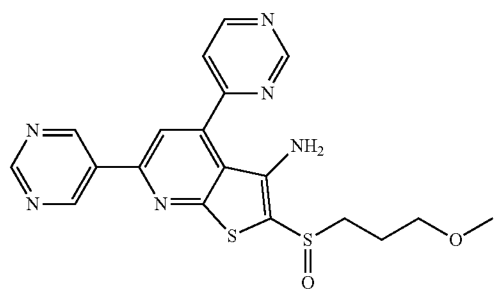 [SMILES: COCCCS(=O)c1sc2nc(-c3cncnc3)cc(-c3ccncn3)c2c1N] | *** |
| 238 | 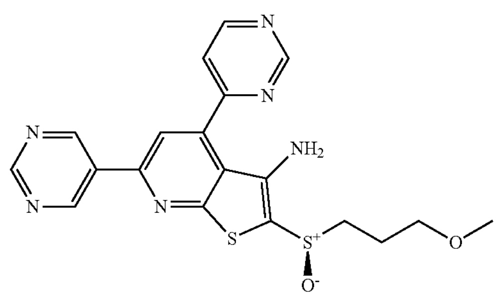 [SMILES: COCCC[S@@+]([O-])c1sc2nc(-c3cncnc3)cc(-c3ccncn3)c2c1N] | *** |
| 239 | 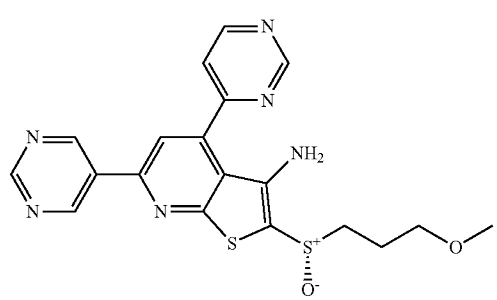 [SMILES: COCCC[S@+]([O-])c1sc2nc(-c3cncnc3)cc(-c3ccncn3)c2c1N] | * |

TABLE 1-continued

| Molecule Name | Structure | PDGH Assay-IC$_{50}$ |
|---|---|---|
| 240 | 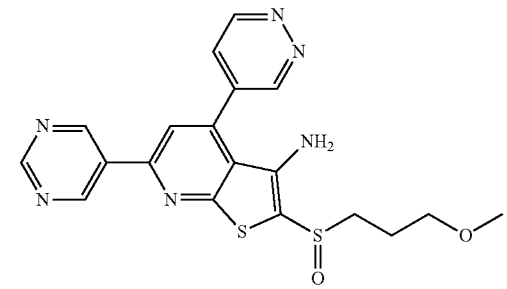 [SMILES: COCCCS(=O)c1sc2nc(-c3cncnc3)cc(-c3ccnnc3)c2c1N] | ** |
| 241 | 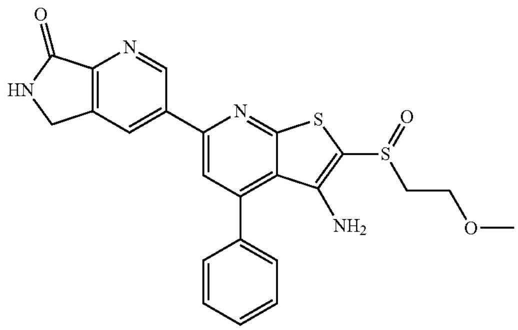 [SMILES: COCCS(=O)c1sc2nc(-c3cnc4c(c3)CNC4=O)cc(-c3ccccc3)c2c1N] | *** |
| 242 | 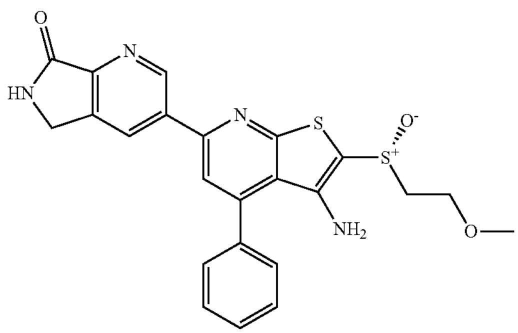 [SMILES: COCC[S@@+]([O-])c1sc2nc(-c3cnc4c(c3)CNC4=O)cc(-c3ccccc3)c2c1N] | *** |
| 243 | 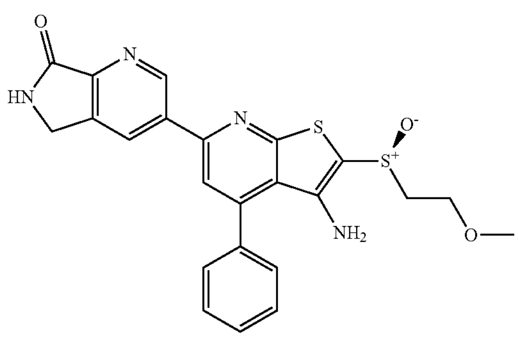 [SMILES: COCC[S@+]([O-])c1sc2nc(-c3cnc4c(c3)CNC4=O)cc(-c3ccccc3)c2c1N] | * |
| 244 | 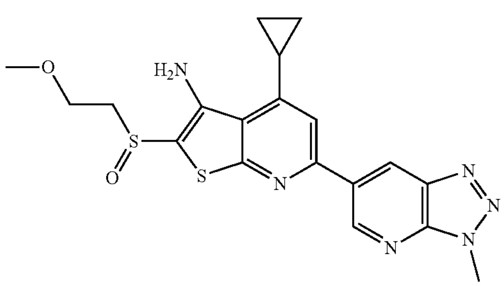 [SMILES: COCCS(=O)c1sc2nc(-c3cnc4c(c3)nnn4C)cc(C3CC3)c2c1N] | *** |

TABLE 1-continued
| Molecule Name | Structure | PDGH Assay-IC$_{50}$ |
|---|---|---|
| 245 | 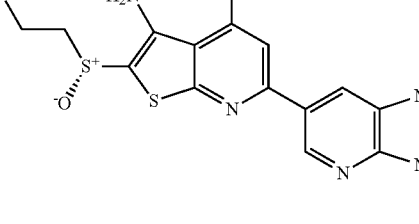 | *** |
| 246 | 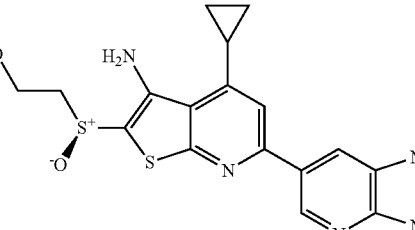 | * |
| 247 | 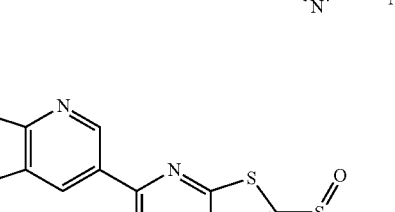 | *** |
| 248 | 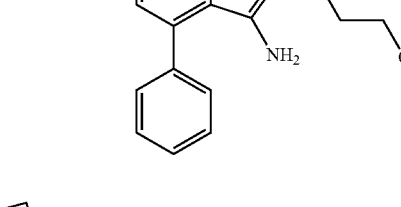 | *** |
| 249 | 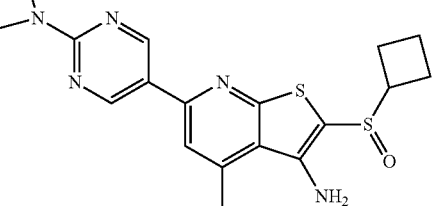 | *** |

TABLE 1-continued

| Molecule Name | Structure | PDGH Assay-IC$_{50}$ |
|---|---|---|
| 250 | 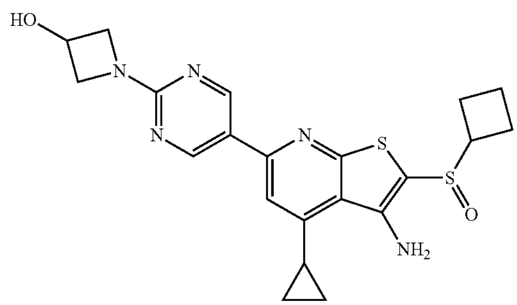 [SMILES: Nc1c(S(=O)C2CCC2)sc2nc(-c3cnc(N4CC(O)C4)nc3)cc(C3CC3)c12] | *** |
| 251 | 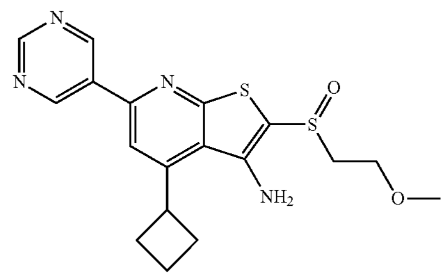 [SMILES: COCCS(=O)c1sc2nc(-c3cncnc3)cc(C3CCC3)c2c1N] | *** |
| 252 | 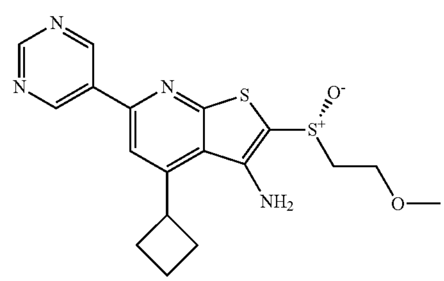 [SMILES: COCC[S@@+]([O-])c1sc2nc(-c3cncnc3)cc(C3CCC3)c2c1N] | *** |
| 253 | 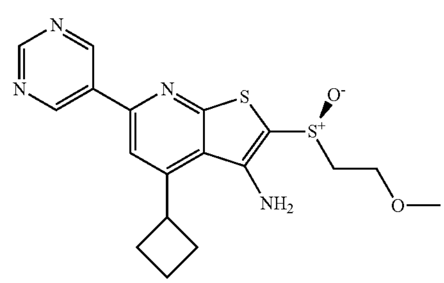 [SMILES: COCC[S@+]([O-])c1sc2nc(-c3cncnc3)cc(C3CCC3)c2c1N] | * |
| 254 | 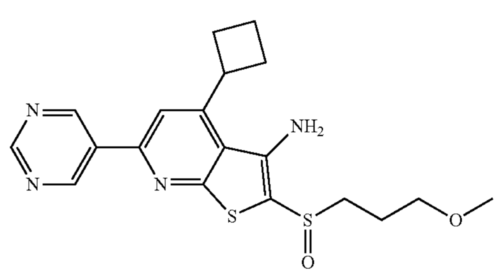 [SMILES: COCCCS(=O)c1sc2nc(-c3cncnc3)cc(C3CCC3)c2c1N] | *** |

TABLE 1-continued

| Molecule Name | Structure | PDGH Assay-IC$_{50}$ |
|---|---|---|
| 255 | 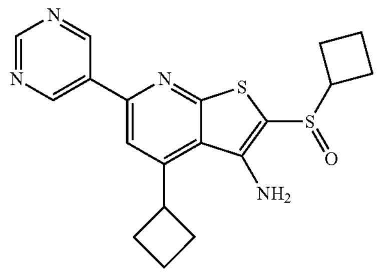 [SMILES: Nc1c(S(=O)C2CCC2)sc2nc(-c3cncnc3)cc(C3CCC3)c12] | *** |
| 256 | 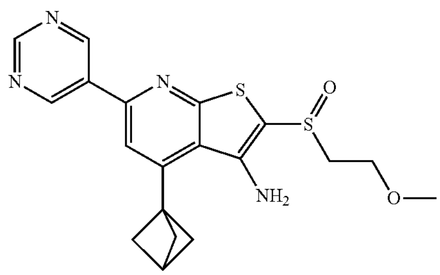 [SMILES: COCCS(=O)c1sc2nc(-c3cncnc3)cc(C34CC(C3)C4)c2c1N] | *** |
| 257 | 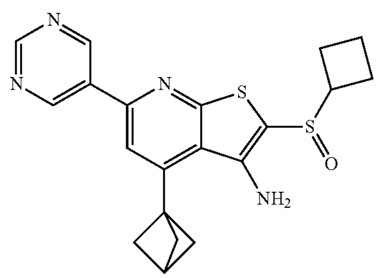 [SMILES: Nc1c(S(=O)C2CCC2)sc2nc(-c3cncnc3)cc(C34CC(C3)C4)c12] | *** |
| 258 | 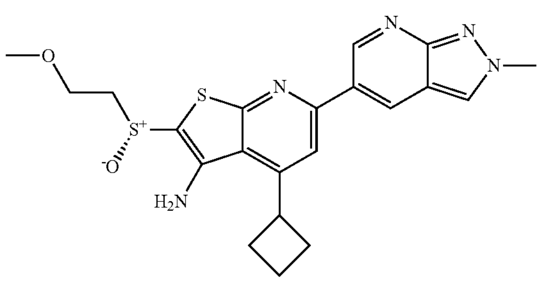 | *** |
| 259 | 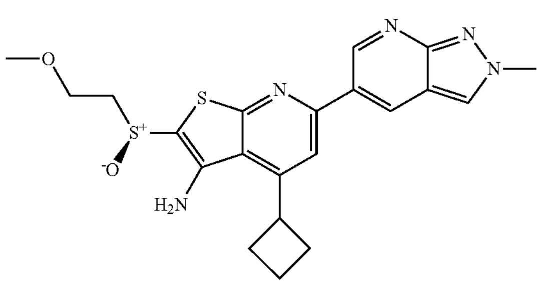 | * |

TABLE 1-continued

| Molecule Name | Structure | PDGH Assay-IC$_{50}$ |
|---|---|---|
| 260 | 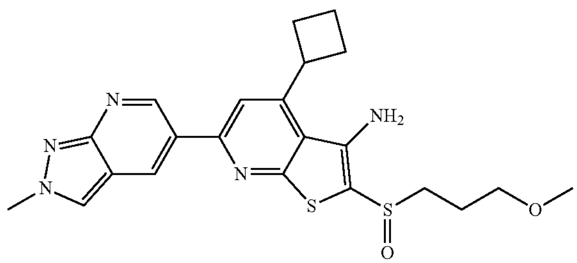 | *** |
| 261 | 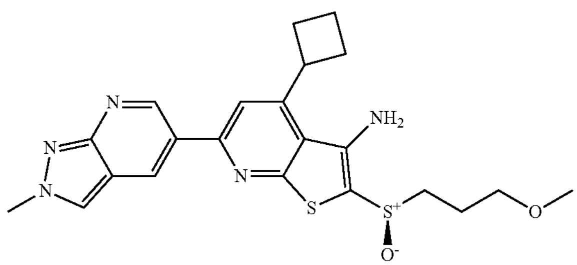 | *** |
| 262 | 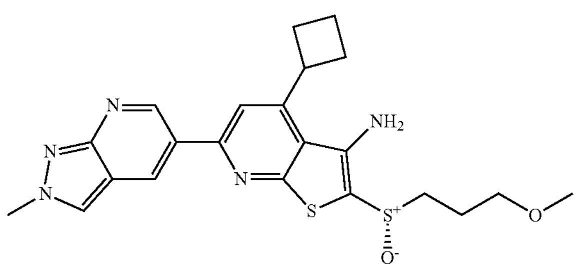 | * |
| 263 | 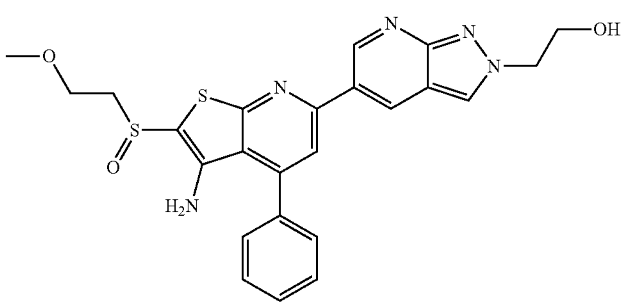 [SMILES: COCCS(=O)c1sc2nc(-c3cnc4nn(CCO)cc4c3)cc(-c3ccccc3)c2c1N] | *** |
| 264 | 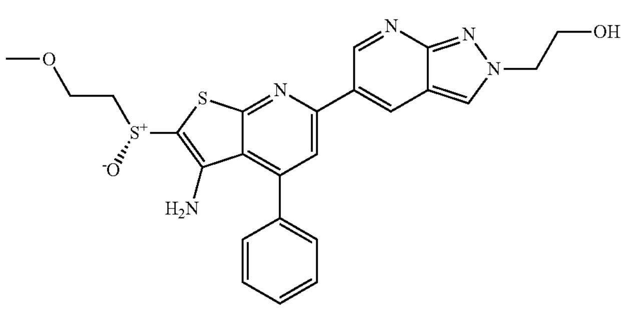 | *** |

TABLE 1-continued

| Molecule Name | Structure | PDGH Assay-IC$_{50}$ |
|---|---|---|
| 265 | 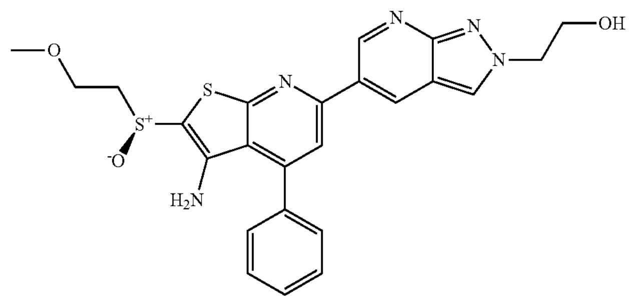 | * |
| 266 | 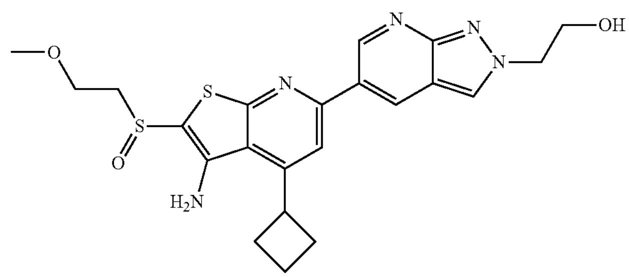 [SMILES: COCCS(=O)c1sc2nc(-c3cnc4nn(CCO)cc4c3)cc(C3CCC3)c2c1N] | *** |
| 267 | 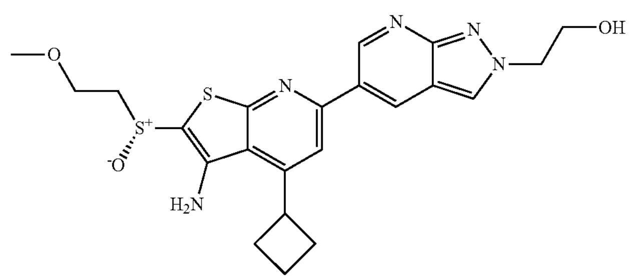 | *** |
| 268 | 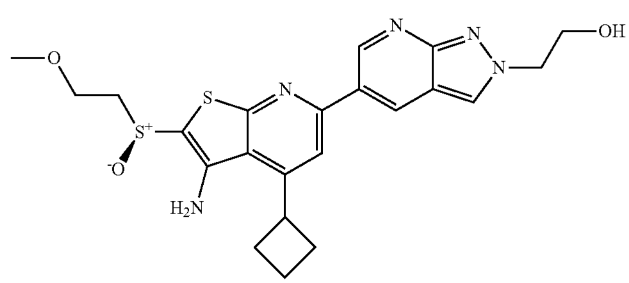 | * |
| 269 | 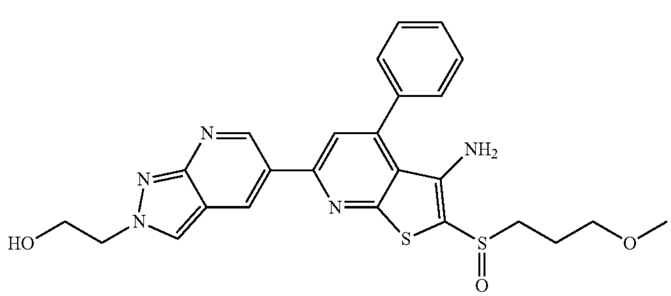 [SMILES: COCCCS(=O)c1sc2nc(-c3cnc4nn(CCO)cc4c3)cc(-c3ccccc3)c2c1N] | *** |

TABLE 1-continued

| Molecule Name | Structure | PDGH Assay-IC$_{50}$ |
|---|---|---|
| 270 | 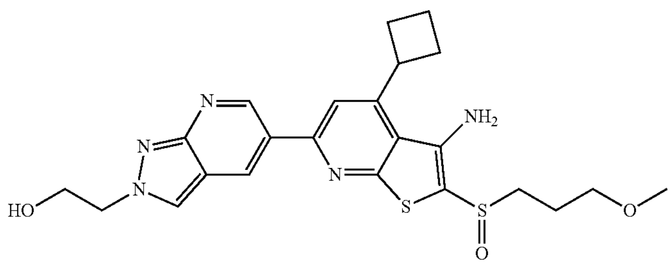 [SMILES: COCCCS(=O)c1sc2nc(-c3cnc4nn(CCO)cc4c3)cc(C3CCC3)c2c1N] | *** |
| 271 | 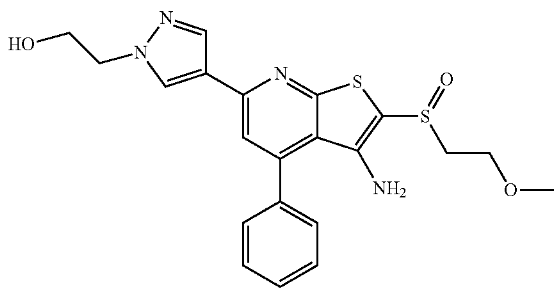 [SMILES: COCCS(=O)c1sc2nc(-c3cnn(CCO)c3)cc(-c3ccccc3)c2c1N] | *** |
| 272 | 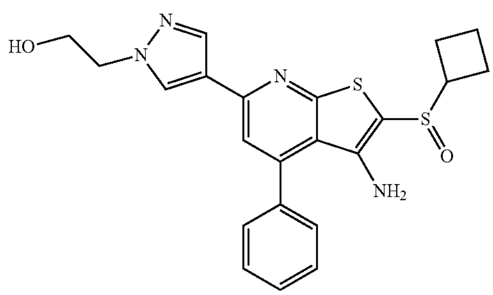 [SMILES: Nc1c(S(=O)C2CCC2)sc2nc(-c3cnn(CCO)c3)cc(-c3ccccc3)c12] | *** |
| 273 | 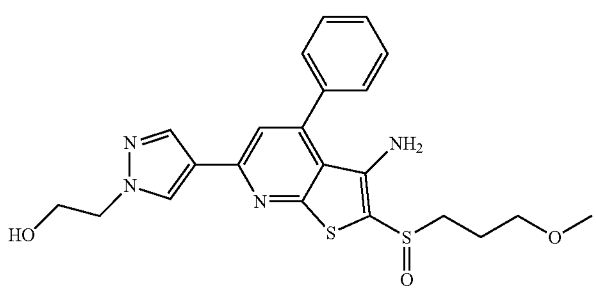 [SMILES: COCCCS(=O)c1sc2nc(-c3cnn(CCO)c3)cc(-c3ccccc3)c2c1N] | *** |
| 274 | 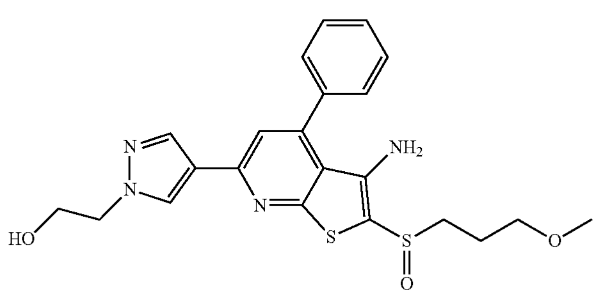 [SMILES: COCCCS(=O)c1sc2nc(-c3cnn(CCO)c3)cc(-c3ccccc3)c2c1N] | *** |

TABLE 1-continued

| Molecule Name | Structure | PDGH Assay-IC$_{50}$ |
|---|---|---|
| 275 | 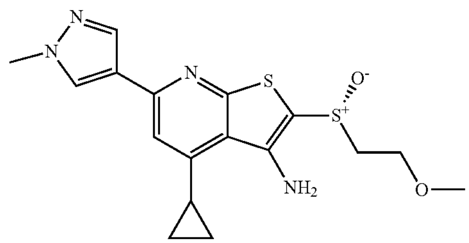 | *** |
| 276 | 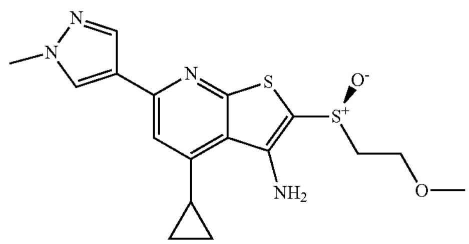 | * |
| 277 | 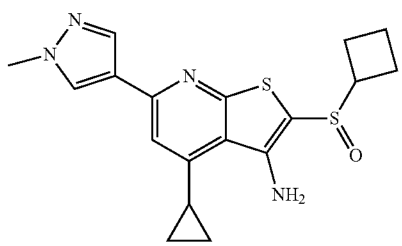 [SMILES: Cn1cc(-c2cc(C3CC3)c3c(N)c(S(=O)C4CCC4)sc3n2)cn1] | *** |
| 278 | 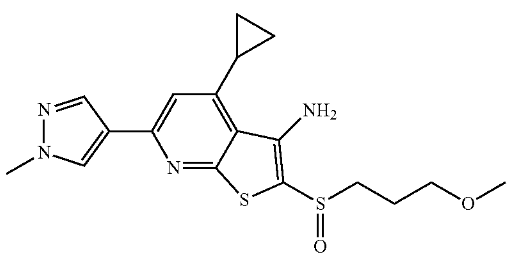 | *** |
| 279 | 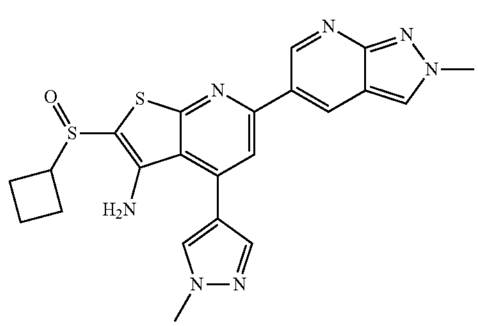 [SMILES: Cn1cc(-c2cc(-c3cnc4nn(C)cc4c3)nc3sc(S(=O)C4CCC4)c(N)c23)cn1] | ** |

TABLE 1-continued

| Molecule Name | Structure | PDGH Assay-IC$_{50}$ |
|---|---|---|
| 280 | 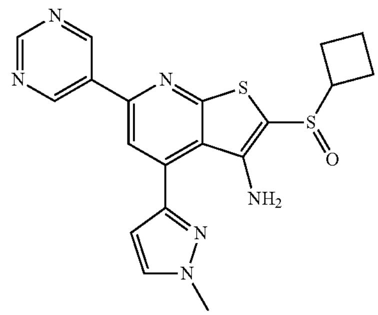 [SMILES: Cn1ccc(-c2cc(-c3cncnc3)nc3sc(S(=O)C4CCC4)c(N)c23)n1] | *** |
| 281 | 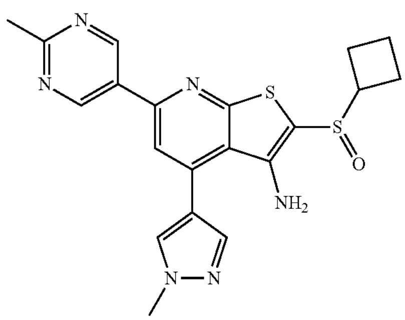 [SMILES: Cc1ncc(-c2cc(-c3cnn(C)c3)c3c(N)c(S(=O)C4CCC4)sc3n2)cn1] | *** |
| 282 | 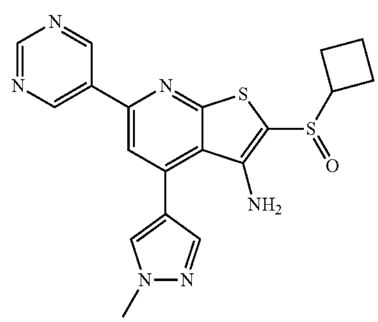 [SMILES: Cn1cc(-c2cc(-c3cncnc3)nc3sc(S(=O)C4CCC4)c(N)c23)cn1] | *** |
| 283 | 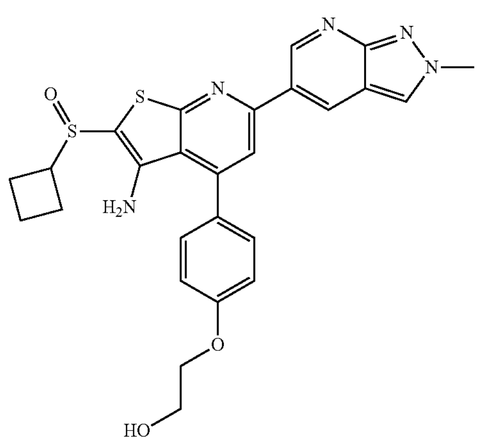 [SMILES: Cn1cc2cc(-c3cc(-c4ccc(OCCO)cc4)c4c(N)c(S(=O)C5CCC5)sc4n3)cnc2n1] | *** |

TABLE 1-continued

| Molecule Name | Structure | PDGH Assay-IC$_{50}$ |
|---|---|---|
| 284 | 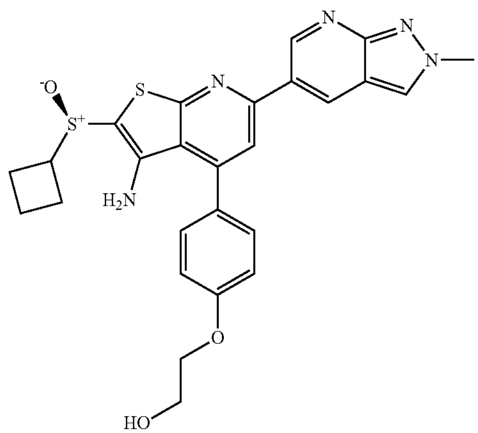 | *** |
| 285 | 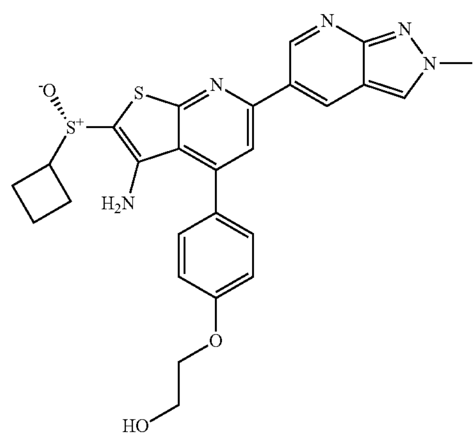 | ** |
| 286 | 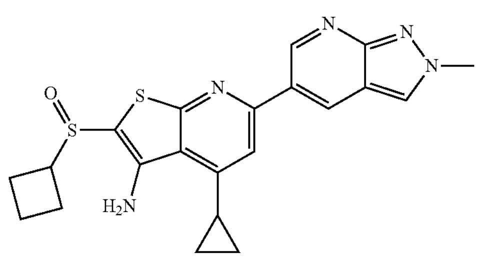 [SMILES: Cn1cc2cc(-c3cc(C4CC4)c4c(N)c(S(=O)C5CCC5)sc4n3)cnc2n1] | *** |
| 287 | 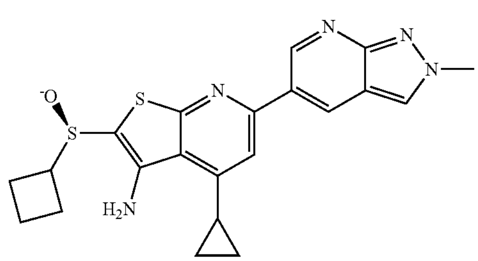 | *** |

TABLE 1-continued

| Molecule Name | Structure | PDGH Assay-IC$_{50}$ |
|---|---|---|
| 288 | 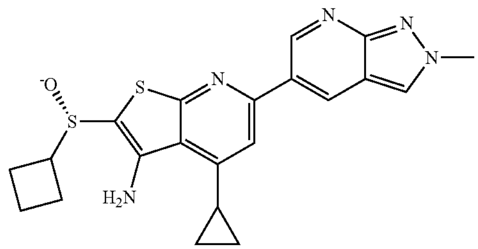 | * |
| 289 | 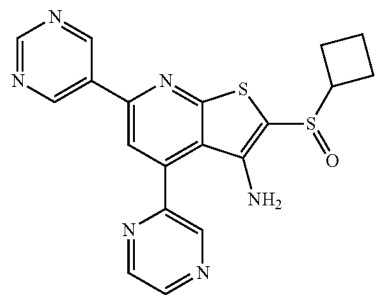 [SMILES: Nc1c(S(=O)C2CCC2)sc2nc(-c3cncnc3)cc(-c3cnccn3)c12] | *** |
| 290 | 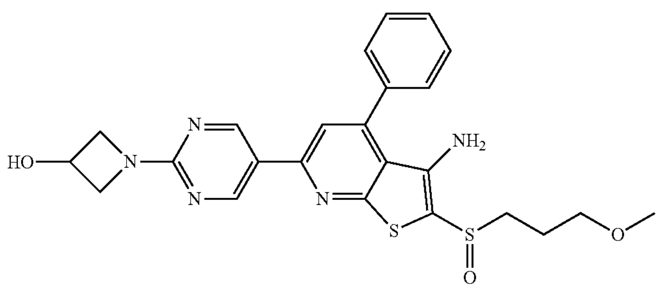 [SMILES: COCCCS(=O)c1sc2nc(-c3cnc(N4CC(O)C4)nc3)cc(-c3ccccc3)c2c1N] | ** |
| 300 | 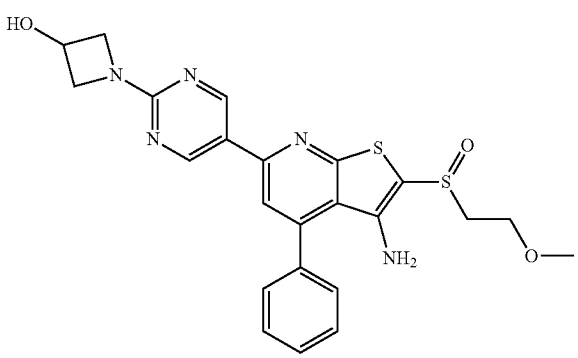 [SMILES: COCCS(=O)c1sc2nc(-c3cnc(N4CC(O)C4)nc3)cc(-c3ccccc3)c2c1N] | ** |
| 301 | 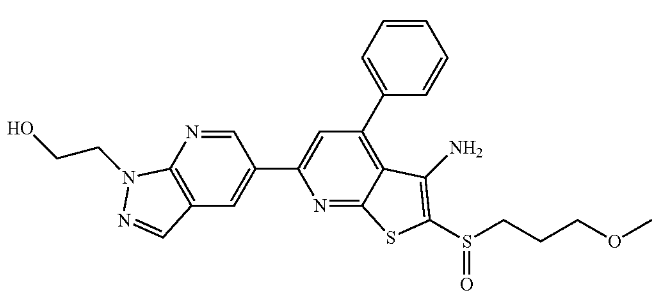 [SMILES: COCCCS(=O)c1sc2nc(-c3cnc4c(cnn4CCO)c3)cc(-c3ccccc3)c2c1N] | ** |

TABLE 1-continued
| Molecule Name | Structure | PDGH Assay-IC$_{50}$ |
|---|---|---|
| 302 | 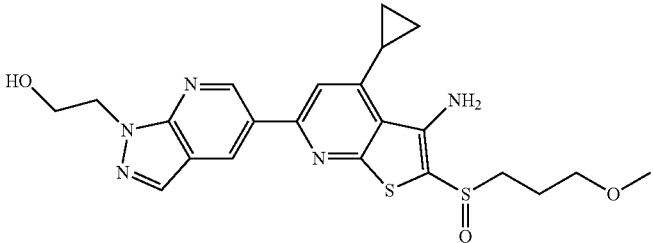 [SMILES: COCCCS(=O)c1sc2nc(-c3cnc4c(cnn4CCO)c3)cc(C3CC3)c2c1N] | ** |
| 303 | 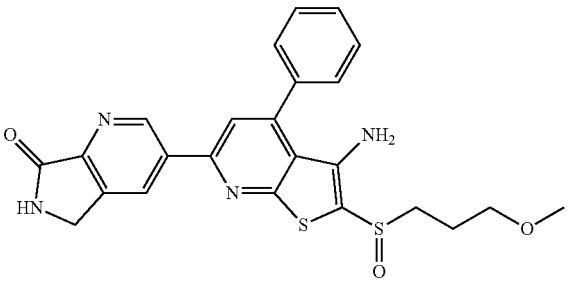 [SMILES: COCCCS(=O)c1sc2nc(-c3cnc4c(c3)CNC4=O)cc(-c3ccccc3)c2c1N] | *** |
| 304 | 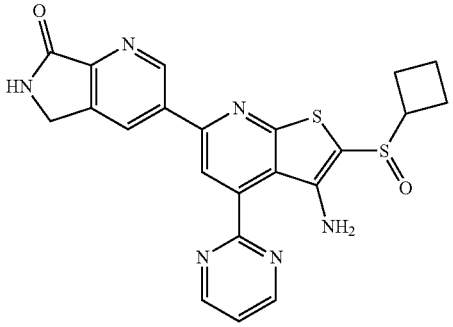 [SMILES: Nc1c(S(=O)C2CCC2)sc2nc(-c3cnc4c(c3)CNC4=O)cc(-c3ncccn3)c12] | ** |
| 305 | 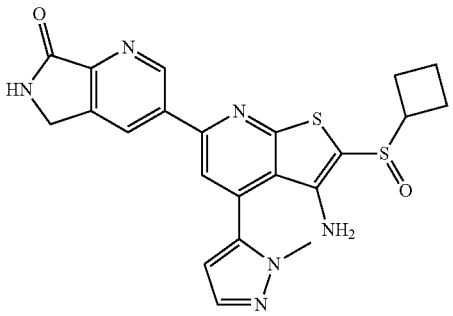 [SMILES: Cn1nccc1-c1cc(-c2cnc3c(c2)CNC3=O)nc2sc(S(=O)C3CCC3)c(N)c12] | *** |
| 306 | 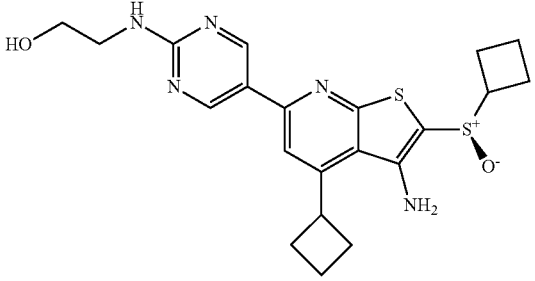 [SMILES: Nc1c([S@+]([O-])C2CCC2)sc2nc(-c3cnc(NCCO)nc3)cc(C3CCC3)c12] | *** |

TABLE 1-continued

| Molecule Name | Structure | PDGH Assay-IC$_{50}$ |
|---|---|---|
| 307 | 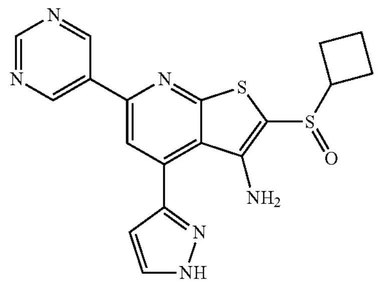 [SMILES: Nc1c(S(=O)C2CCC2)sc2nc(-c3cncnc3)cc(-c3cc[nH]n3)c12] | *** |
| 308 | 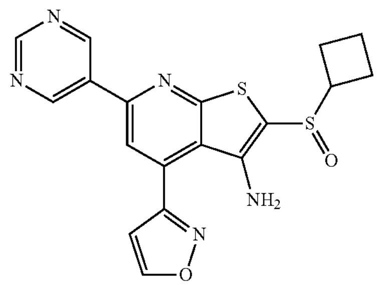 [SMILES: Nc1c(S(=O)C2CCC2)sc2nc(-c3cncnc3)cc(-c3ccon3)c12] | *** |
| 309 | 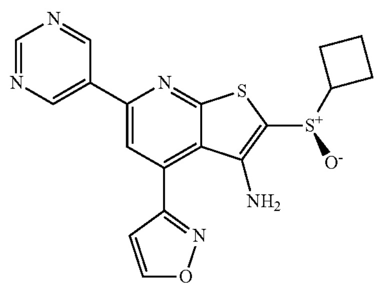 [SMILES: Nc1c([S@+]([O-])C2CCC2)sc2nc(-c3cncnc3)cc(-c3ccon3)c12] | *** |
| 310 | 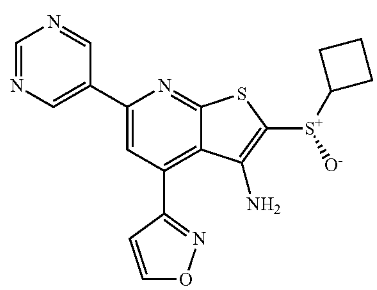 [SMILES: Nc1c([S@@+]([O-])C2CCC2)sc2nc(-c3cncnc3)cc(-c3ccon3)c12] | * |
| 311 | 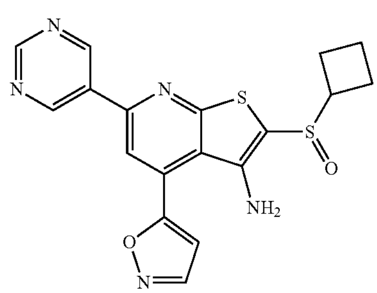 [SMILES: Nc1c(S(=O)C2CCC2)sc2nc(-c3cncnc3)cc(-c3ccno3)c12] | *** |

TABLE 1-continued

| Molecule Name | Structure | PDGH Assay-IC$_{50}$ |
|---|---|---|
| 312 | 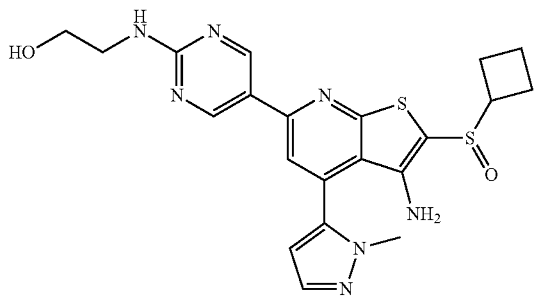 [SMILES: Cn1nccc1-c1cc(-c2cnc(NCCO)nc2)nc2sc(S(=O)C3CCC3)c(N)c12] | *** |
| 313 | 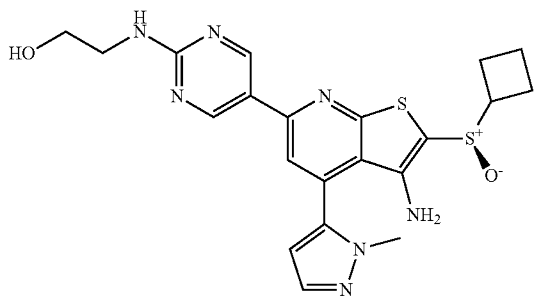 [SMILES: Cn1nccc1-c1cc(-c2cnc(NCCO)nc2)nc2sc([S@+]([O-])C3CCC3)c(N)c12] | *** |
| 314 | 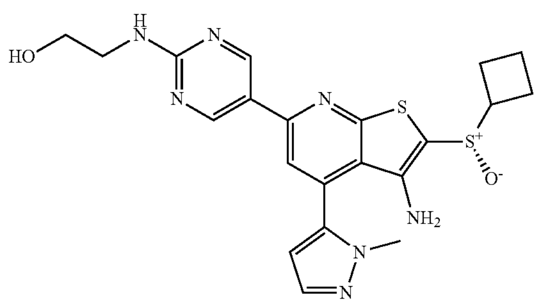 [SMILES: Cn1nccc1-c1cc(-c2cnc(NCCO)nc2)nc2sc([S@@+]([O-])C3CCC3)c(N)c12] | * |
| 315 | 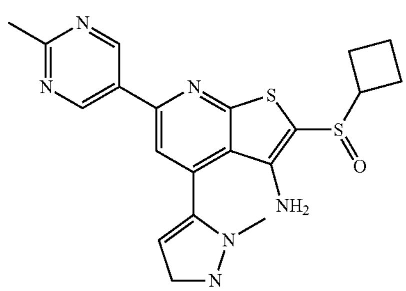 [SMILES: Cc1ncc(-c2cc(C3=CCNN3C)c3c(N)c(S(=O)C4CCC4)sc3n2)cn1] | ** |
| 316 | 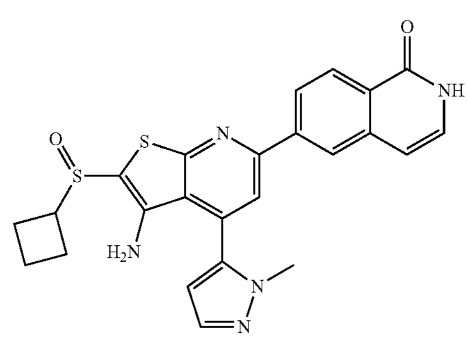 [SMILES: Cn1nccc1-c1cc(-c2ccc3c(=O)[nH]ccc3c2)nc2sc(S(=O)C3CCC3)c(N)c12] | ** |

TABLE 1-continued

| Molecule Name | Structure | PDGH Assay-IC$_{50}$ |
|---|---|---|
| 317 | 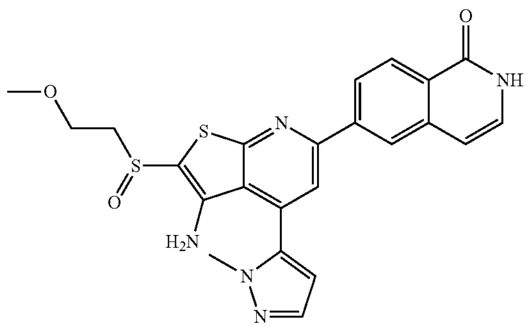 [SMILES: COCCS(=O)c1sc2nc(-c3ccc4c(=O)[nH]ccc4c3)cc(-c3ccnn3C)c2c1N] | *** |
| 318 | 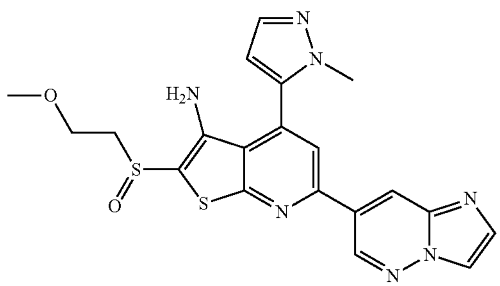 [SMILES: COCCS(=O)c1sc2nc(-c3cnn4ccnc4c3)cc(-c3ccnn3C)c2c1N] | *** |
| 319 | 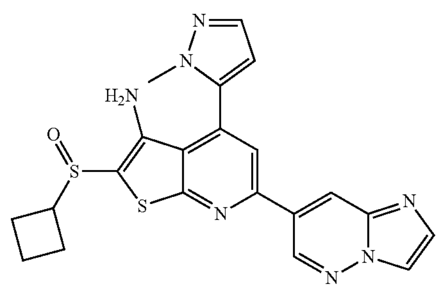 [SMILES: Cn1nccc1-c1cc(-c2cnn3ccnc3c2)nc2sc(S(=O)C3CCC3)c(N)c12] | *** |
| 320 | 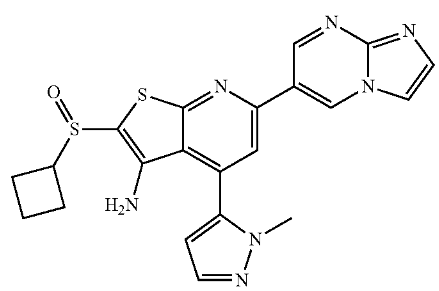 [SMILES: Cn1nccc1-c1cc(-c2cnc3nccn3c2)nc2sc(S(=O)C3CCC3)c(N)c12] | *** |
| 321 | 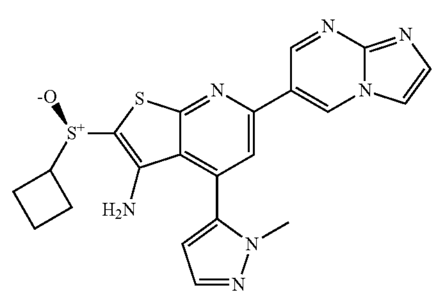 | *** |

TABLE 1-continued

| Molecule Name | Structure | PDGH Assay-IC$_{50}$ |
|---|---|---|
| 322 | 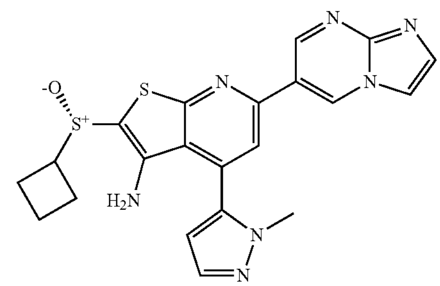 | * |
| 323 | 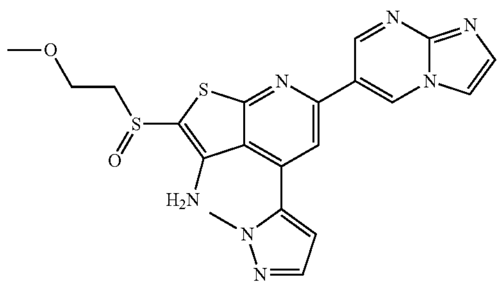 [SMILES: COCCS(=O)c1sc2nc(-c3cnc4nccn4c3)cc(-c3ccnn3C)c2c1N] | *** |
| 324 | 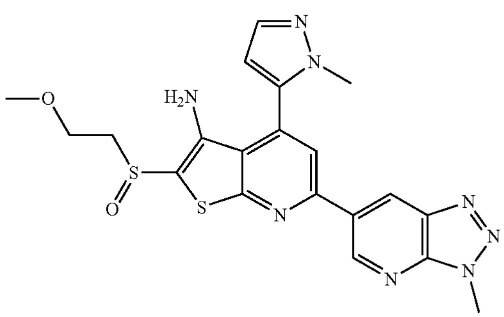 [SMILES: COCCS(=O)c1sc2nc(-c3cnc4c(c3)nnn4C)cc(-c3ccnn3C)c2c1N] | *** |
| 325 | 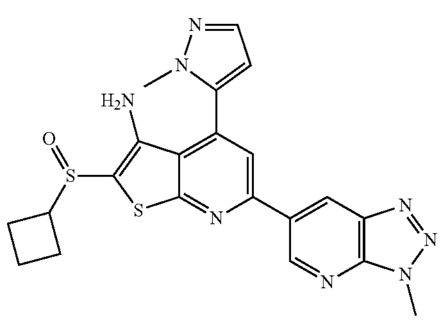 [SMILES: Cn1nccc1-c1cc(-c2cnc3c(c2)nnn3C)nc2sc(S(=O)C3CCC3)c(N)c12] | *** |
| 326 | 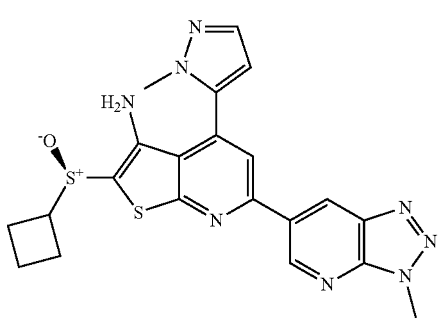 | *** |

TABLE 1-continued

| Molecule Name | Structure | PDGH Assay-IC$_{50}$ |
|---|---|---|
| 327 | 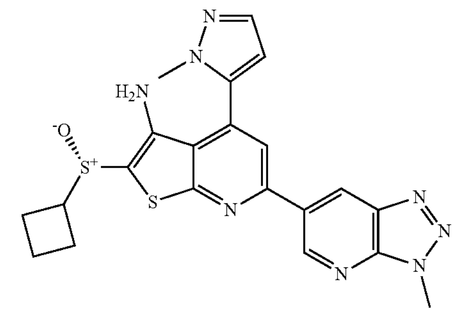 | * |
| 328 | 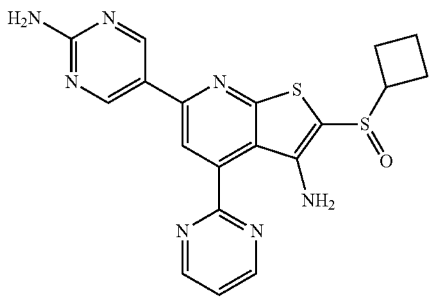 [SMILES: Nc1ncc(-c2cc(-c3ncccn3)c3c(N)c(S(=O)C4CCC4)sc3n2)cn1] | *** |
| 329 | 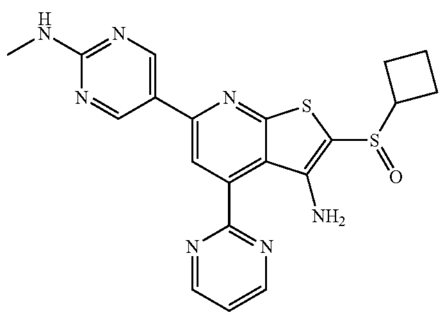 [SMILES: CNc1ncc(-c2cc(-c3ncccn3)c3c(N)c(S(=O)C4CCC4)sc3n2)cn1] | *** |
| 330 | 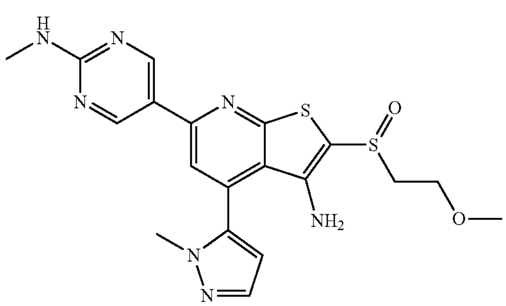 | *** |
| 331 | 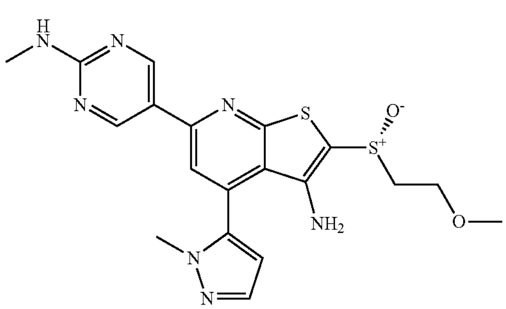 | *** |

TABLE 1-continued

| Molecule Name | Structure | PDGH Assay-IC$_{50}$ |
|---|---|---|
| 332 | 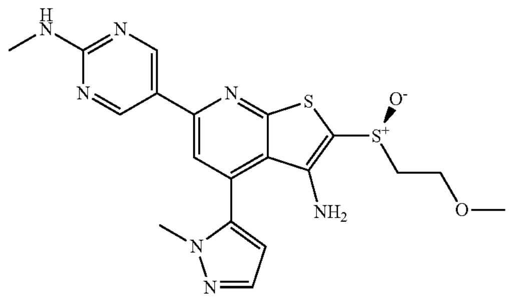 | * |
| 333 | 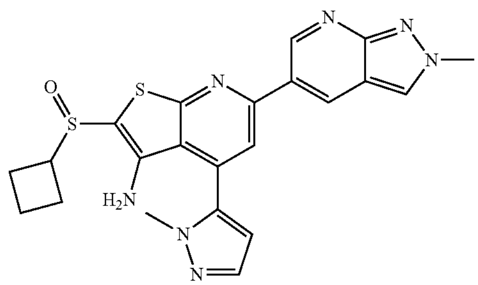 [SMILES: Cn1cc2cc(-c3cc(-c4ccnn4C)c4c(N)c(S(=O)C5CCC5)sc4n3)cnc2n1] | *** |
| 334 | 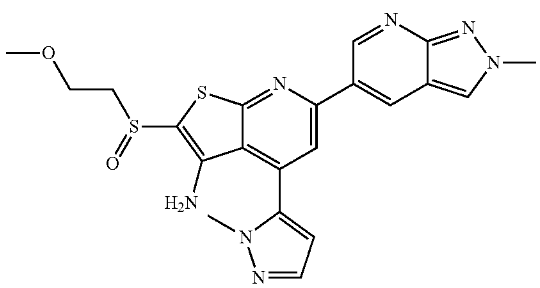 | *** |
| 335 | 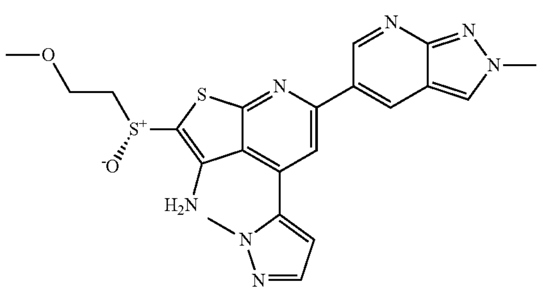 | *** |
| 336 | 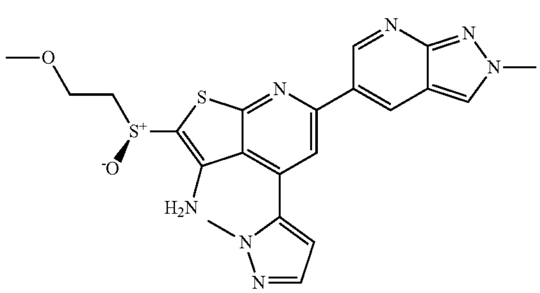 | * |

TABLE 1-continued

| Molecule Name | Structure | PDGH Assay- IC$_{50}$ |
|---|---|---|
| 337 | 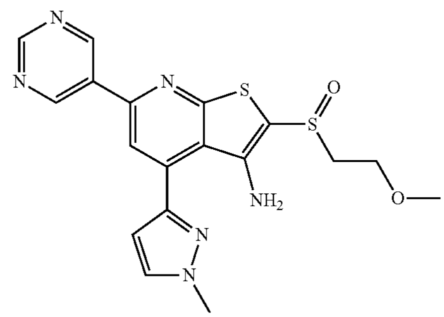 [SMILES: COCCS(=O)c1sc2nc(-c3cncnc3)cc(-c3ccn(C)n3)c2c1N] | *** |
| 338 | 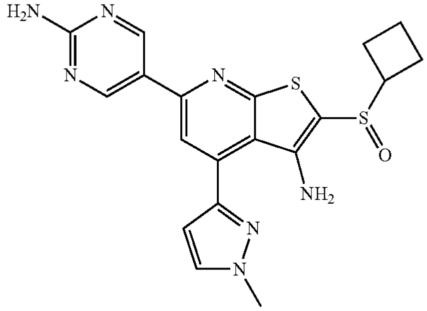 [SMILES: Cn1ccc(-c2cc(-c3cnc(N)nc3)nc3sc(S(=O)C4CCC4)c(N)c23)n1] | *** |
| 339 | 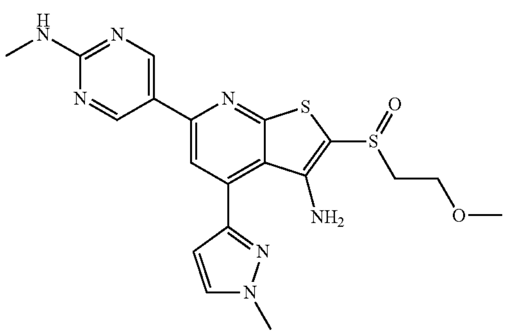 | *** |
| 340 | 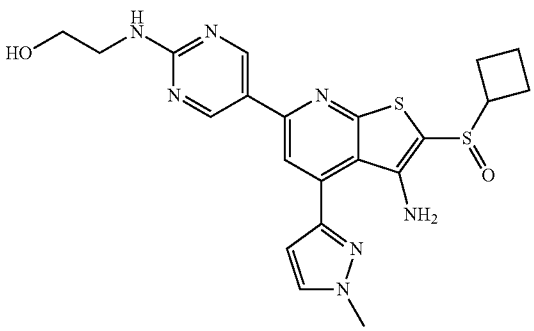 [SMILES: Cn1ccc(-c2cc(-c3cnc(NCCO)nc3)nc3sc(S(=O)C4CCC4)c(N)c23)n1] | *** |

TABLE 1-continued

| Molecule Name | Structure | PDGH Assay-IC$_{50}$ |
|---|---|---|
| 341 | 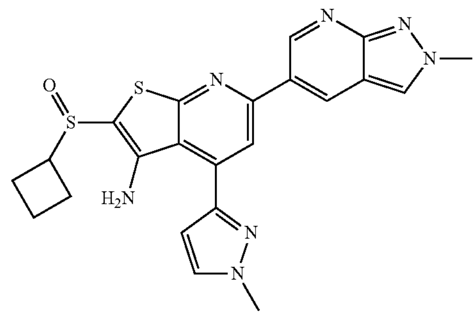 [SMILES: Cn1ccc(-c2cc(-c3cnc4nn(C)cc4c3)nc3sc(S(=O)C4CCC4)c(N)c23)n1] | *** |
| 342 | 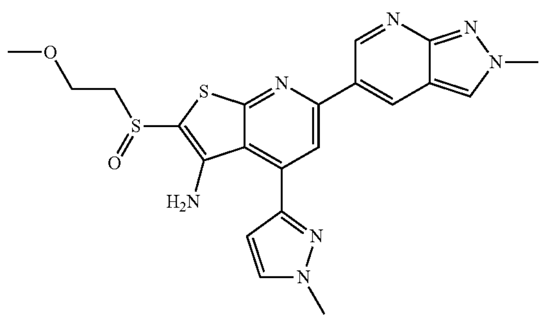 | *** |
| 343 | 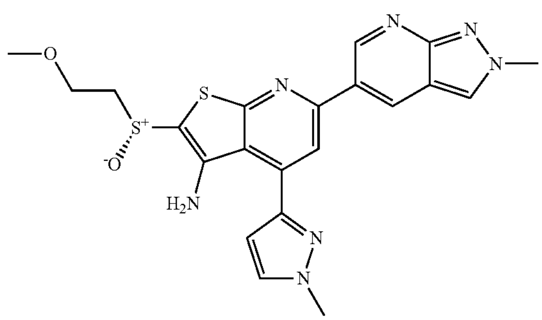 | *** |
| 344 | 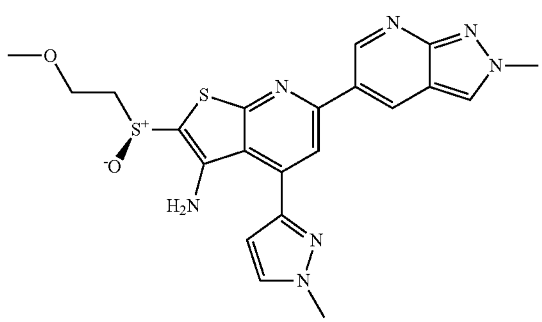 | * |
| 345 | 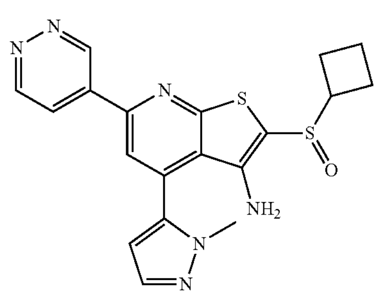 [SMILES: Cn1nccc1-c1cc(-c2ccnnc2)nc2sc(S(=O)C3CCC3)c(N)c12] | *** |

TABLE 1-continued

| Molecule Name | Structure | PDGH Assay-IC$_{50}$ |
|---|---|---|
| 346 | 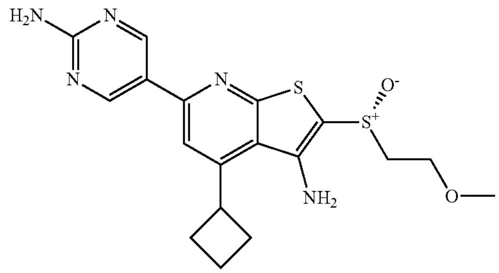 [SMILES: COCC[S@@+]([O-])c1sc2nc(-c3cnc(N)nc3)cc(C3CCC3)c2c1N] | *** |
| 347 | 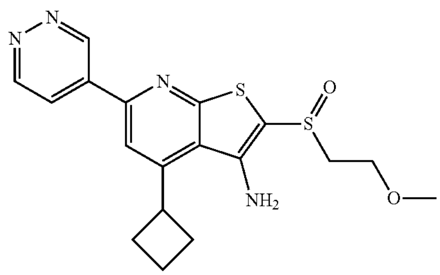 [SMILES: COCCS(=O)c1sc2nc(-c3ccnnc3)cc(C3CCC3)c2c1N] | *** |
| 348 | 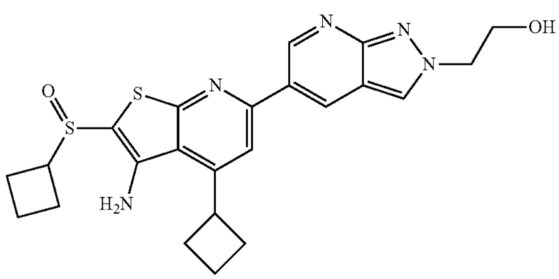 [SMILES: Nc1c(S(=O)C2CCC2)sc2nc(-c3cnc4nn(CCO)cc4c3)cc(C3CCC3)c12] | ** |
| 349 | 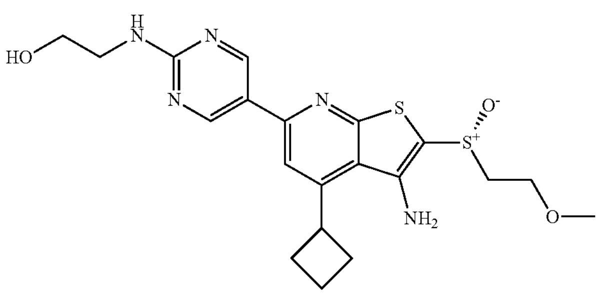 [SMILES: COCC[S@@+]([O-])c1sc2nc(-c3cnc(NCCO)nc3)cc(C3CCC3)c2c1N] | *** |
| 350 | 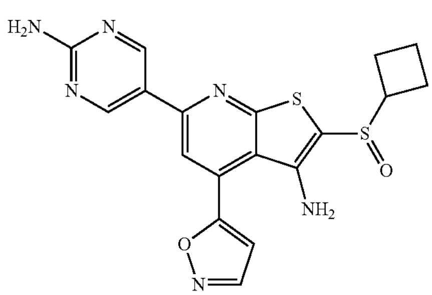 [SMILES: Nc1ncc(-c2cc(-c3ccno3)c3c(N)c(S(=O)C4CCC4)sc3n2)cn1] | *** |

TABLE 1-continued

| Molecule Name | Structure | PDGH Assay-IC$_{50}$ |
|---|---|---|
| 351 | 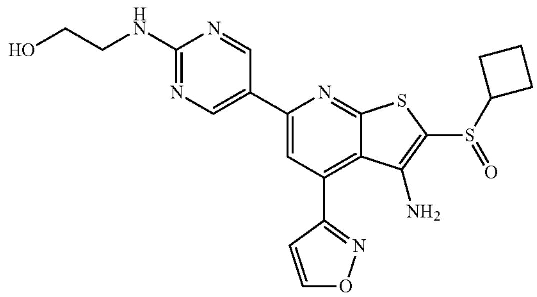 [SMILES: Nc1c(S(=O)C2CCC2)sc2nc(-c3cnc(NCCO)nc3)cc(-c3ccon3)c12] | *** |
| 352 | 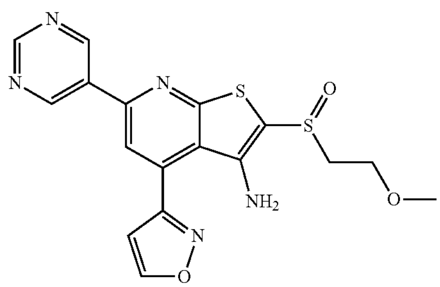 [SMILES: COCCS(=O)c1sc2nc(-c3cncnc3)cc(-c3ccon3)c2c1N] | *** |
| 353 | 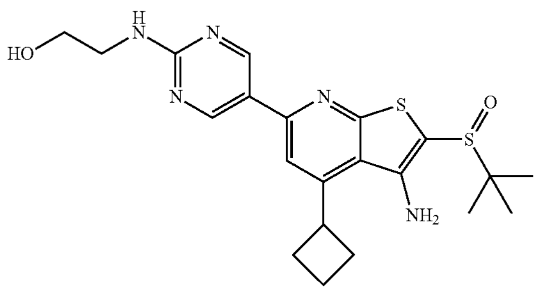 [SMILES: CC(C)(C)S(=O)c1sc2nc(-c3cnc(NCCO)nc3)cc(C3CCC3)c2c1N] | ** |
| 354 | 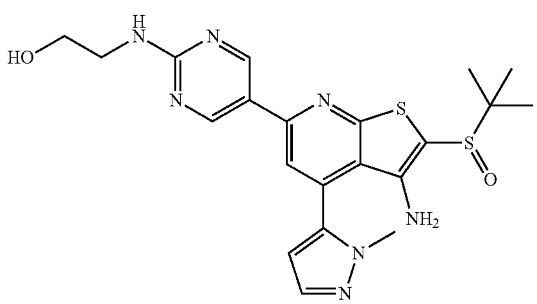 [SMILES: Cn1nccc1-c1cc(-c2cnc(NCCO)nc2)nc2sc(S(=O)C(C)(C)C)c(N)c12] | *** |
| 355 | 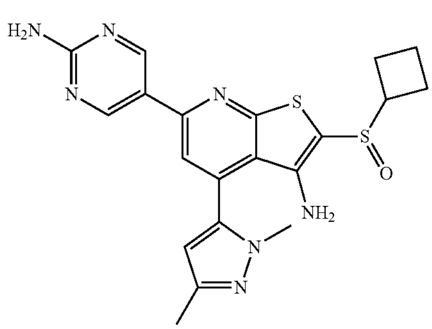 [SMILES: Cc1cc(-c2cc(-c3cnc(N)nc3)nc3sc(S(=O)C4CCC4)c(N)c23)n(C)n1] | *** |

TABLE 1-continued

| Molecule Name | Structure | PDGH Assay-IC$_{50}$ |
|---|---|---|
| 356 | 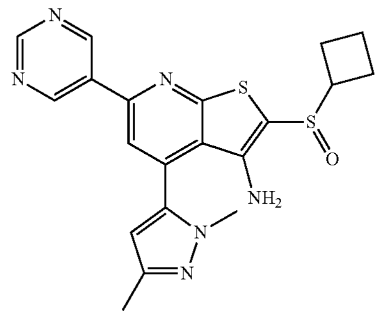 [SMILES: Cc1cc(-c2cc(-c3cncnc3)nc3sc(S(=O)C4CCC4)c(N)c23)n(C)n1] | *** |
| 357 | 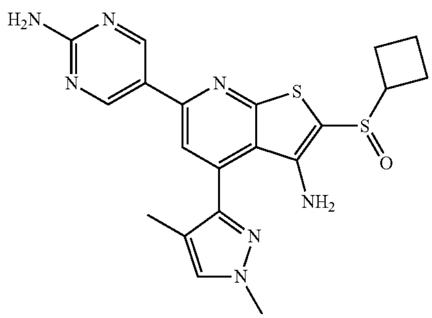 [SMILES: Cc1cn(C)nc1-c1cc(-c2cnc(N)nc2)nc2sc(S(=O)C3CCC3)c(N)c12] | *** |
| 358 | 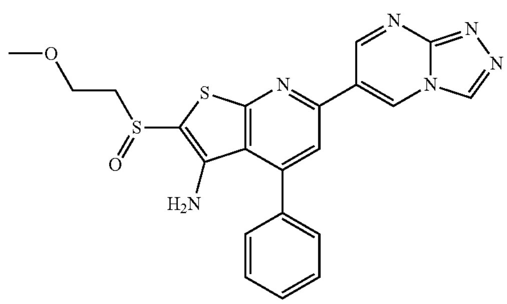 [SMILES: COCCS(=O)c1sc2nc(-c3cnc4nncn4c3)cc(-c3ccccc3)c2c1N] | * |
| 359 | 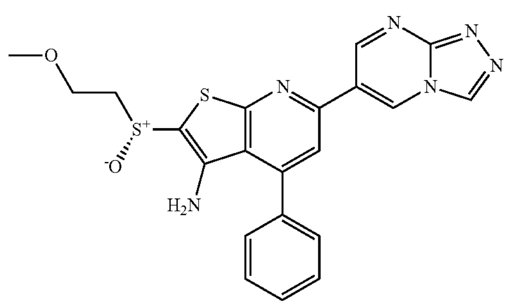 | *** |
| 360 | 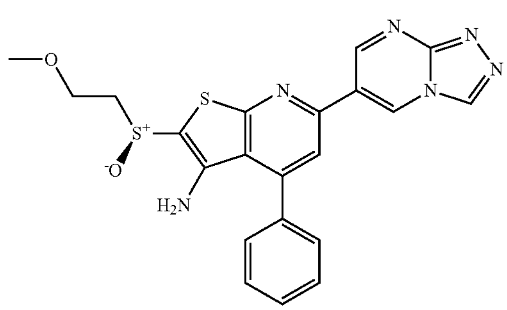 | * |

TABLE 1-continued

| Molecule Name | Structure | PDGH Assay-IC$_{50}$ |
|---|---|---|
| 361 | 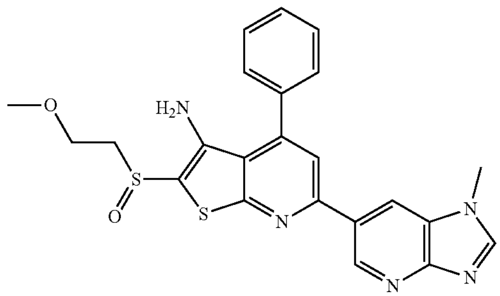 [SMILES: COCCS(=O)c1sc2nc(-c3cnc4ncn(C)c4c3)cc(-c3ccccc3)c2c1N] | *** |
| 362 | 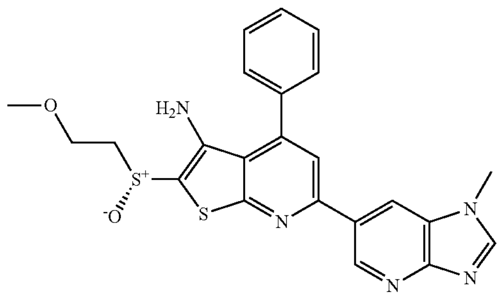 | *** |
| 363 | 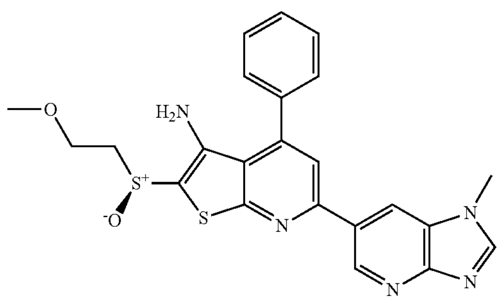 | * |
| 364 | 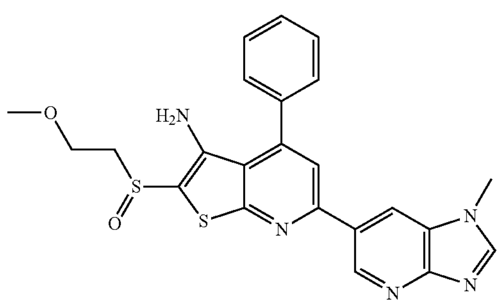 [SMILES: COCCS(=O)c1sc2nc(-c3cnc4ncn(C)c4c3)cc(-c3ccccc3)c2c1N] | *** |
| 365 | 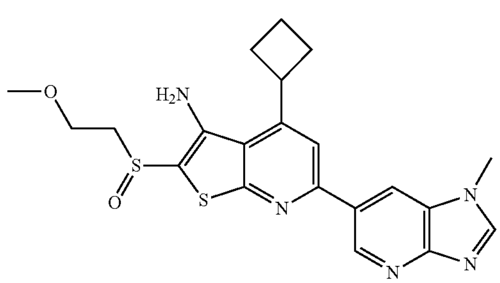 [SMILES: COCCS(=O)c1sc2nc(-c3cnc4ncn(C)c4c3)cc(C3CCC3)c2c1N] | *** |

TABLE 1-continued

| Molecule Name | Structure | PDGH Assay-IC$_{50}$ |
|---|---|---|
| 366 | 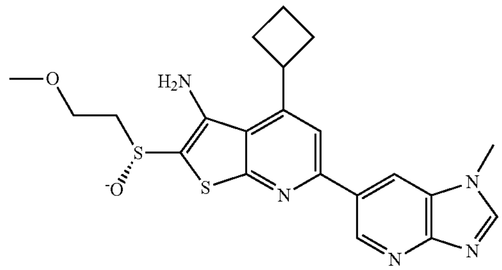 | *** |
| 367 | 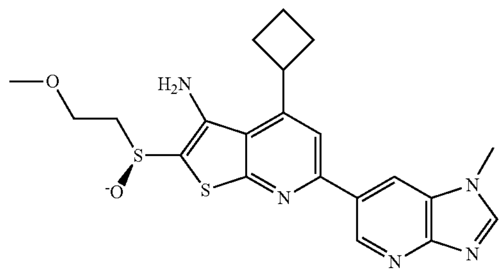 | * |
| 368 | 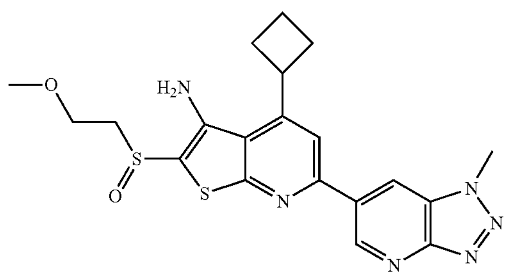 [SMILES: COCCS(=O)c1sc2nc(-c3cnc4nnn(C)c4c3)cc(C3CCC3)c2c1N] | *** |
| 369 | 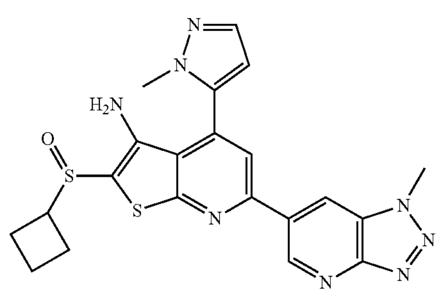 [SMILES: Cn1nccc1-c1cc(-c2cnc3nnn(C)c3c2)nc2sc(S(=O)C3CCC3)c(N)c12] | *** |
| 370 | 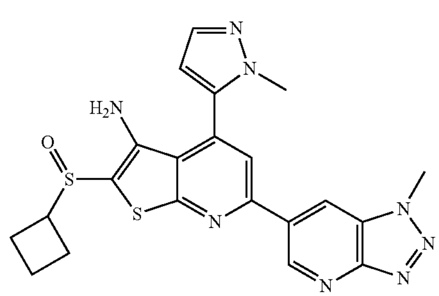 [SMILES: Cn1nccc1-c1cc(-c2cnc3nnn(C)c3c2)nc2sc(S(=O)C3CCC3)c(N)c12] | *** |

TABLE 1-continued

| Molecule Name | Structure | PDGH Assay-IC$_{50}$ |
|---|---|---|
| 371 | 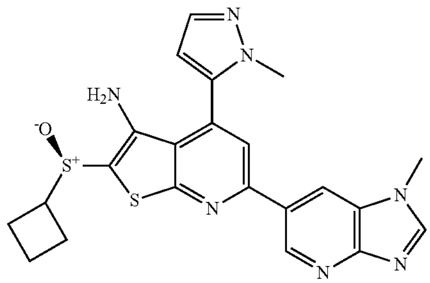 | *** |
| 372 | 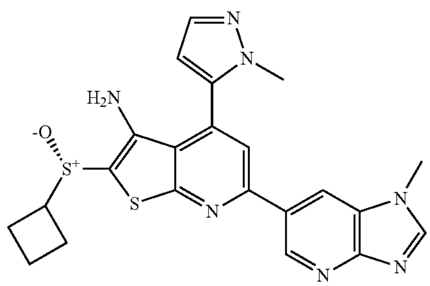 | * |
| 373 | 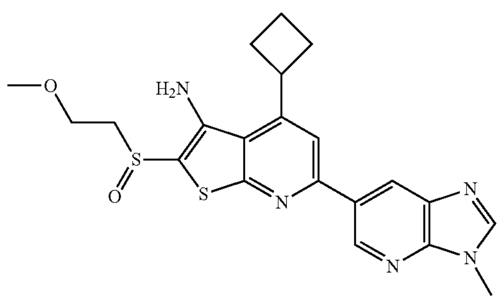 [SMILES: COCCS(=O)c1sc2nc(-c3cnc4c(c3)ncn4C)cc(C3CCC3)c2c1N] | *** |
| 374 | 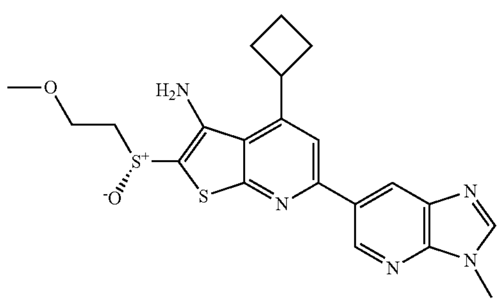 | *** |
| 375 | 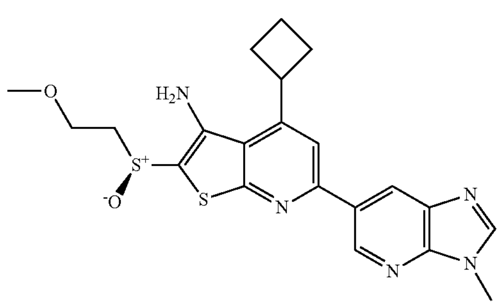 | * |

TABLE 1-continued
| Molecule Name | Structure | PDGH Assay-IC$_{50}$ |
|---|---|---|
| 376 | 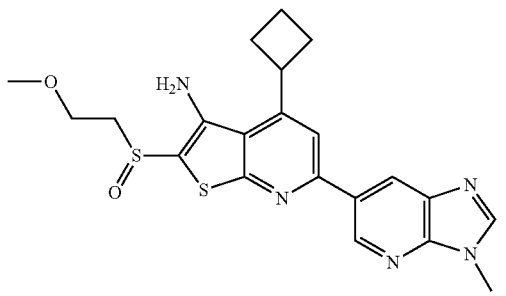 [SMILES: COCCS(=O)c1sc2nc(-c3cnc4c(c3)ncn4C)cc(C3CCC3)c2c1N] | *** |
| 377 | 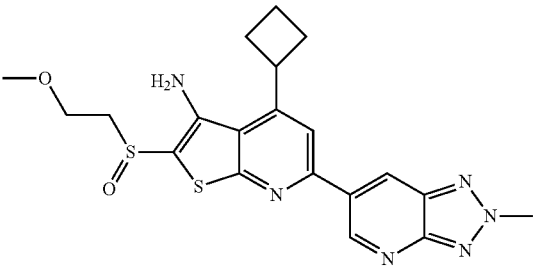 | *** |
| 378 | 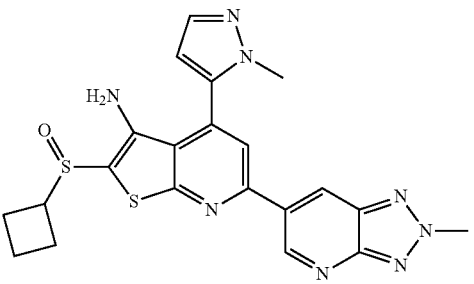 [SMILES: Cn1nc2cc(-c3cc(-c4ccnn4C)c4c(N)c(S(=O)C5CCC5)sc4n3)cnc2n1] | *** |
| 379 | 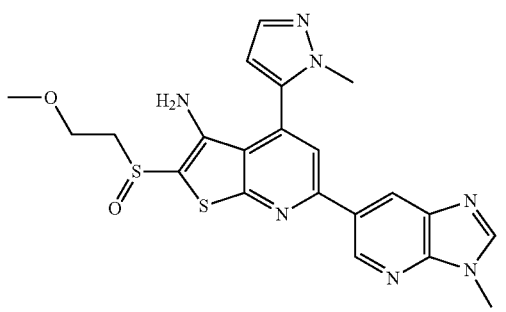 [SMILES: COCCS(=O)c1sc2nc(-c3cnc4c(c3)ncn4C)cc(-c3ccnn3C)c2c1N] | *** |
| 380 | 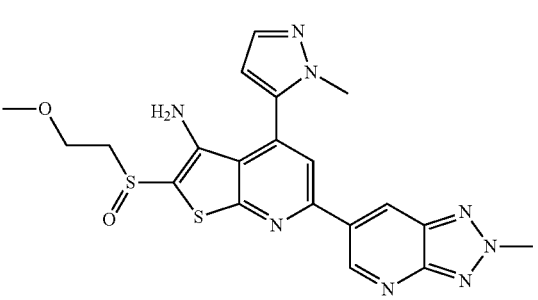 | *** |

TABLE 1-continued
| Molecule Name | Structure | PDGH Assay-IC$_{50}$ |
|---|---|---|
| 381 | 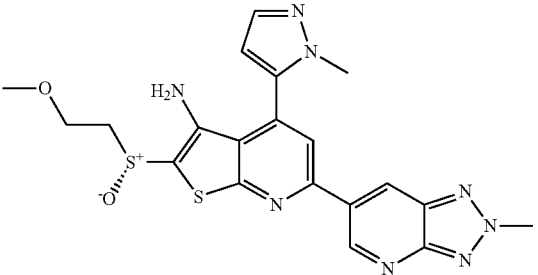 | *** |
| 382 | 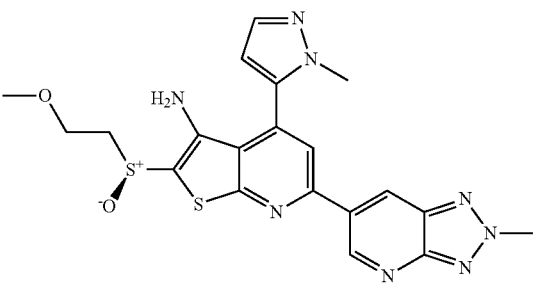 | * |
| 383 | 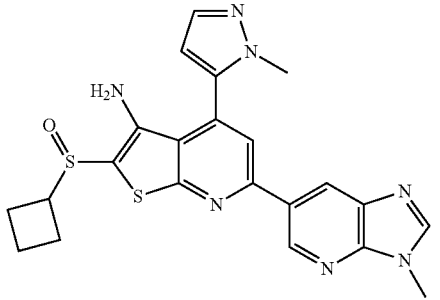 [SMILES: Cn1nccc1-c1cc(-c2cnc3c(c2)ncn3C)nc2sc(S(=O)C3CCC3)c(N)c12] | *** |
| 384 | 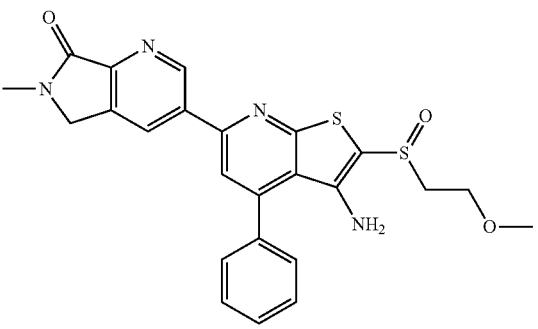 | *** |
| 385 | 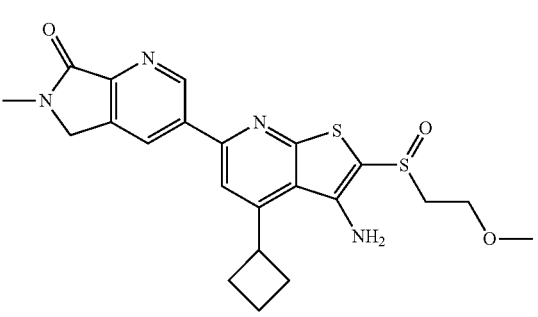 | *** |

TABLE 1-continued

| Molecule Name | Structure | PDGH Assay-IC$_{50}$ |
|---|---|---|
| 386 | 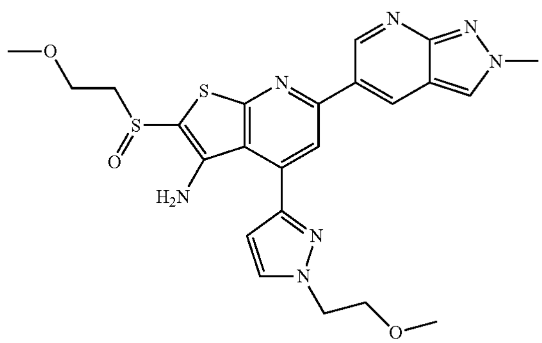 | *** |
| 387 | 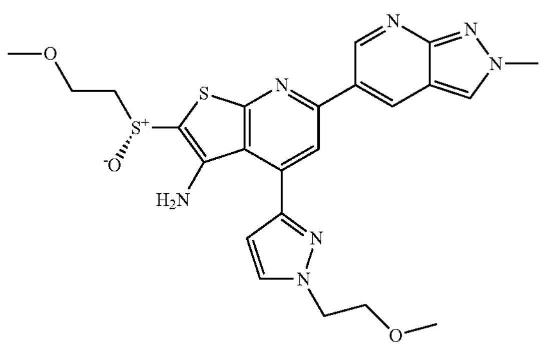 | *** |
| 388 | 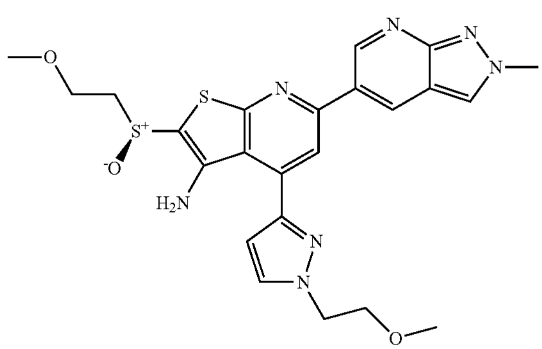 | * |
| 389 | 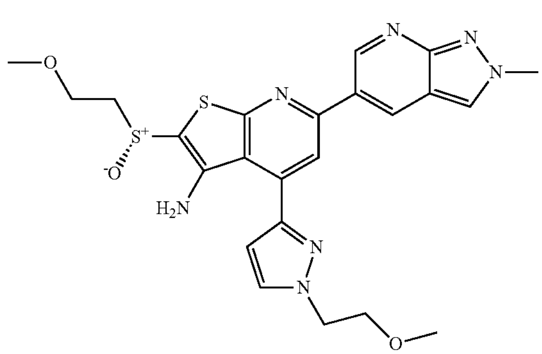 | *** |

TABLE 1-continued

| Molecule Name | Structure | PDGH Assay-IC$_{50}$ |
|---|---|---|
| 390 | 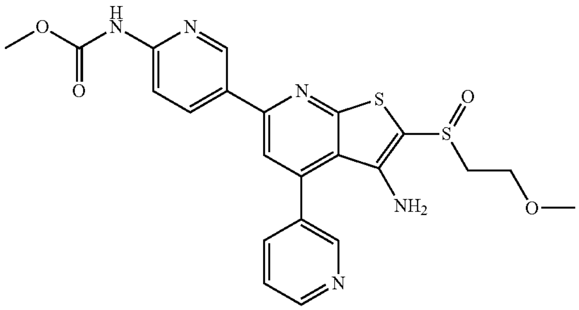 | ** |
| 391 | 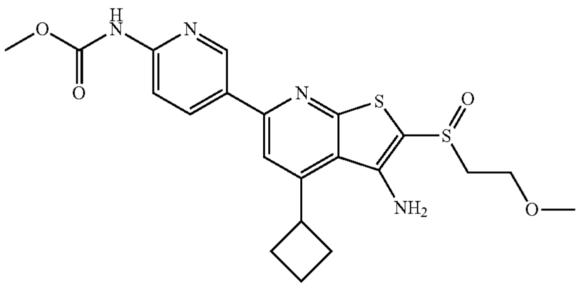 | ** |
| 392 | 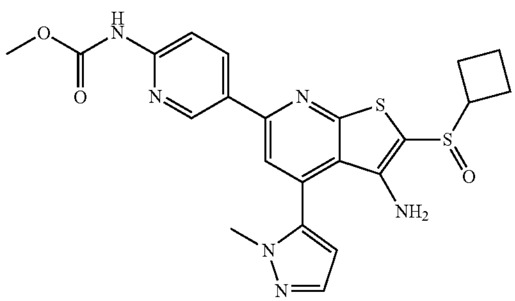 [SMILES: COC(=O)Nc1ccc(-c2cc(-c3ccnn3C)c3c(N)c(S(=O)C4CCC4)sc3n2)cn1] | *** |
| 393 | 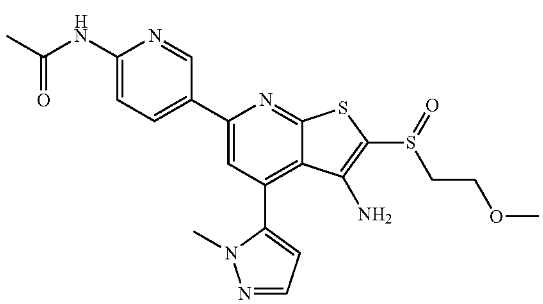 [SMILES: COCCS(=O)c1sc2nc(-c3ccc(NC(C)=O)nc3)cc(-c3ccnn3C)c2c1N] | ** |
| 394 | 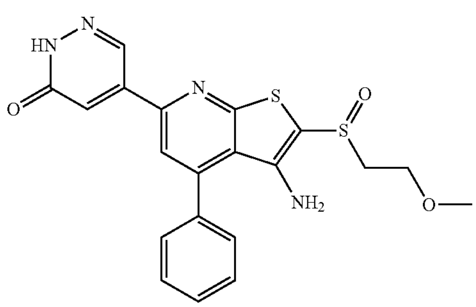 [SMILES: COCCS(=O)c1sc2nc(-c3cn[nH]c(=O)c3)cc(-c3ccccc3)c2c1N] | *** |

TABLE 1-continued

| Molecule Name | Structure | PDGH Assay-IC$_{50}$ |
|---|---|---|
| 395 | 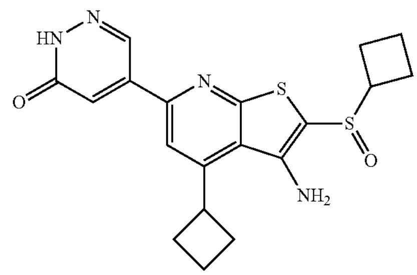 [SMILES: Nc1c(S(=O)C2CCC2)sc2nc(-c3cn[nH]c(=O)c3)cc(C3CCC3)c12] | *** |
| 396 | 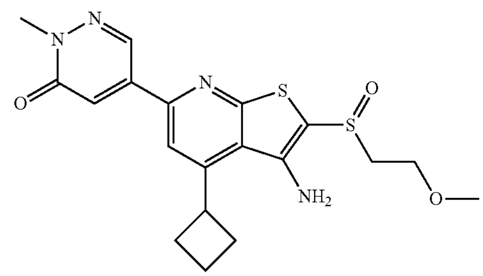 [SMILES: COCCS(=O)c1sc2nc(-c3cnn(C)c(=O)c3)cc(C3CCC3)c2c1N] | *** |
| 397 | 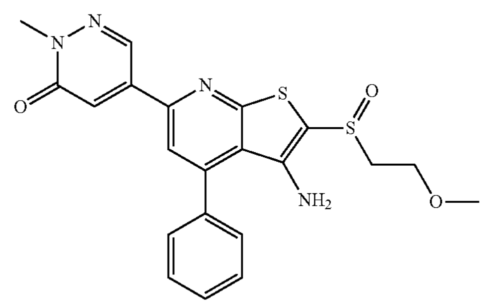 [SMILES: COCCS(=O)c1sc2nc(-c3cnn(C)c(=O)c3)cc(-c3ccccc3)c2c1N] | *** |
| 398 | 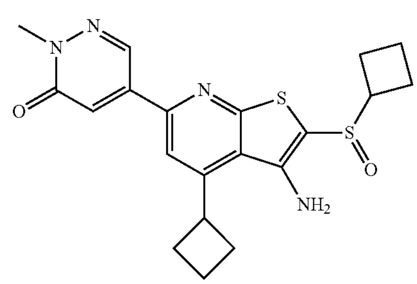 [SMILES: Cn1ncc(-c2cc(C3CCC3)c3c(N)c(S(=O)C4CCC4)sc3n2)cc1=O] | *** |
| 399 | 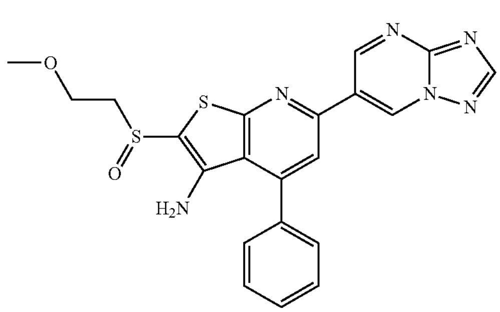 [SMILES: COCCS(=O)c1sc2nc(-c3cnc4ncnn4c3)cc(-c3ccccc3)c2c1N] | *** |

TABLE 1-continued

| Molecule Name | Structure | PDGH Assay-IC$_{50}$ |
|---|---|---|
| 400 | 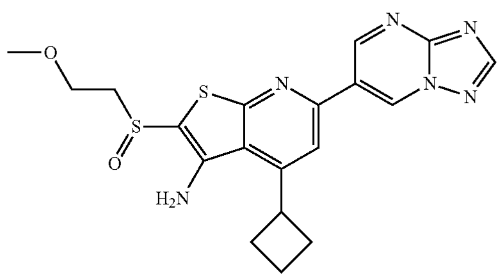 [SMILES: COCCS(=O)c1sc2nc(-c3cnc4ncnn4c3)cc(C3CCC3)c2c1N] | *** |
| 401 | 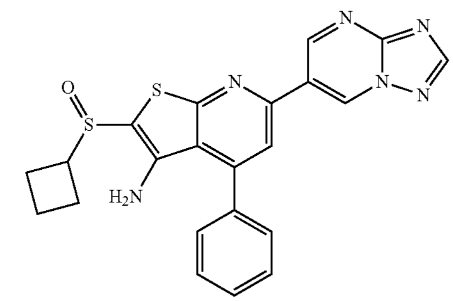 [SMILES: Nc1c(S(=O)C2CCC2)sc2nc(-c3cnc4ncnn4c3)cc(-c3ccccc3)c12] | *** |
| 402 | 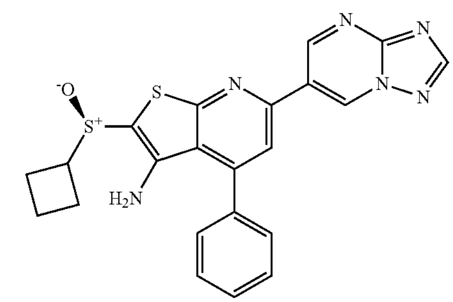 | *** |
| 403 | 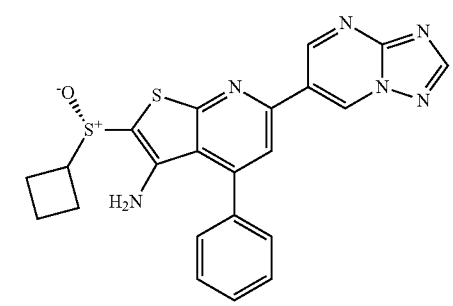 | * |
| 404 | 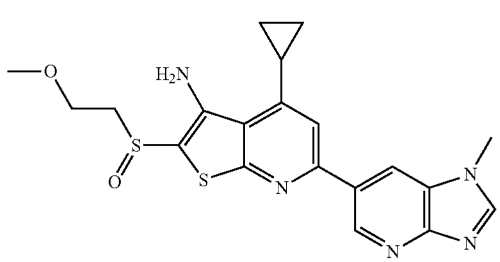 [SMILES: COCCS(=O)c1sc2nc(-c3cnc4ncn(C)c4c3)cc(C3CC3)c2c1N] | *** |

TABLE 1-continued

| Molecule Name | Structure | PDGH Assay-IC$_{50}$ |
|---|---|---|
| 405 | 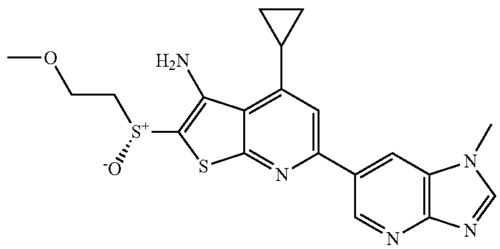 | *** |
| 406 | 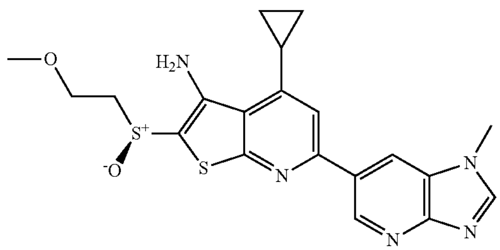 | * |
| 407 | 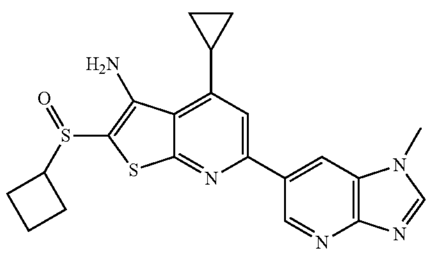 [SMILES: Cn1cnc2ncc(-c3cc(C4CC4)c4c(N)c(S(=O)C5CCC5)sc4n3)cc21] | *** |
| 408 | 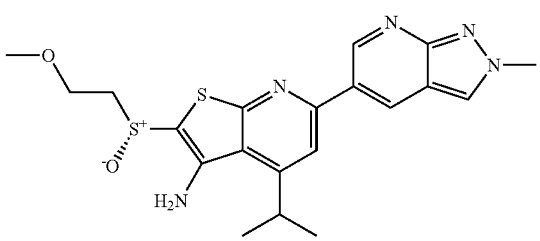 | *** |
| 409 | 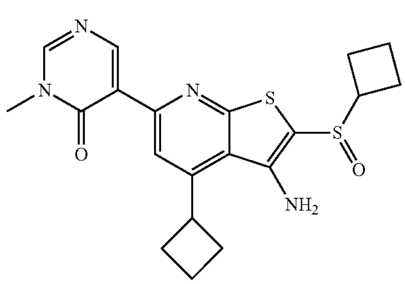 [SMILES: Cn1cncc(-c2cc(C3CCC3)c3c(N)c(S(=O)C4CCC4)sc3n2)c1=O] | *** |

TABLE 1-continued

| Molecule Name | Structure | PDGH Assay-IC$_{50}$ |
|---|---|---|
| 410 | 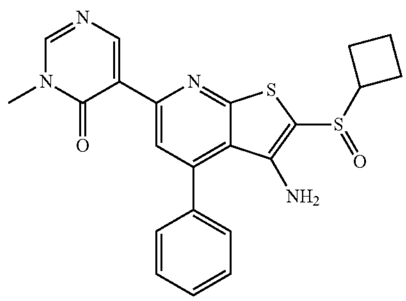 [SMILES: Cn1cncc(-c2cc(-c3ccccc3)c3c(N)c(S(=O)C4CCC4)sc3n2)c1=O] | ** |
| 411 | 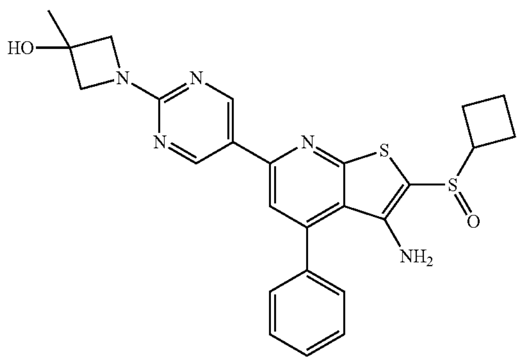 [SMILES: CC1(O)CN(c2ncc(-c3cc(-c4ccccc4)c4c(N)c(S(=O)C5CCC5)sc4n3)cn2)C1] | ** |
| 412 | 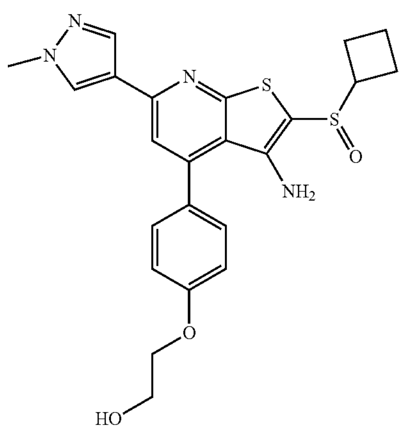 [SMILES: Cn1cc(-c2cc(-c3ccc(OCCO)cc3)c3c(N)c(S(=O)C4CCC4)sc3n2)cn1] | *** |
| 413 | 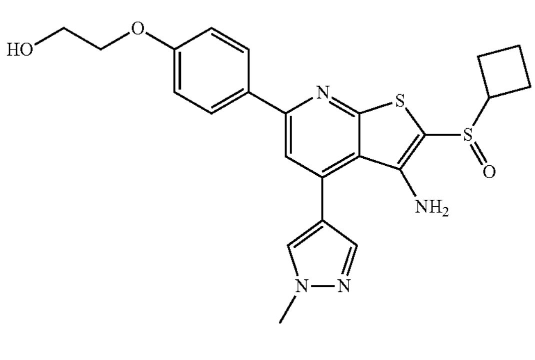 [SMILES: Cn1cc(-c2cc(-c3ccc(OCCO)cc3)nc3sc(S(=O)C4CCC4)c(N)c23)cn1] | *** |

TABLE 1-continued

| Molecule Name | Structure | PDGH Assay-IC$_{50}$ |
| --- | --- | --- |
| 414 | 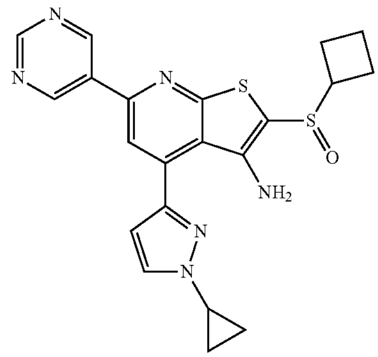 [SMILES: Nc1c(S(=O)C2CCC2)sc2nc(-c3cncnc3)cc(-c3ccn(C4CC4)n3)c12] | *** |
| 415 | 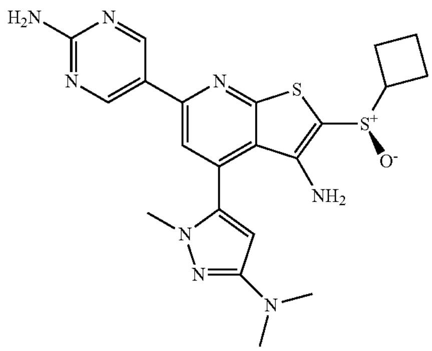 [SMILES: CN(C)c1cc(-c2cc(-c3cnc(N)nc3)nc3sc([S@+]([O-])C4CCC4)c(N)c23)n(C)n1] | *** |
| 416 | 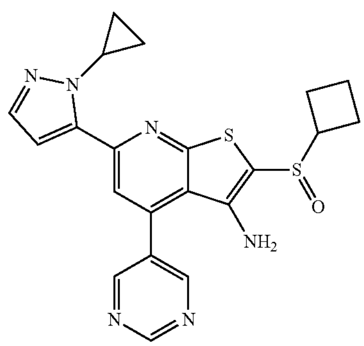 [SMILES: Nc1c(S(=O)C2CCC2)sc2nc(-c3ccnn3C3CC3)cc(-c3cncnc3)c12] | * |
| 417 | 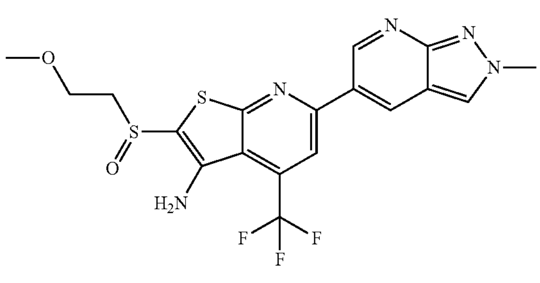 | *** |
| 418 | 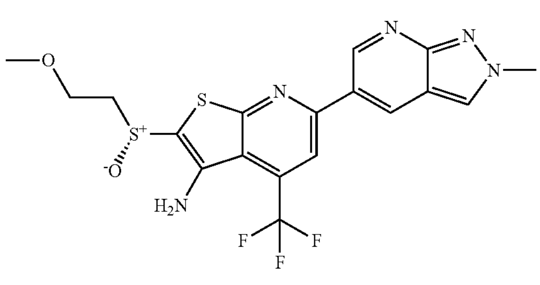 | *** |

TABLE 1-continued

| Molecule Name | Structure | PDGH Assay-IC$_{50}$ |
|---|---|---|
| 419 | 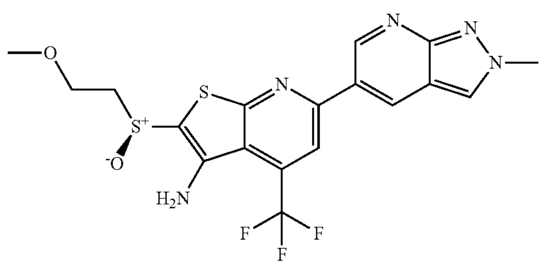 | * |
| 420 | 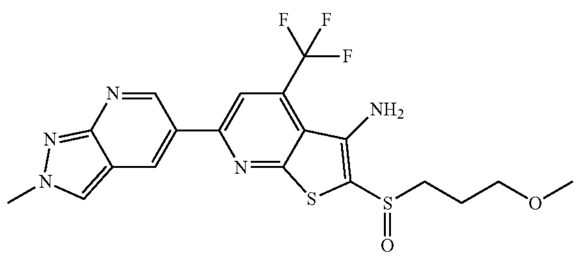 | *** |
| 421 | 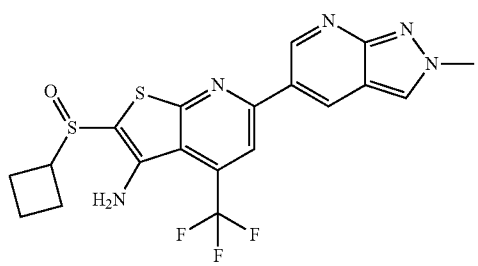 [SMILES: Cn1cc2cc(-c3cc(C(F)(F)F)c4c(N)c(S(=O)C5CCC5)sc4n3)cnc2n1] | *** |
| 422 | 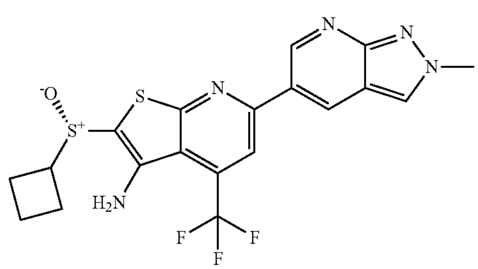 | * |
| 423 | 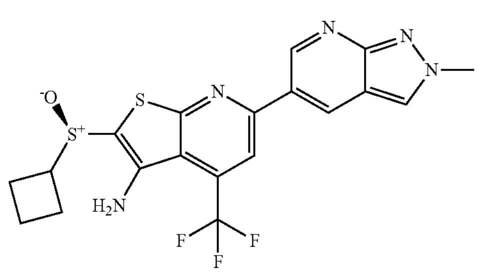 | *** |

TABLE 1-continued
| Molecule Name | Structure | PDGH Assay-IC$_{50}$ |
|---|---|---|
| 424 | 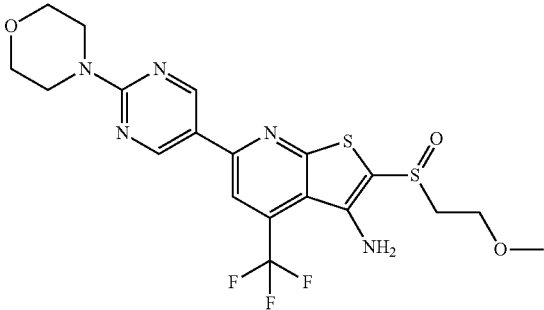 [SMILES: COCCS(=O)c1sc2nc(-c3cnc(N4CCOCC4)nc3)cc(C(F)(F)F)c2c1N] | *** |
| 425 | 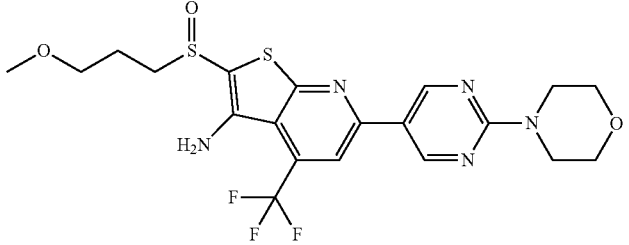 [SMILES: COCCCS(=O)c1sc2nc(-c3cnc(N4CCOCC4)nc3)cc(C(F)(F)F)c2c1N] | ** |
| 426 | 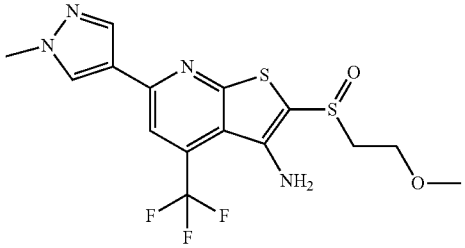 | *** |
| 427 | 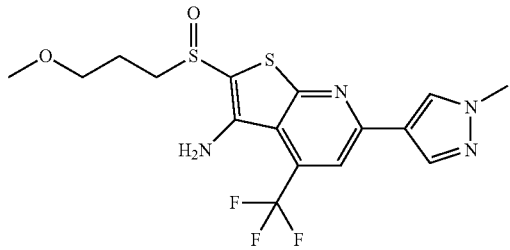 | *** |
| 428 | 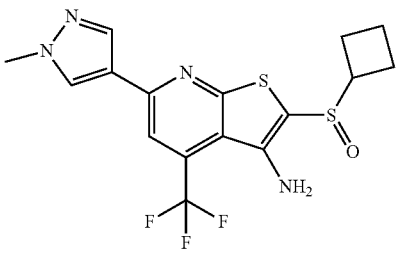 [SMILES: Cn1cc(-c2cc(C(F)(F)F)c3c(N)c(S(=O)C4CCC4)sc3n2)cn1] | *** |

TABLE 1-continued

| Molecule Name | Structure | PDGH Assay-IC$_{50}$ |
|---|---|---|
| 429 | 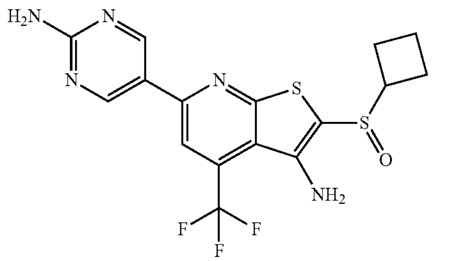 [SMILES: Nc1ncc(-c2cc(C(F)(F)F)c3c(N)c(S(=O)C4CCC4)sc3n2)cn1] | ** |
| 430 | 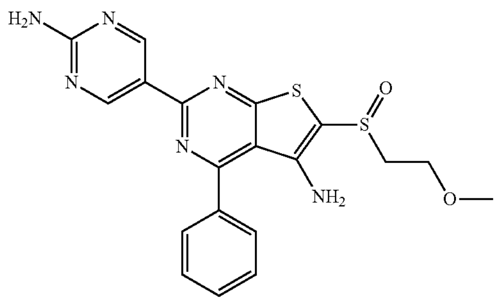 [SMILES: COCCS(=O)c1sc2nc(-c3cnc(N)nc3)nc(-c3ccccc3)c2c1N] | *** |
| 431 | 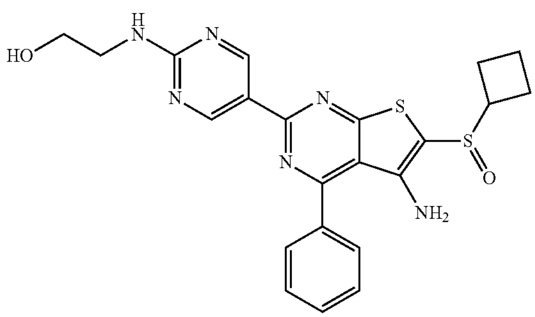 [SMILES: Nc1c(S(=O)C2CCC2)sc2nc(-c3cnc(NCCO)nc3)nc(-c3ccccc3)c12] | ** |
| 432 | 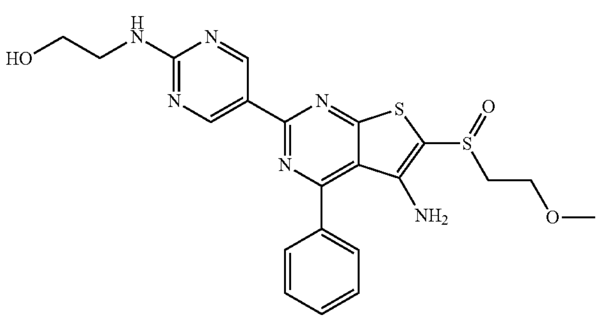 [SMILES: COCCS(=O)c1sc2nc(-c3cnc(NCCO)nc3)nc(-c3ccccc3)c2c1N] | ** |
| 433 | 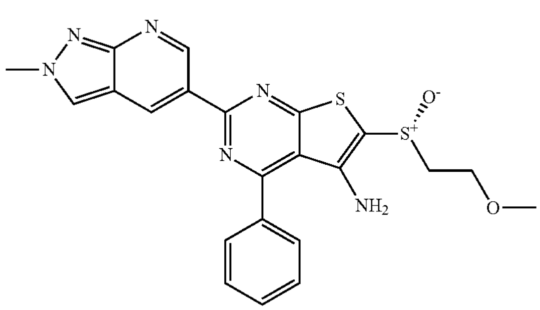 | *** |

TABLE 1-continued

| Molecule Name | Structure | PDGH Assay- IC$_{50}$ |
|---|---|---|
| 434 | 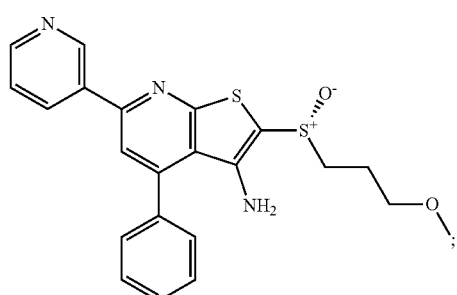 | * |

Example B. Biological Assays

The activity (EC50 in nM) of the compounds was determined for induction of PGE2 from IL1-β treated A549 cells, as assayed in a medium of A549 cells that have been stimulated with by IL1-β for 24 hours. The metabolic stability was determined by incubating the compounds at a concentration of 10 μM in the presence of microsomes derived from mouse livers. Compound concentrations were monitored by HPLC/MS over time, and halflives were calculated from the slope of the best-fit line for Ln[compound] vs time.

Also, reference compounds and selected compounds described herein were given orally to mice at 10 mg/kg (mpk). Colon 15-PGDH activity at 30 minutes was assessed. As shown in Table 2, reference compound A was not sufficiently potent to inhibit colon 15-PGDH activity at 30 minutes and actually showed increased activity as indicated by the −55.2% inhibition. In comparison, compounds described herein demonstrated inhibition of colun 15-PGDH activity at 30 minutes. Similar assays are run at 4 hours.

In Table 2, Reference Compounds A, B, and C have the following structures.

Reference Compounds:

A

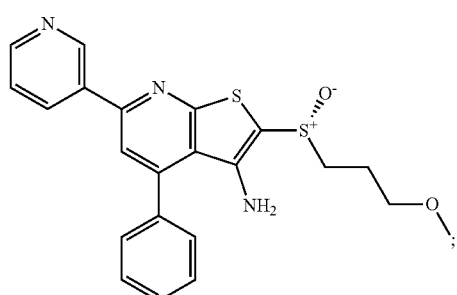

B

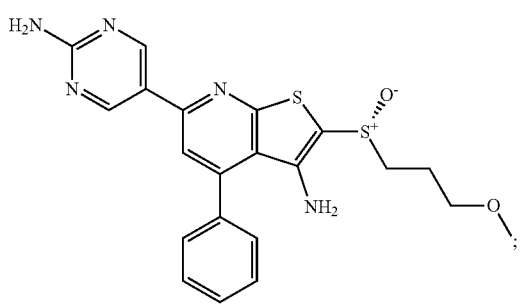

C

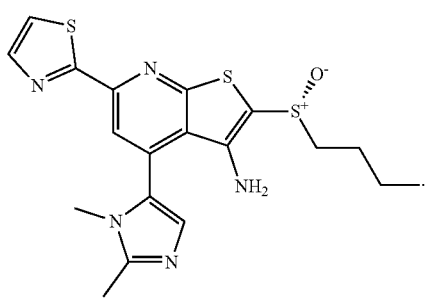

See WO2015/065716 and WO2018/218251 for disclosures of Reference Compounds A-C, the disclosures of each PCT applications are hereby incorporated by reference in their entireties for all purposes.

TABLE 2

| Molecule No. (see Table 1)[1] | Colon enzyme inhibition 30 min following 10 mpk PO | Human microsome stability (T½, min) | hERG IC$_{50}$ (μm) | Elevation of PGE2 in A549 cell culture media (EC$_{50}$, nM) |
|---|---|---|---|---|
| Ref. Compd A | >70% but <90% | <60 | ≤15 | ≤10 |
| Ref. Compd B | >90% | <60 | ≤15 | ≤10 |
| Ref. Compd C | <70% | <60 | ≤15 | >10 |

TABLE 2-continued

| Molecule No. (see Table 1)[1] | Colon enzyme inhibition 30 min following 10 mpk PO | Human microsome stability (T½, min) | hERG IC$_{50}$ (μm) | Elevation of PGE2 in A549 cell culture media (EC$_{50}$, nM) |
|---|---|---|---|---|
| (R)-56 | <70% | ≥60 | >15 | ≤10 |
| (R)-57 | <70% | ≥60 | >15 | ≤10 |
| (R)-44 | >90% | ≥60 | >15 | ≤10 |
| (R)-55 | >90% | ≥60 | >15 | ≤10 |
| (R)-72 | >90% | ≥60 | >15 | ≤10 |
| (R)-73 | >90% | ≥60 | >15 | ≤10 |
| (R)-91 | <70% | ≥60 | >15 | >10 |
| (R)-110 | >90% | ≥60 | >15 | ≤10 |
| (R)-161 | >90% | ≥60 | >15 | ≤10 |
| (R)-195 | >70% but <90% | ≥60 | >15 | ≤10 |
| (R)-145 | >70% but <90% | ≥60 | >15 | ≤10 |
| (R)-224 | >90% | ≥60 | >15 | ≤10 |
| (R)-176 | >90% | ≥60 | >15 | ≤10 |
| (R)-126 | >70% but <90% | ≥60 | >15 | ≤10 |
| (R)-258 | >90% | ≥60 | >15 | ≤10 |
| (R)-326 | >70% but <90% | ≥60 | >15 | ≤10 |
| (R)-331 | N/A | ≥60 | >15 | ≤10 |
| (R)-381 | >90% | ≥60 | >15 | ≤10 |
| (R)-408 | >90% | ≥60 | >15 | ≤10 |

[1]The indication "(R)" in front of the compound number indicates (R) isomer of the compound shown in Table 1. The stereoisomer indication is in relation to the sulfoxide sulfur atom.

The Applicants discovered the IC50 values, alone, are not predictive of in vivo efficacy, such as in disease models. Additional pharmacokinetic and pharmacodynamic properties, such as in vivo inhibition of 15-PGDH, human microsome stability, hERG IC$_{50}$, and EC50 for PGE2 elevation, are important to in vivo efficacy. Without being bound by theory, in certain embodiments, clinical candidates should have two or more of the following characteristics: (i) mouse colon enzyme inhibition 30 minutes following 10 MPK (PO) at ≥70% or ≥90%; (ii) a human microsome stability ≥60 minutes; (iii) hERG IC$_{50}$>15; and (iv) PGE2 elevation EC50≤10 nM. In some embodiments, clinical candidates have three or more of characteristics (i), (ii), (iii), and (iv). In some embodiments, the clinical candidates have characteristics (i), (ii), (iii), and (iv). For example, a compound with a mouse colon enzyme inhibition 30 minutes following 10 MPK of ≥90%, or even ≥70%, may exhibit in vivo efficacy if such compound also demonstrates any combination of two or more of e.g., (ii) a human microsome stability of ≥60 minutes; (iii) hERG IC50 of >15; and/or (iv) EC50 of ≤10 nM. Such compounds with in vivo efficacy are encompassed by the formula disclosed herein, e.g., Formula VIII.

In addition, the blood plasma concentrations of the compounds disclosed herein (e.g., the compounds of Formula VIII and/or Table 2) may be measured using known techniques, to determine, e.g., maximum blood concentrations, time to reach maximum blood concentrations, and area under the blood plasma concentration curve.

Synthesis

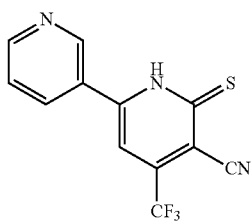 [SMILES: N#Cc1c(C(F)(F)F)cc(-c2cccnc2)[nH]c1=S]

Example 1A: 6-thioxo-4-(trifluoromethyl)-1,6-dihydro-[2,3'-bipyridine]-5-carbonitrile. Cyanothioacetamide (207 mg, 2.07 mmol) was added to a solution of 4,4,4-trifluoro-1-(pyridin-3-yl)butane-1,3-dione (300 mg, 1.38 mmol) and DABCO (155 mg, 1.38 mmol) in EtOH at room temperature. The reaction mixture was stirred under reflux. Once the reaction was completed, the mixture was allowed to stand overnight at 0° C., filtered and collected solid dried to give the title compound in quantitative yield. ESI-MS (m/z): 282.1 [M+H]$^+$.

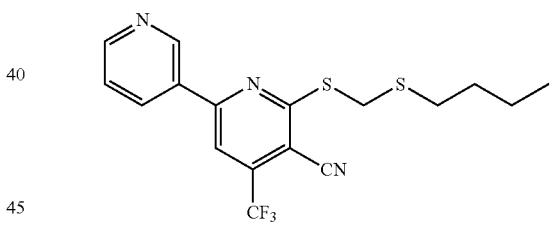

Example 1B: 6-(((butylthio)methyl)thio)-4-(trifluoromethyl)-[2,3'-bipyridine]-5-carbonitrile. A mixture of 6-thioxo-4-(trifluoromethyl)-1,6-dihydro-[2,3'-bipyridine]-5-carbonitrile (4.91 mmol, 1380 mg), butyl(chloromethyl)sulfane (4.91 mmol, 677 mg, 1.0 equiv) and Et$_3$N (7.36 mmol, 750 mg, 1.0 ml, 1.5 equiv) was stirred in dry CH$_3$CN (32.0 mL) for 20 min at 80° C. The reaction mixture was then diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 599 mg of desired product $^1$H NMR (400 MHz, Chloroform-d) δ 9.32 (dt, J=2.4, 0.8 Hz, 1H), 8.79 (ddd, J=4.9, 1.7, 0.7 Hz, 1H), 8.39 (dddd, J=8.1, 2.4, 1.7, 0.6 Hz, 1H), 7.78 (s, 1H), 7.50 (ddt, J=8.1, 4.8, 0.8 Hz, 1H), 4.51 (s, 2H), 2.75 (t, J=7.8 Hz, 2H), 1.72-1.60 (m, 2H), 1.42 (h, J=7.4 Hz, 2H), 0.92 (t, J=7.3, 3H). ESI-MS (m/z): 384.1 [M+H]$^+$.

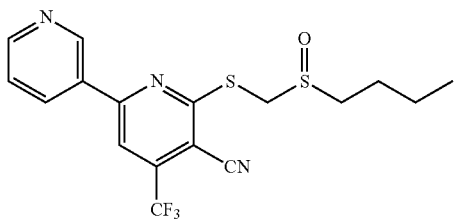 [SMILES: CCCCS(=O)CSc1nc(-c2cccnc2)cc(C(F)(F)F)c1C#N]

Example 1C: 6-(((butylsulfinyl)methyl)thio)-4-(trifluoromethyl)-[2,3'-bipyridine]-5-carbonitrile. To the solution of (((butylthio)methyl)thio)-4-(trifluoromethyl)-[2,3'-bipyridine]-5-carbonitrile (570 mg, 1.49 mmol) in CHCl$_3$/AcOH (1:1, 0.27 M) was added H$_2$O$_2$ (372 µL, 30% solution in water). The reaction mixture was stirred at 32° C. for 40 min. Once complete, the reaction was diluted with EtOAc and was washed with saturated NaHCO$_3$ solution, dried over magnesium sulfate, filtered and concentrated under reduce pressure to give 553 mg (93%) of desired compound. $^1$H NMR (400 MHz, Chloroform-d) δ 9.28 (s, 1H), 8.80 (dd, J=4.8, 1.5 Hz, 1H), 8.49 (ddt, J=8.1, 2.6, 1.5 Hz, 1H), 7.87 (s, 1H), 7.55 (ddt, J=8.0, 4.9, 1.0 Hz, 1H), 4.71 (d, J=13.3 Hz, 1H), 4.54 (d, J=13.3 Hz, 1H), 3.00-2.80 (m, 2H), 1.90-1.75 (m, 2H), 1.61-1.37 (m, 2H), 0.96 (t, J=7.4, 3H). ESI-MS (m/z): 400.0 [M+H]$^+$.

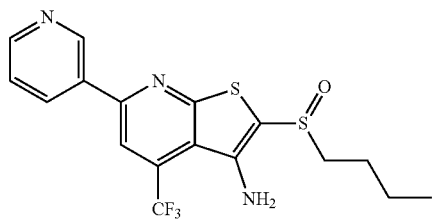

EXAMPLE 1: 2-(butylsulfinyl)-6-(pyridin-3-yl)-4-(trifluoromethyl)thieno[2,3-b]pyridin-3-amine. To the solution of 6-(((butylsulfinyl)methyl)thio)-4-(trifluoromethyl)-[2,3'-bipyridine]-5-carbonitrile (410 mg, 1.03 mmol) in DMF (6.7 mL)/MeOH (3.35 mL) was added KOH (0.62 mmol, 34.7 mg, 347 µL in water). The reaction mixture was stirred at 32° C. for 10 min. Once complete, the reaction was diluted with EtOAc and acidified to pH 7 with 5% aq. solution of AcOH, the organic phase was separated and aqueous layer was extracted twice with EtOAc, dried over magnesium sulfate, filtered and concentrated under reduced pressure. The crude product was purified by flash chromatography to give desired product. $^1$H NMR (400 MHz, Methylene Chloride-d$_2$) δ 9.33 (dd, J=2.4, 0.9 Hz, 1H), 8.72 (dd, J=4.8, 1.7 Hz, 1H), 8.46 (ddd, J=8.0, 2.4, 1.6 Hz, 1H), 8.11 (d, J=0.8 Hz, 1H), 7.49 (ddd, J=8.0, 4.8, 0.9 Hz, 1H), 5.24 (s, 2H), 3.33 (ddd, J=12.9, 9.0, 6.2 Hz, 1H), 3.17 (ddd, J=12.9, 9.1, 6.8 Hz, 1H), 1.90-1.68 (m, 2H), 1.52 (dd, J=7.3, 2.5 Hz, 2H), 0.97 (t, J=7.3 Hz, 3H). ESI-MS (m/z): 400.1 [M+H]$^+$.

Enantiomers of EXAMPLE 1 were separated on a 1 cm Chiralpak AD-H column using 50% EtOH and 50% Hexanes with 5 mL/min flow rate, 400 µL injection (concentration 10 mg/ml) the 1st peak was at 7.8 min and the 2nd peak was at 15.1 min.

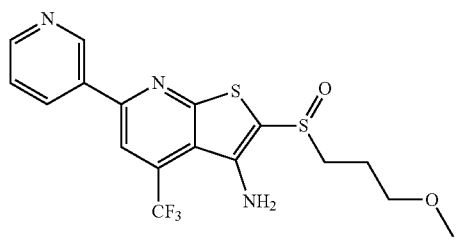 [SMILES: COCCCS(=O)c1sc2nc(-c3cccnc3)cc(C(F)(F)F)c2c1N]

EXAMPLE 2: 2-((3-methoxypropyl)sulfinyl)-6-(pyridin-3-yl)-4-(trifluoromethyl)thieno[2,3-b]pyridin-3-amine was prepared using the synthetic procedures described for the preparation of the analog EXAMPLE 1. $^1$H NMR (500 MHz, Methylene Chloride-d$_2$) δ 9.37 (s, 1H), 8.76 (s, 1H), 8.50 (ddd, J=8.1, 2.3, 1.5 Hz, 1H), 8.14 (s, 1H), 7.53 (dd, J=8.0, 4.7 Hz, 1H), 5.27 (s, 2H), 3.56 (t, J=5.9 Hz, 2H), 3.41 (ddd, J=13.0, 8.4, 6.5 Hz, 1H), 3.37 (s, 3H), 3.30 (ddd, J=13.0, 8.4, 6.3 Hz, 1H), 2.19-1.96 (m, 2H). ESI-MS (m/z): 416.1 [M+H]$^+$.

Enantiomers of EXAMPLE 2 were separated on a 2 cm Chiralpak AD-H column using 100% EtOH with 10 mL/min flow rate, 600 µL injection (concentration 8 mg/ml) the 1st peak was at 20 min and the 2nd peak was at 41 min.

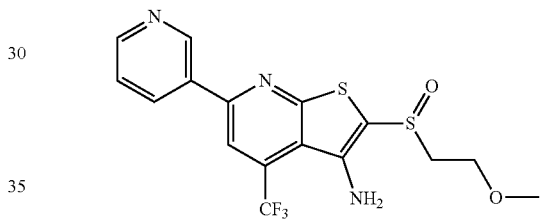

EXAMPLE 3: 2-((2-methoxyethyl)sulfinyl)-6-(pyridin-3-yl)-4-(trifluoromethyl)thieno[2,3-b]pyridin-3-amine was prepared using the synthetic procedures described for the preparation of the analog EXAMPLE 1. $^1$H NMR (500 MHz, Methylene Chloride-d$_2$) δ 9.37 (s, 1H), 8.76 (d, J=4.3 Hz, 1H), 8.54-8.42 (m, 1H), 8.14 (s, 1H), 7.53 (ddd, J=8.0, 4.8, 0.9 Hz, 1H), 5.23 (s, 2H), 3.90 (ddd, J=9.9, 7.6, 3.7 Hz, 1H), 3.71 (ddd, J=10.1, 6.3, 4.0 Hz, 1H), 3.66 (ddd, J=12.9, 6.3, 3.7 Hz, 1H), 3.42 (s, 3H), 3.35 (ddd, J=12.8, 7.6, 4.0 Hz, 1H). ESI-MS (m/z): 402.1. [M+H]$^+$.

Enantiomers of EXAMPLE 3 were separated on a 2 cm Chiralpak AD-H column using 80% EtOH and 20% Hexanes with 10 m/min flow rate, 600 µL injection (concentration 8 mg/ml) the 1st peak was at 21.9 min and the 2nd peak was at 30 min.

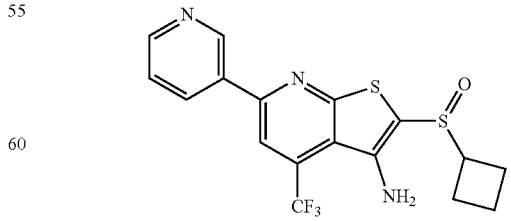

EXAMPLE 4: 2-(cyclobutylsulfinyl)-6-(pyridin-3-yl)-4-(trifluoromethyl)thieno[2,3-b]pyridin-3-amine was prepared using the synthetic procedures described for the preparation of the analog EXAMPLE 1. ¹H NMR (400 MHz, Methylene Chloride-d₂) δ 9.33 (s, 1H), 8.72 (s, 1H), 8.59-8.37 (m, 1H), 8.09 (s, 1H), 7.49 (dd, J=8.0, 4.8 Hz, 1H), 5.18 (s, 2H), 4.04-3.90 (m, 1H), 2.89-2.71 (m, 1H), 2.51-2.36 (m, 1H), 2.36-2.19 (m, 2H), 2.18-1.99 (m, 2H). ESI-MS (m/z): 398.1 [M+H]⁺.

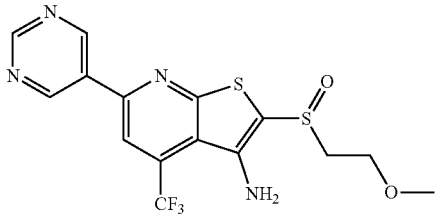 [SMILES: COCCS(=O)c1sc2nc(-c3cncnc3)cc(C(F)(F)F)c2c1N]

EXAMPLE 5: 2-((2-methoxyethyl)sulfinyl)-6-(pyrimidin-5-yl)-4-(trifluoromethyl)thieno[2,3-b]pyridin-3-amine was prepared using the synthetic procedures described for the preparation of the analog EXAMPLE 1. ¹H NMR (400 MHz, Methylene Chloride-d₂) δ 9.46 (s, 2H), 9.30 (s, 1H), 8.10 (s, 1H), 5.21 (s, 2H), 3.87 (ddd, J=9.4, 7.7, 3.5 Hz, 1H), 3.73-3.59 (m, 2H), 3.39 (s, 3H), 3.32 (ddd, J=12.6, 7.6, 3.6 Hz, 1H). ESI-MS (m/z): 403.0 [M+H]⁺.

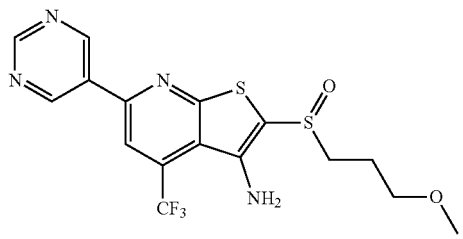 [SMILES: COCCCS(=O)c1sc2nc(-c3cncnc3)cc(C(F)(F)F)c2c1N]

EXAMPLE 6: 2-((3-methoxypropyl)sulfinyl)-6-(pyrimidin-5-yl)-4-(trifluoromethyl)thieno[2,3-b]pyridin-3-amine was prepared using the synthetic procedures described for the preparation of the analog EXAMPLE 1. ¹H NMR (400 MHz, Methylene Chloride-d₂) δ 9.46 (s, 2H), 9.30 (s, 1H), 7.97 (s, 1H), 5.26 (s, 2H), 3.53 (t, J=5.9 Hz, 2H), 3.42-3.35 (m, 1H), 3.34 (s, 3H), 3.27 (ddd, J=13.0, 8.3, 6.3 Hz, 1H), 2.17-1.91 (m, 2H). ESI-MS (m/z): 417.1 [M+H]⁺.

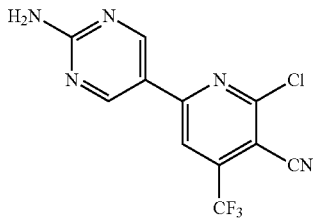

Example 7A: 6-(2-aminopyrimidin-5-yl)-2-chloro-4-(trifluoromethyl)nicotinonitrile. To the solution of 2,6-dichloro-4-(trifluoromethyl)nicotinonitrile (100 mg, 0.416 mmol), (2-aminopyrimidin-5-yl)boronic acid (0.39 mmol, 55.0 mg, 0.95 equiv), [1,1'-bis(diphenylphosphino)ferrocene]dichloropalladium(II) (0.019 mmol, 16 mg, 5 mol %) in degassed dioxane (1.0 mL) was added degassed 2M aqueous solution of sodium carbonate (0.5 mL) and the reaction mixture was stirred for 2.5 h under nitrogen at 100° C. Once complete, the reaction was diluted with EtOAc and water. The organic phase was separated and aqueous layer was extracted twice with EtOAc, dried over magnesium sulfate, filtered and concentrated under reduced pressure to give crude product, which was purified by flash column chromatography in 51% isolated yield (64 mg). ESI-MS (m/z): 300.0 [M+H]⁺.

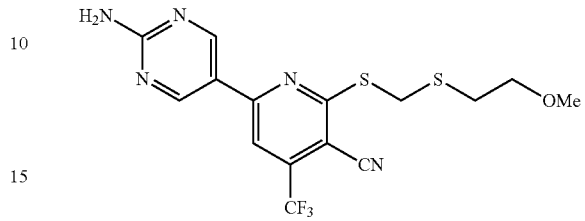

Example 7B: 6-(2-aminopyrimidin-5-yl)-2-((((2-methoxyethyl)thio)methyl)thio)-4-(trifluoromethyl)nicotinonitrile. To the solution of 6-(2-aminopyrimidin-5-yl)-2-chloro-4-(trifluoromethyl)nicotinonitrile (64 mg, 0.214 mmol) in DMF (200 μL) was added sodium sulfide (18.3 mg, 0.24 mmol, 1.1 equiv) and the reaction mixture was stirred at 100° C. for 20 min. The progress of the reaction was followed by LCMS. Once complete (about 20 min), conc. HCl was added and the reaction mixture was stirred in the hood for 10 min. ESI-MS (m/z): 298.0 [M+H]⁺.

The reaction mixture was diluted with CH₃CN (1.50 mL). Et₃N (0.65 mmol, 65.6 mg, 90 μL. 3.0 equiv) was added followed by (chloromethyl)(2-methoxyethyl)sulfane (0.428 mmol, 60 mg, 2.0 equiv). The reaction mixture was stirred at room temperature for 15 min. Once complete, the reaction was diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 24 mg of product (28%). ¹H NMR (400 MHz, Chloroform-d) δ 9.03 (s, 2H), 7.59 (s, 1H), 5.52 (s, 2H), 4.55 (s, 2H), 3.67 (t, J=6.0 Hz, 2H), 3.38 (s, 3H), 2.90 (t, J=6.0 Hz, 2H). ESI-MS (m/z): 402.1 [M+H]⁺.

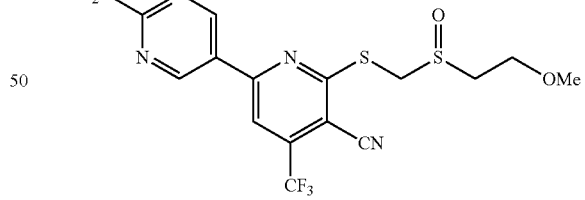

Example 7C: 6-(2-aminopyrimidin-5-yl)-2-((((2-methoxyethyl)sulfinyl)methyl)thio)-4-(trifluoromethyl) nicotinonitrile was prepared via standard oxidation with hydrogen peroxide in 99% isolated yield, using synthetic procedures described for the preparation of the analog EXAMPLE 1. ¹H NMR (400 MHz, Chloroform-d) δ 9.03 (s, 2H), 7.65 (s, 1H), 6.15 (s, 2H), 4.78 (d, J=13.2 Hz, 1H), 4.67 (d, J=13.1 Hz, 1H), 3.98 (ddd, J=10.7, 6.0, 3.6 Hz, 1H), 3.80 (ddd, J=11.0, 8.4, 3.1 Hz, 1H), 3.40 (s, 3H), 3.18 (ddd, J=13.8, 8.5, 3.7 Hz, 1H), 3.07 (ddd, J=13.8, 6.0, 3.1 Hz, 1H). ESI-MS (m/z): 418.1 [M+H]⁺.

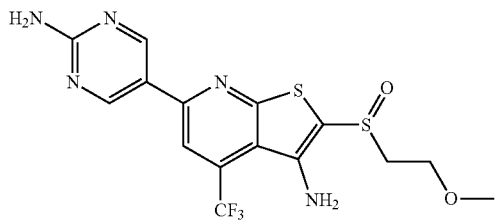

EXAMPLE 7: 6-(2-aminopyrimidin-5-yl)-2-((2-methoxyethyl)sulfinyl)-4-(trifluoromethyl)thieno[2,3-b]pyridin-3-amine was prepared in 71% isolated yield via standard cyclization reaction with potassium hydroxide, using the synthetic procedures described for the preparation of the analog EXAMPLE 1. $^1$H NMR (400 MHz, Acetone-$d_6$) δ 9.14 (s, 2H), 8.25 (s, 1H), 6.59 (s, 2H), 5.40 (s, 2H), 3.85 (ddd, J=10.7, 7.9, 4.2 Hz, 1H), 3.70 (ddd, J=10.5, 5.8, 4.5 Hz, 1H), 3.52 (ddd, J=13.2, 5.9, 4.2 Hz, 1H), 3.35 (s, 3H), 3.33-3.27 (m, 1H). ESI-MS (m/z): 418.1 [M+H]$^+$.

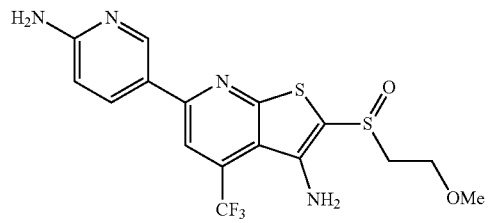

EXAMPLE 10: 6-(6-aminopyridin-3-yl)-2-((2-methoxyethyl)sulfinyl)-4-(trifluoromethyl)thieno[2,3-b]pyridin-3-amine was prepared using the synthetic procedures described for the preparation of the analog EXAMPLE 7. $^1$H NMR (400 MHz, Methylene Chloride-$d_2$) δ 8.82 (s, 1H), 8.26 (dd, J=8.9, 2.3 Hz, 1H), 7.97 (s, 1H), 6.66 (d, J=8.7 Hz, 1H), 5.14 (s, 2H), 4.97 (s, 2H), 3.90-3.80 (m, 1H), 3.71-3.56 (m, 2H), 3.38 (s, 3H), 3.33-3.24 (m, 1H). ESI-MS (m/z): 417.1 [M+H]$^+$.

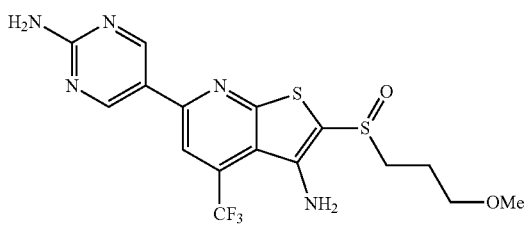

EXAMPLE 8: 6-(2-aminopyrimidin-5-yl)-2-((3-methoxypropyl)sulfinyl)-4-(trifluoromethyl)thieno[2,3-b]pyridin-3-amine was prepared using the synthetic procedures described for the preparation of the analog EXAMPLE 7. $^1$H NMR (400 MHz, Methylene Chloride-$d_2$) δ 9.06 (s, 2H), 7.93 (s, 1H), 5.46 (s, 2H), 5.20 (s, 2H), 3.52 (t, J=5.9 Hz, 2H), 3.41-3.34 (m, 1H), 3.34 (s, 3H), 3.25 (ddd, J=13.2, 8.3, 6.5 Hz, 1H), 2.16-1.88 (m, 2H). ESI-MS (m/z): 432.1 [M+H]$^+$.

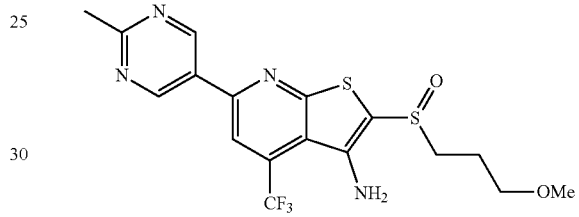

EXAMPLE 11: 2-((3-methoxypropyl)sulfinyl)-6-(2-methylpyrimidin-5-yl)-4-(trifluoromethyl)thieno[2,3-b]pyridin-3-amine was prepared using the synthetic procedures described for the preparation of the analog EXAMPLE 7. $^1$H NMR (400 MHz, Methylene Chloride-$d_2$) δ 9.35 (s, 2H), 8.06 (s, 1H), 5.25 (s, 2H), 3.52 (t, J=5.9 Hz, 2H), 3.42-3.35 (m, 1H), 3.34 (s, 3H), 3.30-3.22 (m, 1H), 2.80 (s, 3H), 2.11-1.90 (m, 2H). ESI-MS (m/z): 431.1 [M+H]$^+$.

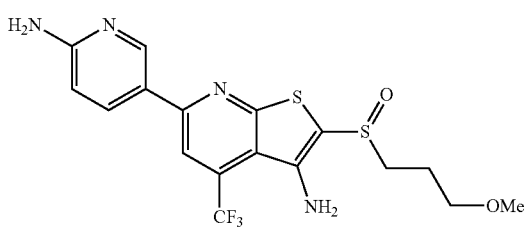 [SMILES: COCCCS(=O)c1sc2nc(-c3ccc(N)nc3)cc(C(F)(F)F)c2c1N]

EXAMPLE 9: 6-(6-aminopyridin-3-yl)-2-((3-methoxypropyl)sulfinyl)-4-(trifluoromethyl)thieno[2,3-b]pyridin-3-amine was prepared using the synthetic procedures described for the preparation of the analog EXAMPLE 7. $^1$H NMR (400 MHz, Methylene Chloride-$d_2$) δ 8.81 (s, 1H), 8.26 (dd, J=8.7, 2.4 Hz, 1H), 7.96 (s, 1H), 6.66 (d, J=9.0 Hz, 1H), 5.18 (s, 2H), 5.03 (s, 2H), 3.52 (t, J=5.9 Hz, 2H), 3.43-3.35 (m, 1H), 3.33 (s, 3H), 3.29-3.18 (m, 1H), 2.05-1.96 (m, 2H). ESI-MS (m/z): 431.1 [M+H]$^+$.

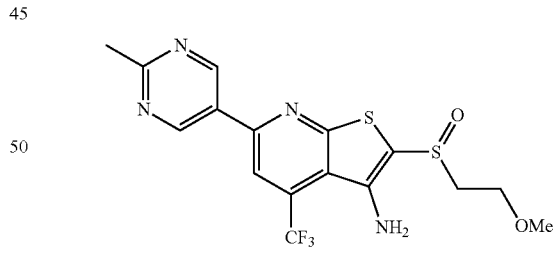

EXAMPLE 12: 2-((2-methoxyethyl)sulfinyl)-6-(2-methylpyrimidin-5-yl)-4-(trifluoromethyl)thieno[2,3-b]pyridin-3-amine was prepared using the synthetic procedures described for the preparation of the analog EXAMPLE 7. $^1$H NMR (400 MHz, Methylene Chloride-$d_2$) δ 9.35 (s, 2H), 8.06 (d, J=1.2 Hz, 1H), 5.20 (s, 2H), 3.87 (ddd, J=9.5, 7.6, 3.4 Hz, 1H), 3.73-3.58 (m, 2H), 3.39 (s, 3H), 3.32 (ddd, J=12.9, 7.6, 3.6 Hz, 1H), 2.81 (s, 3H). ESI-MS (m/z): 417.0 [M+H]$^+$.

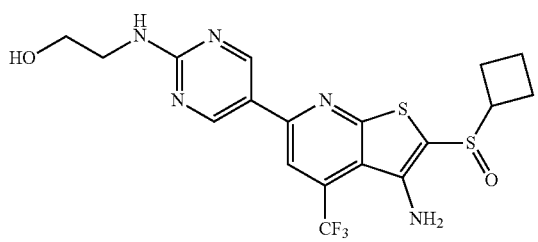 [SMILES: Nc1c(S(=O)C2CCC2)sc2nc(-c3cnc(NCCO)nc3)cc(C(F)(F)F)c12]

EXAMPLE 13: 2-((5-(3-amino-2-(cyclobutylsulfinyl)-4-(trifluoromethyl)thieno[2,3-b]pyridin-6-yl)pyrimidin-2-yl)amino)ethan-1-ol was prepared using the synthetic procedures described for the preparation of the analog EXAMPLE 7. $^1$H NMR (500 MHz, Methylene Chloride-$d_2$) δ 9.06 (s, 2H), 7.92 (s, 1H), 6.03 (s, 1H), 5.17 (s, 2H), 4.06-3.95 (m, 1H), 3.88 (t, J=5.5 Hz, 2H), 3.71 (td, J=5.7, 3.0 Hz, 2H), 2.90-2.77 (m, 1H), 2.50-2.37 (m, 1H), 2.37-2.30 (m, 1H), 2.30-2.22 (m, 1H), 2.17-2.04 (m, 2H). ESI-MS (m/z): 458.1 [M+H]$^+$.

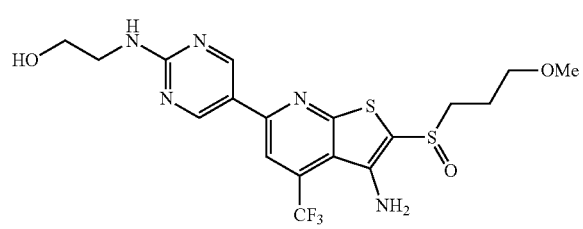 [SMILES: COCCCS(=O)c1sc2nc(-c3cnc(NCCO)nc3)cc(C(F)(F)F)c2c1N]

EXAMPLE 14: 2-((5-(3-amino-2-((3-methoxypropyl)sulfinyl)-4-(trifluoromethyl)thieno[2,3-b]pyridin-6-yl)pyrimidin-2-yl)amino)ethan-1-ol was prepared using the synthetic procedures described for the preparation of the analog EXAMPLE 7. $^1$H NMR (400 MHz, Methylene Chloride-$d_2$) δ 9.03 (s, 2H), 7.89 (s, 1H), 6.01 (s, 1H), 5.19 (s, 2H), 3.95-3.79 (m, 2H), 3.68 (td, J=5.7, 4.4 Hz, 2H), 3.52 (t, J=5.9 Hz, 2H), 3.41-3.31 (m, 1H), 3.33 (s, 3H), 3.24 (ddd, J=13.0, 8.2, 6.5 Hz, 1H), 3.00 (s, 1H), 2.18-1.86 (m, 2H). ESI-MS (m/z): 476.1 [M+H]$^+$.

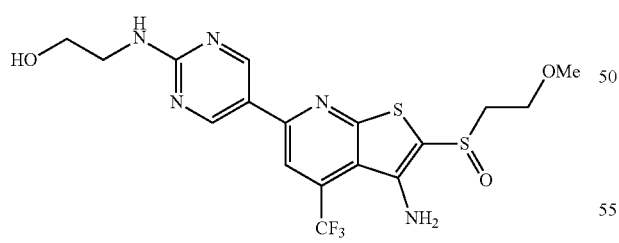

EXAMPLE 15: 2-((5-(3-amino-2-((2-methoxyethyl)sulfinyl)-4-(trifluoromethyl)thieno[2,3-b]pyridin-6-yl)pyrimidin-2-yl)amino)ethan-1-ol was prepared using the synthetic procedures described for the preparation of the analog EXAMPLE 7. $^1$H NMR (400 MHz, Methylene Chloride-$d_2$) δ 9.05 (s, 2H), 7.97 (s, 1H), 6.16 (s, 1H), 5.15 (s, 2H), 3.90-3.78 (m, 3H), 3.73-3.53 (m, 4H), 3.38 (s, 3H), 3.30 (ddd, J=12.1, 7.5, 3.7 Hz, 1H). ESI-MS (m/z): 462.1 [M+H]$^+$.

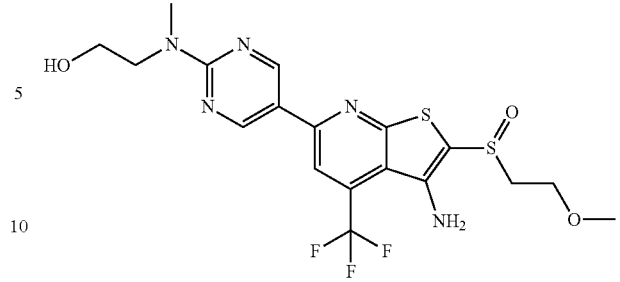

EXAMPLE 16: 2-((5-(3-amino-2-((2-methoxyethyl)sulfinyl)-4-(trifluoromethyl)thieno[2,3-b]pyridin-6-yl)pyrimidin-2-yl)(methyl)amino)ethan-1-ol was prepared using the synthetic procedures described for the preparation of the analog EXAMPLE 7. $^1$H NMR (400 MHz, Methylene Chloride-$d_2$) δ 9.05 (s, 2H), 7.90 (s, 1H), 5.14 (s, 2H), 3.88 (s, 4H), 3.87-3.81 (m, 1H), 3.71-3.56 (m, 2H), 3.38 (s, 3H), 3.32 (s, 3H), 3.31-3.24 (m, 1H). ESI-MS (m/z): 476.1 [M+H]$^+$.

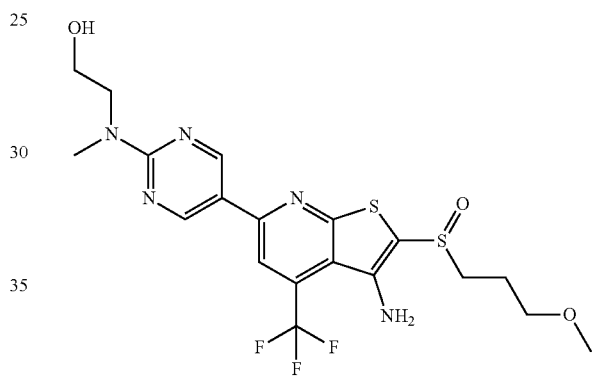

EXAMPLE 17: 2-((5-(3-amino-2-((3-methoxypropyl)sulfinyl)-4-(trifluoromethyl)thieno[2,3-b]pyridin-6-yl)pyrimidin-2-yl)(methyl)amino)ethan-1-ol was prepared using the synthetic procedures described for the preparation of the analog EXAMPLE 7. $^1$H NMR (400 MHz, Methylene Chloride-$d_2$) δ 9.06 (s, 2H), 7.90 (s, 1H), 5.19 (s, 2H), 3.89 (s, 4H), 3.51 (t, J=5.9 Hz, 2H), 3.40-3.34 (m, 1H), 3.33 (s, 3H), 3.32 (s, 3H), 3.24 (ddd, J=13.1, 8.3, 6.6 Hz, 1H), 2.18-1.86 (m, 2H). ESI-MS (m/z): 490.1 [M+H]$^+$.

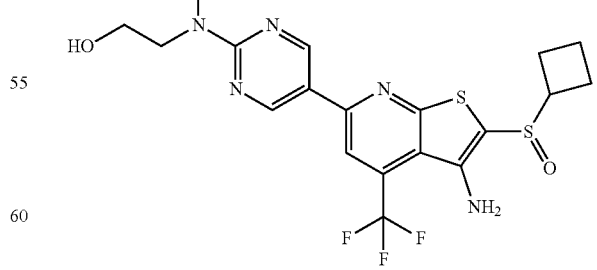

EXAMPLE 18: 2-((5-(3-amino-2-(cyclobutylsulfinyl)-4-(trifluoromethyl)thieno[2,3-b]pyridin-6-yl)pyrimidin-2-yl)(methyl)amino)ethan-1-ol was prepared using the synthetic procedures described for the preparation of the analog EXAMPLE 7. ¹H NMR (400 MHz, Methylene Chloride-d₂) δ 9.04 (s, 2H), 7.89 (s, 1H), 5.13 (s, 2H), 3.97 (p, J=8.1 Hz, 1H), 3.88 (s, 4H), 3.32 (s, 3H), 2.87-2.73 (m, 1H), 2.45-2.35 (m, 1H), 2.35-2.17 (m, 2H), 2.15-1.93 (m, 2H). ESI-MS (m/z): 472.1 [M+H]⁺.

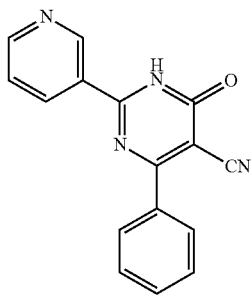

Example 19A: 6-oxo-4-phenyl-2-(pyridin-3-yl)-1,6-dihydropyrimidine-5-carbonitrile. The solution of benzaldehyde (1.00 g, 9.4 mmol), ethyl cyanoacetate (1064 mg, 9.4 mmol) and catalytic amount of piperidine in MeOH (15 mL) was stirred at room temperature overnight. The solvent was evaporated to give the desired product in quantitative yield.

The crude product (3.0 mmol, 603 mg) was dissolved in EtOH (8 mL), nicotinimidamide hydrochloride (1.5 equiv, 4.5 mmol, 706 mg) and potassium carbonate (3.0 equiv, 9 mmol, 1.24 g) were added and the reaction mixture was stirred at 80° C. overnight. Once completed, the reaction mixture was filtered, the obtained solid suspended in water, filtered and dried to give 6-oxo-4-phenyl-2-(pyridin-3-yl)-1,6-dihydropyrimidine-5-carbonitrile (260 mg). ESI-MS (m/z): 275.1 [M+H]+.

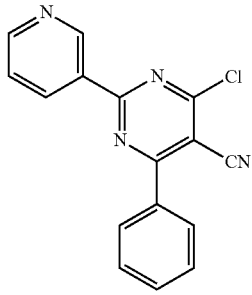 [SMILES: N#Cc1c(Cl)nc(-c2cccnc2)nc1-c1ccccc1]

Example 19B: 4-chloro-6-phenyl-2-(pyridin-3-yl)pyrimidine-5-carbonitrile. The reaction mixture of 6-oxo-4-phenyl-2-(pyridin-3-yl)-1,6-dihydropyrimidine-5-carbonitrile in POCl3 (1 mL) was stirred at 100° C. for 20 min. Once completed (the reaction progress was monitored by LCMS) the reaction mixture was cooled to room temperature and Et2O was added. The formed solid/oil was separated from the liquid, dried and used in the next step without further purification. ESI-MS (m/z): 293.1 [M+H]+.

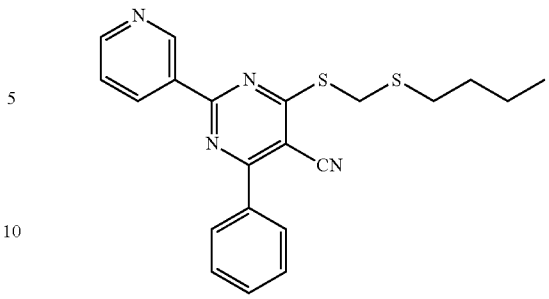

Example 19C: 4-(((butylthio)methyl)thio)-6-phenyl-2-(pyridin-3-yl)pyrimidine-5-carbonitrile. To the crude 4-(((butylthio)methyl)thio)-6-phenyl-2-(pyridin-3-yl)pyrimidine-5-carbonitrile (300 mg, 1.0 mmol) in DMF (1 mL) was added sodium sulfide (85 mg, 1.09 mmol, 1.09 equiv) and the reaction mixture was stirred at 100° C. for 20 min. The progress of the reaction was followed by LCMS. Once complete, conc. HCl was added and the reaction mixture was stirred in the hood for 10 min. ESI-MS (m/z): 291.0 [M+H]+.

The reaction mixture was diluted with CH₃CN (3 mL). Et3N (500 mg, 4.95 mmol) was added followed by butyl (chloromethyl)sulfane (3.0 mmol, 414 mg). The reaction mixture was stirred at room temperature for 15 min. Once complete, the reaction was diluted with EtOAc and water. The organic phase was separated and aqueous layer was extracted twice with EtOAc. The combined extractions were washed with saturated NaCl solution, dried over magnesium sulfate, filtered and concentrated under reduced pressure.

The residue was purified by flash chromatography to give 243 mg of product (62%). ¹H NMR (400 MHz, Chloroform-d) δ 9.83 (s, 1H), 9.43 (d, J=8.8 Hz, 1H), 9.03 (s, 1H), 8.28-8.02 (m, 3H), 7.75-7.47 (m, 3H), 4.53 (s, 2H), 2.76 (t, J=7.4 Hz, 2H), 1.64 (p, J=7.4 Hz, 2H), 1.43 (h, J=7.3 Hz, 2H), 0.92 (t, J=7.4 Hz, 3H). ESI-MS (m/z): 393.1 [M+H]+.

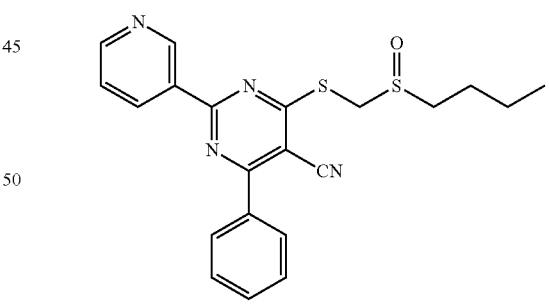

Example 19D: 4-(((butylsulfinyl)methyl)thio)-6-phenyl-2-(pyridin-3-yl)pyrimidine-5-carbonitrile was prepared via standard oxidation with hydrogen peroxide in 98% isolated yield, using synthetic procedures described for the preparation of the analog EXAMPLE 1. ¹H NMR (400 MHz, Chloroform-d) δ 9.76 (s, 1H), 8.86 (d, J=8.1 Hz, ¹H), 8.82 (d, J=6.9 Hz, 1H), 8.19-8.12 (m, 2H), 7.68-7.56 (m, 4H), 4.77 (d, J=13.2 Hz, 1H), 4.59 (d, J=13.3 Hz, 1H), 3.05-2.85 (m, 2H), 1.95-1.74 (m, 2H), 1.64-1.43 (m, 2H), 0.97 (t, J=7.3 Hz, 3H). ESI-MS (m/z): 409.1 [M+H]+.

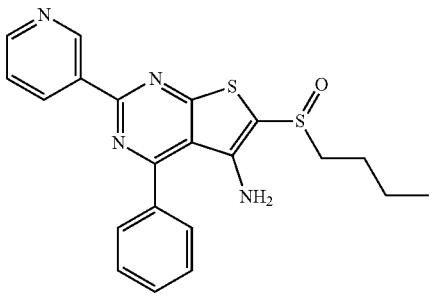 [SMILES: CCCCS(=O)c1sc2nc(-c3cccnc3)nc(-c3ccccc3)c2c1N]

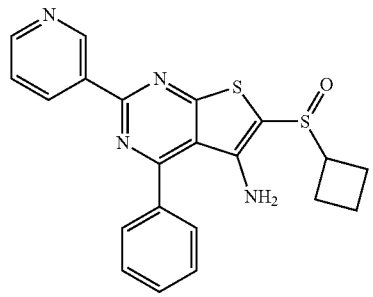

EXAMPLE 19: 6-(butylsulfinyl)-4-phenyl-2-(pyridin-3-yl)thieno[2,3-d]pyrimidin-5-amine. To the solution of 6-(butylsulfinyl)-4-phenyl-2-(pyridin-3-yl)thieno[2,3-d]pyrimidin-5-amine (0.47 mmol, 193 mg) in DMF (3.0 mL) was added KOH (0.35 mmol, 20 mg, 0.75 equiv. in 200 µl of water). The reaction mixture was stirred at r.t. for 20 min (the reaction was monitored by TLC). Once complete, the reaction was diluted with EtOAc and washed with 5% aq. solution of acetic acid. The organic phase was separated and aqueous layer was extracted twice with EtOAc, dried over magnesium sulfate, filtered and concentrated under reduced pressure to give crude product, which was purified by flash chromatography in 48% isolated yield. $^1$H NMR (400 MHz, Methylene Chloride-d2) δ 9.72 (s, 1H), 8.92-8.77 (m, 1H), 8.71 (d, J=4.7 Hz, 1H), 7.85-7.71 (m, 2H), 7.71-7.55 (m, 3H), 7.45 (dd, J=8.0, 4.8 Hz, 1H), 4.83 (s, 2H), 3.28 (ddd, J=12.7, 9.0, 6.1 Hz, 1H), 3.13 (ddd, J=12.8, 9.1, 6.6 Hz, 1H), 1.85-1.59 (m, 2H), 1.59-1.38 (m, 2H), 0.97 (t, J=7.6 Hz, 3H). ESI-MS (m/z): 409.1 [M+H]+.

Enantiomers of EXAMPLE 19 were separated on a 1 cm Chiralpak AD-H column using 75% EtOH and 25% Hexanes with 5 mL/min flow rate, 400 µL injection (concentration 10 mg/ml) the 1st peak was at 5.5 min and the 2nd peak was at 14.7 min.

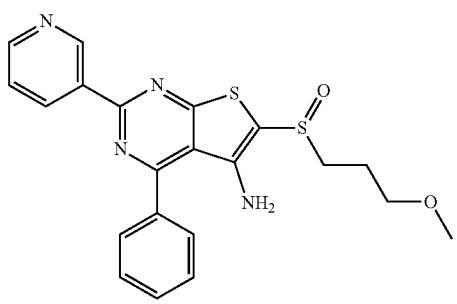 [SMILES: COCCCS(=O)c1sc2nc(-c3cccnc3)nc(-c3ccccc3)c2c1N]

EXAMPLE 20: 6-((3-methoxypropyl)sulfinyl)-4-phenyl-2-(pyridin-3-yl)thieno[2,3-d]pyrimidin-5-amine was prepared using synthetic procedures described for the preparation of the analog EXAMPLE 19. $^1$H NMR (400 MHz, Methylene Chloride-d2) δ 9.72 (dd, J=2.0, 1.0 Hz, 1H), 8.89-8.77 (m, 1H), 8.71 (dd, J=4.7, 1.7 Hz, 1H), 7.83-7.70 (m, 2H), 7.70-7.57 (m, 3H), 7.45 (ddd, J=8.0, 4.8, 1.0 Hz, 1H), 4.83 (s, 2H), 3.50 (t, J=5.9 Hz, 2H), 3.38-3.28 (m, 1H), 3.32 (s, 3H), 3.22 (ddd, J=12.8, 8.1, 6.4 Hz, 1H), 2.09-1.89 (m, 2H). ESI-MS (m/z): 425.1 [M+H]+.

Enantiomers of EXAMPLE 20 were separated on a 1 cm Chiralpak AD-H column using 100% EtOH with 5 m/min flow rate, 500 µL injection (concentration 10 mg/ml) the 1st peak was at 8.34 min and the 2nd peak was at 27.5 min.

EXAMPLE 21: 6-(cyclobutylsulfinyl)-4-phenyl-2-(pyridin-3-yl)thieno[2,3-d]pyrimidin-5-amine was prepared using synthetic procedures described for the preparation of the analog EXAMPLE 19. $^1$H NMR (400 MHz, Methylene Chloride-d2) δ 9.73 (s, 1H), 8.80 (d, J=8.0 Hz, 2H), 7.81-7.67 (m, 2H), 7.69-7.57 (m, 3H), 7.55-7.30 (m, 1H), 4.80 (s, 2H), 3.94 (p, J=8.1 Hz, 1H), 2.89-2.67 (m, 1H), 2.50-2.16 (m, 3H), 2.18-2.01 (m, 2H). ESI-MS (m/z): 407.1 [M+H]+.

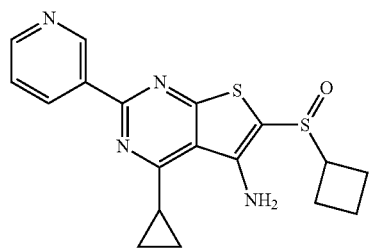 [SMILES: Nc1c(S(=O)C2CCC2)sc2nc(-c3cccnc3)nc(C3CC3)c12]

EXAMPLE 22: 6-(cyclobutylsulfinyl)-4-cyclopropyl-2-(pyridin-3-yl)thieno[2,3-d]pyrimidin-5-amine was prepared using synthetic procedures described for the preparation of the analog EXAMPLE 19. $^1$H NMR (400 MHz, Methylene Chloride-d2) δ 9.70-9.57 (m, 1H), 8.71 (dt, J=8.0, 2.0 Hz, 1H), 8.68 (dd, J=4.9, 1.7 Hz, 1H), 7.47-7.35 (m, 1H), 5.26 (s, 2H), 3.92 (p, J=8.0 Hz, 1H), 2.88-2.73 (m, 1H), 2.68 (tt, J=8.1, 4.7 Hz, 1H), 2.45-2.17 (m, 3H), 2.17-1.99 (m, 2H), 1.64-1.46 (m, 2H), 1.34-1.18 (m, 2H). ESI-MS (m/z): 371.1 [M+H]+.

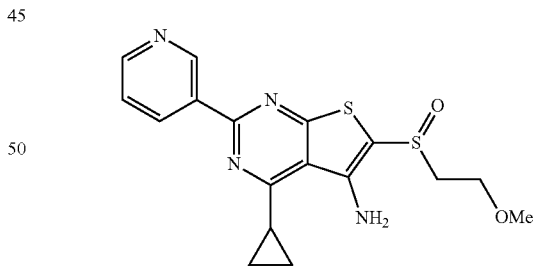

EXAMPLE 23: 4-cyclopropyl-6-((2-methoxyethyl)sulfinyl)-2-(pyridin-3-yl)thieno[2,3-d]pyrimidin-5-amine was prepared using synthetic procedures described for the preparation of the analog EXAMPLE 19. $^1$H NMR (400 MHz, Methylene Chloride-d2) δ 9.63 (dd, J=2.2, 0.9 Hz, 1H), 8.71 (ddd, J=8.0, 2.2, 1.7 Hz, 1H), 8.68 (dd, J=4.8, 1.7 Hz, 1H), 7.42 (ddd, J=8.0, 4.8, 0.9 Hz, 1H), 5.25 (s, 2H), 3.86 (ddd, J=10.5, 7.6, 4.0 Hz, 1H), 3.68 (ddd, J=10.5, 6.3, 4.3 Hz, 1H), 3.58 (ddd, J=13.0, 6.3, 4.0 Hz, 1H), 3.39 (s, 3H), 3.27 (ddd, J=13.1, 7.5, 4.3 Hz, 1H), 2.66 (tt, J=8.0, 4.7 Hz, 1H), 1.59-1.54 (m, 2H), 1.30-1.25 (m, 2H). ESI-MS (m/z): 375.1 [M+H]+.

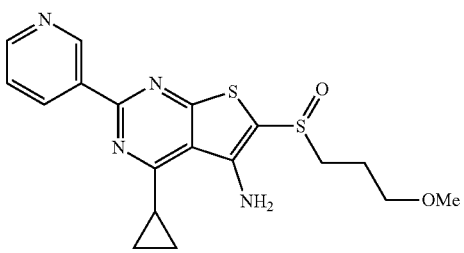 [SMILES: COCCCS(=O)c1sc2nc(-c3cccnc3)nc(C3CC3)c2c1N]

EXAMPLE 24: 4-cyclopropyl-6-((3-methoxypropyl)sulfinyl)-2-(pyridin-3-yl)thieno[2,3-d]pyrimidin-5-amine was prepared using synthetic procedures described for the preparation of the analog EXAMPLE 19. $^1$H NMR (400 MHz, Methylene Chloride-d2) δ 9.63 (dd, J=2.2, 0.9 Hz, 1H), 8.71 (ddd, J=8.0, 2.2, 1.7 Hz, 1H), 8.68 (dd, J=4.8, 1.7 Hz, 1H), 7.41 (ddd, J=8.0, 4.8, 0.9 Hz, 1H), 5.30 (s, 2H), 3.52 (t, J=5.9 Hz, 2H), 3.37-3.28 (m, 1H), 3.34 (s, 3H), 3.22 (ddd, J=13.0, 8.3, 6.4 Hz, 1H), 2.67 (tt, J=8.0, 4.7 Hz, 1H), 2.11-1.91 (m, 2H), 1.60-1.47 (m, 2H), 1.30-1.22 (m, 2H). ESI-MS (m/z): 389.1 [M+H]+.

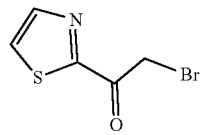

Example 25A: 2-bromo-1-(thiazol-2-yl)ethan-1-one. n-BuLi (24.7 mL, 61.7 mmol, 2.5 M in Hexane) was added dropwise to a solution of 2-thiazole (5.0 g, 59 mmol) in anhydrous diethyl ether (50 mL) at −78° C. After 15 minutes, ethylbromoacetate (6.84 mL, 61.7 mmol) was added, the cold bath was removed and the solution was allowed to warm to room temperature. The reaction mixture was treated with AcOH (7 mL) and then diluted with water (100 mL) and ether (60 mL). The organic layer was separated, dried over Na2SO4, filtered and concentrated under reduced pressure. The crude product was suspended in hexanes and heated to reflux for 15 minutes then the product was decanted off leaving the impure oil. This was repeated 5 times to give a white solid with 88% yield. $^1$H NMR (400 MHz, CDCl3) δ 8.05 (d, J=3.0 Hz, 1H), 7.77 (d, J=3.0 Hz, 1H), 4.71 (s, 2H).

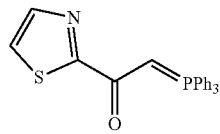

Example 25B: 1-(thiazol-2-yl)-2-(triphenyl-γ5-phosphanylidene)ethan-1-one. To a solution of 2-bromo-1-(thiazol-2-yl)ethan-1-one (10.7 g, 0.0517 mol) in toluene (337.7 mL), triphenylphosphine (14.1 g, 0.0539 mol) was added portion wise. The mixture was stirred at room temperature for 3 hours. The yellowish precipitate was removed by filtration, and was washed several times with toluene and then petroleum ether. Water was added to the precipitate and was treated dropwise with 1N NaOH to pH 10 (at pH 7 there was a color change from yellow to orange). The mixture was stirred for 30 minutes at room temperature. The precipitate was removed by filtration and washed several times with water. The resulting orange solid, was heated at 50° C. under vacuum to remove any water, to give dry product in 96% yield. $^1$H NMR (400 MHz, CDCl3) δ 7.82 (d, J=3.1 Hz, 1H), 7.72 (ddd, J=12.8, 8.3, 1.4 Hz, 6H), 7.61-7.54 (m, 3H), 7.51-7.45 (m, 6H), 7.38 (dd, J=3.1, 1.3 Hz, 1H), 5.00 (d, J=23.3 Hz, 1H). ESI-MS (m/z): 387.9 [M+H]+.

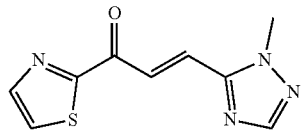

Example 25C: (E)-3-(1-methyl-1H-1,2,4-triazol-5-yl)-1-(thiazol-2-yl)prop-2-en-1-one To a solution of 1,5-dimethyl-1H-imidazole-2-carbaldehyde (2.25 mmol, 250 mg) in 5 ml of CH$_3$CN was added 1-(thiazol-2-yl)-2-(triphenyl-γ5-phosphanylidene)ethan-1-one (2.25 mmol, 871.6 mg, 1.0 equiv.). The reaction mixture was stirred at 90° C. for 48 h. Once complete, solvent was evaporated and residue was purified by flash chromatography to give 306 mg of product $^1$H NMR (400 MHz, Chloroform-d) δ 8.39 (d, J=15.5 Hz, 1H), 8.09 (d, J=3.0 Hz, 1H), 7.97 (s, 1H), 7.82 (d, J=15.6 Hz, 1H), 7.75 (d, J=3.0 Hz, 1H), 4.05 (s, 3H). ESI-MS (m/z): 221.0 [M+H]+.

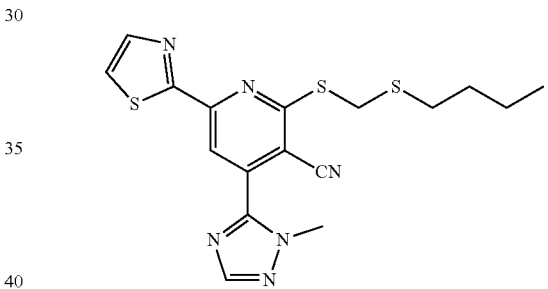

Example 25D: 2-(((butylthio)methyl)thio)-4-(1-methyl-1H-1,2,4-triazol-5-yl)-6-(thiazol-2-yl)nicotinonitrile. To a suspension of (E)-3-(1-methyl-1H-1,2,4-triazol-5-yl)-1-(thiazol-2-yl)prop-2-en-1-one (0.45 mmol, 100 mg) and 2-cyanothioacetamide (1.35 mmol, 135 mg, 3.0 equiv.) in EtOH (1.5 mL) 3 drops of piperidine were added. After being stirred at 80° C. for 2 h, EtOH was evaporated and crude product was redissolved in 2 mL of CH$_3$CN. Butyl(chloromethyl)sulfane (1.30 mmol, 180 mg, 3.0 equiv.) and Et3N (1.30 mmol, 131 mg, 181 µL) were then added and the reaction mixture was stirred at 80° C. for 20 min. Once complete, the reaction was diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 119 mg of the mixture of desired product ESI-MS (m/z): 403.6 [M+H]+ and des CN byproduct: ESI-MS (m/z): 378.1 [M+H]+.

$^1$H NMR (400 MHz, Chloroform-d) δ 8.09 (s, 1H), 8.08 (s, 1H), 8.00 (d, J=3.1 Hz, 1H), 7.61 (d, J=3.1 Hz, 1H), 4.52 (s, 2H), 4.01 (s, 3H), 275 (t, J=7.2 Hz, 2H), 1.69-1.58 (m, 2H), 1.47-1.33 (m, 2H), 0.91 (t, J=7.3 Hz, 3H). ESI-MS (m/z): 403.6 [M+H]+

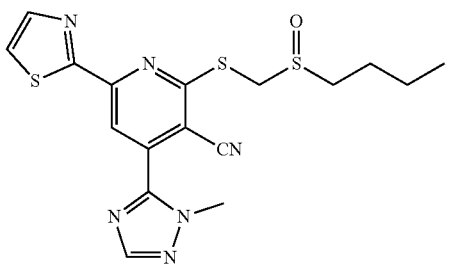 [SMILES: CCCCS(=O)CSc1nc(-c2nccs2)cc(-c2ncnn2C)c1C#N]

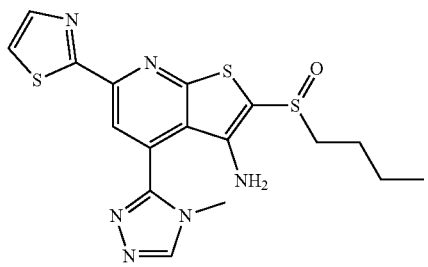

Example 25E: 2-(((butylsulfinyl)methyl)thio)-4-(1-methyl-1H-1,2,4-triazol-5-yl)-6-(thiazol-2-yl)nicotinonitrile. To the solution of the product from the previous step (119 mg) in CHCl$_3$/AcOH (1:1, 0.15 M) was added H$_2$O$_2$ (68 μL, 30% solution in water). The reaction mixture was stirred at 32° C. for 40 min. Once complete, the reaction was diluted with EtOAc and was washed with saturated NaHCO$_3$ solution, dried over magnesium sulfate, filtered and concentrated under reduce pressure to give 89 mg of desired compound and des CN desired compound. $^1$H NMR (400 MHz, Chloroform-d) δ 8.17 (s, 1H), 8.07 (s, 1H), 8.00 (d, J=3.1 Hz, 1H), 7.64 (d, J=3.1 Hz, 1H), 4.69 (d, J=13.2 Hz, 1H), 4.45 (d, J=13.2 Hz, 1H), 4.03 (s, 3H), 3.02-2.88 (m, 1H), 2.88-2.77 (m, 1H), 1.88-1.77 (m, 2H), 1.54-1.41 (m, 2H), 0.95 (t, J=7.3 Hz, 3H). ESI-MS (m/z): 419.0 [M+H]+.

EXAMPLE 26: 2-(butylsulfinyl)-4-(4-methyl-4H-1,2,4-triazol-3-yl)-6-(thiazol-2-yl)thieno[2,3-b]pyridin-3-amine was prepared in 12% isolated yield via standard cyclization reaction with potassium hydroxide, using the synthetic procedures described for the preparation of the analog EXAMPLE 25. $^1$H NMR (400 MHz, Methylene Chloride-d2) δ 8.38 (s, 1H), 8.23 (s, 1H), 7.97 (d, J=3.2 Hz, 1H), 7.60 (d, J=3.1 Hz, 1H), 5.63 (s, 2H), 3.80 (s, 3H), 3.26 (ddd, J=12.9, 9.1, 6.2 Hz, 1H), 3.12 (ddd, J=12.8, 9.1, 6.6 Hz, 1H), 1.89-1.66 (m, 2H), 1.57-1.42 (m, 2H), 0.95 (t, J=7.4 Hz, 3H). ESI-MS (m/z): 419.1 [M+H]+.

Enantiomers of EXAMPLE 26 were separated on a 2 cm Chiralcel OD-H column using 100% EtOH with 10 mL/min flow rate, 600 μL injection (concentration 10 mg/ml) the 1st peak was at 15.0 min and the 2nd peak was at 21.0 min.

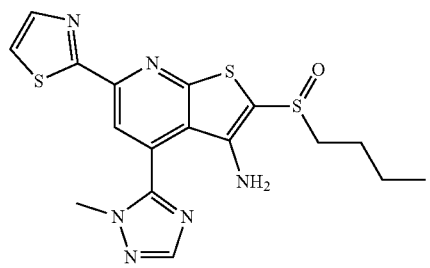 [SMILES: CCCCS(=O)c1sc2nc(-c3nccs3)cc(-c3ncnn3C)c2c1N]

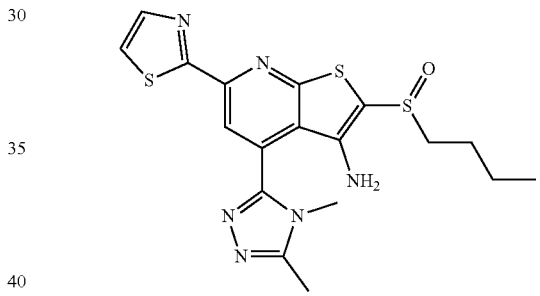

EXAMPLE 25: 2-(butylsulfinyl)-4-(1-methyl-1H-1,2,4-triazol-5-yl)-6-(thiazol-2-yl)thieno[2,3-b]pyridin-3-amine. To the solution of 2-(((butylsulfinyl)methyl)thio)-4-(1-methyl-1H-1,2,4-triazol-5-yl)-6-(thiazol-2-yl)nicotinonitrile (43 mg) in DMF (700 μl)/MeOH (350 μl) was added KOH (0.06 mmol, 3.4 mg, 1.8 M in water). The reaction mixture was stirred at 32° C. for 10 min. Once complete, the reaction was diluted with EtOAc and acidified to pH 7 with 5% aq. solution of AcOH, the organic phase was separated and aqueous layer was extracted twice with EtOAc, dried over magnesium sulfate, filtered and concentrated under reduced pressure. The crude product was purified by flash chromatography to give desired product. $^1$H NMR (400 MHz, Methylene Chloride-d2) δ 8.26 (s, 1H), 8.09 (s, 1H), 7.97 (d, J=3.1 Hz, 1H), 7.60 (d, J=3.1 Hz, 1H), 5.67 (s, 2H), 4.03 (s, 3H), 3.26 (ddd, J=12.7, 9.0, 6.2 Hz, 1H), 3.12 (ddd, J=12.8, 9.0, 6.6 Hz, 1H), 1.86-1.67 (m, 2H), 1.57-1.39 (m, 2H), 0.95 (t, J=7.3 Hz, 3H). EST-MS (m/z): 419.1 [M+H]+.

EXAMPLE 27: 2-(butylsulfinyl)-4-(4,5-dimethyl-4H-1,2,4-triazol-3-yl)-6-(thiazol-2-yl)thieno[2,3-b]pyridin-3-amine was prepared in 12% isolated yield via standard cyclization reaction with potassium hydroxide, using the synthetic procedures described for the preparation of the analog EXAMPLE 25. $^1$H NMR (400 MHz, Methylene Chloride-d2) δ 8.18 (s, 1H), 7.96 (d, J=3.1 Hz, 1H), 7.59 (d, J=3.2 Hz, 1H), 5.71 (s, 2H), 3.65 (s, 3H), 3.26 (ddd, J=12.8, 9.1, 6.1 Hz, 1H), 3.11 (ddd, J=12.8, 9.2, 6.5 Hz, 1H), 2.57 (s, 3H), 1.84-1.66 (m, 2H), 1.56-1.40 (m, 2H), 0.95 (t, J=7.3 Hz, 3H). ESI-MS (m/z): 433.1 [M+H]+.

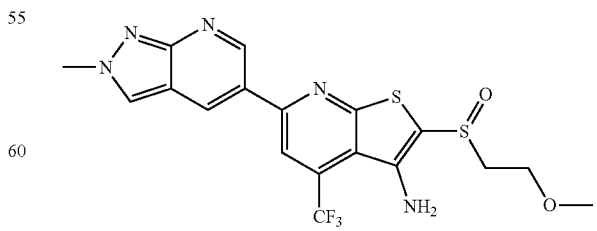

EXAMPLE 28: 2-((2-methoxyethyl)sulfinyl)-6-(2-methyl-2H-pyrazolo[3,4-b]pyridin-5-yl)-4-(trifluoromethyl)thieno[2,3-b]pyridin-3-amine was prepared using the synthetic procedures described for the preparation of EXAMPLE 7. ¹H NMR (400 MHz, Methylene Chloride-d₂) δ 9.43 (d, J=2.4 Hz, 1H), 8.83 (d, J=2.4 Hz, 1H), 8.14 (s, 1H), 8.11 (s, 1H), 5.18 (s, 2H), 4.29 (s, 3H), 3.87 (ddd, J=9.7, 7.5, 3.5 Hz, 1H), 3.74-3.56 (m, 2H), 3.39 (s, 3H), 3.32 (ddd, J=13.0, 7.6, 3.7 Hz, 1H). ESI-MS (m/z): 456.2 [M+H]⁺.

Enantiomers of EXAMPLE 28 were separated on a 2 cm Chiralpak AD-H column using Hexanes 20% and EtOH 80% with 10 m/min flow rate, 600 µL injection (concentration 10 mg/ml). The 1st peak was at 13.0 min and the 2nd peak was at 20.0 min.

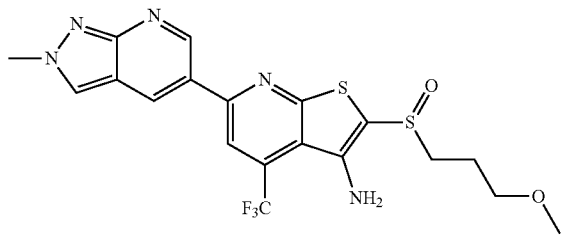

EXAMPLE 29: 2-((3-methoxypropyl)sulfinyl)-6-(2-methyl-2H-pyrazolo[3,4-b]pyridin-5-yl)-4-(trifluoromethyl)thieno[2,3-b]pyridin-3-amine was prepared using the synthetic procedures described for the preparation of EXAMPLE 7. ¹H NMR (400 MHz, Methylene Chloride-d₂) δ 9.43 (d, J=2.3 Hz, 1H), 8.83 (d, J=2.3 Hz, 1H), 8.14 (s, 1H), 8.11 (s, 1H), 5.23 (s, 2H), 4.29 (s, 3H), 3.53 (t, J=5.9 Hz, 2H), 3.43-3.35 (m, 1H), 3.34 (s, 3H), 3.26 (ddd, J=13.0, 8.3, 6.5 Hz, 1H), 2.11-1.96 (m, 2H). ESI-MS (m/z): 470.2 [M+H]⁺.

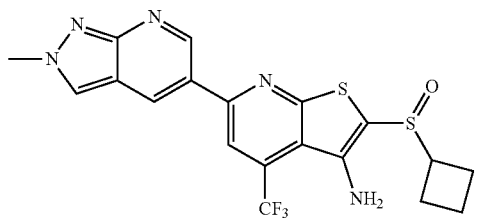 [SMILES: Cn1cc2cc(-c3cc(C(F)(F)F)c4c(N)c(S(=O)C5CCC5)sc4n3)cnc2n1]

EXAMPLE 30: 2-(cyclobutylsulfinyl)-6-(2-methyl-2H-pyrazolo[3,4-b]pyridin-5-yl)-4-(trifluoromethyl)thieno[2,3-b]pyridin-3-amine was prepared using the synthetic procedures described for the preparation of EXAMPLE 7. ¹H NMR (400 MHz, Methylene Chloride-d₂) δ 9.42 (d, J=2.3 Hz, 1H), 8.81 (d, J=2.3 Hz, 1H), 8.12 (s, 1H), 8.11 (s, 1H), 5.17 (s, 2H), 4.29 (s, 3H), 4.05-3.91 (m, 1H), 2.89-2.72 (m, 1H), 2.47-2.36 (m, 1H), 2.36-2.20 (m, 2H), 2.16-2.03 (m, 2H). ESI-MS (m/z): 452.1 [M+H]⁺.

Enantiomers of EXAMPLE 30 were separated on a 2 cm Chiralcel OD-H column using 40% Hexanes and 60% EtOH with 10 mL/min flow rate, 600 µL injection (concentration 10 mg/ml) the 1st peak was at 17.5 min and the 2nd peak was at 23.0 min.

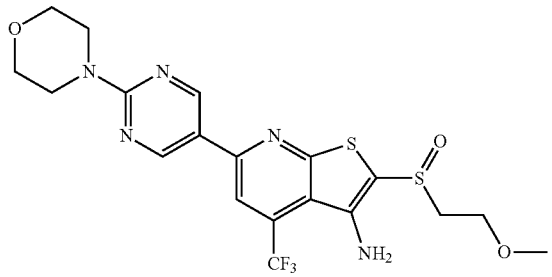 [SMILES: COCCS(=O)c1sc2nc(-c3cnc(N4CCOCC4)nc3)cc(C(F)(F)F)c2c1N]

EXAMPLE 31: 2-((2-methoxyethyl)sulfinyl)-6-(2-morpholinopyrimidin-5-yl)-4-(trifluoromethyl)thieno[2,3-b]pyridin-3-amine was prepared using the synthetic procedures described for the preparation of EXAMPLE 7. ¹H NMR (400 MHz, Methylene Chloride-d₂) δ 9.08 (s, 2H), 7.92 (s, 1H), 5.15 (s, 2H), 3.97-3.90 (m, 4H), 3.86 (ddd, J=9.8, 7.6, 3.7 Hz, 1H), 3.81-3.72 (m, 4H), 3.71-3.57 (m, 2H), 3.38 (s, 3H), 3.29 (ddd, J=12.9, 7.6, 3.9 Hz, 1H). ESI-MS (m/z): 488.2 [M+H]⁺.

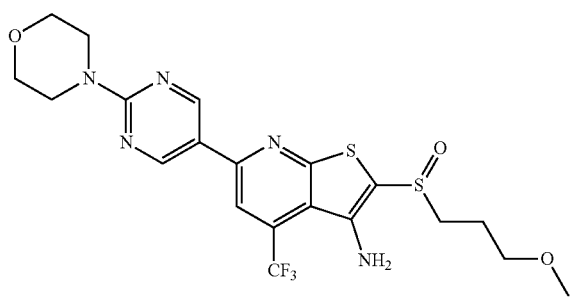 [SMILES: COCCCS(=O)c1sc2nc(-c3cnc(N4CCOCC4)nc3)cc(C(F)(F)F)c2c1N]

EXAMPLE 32: 2-((3-methoxypropyl)sulfinyl)-6-(2-morpholinopyrimidin-5-yl)-4-(trifluoromethyl)thieno[2,3-b]pyridin-3-amine was prepared using the synthetic procedures described for the preparation of EXAMPLE 7. ¹H NMR (400 MHz, Methylene Chloride-d₂) δ 9.08 (s, 2H), 7.92 (s, 1H), 5.19 (s, 2H), 4.00-3.89 (m, 4H), 3.82-3.71 (m, 4H), 3.51 (t, J=5.9 Hz, 2H), 3.41-3.29 (m, 1H), 3.33 (s, 3H), 3.24 (ddd, J=13.0, 8.2, 6.5 Hz, 1H), 2.10-1.95 (m, 2H). ESI-MS (m/z): 502.1 [M+H]⁺.

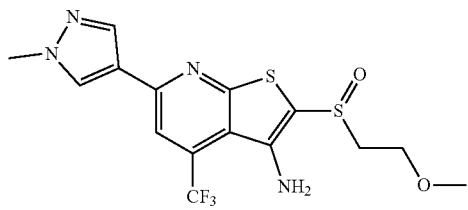

EXAMPLE 33: 2-((2-methoxyethyl)sulfinyl)-6-(1-methyl-1H-pyrazol-4-yl)-4-(trifluoromethyl)thieno[2,3-b]pyridin-3-amine was prepared using the synthetic procedures described for the preparation of EXAMPLE 7. ¹H NMR (400 MHz, Methylene Chloride-d₂) δ 8.09 (s, 1H), 8.05 (d, J=0.8 Hz, 1H), 7.74 (d, J=0.8 Hz, 1H), 5.11 (s, 2H), 3.97 (s, 3H), 3.90-3.80 (m, 1H), 3.71-3.54 (m, 2H), 3.38 (s, 3H), 3.35-3.22 (m, 1H). ESI-MS (m/z): 405.1 [M+H]⁺.

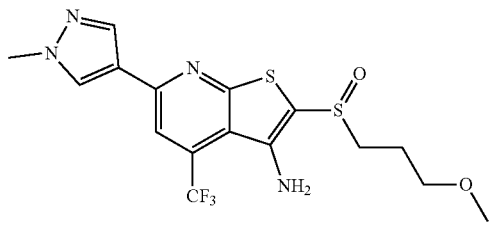

EXAMPLE 34: 2-((3-methoxypropyl)sulfinyl)-6-(1-methyl-1H-pyrazol-4-yl)-4-(trifluoromethyl)thieno[2,3-b]pyridin-3-amine was prepared using the synthetic procedures described for the preparation of EXAMPLE 7. $^{1}$H NMR (400 MHz, Methylene Chloride-d$_2$) δ 8.08 (s, 1H), 8.05 (d, J=0.8 Hz, 1H), 7.74 (d, J=0.8 Hz, 1H), 5.15 (s, 2H), 3.97 (s, 3H), 3.51 (t, J=5.9 Hz, 2H), 3.41-3.29 (m, 1H), 3.33 (s, 3H), 3.22 (ddd, J=13.0, 8.1, 6.7 Hz, 1H), 2.11-1.93 (m, 2H). ESI-MS (m/z): 419.1 [M+H]$^+$.

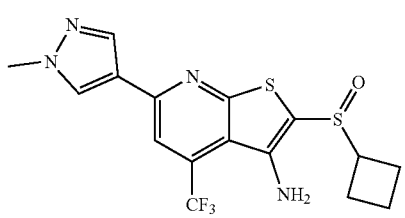 [SMILES: Cn1cc(-c2cc(C(F)(F)F)c3c(N)c(S(=O)C4CCC4)sc3n2)cn1]

EXAMPLE 35: 2-(cyclobutylsulfinyl)-6-(1-methyl-1H-pyrazol-4-yl)-4-(trifluoromethyl)thieno[2,3-b]pyridin-3-amine was prepared using the synthetic procedures described for the preparation of EXAMPLE 7. $^{1}$H NMR (400 MHz, Methylene Chloride-d$_2$) δ 8.07 (s, 1H), 8.04 (s, 1H), 7.73 (s, 1H), 5.10 (s, 2H), 4.06-3.88 (m, 1H), 3.97 (s, 3H), 2.89-2.67 (m, 1H), 2.47-2.15 (m, 3H), 2.15-1.94 (m, 2H). ESI-MS (m/z): 401.1 [M+H]$^+$.

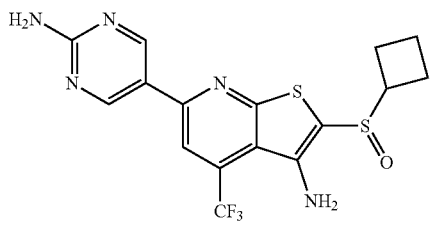 [SMILES: Nc1ncc(-c2cc(C(F)(F)F)c3c(N)c(S(=O)C4CCC4)sc3n2)cn1]

EXAMPLE 36: 6-(2-aminopyrimidin-5-yl)-2-(cyclobutylsulfinyl)-4-(trifluoromethyl)thieno[2,3-b]pyridin-3-amine was prepared using the synthetic procedures described for the preparation of EXAMPLE 7. $^{1}$H NMR (400 MHz, Methylene Chloride-d$_2$) δ 9.05 (s, 2H), 7.92 (s, 1H), 5.40 (s, 2H), 5.15 (s, 2H), 3.97 (p, J=8.0 Hz, 1H), 2.87-2.68 (m, 1H), 2.51-2.35 (m, 1H), 2.35-2.14 (m, 2H), 2.14-1.92 (m, 2H). ESI-MS (m/z): 414.1 [M+H]$^+$.

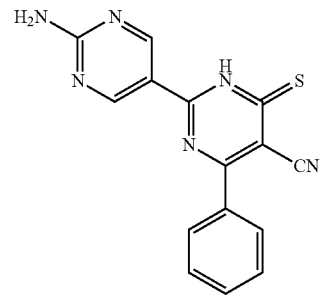

EXAMPLE 37A: 2-(4-aminophenyl)-4-phenyl-6-thioxo-1,6-dihydropyrimidine-5-carbonitrile. A mixture of NaOiPr (1.75 mmol, 1.0 equiv, prepared in situ from sodium and dry iPrOH), 2-aminopyrimidine-5-carbothioamide (1.75 mmol, 270 mg, 1.0 equiv) and 2-(mehoxy(phenyl)methylene)malononitrile (1.75 mmol, 322 mg, 1.0 equiv) in iPrOH (30 mL) was stirred for overnight at r.t. The reaction was acidified with con. HCl and then evaporated to give crude product as a solid (380 mg). ESI-MS (m/z): 307.1 [M+H]$^+$.

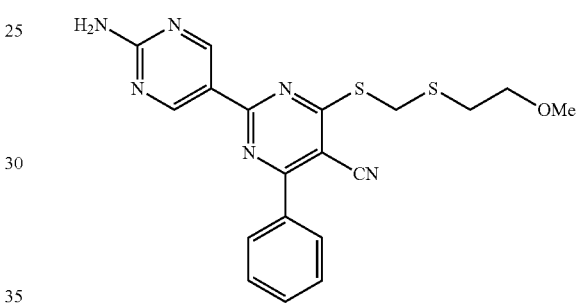

EXAMPLE 37B: 2-(4-aminophenyl)-6-((((2-methoxyethyl)thio)methyl)thio)-4-phenyl-1,6-dihydropyrimidine-5-carbonitrile. A mixture of 2-(4-aminophenyl)-6-mercapto-4-phenyl-1,6-dihydropyrimidine-5-carbonitrile (0.33 mmol, 100 mg), (chloromethyl)(2-methoxyethyl)sulfane (0.36 mmol, 50 mg, 1.1 equiv) and Et$_3$N (0.98 mmol, 140 μl, 3.0 equiv) was stirred in dry CH$_3$CN (3 mL) for 20 min at room temperature. The reaction mixture was then diluted with EtOAc and water. The organic phase was separated and aqueous layer, dried over magnesium sulfate, filtered and concentrated under reduced pressure. The residue was purified by flash chromatography to give 37 mg of desired product. $^{1}$H NMR (400 MHz, Chloroform-d) δ 9.42 (s, 2H), 8.25-7.94 (m, 2H), 7.81-7.48 (m, 3H), 5.72 (s, 2H), 4.61 (s, 2H), 3.69 (t, J=6.0 Hz, 2H), 3.39 (s, 3H), 2.92 (t, J=6.0 Hz, 2H). ESI-MS (m/z): 411.0 [M+H]$^+$.

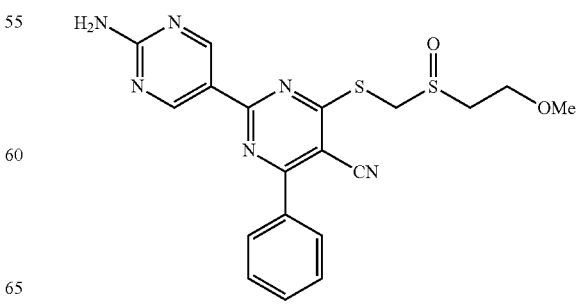

EXAMPLE 37C: 2-(4-aminophenyl)-6-((((2-methoxyethyl)sulfinyl)methyl)thio)-4-phenyl-1,6-dihydropyrimidine-5-carbonitrile To the solution of 2-(4-aminophenyl)-6-((((2-methoxyethyl)thio)methyl)thio)-4-phenyl-1,6-dihydropyrimidine-5-carbonitrile (30 mg, 0.073 mmol) in CHCl$_3$ (135 µl) and AcOH (135 µl) was added H$_2$O$_2$ (17 µL, 30% solution in water). The reaction mixture was stirred at 32° C. for 40 min. Once complete, the reaction was diluted with EtOAc and was washed with saturated NaHCO$_3$ solution, dried over magnesium sulfate, filtered and concentrated under reduce pressure to give 18 mg of desired compound. EST-MS (m/z): 427.0 [M+H]$^+$.

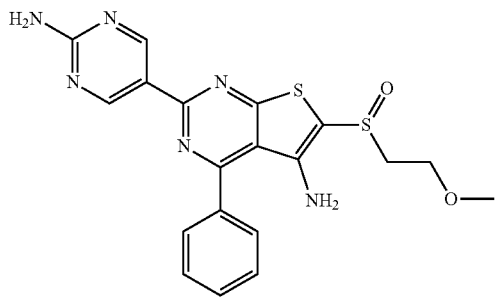

EXAMPLE 37: 2-(2-aminopyrimidin-5-yl)-6-((2-methoxyethyl)sulfinyl)-4-phenylthieno[2,3-d]pyrimidin-5-amine was prepared using the KOH cyclization procedure described for the preparation of the analog EXAMPLE 19. $^1$H NMR (400 MHz, Methylene Chloride-d$_2$) δ 9.37 (s, 2H), 7.81-7.68 (m, 2H), 7.68-7.56 (m, 3H), 5.46 (s, 2H), 4.75 (s, 2H), 3.83 (ddd, J=11.0, 7.6, 4.0 Hz, 1H), 3.66 (ddd, J=10.6, 6.3, 4.3 Hz, 1H), 3.56 (ddd, J=13.1, 6.2, 4.0 Hz, 1H), 3.36 (s, 3H), 3.26 (ddd, J=13.2, 7.6, 4.3 Hz, 1H). ESI-MS (m/z): 427.1 [M+H]$^+$.

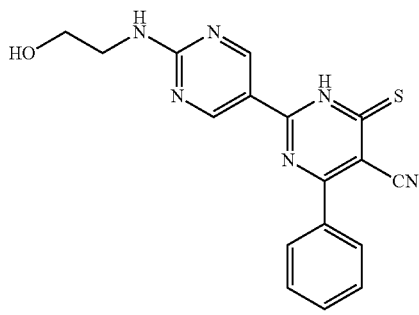

EXAMPLE 38A: 2'-((2-hydroxyethyl)amino)-4-phenyl-6-thioxo-1,6-dihydro-[2,5'-bipyrimidine]-5-carbonitrile was prepared from 2-((2-hydroxyethyl)amino)pyrimidine-5-carbothioamide and 2-(mehoxy(phenyl)methylene)malononitrile, using the procedure described for the preparation of the analog EXAMPLE 37. ESI-MS (m/z): 351.1 [M+H]$^+$.

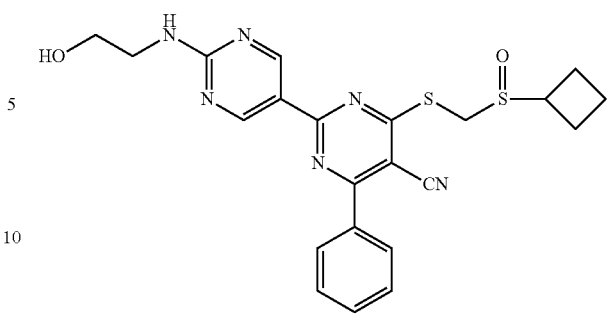

EXAMPLE 38B: 4-(((cyclobutylsulfinyl)methyl)thio)-2'-((2-hydroxyethyl)amino)-6-phenyl-[2,5'-bipyrimidine]-5-carbonitrile. A mixture of 2'-((2-hydroxyethyl)amino)-4-phenyl-6-thioxo-1,6-dihydro-[2,5'-bipyrimidine]-5-carbonitrile (0.11 mmol, 40 mg), ((chloromethyl)sulfinyl)cyclobutane (0.42 mmol, 21 mg, 1.2 equiv) and Et$_3$N (0.98 mmol, 46 µl, 3.0 equiv) was stirred in dry CH$_3$CN (3 mL) for 2 h at 80° C. The reaction mixture was then diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 26 mg of desired product. $^1$H NMR (400 MHz, Chloroform-d) δ 12.04 (s, 1H), 9.44 (s, 2H), 8.21-7.92 (m, 2H), 7.80-7.42 (m, 3H), 4.66 (d, J=13.3 Hz, 1H), 4.06 (d, J=13.0 Hz, 1H), 3.94-3.82 (m, 2H), 3.82-3.66 (m, 3H), 2.90-2.70 (m, 1H), 2.57-2.38 (m, 1H), 2.33-2.02 (m, 4H). ESI-MS (m/z): 467.1 [M+H]$^+$.

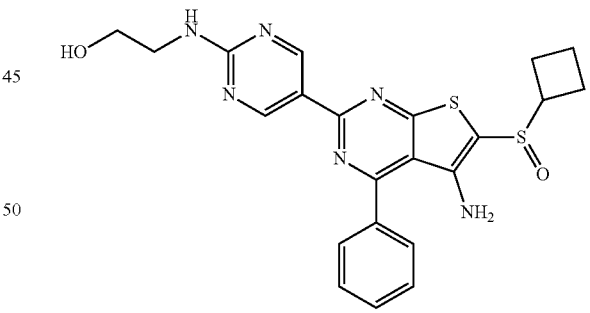

EXAMPLE 38: 2-((5-(5-amino-6-(cyclobutylsulfinyl)-4-phenylthieno[2,3-d]pyrimidin-2-yl)pyrimidin-2-yl)amino)ethan-1-ol was prepared using the KOH cyclization procedure described for the preparation of the analog EXAMPLE 19. $^1$H NMR (400 MHz, Methylene Chloride-d$_2$) δ 9.31 (s, 2H), 7.76-7.66 (m, 2H), 7.66-7.56 (m, 3H), 5.98 (t, J=6.1 Hz, 1H), 4.74 (s, 2H), 4.00-3.78 (m, 3H), 3.78-3.56 (m, 2H), 2.86-2.64 (m, 1H), 2.44-1.89 (m, 5H)). ESI-MS (m/z): 467.1 [M+H]$^+$.

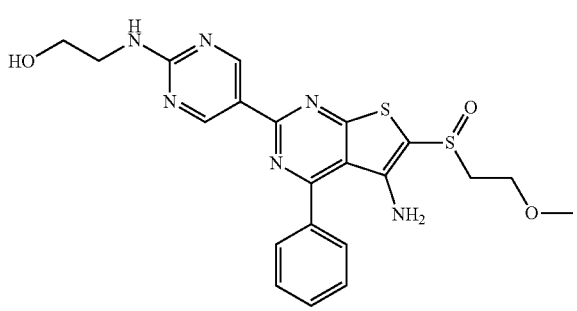 [SMILES: COCCS(=O)c1sc2nc(-c3cnc(NCCO)nc3)nc(-c3ccccc3)c2c1N]

EXAMPLE 39: 2-((5-(5-amino-6-((2-methoxyethyl)sulfinyl)-4-phenylthieno[2,3-d]pyrimidin-2-yl)pyrimidin-2-yl)amino)ethan-1-ol was prepared using the synthetic procedures described for the preparation of EXAMPLE 38. $^1$H NMR (400 MHz, Methylene Chloride-d$_2$) δ 9.32 (s, 2H), 7.75-7.68 (m, 2H), 7.66-7.58 (m, 3H), 6.06 (t, J=6.3 Hz, 1H), 4.74 (s, 2H), 3.91-3.77 (m, 3H), 3.73-3.59 (m, 3H), 3.54 (ddd, J=13.0, 6.1, 4.0 Hz, 1H), 3.36 (s, 3H), 3.24 (ddd, J=13.0, 7.7, 4.3 Hz, 1H). ESI-MS (m/z): 471.1 [M+H]$^+$.

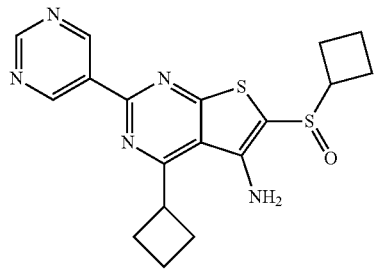 [SMILES: Nc1c(S(=O)C2CCC2)sc2nc(-c3cncnc3)nc(C3CCC3)c12]

EXAMPLE 40: 4-cyclobutyl-6-(cyclobutylsulfinyl)-2-(pyrimidin-5-yl)thieno[2,3-d]pyrimidin-5-amine was prepared using synthetic procedures described for the preparation of EXAMPLE 19. $^1$H NMR (400 MHz, Methylene Chloride-d$_2$) δ 9.82 (s, 2H), 9.29 (s, 1H), 5.17 (s, 2H), 4.25 (p, J=8.2 Hz, 1H), 3.92 (p, J=8.1 Hz, 1H), 2.91-2.71 (m, 2H), 2.57-2.41 (m, 2H), 2.42-1.91 (m, 8H). ESI-MS (m/z): 386.1 [M+H]$^+$.

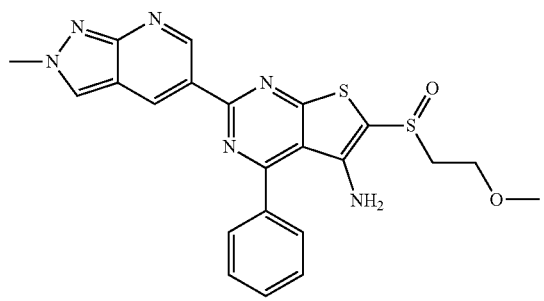

EXAMPLE 41: 6-((2-methoxyethyl)sulfinyl)-2-(2-methyl-2H-pyrazolo[3,4-b]pyridin-5-yl)-4-phenylthieno[2,3-d]pyrimidin-5-amine was prepared using synthetic procedures described for the preparation of EXAMPLE 38. $^1$H NMR (400 MHz, Methylene Chloride-d$_2$) δ 9.82 (d, J=2.2 Hz, 1H), 9.27 (d, J=2.2 Hz, 1H), 8.09 (s, 1H), 7.80-7.74 (m, 2H), 7.68-7.61 (m, 3H), 4.78 (s, 2H), 4.27 (s, 3H), 3.84 (ddd, J=10.5, 7.6, 4.0 Hz, 1H), 3.67 (ddd, J=10.5, 6.3, 4.3 Hz, 1H), 3.58 (ddd, J=13.1, 6.3, 4.0 Hz, 1H), 3.37 (s, 3H), 3.28 (ddd, J=13.0, 7.6, 4.3 Hz, 1H). ESI-MS (m/z): 465.1 [M+H]$^+$.

Enantiomers of EXAMPLE 41 were separated on a 2 cm Chiralpak AD-H column using Hexanes:EtOH (1:1) with 10 m/min flow rate, 600 µL injection (concentration 8 mg/ml) the 1st peak was at 22.0 min and the 2nd peak was at 35.0 min.

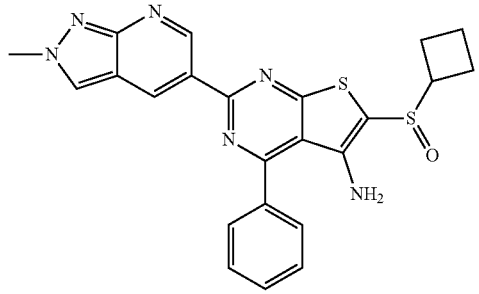 [SMILES: Cn1cc2cc(-c3nc(-c4ccccc4)c4c(N)c(S(=O)C5CCC5)sc4n3)cnc2n1]

EXAMPLE 42: 6-(cyclobutylsulfinyl)-2-(2-methyl-2H-pyrazolo[3,4-b]pyridin-5-yl)-4-phenylthieno[2,3-d]pyrimidin-5-amine was prepared using synthetic procedures described for the preparation of the analog EXAMPLE 19. $^1$H NMR (400 MHz, Methylene Chloride-d$_2$) δ 9.82 (s, 1H), 9.26 (s, 1H), 8.09 (s, 1H), 7.83-7.71 (m, 2H), 7.71-7.57 (m, 3H), 4.78 (s, 2H), 4.27 (s, 3H), 4.03-3.88 (m, 1H), 2.83-2.70 (m, 1H), 2.47-1.92 (m, 5H). ESI-MS (m/z): 461.1 [M+H]$^+$.

General Procedure A

Step 1: Aldol Reaction

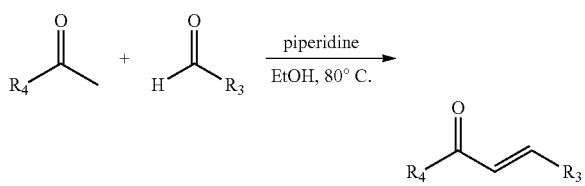

To a solution of the ketone (1.0 equiv) and the aldehyde (2.0 equiv) in ethanol was added piperidine (3.0 equiv). The mixture was stirred at 80° C. for 2 hours. After cooling, the mixture was concentrated and the residue was triturated with a 4:1 mixture of petroleum ether:ethyl acetate. The solid was filtered to give the enone.

Step 2: Condensation with 2-Cyanothioacetamide and Oxidation

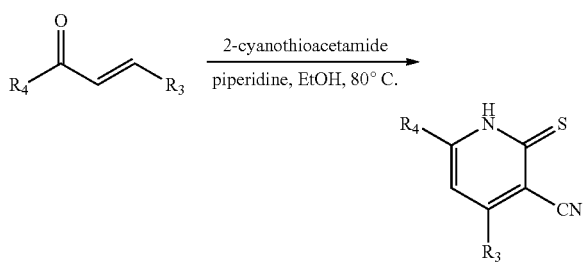

To a solution of the enone (1.0 equiv) in ethanol was added 2-cyanothioacetamide (3.0 equiv) and piperidine (2.0 equiv). The reaction mixture was stirred at 80° C. for 1 hour under an oxygen atmosphere (15 psi). The mixture was concentrated to give the crude pyridinethione.

Step 3: Preparation of α-Chlorosulfides

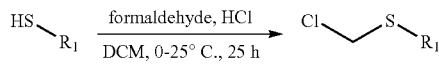

Hydrogen chloride gas was bubbled into a solution of the appropriate thiol (1.0 equiv) and formaldehyde (1.0 equiv) in dichloromethane. The mixture was stirred at 0° C. for 1 hour. The mixture was warmed to 25° C. and stirred for 24 hours. The mixture was concentrated to give the target compound.

Step 4: Alkylation

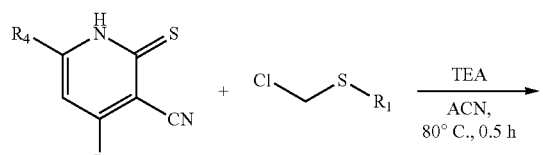

To a solution of the pyridinethione (1.0 equiv) in acetonitrile were added triethylamine (3.0 equiv) and the appropriate chloromethylsulfide (2.0 equiv). The mixture was stirred at 80° C. for 0.5 hour. The mixture was concentrated and the residue was purified by reversed-phase HPLC to give the target compound.

Step 5: Oxidation to Sulfoxide

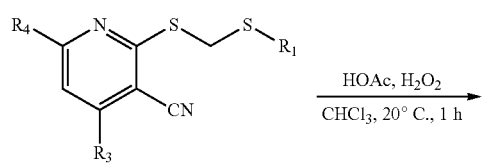

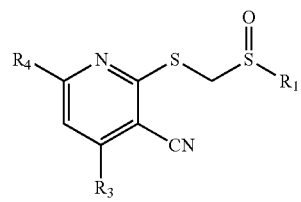

To a solution of the pyridinethiomethylsulfane (1 equiv) in chloroform was added acetic acid (25 equiv) and hydrogen peroxide (30% purity, 1.5 equiv). The mixture was stirred at 20° C. for 1 hour. The mixture was neutralized with saturated sodium bicarbonate solution and extracted with dichloromethane. The combined organic phases were concentrated to give the target sulfoxide.

Step 6: Cyclization

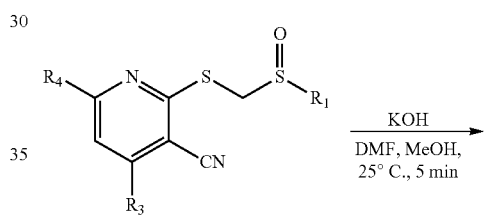

To a solution of the sulfoxide (1 equiv) in methanol and N,N-dimethylformamide was added potassium hydroxide solution (5%, 0.6 equiv). The mixture was stirred at 20° C. for 5 minutes. The mixture was neutralized with aqueous acetic acid (10%) and concentrated. The residue was purified by reversed-phase HPLC to give the final target compound.

The following compounds were prepared from known starting materials using General Procedure A. For select compounds, the enantiomers were resolved from the racemate using chiral supercritical fluid chromatography (SFC) and are reported with enantiomeric excess (ee) and/or optical rotation values. In some cases, only the more active R-(+) isomer was prepared/isolated.

| Ex. No. | Structure | 400 MHz NMR (δ; CDCl₃ unless otherwise noted) | LCMS (ES⁺; MH⁺) | Chiral compound info |
|---|---|---|---|---|
| 43 | 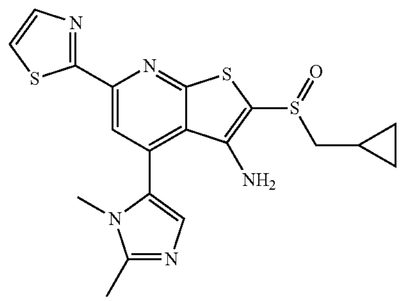 [SMILES: Cc1ncc(-c2cc(-c3nccs3)nc3sc(S(=O)CC4CC4)c(N)c23)n1C] | 8.10 (s, 1H), 7.97 (d, J = 3.2 Hz, 1H), 7.55 (d, J = 3.2 Hz, 1H), 7.16 (s, 1H), 4.82 (s, 2H), 3.44 (s, 3H), 3.14-3.26 (m, 2H), 2.53 (s, 3H), 1.06-1.08 (m, 1H), 0.71-0.74 (m, 2H), 0.36-0.46 (m, 2H). | 430.1 | |
| 44 | 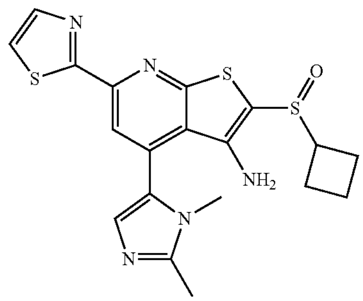 [SMILES: Cc1ncc(-c2cc(-c3nccs3)nc3sc(S(=O)C4CCC4)c(N)c23)n1C] | DMSO-d6 8.06 (s, 1H), 7.95 (d, J = 3.2 Hz, 1H), 7.53 (d, J = 3.2 Hz, 1H), 7.16 (s, 1H), 4.75 (s, 2H), 3.91-3.99 (m, 1H), 3.41 (s, 3H), 2.50-2.83 (m, 1H), 2.40 (s, 3H), 2.07-2.38 (m, 5 H). | 430.1 | R-isomer: [α] = +143.2° S-isomer: [α] = −147.3° |
| 45 | 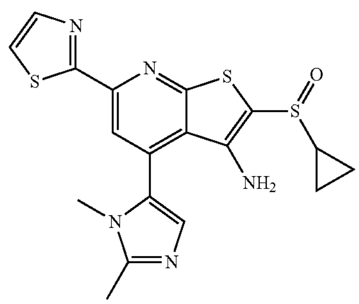 [SMILES: Cc1ncc(-c2cc(-c3nccs3)nc3sc(S(=O)C4CC4)c(N)c23)n1C] | 8.07 (s, 1H), 7.95 (d, J = 3.2 Hz, 1H), 7.53 (d, J = 3.2 Hz, 1H), 7.14 (s, 1H), 4.76 (s, 2H), 3.43 (s, 3H), 2.66 (m, 1H), 2.51 (s, 3H), 1.41-1.43 (m, 1H), 1.22-1.12 (m, 3H) | 416.1 | |
| 46 | 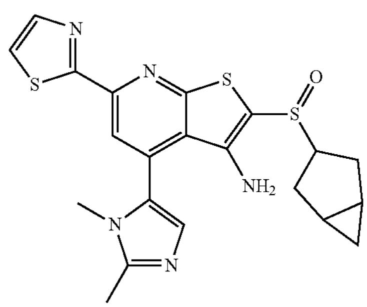 [SMILES: Cc1ncc(-c2cc(-c3nccs3)nc3sc(S(=O)C4CC5CC5C4)c(N)c23)n1C] | 8.07 (s, 1H), 7.96 (d, J = 3.2 Hz, 1H), 7.54 (d, J = 3.2 Hz, 1H), 7.14 (s, 1H), 4.72 (s, 2H), 4.03 (s, 1H), 3.42 (s, 3H), 2.53- 2.60 (m, 1H), 2.51 (s, 3H), 2.20-2.45 (m, 2H), 1.73-1.83 (m, 1H), 1.48-1.49 (m, 2H), 1.38-1.39 (m, 1H), 0.61-0.65 (m, 1H), 0.38-0.42 (m, 1H) | 456.1 | |
| 47 | 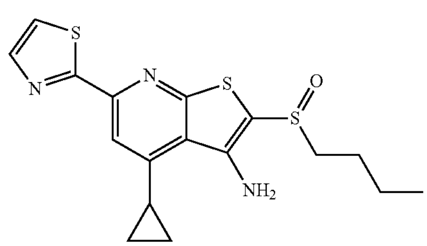 [SMILES: CCCCS(=O)c1sc2nc(-c3nccs3)cc(C3CC3)c2c1N] | 7.96-7.95 (m, 2H), 7.50 (d, J = 3.2 Hz, 1H), 5.61 (s, 2H), 3.38-3.31 (m, 1H), 3.22-3.15 (m, 1H), 2.58-2.51 (m, 1H), 1.87-1.73 (m, 2H), 1.59-1.48 (m, 2H), 1.23-1.19 (m, 2H), 1.19-1.07 (m, 2H), 0.99 (d, J = 7.2 Hz, 3H) | 378.2 | |

| Ex. No. | Structure | 400 MHz NMR (δ; CDCl₃ unless otherwise noted) | LCMS (ES⁺; MH⁺) | Chiral compound info |
|---|---|---|---|---|
| 48 | 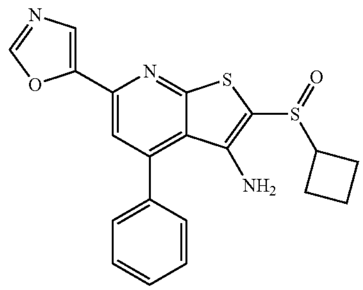 [SMILES: Nc1c(S(=O)C2CCC2)sc2nc(-c3cnco3)cc(-c3ccccc3)c12] | 8.01 (s, 1H), 7.82 (s, 1H), 7.58-7.54 (m, 3H), 7.50 (s, 1H), 7.50-7.45 (m, 2H), 4.59 (s, 2H), 4.01-3.93 (m, 1H), 2.85-2.74 (m, 1H), 2.44-2.31 (m, 2H), 2.30-2.18 (m, 1H), 2.14-2.02 (m, 2H). | 396.1 | |
| 49 | 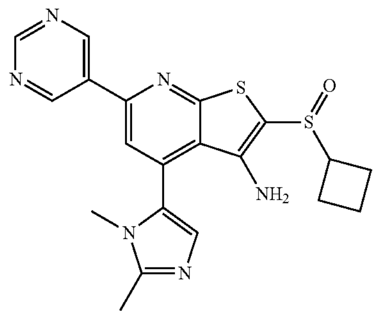 [SMILES: Cc1ncc(-c2cc(-c3cncnc3)nc3sc(S(=O)C4CCC4)c(N)c23)n1C] | 9.42 (s, 2H), 9.31 (s, 1H), 7.59 (s, 1H), 7.15 (s, 1H), 4.73 (s, 2H), 3.91-3.99 (m, 1H), 3.40 (s, 3H), 2.84 (s, 1H), 2.52 (s, 3H), 2.27-2.48 (m, 3H), 2.03-2.15 (m, 2H) | 425.1 | |
| 50 | 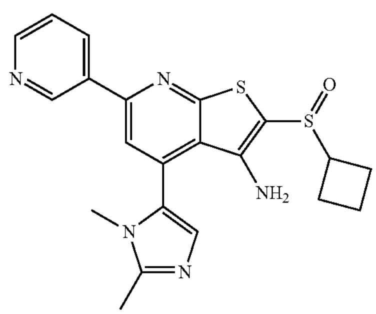 [SMILES: Cc1ncc(-c2cc(-c3cccnc3)nc3sc(S(=O)C4CCC4)c(N)c23)n1C] | 9.28 (d, J = 2.4 Hz, 1H), 8.71 (dd, J₁ = 1.6, J₂ = 4.8 Hz, 1H), 8.42-8.45 (m, 1H), 7.60 (s, 1H), 7.45 (dd, J₁ = 3.2, J₂ = 4.8 Hz, 1H), 7.14 (s, 1H), 4.70 (s, 2H), 3.91-3.99 (m, 1H), 3.40 (s, 3H), 2.52 (s, 1H), 2.52 (s, 3H), 2.26-2.46 (m, 3H), 2.05-2.17 (m, 2H). | 424.1 | |
| 51 | 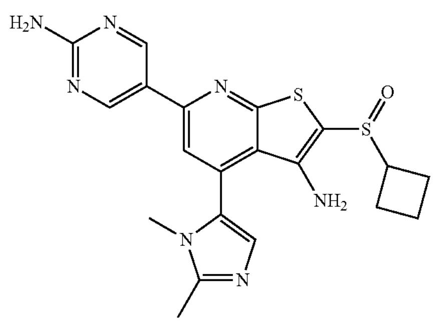 [SMILES: Cc1ncc(-c2cc(-c3cnc(N)nc3)nc3sc(S(=O)C4CCC4)c(N)c23)n1C] | 9.02 (s, 2H), 7.43 (s, 1H), 7.12 (s, 1H), 5.31 (s, 2H), 4.65 (s, 2H), 3.98-3.90 (m, 1H), 3.38 (s, 3H), 2.82-2.83 (m, 1H), 2.51 (s, 3H), 2.40-2.35 (m, 2H), 2.12-2.11 (m, 1H), 2.09-2.06 (m, 2H) | 440.2 | |
| 52 | 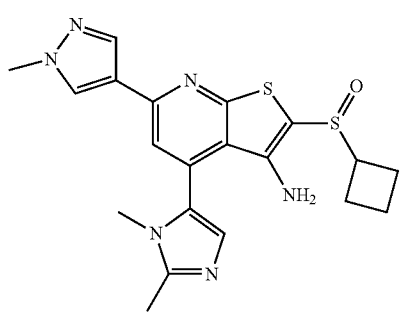 [SMILES: Cc1ncc(-c2cc(-c3cnn(C)c3)nc3sc(S(=O)C4CCC4)c(N)c23)n1C] | DMSO-d6 8.46 (m, 1H), 8.14 (s, 1H), 7.60 (s, 1H), 7.03 (s, 1H), 5.12 (s, 2H), 3.88 (s, 3H), 3.78-3.84 (m, 1H), 3.36 (s, 3H), 2.61-2.64 (m, 1H), 2.40 (s, 3H), 2.13-2.18 (m, 3H), 1.90-2.01 (m, 2H). | 427.2 | |

-continued

| Ex. No. | Structure | 400 MHz NMR (δ; CDCl₃ unless otherwise noted) | LCMS (ES⁺; MH⁺) | Chiral compound info |
|---|---|---|---|---|
| 53 | 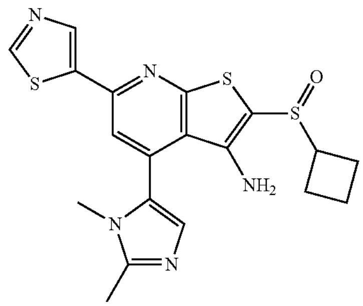 [SMILES: Cc1ncc(-c2cc(-c3cncs3)nc3sc(S(=O)C4CCC4)c(N)c23)n1C] | 8.90 (s, 1H), 8.42 (s, 1H), 7.50 (s, 1H), 7.13 (s, 1H), 4.66 (s, 2H), 3.91-3.95 (m, 1H), 3.39 (s, 3H), 2.82 (s, 1H), 2.51 (s, 3H), 2.36-2.43 (m, 2H), 2.26-2.28 (m, 1H), 2.03-2.14 (m, 2H) | 430.1 | |
| 54 | 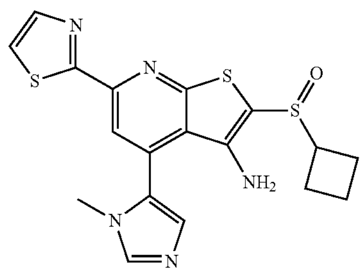 [SMILES: Cn1cncc1-c1cc(-c2nccs2)nc2sc(S(=O)C3CCC3)c(N)c12] | 8.1 (s, 1H), 7.95 (d, J = 2.8 Hz, 1H), 7.68 (s, 1H), 7.53 (d, J = 3.2 Hz, 1H), 4.66 (s, 2H), 3.91-3.99 (m, 1H), 3.54 (s, 3H), 2.83-2.88 (m, 1H), 2.08-2.42 (m, 5H). | 416.2 | |
| 55 | 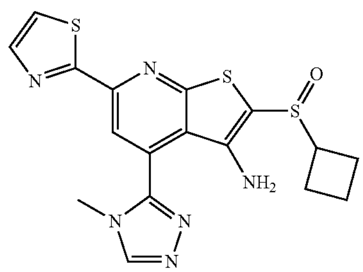 [SMILES: Cn1cnnc1-c1cc(-c2nccs2)nc2sc(S(=O)C3CCC3)c(N)c12] | 8.37 (s, 1H), 8.19 (s, 1H), 7.96 (d, J = 3.2 Hz, 1H), 7.56 (d, J = 3.2 Hz, 1H), 5.58 (s, 2H), 3.97-3.93 (m, 1H), 3.83 (s, 3H), 2.87-2.81 (m, 1H), 2.41-2.38 (m, 1H), 2.34-2.25 (m, 2H), 2.11-2.06 (m, 2H) | 417.1 | |
| 56 | 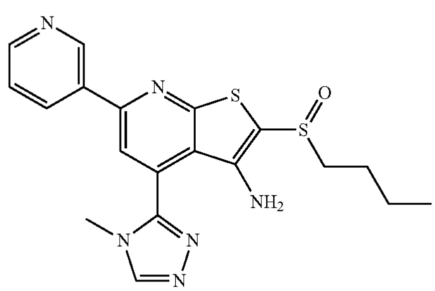 [SMILES: CCCCS(=O)c1sc2nc(-c3cccnc3)cc(-c3nncn3C)c2c1N] | DMSO-d6 9.42 (d, J = 1.6 Hz, 1H), 8.91 (s, 1H), 8.71 (d, J = 4.8 Hz, 1H), 8.62 (d, J = 8.0 Hz, 1H), 8.34 (s, 1H), 7.60 (dd, J = 4.8, 7.6 Hz, 1H), 6.10 (s, 2H), 3.82 (s, 3H), 3.12-3.19 (m, 1H), 3.00-3.07 (m, 1H), 1.54-1.65 (m, 2H), 1.39-1.48 (m, 2H), 0.89 (t, J = 7.2 Hz, 3H) | 413.2 | |
| 57 | 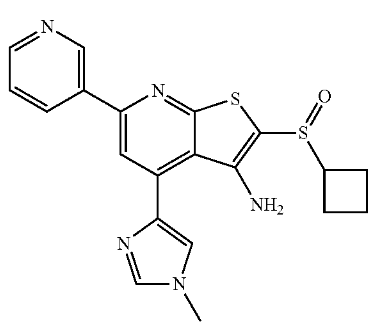 [SMILES: Cn1cnc(-c2cc(-c3cccnc3)nc3sc(S(=O)C4CCC4)c(N)c23)c1] | 9.18 (d, J = 1.6 Hz, 1H), 8.61 (d, J₁ = 1.6 Hz, J₁ = 4.8 Hz,, 1H), 8.38-8.41 (m, J = 1.94, 8.13 Hz, 1H), 7.66 (s, 1H), 7.56 (s, 1H), 7.35-7.39 (m, 2H), 6.84 (s, 2H), 3.87-3.95 (m, 1H), 3.78 (s, 3H), 2.71-2.81 (m, 1H), 2.25-2.35 (m, 2H), 2.11-2.17 (m, 1H), 1.96-2.04 (m, 2H). | 448.1 | |

| Ex. No. | Structure | 400 MHz NMR (δ; CDCl₃ unless otherwise noted) | LCMS (ES⁺; MH⁺) | Chiral compound info |
|---|---|---|---|---|
| 58 | 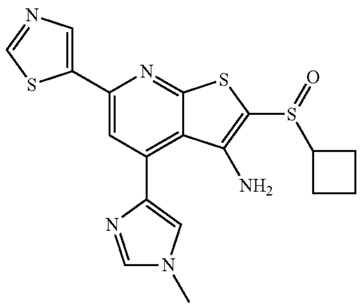 [SMILES: Cn1cnc(-c2cc(-c3cncs3)nc3sc(S(=O)C4CCC4)c(N)c23)c1] | 8.87 (s, 1H), 8.41 (s, 1H), 7.63 (s, 2H), 7.46 (s, 1H), 6.87 (s, 2H), 3.92-4.00 (m, 1H), 3.85 (s, 3H), 2.77-2.86 (m, 1H), 2.33-2.40 (m, 2H), 2.17-2.23 (m, 1H), 2.02-2.11 (m, 2H) | 416.2 | |
| 59 | 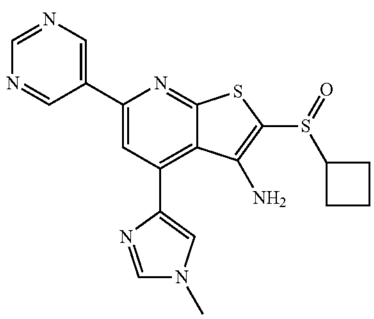 [SMILES: Cn1cnc(-c2cc(-c3cncnc3)nc3sc(S(=O)C4CCC4)c(N)c23)c1] | 9.34 (s, 2H), 9.21 (s, 1H), 7.63 (s, 1H), 7.56 (s, 1H), 7.40 (s, 1H), 6.86 (s, 2H), 3.87-3.95 (m, 1H), 3.79 (s, 3H), 2.73-2.79 (m, 1H), 2.28-2.31 (m, 2H), 1.98-2.02 (m, 3H) | 411.1 | R-isomer: 98.1% ee; [α] = +114.3° S-isomer: 100% ee; [α] = −17.7° |
| 60 | 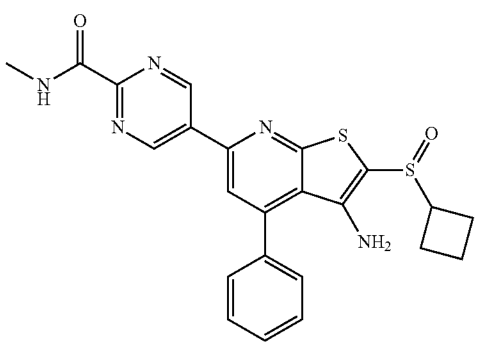 [SMILES: CNC(=O)c1ncc(-c2cc(-c3ccccc3)c3c(N)c(S(=O)C4CCC4)sc3n2)cn1] | 9.52 (s, 2H), 8.10 (d, J = 5.2 Hz, 1H), 7.61 (s, 1H), 7.60-7.56 (m, 3H), 7.52-7.48 (m, 2H), 4.63 (s, 2H), 4.02-3.94 (m, 1H), 3.12 (d, J = 4.8 Hz, 3H), 2.87-2.73 (m, 1H), 2.47-2.31 (m, 2H), 2.31-2.19 (m, 1H), 2.15-2.00 (m, 2H) | 464.0 | |
| 61 | 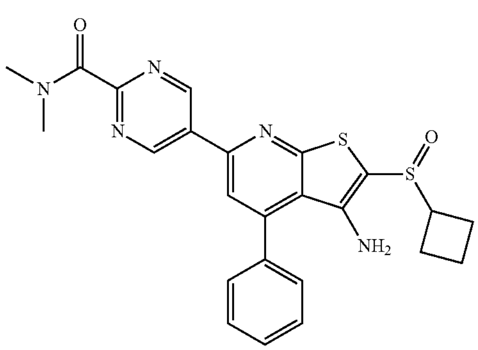 [SMILES: CN(C)C(=O)c1ncc(-c2cc(-c3ccccc3)c3c(N)c(S(=O)C4CCC4)sc3n2)cn1] | 9.48 (s, 2H), 7.61 (s, 1H), 7.60-7.54 (m, 3H), 7.51-7.49 (m, 2H), 4.63 (s, 2H), 4.02-3.94 (m, 1H), 3.19 (s, 3H), 3.00 (s, 3H), 2.86-2.75 (m, 1H), 2.45-2.32 (m, 2H), 2.30-2.20 (m, 1H), 2.16-2.04 (m, 2H) | 478.0 | |

-continued

| Ex. No. | Structure | 400 MHz NMR (δ; CDCl₃ unless otherwise noted) | LCMS (ES⁺; MH⁺) | Chiral compound info |
|---|---|---|---|---|
| 62 | 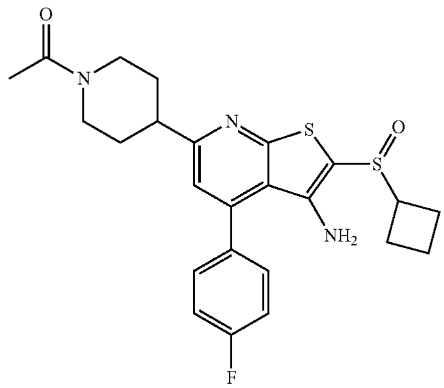 [SMILES: CC(=O)N1CCC(c2cc(-c3ccc(F)cc3)c3c(N)c(S(=O)C4CCC4)sc3n2)CC1] | 7.43-7.40 (m, 2H), 7.22 (t, J = 8.8 Hz, 2H), 6.95 (s, 1H), 4.78 (d, J = 13.2 Hz, 1H), 4.53 (d, J = 5.2 Hz, 2H), 4.0-4.0 (m, 2H), 3.25-3.18 (m, 1H), 3.10-3.02 (m, 1H), 2.82-2.66 (m, 2H), 2.40-2.29 (m, 2H), 2.27-2.18 (m, 1H), 2.13 (s, 3H), 2.09-2.00 (m, 4H), 1.92-1.73 (m, 2H) | 472.2 | |
| 63 | 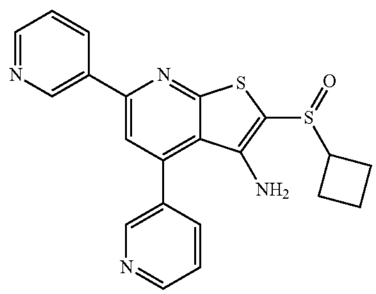 [SMILES: Nc1c(S(=O)C2CCC2)sc2nc(-c3cccnc3)cc(-c3cccnc3)c12] | 9.30 (d, J = 1.6 Hz, 1H), 8.84-8.82 (m, 2H), 8.71 (dd, J = 1.6, 4.8 Hz, 1H), 8.51-8.48 (m, 1H), 7.89 (d, J = 7.6 Hz, 1H), 7.59 (s, 1H), 7.52-7.37 (m, 2H), 4.51 (s, 2H), 4.03-3.94 (m, 1H), 2.86-2.79 (m, 1H), 2.41-2.29 (m, 5H). | 407.2 | |
| 64 | 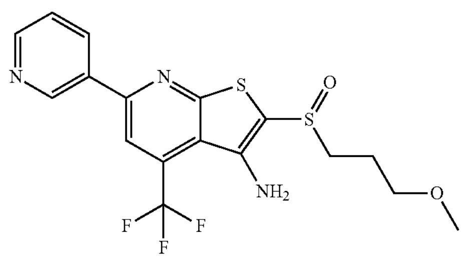 [SMILES: COCCCS(=O)c1sc2nc(-c3cccnc3)cc(C(F)(F)F)c2c1N] | 9.33 (d, J = 1.6 Hz, 1H), 8.74 (dd, J₁ = 1.6, J₁ = 4.8 Hz, 1H), 8.47-8.44 (m, 1H), 8.06 (s, 1H), 7.50-7.47 (m, 1H), 5.30 (s, 2H), 3.55 (t, J = 6.0 Hz, 2H), 3.47-3.40 (m, 1H), 3.34-3.26 (s, 3H), 3.35-3.26 (m, 1H), 2.13-2.02 (m, 2H) | 416.0 | R-isomer: 100% ee; [α] = +46.5° S-isomer: 100% ee; [α] = −60.8° |
| 65 | 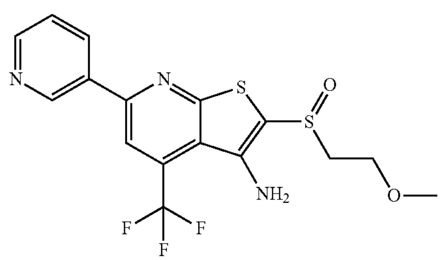 [SMILES: COCCS(=O)c1sc2nc(-c3cccnc3)cc(C(F)(F)F)c2c1N] | 9.33 (d, J = 2.0 Hz, 1H), 8.75 (dd, J₁ = 1.6, J₂ = 4.8 Hz, 1H), 8.48-8.45 (m, 1H), 8.07 (s, 1H), 7.51-7.47 (m, 1H), 5.26 (s, 2H), 3.93-3.87 (m, 1H), 3.74-3.65 (m, 2H), 3.42 (s, 3H), 3.37-3.30 (m, 1H) | 402.0 | R-isomer: 98.7% ee; [α] = +86.9° S-isomer: 100% ee; [α] = −88.5° |
| 66 | 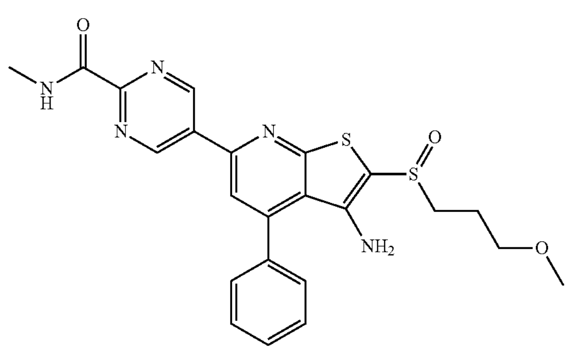 | 9.54 (s, 2H), 8.12-8.10 (m, 1H), 7.63 (s, 1H), 7.60-7.59 (m, 3H), 7.53-7.50 (m, 2H), 4.67 (s, 2H), 3.52 (t, J = 6.0 Hz, 2H), 3.41-3.36 (m, 1H), 3.35 (s, 3H), 3.29-3.22 (m, 1H), 3.13 (d, J = 4.0 Hz, 3H), 2.08-2.01 (m, 2H). | 482.1 | R-isomer: 98% ee; [α] = +60.098°; S-isomer: 98% ee; [α] = −58.480° |

-continued

| Ex. No. | Structure | 400 MHz NMR (δ; CDCl₃ unless otherwise noted) | LCMS (ES⁺; MH⁺) | Chiral compound info |
|---|---|---|---|---|
| 67 | 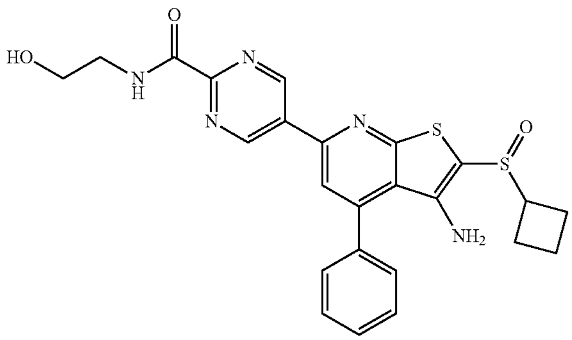 [SMILES: Nc1c(S(=O)C2CCC2)sc2nc(-c3cnc(C(=O)NCCO)nc3)cc(-c3ccccc3)c12] | 9.53 (s, 2H), 8.49 (s, 1H), 7.62-7.51 (m, 6H), 4.63 (s, 1H), 3.98-3.96 (m, 1H), 3.92-3.90 (m, 2H), 3.77-3.73 (m, 2H), 2.80-2.75 (m, 1H), 2.49-2.07 (m, 6H). | 494.1 | |
| 68 | 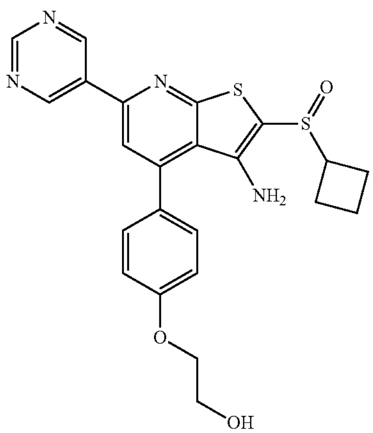 [SMILES: Nc1c(S(=O)C2CCC2)sc2nc(-c3cncnc3)cc(-c3ccc(OCCO)cc3)c12] | DMSO-d6 9.55 (s, 2H), 9.27 (s, 1H), 7.98 (s, 1H), 7.51 (d, J = 8.4 Hz, 2H), 7.16 (d, J = 8.8 Hz, 2H), 5.05 (s, 2H), 4.91 (t, J = 5.6 Hz, 1H), 4.10 (t, J = 4.8 Hz, 2H), 3.86 (t, J = 8.4 Hz, 1H), 3.79-3.75 (m, 2H), 2.64-2.61 (m, 1H), 2.20-2.13 (m, 3H), 2.05-1.98 (m, 1H), 1.92-1.90 (m, 1H) | 467.2 | |
| 69 | 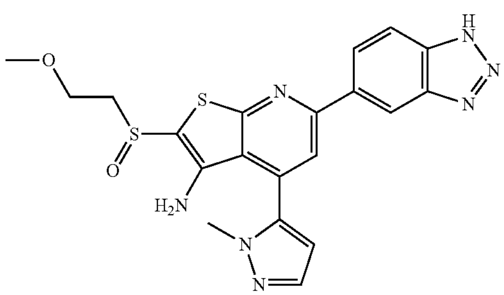 [SMILES: COCCS(=O)c1sc2nc(-c3ccc4[nH]nnc4c3)cc(-c3ccnn3C)c2c1N] | DMSO-d6 .66 (d, J = 0.8 Hz, 1H), 8.11-8.09 (m, 2H), 7.84 (d, J = 8.4 Hz, 1H), 7.69 (d, J = 1.6 Hz, 1H), 6.65 (s, 1H), 5.01 (s, 2H), 3.77-3.71 (m, 4H), 3.66-3.61 (m, 1H), 3.41-3.35 (m, 1H), 3.28 (s, 3H), 3.25-3.22 (m, 1H). | 454.2 | |
| 70 | 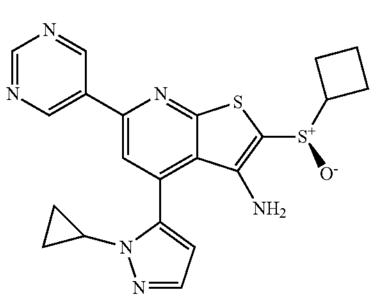 [SMILES: Nc1c([S@+]([O-])C2CCC2)sc2nc(-c3cncnc3)cc(-c3ccnn3C3CC3)c12] | 9.44 (s, 2H), 9.31 (s, 1H), 7.68 (s, 1H), 7.63 (s, 1H), 6.49 (d, J = 1.2 Hz, 1H), 4.65-4.59 (m, 2H), 3.99-3.92 (m, 1H), 3.43-3.40 (m, 1H), 2.88-2.78 (m, 1H), 2.44-2.23 (m, 3H), 2.16-2.06 (m, 2H), 1.29-1.07 (m, 2H), 0.88-0.79 (m, 2H). | 437.1 | R-isomer: [α] = +154.740°; |

-continued

| Ex. No. | Structure | 400 MHz NMR (δ; CDCl₃ unless otherwise noted) | LCMS (ES⁺; MH⁺) | Chiral compound info |
|---|---|---|---|---|
| 71 | 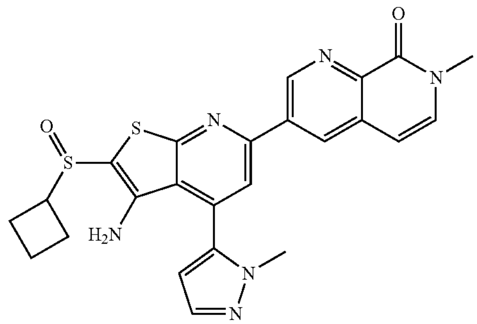 [SMILES: Cn1nccc1-c1cc(-c2cnc3c(=O)n(C)ccc3c2)nc2sc(S(=O)C3CCC3)c(N)c12] | DMSO-d6<br>9.57 (d, J = 2.0 Hz, 1H), 8.95 (d, J = 2.0 Hz, 1H), 8.26 (s, 1H), 7.72 (d, J = 2.0 Hz, 1H), 7.65 (d, J = 7.2 Hz, 1H), 6.73 (d, J = 7.2 Hz, 1H), 6.69 (s, 1H), 5.05 (s, 2H), 3.95-3.85 (m, 1H), 3.74 (s, 3H), 3.57 (s, 3H), 2.70-2.63 (m, 1H), 2.28-2.11 (m, 3H), 2.10-1.99 (m, 1H), 1.99-1.87 (m, 1H). | 491.1 | R-isomer: [α] = +166.952°; |
| 72 | 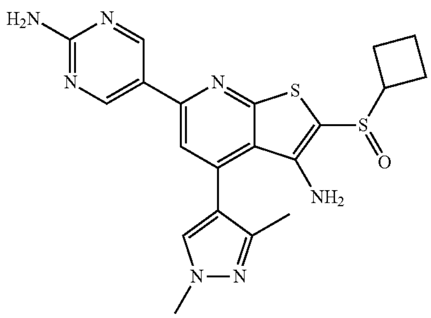 [SMILES: Cc1nn(C)cc1-c1cc(-c2cnc(N)nc2)nc2sc(S(=O)C3CCC3)c(N)c12] | 9.00 (s, 2H), 7.50 (s, 1H), 7.33 (s, 1H), 5.41 (s, 2H), 4.84 (s, 2H), 4.02-3.93 (m, 4H), 2.88-2.77 (m, 1H), 2.44-2.35 (m, 2H), 2.30-2.25 (m, 1H), 2.24 (s, 3H), 2.15-2.05 (m, 2H). | 440.0 | |
| 73 | 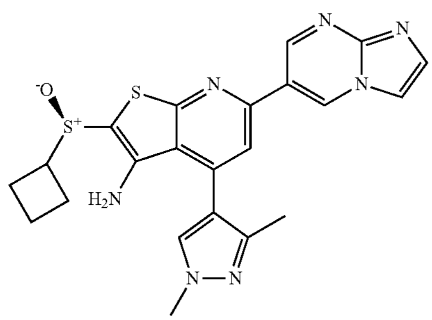 | 9.33 (d, J = 2.4 Hz, 1H), 9.15 (d, J = 2.4 Hz, 1H), 7.89 (s, 1H), 7.67 (d, J = 1.6 Hz, 1H), 7.53 (s, 1H), 7.50 (s, 1H), 4.87 (s, 2H), 3.99 (s, 3H), 3.97-3.94 (m, 2H), 2.88-2.78 (m, 1H), 2.45-2.34 (m, 2H), 2.31-2.22 (m, 4H), 2.13-2.05 (m, 2H) | 464.0 | R-isomer: [α] = +93.331° |
| 74 | 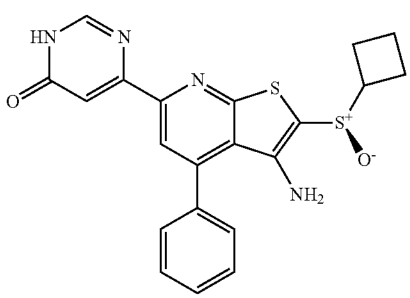 [SMILES: Nc1c([S@+]([O-])C2CCC2)sc2nc(-c3cc(=O)[nH]cn3)cc(-c3ccccc3)c12] | 8.26-8.24 (m, 1H), 8.19 (s, 1H), 7.70-7.68 (m, 1H), 7.58-7.54 (m, 3H), 7.53-7.48 (m, 2H), 4.67 (s, 2H), 4.05-3.95 (m, 1H), 2.87-2.76 (m, 1H), 2.46-2.34 (m, 2H), 2.32-2.22 (m, 1H), 2.16-2.05 (m, 2H). | 423.1 | R-isomer: [α] = +42.7545°; |
| 75 | 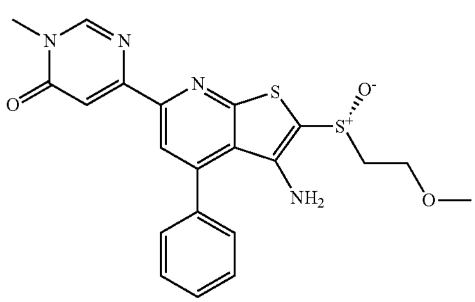 [SMILES: COCC[S@@+]([O-])c1sc2nc(-c3cc(=O)n(C)cn3)cc(-c3ccccc3)c2c1N] | 8.21 (s, 1H), 8.14 (s, 1H), 7.67-7.66 (m, 1H), 7.57-7.54 (m, 3H), 7.53-7.48 (m, 2H), 4.65 (s, 2H), 3.91-3.85 (m, 1H), 3.75-3.68 (m, 1H), 3.65-3.61 (m, 1H), 3.60 (s, 3H), 3.41 (s, 3H), 3.34-3.27 (m, 1H). | 441.2 | R-isomer: [α] = +62.306° |

-continued
| Ex. No. | Structure | 400 MHz NMR (δ; CDCl₃ unless otherwise noted) | LCMS (ES⁺; MH⁺) | Chiral compound info |
|---|---|---|---|---|
| 76 | 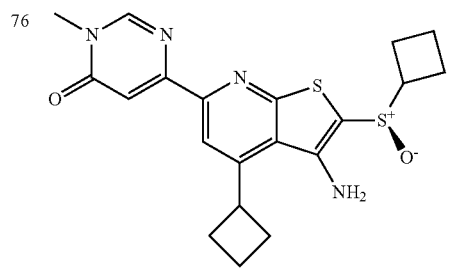 | 8.23 (s, 1H), 8.21 (s, 1H), 7.54 (s, 1H), 5.17 (s, 2H), 4.27-4.19 (m, 1H), 3.99-3.92 (m, 1H), 3.59 (s, 3H), 2.87-2.77 (m, 1H), 2.52-2.45 (m, 3H), 2.44-2.32 (m, 3H), 2.30-2.20 (m, 1H), 2.19-2.13 (m, 1H), 2.12-2.04 (m, 2H), 2.03-1.95 (m, 1H). | 415.0 | R-isomer: [α] = +89.571°; |
| 77 | 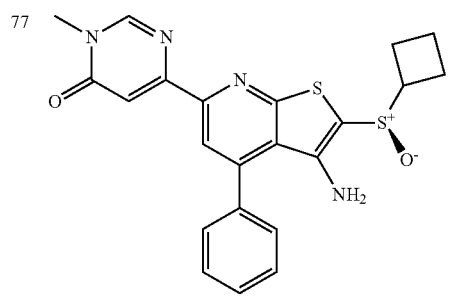 | 8.20 (s, 1H), 8.12 (s, 1H), 7.65 (s, 1H), 7.58-7.53 (m, 3H), 7.50 (s, 2H), 4.65 (s, 2H), 4.04-3.94 (m, 1H), 3.60 (s, 3H), 2.86-2.75 (m, 1H), 2.44-2.32 (m, 2H), 2.32-2.20 (m, 1H), 2.15-2.03 (m, 2H). | 437.2 | R-isomer: [α] = +163.247°; |
| 78 | 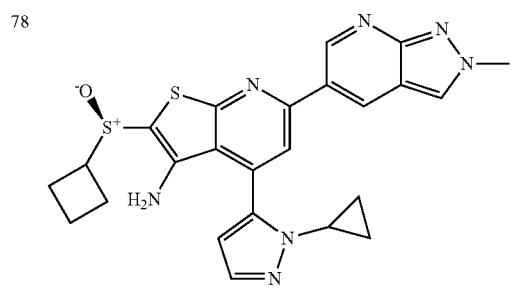 | 9.41 (d, J = 2.4 Hz, 1H), 8.80 (d, J = 2.0 Hz, 1H), 8.04 (s, 1H), 7.72 (s, 1H), 7.62 (d, J = 1.6 Hz, 1H), 6.49 (d, J = 8.0 Hz, 1H), 4.62-4.52 (m, 2H), 4.31 (s, 3H), 3.99-3.91 (m, 1H), 3.43 (s, 1H), 2.87-2.78 (m, 1H), 2.45-2.31 (m, 2H), 2.30-2.21 (m, 1H), 2.14-2.03 (m, 2H), 1.30-1.07 (m, 2H), 0.89-0.80 (m, 2H) | 490.1 | R-isomer: [α] = +89.571°; |
| 79 | 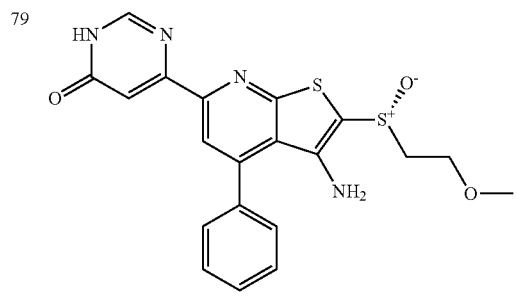 | | 427.1 | R-isomer: [α] = +60.503° |
| 80 | 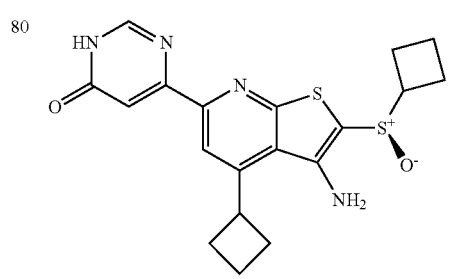 | | 401.1 | R-isomer: [α] = +22.781° |

| Ex. No. | Structure | 400 MHz NMR (δ; CDCl₃ unless otherwise noted) | LCMS (ES⁺; MH⁺) | Chiral compound info |
|---|---|---|---|---|
| 81 | 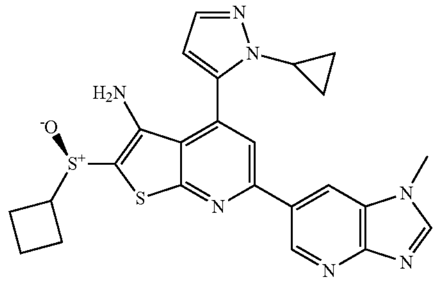 | | 490.2 | R-isomer: [α] = +153.402° |
| 82 | 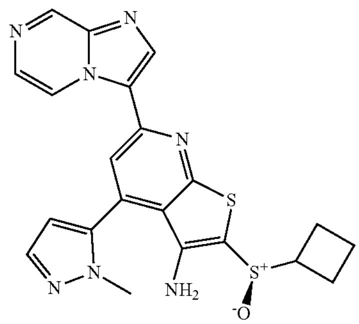 | | 450.2 | R-isomer: [α] = +214.635° |

General Procedure B

Step 1: Condensation to Form Hydroxypyridine

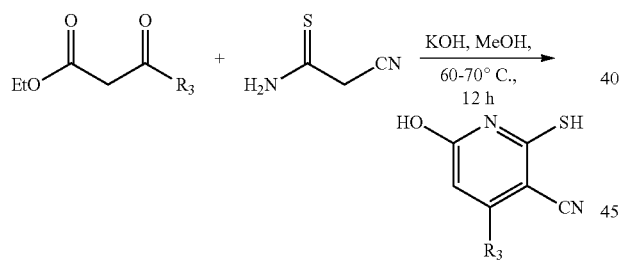

To a solution of potassium hydroxide (1.2 eq) in methanol at 60° C. was added a methanol solution of the R-keto ester (1.0 eq) and 2-cyanothioacetamide (1.0 eq). The reaction was stirred at 70° C. for 12 hours. The mixture was concentrated, dissolved in water and acidified to pH 4 with concentrated hydrochloric acid. The solid was filtered to give the target compound.

Step 2: Alkylation

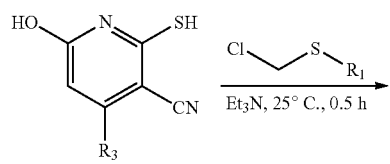

To a solution of the hydroxypyridine (1.0 eq) in acetonitrile were added triethylamine (2.0 eq) and the appropriate chloromethylsulfide (2.0 eq). The mixture was stirred at 25° C. for 15 minutes. The mixture was concentrated and the crude product was purified by prep-HPLC to give the target compound.

Step 3: Triflation

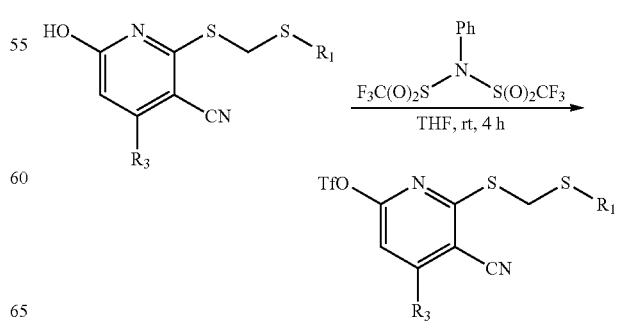

To a solution of the alkylated hydroxypyridine (1.0 eq) in tetrahydrofuran was added potassium tert-butoxide (1.2 eq) and 1,1,1-trifluoro-N-phenyl-N-(trifluoromethylsulfonyl)methanesulfonamide (1.2 eq). The mixture was stirred at 25° C. for 3 hours and concentrated. Water was added and the mixture extracted with dichloromethane. The combined organic layers were concentrated. The residue was purified by column chromatography to give the target compound.

Step 4: Suzuki Reaction

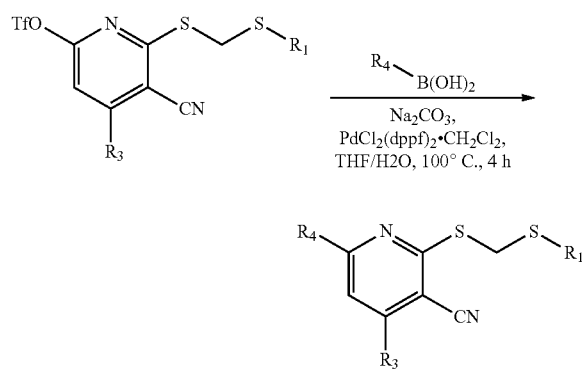

To a solution of the triflate (1.0 eq) in tetrahydrofuran and water was added sodium carbonate (2.0 eq). 1,1'-bis(diphenylphosphino)ferrocene-palladium(II) dichloride dichloromethane complex (0.05 eq) and the appropriate boronic acid (1.5 eq) were added. The reaction was stirred at 100° C. for 3 hours under nitrogen atmosphere. The mixture was concentrated and water was added. The mixture was extracted with dichloromethane and the combined organic phases were concentrated. The residue was purified by column chromatography to provide the target compound.

Step 5: Oxidation to Sulfoxide

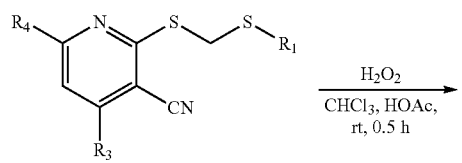

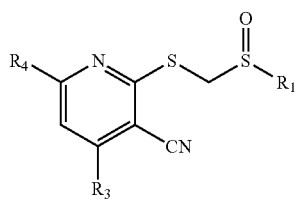

The sulfide was converted to the sulfoxide using the same procedure described in General Procedure A.

Step 6: Cyclization

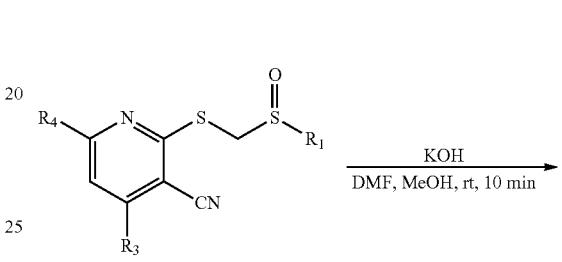

The sulfoxide was cyclized to the final target compound using the same procedure described in General Procedure A.

The following compounds were prepared from known starting materials using General Procedure B. For select compounds, the enantiomers were resolved from the racemate using chiral supercritical fluid chromatography (SFC) and are reported with enantiomeric excess (ee) and/or optical rotation values. In some cases, only the more active R-(+) isomer was prepared/isolated.

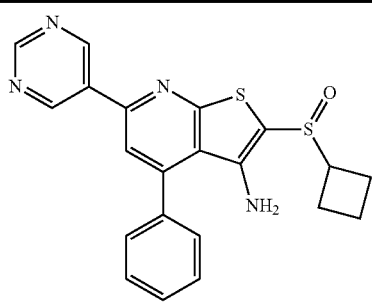

| Ex. No. | Structure | 400 MHz NMR (δ; CDCl$_3$ unless otherwise noted) | LCMS (ES$^+$; MH$^+$) | Chiral info |
|---|---|---|---|---|
| 83 | 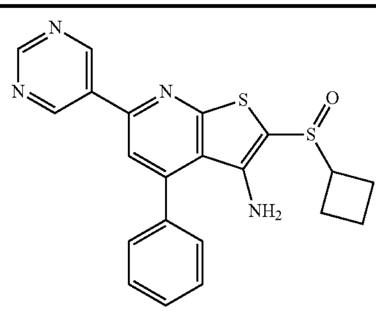 | 9.43 (s, 2H), 9.29 (s, 1H), 7.58 (s, 4H), 7.50 (s, 2H), 4.63 (s, 2H), 3.94-4.02 (m, 1H), 2.78-2.83 (m, 1H), 2.07-2.39 (m, 5H). | 407.1 | |

-continued

| Ex. No. | Structure | 400 MHz NMR (δ; CDCl₃ unless otherwise noted) | LCMS (ES⁺; MH⁺) | Chiral info |
|---|---|---|---|---|
| 84 | 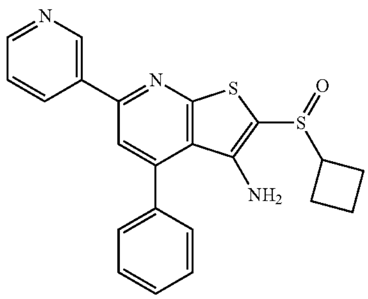 [SMILES: Nc1c(S(=O)C2CCC2)sc2nc(-c3cccnc3)cc(-c3ccccc3)c12] | 9.29 (d, J = 2.4 Hz, 1H), 8.69 (d, J = 4.0 Hz, 1H), 8.45 (d, J = 8.4 Hz, 1H), 7.59 (s, 1H), 7.56-7.45 (m, 5H), 7.43-7.42 (m, 1H), 4.60 (s, 2H), 4.02-3.93 (m, 1H), 2.82-2.77 (m, 1H), 2.38-2.25 (m, 2H), 2.10-2.06 (m, 1H), 2.10-2.05 (m, 2H). | 406.2 | |
| 85 | 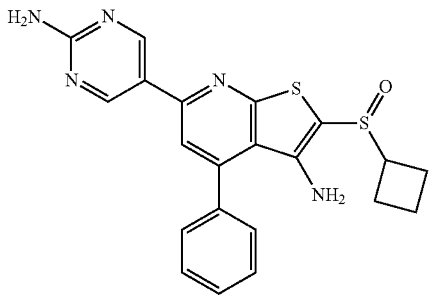 [SMILES: Nc1ncc(-c2cc(-c3ccccc3)c3c(N)c(S(=O)C4CCC4)sc3n2)cn1] | 9.03 (s, 2H), 7.49-7.55 (m, 5H), 7.41 (s, 1H), 5.32 (s, 2H), 4.57 (s, 2H), 3.93-4.01 (m, 1H), 2.77-2.82 (m, 1H), 2.35-2.38 (s, 2H), 2.25-2.26 (m, 1H), 2.06-2.10 (m, 2H). | 422.1 | |
| 86 | 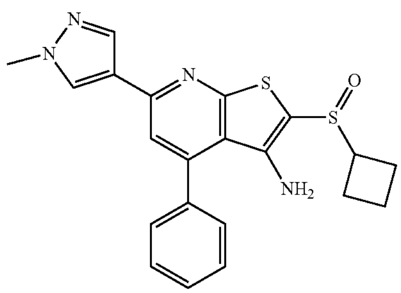 [SMILES: Cn1cc(-c2cc(-c3ccccc3)c3c(N)c(S(=O)C4CCC4)sc3n2)cn1] | 8.04 (s, 1H), 8.00 (s, 1H), 7.47-7.54 (m, 5H), 7.26 (s, 1H), 4.51 (s, 2H), 3.91-3.98 (m, 1H), 2.76-2.83 (m, 1H), 2.23-2.38 (m, 3H), 2.05-2.09 (m, 2H). | 409.2 | |
| 87 | 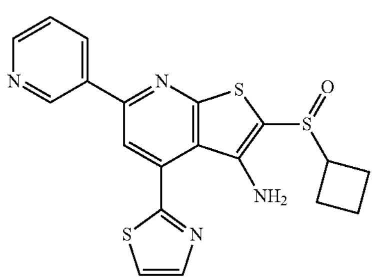 [SMILES: Nc1c(S(=O)C2CCC2)sc2nc(-c3cccnc3)cc(-c3nccs3)c12] | 9.31 (d, J = 2.0 Hz, 1H), 8.73 (d, J = 3.2 Hz, 1H), 8.476 (d, J = 8.0 Hz, 1H), 8.06 (d, J = 3.2 Hz, 1H), 7.99 (s, 1H), 7.64 (d, J = 3.2 Hz, 1H), 7.46-7.49 (m, 1H), 6.67 (s, 2H), 3.95-4.03 (m, 1H), 2.82-2.89 (m, 1H), 2.36-2.40 (m, 2H), 2.24-2.25 (m, 1H), 2.07-2.11 (m, 2H). | 413.1 | |
| 88 | 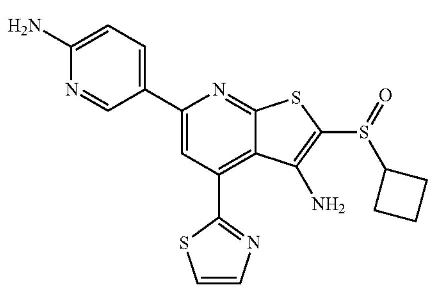 [SMILES: Nc1ccc(-c2cc(-c3nccs3)c3c(N)c(S(=O)C4CCC4)sc3n2)cn1] | 8.82 (d, J = 2.0 Hz, 1H), 8.18-8.24 (m, 3H), 8.04 (s, 1H), 6.77 (s, 1H), 6.54-6.58 (m, 1H), 3.83-3.91 (m, 1H), 2.59-2.66 (m, 1H), 1.93-2.21 (m, 5H). | 428.1 | |

-continued

| Ex. No. | Structure | 400 MHz NMR (δ; CDCl₃ unless otherwise noted) | LCMS (ES⁺; MH⁺) | Chiral info |
|---|---|---|---|---|
| 89 | 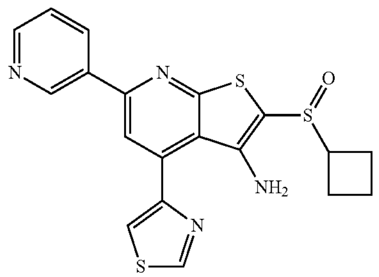 [SMILES: Nc1c(S(=O)C2CCC2)sc2nc(-c3cccnc3)cc(-c3cscn3)c12] | 9.30 (d, J = 2.0 Hz, 1H), 9.06 (d, J = 2.0 Hz, 1H), 8.70 (d, J₁ = 1.6 Hz, J₂ = 4.8 Hz, 1H), 8.46-8.49 (m, 1H), 7.82-7.84 (m, 2H), 7.45 (d, J₁ = 4.8 Hz, J₂ = 8.0 Hz, 1H), 5.93 (s, 2H), 3.93-4.01 (m, 1H), 2.81-2.88 (m, 1H), 2.35-2.43 (m, 2H), 2.23-2.25 (m, 1H), 2.06-2.10 (m, 2H). | 413.2 | |
| 90 | 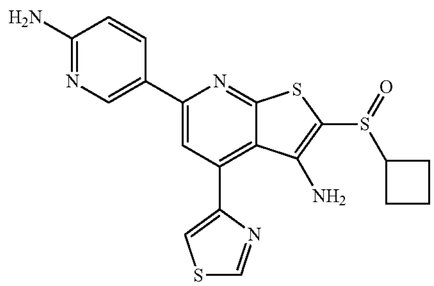 [SMILES: Nc1ccc(-c2cc(-c3cscn3)c3c(N)c(S(=O)C4CCC4)sc3n2)cn1] | 9.46 (d, J = 2.0 Hz, 1H), 8.84 (d, J = 2.4 Hz, 1H), 8.56 (d, J = 2.0 Hz, 1H), 8.23 (dd, J₁ = 8.8 Hz, J₂ = 2.4 Hz, 1H), 7.98 (s, 1H), 6.57 (d, J = 8.8 Hz, 1H), 6.46 (s, 2H), 6.37 (s, 2H), 3.82-3.90 (m, 1H), 2.58-2.65 (m, 1H), 2.14-2.22 (m, 3H), 1.92-2.03 (m, 2H). | 428.2 | |
| 91 | 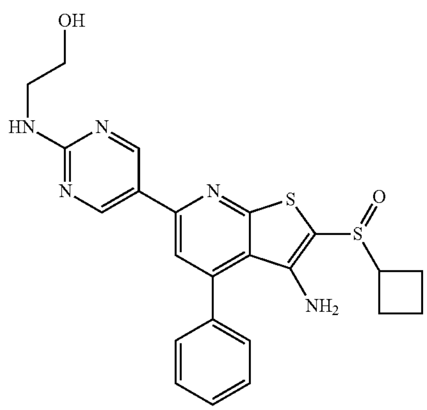 [SMILES: Nc1c(S(=O)C2CCC2)sc2nc(-c3cnc(NCCO)nc3)cc(-c3ccccc3)c12] | 9.00 (s, 2H), 7.55-7.58 (m, 4H), 7.47 (s, 1H), 7.38 (s, 1H), 5.85 (s, 1H), 4.57 (s, 2H), 3.69-3.98 (m, 5H), 2.77-2.79 (m, 1H), 2.37-2.40 (m, 2H), 2.34-2.37 (m, 1H), 2.07-2.11 (m, 2H). | 466.3 | R-isomer: 100% ee; [α] = +3.2° S-isomer: 95.2% ee; [α] = −0.7° |
| 92 | 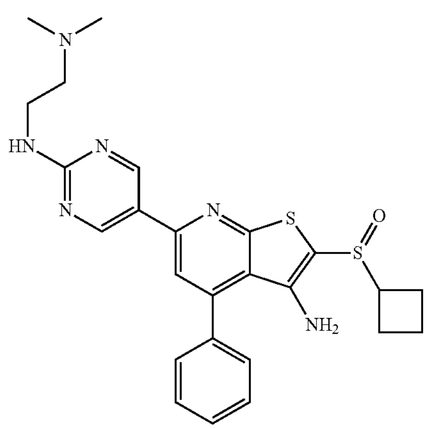 [SMILES: CN(C)CCNc1ncc(-c2cc(-c3ccccc3)c3c(N)c(S(=O)C4CCC4)sc3n2)cn1] | 8.45 (d, J = 4.9 Hz, 2H), 7.55 (s, 1H), 7.52-7.46 (m, 5H), 6.78 (t, J = 4.8 Hz, 1H), 4.64-4.55 (m, 2H), 4.49 (s, 2H), 3.99-3.89 (m, 1H), 2.85-2.71 (m, 3H), 2.48-2.28 (m, 8H), 2.28-2.16 (m, 2H), 2.13-2.00 (m, 2H). | 493.2 | |

-continued
| Ex. No. | Structure | 400 MHz NMR (δ; CDCl₃ unless otherwise noted) | LCMS (ES⁺; MH⁺) | Chiral info |
|---|---|---|---|---|
| 93 | 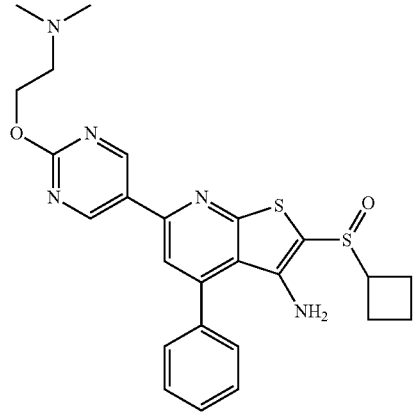 [SMILES: CN(C)CCOc1ncc(-c2cc(-c3ccccc3)c3c(N)c(S(=O)C4CCC4)sc3n2)cn1] | 9.21 (s, 2H), 7.56-7.48 (m, 6H), 4.58 (t, J = 5.6 Hz, 2H), 3.99-3.93 (m, 1H), 2.84-2.79 (m, 3H), 2.38-2.35 (m, 8H), 2.10-2.06 (m, 3H). | 494.2 | |
| 94 | 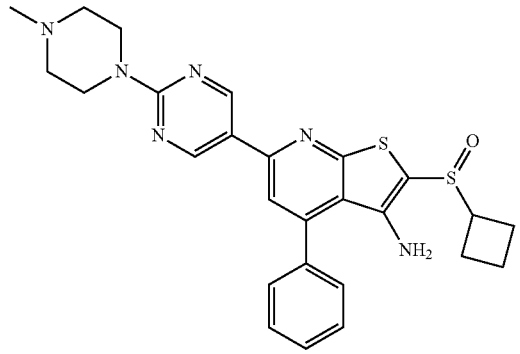 [SMILES: CN1CCN(c2ncc(-c3cc(-c4ccccc4)c4c(N)c(S(=O)C5CCC5)sc4n3)cn2)CC1] | 9.02 (s, 2H), 7.55 (m, 3H), 7.48 (m, 2H), 7.38 (s, 1H), 4.54 (s, 2H), 4.02-3.92 (m, 5H), 2.85-2.72 (m, 1H), 2.52 (m, 4H), 2.42-2.31 (m, 5H), 2.29-2.19 (m, 1H), 2.14-2.03 (m, 2H). | 505.3 | R-isomer: [α] = +57.4° S-isomer: [α] = −35.0° |
| 95 | 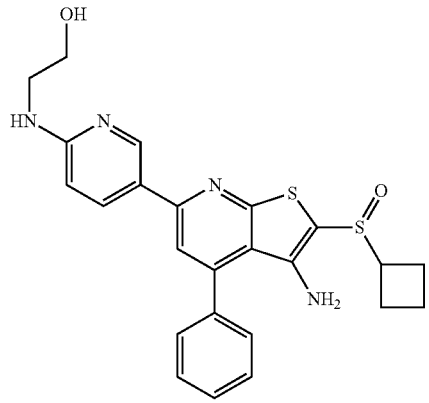 | 8.72 (d, J = 2.0 Hz, 1H), 8.24 (dd, J₁ = 2.0 Hz, J₂ = 11.2 Hz, 1H), 7.54-7.49 (m, 5H), 7.14 (s, 1H), 6.57 (d, J = 8.8 Hz, 1H), 5.24 (s, 1H), 5.54 (s, 2H), 3.97-3.93 (m, 1H), 3.65 (t, J = 4.8 Hz, 2H), 3.62-3.58 (m, 2H), 2.78-2.76 (m, 1H), 2.38-2.33 (m, 2H), 2.23 (s, 1H), 2.09-2.04 (m, 2H). | 465.0 | |
| 96 | 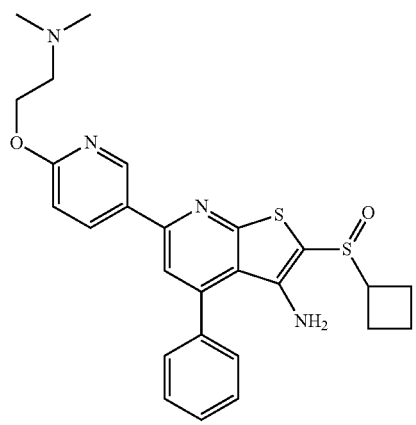 [SMILES: CN(C)CCOc1ccc(-c2cc(-c3ccccc3)c3c(N)c(S(=O)C4CCC4)sc3n2)cn1] | 8.83 (d, J = 2.4 Hz, 1H), 8.34 (dd, J₁ = 2.4 Hz, J₂ = 8.8 Hz, 1H), 7.55-7.49 (m, 6H), 6.90 (d, J = 8.8 Hz, 1H), 4.56 (s , 2H), 4.51 (t, J = 6 Hz, 1H), 4.01-3.93 (m, 1H), 2.82-2.76 (m, 2H), 2.40-2.35 (m, 8H), 2.24-2.05 (m, 3H). | 493.0 | |

| Ex. No. | Structure | 400 MHz NMR (δ; CDCl₃ unless otherwise noted) | LCMS (ES⁺; MH⁺) | Chiral info |
|---|---|---|---|---|
| 97 | 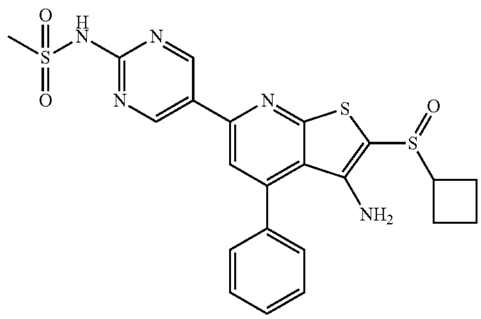 [SMILES: CS(=O)(=O)Nc1ncc(-c2cc(-c3ccccc3)c3c(N)c(S(=O)C4CCC4)sc3n2)cn1] | DMSO-d₆ 9.19 (s, 2H), 7.18 (s, 1H), 7.58-7.61 (m, 5H), 4.91 (s, 1H), 3.81-3.89 (m, 1H), 3.15 (s, 3H), 1.61-2.66 (m, 1H), 2.14-2.21 (m, 2H), 2.01-2.03 (m, 1H), 1.91-1.94 (m, 2H). | 500.1 | R-isomer: 98.2% ee; [α] = +47.6° S-isomer: 93.0% ee; [α] = −66.1° |
| 98 | 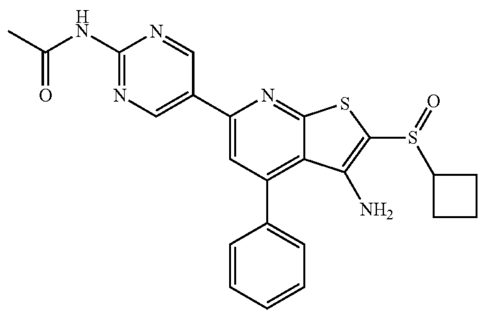 [SMILES: CC(=O)Nc1ncc(-c2cc(-c3ccccc3)c3c(N)c(S(=O)C4CCC4)sc3n2)cn1] | 9.27 (s, 2H), 8.23 (brs, 1H), 7.50-7.58 (m, 6H), 4.60 (s, 2H), 3.94-4.02 (m, 1H), 2.55-2.85 (m, 1H), 2.38 (s, 3H), 2.34-2.36 (m, 2H), 2.24-2.25 (m, 1H), 2.07-2.11 (m, 2H). | 464.2 | |
| 99 | 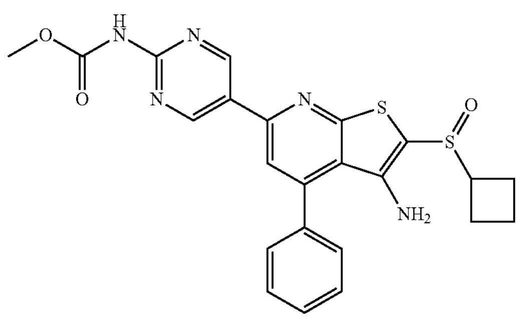 [SMILES: COC(=O)Nc1ncc(-c2cc(-c3ccccc3)c3c(N)c(S(=O)C4CCC4)sc3n2)cn1] | 9.29 (s, 2H), 9.02 (brs, 1H), 7.44-7.57 (m, 6H), 4.60 (s, 2H), 3.91-3.99 (m, 1H), 3.88 (s, 3H), 2.78-2.83 (m, 1H), 2.24-2.38 (m, 3H), 2.04-2.10 (m, 2H). | 480.1 | |
| 100 | 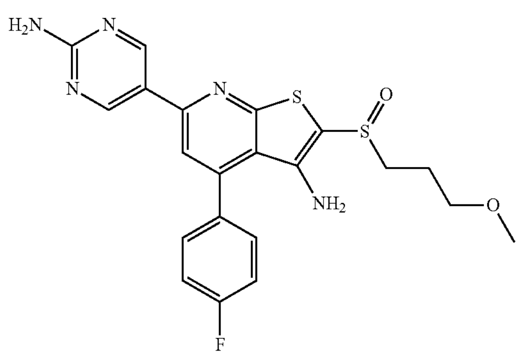 [SMILES: COCCCS(=O)c1sc2nc(-c3cnc(N)nc3)cc(-c3ccc(F)cc3)c2c1N] | 9.03 (s, 2H), 7.50-7.47 (m, 2H), 7.39 (s, 1H), 7.28-7.27 (m, 1H), 7.25-7.23 (m, 1H), 5.34 (s, 2H), 4.58 (s, 2H), 3.53-3.50 (m, 2H), 3.40-3.30 (m, 4H), 3.27-3.20 (m, 1H), 2.07-2.00 (m, 2H) | 458.2 | R-isomer: 100% ee; [α] = +29.3° S-isomer: 100% ee; [α] = −28.5° |

| Ex. No. | Structure | 400 MHz NMR (δ; CDCl₃ unless otherwise noted) | LCMS (ES⁺; MH⁺) | Chiral info |
|---|---|---|---|---|
| 101 | 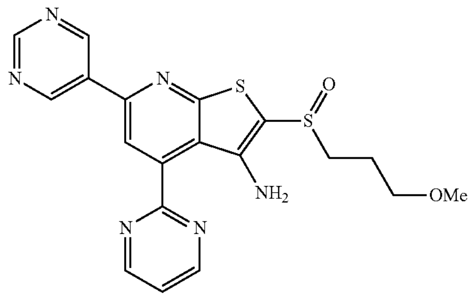 [SMILES: COCCCS(=O)c1sc2nc(-c3cncnc3)cc(-c3ncccn3)c2c1N] | 9.51 (s, 2H), 9.31 (s, 1H), 9.01 (d, J = 4.8 Hz, 2H), 8.51 (s, 1H), 7.49 (t, J = 4.8 Hz, 1H), 6.50 (s, 2H), 3.53 (t, J = 5.6 Hz, 1H), 4.43-3.36 (m, 1H), 3.36 (s, 3H), 3.31-3.22 (m, 1H), 2.09-2.02 (m, 2H). | 427.0 | R-isomer: 100% ee; [α] = +84.6° S-isomer: 100% ee; [α] = −160.5° |
| 102 | 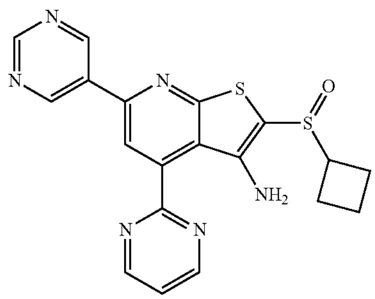 [SMILES: Nc1c(S(=O)C2CCC2)sc2nc(-c3cncnc3)cc(-c3ncccn3)c12] | 9.52 (s, 2H), 9.32 (s, 1H), 9.02 (d, J = 4.8 Hz, 2H), 8.50 (s, 1H), 7.51 (t, J = 4.8 Hz, 1H), 4.05-3.96 (m, 1H), 2.89-2.81 (m, 1H), 2.50-2.06 (m, 5H). | 409.0 | |
| 103 | 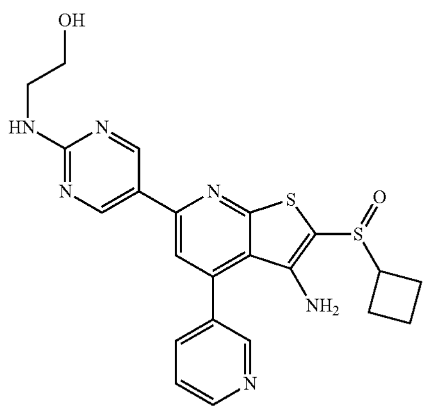 [SMILES: Nc1c(S(=O)C2CCC2)sc2nc(-c3cnc(NCCO)nc3)cc(-c3cccnc3)c12] | 8.97 (s, 2H), 8.81 (dd, J₁ = 1.6, J₂ = 4.8 Hz, 2H), 7.86 (s, 1H), 7.52-7.49 (m, 1H), 7.34 (s, 1H), 5.91 (t, J = 6.0 Hz, 1H), 4.46 (s, 2H), 3.95-3.87 (m, 3H), 3.74-3.62 (m, 3H), 2.83-2.74 (m, 1H), 2.42-2.32 (m, 2H), 2.26-2.18 (m, 1H), 2.13-2.05 (m, 2H) | 467.0 | R-isomer: 100% ee; [α] = +83.4° S-isomer: 96.5% ee; [α] = −71.0° |
| 104 | 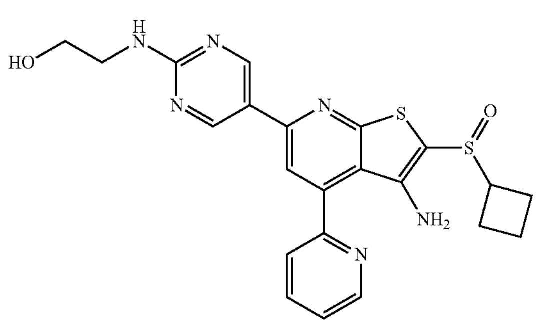 [SMILES: Nc1c(S(=O)C2CCC2)sc2nc(-c3cnc(NCCO)nc3)cc(-c3ccccn3)c12] | 9.03 (s, 2H), 8.77 (d, J = 4 Hz, 1H), 7.97-7.95 (m, 1H), 7.72 (d, J = 8 Hz, 1H), 7.53 (s, 1H), 7.50-7.49 (m, 1H), 5.83 (t, J = 6 Hz, 1H), 5.58 (s, 2H), 3.96-3.88 (m, 3H), 3.71-3.69 (m, 2H), 3.41 (s, 1H), 2.82-2.79 (m, 1H), 2.37-2.33 (m, 2H), 2.09-2.05 (m, 3H). | 467.0 | R-isomer: 98.5% ee; [α] = +128.3° S-isomer: 95.8% ee; [α] = −121.9° |

-continued

| Ex. No. | Structure | 400 MHz NMR (δ; CDCl₃ unless otherwise noted) | LCMS (ES⁺; MH⁺) | Chiral info |
|---|---|---|---|---|
| 105 | 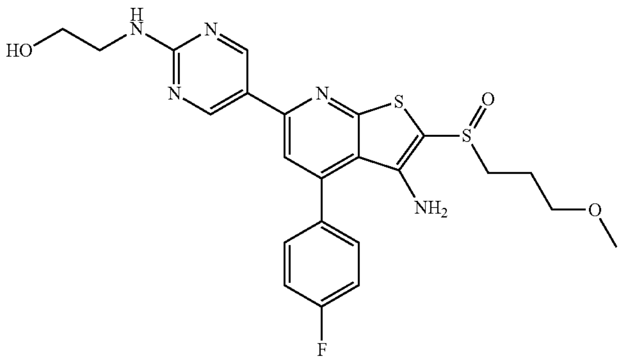 [SMILES: COCCCS(=O)c1sc2nc(-c3cnc(NCCO)nc3)cc(-c3ccc(F)cc3)c2c1N] | 8.99 (s, 2H), 7.52-7.47 (m, 2H), 7.34 (s, 1H), 7.31-7.27 (m, 1H), 7.27-7.21 (m, 1H), 6.01 (t, J = 5.8 Hz, 1H), 4.57 (br s, 2H), 3.89-3.87 (m, 2H), 3.70-3.69 (m, 2H), 3.52-3.49 (m, 2H), 3.33 (s, 4H), 3.22-3.16 (m, 1H), 2.05-2.00 (m, 2H) | 502.1 | |
| 106 | 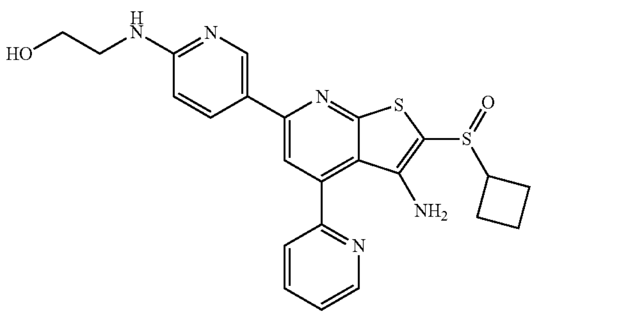 [SMILES: Nc1c(S(=O)C2CCC2)sc2nc(-c3ccc(NCCO)nc3)cc(-c3ccccn3)c12] | 8.76 (s, 2H), 8.27 (dd, J₁ = 2.4 Hz, J₂ = 8.8 Hz, 1H), 7.95-7.96 (m, 1H), 7.73 (d, J = 8 Hz, 1H), 7.58 (s, 1H), 7.47-7.49 (m, 1H), 6.57 (d, J = 8.8 Hz, 1H), 5.60 (s, 2H), 5.15 (m, 1H), 3.92-3.96 (m, 1H), 3.86 (t, J = 4.8 Hz, 2H), 3.59-3.62 (m, 2H), 2.78-2.83 (m, 1H), 2.36-2.39 (m, 2H), 2.05-2.09 (m, 3H). | 466.0 | R-isomer: 100% ee; [α] = +21.0° S-isomer: 100% ee; [α] = −52.9° |
| 107 | 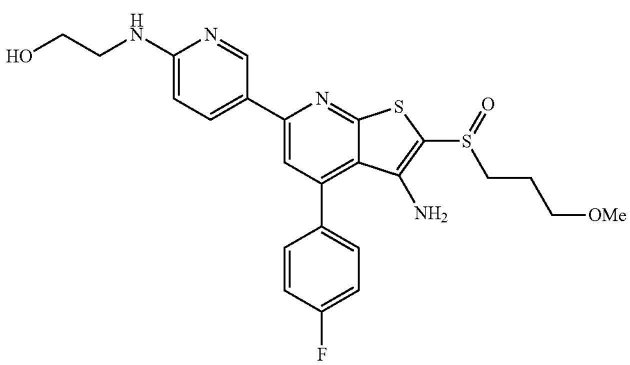 [SMILES: COCCCS(=O)c1sc2nc(-c3ccc(NCCO)nc3)cc(-c3ccc(F)cc3)c2c1N] | 8.58 (d, J = 2.0 Hz, 1H), 8.18 (dd, J₁ = 2.0, J₁ = 8.8 Hz, 1H), 7.59-7.37 (m, 2H), 7.29 (s, 2H), 7.26 (s, 1H), 6.53 (d, J = 3.6 Hz, 1H), 5.36 (t, J = 6.4 Hz, 1H), 4.54 (s, 2H), 3.90-3.80 (m, 2H), 3.57-3.55 (m, 2H), 3.52-3.47 (m, 2H), 3.36-3.29 (m, 4H), 3.21-3.14 (m, 1H), 2.02-1.95 (m, 2H) | 501.0 | |
| 108 | 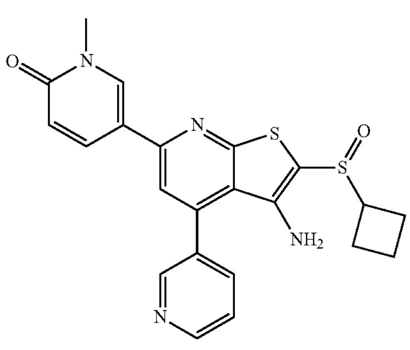 [SMILES: Cn1cc(-c2cc(-c3cccnc3)c3c(N)c(S(=O)C4CCC4)sc3n2)ccc1=O] | DMSO-d₆ 8.81-8.74 (m, 3H), 8.31 (dd, J = 2.0, 9.2 Hz, 1H), 8.01-7.99 (m, 1H), 7.77 (s, 1H), 7.59 (dd, J = 4.8, 7.6 Hz, 1H), 6.52 (d, J = 9.6 Hz, 1H), 4.89 (s, 2H), 3.89-3.81 (m, 1H), 3.54 (s, 3H), 2.64-2.61 (m, 1H), 2.24-2.12 (m, 3H), 2.08-1.97 (m, 1H), 1.96-1.86 (m, 1H) | 437.1 | |

-continued

| Ex. No. | Structure | 400 MHz NMR (δ; CDCl₃ unless otherwise noted) | LCMS (ES⁺; MH⁺) | Chiral info |
|---|---|---|---|---|
| 109 | 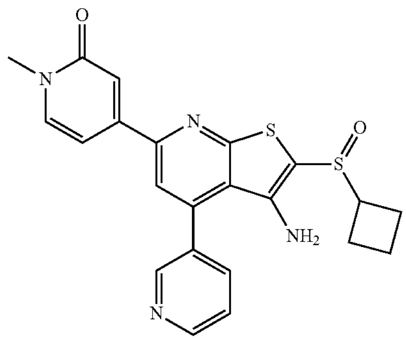 [SMILES: Cn1ccc(-c2cc(-c3cccnc3)c3c(N)c(S(=O)C4CCC4)sc3n2)cc1=O] | DMSO-d₆ 8.79 (d, J = 2.0 Hz, 1H), 8.77-8.72 (m, 1H), 8.03-8.01 (m, 1H), 7.96 (s, 1H), 7.83 (d, J = 7.2 Hz, 1H), 7.59 (dd, J = 4.8, 7.2 Hz, 1H), 7.25 (d, J = 1.6 Hz, 1H), 7.04 (dd, J = 1.6, 7.2 Hz, 1H), 4.95 (s, 2H), 3.92-3.84 (m, 1H), 3.48 (s, 3H), 2.64-2.62 (m, 1H), 2.26-2.10 (m, 3H), 2.09-1.97 (m, 1H), 1.97-1.86 (m, 1H) | 437.1 | |
| 110 | 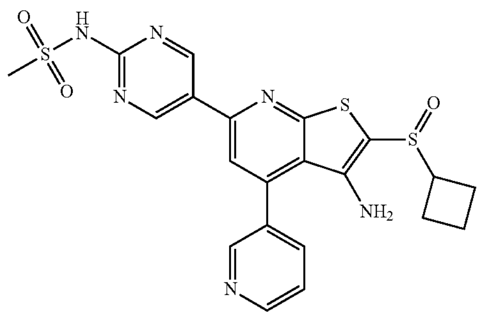 [SMILES: CS(=O)(=O)Nc1ncc(-c2cc(-c3cccnc3)c3c(N)c(S(=O)C4CCC4)sc3n2)cn1] | DMSO-d₆ 9.29 (s, 2H), 8.79 (d, J = 1.6 Hz, 1H), 8.75 (d, J = 4.0 Hz, 1H), 8.02 (d, J = 8.0 Hz, 1H), 7.94 (s, 1H), 7.61-7.58 (m, 1H), 4.93 (s, 2H), 3.91-3.83 (m, 1H), 3.27 (s, 3H), 2.66-2.61 (m, 1H), 2.18-2.16 (m, 3H), 2.07-1.98 (m, 1H), 1.95-1.89 (m, 1H) | 501.0 | |
| 111 | 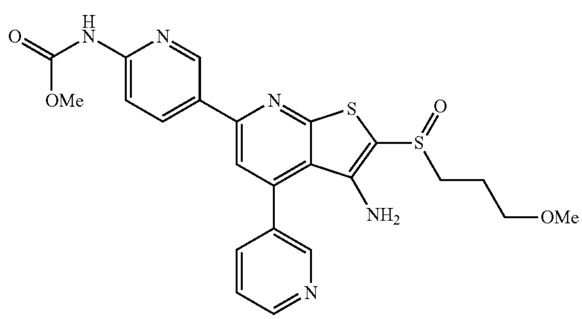 [SMILES: COCCCS(=O)c1sc2nc(-c3ccc(NC(=O)OC)nc3)cc(-c3cccnc3)c2c1N] | 8.99 (d, J = 1.6 Hz, 1H), 8.85-8.79 (m, 2H), 8.45 (dd, J = 2.0, 8.4 Hz, 1H), 8.13 (d, J = 8.8 Hz, 1H), 7.88 (d, J = 8.0 Hz, 1H), 7.55-7.49 (m, 2H), 4.52 (s, 2H), 3.85 (s, 3H), 3.53 (t, J = 6.0 Hz, 2H), 3.42-3.35 (m, 1H), 3.35 (s, 3H), 3.29-3.21 (m, 1H), 2.09-2.00 (m, 2H) | 498.2 | |
| 112 | 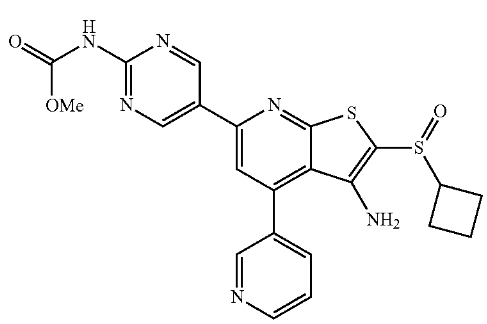 [SMILES: COC(=O)Nc1ncc(-c2cc(-c3cccnc3)c3c(N)c(S(=O)C4CCC4)sc3n2)cn1] | 9.28 (s, 2H), 8.84-8.83 (m, 1H), 8.80 (d, J = 1.6 Hz, 1H), 7.89-7.85 (m, 2H), 7.54-7.50 (m, 1H), 7.47 (s, 1H), 4.50 (br s, 2H), 3.99-3.95 (m, 1H), 3.88 (s, 3H), 2.86-2.76 (m, 1H), 2.45-2.32 (m, 2H), 2.29-2.25 (m, 1H), 2.12-2.06 (m, 2H) | 481.1 | |

| Ex. No. | Structure | 400 MHz NMR (δ; CDCl₃ unless otherwise noted) | LCMS (ES⁺; MH⁺) | Chiral info |
|---|---|---|---|---|
| 113 | 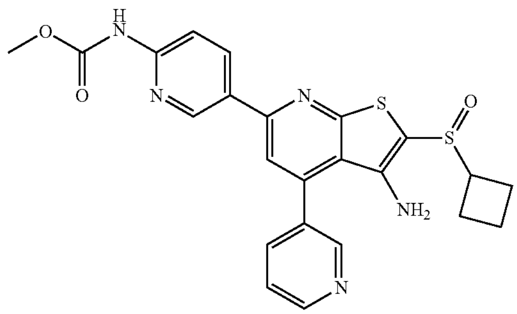 [SMILES: COC(=O)Nc1ccc(-c2cc(-c3cccnc3)c3c(N)c(S(=O)C4CCC4)sc3n2)cn1] | 8.98 (s, 1H), 8.82-8.81 (m, 2H), 8.46 (br d, J = 8.4 Hz, 1H), 8.14 (d, J = 8.8 Hz, 1H), 7.87 (br d, J = 4.6 Hz, 1H), 7.55-7.47 (m, 2H), 4.49 (br s, 2H), 3.96 (t, J = 8.0 Hz, 1H), 3.84 (s, 3H), 2.82-2.80 (m, 1H), 2.39-2.34 (m, 2H), 2.11-2.10 (m, 1H), 2.09-2.07 (m, 2H) | 480.1 | |
| 114 | 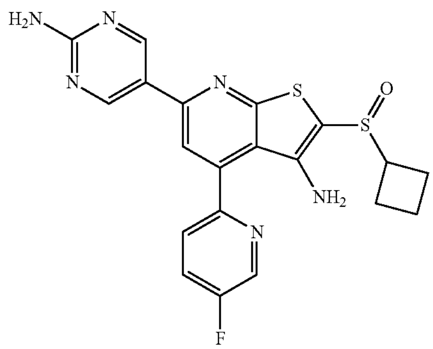 [SMILES: Nc1ncc(-c2cc(-c3ccc(F)cn3)c3c(N)c(S(=O)C4CCC4)sc3n2)cn1] | 9.04 (s, 2H), 8.64 (d, J = 2.8 Hz, 1H), 7.78-7.73 (m, 1H), 7.72-7.65 (m, 1H), 7.52 (s, 1H), 5.44 (s, 2H), 5.36 (s, 2H), 3.98-3.90 (m, 1H), 2.88-2.76 (m, 1H), 2.45-2.29 (m, 2H), 2.26-2.21 (m, 1H), 2.15-2.01 (m, 2H) | 441.0 | |
| 115 | 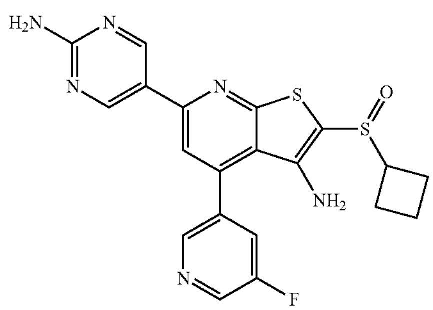 [SMILES: Nc1ncc(-c2cc(-c3cncc(F)c3)c3c(N)c(S(=O)C4CCC4)sc3n2)cn1] | DMSO-d₆ 9.06 (s, 2H), 8.74 (d, J = 2.8 Hz, 1H), 8.64-8.62 (m, 1H), 8.07-7.97 (m, 1H), 7.87 (s, 1H), 7.18 (s, 2H), 5.01 (s, 2H), 3.89-3.81 (m, 1H), 2.63-2.61 (m, 1H), 2.26-2.10 (m, 3H), 2.08-1.98 (m, 1H), 1.96-1.90 (m, 1H) | 441.1 | |
| 116 | 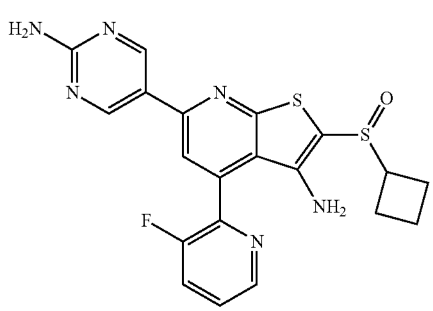 [SMILES: Nc1ncc(-c2cc(-c3ncccc3F)c3c(N)c(S(=O)C4CCC4)sc3n2)cn1] | DMSO-d₆ 9.05 (s, 2H), 8.71-8.64 (m, 1H), 8.12-8.02 (m, 2H), 7.77-7.73 (m, 1H), 7.19 (s, 2H), 5.23 (s, 2H), 3.91-3.83 (m, 1H), 2.67-2.60 (m, 1H), 2.25-2.11 (m, 3H), 2.08-1.97 (m, 1H), 1.96-1.86 (m, 1H) | 441.0 | |

-continued

| Ex. No. | Structure | 400 MHz NMR (δ; CDCl₃ unless otherwise noted) | LCMS (ES⁺; MH⁺) | Chiral info |
|---|---|---|---|---|
| 117 | 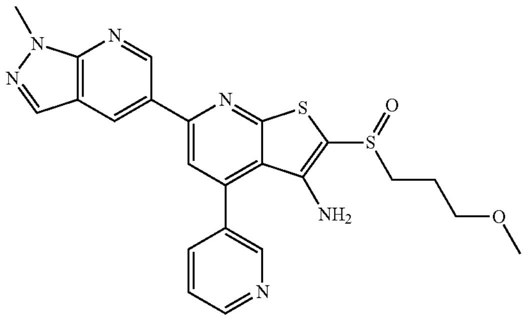 [SMILES: COCCCS(=O)c1sc2nc(-c3cnc4c(cnn4C)c3)cc(-c3cccnc3)c2c1N] | 9.29 (d, J = 2.0 Hz, 1H), 8.86-8.82 (m, 2H), 8.81 (d, J = 2.0 Hz, 1H), 8.10 (s, 1H), 7.90 (d, J = 7.6 Hz, 1H), 7.61 (s, 1H), 7.53 (dd, J = 4.8, 8.0 Hz, 1H), 4.53 (s, 2H), 4.22 (s, 3H), 3.53 (t, J = 6.0 Hz, 2H), 3.43-3.36 (m, 1H), 3.35 (s, 3H), 3.31-3.22 (m, 1H), 2.11-2.00 (m, 2H) | 479.1 | |
| 118 | 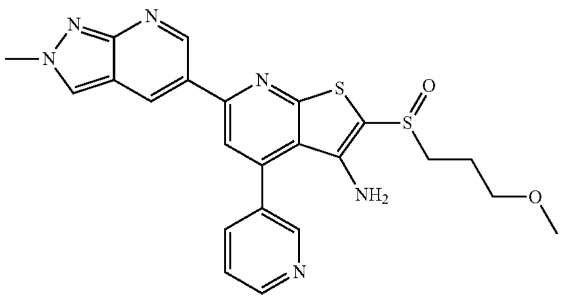 | 9.41 (d, J = 2.0 Hz, 1H), 8.85-8.80 (m, 3H), 8.04 (s, 1H), 7.90 (d, J = 7.6 Hz, 1H), 7.62 (s, 1H), 7.53 (dd, J = 5.2, 7.2 Hz, 1H), 4.52 (s, 2H), 4.31 (s, 3H), 3.53 (t, J = 6.0 Hz, 2H), 3.42-3.36 (m, 1H), 3.35 (s, 3H), 3.30-3.21 (m, 1H), 2.09-2.01 (m, 2H) | 479.1 | |
| 119 | 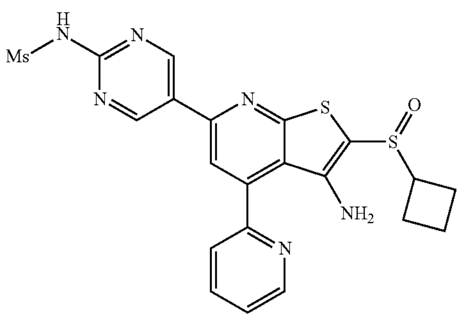 [SMILES: CS(=O)(=O)Nc1ncc(-c2cc(-c3ccccn3)c3c(N)c(S(=O)C4CCC4)sc3n2)cn1] | 9.33 (s, 2H), 8.80 (d, J = 5.6 Hz, 1H), 8.02-7.99 (m, 1H), 7.74 (d, J = 10.4 Hz, 1H), 7.64 (s, 1H), 7.53-7.49 (m, 1H), 5.63 (s, 2H), 2.86-2.80 (m, 1H), 2.41-2.04 (m, 5H). | 501.0 | |
| 120 | 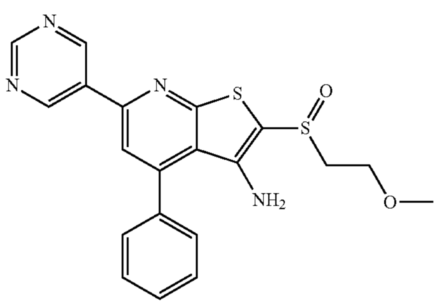 [SMILES: COCCS(=O)c1sc2nc(-c3cncnc3)cc(-c3ccccc3)c2c1N] | 9.44 (s, 2H), 9.29 (s, 1H), 7.59-7.58 (m, 4H), 7.50 (s, 2H), 4.63 (s, 2H), 3.87-3.85 (m, 1H), 3.72-3.70 (m, 1H), 3.60-3.59 (m, 1H), 3.40 (s, 3H), 3.30-3.28 (m, H) | 411.0 | R-isomer: 100% ee; [α] = +124.7° S-isomer: 100% ee; [α] = −85.5° |
| 121 | 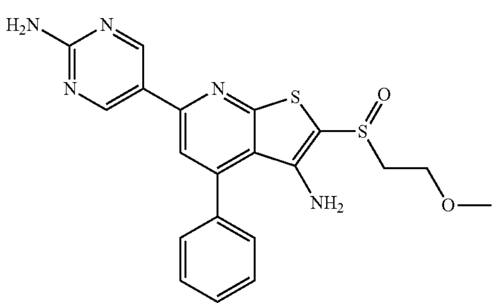 [SMILES: COCCS(=O)c1sc2nc(-c3cnc(N)nc3)cc(-c3ccccc3)c2c1N] | 9.03 (s, 2H), 7.56-7.55 (m, 3H), 7.49 (s, 2H), 7.42 (s, 1H), 5.33 (s, 2H), 4.57 (s, 2H), 3.86-3.84 (m, 1H), 3.70-3.69 (m, 1H), 3.59-3.58 (m, 1H), 3.39 (s, 3H), 3.29-3.27 (m, 1H) | 426.0 | R-isomer: 100% ee; [α] = +49.8° S-isomer: 100% ee; [α] = −54.6° |

-continued
| Ex. No. | Structure | 400 MHz NMR (δ; CDCl₃ unless otherwise noted) | LCMS (ES⁺; MH⁺) | Chiral info |
|---|---|---|---|---|
| 122 | 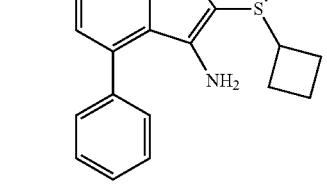 | 9.31 (s, 2H), 7.57-7.50 (m, 6H), 4.61 (s, 2H), 4.02-3.92 (m, 1H), 2.83 (s, 3H), 2.42-2.35 (m, 2H), 2.28-2.25 (m, 1H), 2.11-2.04 (m, 2H). | 421.0 | |
| 123 | 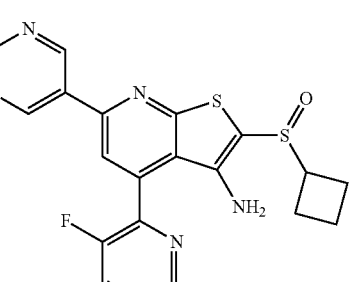 | DMSO-d₆ 9.01 (s, 2H), 8.63 (d, J = 4.0 Hz, 1H), 8.05-8.01 (m, 2H), 7.73-7.69 (m, 1H), 7.15 (s, 2H), 5.19 (s, 2H), 3.85-3.81 (t, J = 8.0 Hz, 1H), 2.64-2.57 (m, 1H), 2.19-2.08 (m, 3H), 2.01-1.83 (m, 2H). | 441.1 | |
| 124 | 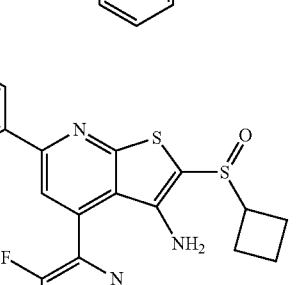 | 9.44 (s, 2H), 9.31 (s, 1H), 8.64-8.63 (m, 1H), 7.80 (d, J = 2.4 Hz, 1H), 7.77-7.71 (m, 1H), 7.58-7.54 (m, 1H), 5.60-4.92 (m, 2H), 2.91-2.72 (m, 1H), 2.52-1.93 (m, 6H). | 426.2 | |
| 125 | 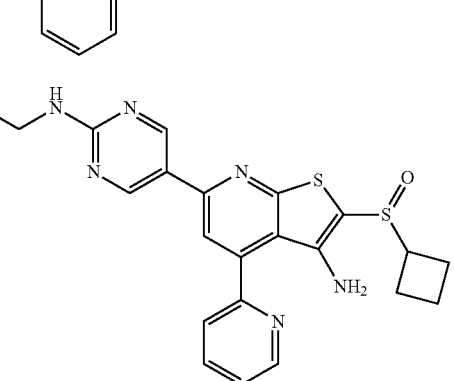 | 9.02 (s, 2H), 8.64 (d, J = 2.8 Hz, 1H), 7.74-7.72 (m, 1H), 7.71-7.68 (m, 1H), 7.49 (s, 1H), 5.83 (s, 1H), 5.43 (s, 2H), 3.98-3.88 (m, 3H), 3.71-3.68 (m, 2H), 3.52-3.38 (m, 1H), 2.84-2.79 m, 1H), 2.43-2.29 (m, 2H), 2.26-2.19 (m, 1H), 2.12-2.03 (m, 2H) | 485.0 | |
| 126 | 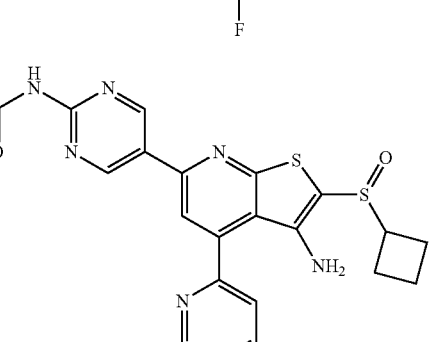 | 9.30 (s, 2H), 8.80-8.79 (m, 1H), 8.01-7.97 (m, 2H), 7.73 (d, J = 8.0 Hz, 1H), 7.55-7.46 (m, 1H), 5.62 (s, 2H), 3.99-3.91 (m, 1H), 3.79 (s, 3H), 2.85-2.97 (s, 1H), 2.48-2.11 (m, 5H). | 427.0 | |

| Ex. No. | Structure | 400 MHz NMR (δ; CDCl₃ unless otherwise noted) | LCMS (ES⁺; MH⁺) | Chiral info |
|---|---|---|---|---|
| 127 | 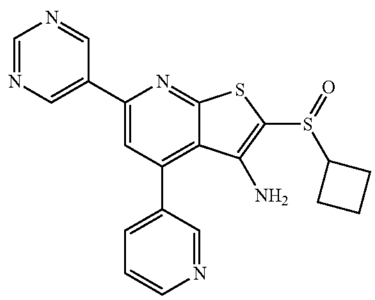 [SMILES: Nc1c(S(=O)C2CCC2)sc2nc(-c3cncnc3)cc(-c3cccnc3)c12] | 9.44 (s, 2H), 9.32 (s, 1H), 8.85-8.81 (m, 2H), 7.89-7.87 (m, 1H), 7.59 (s, 1H), 7.55-7.51 (m, 1H), 4.54 (s, 2H), 4.03-3.93 (m, 1H), 2.86-2.77 (m, 1H), 2.45-2.23 (m, 3H), 2.15-2.06 (m, 2H). | 408.0 | |
| 128 | 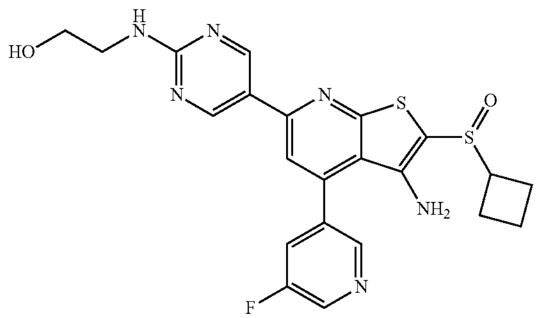 [SMILES: Nc1c(S(=O)C2CCC2)sc2nc(-c3cnc(NCCO)nc3)cc(-c3cncc(F)c3)c12] | 8.92 (s, 2H), 8.76-8.63 (m, 2H), 7.73-7.55 (m, 1H), 7.29 (s, 1H), 6.04 (t, J = 5.6 Hz, 1H), 4.45 (s, 2H), 3.98-3.82 (m, 4H), 3.76-3.63 (m, 2H), 2.84-2.72 (m, 1H), 2.41-2.30 (m, 2H), 2.29-2.17 (m, 1H), 2.13-2.03 (m, 2H) | 485.2 | |
| 129 | 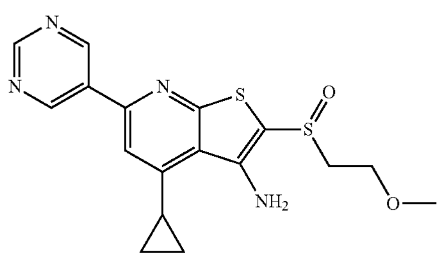 [SMILES: COCCS(=O)c1sc2nc(-c3cncnc3)cc(C3CC3)c2c1N] | 9.38 (s, 2H), 9.28 (s, 1H), 7.47 (s, 1H), 5.58 (s, 2H), 3.91-3.89 (m, 1H), 3.75-3.73 (m, 1H), 3.67-3.61 (m, 1H), 3.43 (s, 3H), 3.35-3.29 (m, 1H), 2.58-2.54 (m, 1H), 1.25-1.23 (m, 2H), 1.11-1.06 (m, 2H). | 375.0 | R-isomer: 94.0% ee; [α] = +78.0° S-isomer: 96.1% ee; [α] = −91.3° |
| 130 | 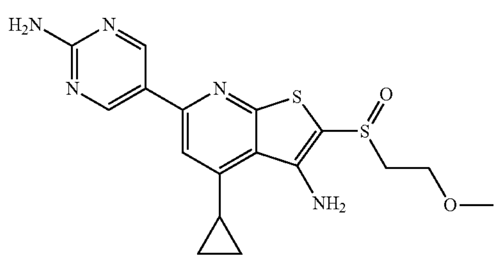 [SMILES: COCCS(=O)c1sc2nc(-c3cnc(N)nc3)cc(C3CC3)c2c1N] | 8.98 (s, 2H), 7.32 (s, 1H), 5.54 (s, 2H), 5.30 (s, 2H), 3.90-3.88 (m, 1H), 3.73-3.71 (m, 1H), 3.63-3.61 (m, 1H), 3.43 (s, 3H), 3.30-3.27 (m, 1H), 2.53-2.49 (m, 1H), 1.26 (s, 1H), 1.21-1.19 (m, 2H), 1.08-1.03 (m, 2H). | 390.0 | R-isomer: 100% ee; [α] = +57.1° S-isomer: 100% ee; [α] = −22.5° |
| 131 | 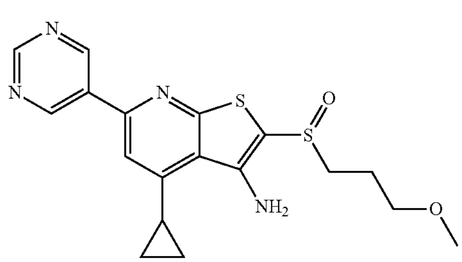 [SMILES: COCCCS(=O)c1sc2nc(-c3cncnc3)cc(C3CC3)c2c1N] | 9.37 (s, 2H), 9.28 (s, 1H), 7.46 (s, 1H), 5.62 (s, 2H), 3.55 (t, J = 4.0 Hz, 2H), 3.44-3.39 (m, 1H), 3.36 (s, 3H), 3.31-3.24 (m, 1H), 2.60-2.53 (m, 1H), 2.11-2.05 (m, 2H), 1.26-1.21 (m, 2H), 1.14-1.02 (m, 2H). | 389.0 | R-isomer: 100% ee; [α] = +72.5° S-isomer: 98.0% ee; [α] = −67.5° |

| Ex. No. | Structure | 400 MHz NMR (δ; CDCl₃ unless otherwise noted) | LCMS (ES⁺; MH⁺) | Chiral info |
|---|---|---|---|---|
| 132 | 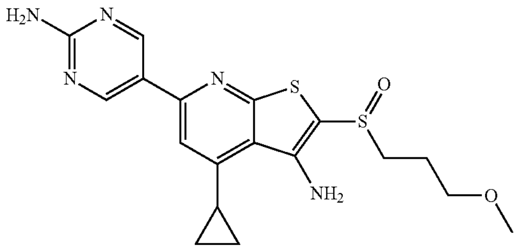 [SMILES: COCCCS(=O)c1sc2nc(-c3cnc(N)nc3)cc(C3CC3)c2c1N] | 8.98 (s, 2H), 7.31 (s, 1H), 5.57 (s, 2H), 5.32 (s, 2H), 3.54 (t, J = 6.1 Hz, 2H), 3.44-3.37 (m, 1H), 3.36 (s, 3H), 3.31-3.22 (m, 1H), 2.55-2.48 (m, J = 5.4, 8.3 Hz, 1H), 2.11-2.02 (m, 2H), 1.23-1.16 (m, 2H), 1.12-0.98 (m, 2H). | 404.0 | R-isomer: 98.2% ee; [α] = +38.4° S-isomer: 98.9% ee; [α] = −32.8° |
| 133 | 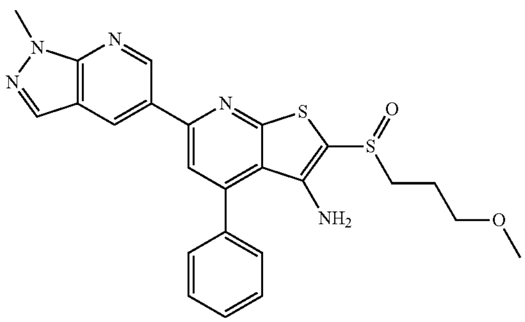 [SMILES: COCCCS(=O)c1sc2nc(-c3cnc4c(cnn4C)c3)cc(-c3ccccc3)c2c1N] | 9.29 (d, J = 2.1 Hz, 1H), 8.81 (d, J = 2.0 Hz, 1H), 8.10 (s, 1H), 7.62 (s, 1H), 7.60-7.49 (m, 5H), 4.63 (s, 2H), 4.22 (s, 3H), 3.55-3.50 (m, 2H), 3.42-3.36 (m, 1H), 3.35 (s, 3H), 3.30-3.20 (m, 1H), 2.07-2.01 (m, 2H). | 478.1 | |
| 134 | 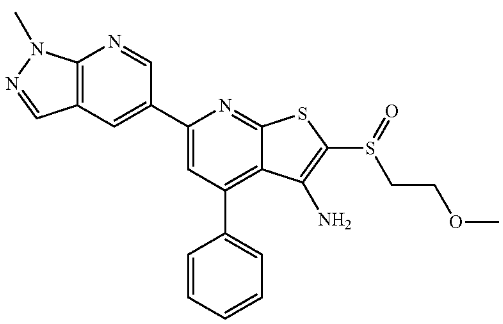 [SMILES: COCCS(=O)c1sc2nc(-c3cnc4c(cnn4C)c3)cc(-c3ccccc3)c2c1N] | 9.29 (d, J = 2.0 Hz, 1H), 8.82 (d, J = 2.0 Hz, 1H), 8.10 (s, 1H), 7.63 (s, 1H), 7.58-7.57 (m, 5H), 4.60 (s, 2H), 4.22 (s, 3H), 3.91-3.83 (m, 1H), 3.75-3.66 (m, 1H), 3.66-3.57 (m, 1H), 3.40 (s, 3H), 3.33-3.24 (m, 1H) | 464.1 | |
| 135 | 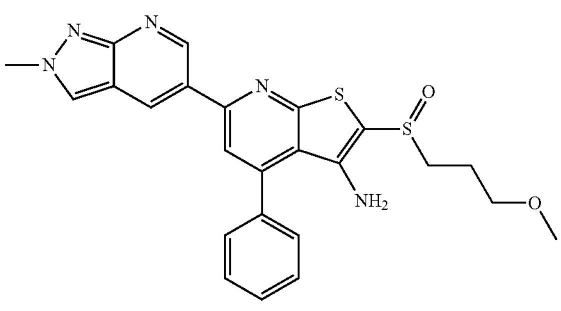 | 9.40 (d, J = 4.0 Hz, 1H), 8.78 (d, J = 4.0 Hz, 1H), 8.01 (s, 1H), 7.61 (s, 1H), 7.56-7.55 (m, 3H), 7.53-7.51 (m, 2H), 4.62 (s, 2H), 4.30 (s, 3H), 3.51 (t, J = 5.6 Hz, 2H), 3.38-3.35 (m, 1H), 3.34 (s, 3H), 3.25-3.23 (m, 1H), 2.06-2.00 (m, 2H). | 478.0 | |
| 136 | 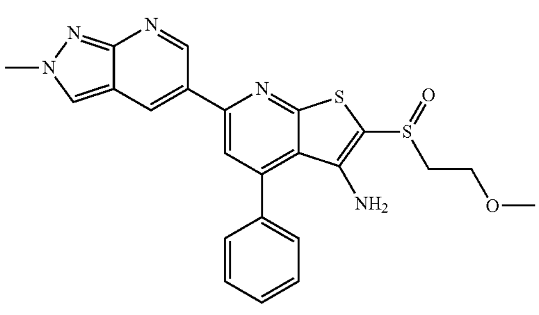 | 9.40 (d, J = 4.0 Hz, 1H), 8.82 (d, J = 4.0 Hz, 1H), 8.03 (s, 1H), 7.64 (s, 1H), 7.57-7.55 (m, 3H), 7.52 (s, 2H), 4.60 (s, 2H), 4.31 (s, 3H), 3.87-3.85 (m, 1H), 3.72-3.70 (m, 1H), 3.61-3.60 (m, 1H), 3.40 (s, 3H), 3.31-3.29 (m, 1H). | 464.0 | R-isomer: 100% ee; [α] = +40.2° S-isomer: 94.6% ee; [α] = −45.4° |

| Ex. No. | Structure | 400 MHz NMR (δ; CDCl₃ unless otherwise noted) | LCMS (ES⁺; MH⁺) | Chiral info |
|---|---|---|---|---|
| 137 | 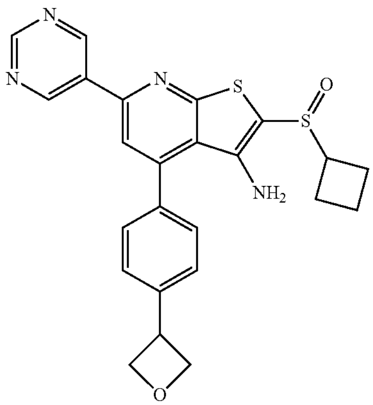 [SMILES: Nc1c(S(=O)C2CCC2)sc2nc(-c3cncnc3)cc(-c3ccc(C4COC4)cc3)c12] | DMSO-d₆ 9.55 (s, 2H), 9.27 (s, 1H), 8.03 (s, 1H), 7.65-7.60 (m, 4H), 5.05-4.97 (m, 4H), 4.71-4.68 (m, 2H), 4.44-4.34 (m, 1H), 3.86 (m, 1H), 2.65-2.57 (m, 1H), 2.24-2.10 (m, 3H), 2.06-1.96 (m, 1H), 1.91 (m, 1H) | 436.2 | |
| 138 | 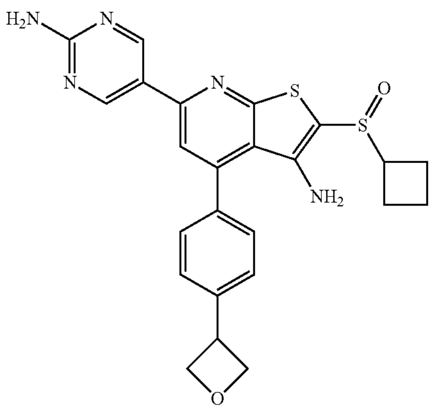 [SMILES: Nc1ncc(-c2cc(-c3ccc(C4COC4)cc3)c3c(N)c(S(=O)C4CCC4)sc3n2)cn1] | DMSO-d₆ 9.05 (s, 2H), 7.75 (s, 1H), 7.67-7.53 (m, 4H), 7.13 (s, 2H), 5.01 (m, 2H), 4.94 (s, 2H), 4.70 (t, J = 6.2 Hz, 2H), 4.39 (m, 1H), 3.84 (m, 1H), 2.72-2.54 (m, 2H), 2.18-2.10 (m, 2H), 2.07-1.85 (m, 2H) | 478.0 | |
| 139 | 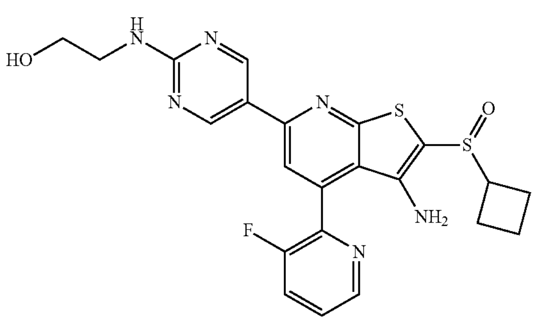 [SMILES: Nc1c(S(=O)C2CCC2)sc2nc(-c3cnc(NCCO)nc3)cc(-c3ncccc3F)c12] | 9.01 (s, 2H), 8.61 (dd, J₁ = 1.2 Hz, J₂ = 4.8 Hz, 1H), 7.70-7.68 (m, 1H), 7.60 (d, J = 2.4 Hz, 1H), 7.55-7.52 (m, 1H), 5.85 (s, 1H), 2.13 (s, 2H), 3.93-3.87 (m, 3H), 3.71-3.67 (m, 2H), 3.45-3.35 (m, 1H), 2.80-2.79 (m, 1H), 2.44-1.99 (m, 5H). | 485.0 | R-isomer: 100% ee; [α] = +3.8° S-isomer: 97.7% ee; [α] = −69.4° |
| 140 | 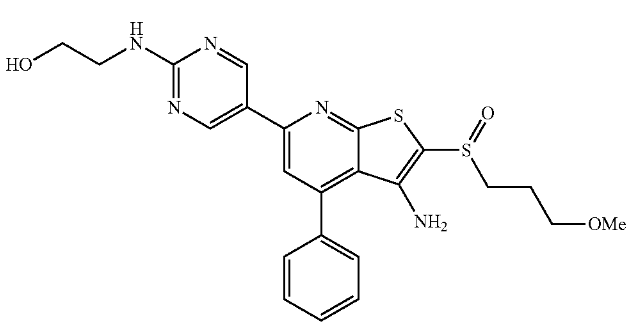 [SMILES: COCCCS(=O)c1sc2nc(-c3cnc(NCCO)nc3)cc(-c3ccccc3)c2c1N] | 8.95 (s, 2H), 7.57-7.56 (m, 4H), 7.44 (m, 1H), 7.33 (s, 1H), 5.97 (t, J = 6.0 Hz, 1H), 4.59 (s, 2H), 3.90-3.88 (m, 3H), 3.70-3.66 (m, 2H), 3.51-3.48 (m, 2H), 3.33 (s, 3H), 3.20-3.17 (m, 1H), 2.03-1.97 (m, 3H). | 484.0 | |

| Ex. No. | Structure | 400 MHz NMR (δ; CDCl₃ unless otherwise noted) | LCMS (ES⁺; MH⁺) | Chiral info |
|---|---|---|---|---|
| 141 | 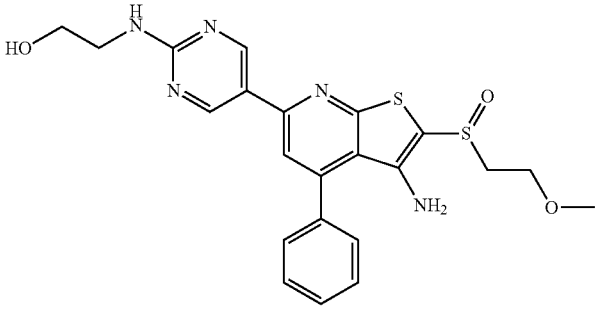 [SMILES: COCCS(=O)c1sc2nc(-c3cnc(NCCO)nc3)cc(-c3ccccc3)c2c1N] | 8.96 (s, 2H), 7.56-7.48 (m, 4H), 7.48-7.41 (m, 1H), 7.35 (s, 1H), 6.01 (t, J = 5.6 Hz, 1H), 4.57 (s, 2H), 3.94-3.80 (m, 4H), 3.70-3.65 (m, 2H), 3.59-3.54 (m, 1H), 3.38 (s, 3H), 3.29-3.19 (m, 1H) | 470.0 | R-isomer: 100% ee; [α] = +40.533°; S-isomer: 99% ee; [α] = −39.950°; |
| 142 | 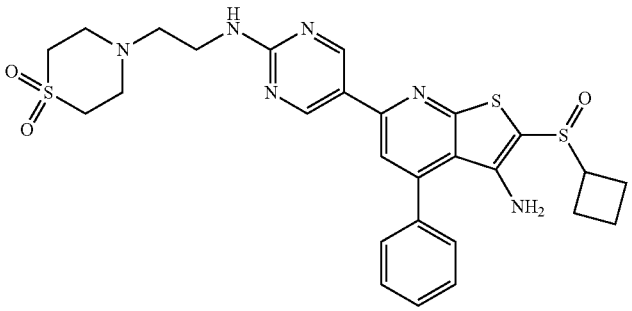 [SMILES: Nc1c(S(=O)C2CCC2)sc2nc(-c3cnc(NCCN4CCS(=O)(=O)CC4)nc3)cc(-c3ccccc3)c12] | DMSO-d₆ 9.09 (s, 2H), 7.75 (s, 1H), 7.61-7.55 (m, 5H), 4.91 (s, 2H), 3.88-3.80 (m, 1H), 3.50-3.46 (m, 2H), 3.09-3.07 (m, 4H), 2.98-2.97 (m, 4H), 2.71-2.67 (m, 2H), 2.21-2.14 (m, 2H), 2.05-1.89 (m, 2H). | 583.3 | |
| 143 | 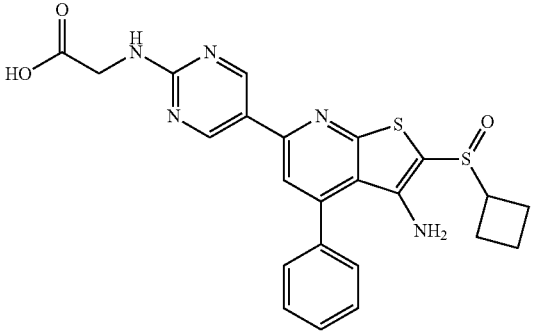 [SMILES: Nc1c(S(=O)C2CCC2)sc2nc(-c3cnc(NCC(=O)O)nc3)cc(-c3ccccc3)c12] | DMSO-d₆ 9.09 (s, 2H), 7.76 (s, 1H), 7.61-7.56 (m, 5H), 4.91 (s, 2H), 3.87-3.80 (m, 3H), 2.66-2.64 (m, 1H), 2.21-2.13 (m, 3H), 2.02-2.00 (m, 1H), 1.92-1.91 (m, 1H). | 480.1 | |
| 144 | 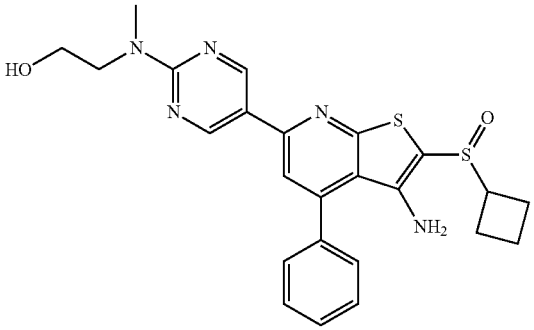 [SMILES: CN(CCO)c1ncc(-c2cc(-c3ccccc3)c3c(N)c(S(=O)C4CCC4)sc3n2)cn1] | 9.02 (s, 2H), 7.56-7.55 (m, 3H), 7.48 (s, 2H), 7.37 (s, 1H), 4.55 (s, 2H), 3.98-3.93 (m, 3H), 3.89-3.86 (m, 2H), 3.32 (s, 3H), 2.83-2.74 (m, 1H), 2.39-2.34 (m, 2H), 2.26-2.22 (m, 1H), 2.10-2.06 (m, 2H). | 480.1 | R-isomer: 100% ee; [α] = +80.2° S-isomer: 98.3% ee; [α] = −64.3° |

-continued

| Ex. No. | Structure | 400 MHz NMR (δ; CDCl₃ unless otherwise noted) | LCMS (ES⁺; MH⁺) | Chiral info |
|---|---|---|---|---|
| 145 | (structure) | 8.98 (s, 2H), 7.60-7.44 (m, 5H), 7.36 (s, 1H), 5.96 (s, 1H), 4.55 (s, 2H), 3.96-3.92 (m, 1H), 3.78-3.72 (m, 6H), 3.64-3.64 (m, 2H), 2.80-2.75 (m, 1H), 2.65 (s, 1H), 2.35-2.34 (m, 2H), 2.23-2.22 (m, 1H), 2.09-2.05 (m, 2H) | 510.2 | R-isomer: 100% ee; [α] = +86.3° S-isomer: 100% ee; [α] = −83.1° |
| 146 | (structure) | 8.93 (s, 2H), 7.50-7.45 (m, 3H), 7.40 (m, 2H), 7.31 (m, 1H), 5.79 (m, 1H), 4.50-4.44 (m, 2H), 3.88 (m, 1H), 3.69-3.57 (m, 4H), 3.46 (m, 2H), 2.85-2.80 (m, 2H), 2.75-2.65 (m, 1H), 2.35-2.23 (m, 2H), 2.20-2.10 (m, 1H), 2.04-1.93 (m, 2H). | 509.1 | |
| 147 | (structure) | DMSO-d₆ 9.08 (s, 2H), 7.75 (s, 1H), 7.60-7.56 (m, 5H), 4.90 (s, 2H), 4.47 (t, J = 5.2 Hz, 2H), 3.86-3.82 (m, 1H), 3.50-3.45 (m, 4H), 3.40-3.36 (m, 2H), 2.73-2.68 (m, 1H), 2.18-2.14 (m, 3H), 2.03-2.00 (m, 1H), 1.87-1.84 (m, 2H). | 510.2 | |
| 148 | (structure) | DMSO-d₆ 9.07 (s, 2H), 7.84 (d, J = 1.6 Hz, 1H), 7.68-7.55 (m, 3H), 7.49-7.40 (m, 2H), 4.83 (d, J = 3.2 Hz, 2H), 4.72 (t, J = 5.6 Hz, 1H), 3.84 (t, J = 8.0 Hz, 1H), 3.54-3.52 (m, 2H), 3.44-3.41 (m, 2H), 2.64-2.58 (m, 1H), 2.17-2.13 (m, 3H), 2.06-1.97 (m, 1H), 1.95-1.86 (m, 1H) | 484.1 | |

| Ex. No. | Structure | 400 MHz NMR (δ; CDCl₃ unless otherwise noted) | LCMS (ES⁺; MH⁺) | Chiral info |
|---|---|---|---|---|
| 149 | 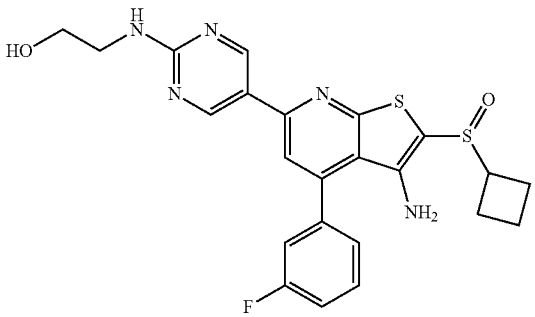 [SMILES: Nc1c(S(=O)C2CCC2)sc2nc(-c3cnc(NCCO)nc3)cc(-c3cccc(F)c3)c12] | DMSO-d₆ 9.08 (s, 2H), 7.79 (s, 1H), 7.63-7.59 (m, 2H), 7.59-7.38 (m, 3H), 4.92 (s, 2H), 4.78-4.67 (m, 1H), 3.86-3.81 (m, 1H), 3.53 (s, 2H), 3.44-3.39 (m, 2H), 2.66-2.60 (m, 1H), 2.21-2.13 (m, 3H), 2.02-1.92 (m, 2H). | 484.1 | |
| 150 | 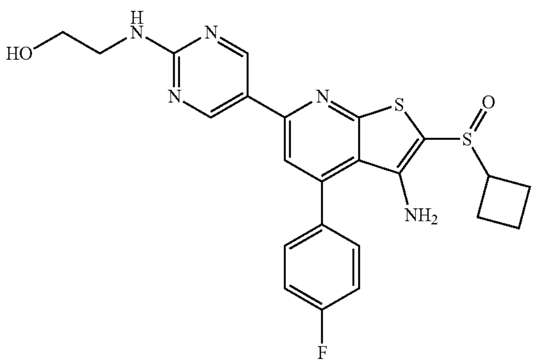 [SMILES: Nc1c(S(=O)C2CCC2)sc2nc(-c3cnc(NCCO)nc3)cc(-c3ccc(F)cc3)c12] | DMSO-d₆ 9.08 (s, 2H), 7.75 (s, 1H), 7.65-7.58 (m, 3H), 7.43 (m, 2H), 4.91 (s, 2H), 4.74 (s, 1H), 3.88-3.79 (m, 1H), 3.54 (t, J = 6.0 Hz, 2H), 3.42 (t, J = 6.2 Hz, 2H), 2.67-2.58 (m, 1H), 2.22-2.13 (m, 3H), 2.06-1.97 (m, 1H), 1.92 (m, 1H). | 484.0 | |
| 151 | 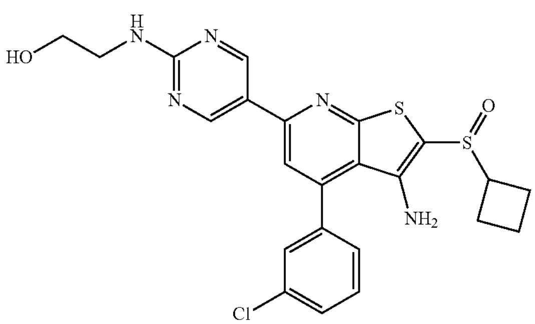 [SMILES: Nc1c(S(=O)C2CCC2)sc2nc(-c3cnc(NCCO)nc3)cc(-c3cccc(Cl)c3)c12] | DMSO-d₆ 9.09 (s, 2H), 7.80 (s, 1H), 7.70 (s, 1H), 7.68-7.56 (m, 3H), 7.56-7.49 (m, 1H), 4.92 (s, 2H), 4.74 (t, J = 5.4 Hz, 1H), 3.91-3.78 (m, 1H), 3.58-3.50 (m, 2H), 3.42 (m, 2H), 2.70-2.58 (m, 1H), 2.23-2.10 (m, 3H), 2.09-1.97 (m, 1H), 1.97-1.86 (m, 1H) | 500.1 | |
| 152 | 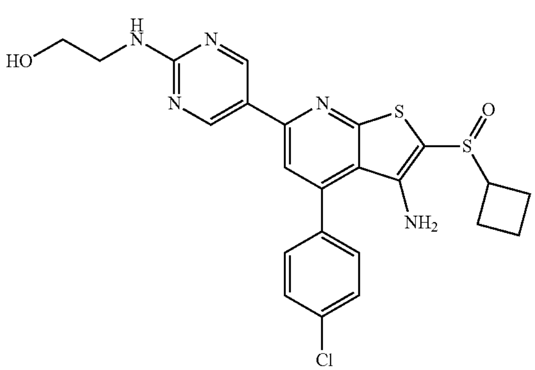 [SMILES: Nc1c(S(=O)C2CCC2)sc2nc(-c3cnc(NCCO)nc3)cc(-c3ccc(Cl)cc3)c12] | DMSO-d₆ 9.08 (s, 2H), 7.76 (s, 1H), 7.67-7.64 (m, 2H), 7.61-7.59 (m, 2H), 4.92 (s, 2H), 4.74 (t, J = 5.6 Hz, 1H), 3.89-3.80 (m, 1H), 3.54 (q, J = 6.0 Hz, 2H), 3.45-3.41 (m, 2H), 2.67-2.60 (m, 1H), 2.23-2.11 (m, 3H), 2.06-1.98 (m, 1H), 1.97-1.87 (m, 1H) | 500.0 | |

| Ex. No. | Structure | 400 MHz NMR (δ; CDCl₃ unless otherwise noted) | LCMS (ES⁺; MH⁺) | Chiral info |
|---|---|---|---|---|
| 153 | 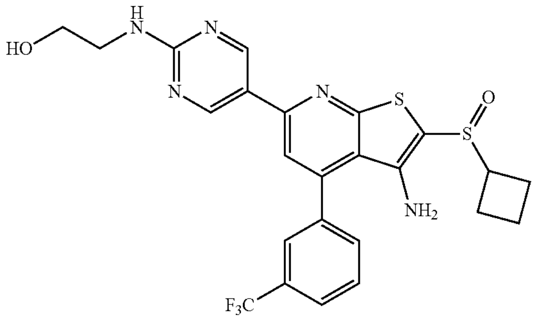 [SMILES: Nc1c(S(=O)C2CCC2)sc2nc(-c3cnc(NCCO)nc3)cc(-c3cccc(C(F)(F)F)c3)c12] | 9.01 (s, 2H), 7.86-7.68 (m, 4H), 7.37 (s, 1H), 5.85 (t, J = 6.0 Hz, 1H), 4.52-4.41 (m, 2H), 4.00-3.94 (m, 1H), 3.93-3.88 (m, 2H), 3.74-3.68 (m, 2H), 2.86-2.74 (m, 1H), 2.45-2.33 (m, 2H), 2.32-2.20 (m, 1H), 2.15-2.05 (m, 2H) | 534.3 | |
| 154 | 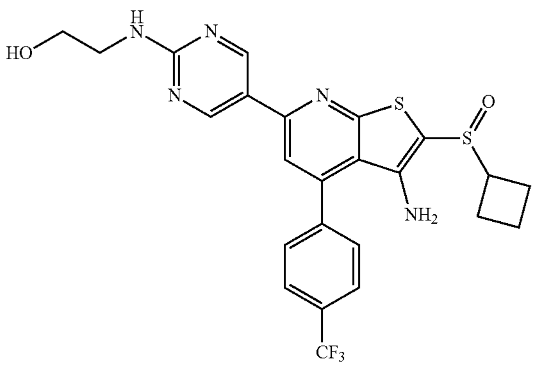 [SMILES: Nc1c(S(=O)C2CCC2)sc2nc(-c3cnc(NCCO)nc3)cc(-c3ccc(C(F)(F)F)cc3)c12] | DMSO-d₆ 9.09 (s, 2H), 7.95 (d, J = 8.4 Hz, 2H), 7.86-7.78 (m, 3H), 7.63 (t, J = 5.8 Hz, 1H), 4.87 (s, 2H), 4.74 (m, 1H), 3.85 (m, 1H), 3.54 (m, 2H), 3.42 (m, 2H), 2.69-2.61 (m, 1H), 2.23-2.10 (m, 3H), 2.09-1.97 (m, 1H), 1.97-1.85 (m, 1H) | 534.2 | |
| 155 | 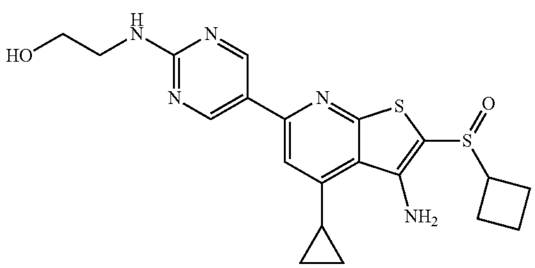 [SMILES: Nc1c(S(=O)C2CCC2)sc2nc(-c3cnc(NCCO)nc3)cc(C3CC3)c12] | DMSO-d₆ 9.03 (s, 2H), 7.56 (t, J = 5.6 Hz, 1H), 7.47 (s, 1H), 5.97 (s, 2H), 4.73 (t, J = 5.6 Hz, 1H), 3.90-3.86 (m, 1H), 3.55-3.52 (m, 2H), 3.45-3.42 (m, 2H), 2.64-2.61 (m, 2H), 2.21-2.15 (m, 3H), 2.08-1.82 (m, 2H), 1.13-1.07 (m, 4H). | 430.1 | R-isomer: 99% ee; [α] = +165.085° S-isomer: 99% ee; [α] = −142.011° |
| 156 | 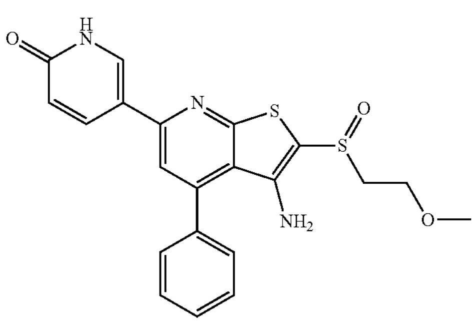 [SMILES: COCCS(=O)c1sc2nc(-c3ccc(=O)[nH]c3)cc(-c3ccccc3)c2c1N] | DMSO-d₆ 8.38 (d, J = 2.4 Hz, 1H), 8.31 (dd, J = 2.4 Hz, J = 9.6 Hz, 1H), 7.73 (s, 1H), 7.61-7.54 (m, 5H), 6.43 (d, J = 10.0 Hz, 1H), 4.94 (s, 2H), 3.75-3.69 (m, 1H), 3.64-3.59 (m, 1H), 3.27 (s, 3H), 3.22-3.13 (m, 2H) | 426.1 | |

| Ex. No. | Structure | 400 MHz NMR (δ; CDCl₃ unless otherwise noted) | LCMS (ES⁺; MH⁺) | Chiral info |
|---|---|---|---|---|
| 157 | 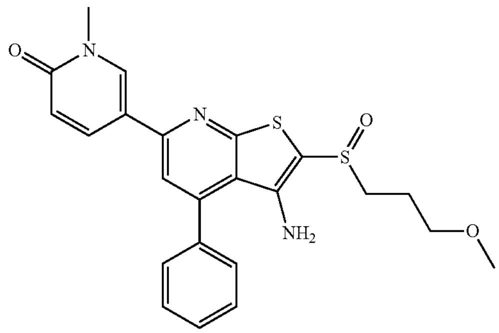 [SMILES: COCCCS(=O)c1sc2nc(-c3ccc(=O)n(C)c3)cc(-c3ccccc3)c2c1N] | DMSO-d₆ 8.76 (d, J = 2.4 Hz, 1H), 8.32 (dd, J₁ = 9.6 Hz, J₂ = 2.4 Hz, 1H), 7.73 (s, 1H), 7.62-7.57 (m, 5H), 6.52 (d, J = 9.6 Hz, 1H), 4.92 (s, 2H), 3.55 (s, 3H), 3.42 (t, J = 6.0 Hz, 2H), 3.22 (s, 3H), 3.18-3.11 (m, 1H), 3.05-2.98 (m, 1H), 1.85-1.80 (m, 2H). | 454.2 | R-isomer: 100% ee; [α] = +42.2° S-isomer: 100% ee; [α] = −42.2° |
| 158 | 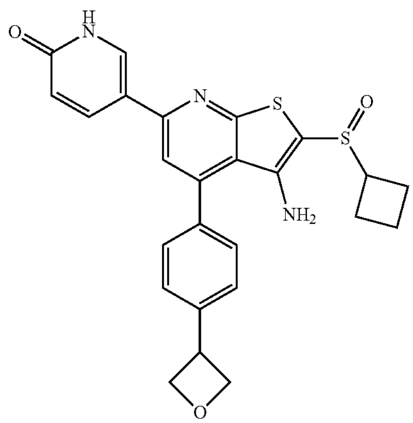 [SMILES: Nc1c(S(=O)C2CCC2)sc2nc(-c3ccc(=O)[nH]c3)cc(-c3ccc(C4COC4)cc3)c12] | DMSO-d₆ 8.35 (d, J = 2.8 Hz, 1H), 8.29 (dd, J₁ = 9.6 Hz, J₂ = 2.8 Hz, 1H), 7.70 (s, 1H), 7.63-7.55 (m, 4H), 6.43 (d, J = 9.2 Hz, 1H), 5.01 (dd, J₁ = 8.8 Hz, J₂ = 6.4 Hz, 2H), 4.93 (s, 2H), 4.69 (t, J = 6.0 Hz, 2H), 4.43-4.36 (m, 1H), 3.83 (t, J = 7.2 Hz, 1H), 2.65-2.60 (m, 1H), 2.20-2.12 (m, 3H), 2.05-1.98 (m, 1H), 1.96-1.88 (m, 1H). | 478.3 | |
| 159 | 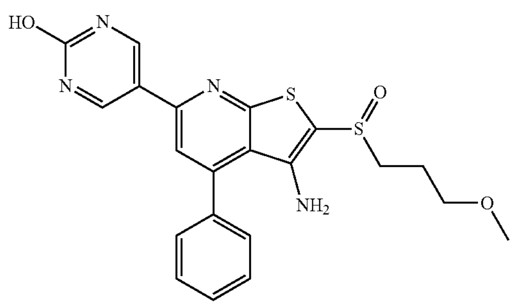 [SMILES: COCCCS(=O)c1sc2nc(-c3cnc(O)nc3)cc(-c3ccccc3)c2c1N] | DMSO-d₆ 9.38 (s, 2H), 7.95 (s, 1H), 7.61 (s, 5H), 4.95 (s, 2H), 4.69 (s, 1H), 4.01 (s, 3H), 3.49 (t, J = 6.2 Hz, 2H), 3.17 (m, 1H), 3.09-2.98 (m, 1H), 1.82-1.64 (m, 2H). | 441.1 | |
| 160 | 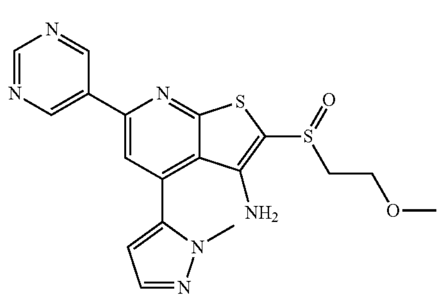 [SMILES: COCCS(=O)c1sc2nc(-c3cncnc3)cc(-c3ccnn3C)c2c1N] | 9.37 (s, 2H), 9.25 (s, 1H), 7.62 (d, J = 2.0 Hz, 1H), 7.58 (s, 1H), 6.45-6.43 (m, 1H), 4.48 (d, J = 28.8 Hz, 2H), 3.82-3.79 (m, 1H), 3.70 (s, 3H), 3.65-3.52 (m, 2H), 3.34 (s, 3H), 3.21-3.19 (m, 1H). | 415.0 | |

| Ex. No. | Structure | 400 MHz NMR (δ; CDCl₃ unless otherwise noted) | LCMS (ES⁺; MH⁺) | Chiral info |
|---|---|---|---|---|
| 161 | 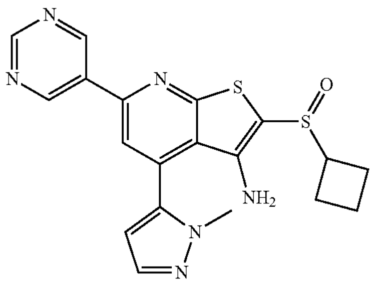 [SMILES: Cn1nccc1-c1cc(-c2cncnc2)nc2sc(S(=O)C3CCC3)c(N)c12] | 9.44 (s, 2H), 9.32 (s, 1H), 7.69 (s, 1H), 7.63 (m, 1H), 6.50 (m, 1H), 4.65-4.50 (m, 2H), 3.95 (m, 1H), 3.76 (s, 3H), 2.89-2.78 (m, 1H), 2.48-2.22 (m, 3H), 2.17-2.04 (m, 2H) | 411.2 | R-isomer: 100% ee; [α] = +155.822°; S-isomer: 99% ee; [α] = −152.807°; |
| 162 | 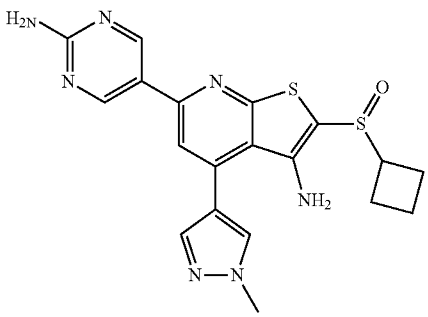 [SMILES: Cn1cc(-c2cc(-c3cnc(N)nc3)nc3sc(S(=O)C4CCC4)c(N)c23)cn1] | DMSO-d₆ 9.02 (s, 2H), 8.15 (s, 1H), 7.81 (s, 1H), 7.72 (s, 1H), 7.12 (s, 2H), 5.36 (s, 2H), 3.95 (s, 3H), 3.89-3.81 (m, 1H), 2.68-2.59 (m, 1H), 2.23-2.14 (m, 3H), 2.07-1.98 (m, 1H), 1.96-1.88 (m, 1H) | 426.2 | R-isomer: 100% ee; [α] = +147.330°; S-isomer: 100% ee; [α] = −115.373°; |
| 163 | 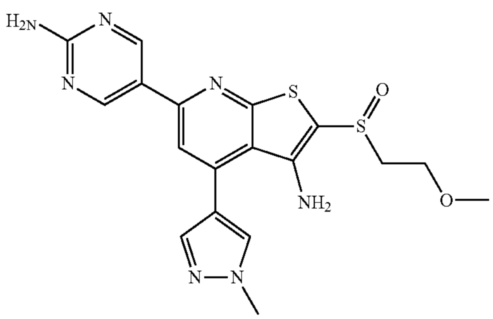 [SMILES: COCCS(=O)c1sc2nc(-c3cnc(N)nc3)cc(-c3cnn(C)c3)c2c1N] | DMSO-d₆ 9.03 (s, 2H), 8.15 (s, 1H), 7.81 (s, 1H), 7.73 (s, 1H), 7.12 (s, 2H), 5.37 (s, 2H), 3.95 (s, 3H), 3.76-3.70 (m, 1H), 3.64-3.60 (m, 1H), 3.40-3.36 (m, 1H), 3.28 (s, 3H), 3.22-3.17 (m, 1H). | 430.2 | |
| 164 | 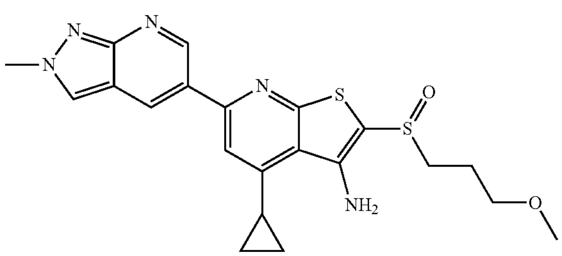 | 9.36 (d, J = 2.0 Hz, 1H), 8.75 (d, J = 2.0 Hz, 1H), 8.03 (s, 1H), 7.52 (s, 1H), 5.60 (s, 2H), 4.32 (s, 3H), 3.58-3.54 (m, 2H), 3.45-3.39 (m, 1H), 3.38 (s, 3H), 3.33-3.24 (m, 1H), 2.61-2.51 (m, 1H), 2.13-2.05 (m, 2H), 1.25-1.18 (m, 2H), 1.17-1.03 (m, 2H) | 442.1 | R-isomer: 99.1% ee; [α] = +90.130°; S-isomer: 98.6% ee; [α] = −91.799°; |
| 165 | 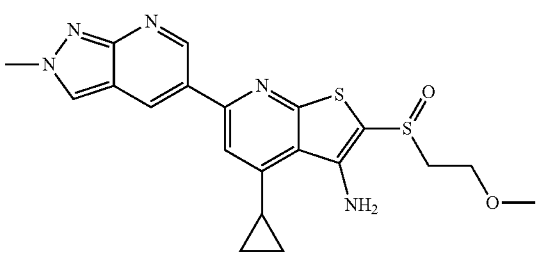 | 9.33 (d, J = 4.0 Hz, 1H), 8.74 (d, J = 4.0 Hz, 1H), 8.01 (s, 1H), 7.51 (s, 1H), 5.54 (s, 2H), 4.30 (s, 3H), 3.91-3.89 (m, 2H), 3.74-3.70 (m, 1H), 3.66-3.61 (m, 1H), 3.43 (s, 3H), 3.34-3.28 (m, 1H), 2.55-2.50 (m, 1H), 1.23-1.20 (m, 2H), 1.11-1.06 (m, 1H). | 428.1 | R-isomer: 100% ee; [α] = +88.226°; S-isomer: 97% ee; [α] = −96.320° |

-continued

| Ex. No. | Structure | 400 MHz NMR (δ; CDCl₃ unless otherwise noted) | LCMS (ES⁺; MH⁺) | Chiral info |
|---|---|---|---|---|
| 166 | 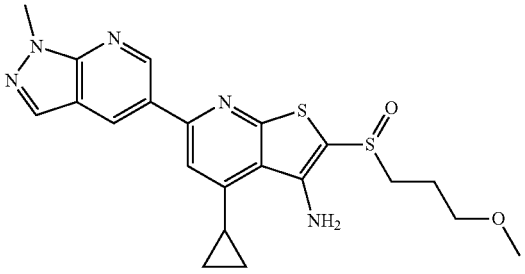 [SMILES: COCCCS(=O)c1sc2nc(-c3cnc4c(cnn4C)c3)cc(C3CC3)c2c1N] | 9.23 (d, J = 2.0 Hz, 1H), 8.73 (d, J = 2.0 Hz, 1H), 8.10 (s, 1H), 7.49 (d, J = 0.8 Hz, 1H), 5.60 (s, 2H), 4.22 (s, 3H), 3.59-3.53 (m, 2H), 3.46-3.39 (m, 1H), 3.38 (s, 3H), 3.33-3.24 (m, 1H), 2.61-2.53 (m, 1H), 2.13-2.05 (m, 2H), 1.26-1.18 (m, 2H), 1.17-1.10 (m, 1H), 1.09-1.03 (m, 1H). | 442.1 | R-isomer: 100% ee; [α] = +97.440°; S-isomer: 98.3% ee; [α] = −105 808°; |
| 167 | 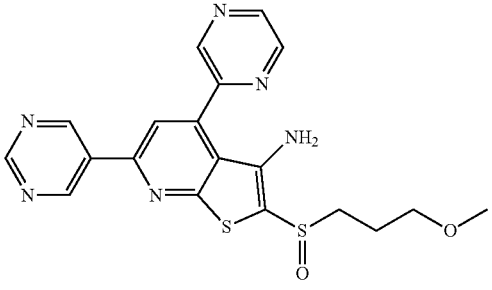 [SMILES: COCCCS(=O)c1sc2nc(-c3cncnc3)cc(-c3cnccn3)c2c1N] | CD₃OD 9.62 (s, 2H), 9.28 (s, 1H), 9.22 (d, J = 1.6 Hz, 1H), 8.87-8.84 (m, 2H), 8.24 (s, 1H), 3.54 (t, J = 6.0 Hz, 2H), 3.42-3.38 (m, 1H), 3.35 (s, 3H), 3.29-3.22 (m, 1H), 2.05-1.96 (m, 2H). | 427.1 | R-isomer: 100% ee; [α] = +138.624°; S-isomer: 100% ee; [α] = −130.813° |
| 168 | 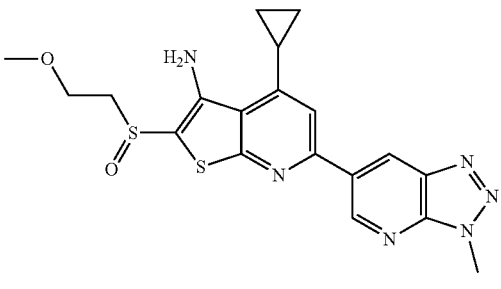 [SMILES: COCCS(=O)c1sc2nc(-c3cnc4c(c3)nnn4C)cc(C3CC3)c2c1N] | 9.43 (d, J = 1.6 Hz, 1H), 8.91 (d, J = 1.6 Hz, 1H), 7.53 (s, 1H), 5.58 (s, 2H), 4.42 (s, 3H), 3.94-3.88 (m, 1H), 3.76-3.71 (m, 1H), 3.67-3.62 (m, 1H), 3.43 (s, 3H), 3.35-3.29 (m, 1H), 2.61-2.54 (m, 1H), 1.27-1.22 (m, 2H), 1.16-1.12 (m, 1H), 1.09-1.04 (m, 1H). | 429.0 | R-isomer: 100% ee; [α] = +56.429°; S-isomer: 98% ee; [α] = −44.012° |
| 169 | 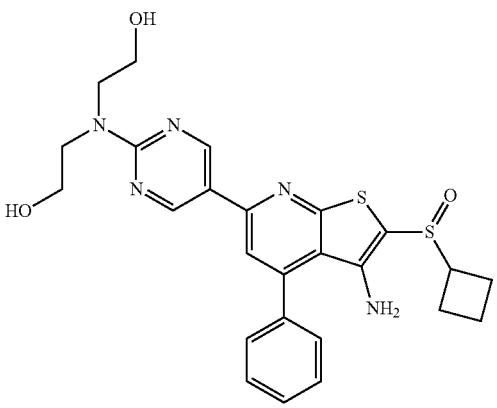 [SMILES: Nc1c(S(=O)C2CCC2)sc2nc(-c3cnc(N(CCO)CCO)nc3)cc(-c3ccccc3)c12] | 9.01 (s, 2H), 7.56-7.55 (m, 3H), 7.48 (s, 2H), 7.37 (s, 1H), 4.55 (s, 2H), 3.98-3.95 (m, 4H), 3.92-3.90 (m, 4H), 3.78-3.73 (m, 1H), 2.83-2.76 (m, 1H), 2.39-2.34 (m, 2H), 2.25-2.22 (m, 1H), 2.10-2.06 (m, 2H). | 510.1 | R-isomer: 98% ee; [α] = +73.795. S-isomer: 96% ee; [α] = −86.782. |

| Ex. No. | Structure | 400 MHz NMR (δ; CDCl₃ unless otherwise noted) | LCMS (ES⁺; MH⁺) | Chiral info |
|---|---|---|---|---|
| 170 | 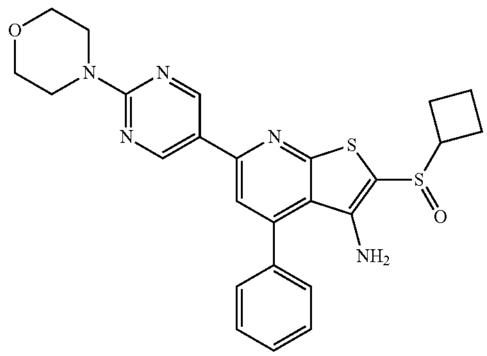 [SMILES: Nc1c(S(=O)C2CCC2)sc2nc(-c3cnc(N4CCOCC4)nc3)cc(-c3ccccc3)c12] | 9.05 (s, 2H), 7.57-7.56 (m, 3H), 7.50-7.49 (m, 2H), 7.40 (s, 1H), 4.56 (s, 2H), 4.00-3.93 (m, 5H), 3.83-3.80 (m, 4H), 2.80-2.78 (m, 1H), 2.41-2.36 (m, 2H), 2.28-2.24 (m, 1H), 2.11-2.07 (m, 2H). | 492.1 | |
| 171 | 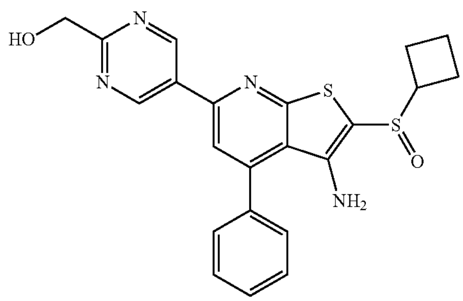 [SMILES: Nc1c(S(=O)C2CCC2)sc2nc(-c3cnc(CO)nc3)cc(-c3ccccc3)c12] | DMSO-d6 9.54 (s, 2H), 8.04 (s, 1H), 7.62 (s, 5H), 5.43 (t, J = 6.4 Hz, 1H), 4.96 (s, 2H), 4.69 (m, J = 6.0 Hz, 2H), 3.91-3.83 (m, 1H), 2.68-2.63 (m, 1H), 2.18-2.15 (m, 3H), 2.01-1.90 (m, 2H). | 437.2 | |
| 172 | 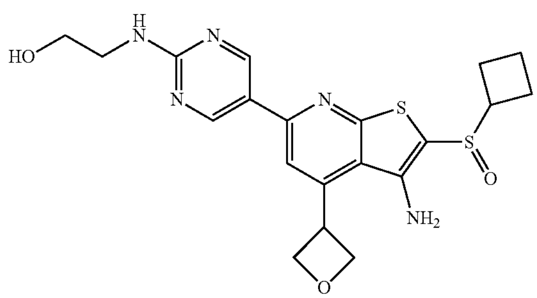 [SMILES: Nc1c(S(=O)C2CCC2)sc2nc(-c3cnc(NCCO)nc3)cc(C3COC3)c12] | DMSO-d6 9.10 (s, 2H), 7.81 (s, 1H), 7.58-7.55 (m, 1H), 5.58 (s, 2H), 5.24-5.22 (m, 1H), 5.01-4.95 (m, 3H), 4.93-4.71 (m, 2H), 3.83-3.81 (m, 1H), 3.57-3.54 (m, 2H), 3.47-3.44 (m, 2H), 2.63-2.60 (m, 1H), 2.20-2.14 (m, 3H), 2.02-1.91 (m, 2H). | 446.1 | |
| 173 | 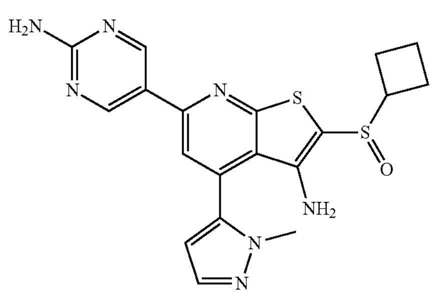 [SMILES: Cn1nccc1-c1cc(-c2cnc(N)nc2)nc2sc(S(=O)C3CCC3)c(N)c12] | 9.05 (s, 2H), 7.68 (d, J = 1.6 Hz, 1H), 7.48 (s, 1H), 6.49 (s, 1H), 5.33 (s, 2H), 4.52 (d, J = 37.6 Hz, 2H), 4.00-3.92 (m, 1H), 3.76 (s, 3H), 2.88-2.81 (m, 1H), 2.42-2.39 (m, 2H), 2.38-2.37 (m, 1H), 2.13-2.09 (m, 2H). | 426.0 | R-isomer: 100% ee; [α] = +156.573°; S-isomer: 97% ee; [α] = −174.310°; |
| 174 | 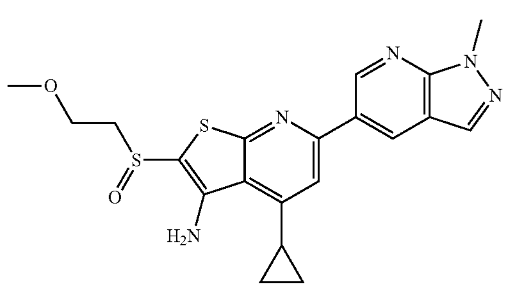 [SMILES: COCCS(=O)c1sc2nc(-c3cnc4c(cnn4C)c3)cc(C3CC3)c2c1N] | 9.23 (d, J = 2.0 Hz, 1H), 8.75 (d, J = 2.0 Hz, 1H), 8.11 (s, 1H), 7.51 (s, 1H), 5.56 (s, 1H), 4.22 (s, 3H), 3.91-3.89 (m, 1H), 3.74-3.73 (m, 1H), 3.66-3.63 (m, 1H), 3.44 (s, 3H), 3.34-3.29 (m, 1H), 2.57-2.53 (m, 1H), 1.23-1.21 (m, 2H), 1.12-1.10 (m, 1H), 1.08-1.07 (m, 1H). | 428.1 | R-isomer: 100% ee; [α] = +73.395. S-isomer: 100% ee; [α] = −59.486. |

-continued

| Ex. No. | Structure | 400 MHz NMR (δ; CDCl₃ unless otherwise noted) | LCMS (ES⁺; MH⁺) | Chiral info |
|---|---|---|---|---|
| 175 | 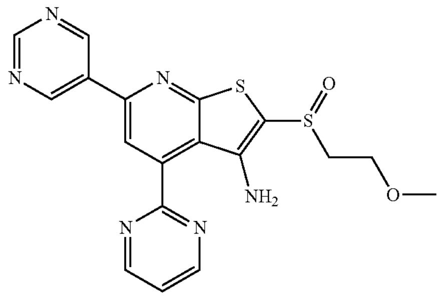 [SMILES: COCCS(=O)c1sc2nc(-c3cncnc3)cc(-c3ncccn3)c2c1N] | 9.56 (d, J = 4.0 Hz, 2H), 9.32 (s, 1H), 9.16 (d, J = 4.8 Hz, 2H), 8.53 (s, 1H), 7.77 (t, J = 4.8 Hz, 1H), 6.32 (s, 2H), 3.76-3.74 (m 1H), 3.64 (m, 1H), 3.44-3.41 (m, 1H), 3.40-3.26 (m, 4H). | 413.0 | R-isomer: 100% ee; [α] = +127.997. S-isomer: 100% ee; [α] = −231.162. |
| 176 | 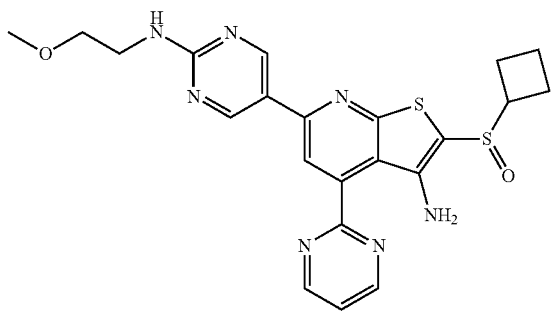 [SMILES: COCCNc1ncc(-c2cc(-c3ncccn3)c3c(N)c(S(=O)C4CCC4)sc3n2)cn1] | 9.08 (s, 2H), 8.98 (d, J = 5.2 Hz, 2H), 8.27 (s, 1H), 7.46 (t, J = 4.8 Hz, 1H), 6.32 (s, 2H), 5.73 (t, J = 5.6 Hz, 1H), 4.00-3.96 (m 1H), 3.74-3.70 (m, 2H), 3.63-3.60 (m, 2H), 3.41 (s, 3H), 2.86-2.80 (m, 1H), 2.40-2.35 (m, 2H), 2.20-2.15 (m, 1H), 2.10-2.06 (m, 2H). | 379.0 | |
| 177 | 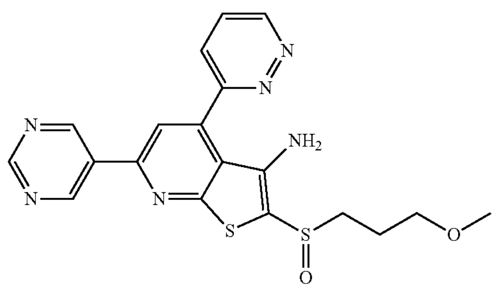 [SMILES: COCCCS(=O)c1sc2nc(-c3cncnc3)cc(-c3cccnn3)c2c1N] | DMSO-d6 9.63 (s, 2H), 9.48-7.46 (m, 1H), 9.32 (s, 1H), 8.39-8.36 (m, 2H), 8.10-8.06 (m, 1H), 5.87 (s, 2H), 3.43 (t, J = 6.4 Hz, 2H), 3.22 (s, 3H), 3.21-3.14 (m, 1H), 3.13-3.04 (m, 1H), 1.88-1.81 (m, 2H). | 427.2 | |
| 178 | 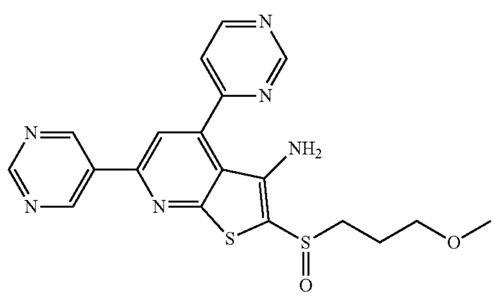 [SMILES: COCCCS(=O)c1sc2nc(-c3cncnc3)cc(-c3ccncn3)c2c1N] | 9.47 (s, 2H), 9.44 (d, J = 1.2 Hz, 1H), 9.34 (s, 1H), 9.06 (d, J = 4.8 Hz, 1H), 7.80 (dd, J1 = 4.8 Hz, J2 = 1.2 Hz, 1H), 7.77 (s, 1H), 5.68 (s, 2H), 3.54 (t, J = 6.0 Hz, 2H), 3.37 (m, 1H), 3.36 (s, 3H), 3.31-3.23 (m, 1H), 2.11-2.03 (m, 2H); | 427.1 | R-isomer: 98.6% ee; [α] = +124.899°; S-isomer: 100% ee; [α] = −141.197°; |
| 179 | 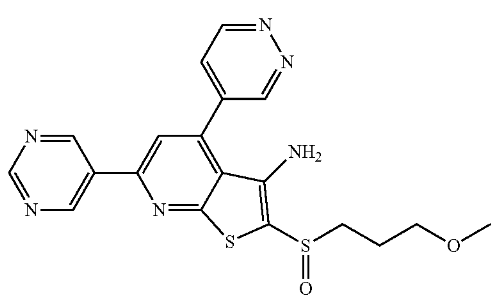 [SMILES: COCCCS(=O)c1sc2nc(-c3cncnc3)cc(-c3ccnnc3)c2c1N] | DMSO-d6 9.60 (s, 2H), 9.51-9.50 (m, 1H), 9.44-9.43 (m, 1H), 9.31 (s, 1H), 8.22 (s, 1H), 7.96-7.94 (m, 1H), 5.16 (s, 2H), 3.45 (t, J = 6.0 Hz, 2H), 3.24 (s, 3H), 3.21-3.16 (m, 1H), 3.13-3.06 (m, 1H), 1.89 (s, 2H). | 427.0 | |

-continued

| Ex. No. | Structure | 400 MHz NMR (δ; CDCl₃ unless otherwise noted) | LCMS (ES⁺; MH⁺) | Chiral info |
|---|---|---|---|---|
| 180 | 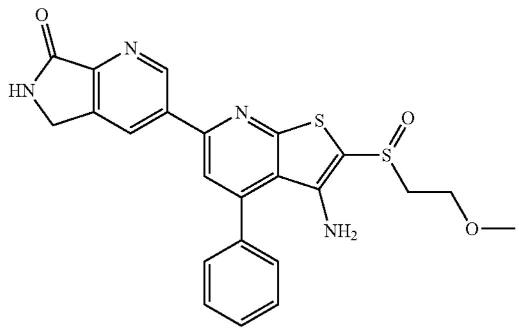 [SMILES: COCCS(=O)c1sc2nc(-c3cnc4c(c3)CNC4=O)cc(-c3ccccc3)c2c1N] | 9.44 (s, 1H), 8.73 (s, 1H), 7.71 (s, 1H), 7.62-7.48 (m, 5H), 6.74 (s, 1H), 4.62 (s, 2H), 4.60 (s, 2H), 3.95-3.83 (m, 1H), 3.74-3.69 (m, 1H), 3.65-3.57 (m, 1H), 3.40 (s, 3H), 3.29 (m, 1H). | 465.1 | R-isomer: 98% ee; [α] = +49.923°; S-isomer: 98% ee; [α] = −43.697° |
| 181 | 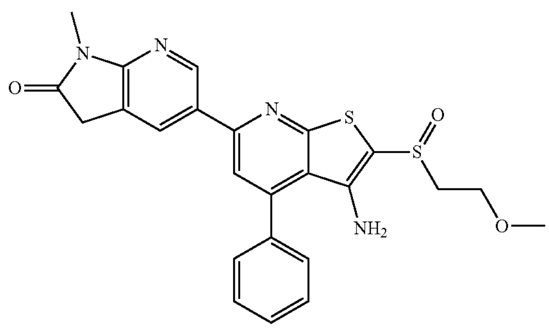 [SMILES: COCCS(=O)c1sc2nc(-c3cnc4c(c3)CC(=O)N4C)cc(-c3ccccc3)c2c1N] | 8.86 (d, J = 1.6 Hz, 1H), 8.38 (d, J = 0.8 Hz, 1H), 7.61-7.57 (m, 3H), 7.55 (s, 1H), 7.52 (s, 2H), 4.60 (s, 2H), 3.91-3.85 (m, 1H), 3.74-3.68 (m, 1H), 3.65 (s, 2H), 3.64-3.58 (m, 1H), 3.41 (s, 3H), 3.38 (s, 3H), 3.32-3.25 (m, 1H). | 479.2 | |
| 182 | 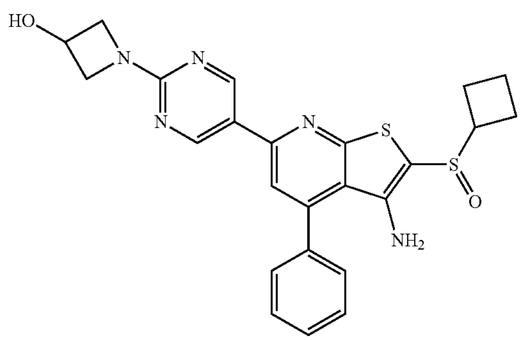 [SMILES: Nc1c(S(=O)C2CCC2)sc2nc(-c3cnc(N4CC(O)C4)nc3)cc(-c3ccccc3)c12] | 8.99 (s, 2H), 7.56-7.49 (m, 5H), 7.36 (s, 1H), 4.85-4.81 (m, 1H), 4.55-4.48 (m, 4H), 4.13-4.09 (m, 2H), 3.98-3.94 (m, 1H), 2.81-2.75 (m, 1H), 2.47-2.45 (m, 1H), 2.41-2.31 (m, 2H), 2.28-2.18 (m, 1H), 2.09-2.05 (m, 2H). | 478.1 | |
| 183 | 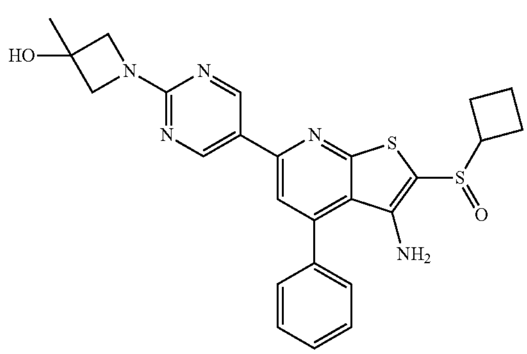 [SMILES: CC1(O)CN(c2ncc(-c3cc(-c4ccccc4)c4c(N)c(S(=O)C5CCC5)sc4n3)cn2)C1] | DMSO-d6 9.12 (s, 2H), 7.76 (s, 1H), 7.64-7.51 (m, 5H), 5.70 (s, 1H), 4.90 (s, 2H), 4.06-3.93 (m, 4H), 3.84 (m, 1H), 2.64 (m, 1H), 2.17 (m, 3H), 2.09-1.97 (m, 1H), 1.97-1.84 (m, 1H), 1.45 (s, 3H). | 492.2 | |

-continued

| Ex. No. | Structure | 400 MHz NMR (δ; CDCl₃ unless otherwise noted) | LCMS (ES⁺; MH⁺) | Chiral info |
|---|---|---|---|---|
| 184 | 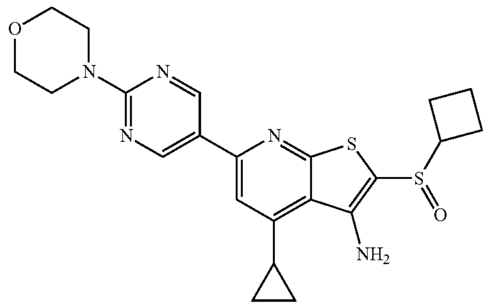 [SMILES: Nc1c(S(=O)C2CCC2)sc2nc(-c3cnc(N4CCOCC4)nc3)cc(C3CC3)c12] | 8.99 (s, 2H), 7.28 (s, 1H), 5.53 (s, 2H), 4.01-3.97 (m, 1H), 3.93-3.90 (m, 4H), 3.81-3.79 (m, 4H), 2.83-2.80 (m 1H), 2.51-2.50 (m, 1H), 2.43-2.40 (m, 2H), 2.35-2.28 (m, 1H), 2.12-2.08 (m, 2H), 1.18-1.16 (m, 2H), 1.05-1.00 (m, 2H). | 456.1 | |
| 185 | 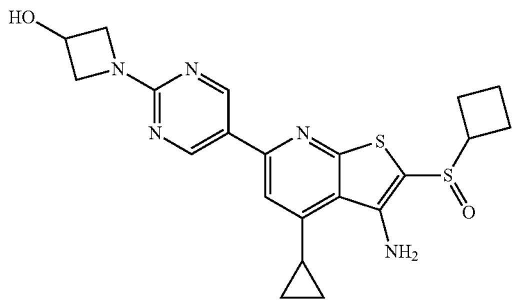 [SMILES: Nc1c(S(=O)C2CCC2)sc2nc(-c3cnc(N4CC(O)C4)nc3)cc(C3CC3)c12] | 8.94 (s, 2H), 7.27 (s, 1H), 5.53 (s, 2H), 4.84-4.83 (m, 1H), 4.52-4.47 (m, 2H), 4.12-4.09 (m, 2H), 3.98-3.96 (m 1H), 2.81-2.80 (m, 1H), 2.52-2.50 (m, 1H), 2.42-2.31 (m, 3H), 2.38-2.26 (m, 1H), 2.11-2.08 (m, 2H), 1.18-1.16 (m, 2H), 1.08-1.00 (m, 2H). | 442.0 | |
| 186 | 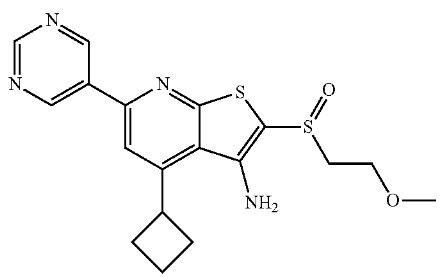 | 9.42 (s, 2H), 9.30 (s, 1H), 7.66 (s, 1H), 5.15 (s, 2H), 4.28-4.20 (m, 1H), 3.92-3.87 (m, 1H), 3.74-3.68 (m, 1H), 3.65-3.59 (m, 1H), 3.42 (s, 3H), 3.32-3.27 (m, 1H), 2.57-2.50 (m, 2H), 2.48-2.39 (m, 2H), 2.27-2.14 (m, 1H), 2.09-1.99 (m, 1H). | 389.1 | R-isomer: 99% ee; [α] = +55.025°; S-isomer: 100% ee; [α] = −49.891°; |
| 187 | 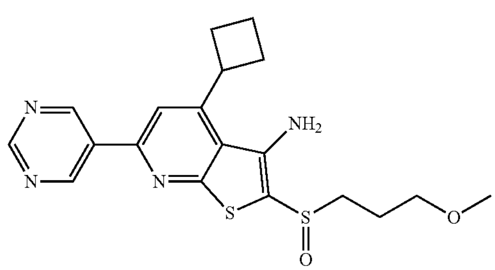 [SMILES: COCCCS(=O)c1sc2nc(-c3cncnc3)cc(C3CCC3)c2c1N] | 9.40 (s, 2H), 9.28 (s, 1H), 7.64 (s, 1H), 5.19 (s, 2H), 4.28-4.19 (m, 1H), 3.53 (t, J = 6.4 Hz, 2H), 3.41-3.37 (m, 1H), 3.35 (s, 3H), 3.28-3.21 (m, 1H), 2.55-2.49 (m, 2H), 2.47-2.35 (m, 2H), 2.24-2.13 (m, 1H), 2.09-1.98 (m, 3H). | 403.1 | |
| 188 | 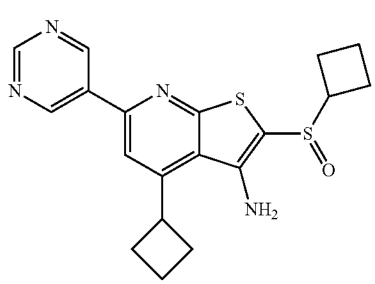 | DMSO-d6 9.55 (s, 2H), 9.29 (s, 1H), 7.98 (s, 1H), 5.77 (s, 2H), 4.50-4.41 (m, 1H), 3.92-3.84 (m, 1H), 2.67-2.60 (m, 2H), 2.46-2.34 (m, 4H), 2.21-2.13 (m, 2H), 2.10-1.99 (m, 2H), 1.97-1.82 (m, 2H). | 385.3 | |

-continued

| Ex. No. | Structure | 400 MHz NMR (δ; CDCl₃ unless otherwise noted) | LCMS (ES⁺; MH⁺) | Chiral info |
|---|---|---|---|---|
| 189 | 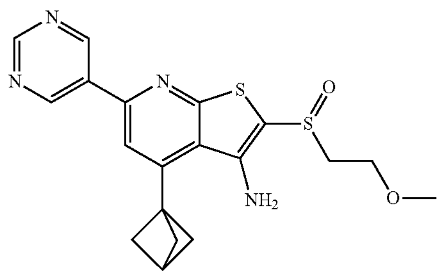 [SMILES: COCCS(=O)c1sc2nc(-c3cncnc3)cc(C34CC(C3)C4)c2c1N] | 9.42 (s, 2H), 9.31 (s, 1H), 7.48 (s, 1H), 5.38 (s, 2H), 3.96-3.89 (m, 1H), 3.77-3.71 (m, 1H), 3.69-3.63 (m, 1H), 3.45 (s, 3H), 3.37-3.29 (m, 1H), 2.79 (s, 1H), 2.47 (s, 6H). | 401.0 | |
| 190 | 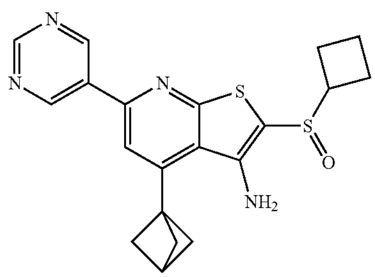 [SMILES: Nc1c(S(=O)C2CCC2)sc2nc(-c3cncnc3)cc(C34CC(C3)C4)c12] | 9.38 (s, 2H), 9.28 (s, 1H), 7.43 (s, 1H), 5.35 (s, 2H), 4.03-3.95 (m, 1H), 2.88-2.77 (m, 1H), 2.76 (s, 1H), 2.47-2.41 (m, 7H), 2.39-2.33 (m, 1H), 2.31-2.22 (m, 1H), 2.14-2.06 (m, 2H). | 397.1 | |
| 191 | 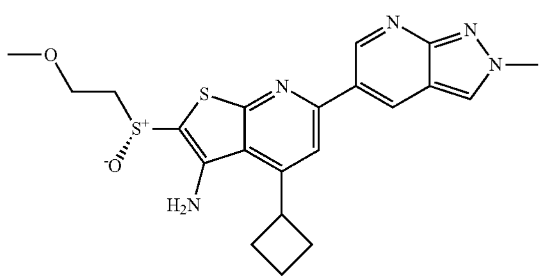 | 9.36 (d, J = 2.4 Hz, 1H), 8.70 (d, J = 2.4 Hz, 1H), 7.99 (s, 1H), 7.66 (s, 1H), 5.09 (s, 2H), 4.30 (s, 3H), 4.25-4.16 (m, 1H), 3.91-3.85 (m, 1H), 3.71-3.66 (m, 1H), 3.64-3.58 (m, 1H), 3.41 (s, 3H), 3.30-3.23 (m, 1H), 2.58-2.43 (m, 3H), 2.41-2.32 (m, 1H), 2.23-2.12 (m, 1H), 2.05-1.96 (m, 1H). | 427.1 | R-isomer: 99% ee; [α] = +119.373°; S-isomer: 99% ee; [α] = −131.920°; |
| 192 | 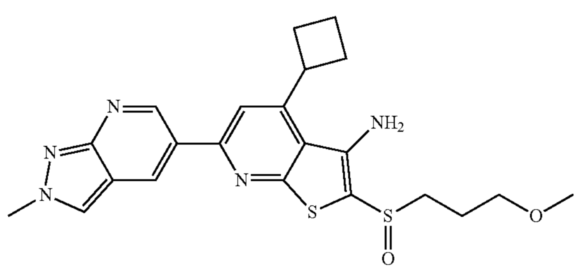 | DMSO-d6 9.42 (d, J = 2.4 Hz, 1H), 9.03 (d, J = 2.0 Hz, 1H), 8.56 (s, 1H), 7.93 (s, 1H), 5.76 (s, 2H), 4.48-4.38 (m, 1H), 4.26 (s, 3H), 3.45 (t, J = 6.4 Hz, 2H), 3.24 (s, 3H), 3.20-3.12 (m, 1H), 3.09-3.00 (m, 1H), 2.45-2.32 (m, 4H), 2.15-2.02 (m, 1H), 1.91-1.82 (m, 3H). | 456.2 | R-isomer: 100% ee; [α] = +23.834°; S-isomer: 97% ee; [α] = −24.371°; |
| 193 | 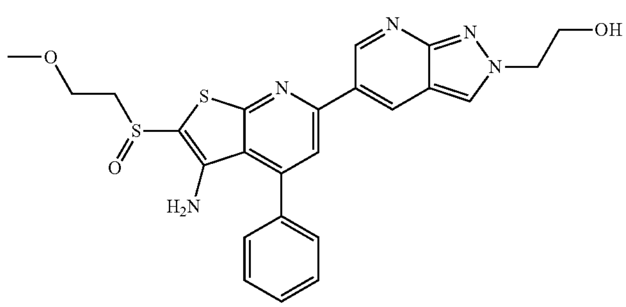 [SMILES: COCCS(=O)c1sc2nc(-c3cnc4nn(CCO)cc4c3)cc(-c3ccccc3)c2c1N] | 9.29 (d, J = 2.0 Hz, 1H), 8.72 (d, J = 2.4 Hz, 1H), 8.10 (s, 1H), 7.64-7.54 (m, 5H), 7.53-7.45 (m, 1H), 4.65-4.57 (m, 4H), 4.37-4.21 (m, 2H), 3.97 (s, 1H), 3.90-3.83 (m, 1H), 3.73-3.67 (m, 1H), 3.62-3.55 (m, 1H), 3.41 (s, 3H), 3.31-3.23 (m, 1H). | 494.1 | R-isomer: 97.1% ee; [α] = +48.528°; S-isomer: 97% ee; [α] = −32.462°; |

| Ex. No. | Structure | 400 MHz NMR (δ; CDCl₃ unless otherwise noted) | LCMS (ES⁺; MH⁺) | Chiral info |
|---|---|---|---|---|
| 194 | 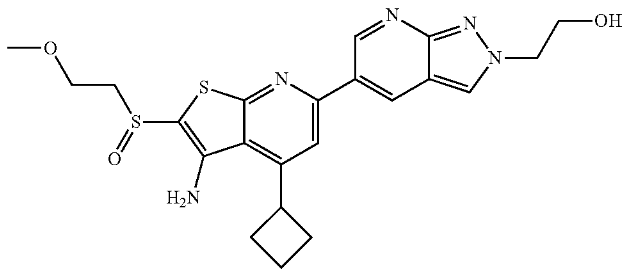 [SMILES: COCCS(=O)c1sc2nc(-c3cnc4nn(CCO)cc4c3)cc(C3CCC3)c2c1N] | 8.92 (d, J = 2.0 Hz, 1H), 8.36 (d, J = 2.0 Hz, 1H), 8.09 (s, 1H), 7.36 (s, 1H), 5.35-5.32 (m, 1H), 5.11 (s, 2H), 4.59-4.57 (m, 2H), 4.43 (m, 2H), 4.24-4.16 (m, 1H), 3.90-3.85 (m, 1H), 3.68-3.63 (m, 1H), 3.65-3.55 (m, 1H), 3.41 (s, 3H), 3.25-3.18 (m, 1H), 2.57-2.52 (m, 2H), 2.44-2.35 (m, 1H), 2.16-2.10 (m, 2H), 1.94-1.87 (m, 1H). | 472.1 | R-isomer: 100% ee; [α] = +46.840°; S-isomer: 99% ee; [α] = −44.093°; |
| 195 | 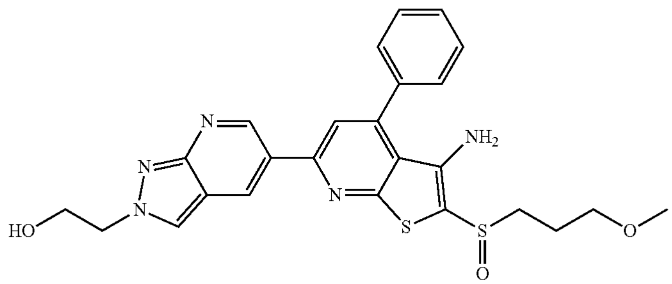 [SMILES: COCCCS(=O)c1sc2nc(-c3cnc4nn(CCO)cc4c3)cc(-c3ccccc3)c2c1N] | 9.33 (d, J = 2.4 Hz, 1H), 8.77 (d, J = 2.4 Hz, 1H), 8.10 (s, 1H), 7.60 (s, 2H), 7.59-7.55 (m, 3H), 7.53-7.45 (m, 1H), 4.67 (s, 2H), 4.62-4.58 (m, 2H), 4.35-4.18 (m, 2H), 3.73-3.66 (m, 1H), 3.55-3.49 (m, 2H), 3.39-3.35 (m, 1H), 3.34 (s, 3H), 3.26-3.17 (m, 1H), 2.07-1.98 (m, 2H). | 508.2 | |
| 196 | 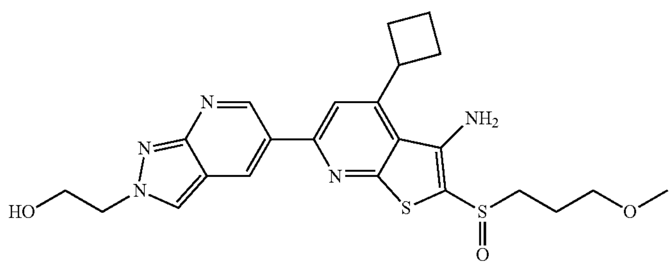 [SMILES: COCCCS(=O)c1sc2nc(-c3cnc4nn(CCO)cc4c3)cc(C3CCC3)c2c1N] | 9.21 (s, 1H), 8.61 (s, 1H), 8.10 (s, 1H), 7.57 (s, 1H), 5.15 (s, 2H), 4.60 (m, 2H), 4.33 (s, 2H), 4.27-4.18 (m, 1H), 4.13-4.05 (m, 1H), 3.53 (t, J = 5.6 Hz, 2H), 3.42-3.38 (m, 1H), 3.36 (s, 1H), 3.27-3.18 (m, 1H), 2.60-2.42 (m, 3H), 2.36-2.27 (m, 1H), 2.24-2.13 (m, 1H), 2.09-1.95 (m, 3H). | 486.1 | |
| 197 | 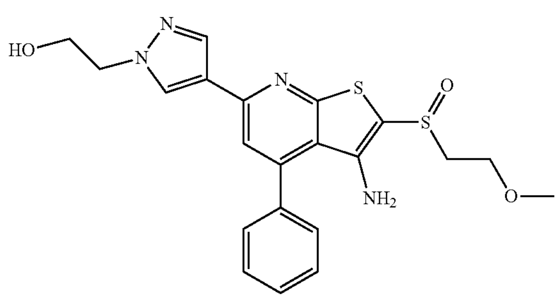 [SMILES: COCCS(=O)c1sc2nc(-c3cnn(CCO)c3)cc(-c3ccccc3)c2c1N] | 8.13 (s, 1H), 8.05 (s, 1H), 7.58-7.52 (m, 3H), 7.48-7.45 (m, 2H), 7.29 (s, 1H), 4.53 (s, 2H), 4.33 (t, J = 3.2 Hz, 2H), 4.09-4.05 (m, 2H), 3.88-3.82 (m, 1H), 3.71-3.65 (m, 1H), 3.62-3.55 (m, 1H), 3.39 (s, 3H), 3.29-3.21 (m, 1H), 2.95-2.89 (m, 1H) | 443.2 | |
| 198 | 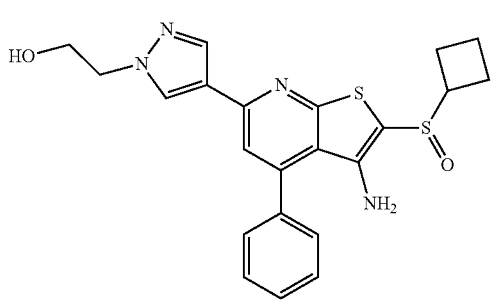 [SMILES: Nc1c(S(=O)C2CCC2)sc2nc(-c3cnn(CCO)c3)cc(-c3ccccc3)c12] | MeOD 8.35 (s, 1H), 8.15 (s, 1H), 7.61-7.56 (m, 3H), 7.54-7.50 (m, 2H), 7.49 (s, 1H), 4.29 (t, J = 5.2 Hz, 2H), 3.99-3.89 (m, 3H), 2.81-2.70 (m, 1H), 2.44-2.32 (m, 1H), 2.32-2.22 (m, 2H), 2.17-2.00 (m, 2H). | 439.2 | |

-continued

| Ex. No. | Structure | 400 MHz NMR (δ; CDCl₃ unless otherwise noted) | LCMS (ES⁺; MH⁺) | Chiral info |
|---|---|---|---|---|
| 199 | 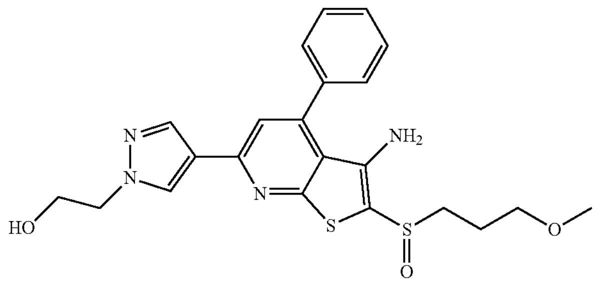 [SMILES: COCCCS(=O)c1sc2nc(-c3cnn(CCO)c3)cc(-c3ccccc3)c2c1N] | 8.13 (s, 1H), 8.05 (s, 1H), 7.57-7.52 (m, 3H), 7.48 (s, 2H), 7.28 (s, 1H), 4.55 (s, 2H), 4.32 (m, 2H), 4.09-4.03 (m, 2H), 3.52-3.49 (m, 2H), 3.39-3.45 (m, 1H), 3.34 (s, 3H), 3.26-3.16 (m, 1H), 2.92 (t, J = 5.6 Hz, 1H), 2.06-1.98 (m, 2H). | 457.0 | |
| 200 | 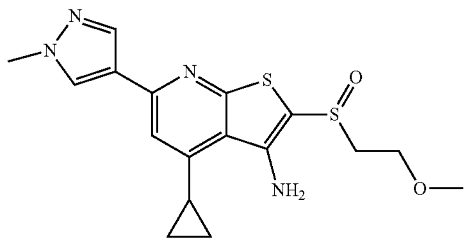 | 8.02 (s, 1H), 8.00 (s, 1H), 7.18 (s, 1H), 5.51 (s, 2H), 3.99 (s, 3H), 3.93-3.87 (m, 1H), 3.75-3.69 (m, 1H), 3.66-3.59 (m, 1H), 3.43 (s, 3H), 3.33-3.26 (m, 1H), 2.52-2.43 (m, 1H), 1.20-1.15 (m, 2H), 1.06-1.02 (m, 2H). | 377.0 | R-isomer: 100% ee; [α] = +60.777°; S-isomer: 99% ee; [α] = −68.241°; |
| 201 | 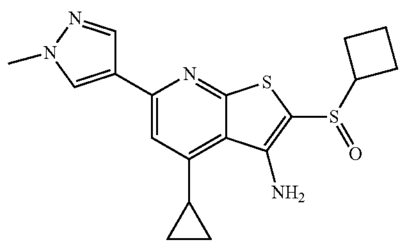 [SMILES: Cn1cc(-c2cc(C3CC3)c3c(N)c(S(=O)C4CCC4)sc3n2)cn1] | 8.00 (d, J = 5.6 Hz, 2H), 7.16 (s, 1H), 5.51 (s, 2H), 4.03-3.95 (m, 4H), 2.84-2.80 (m, 1H), 2.49-2.41 (m, 3H), 2.40-2.38 (m, 1H), 2.12-2.08 (m, 2H), 1.17-1.15 (m, 2H), 1.06-1.01 (m, 2H). | 373.1 | |
| 202 | 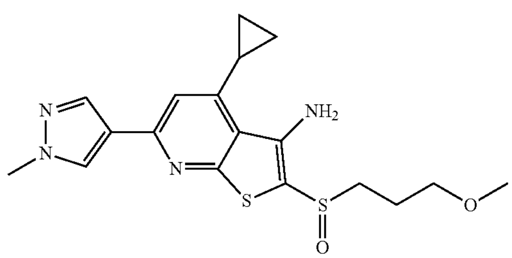 | 8.00 (s, 1H), 7.98 (s, 1H), 7.15 (s, 1H), 5.52 (s, 2H), 3.98 (s, 3H), 3.53 (m, 2H), 3.39-3.35 (m, 4H), 3.28-3.21 (m, 1H), 2.49-2.45 (m, 1H), 2.08-2.01 (m, 2H), 1.16-1.14 (m, 2H), 1.05-1.00 (m, 2H). | 391.0 | |
| 203 | 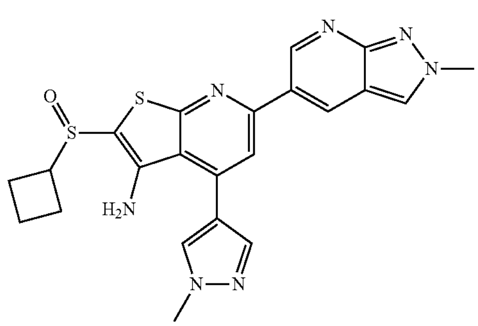 [SMILES: Cn1cc(-c2cc(-c3cnc4nn(C)cc4c3)nc3sc(S(=O)C4CCC4)c(N)c23)cn1] | DMSO-d6 8.70 (d, J = 1.6 Hz, 1H), 8.57 (s, 1H), 8.47 (s, 1H), 8.38 (d, J = 2.0 Hz, 1H), 8.14 (s, 1H), 7.66 (s, 1H), 4.92 (s, 2H), 4.27 (s, 3H), 3.89-3.82 (m, 4H), 2.66-2.63 (m, 1H), 2.19-2.14 (m, 3H), 2.03-2.00 (m, 1H), 1.98-1.94 (m, 1H). | 464.1 | |

| Ex. No. | Structure | 400 MHz NMR (δ; CDCl$_3$ unless otherwise noted) | LCMS (ES$^+$; MH$^+$) | Chiral info |
|---|---|---|---|---|
| 204 | 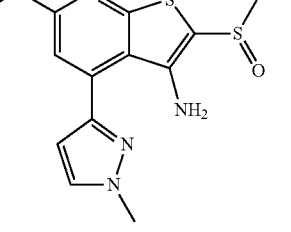 | 9.45 (s, 2H), 9.31 (s, 1H), 7.81 (s, 1H), 7.59 (d, J = 2.0 Hz, 1H), 6.76 (d, J = 2.4 Hz, 1H), 6.45 (s, 2H), 4.07 (s, 3H), 4.01 (t, J = 8.0 Hz, 1H), 2.89-2.80 (m, 1H), 2.47-2.34 (m, 2H), 2.31-2.21 (m, 1H), 2.15-2.04 (m, 2H). | 411.0 | |
| 205 | 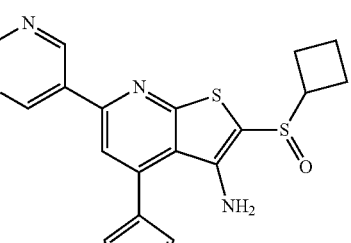 | 9.29 (s, 2H), 7.76 (s, 1H), 7.70 (s, 1H), 7.50 (s, 1H), 4.95 (s, 2H), 4.06 (s, 3H), 4.03-3.95 (m, 1H), 2.85-2.80 (m, 4H), 2.44-2.36 (m, 2H), 2.31-2.26 (m, 1H), 2.14-2.10 (m, 2H). | 425.0 | |
| 206 | 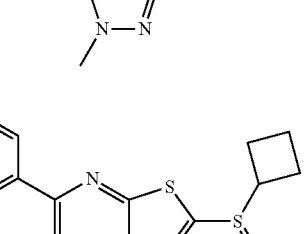 | 9.40 (s, 2H), 9.29 (s, 1H), 7.76 (s, 1H), 7.71 (s, 1H), 7.53 (s, 1H), 4.97 (s, 2H), 4.06 (s, 3H), 4.01-3.95 (m, 1H), 2.87-2.80 (m, 1H), 2.42-2.37 (m, 2H), 2.28-2.26 (m, 1H), 2.13-2.08 (m, 2H). | 411.0 | |
| 207 | 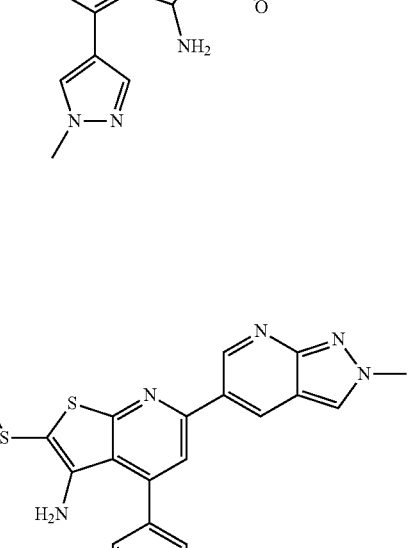 | DMSO-d6 9.41 (d, J = 2.4 Hz, 1H), 9.03 (d, J = 2.4 Hz, 1H), 8.54 (s, 1H), 7.89 (s, 1H), 7.52 (d, J = 8.8 Hz, 2H), 7.16 (d, J = 8.8 Hz, 2H), 5.04 (s, 2H), 4.94 (t, J = 5.4 Hz, 1H), 4.23 (s, 3H), 4.11-4.07 (m, 2H), 3.91-3.82 (m, 1H), 3.79-3.75 (m, 2H), 2.66-2.60 (m, 1H), 2.23-2.14 (m, 3H), 2.06-1.97 (m, 1H), 1.96-1.88 (m, 1H). | 520.0 | R-isomer: 97% ee; [α] = +50.037°; S-isomer: 95% ee; [α] = −47.384°; |

-continued

| Ex. No. | Structure | 400 MHz NMR (δ; CDCl₃ unless otherwise noted) | LCMS (ES⁺; MH⁺) | Chiral info |
|---|---|---|---|---|
| 208 | 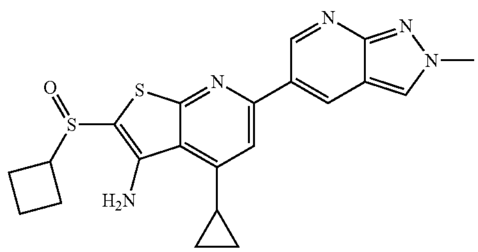 [SMILES: Cn1cc2cc(-c3cc(C4CC4)c4c(N)c(S(=O)C5CCC5)sc4n3)cnc2n1] | 9.32 (d, J = 2.4 Hz, 1H), 8.70 (d, J = 2.4 Hz, 1H), 8.00 (s, 1H), 7.47 (s, 1H), 5.54 (s, 2H), 4.29 (s, 3H), 4.03-3.95 (m, 1H), 2.84-2.83 (m, 1H), 2.54-2.50 (m, 1H), 2.41-2.38 (m, 2H), 2.30-2.25 (m, 1H), 2.12-2.08 (m, 2H), 1.21-1.19 (m, 2H), 1.10-1.04 (m, 2H). | 424.2 | R-isomer: 99% ee; [α] = +86.00° S-isomer: 99% ee; [α] = −110.40° |
| 209 | 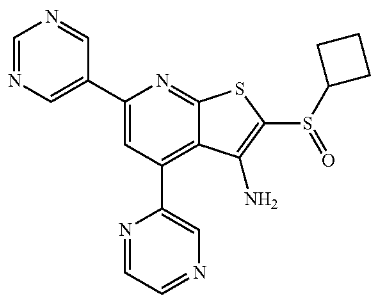 [SMILES: Nc1c(S(=O)C2CCC2)sc2nc(-c3cncnc3)cc(-c3cnccn3)c12] | DMSO-d6 9.62 (s, 2H), 9.31 (s, 1H), 9.28 (d, J = 1.2 Hz, 1H), 8.91-8.89 (m, 2H), 8.37 (s, 1H), 5.78 (s, 2H), 3.93-3.89 (m, 1H), 2.68-2.60 (m, 1H), 2.30-2.21 (m, 1H), 2.21-2.07 (m, 2H), 2.07-1.98 (m, 1H), 1.97-1.87 (m, 1H). | 409.0 | |
| 210 | 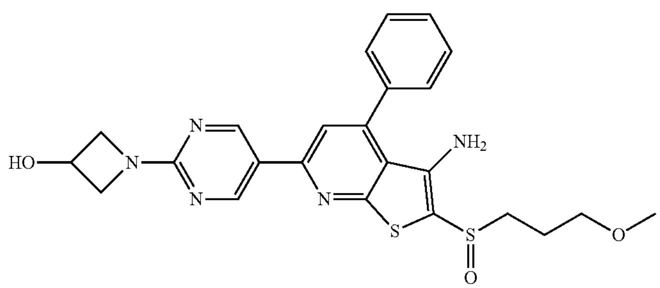 [SMILES: COCCCS(=O)c1sc2nc(-c3cnc(N4CC(O)C4)nc3)cc(-c3ccccc3)c2c1N] | 8.93 (s, 2H), 7.60-7.52 (m, 5H), 7.35 (s, 1H), 4.84-4.76 (m, 1H), 4.61 (s, 2H), 4.53-4.45 (m, 2H), 4.11 (m, 2H), 3.54-3.48 (m, 2H), 3.40-3.35 (m, 1H), 3.34 (s, 3H), 3.27-3.17 (m, 2H), 2.06-1.97 (m, 2H). | 496.1 | |
| 211 | 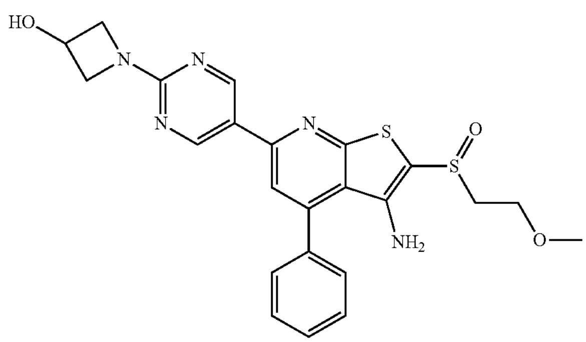 [SMILES: COCCS(=O)c1sc2nc(-c3cnc(N4CC(O)C4)nc3)cc(-c3ccccc3)c2c1N] | 8.98 (s, 2H), 7.60-7.56 (m, 3H), 7.54-7.50 (m, 2H), 7.38 (s, 1H), 4.87-4.79 (m, 1H), 4.58 (s, 2H), 4.53-4.48 (m, 2H), 4.12 (m, 2H), 3.89-3.83 (m, 1H), 3.72-3.66 (m, 1H), 3.64-3.57 (m, 1H), 3.40 (s, 3H), 3.31-3.24 (m, 1H), 2.72 (d, J = 6.4 Hz, 1H). | 482.1 | |
| 212 | 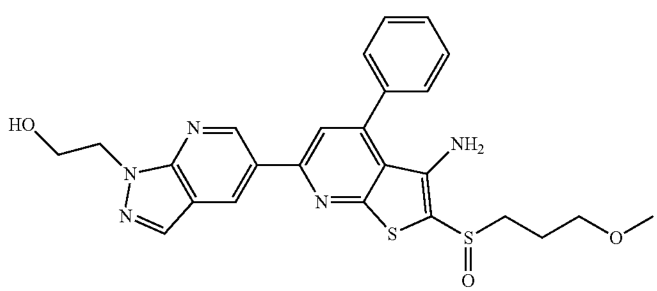 [SMILES: COCCCS(=O)c1sc2nc(-c3cnc4c(cnn4CCO)c3)cc(-c3ccccc3)c2c1N] | DMSO-d6 9.39-3.38 (d, 1H), 9.07-9.06 (d, 1H), 8.26 (s, 1H), 7.98 (s, 1H), 7.61 (s, 5H), 4.95 (s, 2H), 4.87 (t, J = 5.6 Hz, 1H), 4.54 (t, J = 6.0 Hz, 2H), 3.91-3.85 (m, 2H), 3.42 (t, J = 2.4 Hz, 2H), 3.21 (s, 3H), 3.18-3.11 (m, 1H), 3.07-2.99 (m, 1H), 1.88-1.78 (m, 2H). | 508 | |

-continued
| Ex. No. | Structure | 400 MHz NMR (δ; CDCl₃ unless otherwise noted) | LCMS (ES⁺; MH⁺) | Chiral info |
|---|---|---|---|---|
| 213 | 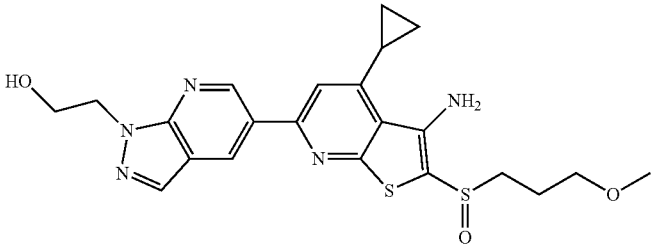 [SMILES: COCCCS(=O)c1sc2nc(-c3cnc4c(cnn4CCO)c3)cc(C3CC3)c2c1N] | 9.19 (d, J = 4.0 Hz, 1H), 8.77 (s, 1H), 8.11 (s, 1H), 7.48 (s, 1H), 5.59 (s, 2H), 4.75-4.73 (m, 2H), 4.22-4.18 (m, 3H), 3.56-3.53 (m, 2H), 3.42-3.37 (m, 4H), 3.31-3.27 (m, 1H), 2.57-2.55 (m, 1H), 2.11-2.06 (m, 2H), 1.23-1.21 (m, 2H), 1.13-1.06 (m, 2H). | 472.2 | |
| 214 | 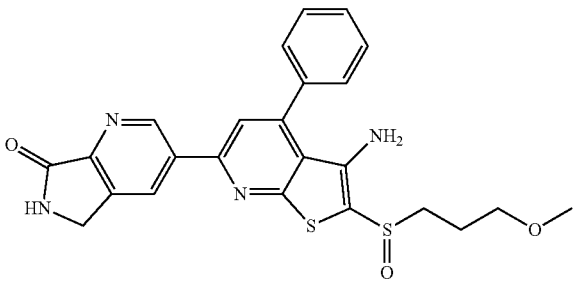 [SMILES: COCCCS(=O)c1sc2nc(-c3cnc4c(c3)CNC4=O)cc(-c3ccccc3)c2c1N] | 9.45 (s, 1H), 8.73 (d, J = 2.0 Hz, 1H), 7.72 (s, 1H), 7.63-7.50 (m, 5H), 6.90 (s, 1H), 4.68 (s, 2H), 4.62 (s, 2H), 3.56-3.51 (m, 2H), 3.43-3.37 (m, 1H), 3.36 (s, 3H), 3.30-3.22 (m, 1H), 2.11-2.02 (m, 2H). | 479.0 | |
| 215 | 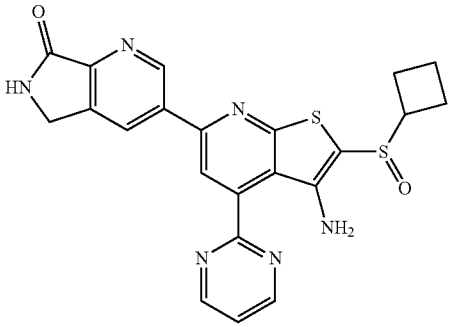 [SMILES: Nc1c(S(=O)C2CCC2)sc2nc(-c3cnc4c(c3)CNC4=O)cc(-c3ncccn3)c12] | DMSO-d6 9.48 (d, J = 1.6 Hz, 1H), 9.15 (d, J = 4.8 Hz, 2H), 9.08 (s, 1H), 8.81 (s, 1H), 8.54 (s, 1H), 7.78-7.74 (m, 1H), 6.34 (d, J = 5.6 Hz, 2H), 4.50 (s, 2H), 3.95-3.89 (m, 1H), 2.68-2.66 (m, 1H), 2.19-2.12 (m, 3H), 2.07-1.92 (m, 2H). | 463.0 | |
| 216 | 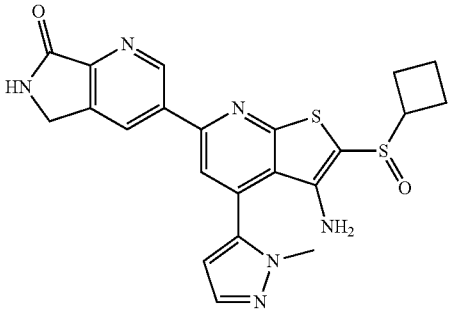 [SMILES: Cn1nccc1-c1cc(-c2cnc3c(c2)CNC3=O)nc2sc(S(=O)C3CCC3)c(N)c12] | DMSO-d6 9.53 (d, J = 2.0 Hz, 1H), 9.07 (s, 1H), 8.85 (d, J = 1.6 Hz, 1H), 8.22 (s, 1H), 7.70 (d, J = 1.6 Hz, 1H), 6.67 (s, 1H), 5.04 (s, 2H), 4.50 (s, 2H), 3.93-3.85 (m, 1H), 3.73 (s, 3H), 2.68-2.66 (m, 1H), 2.23-2.16 (m, 3H), 2.15-1.90 (m, 2H). | 465.0 | |
| 217 | 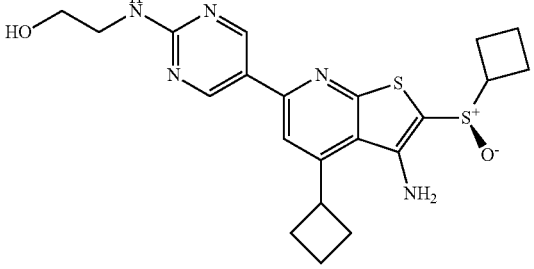 | 8.93 (s, 2H), 7.39 (s, 1H), 6.03-6.01 (m, 1H), 5.12 (s, 2H), 4.24-4.15 (m, 1H), 4.00-3.90 (m, 4H), 3.72-3.68 (m, 2H), 2.88-2.78 (m, 1H), 2.53-2.47 (m, 2H), 2.45-2.36 (m, 3H), 2.32-2.22 (m, 2H), 2.20-2.05 (m, 3H), 2.02-1.95 (m, 1H). | 444.4 | R-isomer: 99% ee; [α] = +158.691°; S-isomer: 100% ee; [α] = −151.194°; |

| Ex. No. | Structure | 400 MHz NMR (δ; CDCl₃ unless otherwise noted) | LCMS (ES⁺; MH⁺) | Chiral info |
|---|---|---|---|---|
| 218 | 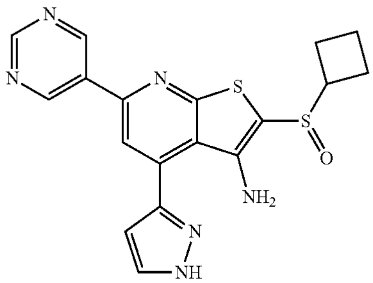 [SMILES: Nc1c(S(=O)C2CCC2)sc2nc(-c3cncnc3)cc(-c3cc[nH]n3)c12] | DMSO-d6 9.60 (s, 2H), 9.31 (s, 1H), 8.30 (s, 1H), 8.09 (d, J = 2.4 Hz, 1H), 7.25-7.23 (m, 3H), 3.91-3.87 (m, 1H), 2.68-2.67 (m, 1H), 2.23-2.13 (m, 3H), 2.06-1.99 (m, 1H), 1.97-1.89 (m, 1H). | 397.1 | |
| 219 | 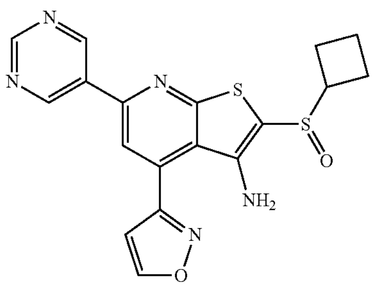 [SMILES: Nc1c(S(=O)C2CCC2)sc2nc(-c3cncnc3)cc(-c3ccon3)c12] | DMSO-d6 9.60 (s, 2H), 9.32-9.31 (m, 2H), 8.36 (s, 1H), 7.43 (s, 1H), 6.21 (s, 2H), 3.91 (t, J = 8.0 Hz, 1H), 2.67-2.62 (m, 1H), 2.27-2.07 (m, 3H), 2.05-1.98 (m, 1H), 1.96-1.86 (m, 1H). | 398.1 | R-isomer: 99% ee; [α] = +222.308°; S-isomer: 100% ee; [α] = −277.961°; |
| 220 | 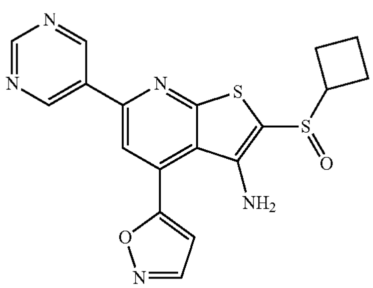 [SMILES: Nc1c(S(=O)C2CCC2)sc2nc(-c3cncnc3)cc(-c3ccno3)c12] | 9.44 (s, 2H), 9.32 (s, 1H), 8.52 (d, J = 1.6 Hz, 1H), 7.85 (s, 1H), 6.80 (d, J = 1.6 Hz, 1H), 5.15 (s, 2H), 4.02-3.94 (m, 1H), 2.87-2.82 (m, 1H), 2.49-2.39 (m, 1H), 2.38-2.32 (m, 1H), 2.31-2.23 (m, 1H), 2.15-2.06 (m, 2H). | 398.1 | |
| 221 | 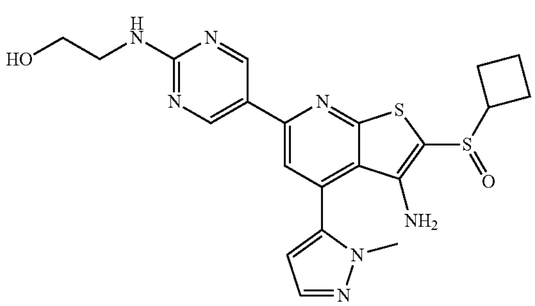 [SMILES: Cn1nccc1-c1cc(-c2cnc(NCCO)nc2)nc2sc(S(=O)C3CCC3)c(N)c12] | DMSO-d6 9.10 (s, 2H), 7.93 (s, 1H), 7.69 (s, 1H), 7.68-7.63 (m, 1H), 6.63 (s, 1H), 4.98 (s, 2H), 4.73 (t, J = 5.6 Hz, 1H), 3.88-3.84 (m, 1H), 3.70 (s, 3H), 3.56-3.53 (m, 2H), 3.46-3.43 (m, 2H), 2.65-2.64 (m, 1H), 2.20-2.16 (m, 3H), 2.15-1.90 (m, 2H). | 470.2 | R-isomer: 99% ee; [α] = +101.844°; S-isomer: 99% ee; [α] = −86.901°; |
| 222 | 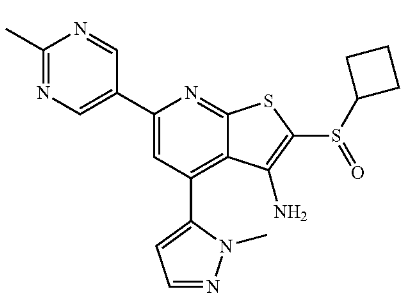 [SMILES: Cc1ncc(-c2cc(-c3ccnn3C)c3c(N)c(S(=O)C4CCC4)sc3n2)cn1] | DMSO-d6 9.47 (s, 2H), 8.18 (s, 1H), 7.70 (d, J = 2.0 Hz, 1H), 6.66 (s, 1H), 5.05 (s, 2H), 3.93-3.85 (m, 1H), 3.72 (s, 3H), 2.72 (s, 3H), 2.67-2.66 (m, 1H), 2.23-2.16 (m, 3H), 2.15-1.90 (m, 2H). | 425.2 | |

| Ex. No. | Structure | 400 MHz NMR (δ; CDCl₃ unless otherwise noted) | LCMS (ES⁺; MH⁺) | Chiral info |
|---|---|---|---|---|
| 223 | 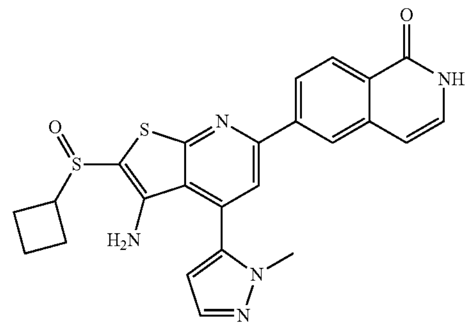 [SMILES: Cn1nccc1-c1cc(-c2ccc3c(=O)[nH]ccc3c2)nc2sc(S(=O)C3CCC3)c(N)c12] | 8.29-8.28 (m, 1H), 8.53 (d, J = 8.4 Hz, 1H), 8.33 (s, 1H), 8.21 (d, J = 8.4 Hz, 1H), 7.75 (s, 1H), 7.68 (s, 1H), 7.14 (t, J = 6.4 Hz, 1H), 6.65 (d, J = 7.2 Hz, 1H), 6.51 (s, 1H), 4.66-4.47 (m, 2H), 4.03-3.89 (m, 1H), 3.82-3.71 (s, 3H), 2.92-2.76 (m, 1H), 2.50-2.18 (m, 3H), 2.15-1.99 (m, 2H). | 476.3 | |
| 224 | 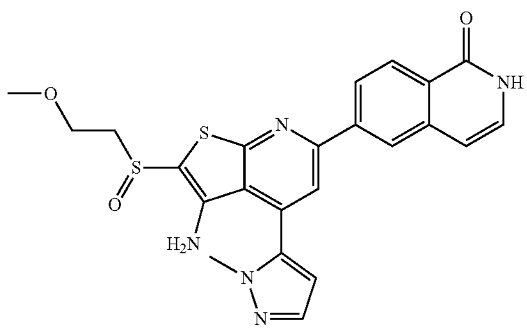 [SMILES: COCCS(=O)c1sc2nc(-c3ccc4c(=O)[nH]ccc4c3)cc(-c3ccnn3C)c2c1N] | DMSO-d6 (m, 1H), 8.59 (d, J = 1.6 Hz, 1H), 8.38-8.36 (m, 1H), 8.32-8.30 (m, 1H), 8.19 (s, 1H), 7.72 (d, J = 2 Hz, 1H), 7.26-7.23 (m, 1H), 6.71-6.68 (m, 2H), 5.06 (s, 2H), 3.79-3.76 (m, 1H), 3.74 (s, 3H), 3.68-3.63 (m, 1H), 3.43-3.38 (m, 1H), 3.29 (s, 3H), 3.27-3.22 (m, 1H) | 480.1 | |
| 225 | 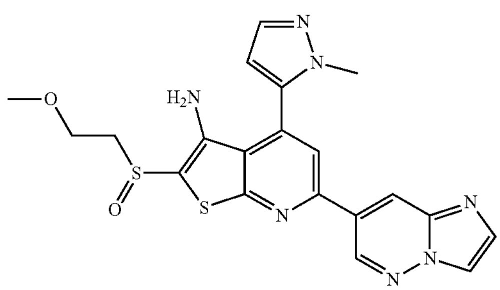 [SMILES: COCCS(=O)c1sc2nc(-c3cnn4ccnc4c3)cc(-c3ccnn3C)c2c1N] | 9.28 (d, J = 2.0 Hz, 1H), 8.56 (d, J = 2.0 Hz, 1H), 8.08 (s, 1H), 7.90 (d, J = 1.2 Hz, 1H), 7.73-7.68 (m, 2H), 6.52 (s, 1H), 4.59-4.53 (m, 2H), 3.89 (m, 1H), 3.79 (s, 3H), 3.76-3.69 (m, 1H), 3.65-3.58 (m, 1H), 3.41 (s, 3H), 3.29 (m, 1H) | 454.1 | |
| 226 | 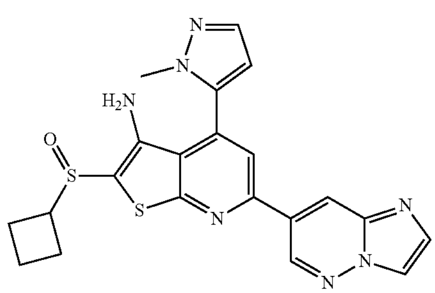 [SMILES: Cn1nccc1-c1cc(-c2cnn3ccnc3c2)nc2sc(S(=O)C3CCC3)c(N)c12] | 9.27 (d, J = 2.0 Hz, 1H), 8.55 (d, J = 2.0 Hz, 1H), 8.08 (s, 1H), 7.89 (d, J = 0.8 Hz, 1H), 7.69 (d, J = 1.6 Hz, 2H), 7.68 (s, 1H), 6.51 (s, 1H), 4.56 (d, J = 38.4 Hz, 2H), 3.98-3.94 (m, 1H), 3.77 (s, 3H), 2.90-2.77 (m, 1H), 2.47-2.22 (m, 3H), 2.17-2.03 (m, 2H). | 450.1 | |
| 227 | 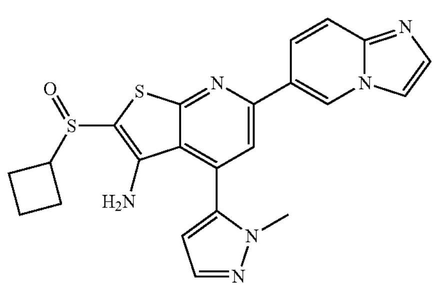 [SMILES: Cn1nccc1-c1cc(-c2ccc3nccn3c2)nc2sc(S(=O)C3CCC3)c(N)c12] | DMSO-d6 9.88 (d, J = 2.8 Hz, 1H), 9.36 (d, J = 2.4 Hz, 1H), 8.15 (s, 1H), 8.01 (s, 1H), 7.80 (s, 1H), 7.70 (d, J = 1.6 Hz, 1H), 6.66 (s, 1H), 5.05 (s, 2H), 3.90-3.84 (m, 1H), 3.74 (s, 3H), 2.67-2.61 (m, 1H), 2.26-2.12 (m, 3H), 2.09-1.88 (m, 2H) | 450.1 | R-isomer: 98% ee; [α] = +64.999°; S-isomer: 99% ee; [α] = −223.632° |

| Ex. No. | Structure | 400 MHz NMR (δ; CDCl₃ unless otherwise noted) | LCMS (ES⁺; MH⁺) | Chiral info |
|---|---|---|---|---|
| 228 | 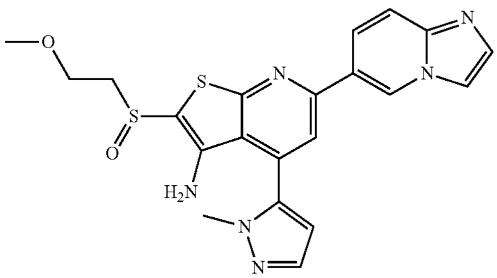 [SMILES: COCCS(=O)c1sc2nc(-c3ccc4nccn4c3)cc(-c3ccnn3C)c2c1N] | DMSO-d6 9.91 (d, J = 2.4 Hz, 1H), 9.38 (d, J = 2.8 Hz, 1H), 8.18 (s, 1H), 8.03 (d, J = 1.2 Hz, 1H), 7.82 (d, J = 1.6 Hz, 1H), 7.72 (d, J = 2.0 Hz, 1H), 6.67 (d, J = 1.2 Hz, 1H), 5.09 (s, 2H), 3.77-3.73 (m, 4H), 3.66 (m, 1H), 3.39-3.37 (m, 1H), 3.29-3.24 (m, 4H). | 454.2 | |
| 229 | 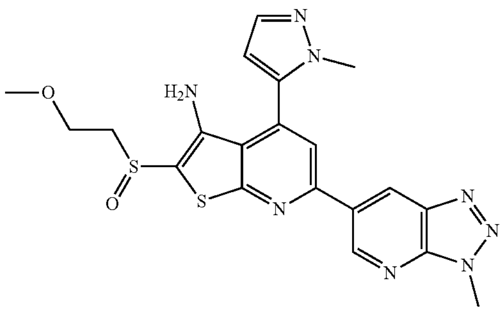 [SMILES: COCCS(=O)c1sc2nc(-c3cnc4c(c3)nnn4C)cc(-c3ccnn3C)c2c1N] | DMSO-d6 9.64 (d, J = 1.6 Hz, 1H), 9.35 (d, J = 1.6 Hz, 1H), 8.30 (s, 1H), 7.71 (d, J = 1.6 Hz, 1H), 6.67 (s, 1H), 5.07 (s, 2H), 4.36 (s, 3H), 3.78-3.72 (m, 4H), 3.67-3.62 (m, 1H), 3.41-3.37 (m, 1H), 3.28 (s, 3H), 3.26-3.21 (m, 1H). | 469.3 | |
| 230 | 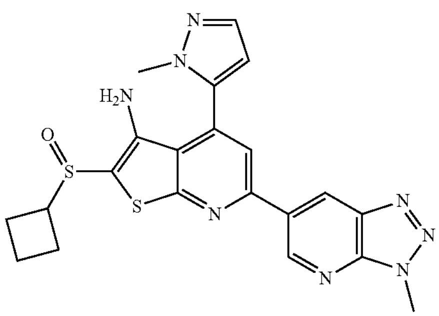 [SMILES: Cn1nccc1-c1cc(-c2cnc3c(c2)nnn3C)nc2sc(S(=O)C3CCC3)c(N)c12] | DMSO-d6 9.62 (s, 1H), 9.33 (d, J = 1.6 Hz, 1H), 8.27 (s, 1H), 7.70 (d, J = 2.0 Hz, 1H), 6.67 (s, 1H), 5.04 (s, 2H), 4.36 (s, 3H), 3.93-3.85 (m, 1H), 3.74 (s, 3H), 2.70-2.65 (m, 1H), 2.25-2.12 (m, 3H), 2.08-1.99 (m, 1H), 1.97-1.88 (m, 1H). | 465.2 | R-isomer: 97% ee; [α] = +146.313°; S-isomer: 100% ee; [α] = −145.920°; |
| 231 | 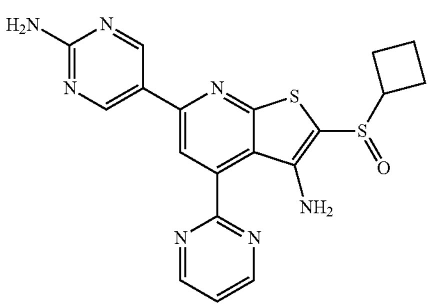 [SMILES: Nc1ncc(-c2cc(-c3ncccn3)c3c(N)c(S(=O)C4CCC4)sc3n2)cn1] | DMSO-d6 9.12 (d, J = 5.2 Hz, 2H), 9.02 (s, 2H), 8.23 (s, 1H), 7.73 (t, J = 4.8 Hz, 1H), 7.18 (s, 2H), 6.21 (s, 2H), 3.88 (t, J = 6.0 Hz, 1H), 2.66-2.61 (m, 1H), 2.21-2.16 (m, 3H), 2.02-1.90 (m, 2H). | 424.2 | |
| 232 | 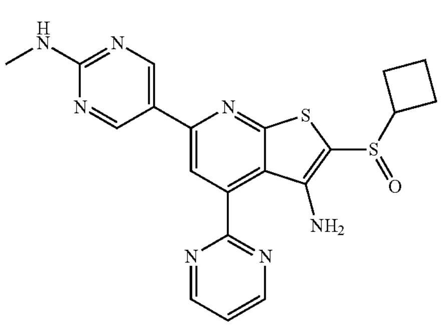 [SMILES: CNc1ncc(-c2cc(-c3ncccn3)c3c(N)c(S(=O)C4CCC4)sc3n2)cn1] | 9.09 (s, 2H), 8.98 (d, J = \4.8 Hz, 2H), 8.27 (s, 1H), 7.46 (t, J = 4.8 Hz, 1H), 6.32 (s, 2H), 5.40-5.38 (m, 1H), 3.98 (t, J = 8.0 Hz, 1H), 3.11-3.09 (m, 3H), 2.85-2.80 (m, 1H), 2.39-2.34 (m, 2H), 2.27-2.25 (m, 1H), 2.10-2.05 (m, 2H). | 438.2 | |

-continued

| Ex. No. | Structure | 400 MHz NMR (δ; CDCl₃ unless otherwise noted) | LCMS (ES⁺; MH⁺) | Chiral info |
|---|---|---|---|---|
| 233 | 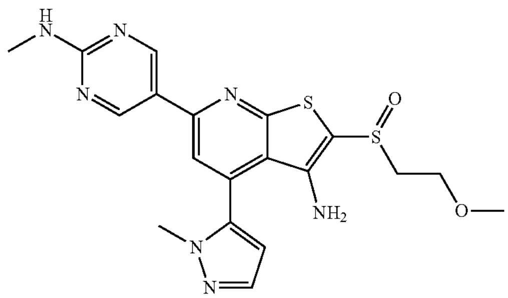 | 9.03 (s, 2H), 7.67 (d, J = 2.0 Hz, 1H), 7.45 (s, 1H), 6.49-6.48 (m, 1H), 5.43 (t, J = 4.8 Hz, 1H), 4.52-4.45 (m, 2H), 3.83-3.81 (m, 1H), 3.76 (s, 3H), 3.75-3.71 (m, 1H), 3.61-3.58 (m, 1H), 3.40 (s, 3H), 3.29-3.23 (m, 1H), 3.11-3.10 (m, 3H). | 444.2 | R-isomer: 98% ee; [α] = +95.687. S-isomer: 98% ee; [α] = −111.509. |
| 234 | 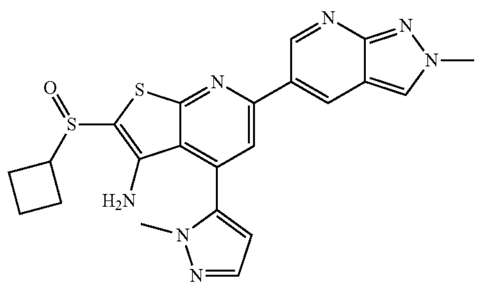 [SMILES: Cn1cc2cc(-c3cc(-c4ccnn4C)c4c(N)c(S(=O)C5CCC5)sc4n3)cnc2n1] | DMSO-d6 9.44 (d, J = 1.6 Hz, 1H), 9.06 (d, J = 1.6 Hz, 1H), 8.57 (s, 1H), 8.12 (s, 1H), 7.69 (s, 1H), 6.65 (s, 1H), 5.01 (s, 2H), 4.24 (s, 3H), 3.89-3.83 (m, 1H), 3.72 (s, 3H), 2.67-2.60 (m, 1H), 2.24-2.15 (m, 3H), 2.07-1.99 (m, 1H), 1.96-1.88 (m, 1H). | 464.3 | |
| 235 | 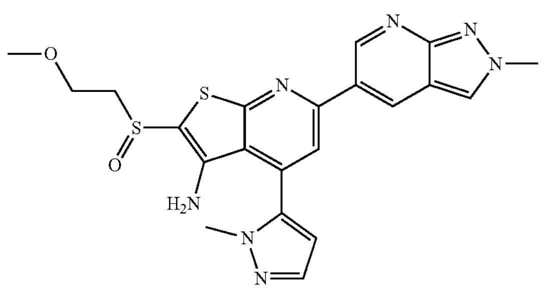 | DMSO-d6 9.45 (d, J = 2.0 Hz, 1H), 9.08 (d, J = 2.0 Hz, 1H), 8.57 (s, 1H), 8.14 (s, 1H), 7.70 (s, 1H), 6.66 (s, 1H), 5.04 (s, 2H), 4.24 (s, 3H), 3.77-3.72 (m, 4H), 3.65-3.62 (m, 1H), 3.41-3.36 (m, 1H), 3.28 (s, 3H), 3.26-3.19 (m, 1H). | 468.3 | R-isomer: 100% ee; [α] = +42.112°; S-isomer: 96% ee; [α] = −39.840°; |
| 236 | 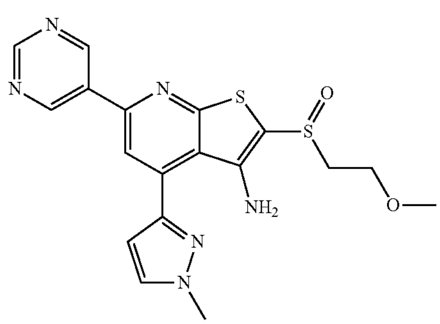 [SMILES: COCCS(=O)c1sc2nc(-c3cncnc3)cc(-c3ccn(C)n3)c2c1N] | DMSO-d6 9.60 (s, 2H), 9.31 (s, 1H), 8.29 (s, 1H), 8.03 (d, J = 2.0 Hz, 1H), 7.22 (d, J = 2.0 Hz, 1H), 7.05 (s, 2H), 4.02 (s, 3H), 3.78-3.71 (m, 1H), 3.66-3.59 (m, 1H), 3.43-3.36 (m, 1H), 3.29 (s, 3H), 3.28-3.20 (m, 1H). | 415.0 | |
| 237 | 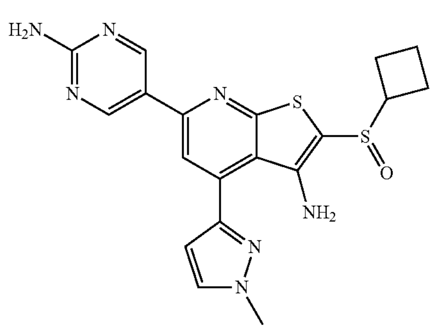 [SMILES: Cn1ccc(-c2cc(-c3cnc(N)nc3)nc3sc(S(=O)C4CCC4)c(N)c23)n1] | DMSO-d6 9.08 (s, 2H), 7.99 (s, 2H), 7.14 (s, 3H), 6.92 (s, 2H), 4.00 (s, 3H), 3.93-3.82 (s, 1H), 2.69-2.58 (m, 1H), 2.25-2.12 (m, 3H), 2.09-1.88 (m, 2H). | 426.1 | |

| Ex. No. | Structure | 400 MHz NMR (δ; CDCl₃ unless otherwise noted) | LCMS (ES⁺; MH⁺) | Chiral info |
|---|---|---|---|---|
| 238 | 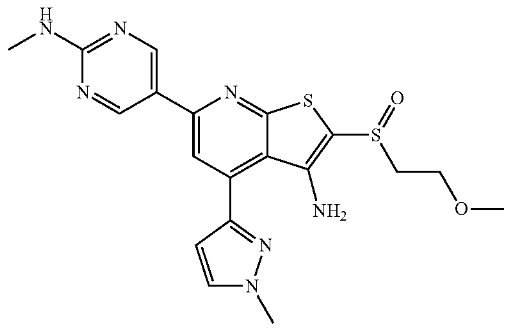 | DMSO-d6 9.12 (s, 2H), 8.03-7.99 (m, 2H), 7.66-7.60 (m, 1H), 7.15 (d, J = 2.4 Hz, 1H), 6.96 (s, 2H), 4.00 (s, 3H), 3.78-3.69 (m, 1H), 3.64-3.57 (m, 1H), 3.36 (s, 1H), 3.29 (s, 3H), 3.25-3.17 (m, 1H), 2.90 (d, J = 4.8 Hz, 3H) | 444.1 | |
| 239 | 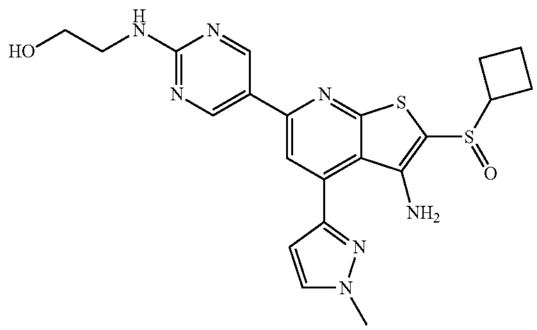 [SMILES: Cn1ccc(-c2cc(-c3cnc(NCCO)nc3)nc3sc(S(=O)C4CCC4)c(N)c23)n1] | DMSO-d6 9.10 (s, 2H), 8.01-7.97 (m, 2H), 7.60-7.55 (m, 1H), 7.13 (d, J = 2.4 Hz, 1H), 6.92 (s, 2H), 4.75-4.68 (m, 1H), 4.00 (s, 3H), 3.92-3.82 (m, 1H), 3.60-3.53 (m, 2H), 3.48-3.41 (m, 2H), 2.70-2.60 (m, 1H), 2.23-2.13 (m, 3H), 2.06-1.88 (m, 2H). | 470.1 | |
| 240 | 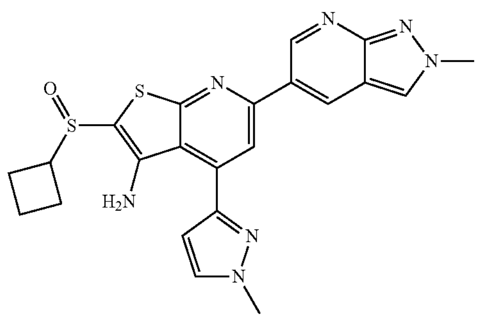 [SMILES: Cn1ccc(-c2cc(-c3cnc4nn(C)cc4c3)nc3sc(S(=O)C4CCC4)c(N)c23)n1] | DMSO-d6 9.44 (d, J = 2.0 Hz, 1H), 9.05 (d, J = 2.0 Hz, 1H), 8.57 (s, 1H), 8.19 (s, 1H), 8.01 (d, J = 2.4 Hz, 1H), 7.19 (d, J = 2.0 Hz, 1H), 6.95 (s, 2H), 4.25 (s, 3H), 4.01 (s, 3H), 3.93-3.84 (m, 1H), 2.69-2.60 (m, 1H), 2.25-2.13 (m, 3H), 2.08-2.01 (m, 1H), 1.99-1.91 (m, 1H). | 464.2 | |
| 241 | 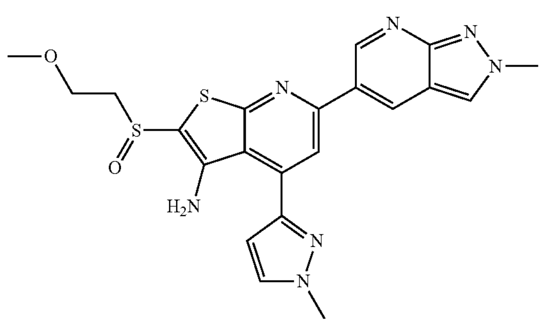 | DMSO-d6 9.45 (d, J = 2.0 Hz, 1H), 9.06 (d, J = 2.4 Hz, 1H), 8.58 (s, 1H), 8.21 (s, 1H), 8.02 (d, J = 2.4 Hz, 1H), 7.21 (d, J = 2.0 Hz, 1H), 6.99 (s, 2H), 4.25 (s, 3H), 4.01 (s, 3H), 3.73-3.72 (m, 1H), 3.63-3.61 (m, 1H), 3.38-3.37 (m, 1H), 3.36 (s, 3H), 3.29-3.23 (m, 1H). | 468.1 | R-isomer: 100% ee; [α] = +79.150. S-isomer: 100% ee; [α] = −82.080. |
| 242 | 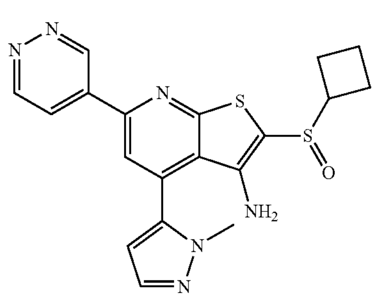 [SMILES: Cn1nccc1-c1cc(-c2ccnnc2)nc2sc(S(=O)C3CCC3)c(N)c12] | DMSO-d6 10.03 (m, 1H), 9.41 (m, 1H), 8.45 (m, 1H), 8.32 (s, 1H), 7.71 (d, J = 2.0 Hz, 1H), 6.67 (s, 1H), 5.07 (s, 2H), 3.94-3.86 (m, 1H), 3.73 (s, 3H), 2.68-2.66 (m, 1H), 2.24-2.16 (m, 3H), 2.15-1.93 (m, 2H). | 411.0 | |

| Ex. No. | Structure | 400 MHz NMR (δ; CDCl₃ unless otherwise noted) | LCMS (ES⁺; MH⁺) | Chiral info |
|---|---|---|---|---|
| 243 | 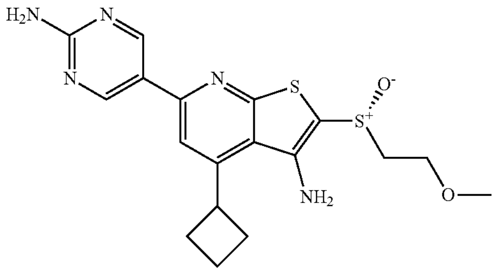 [SMILES: COCC[S@@+]([O-])c1sc2nc(-c3cnc(N)nc3)cc(C3CCC3)c2c1N] | 9.02 (s, 2H), 7.50 (s, 1H), 5.34 (s, 2H), 5.10 (s, 2H), 4.21-4.16 (m, 1H), 3.88-3.86 (m, 1H), 3.70-3.69 (m, 1H), 3.67-3.61 (m, 1H), 3.41 (s, 3H), 3.28-3.22 (m, 1H), 2.52-2.42 (m, 4H), 2.41-2.39 (m, 1H), 2.16-2.00 (m, 1H). | 404.2 | |
| 244 | 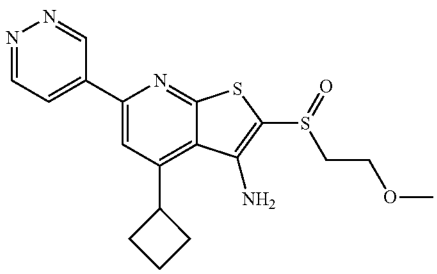 [SMILES: COCCS(=O)c1sc2nc(-c3ccnnc3)cc(C3CCC3)c2c1N] | 9.90 (dd, J1 = 2.4 Hz, J2 = 1.2 Hz, 1H), 9.36 (dd, J1 = 5.2 Hz, J2 = 1.2 Hz, 1H), 8.19 (dd, J1 = 5.6 Hz, J2 = 2.4 Hz, 1H), 7.78 (s, 1H), 5.18 (s, 2H), 4.31-4.22 (m, 1H), 3.95-3.88 (m, 1H), 3.76-3.69 (m, 1H), 3.68-3.60 (m, 1H), 3.44 (s, 3H), 3.35-3.27 (m, 1H), 2.61-2.52 (m, 2H), 2.51-2.40 (m, 2H), 2.29-2.16 (m, 1H), 2.11-2.00 (m, 1H). | 389.0 | |
| 245 | 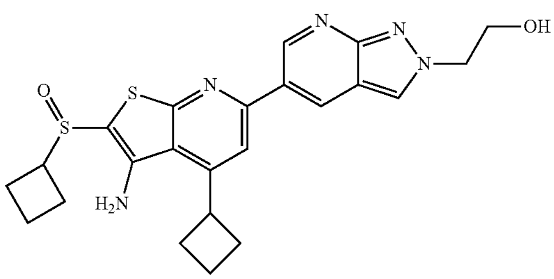 [SMILES: Nc1c(S(=O)C2CCC2)sc2nc(-c3cnc4nn(CCO)cc4c3)cc(C3CCC3)c12] | DMSO-d6 9.42 (d, J = 2.4 Hz, 1H), 9.03 (d, J = 2.4 Hz, 1H), 8.56 (s, 1H), 7.92 (s, 1H), 5.75 (s, 2H), 4.54 (t, J = 5.4 Hz, 2H), 4.47-4.39 (m, 1H), 3.93 (t, J = 5.4 Hz, 2H), 3.89-3.83 (m, 1H), 2.68-2.60 (m, 1H), 2.47-2.43 (m, 2H), 2.39-2.33 (m, 2H), 2.24-2.13 (m, 3H), 2.11-1.99 (m, 2H), 1.97-1.83 (m, 2H). | 468.1 | |
| 246 | 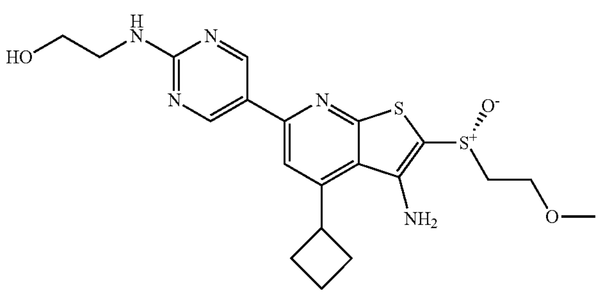 [SMILES: COCC[S@@+]([O-])c1sc2nc(-c3cnc(NCCO)nc3)cc(C3CCC3)c2c1N] | 8.97 (s, 2H), 7.44 (s, 1H), 5.98-5.91 (m, 1H), 5.10 (s, 2H), 4.24-4.13 (m, 1H), 3.95-3.86 (m, 3H), 3.82 (s, 1H), 3.73-3.66 (m, 3H), 3.65-3.58 (m, 1H), 3.42 (s, 3H), 3.31-3.23 (m, 1H), 2.56-2.46 (m, 2H), 2.45-2.30 (m, 2H), 2.24-2.11 (m, 1H), 2.05-1.95 (s, 1H) | 448.1 | R-isomer: 98.2% ee; [α] = +35.337; S-isomer: 94.8% ee; [α] = −36.966. |
| 247 | 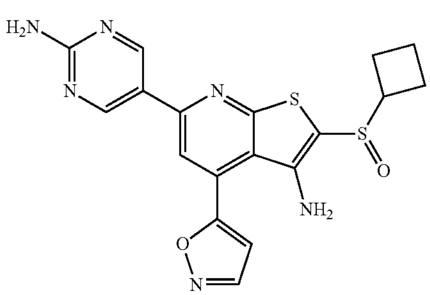 [SMILES: Nc1ncc(-c2cc(-c3ccno3)c3c(N)c(S(=O)C4CCC4)sc3n2)cn1] | 9.04 (s, 2H), 8.50 (d, J = 2.0 Hz, 1H), 7.68 (s, 1H), 6.76 (d, J = 1.6 Hz, 1H), 5.34 (s, 2H), 5.09 (s, 2H), 3.97 (t, J = 8.4 Hz, 1H), 2.86-2.79 (m, 1H), 2.43-2.32 (m, 2H), 2.32-2.20 (m, 1H), 2.14-2.03 (m, 2H). | 413.1 | |

-continued
| Ex. No. | Structure | 400 MHz NMR (δ; CDCl₃ unless otherwise noted) | LCMS (ES⁺; MH⁺) | Chiral info |
|---|---|---|---|---|
| 248 | 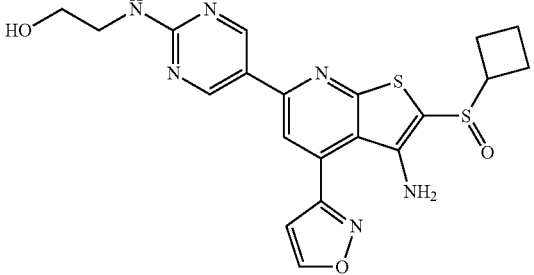 | DMSO-d6 9.29 (d, J = 1.6 Hz, 1H), 9.12 (s, 2H), 8.09 (s, 1H), 7.64 (t, J = 5.6 Hz, 1H), 7.39 (d, J = 2.0 Hz, 1H), 6.14 (s, 2H), 4.71 (t, J = 5.6 Hz, 1H), 3.90-3.86 (m, 1H), 3.58-3.53 (m, 2H), 3.46-3.42 (m, 2H), 2.70-2.61 (m, 1H), 2.25-2.11 (m, 3H), 2.05-1.98 (m, 1H), 1.95-1.89 (m, 1H). | 457.2 | |
| 249 | 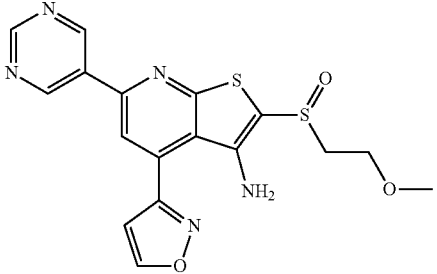 [SMILES: COCCS(=O)c1sc2nc(-c3cncnc3)cc(-c3ccon3)c2c1N] | DMSO-d6 9.62 (s, 2H), 9.34 (d, J = 1.6 Hz, 1H), 9.33 (s, 1H), 8.39 (s, 1H), 7.45 (d, J = 1.6 Hz, 1H), 6.26 (s, 2H), 3.80-3.73 (m, 1H), 3.69-3.62 (m, 1H), 3.44-3.37 (m, 1H), 3.29 (s, 3H), 3.28-3.23 (m, 1H). | 402.0 | |
| 250 | 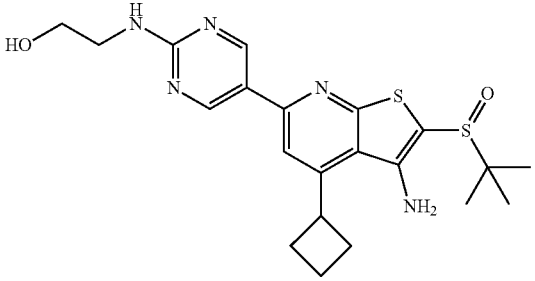 [SMILES: CC(C)(C)S(=O)c1sc2nc(-c3cnc(NCCO)nc3)cc(C3CCC3)c2c1N] | 8.92 (s, 2H), 7.38 (s, 1H), 6.16-6.13 (m, 1H), 5.25 (s, 2H), 4.22-4.14 (m, 1H), 3.98-3.88 (m, 1H), 3.76-3.64 (m, 2H), 2.54-2.37 (m, 3H), 2.34-2.25 (m, 1H), 2.20-2.09 (m, 1H), 2.04-1.94 (m, 2H), 1.40 (s, 9H). | 446.1 | |
| 251 | 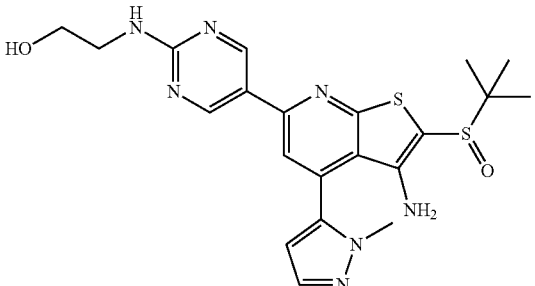 | DMSO-d6 9.10 (s, 2H), 7.92 (s, 1H), 7.67 (d, J = 1.6 Hz, 1H), 7.66-7.61 (m, 1H), 6.63 (s, 1H), 4.89 (s, 2H), 4.73 (t, J = 5.6 Hz, 1H), 3.69 (s, 3H), 3.58-3.51 (m, 2H), 3.46-3.40 (m, 2H), 1.27 (s, 9H). | 472.1 | |
| 252 | 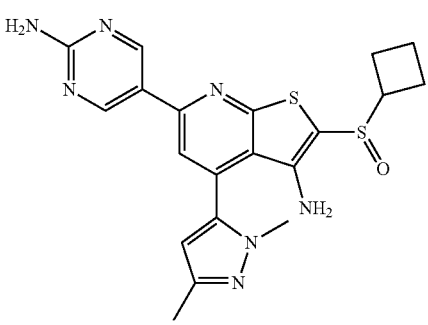 [SMILES: Cc1cc(-c2cc(-c3cnc(N)nc3)nc3sc(S(=O)C4CCC4)c(N)c23)n(C)n1] | 9.03 (s, 2H), 7.44 (s, 1H), 6.25 (d, J = 4.4 Hz, 1H), 5.31 (s, 2H), 4.64-4.55 (m, 2H), 3.96-3.92 (m, 1H), 3.66 (s, 3H), 2.89-2.75 (m, 1H), 2.42-2.31 (m, 5H), 2.30-2.20 (m, 1H), 2.15-2.04 (m, 2H). | 440.1 | |

| Ex. No. | Structure | 400 MHz NMR (δ; CDCl₃ unless otherwise noted) | LCMS (ES⁺; MH⁺) | Chiral info |
|---|---|---|---|---|
| 253 | 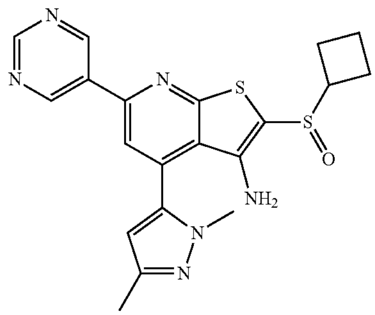 [SMILES: Cc1cc(-c2cc(-c3cncnc3)nc3sc(S(=O)C4CCC4)c(N)c23)n(C)n1] | 9.43 (s, 2H), 9.31 (s, 1H), 7.61 (s, 1H), 6.27 (s, 1H), 4.66 (d, J = 26.4 Hz, 2H), 4.03-3.88 (m, 1H), 3.68 (s, 3H), 2.90-2.78 (m, 1H), 2.48-2.32 (m, 5H), 2.30-2.22 (m, 1H), 2.16-2.05 (m, 2H). | 425.2 | |
| 254 | 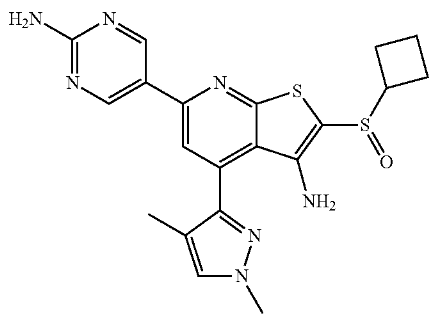 [SMILES: Cc1cn(C)nc1-c1cc(-c2cnc(N)nc2)nc2sc(S(=O)C3CCC3)c(N)c12] | DMSO-d6 9.03 (s, 2H), 7.82 (s, 1H), 7.77 (s, 1H), 7.14 (s, 2H), 6.00 (s, 2H), 3.93 (s, 3H), 3.87-3.81 (m, 1H), 2.66-2.57 (m, 1H), 2.22-2.13 (m, 3H), 2.11 (s, 3H), 2.06-1.97 (m, 1H), 1.97-1.88 (m, 1H) | 440.0 | |
| 255 | 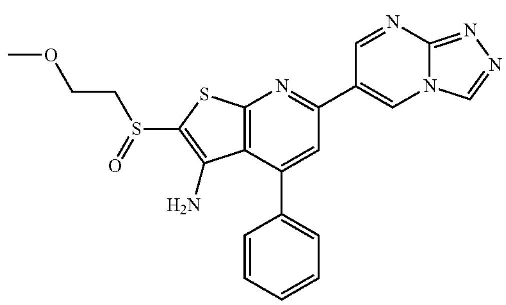 [SMILES: COCCS(=O)c1sc2nc(-c3cnc4nncn4c3)cc(-c3ccccc3)c2c1N] | DMSO-d6 10.21 (d, J = 2.8 Hz, 1H), 9.72 (d, J = 2.4 Hz, 1H), 8.77 (s, 1H), 8.17 (s, 1H), 7.63 (m, 5H), 5.02 (s, 2H), 3.78-3.71 (m, 1H), 3.68-3.61 (m, 1H), 3.42-3.37 (m, H), 3.28 (s, 3H), 3.26-3.20 (m, 1H). | 451.1 | R-isomer: 100% ee; [α] = +40.213°; S-isomer: 100% ee; [α] = −75.514°; |
| 256 | 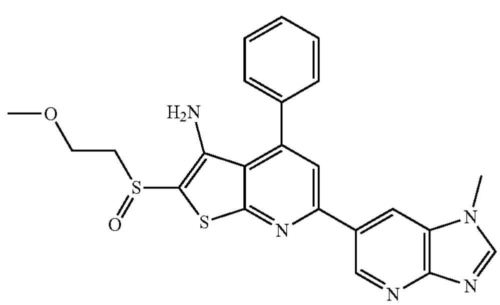 [SMILES: COCCS(=O)c1sc2nc(-c3cnc4ncn(C)c4c3)cc(-c3ccccc3)c2c1N] | 9.22 (d, J = 2.0 Hz, 1H), 8.62 (d, J = 2.4 Hz, 1H), 8.16 (s, 1H), 7.70 (s, 1H), 7.59-7.54 (m, 5H), 4.61 (s, 2H), 3.99 (s, 3H), 3.3.90-3.85 (m, 1H), 3.74-3.68 (m, 1H), 3.64-3.58 (m, 1H), 3.41 (s, 3H), 3.32-3.25 (m, 1H). | 464.1 | R-isomer: 100% ee; [α] = +28.687°; S-isomer: 98% ee; [α] = −31.782°; |
| 257 | 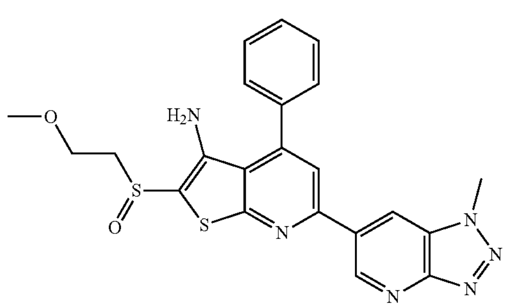 [SMILES: COCCS(=O)c1sc2nc(-c3cnc4nnn(C)c4c3)cc(-c3ccccc3)c2c1N] | DMSO-d6 9.58 (d, J = 2.0 Hz, 1H), 9.22 (d, J = 2.0 Hz, 1H), 8.13 (s, 1H), 7.64 (s, 5H), 5.01 (s, 2H), 4.42 (s, 3H), 3.78-3.72 (m, 1H), 3.67-3.62 (m, 1H), 3.41-3.31 (m, 1H), 3.29 (s, 3H), 3.27-3.20 (m, 1H). | 465.0 | |

-continued

| Ex. No. | Structure | 400 MHz NMR (δ; CDCl₃ unless otherwise noted) | LCMS (ES⁺; MH⁺) | Chiral info |
|---|---|---|---|---|
| 258 | 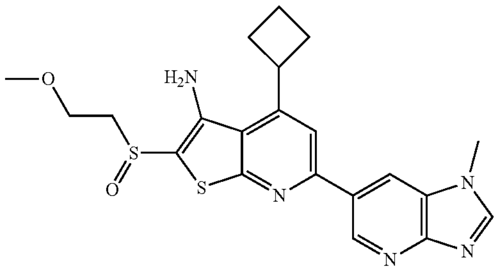 [SMILES: COCCS(=O)c1sc2nc(-c3cnc4ncn(C)c4c3)cc(C3CCC3)c2c1N] | 9.14 (d, J = 2.0 Hz, 1H), 8.34 (d, J = 2.0 Hz, 1H), 8.08 (s, 1H), 7.67 (s, 1H), 5.09 (s, 2H), 4.27-4.18 (m, 1H), 3.93 (s, 3H), 3.90-3.84 (m, 1H), 3.68-3.63 (m, 1H), 3.62-3.56 (m, 1H), 3.40 (s, 3H), 3.26-3.20 (m, 1H), 2.58-2.42 (m, 3H), 2.34-2.27 (m, 1H), 2.21-2.12 (m, 1H), 2.03-1.99 (m, 1H). | 442.0 | R-isomer: 100% ee; [α] = +95.240°; S-isomer: 98% ee; [α] = −91.873°; |
| 259 | 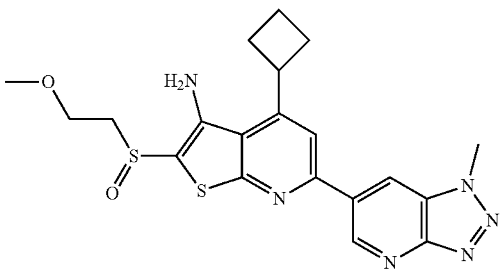 [SMILES: COCCS(=O)c1sc2nc(-c3cnc4nnn(C)c4c3)cc(C3CCC3)c2c1N] | DMSO-d6 9.54 (d, J = 2.0 Hz, 1H), 9.14 (d, J = 2.0 Hz, 1H), 8.06 (s, 1H), 5.80 (s, 2H), 4.52-4.44 (m, 4H), 3.78-3.72 (m, 1H), 3.65-3.60 (m, 1H), 3.42-3.36 (m, 1H), 3.29 (s, 3H), 3.26-3.19 (m, 1H), 2.47-2.35 (m, 4H), 2.15-2.04 (m, 1H), 1.91-1.83 (m, 1H). | 443.0 | |
| 260 | 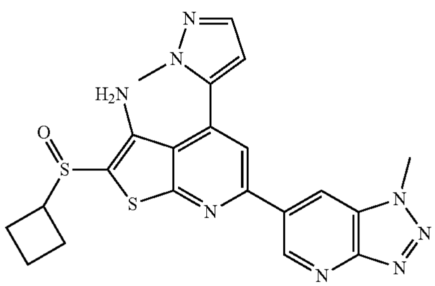 [SMILES: Cn1nccc1-c1cc(-c2cnc3nnn(C)c3c2)nc2sc(S(=O)C3CCC3)c(N)c12] | DMSO-d6 9.57 (d, J = 2.0 Hz, 1H), 9.22 (d, J = 2.4 Hz, 1H), 8.28 (s, 1H), 7.71 (d, J = 2.0 Hz, 1H), 6.68 (s, 1H), 5.05 (s, 2H), 4.42 (s, 3H), 3.93-3.85 (m, 1H), 3.73 (s, 3H), 2.68-2.63 (m, 1H), 2.26-2.12 (m, 3H), 2.08-1.99 (m, 1H), 1.96-1.88 (m, 1H). | 465.2 | |
| 261 | 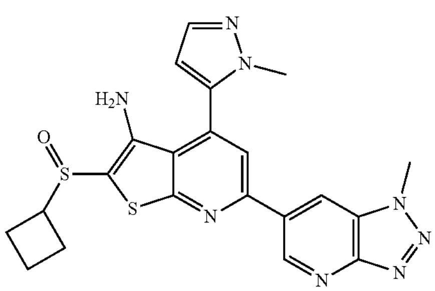 [SMILES: Cn1nccc1-c1cc(-c2cnc3nnn(C)c3c2)nc2sc(S(=O)C3CCC3)c(N)c12] | 9.21 (d, J = 2.0 Hz, 1H), 8.64 (d, J = 2.0 Hz, 1H), 8.19 (s, 1H), 7.75 (s, 1H), 7.69 (d, J = 2.0 Hz, 1H), 6.52 (m, 1H), 4.60-4.49 (m, 2H), 4.00 (s, 3H), 3.98-3.92 (m, 1H), 3.78 (s, 3H), 2.89-2.77 (m, 1H), 2.47-2.32 (m, 2H), 2.31-2.21 (m, 1H), 2.16-2.04 (m, 2H). | 464.1 | R-isomer: 100% ee; [α] = +77.141°; S-isomer: 97% ee; [α] = −59.110° |
| 262 | 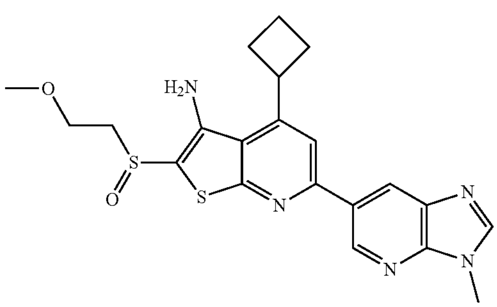 [SMILES: COCCS(=O)c1sc2nc(-c3cnc4c(c3)ncn4C)cc(C3CCC3)c2c1N] | 9.15 (d, J = 2.0 Hz, 1H), 8.67 (d, J = 2.0 Hz, 1H), 8.09 (s, 1H), 7.66 (s, 1H), 5.11 (s, 2H), 4.23-4.14 (m, 1H), 3.96 (s, 3H), 3.90-3.84 (m, 1H), 3.70-3.65 (m, 1H), 3.63-3.57 (m, 1H), 3.40 (s, 3H), 3.30-3.24 (m, 1H), 2.55-2.48 (m, 2H), 2.42-2.35 (m, 1H), 2.22-2.10 (m, 2H), 2.05-1.96 (m, 1H) | 442.0 | R-isomer: 100% ee; [α] = +106.108°; S-isomer: 99% ee; [α] = −96.478°; |

| Ex. No. | Structure | 400 MHz NMR (δ; CDCl₃ unless otherwise noted) | LCMS (ES⁺; MH⁺) | Chiral info |
|---|---|---|---|---|
| 263 | 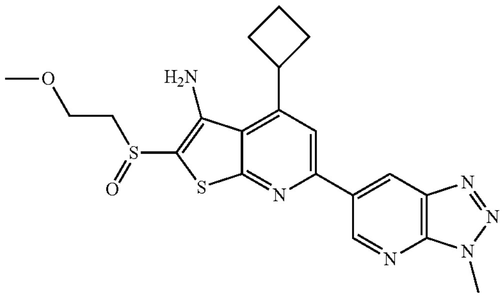 [SMILES: COCCS(=O)c1sc2nc(-c3cnc4c(c3)nnn4C)cc(C3CCC3)c2c1N] | DMSO-d6<br>9.54 (d, J = 6.0 Hz, 1H), 9.30 (d, J = 2.0 Hz, 1H), 8.01 (s, 1H), 5.76 (s, 2H), 4.47-4.38 (m, 1H), 4.35 (s, 3H), 3.78-3.73 (m, 1H), 3.64-3.59 (m, 1H), 3.42-3.36 (m, 1H), 3.29 (s, 3H), 3.25-3.19 (m, 1H), 2.50-2.36 (m, 4H), 2.13-2.02 (m, 1H), 1.90-1.82 (m, 1H). | 443.2 | |
| 264 | 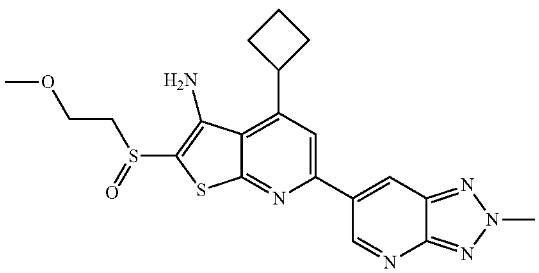 | DMSO-d6<br>9.60 (d, J = 2.0 Hz, 1H), 9.21 (d, J = 2.4 Hz, 1H), 8.04 (s, 1H), 5.77 (s, 2H), 4.60 (s, 3H), 4.50-4.41 (m, 1H), 3.78-.372 (m, 1H), 3.64-3.59 (m, 1H), 3.42-3.36 (m, 1H), 3.29 (s, 3H), 3.25-3.19 (m, 1H), 2.46-2.35 (m, 4H), 2.14-2.02 (m, 1H), 1.90-1.82 (m, 1H). | 443.2 | |
| 265 | 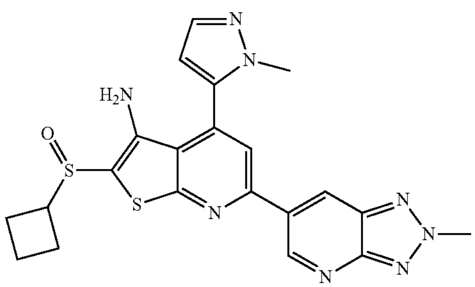 [SMILES: Cn1nc2cc(-c3cc(-c4ccnn4C)c4c(N)c(S(=O)C5CCC5)sc4n3)cnc2n1] | DMSO-d6<br>9.64 (d, J = 2.0 Hz, 1H), 9.21 (d, J = 2.4 Hz, 1H), 8.26 (s, 1H), 7.70 (d, J = 1.6 Hz, 1H), 6.66 (s, 1H), 5.03 (s, 2H), 4.59 (s, 3H), 3.93-3.85 (m, 1H), 3.74 (s, 3H), 2.74-2.61 (m, 1H), 2.26-2.13 (m, 3H), 2.06-1.99 (m, 1H), 1.97-1.87 (m, 1H). | 465.2 | |
| 266 | 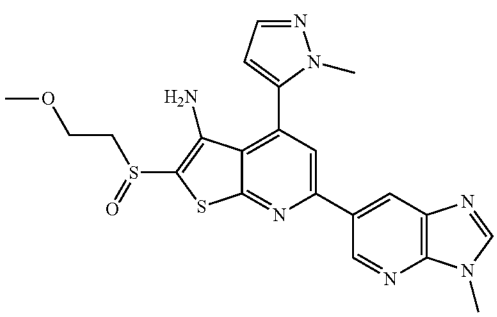 [SMILES: COCCS(=O)c1sc2nc(-c3cnc4c(c3)ncn4C)cc(-c3ccnn3C)c2c1N] | DMSO-d6<br>9.28 (d, J = 2.0 Hz, 1H), 8.89 (d, J = 2.0 Hz, 1H), 8.53 (s, 1H), 8.19 (s, 1H), 7.70 (d, J = 1.6 Hz, 1H), 6.67 (s, 1H), 5.05 (s, 2H), 3.91 (s, 3H), 3.79-3.71 (m, 4H), 3.67-3.60 (m, 1H), 3.38 (s, 1H), 3.29 (s, 3H), 3.26-3.19 (m, 1H). | 468.0 | |
| 267 | 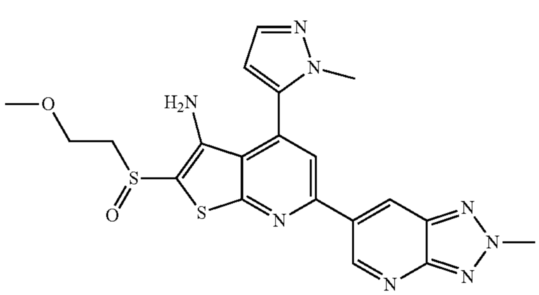 | DMSO-d6<br>9.65 (d, J = 2.0 Hz, 1H), 9.23 (d, J = 2.4 Hz, 1H), 8.28 (s, 1H), 7.71 (d, J = 2.0 Hz, 1H), 6.67 (s, 1H), 5.07 (s, 2H), 4.59 (s, 3H), 3.78-3.72 (m, 4H), 3.67-3.62 (m, 1H), 3.42-3.38 (m, 1H), 3.28 (s, 3H), 3.26-3.20 (m, 1H). | 469.2 | R-isomer: 98% ee; [α] = +106.322°; S-isomer: 95% ee; [α] = −98.728°; |

-continued

| Ex. No. | Structure | 400 MHz NMR (δ; CDCl₃ unless otherwise noted) | LCMS (ES⁺; MH⁺) | Chiral info |
|---|---|---|---|---|
| 268 | 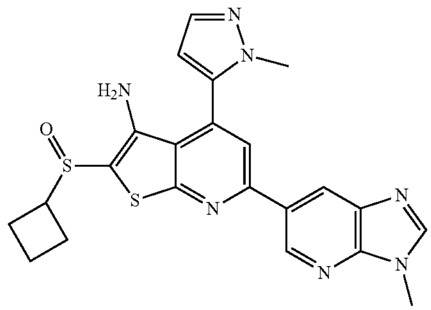 [SMILES: Cn1nccc1-c1cc(-c2cnc3c(c2)ncn3C)nc2sc(S(=O)C3CCC3)c(N)c12] | 9.19 (d, J = 2.0 Hz, 1H), 8.75 (d, J = 1.6 Hz, 1H), 8.13 (s, 1H), 7.69 (d, J = 1.6 Hz, 1H), 7.67 (s, 1H), 6.52 (m, 1H), 4.61-4.51 (m, 2H), 4.00 (s, 3H), 3.97-3.93 (m, 1H), 3.79 (s, 3H), 2.89-2.79 (m, 1H), 2.47-2.33 (m, 2H), 2.31-2.22 (m, 1H), 2.15-2.04 (m, 2H). | 464.0 | |
| 269 | 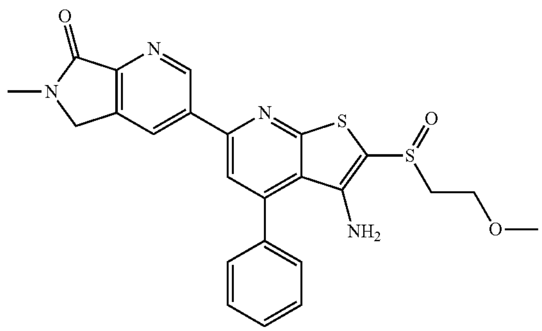 | 9.38 (s, 1H), 8.68 (d, J = 1.6 Hz, 1H), 7.70 (s, 1H), 7.61-7.56 (m, 3H), 7.53 (m, 2H), 4.63 (s, 2H), 4.50 (s, 2H), 3.87 (m, 1H), 3.74-3.68 (m, 1H), 3.61 (m, 1H), 3.40 (s, 3H), 3.32 (s, 3H), 3.31-3.25 (m, 1H). | 479.2 | |
| 270 | 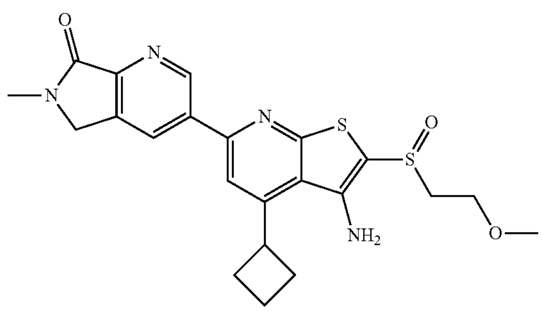 | 9.36 (d, J = 2.0 Hz, 1H), 8.55 (d, J = 1.6 Hz, 1H), 7.72 (s, 1H), 5.14 (s, 2H), 4.48 (s, 2H), 4.25 (m, 1H), 3.89 (m, 1H), 3.73-3.66 (m, 1H), 3.66-3.59 (m, 1H), 3.42 (s, 3H), 3.33 (s, 3H), 3.28 (m, 1H), 2.59-2.47 (m, 3H), 2.46-2.36 (m, 1H), 2.26-2.15 (m, 1H), 2.09-1.98 (m, 1H) | 457.2 | |
| 271 | 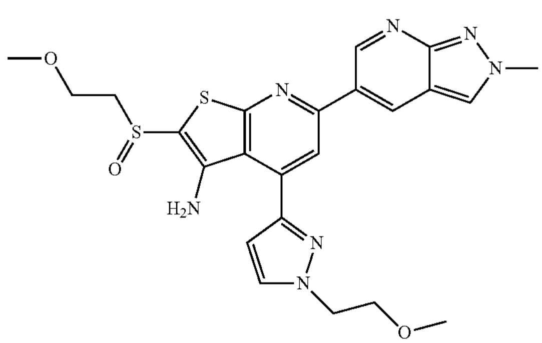 | 9.40 (d, J = 2.4 Hz, 1H), 8.84 (d, J = 2.4 Hz, 1H), 8.04 (s, 1H), 7.89 (s, 1H), 7.67 (d, J = 2.4 Hz, 1H), 6.76 (d, J = 2.4 Hz, 1H), 6.46 (s, 2H), 4.41 (t, J = 4.8 Hz, 2H), 4.31 (s, 3H), 3.90-3.85 (m, 1H), 3.82-3.80 (m, 2H), 3.72-3.67 (m, 1H), 3.65-3.59 (m, 1H), 3.41 (s, 3H), 3.39 (s, 3H), 3.34-3.27 (m, 1H). | 512.2 | R-isomer: 99% ee; [α] = +61.878°; S-isomer: 99% ee; [α] = −59.924°; |

-continued

| Ex. No. | Structure | 400 MHz NMR (δ; CDCl₃ unless otherwise noted) | LCMS (ES⁺; MH⁺) | Chiral info |
|---|---|---|---|---|
| 272 | 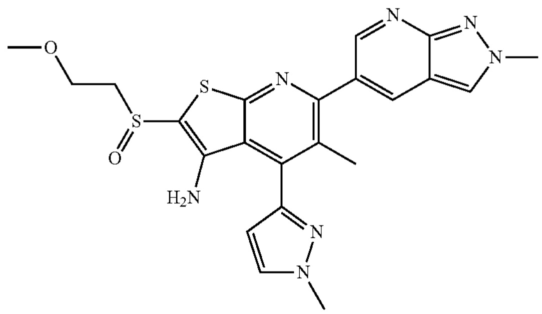 | 8.91 (d, J = 2.0 Hz, 1H), 8.29 (d, J = 2.0 Hz, 1H), 8.02 (s, 1H), 7.64 (d, J = 2.0 Hz, 1H), 6.48 (d, J = 2.0 Hz, 1H), 4.82 (s, 2H), 4.33 (s, 3H), 4.07 (s, 3H), 3.90-3.82 (m, 1H), 3.71-3.64 (m, 1H), 3.62-3.55 (m, 1H), 3.40 (s, 3H), 3.31-3.23 (m, 1H), 2.25 (s, 3H). | 482.2 | |
| 273 | 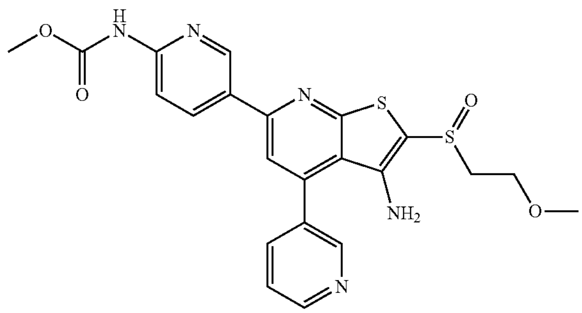 | DMSO-d6 10.51 (s, 1H), 9.13 (d, J = 1.6 Hz, 1H), 8.81 (d, J = 1.6 Hz, 1H), 8.77-8.76 (m, 1H), 8.62-8.59 (m, 1H), 8.05-8.03 (m, 1H), 8.00-7.97 (m, 2H), 7.62-7.59 (m, 1H), 4.94 (s, 2H), 3.77-3.72 (m, 1H), 3.70 (s, 3H), 3.66-3.61 (m, 1H), 3.41-3.37 (m, 1H), 3.28 (s, 3H), 3.25-3.19 (m, 1H). | 484.1 | |
| 274 | 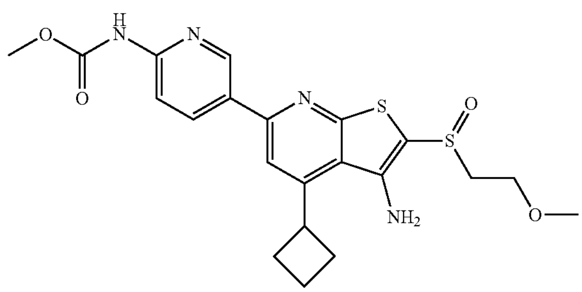 | 9.00 (d, J = 2.0 Hz, 1H), 8.50-8.32 (m, 2H), 8.14 (d, J = 8.8 Hz, 1H), 7.61 (s, 1H), 5.12 (s, 2H), 4.26-4.18 (m, 1H), 3.93-3.91 (m, 1H), 3.89 (s, 3H), 3.76-3.68 (m, 1H), 3.66-3.60 (m, 1H), 3.43 (s, 3H), 3.33-3.25 (m, 1H), 2.57-2.35 (m, 4H), 2.25-2.16 (m, 1H), 2.06-1.98 (m, 1H). | 461.1 | |
| 275 | 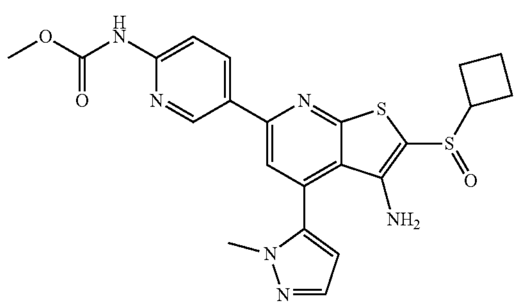 [SMILES: COC(=O)Nc1ccc(-c2cc(-c3ccnn3C)c3c(N)c(S(=O)C4CCC4)sc3n2)cn1] | 9.02 (s, 1H), 8.45-8.42 (m, 1H), 8.25 (m, 1H), 8.15-8.13 (m, 1H), 7.67 (s, 1H), 7.57 (s, 1H), 6.51-6.48 (m, 1H), 4.57-4.47 (m, 2H), 3.97-3.91 (m, 1H), 3.86 (s, 3H), 3.75 (s, 3H), 2.85-2.80 (m, 1H), 2.40-2.35 (m, 2H), 2.29-2.26 (m, 1H), 2.15-2.04 (m, 2H). | 483.1 | |
| 276 | 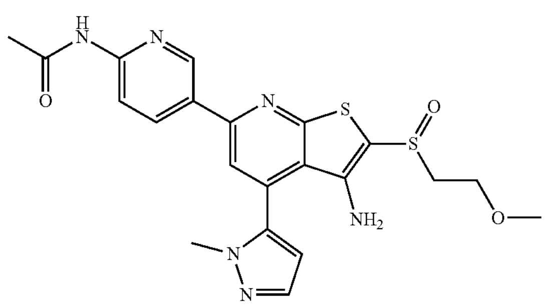 [SMILES: COCCS(=O)c1sc2nc(-c3ccc(NC(C)=O)nc3)cc(-c3ccnn3C)c2c1N] | 9.05-9.01 (m, 1H), 8.48-8.42 (m, 1H), 8.39-8.34 (m, 1H), 8.10 (s, 1H), 7.70 (d, J = 2.0 Hz, 1H), 7.61 (s, 1H), 6.54-6.47 (m, 1H), 4.60-4.47 (m, 2H), 3.94-3.86 (m, 1H), 3.78 (s, 3H), 3.76-3.68 (m, 1H), 3.66-3.58 (m, 1H), 3.42 (s, 3H), 3.33-3.26 (m, 1H), 2.28 (s, 3H) | 471.1 | |

| Ex. No. | Structure | 400 MHz NMR (δ; CDCl₃ unless otherwise noted) | LCMS (ES⁺; MH⁺) | Chiral info |
|---|---|---|---|---|
| 277 | 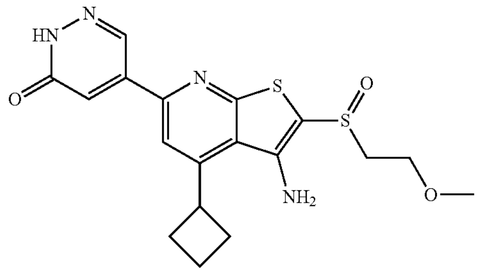 [SMILES: COCCS(=O)c1sc2nc(-c3cn[nH]c(=O)c3)cc(C3CCC3)c2c1N] | 11.05-10.79 (m, 1H), 8.69 (d, J = 2.0 Hz, 1H), 7.66 (s, 1H), 7.49 (d, J = 2.0 Hz, 1H), 5.16 (s, 2H), 4.27-4.18 (m, 1H), 3.92-3.87 (m, 1H), 3.73-3.68 (m, 1H), 3.66-3.60 (m, 1H), 3.42 (s, 3H), 3.33-3.27 (m, 1H), 2.57-2.50 (m, 2H), 2.45-2.34 (m, 2H), 2.25-2.16 (m, 1H), 2.08-1.99 (m, 1H). | 405.0 | |
| 278 | 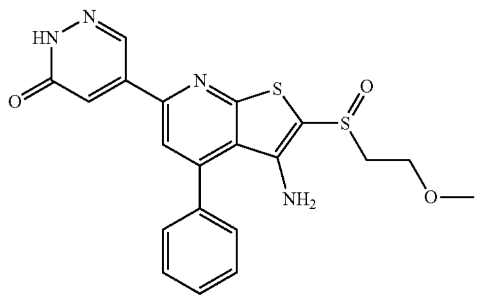 [SMILES: COCCS(=O)c1sc2nc(-c3cn[nH]c(=O)c3)cc(-c3ccccc3)c2c1N] | 10.50-10.46 (m, 1H), 8.69 (d, J = 2.0 Hz, 1H), 7.59-7.57 (m, 4H), 7.49-7.47 (m, 3H), 4.65 (s, 2H), 3.90-3.85 (m, 1H), 3.73-3.68 (m, 1H), 3.64-3.58 (m, 1H), 3.40 (s, 3H), 3.33-3.26 (m, 1H) | 427.0 | |
| 279 | 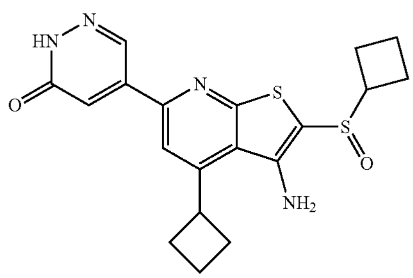 [SMILES: Nc1c(S(=O)C2CCC2)sc2nc(-c3cn[nH]c(=O)c3)cc(C3CCC3)c12] | 10.73-10.69 (m, 1H), 8.69 (d, J = 2.4 Hz, 1H), 7.66 (s, 1H), 7.49 (d, J = 2.0 Hz, 1H), 5.20 (s, 2H), 4.29-4.20 (m, 1H), 4.02-3.94 (m, 1H), 2.89-2.79 (m, 1H), 2.57-2.48 (m, 2H), 2.46-2.33 (m, 4H), 2.31-2.23 (m, 1H), 2.21-2.15 (m, 1H), 2.13-1.99 (m, 3H). | 401.0 | |
| 280 | 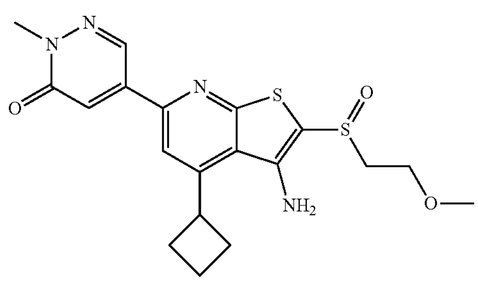 [SMILES: COCCS(=O)c1sc2nc(-c3cnn(C)c(=O)c3)cc(C3CCC3)c2c1N] | DMSO-d6 8.67 (d, J = 2.0 Hz, 1H), 7.97 (s, 1H), 7.77 (d, J = 2.4 Hz, 1H), 5.79 (s, 2H), 4.48-4.39 (m, 1H), 3.77-3.72 (m, 4H), 3.63-3.58 (m, 1H), 3.41-3.36 (m, 1H), 3.28 (s, 3H), 3.25-3.18 (m, 1H), 2.44-2.32 (m, 4H), 2.09-2.17 (m, 1H), 1.87-1.79 (m, 1H). | 419.0 | |
| 281 | 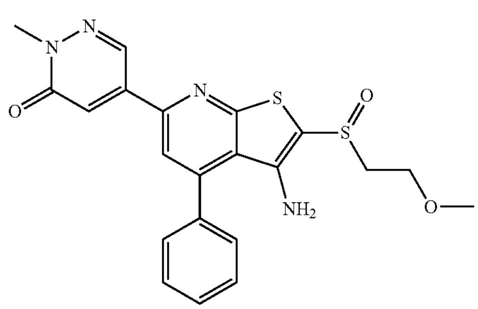 [SMILES: COCCS(=O)c1sc2nc(-c3cnn(C)c(=O)c3)cc(-c3ccccc3)c2c1N] | 8.67-8.65 (m, 1H), 7.62-7.58 (m, 3H), 7.57 (s, 1H), 7.52-7.46 (m, 3H), 4.66 (s, 2H), 3.92-3.85 (m, 4H), 3.75-3.68 (m, 1H), 3.66-3.59 (m, 1H), 3.42 (s, 3H), 3.34-3.26 (m, 1H). | 441.1 | |

| Ex. No. | Structure | 400 MHz NMR (δ; CDCl₃ unless otherwise noted) | LCMS (ES⁺; MH⁺) | Chiral info |
|---|---|---|---|---|
| 282 | 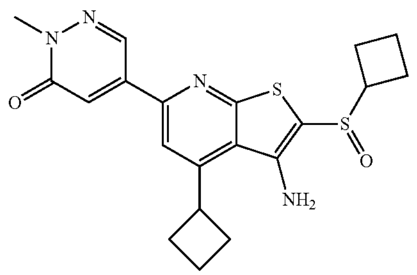 [SMILES: Cn1ncc(-c2cc(C3CCC3)c3c(N)c(S(=O)C4CCC4)sc3n2)cc1=O] | 8.64 (d, J = 2.0 Hz, 1H), 7.65 (s, 1H), 7.48 (d, J = 2.4 Hz, 1H), 5.19 (s, 2H), 4.28-4.19 (m, 1H), 4.02-3.94 (m, 1H), 3.88 (s, 3H), 2.88-2.79 (m, 1H), 2.56-2.47 (m, 2H), 2.46-2.35 (m, 4H), 2.31-2.25 (m, 1H), 2.23-2.15 (m, 1H), 2.11-2.00 (m, 3H). | 403.1 | |
| 283 | 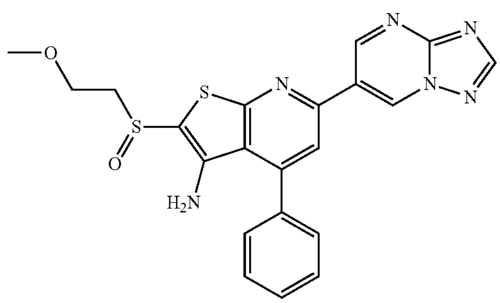 [SMILES: COCCS(=O)c1sc2nc(-c3cnc4ncnn4c3)cc(-c3ccccc3)c2c1N] | 9.69-9.63 (m, 1H), 9.58-9.52 (m, 1H), 8.59 (s, 1H), 7.63 (s, 1H), 7.63-7.59 (m, 3H), 7.52 (m, 2H), 4.64 (s, 2H), 3.92-3.84 (m, 1H), 3.74-3.69 (m, 1H), 3.65-3.59 (m, 1H), 3.41 (s, 3H), 3.30 (m, 1H). | 451.1 | |
| 284 | 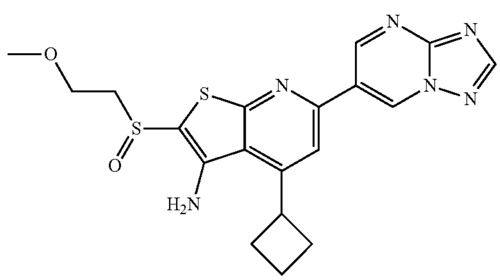 [SMILES: COCCS(=O)c1sc2nc(-c3cnc4ncnn4c3)cc(C3CCC3)c2c1N] | 9.62 (d, J = 2.4 Hz, 1H), 9.57 (d, J = 2.4 Hz, 1H), 8.59 (s, 1H), 7.70 (s, 1H), 5.15 (s, 2H), 4.29-4.23 (m, 1H), 3.93-3.87 (m, 1H), 3.74-3.69 (m, 1H), 3.66-3.60 (m, 1H), 3.43 (s, 3H), 3.33-3.27 (m, 1H), 2.60-2.51 (m, 2H), 2.49-2.39 (m, 2H), 2.27-2.16 (m, 1H), 2.10-2.01 (m, 1H). | 429.2 | |
| 285 | 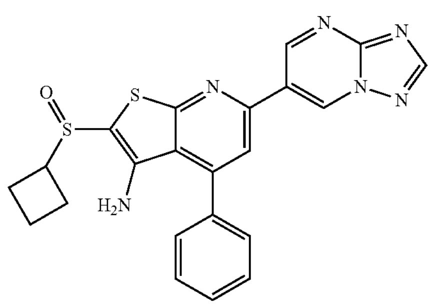 [SMILES: Nc1c(S(=O)C2CCC2)sc2nc(-c3cnc4ncnn4c3)cc(-c3ccccc3)c12] | DMSO-d6 10.19 (d, J = 2.4 Hz, 1H), 9.71 (d, J = 2.4 Hz, 1H), 8.76 (s, 1H), 8.14 (s, 1H), 7.62 (brs, 5H), 4.99 (s, 2H), 3.90-3.83 (m, 1H), 2.65-2.60 (m, 1H), 2.25-2.11 (m, 3H), 2.07-1.98 (m, 1H), 1.92 (m, 1H). | 447.1 | R-isomer: 99% ee; [α] = +114.673°; S-isomer: 98% ee; [α] = −131.825° |
| 286 | 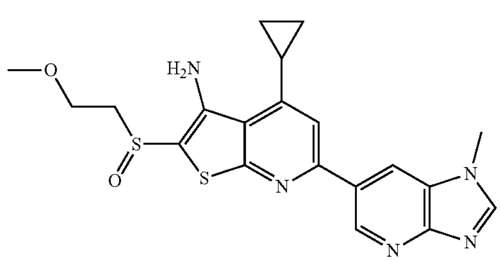 [SMILES: COCCS(=O)c1sc2nc(-c3cnc4ncn(C)c4c3)cc(C3CC3)c2c1N] | DMSO-d6 9.25 (d, J = 2.0 Hz, 1H), 8.77 (d, J = 2.0 Hz, 1H), 8.52 (s, 1H), 7.74 (s, 1H), 6.03 (s, 2H), 3.98 (s, 3H), 3.79-3.73 (m, 1H), 3.67-3.62 (m, 1H), 3.42-3.36 (m, 1H), 3.31 (s, 3H), 3.26-3.20 (m, 1H), 2.73-2.66 (m, 1H), 1.20-1.12 (m, 4H). | 428.2 | R-isomer: 100% ee; [α] = +37.928°; S-isomer: 98% ee; [α] = −47.481°; |

-continued

| Ex. No. | Structure | 400 MHz NMR (δ; CDCl₃ unless otherwise noted) | LCMS (ES⁺; MH⁺) | Chiral info |
|---|---|---|---|---|
| 287 | 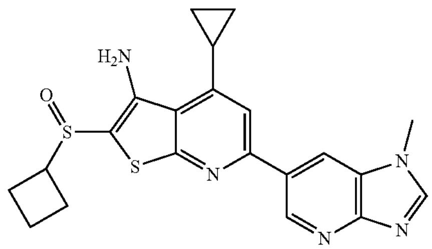 [SMILES: Cn1cnc2ncc(-c3cc(C4CC4)c4c(N)c(S(=O)C5CCC5)sc4n3)cc21] | 9.14 (d, J = 2.4 Hz, 1H), 8.51 (d, J = 2.0 Hz, 1H), 8.14 (s, 1H), 7.55 (s, 1H), 5.54 (s, 2H), 4.02-3.94 (m, 4H), 2.89-2.79 (m, 1H), 2.60-2.54 (m, 1H), 2.46-2.35 (m, 2H), 2.31-2.21 (m, 1H), 2.15-2.06 (m, 2H), 1.25-1.20 (m, 2H), 1.16-1.11 (m, 1H), 1.07-1.01 (m, 1H). | 424.0 | R-isomer: 100% ee; [α] = +84.195°; S-isomer: 97% ee; [α] = −78.173°; |
| 288 | 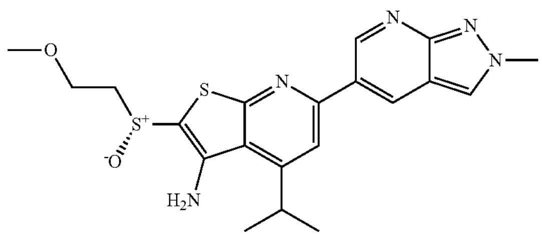 | 9.37 (d, J = 2.0 Hz, 1H), 8.74 (d, J = 2.0 Hz, 1H), 8.03 (s, 1H), 7.69 (s, 1H), 5.09 (s, 2H), 4.31 (s, 3H), 3.94-3.87 (m, 1H), 3.84-3.75 (m, 1H), 3.74-3.60 (m, 2H), 3.43 (s, 3H), 3.34-3.26 (m, 1H), 1.50 (m, 6H). | 430.2 | R-isomer: 100% ee; [α] = +30.365°; S-isomer: 98.9% ee; [α] = −45.960° |
| 289 | 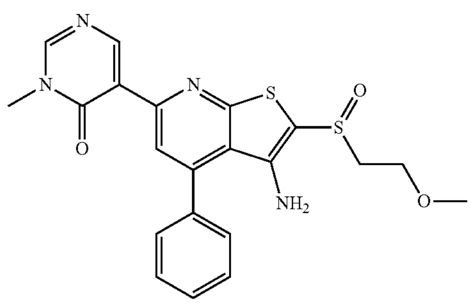 | 9.08 (s, 1H), 8.42 (s, 1H), 8.27 (s, 1H), 7.53 (s, 5H), 4.63 (s, 2H), 3.90-3.85 (m, 1H), 3.73-3.68 (m, 1H), 3.65 (s, 3H), 3.62-3.59 (m, 1H), 3.41 (s, 3H), 3.32-3.26 (m, 1H). | 441.0 | |
| 290 | 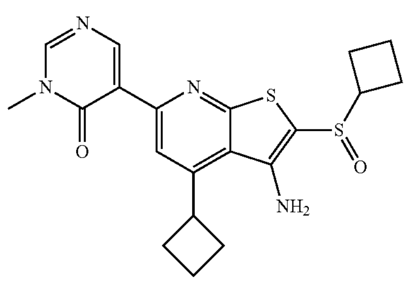 [SMILES: Cn1cncc(-c2cc(C3CCC3)c3c(N)c(S(=O)C4CCC4)sc3n2)c1=O] | 9.00 (s, 1H), 8.53 (s, 1H), 8.25 (s, 1H), 5.13 (s, 2H), 4.23-4.15 (m, 1H), 4.00-3.92 (m, 1H), 3.66 (s, 3H), 2.86-2.79 (m, 1H), 2.50-2.42 (m, 4H), 2.40-2.32 (m, 2H), 2.29-2.20 (m, 1H), 2.16-2.05 (m, 3H), 2.02-1.95 (m, 1H). | 415.0 | |
| 291 | 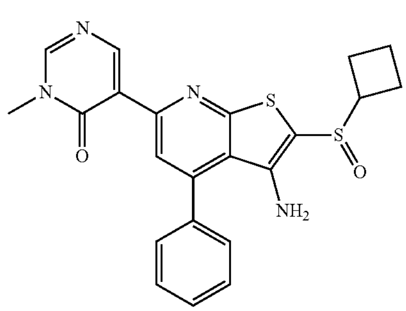 [SMILES: Cn1cncc(-c2cc(-c3ccccc3)c3c(N)c(S(=O)C4CCC4)sc3n2)c1=O] | 9.06 (s, 1H), 8.39 (s, 1H), 8.25 (s, 1H), 7.52-7.50 (m, 5H), 4.60 (s, 2H), 4.01-3.93 (m, 1H), 3.63 (s, 3H), 2.84-2.77 (m, 1H), 2.43-2.33 (m, 2H), 2.30-2.18 (m, 1H), 2.13-2.02 (m, 2H). | 437.2 | |

-continued

| Ex. No. | Structure | 400 MHz NMR (δ; CDCl₃ unless otherwise noted) | LCMS (ES⁺; MH⁺) | Chiral info |
|---|---|---|---|---|
| 292 | 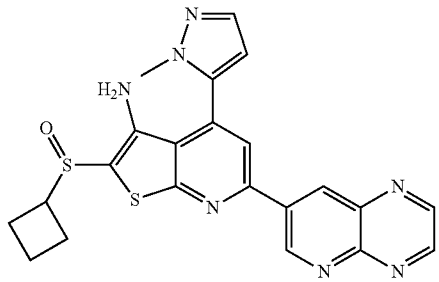 [SMILES: Cn1nccc1-c1cc(-c2cnc3nccnc3c2)nc2sc(S(=O)C3CCC3)c(N)c12] | 10.02 (d, J = 2.4 Hz, 1H), 9.13 (d, J = 2.0 Hz, 1H), 9.12 (d, J = 2.4 Hz, 1H), 9.04 (d, J = 1.6 Hz, 1H), 7.86 (s, 1H), 7.72 (d, J = 2.0 Hz, 1H), 6.55 (s, 1H), 4.69-4.53 (m, 2H), 4.04-3.94 (m, 1H), 3.81 (s, 3H), 2.93-2.79 (m, 1H), 2.49-2.25 (m, 3H), 2.21-2.03 (m, 2H). | 462.2 | |
| 293 | 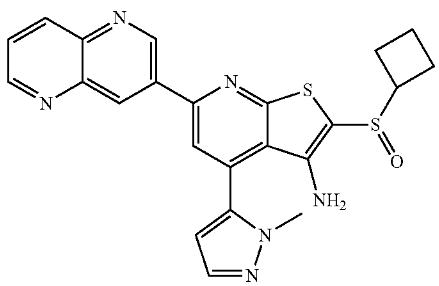 [SMILES: Cn1nccc1-c1cc(-c2cnc3cccnc3c2)nc2sc(S(=O)C3CCC3)c(N)c12] | 9.81 (d, J = 2.4 Hz, 1H), 9.07 (dd, J1 = 4.4 Hz, J2 = 1.6 Hz, 1H), 9.02 (d, J = 2.4 Hz, 1H), 8.50 (d, J = 8.4 Hz, 1H), 7.83 (s, 1H), 7.76-7.69 (m, 2H), 6.55 (s, 1H), 4.71-4.51 (m, 2H), 4.04-3.93 (m, 1H), 3.81 (s, 3H), 2.92-2.80 (m, 1H), 2.50-2.23 (m, 3H), 2.20-2.03 (m, 2H). | 461.2 | |
| 294 | 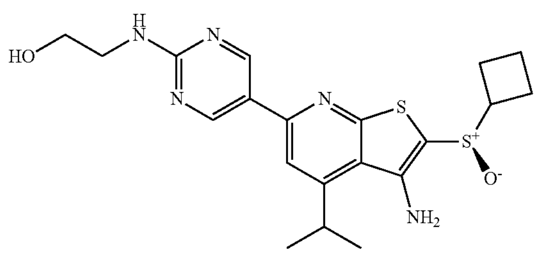 [SMILES: CC(C)c1cc(-c2cnc(NCCO)nc2)nc2sc([S@+]([O-])C3CCC3)c(N)c12] | | 432.1 | R-isomer: 100% ee; [α] = +177.876° |

The following compounds were prepared from known starting materials in a manner similar to that used for EXAMPLE 25. For select compounds, the enantiomers were resolved from the racemate using chiral supercritical fluid chromatography (SFC) and are reported with enantiomeric excess (ee) and/or optical rotation values. In some cases, only the more active R-(+) isomer was prepared/isolated.

| Ex. No. | Structure | 400 MHz NMR (δ; CDCl₃ unless otherwise noted) | LCMS (ES⁺; MH⁺) | Chiral info |
|---|---|---|---|---|
| 295 | 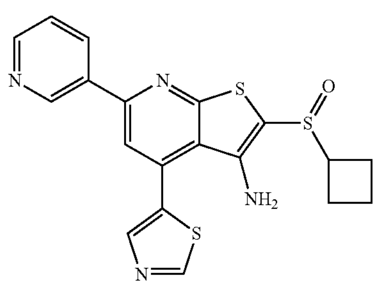 [SMILES: Nc1c(S(=O)C2CCC2)sc2nc(-c3cccnc3)cc(-c3cncs3)c12] | DMSO-d6 9.36-9.38 (m, 2 H), 8.67 (d, J = 6.4 Hz, 1H), 8.56 (dd, J1 = 2.4 Hz, J2 = 8.0 Hz, 1H), 8.20 (s, 1H), 8.05 (s, 1H), 7.53-7.56 (m, 1H), 5.19 (s, 2H), 3.85-3.93 (m, 1H), 2.63-2.70 (m, 1H), 2.14-2.23 (m, 3H), 1.90-2.03 (m, 2H). | 413.0 | |

| Ex. No. | Structure | 400 MHz NMR (δ; CDCl₃ unless otherwise noted) | LCMS (ES⁺; MH⁺) | Chiral info |
|---|---|---|---|---|
| 296 | 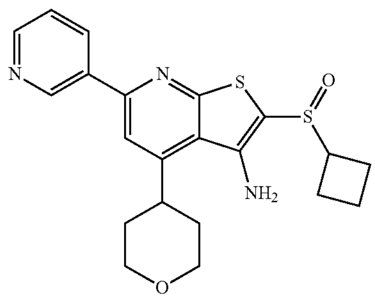 [SMILES: Nc1c(S(=O)C2CCC2)sc2nc(-c3cccnc3)cc(C3CCOCC3)c12] | 9.14 (d, J = 1.6 Hz, 1H), 8.58 (d, J = 6.4 Hz, 1H), 8.26-8.29 (m, 1H), 7.51 (s, 1H), 7.31-7.34 (m, 1H), 4.96 (s, 2H), 4.06-4.11 (m, 2H), 3.82-3.90 (m, 1H), 3.51-3.59 (m, 3H), 2.68-2.78 (m, 1H), 2.12-2.37 (m, 3H), 1.95-2.04 (m, 2H), 1.86-1.93 (m, 4H). | 414.2 | |
| 297 | 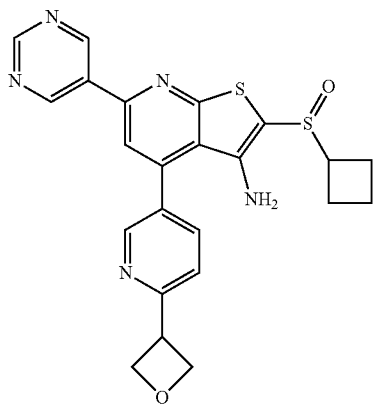 [SMILES: Nc1c(S(=O)C2CCC2)sc2nc(-c3cncnc3)cc(-c3ccc(C4COC4)nc3)c12] | 9.44 (s, 2H), 9.31 (s, 1H), 8.83 (d, J = 2.0 Hz, 1H), 7.85 (dd, J₁ = 2.4 Hz, J₂ = 8.0 Hz, 1H), 7.57 (s, 1H), 7.48 (d, J = 8.0 Hz, 1H), 5.18-5.14 (m, 2H), 5.03 (t, J = 6.0 Hz, 2H), 4.58 (s, 2H), 4.57-4.42 (m, 1H), 4.02-3.94 (m, 1H), 2.87-2.81 (m, 1H), 2.43-2.38 (m, 3H), 2.13-2.08 (m, 1H). | 464.1 | |
| 298 | 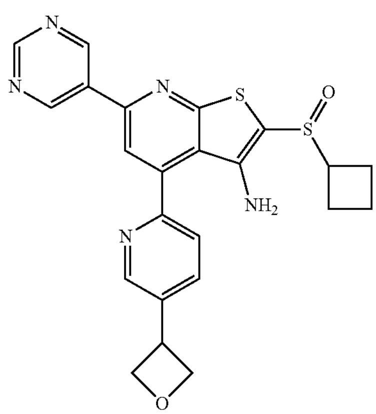 [SMILES: Nc1c(S(=O)C2CCC2)sc2nc(-c3cncnc3)cc(-c3ccc(C4COC4)cn3)c12] | 9.46 (s, 2H), 9.32 (s, 1H), 8.76 (d, J = 2.4 Hz, 1H), 8.18 (dd, J₁ = 2.4 Hz, J₂ = 8.4 Hz 1H), 7.83 (d, J = 8.0 Hz, 1H), 7.74 (s, 1H), 5.69 (m, 2H), 5.26-5.22 (m, 2H), 4.83 (t, J = 8.0 Hz, 1H), 4.42-4.37 (m, 1H), 3.99-3.88 (m, 1H), 2.45-2.36 (m, 2H), 2.35-2.21 (m, 1H), 2.14-2.07 (m, 2H). | 464.1 | |
| 299 | 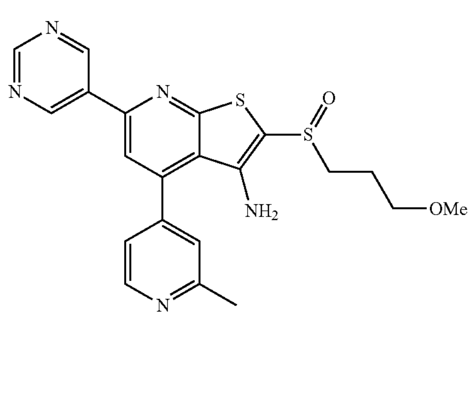 [SMILES: COCCCS(=O)c1sc2nc(-c3cncnc3)cc(-c3ccnc(C)c3)c2c1N] | DMSO-d6<br>9.58 (s, 2H), 9.30 (s, 1H), 8.65 (d, J = 4.8 Hz, 1H), 8.09 (s, 1H), 7.53 (s, 1H), 7.44 (d, J = 5.2 Hz, 1H), 5.02 (s, 2H), 3.43 (t, J = 6.4 Hz, 2H), 3.23 (s, 3H), 3.21-314 (m, 1H), 3.11-3.05 (m, 1H), 2.59 (s, 3H), 1.89-1.82 (m, 2H) | 440.0 | R-isomer: 100% ee; [α] = +65.7° S-isomer: 100% ee; [α] = −49.5° |

-continued

| Ex. No. | Structure | 400 MHz NMR (δ; CDCl₃ unless otherwise noted) | LCMS (ES⁺; MH⁺) | Chiral info |
|---|---|---|---|---|
| 300 | 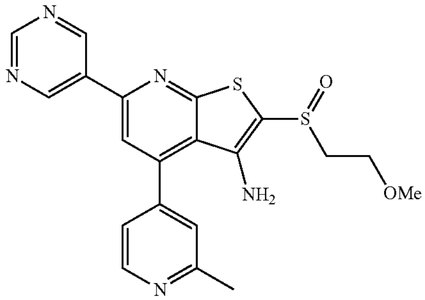 [SMILES: COCCS(=O)c1sc2nc(-c3cncnc3)cc(-c3ccnc(C)c3)c2c1N] | DMSO-d6<br>9.58 (s, 2H), 9.29 (s, 1H), 8.65 (d, J = 4.8 Hz, 1H), 8.09 (s, 1H), 7.52 (s, 1H), 7.44 (d, J = 5.2 Hz, 1H), 5.02 (s, 2H), 3.78-3.72 (m, 1H), 3.66-3.61 (m, 1H), 3.42-3.36 (m, 1H), 3.28 (s, 3H), 3.27-3.20 (m, 1H), 2.59 (s, 3H) | 426.0 | |
| 301 | 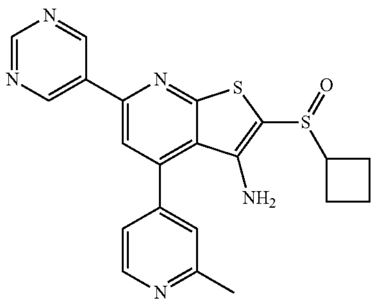 [SMILES: Cc1cc(-c2cc(-c3cncnc3)nc3sc(S(=O)C4CCC4)c(N)c23)ccn1] | 9.41 (s, 2H), 9.28 (s, 1H), 8.71-8.70 (m, 1H), 7.53 (s, 1H), 7.31-7.27 (m, 1H), 7.26 (s, 1H), 4.61 (s, 2H), 4.00-3.92 (m, 1H), 2.84-2.77 (m, 1H), 2.69 (s, 3H), 2.27-2.25 (m, 2H), 2.11-2.09 (m, 1H), 2.08-2.07 (m, 2H). | 422.0 | |

The following compounds were prepared from known starting materials in a manner similar to that used for EXAMPLE 7. In some cases, only the more active R-(+) isomer was prepared/isolated.

| Ex. No. | Structure | 400 MHz NMR (δ; CDCl₃ unless otherwise noted) | LCMS (ES⁺; MH⁺) | Chiral info |
|---|---|---|---|---|
| 302 | 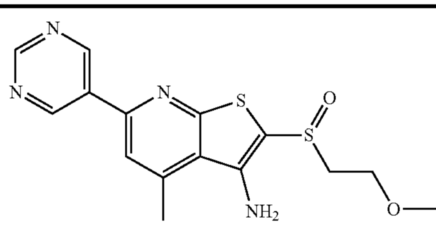 | 9.39 (s, 2H), 9.29 (s, 1H), 7.49 (s, 1H), 5.15 (s, 2H), 3.91 (m, 1H), 3.77-3.69 (m, 1H), 3.66-3.59 (m, 1H), 3.44 (s, 3H), 3.31 (m, 1H), 2.91 (s, 3H) | 349.1 | |
| 303 | 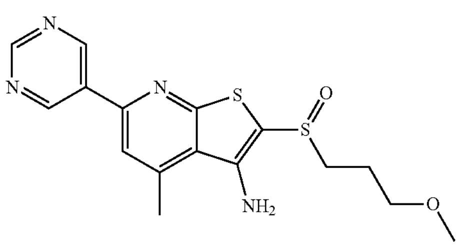 [SMILES: COCCCS(=O)c1sc2nc(-c3cncnc3)cc(C)c2c1N] | 9.41 (s, 2H), 9.30 (s, 1H), 7.50 (s, 1H), 5.20 (s, 2H), 3.59-3.53 (m, 2H), 3.43-3.35 (m, 4H), 3.32-3.24 (m, 1H), 2.91 (s, 3H), 2.14-2.04 (m, 2H). | 363.2 | |
| 304 | 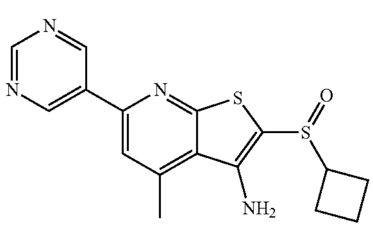 [SMILES: Cc1cc(-c2cncnc2)nc2sc(S(=O)C3CCC3)c(N)c12] | 9.39 (s, 2H), 9.28 (s, 1H), 7.48 (s, 1H), 5.17 (s, 2H), 3.98 (m, 1H), 2.89 (s, 3H), 2.87-2.77 (m, 1H), 2.47-2.33 (m, 2H), 2.32-2.22 (m, 1H), 2.16-2.04 (m, 2H). | 345.1 | R-isomer: 100% ee; [α] = +175.431°; S-isomer: 100% ee; [α] = −195.207°; |

-continued

| Ex. No. | Structure | 400 MHz NMR (δ; CDCl₃ unless otherwise noted) | LCMS (ES⁺; MH⁺) | Chiral info |
|---|---|---|---|---|
| 305 | 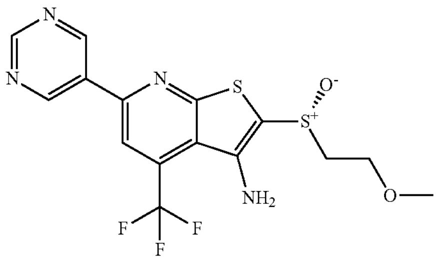 [SMILES: COCC[S@@+]([O-])c1sc2nc(-c3cncnc3)cc(C(F)(F)F)c2c1N] | 9.47 (s, 2H), 9.35 (s, 1H), 8.06 (s, 1H), 5.29 (s, 2H), 3.95-3.88 (m, 1H), 3.76-3.65 (m, 2H), 3.43 (s, 3H), 3.39-3.31 (m, 1H). | 403.0 | R-isomer: 100% ee; [α] = +73.873°; |
| 306 | 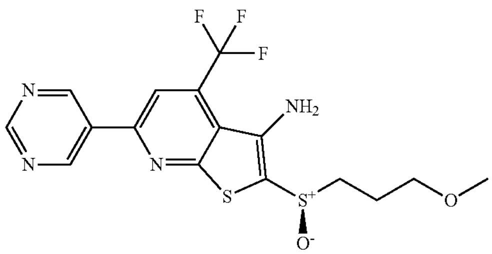 [SMILES: COCCC[S@@+]([O-])c1sc2nc(-c3cncnc3)cc(C(F)(F)F)c2c1N] | 9.47 (s, 2H), 9.35 (s, 1H), 8.06 (s, 1H), 5.34 (s, 2H), 3.57-3.55 (m, 2H), 3.48-3.41 (m, 1H), 3.37 (s, 3H), 3.35-3.28 (m, 1H), 2.18-2.01 (m, 2H). | 417.0 | R-isomer: 100% ee; [α] = +75.521° |
| 307 | 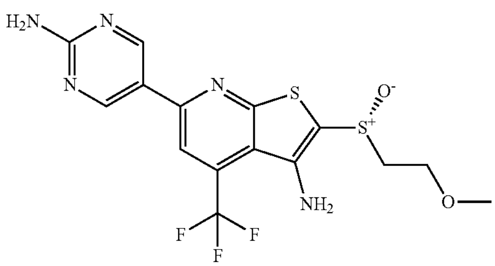 [SMILES: COCC[S@@+]([O-])c1sc2nc(-c3cnc(N)nc3)cc(C(F)(F)F)c2c1N] | 9.08 (s, 2H), 7.91 (s, 1H), 5.39 (s, 2H), 5.24 (s, 2H), 3.95-3.89 (m, 1H), 3.76-3.65 (m, 2H), 3.44 (s, 3H), 3.38-3.30 (m, 1H) | 418.0 | R-isomer: 100% ee; [α] = +44.975°; S-isomer: 100% ee; [α] = −44.803° |
| 308 | 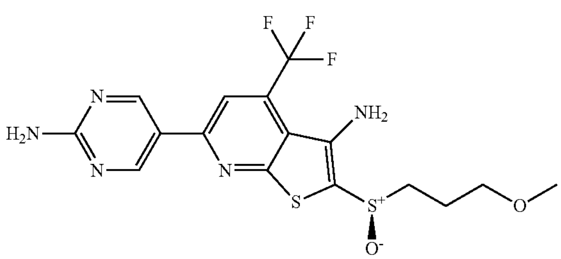 [SMILES: COCCC[S@@+]([O-])c1sc2nc(-c3cnc(N)nc3)cc(C(F)(F)F)c2c1N] | 9.08 (s, 2H), 7.90 (s, 1H), 5.37 (s, 2H), 5.29 (s, 2H), 3.58-3.54 (m, 2H), 3.48-3.40 (m, 1H), 3.38 (s, 3H), 3.34-3.28 (m, 1H), 2.14-2.05 (m, 2H). | 432.0 | R-isomer: 100% ee; [α] = +124.298°; S-isomer: 100% ee; [α] = −122.651° |
| 309 | 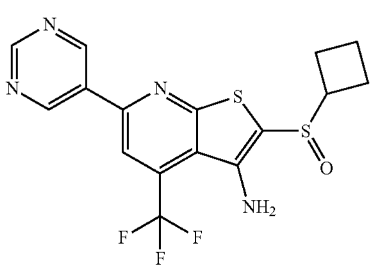 [SMILES: Nc1c(S(=O)C2CCC2)sc2nc(-c3cncnc3)cc(C(F)(F)F)c12] | 9.46 (s, 2H), 9.35 (s, 1H), 8.05 (s, 1H), 5.28 (s, 2H), 4.07-4.00 (m, 1H), 2.92-2.80 (m, 1H), 2.52-2.24 (m, 3H), 2.07 (s, 2H) | 399.0 | |
| 310 | 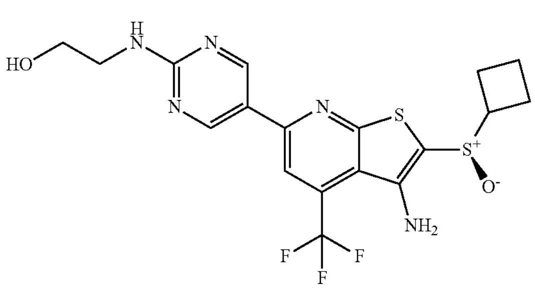 [SMILES: Nc1c([S@+]([O-])C2CCC2)sc2nc(-c3cnc(NCCO)nc3)cc(C(F)(F)F)c12] | 9.04 (s, 2H), 7.85 (s, 1H), 5.89-5.86 (m, 1H), 5.21 (s, 2H), 4.05-3.97 (m, 1H), 3.92-3.88 (m, 2H), 3.74-3.70 (m, 2H), 3.16 (t, J = 5.6 Hz, 1H), 2.89-2.80 (m, 1H), 2.49-2.20 (m, 2H), 2.17-2.04 (m, 2H). | 458.0 | R-isomer: 100% ee; [α] = +80.486°; |

-continued

| Ex. No. | Structure | 400 MHz NMR (δ; CDCl₃ unless otherwise noted) | LCMS (ES⁺; MH⁺) | Chiral info |
|---|---|---|---|---|
| 311 | 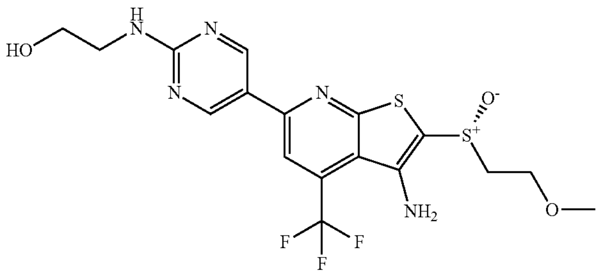 [SMILES: COCC[S@@+]([O-])c1sc2nc(-c3cnc(NCCO)nc3)cc(C(F)(F)F)c2c1N] | 9.07 (s, 2H), 7.88 (s, 1H), 5.88 (t, J = 5.6 Hz, 1H), 5.24 (s, 2H), 3.95-3.89 (m, 3H), 3.76-3.65 (m, 4H), 3.44 (s, 3H), 3.38-3.28 (m, 1H), 3.12 (t, J = 4.8 Hz, 1H) | 462.0 | R-isomer: 100% ee; [α] = +39.407°; S-isomer: 100% ee; [α] = −46.148°; |
| 312 | 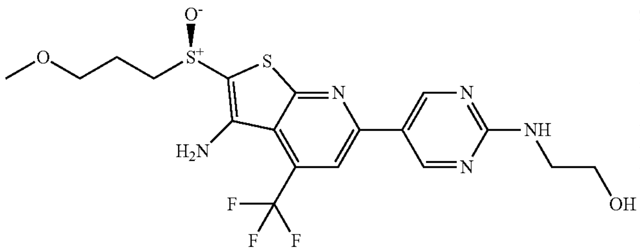 [SMILES: COCCC[S@@+]([O-])c1sc2nc(-c3cnc(NCCO)nc3)cc(C(F)(F)F)c2c1N] | 9.06 (s, 2H), 7.88 (s, 1H), 5.92-5.88 (m, 1H), 5.28 (s, 2H), 3.95-3.88 (m, 2H), 3.76-3.70 (m, 2H), 3.56 (t, J = 5.6 Hz, 2H), 3.48-3.40 (m, 1H), 3.38 (s, 3H), 3.34-3.26 (m, 1H), 3.16-3.07 (m, 1H), 2.09 (m, 2H). | 476.0 | R-isomer: 100% ee; [α] = +11.507°; S-isomer: 99% ee; [α] = −11.463°; |
| 313 | 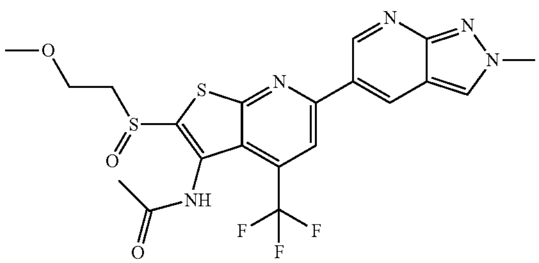 | 9.30 (d, J = 2.4 Hz, 1H), 8.63 (d, J = 2.4 Hz, 1H), 8.16 (s, 1H), 8.11 (s, 1H), 8.00 (s, 1H), 4.32 (s, 3H), 4.10-4.02 (m, 1H), 3.93-3.86 (m, 1H), 3.81-3.73 (m, 1H), 3.49 (s, 3H), 3.38-3.31 (m, 1H), 2.29 (s, 3H). | 498.0 | |

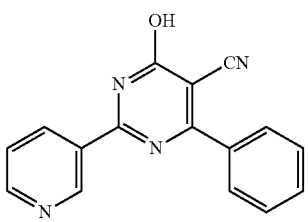 [SMILES: N#Cc1c(O)nc(-c2cccnc2)nc1-c1ccccc1]

Example 314A: 4-hydroxy-6-phenyl-2-(pyridin-3-yl)pyrimidine-5-carbonitrile. A mixture of ethyl (Z)-2-cyano-3-phenyl-prop-2-enoate (5.00 g, 24.8 mmol), pyridine-3-carboxamidine (5.87 g, 37.20 mmol, HCl), potassium carbonate (10.30 g, 74.50 mmol) in ethanol (50 mL) was stirred at 80° C. for 15 hours. The reaction mixture was filtered, the filter cake was collected and dissolved with water, then conc. hydrochloric acid was added, the white solid formed and filtered. The filtered cake was dried to provide the product (5.30 g, 78% yield) as a white solid.

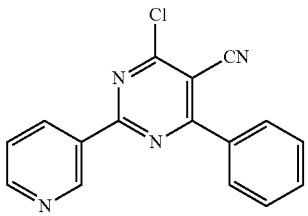 [SMILES: N#Cc1c(Cl)nc(-c2cccnc2)nc1-c1ccccc1]

Example 314B: 4-chloro-6-phenyl-2-(pyridin-3-yl)pyrimidine-5-carbonitrile. To a solution of 4-hydroxy-6-phenyl-2-(3-pyridyl)pyrimidine-5-carbonitrile (5.00 g) in phosphorus oxychloride (50 mL) was stirred at 100° C. for 0.5 hour to provide the product (3.00 g, 98% purity) as a white solid.

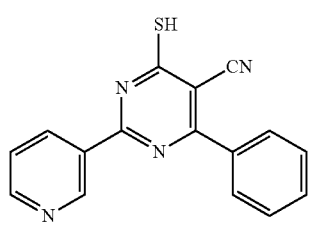 [SMILES: N#Cc1c(S)nc(-c2cccnc2)nc1-c1ccccc1]

Example 314C: 4-mercapto-6-phenyl-2-(pyridin-3-yl)pyrimidine-5-carbonitrile. To a solution of Example 150B (3.00 g) in dimethyl formamide (20 mL) was added sodium sulfide (1.15 g). The mixture was stirred at 80° C. for 2 hours to provide the product (3.50 g, zrude) as a yellow solid.

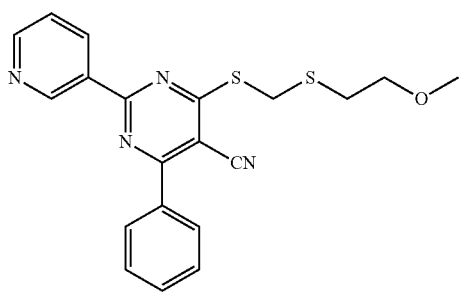 [SMILES: COCCSCSc1nc(-c2cccnc2)nc(-c2ccccc2)c1C#N]

Example 314D: 4-((((2-methoxyethyl)thio)methyl)thio)-6-phenyl-2-(pyridine-3-yl)pyrimidine-5-carbonitrile. Prepared using the General Procedure, step 4 starting from Example 314C (3.00 g) and 1-(chloromethylsulfanyl)-2-methoxy-ethane (3.63 g) to provide the product (1.70 g, 33% yield) as a white solid. $^1$H NMR (400 MHz, CDCl$_3$) δ 9.70-9.68 (m, 1H), 8.72-8.71 (m, 2H), 8.06-8.04 (m, 2H), 7.54-7.50 (m, 4H), 4.60 (s, 2H), 3.63 (t, J=6.0 Hz, 2H), 3.32 (s, 3H), 2.88-2.84 (m, 2H).

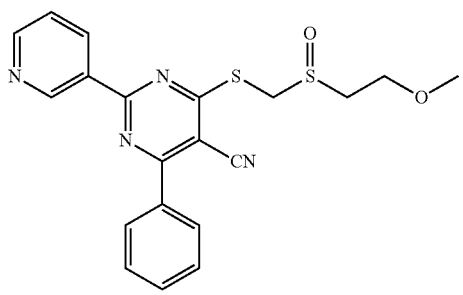 [SMILES: COCCS(=O)CSc1nc(-c2cccnc2)nc(-c2ccccc2)c1C#N]

Example 314E: 4-((((2-methoxyethylsulfinyl)methyl)thio)-6-phenyl-2-(pyridin-3-yl)pyrimidine-5-carbonitrile. Prepared using the General Procedure, step 5 starting from Example 314D (1.70 g, 3.02 mmol) and hydrogen peroxide (769 mg) to provide the product (1.60 g, 91% yield) as a yellow solid.

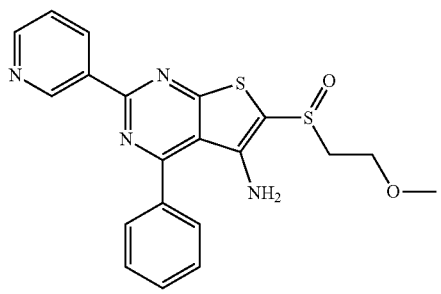 [SMILES: COCCS(=O)c1sc2nc(-c3cccnc3)nc(-c3ccccc3)c2c1N]

EXAMPLE 314: 6-((2-methoxyethyl)sulfinyl)-4-phenyl-2-(pyridin-3-yl)thieno[2,3-d]pyrimidin-5-amine. Prepared using the General Procedure, step 6 starting from Example 314E (1.50 g) to provide the product (600 mg, 56% yield) as a yellow solid.
$^1$H NMR: (400 MHz, CDCl$_3$) δ 9.76 (d, J=2.0 Hz, 1H), 8.84-8.81 (m, $^1$H), 8.73-8.72 (m, $^1$H), 7.74-7.72 (m, 2H), 7.63-7.61 (m, 3H), 7.43 (m, 1H), 4.85 (s, 2H), 3.88-3.86 (m, 1H), 3.73-3.71 (m, 1H), 3.61-3.60 (m, 1H), 3.40 (s, 3H), 3.29-3.28 (m, 1H). LCMS: (ES$^+$) m/z (M+H)$^+$+=411.0.

The enantiomers were resolved by SFC to give the R isomer (99% ee, [α]=+98.739°) and the S isomer (99% ee, [α]=−94.777°).

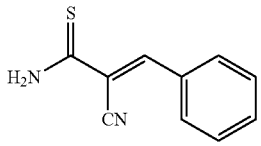 [SMILES: N#C/C(=C\c1ccccc1)C(N)=S]

EXAMPLE 315A: (E)-2-cyano-3-phenylprop-2-enethioamide. To a solution of benzaldehyde (5 g, 47.12 mmol) and 2-cyanothioacetamide (4.72 g, 47.12 mmol) in EtOH (50 mL) was added TEA (476.76 mg, 4.71 mmol). The mixture solution was stirred at 30° C. for 2 hours. The mixture was purified by reversed-phase column (TFA condition) to give the target compound (2.5 g, 28% yield) as a white solid.

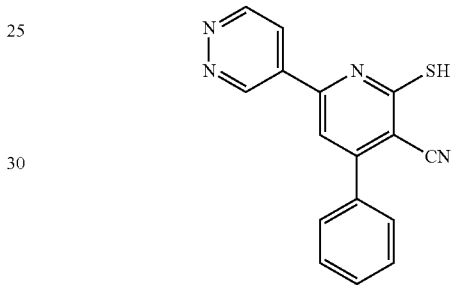

EXAMPLE 315B: 2-mercapto-4-phenyl-6-(pyridazin-4-yl)nicotinonitrile. To a solution of Example 315A (2.2 g, 11.69 mmol) and 1-pyridazin-4-ylethanone (1.43 g, 11.69 mmol) in EtOH (45 mL) was added TEA (118.26 mg, 1.17 mmol, 162.66 μL). The mixture solution was stirred at 80° C. for 16 hours. The solution was concentrated and purified by reversed-phase column (basic condition) to give the target compound (0.5 g, 13% yield) as yellow solid.

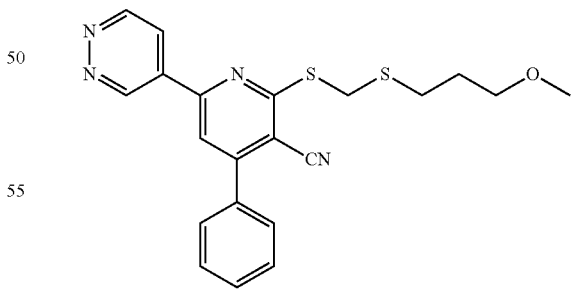

EXAMPLE 315C: 2-((((3-methoxypropyl)thio)methyl)thio)-4-phenyl-6-(pyridazin-4-yl)nicotinonitrile. The title compound was prepared by the general procedure starting from Example 315B (0.50 g, 1.72 mmol) and (chloromethyl)(3-methoxypropyl)sulfane (320 mg, 2.07 mmol) to give the target compound (0.30 g, 43% yield) as a brown solid.

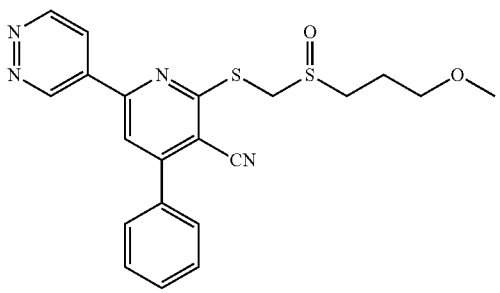 [SMILES: COCCCS(=O)CSc1nc(-c2ccnnc2)cc(-c2ccccc2)c1C#N]

EXAMPLE 315D: 2-((((3-methoxypropyl)sulfinyl)methyl)thio)-4-phenyl-6-(pyridazin-4-yl)nicotinonitrile.

starting from Example 315D (300 mg, 0.71 mmol) to give the target compound (70 mg, 23% yield) as a yellow solid. LCMS: (ES+) m/z (M+H)+=425.0 HPLC: tR=1.912 min $^1$H NMR (400 MHz, DMSO-$d_6$) δ 10.03 (d, J=1.2 Hz, 1H), 9.40-9.39 (m, 1H), 8.47-8.45 (m, 1H), 8.17 (s, 1H), 7.65-7.61 (m, 5H), 5.01 (s, 2H), 3.44-3.41 (m, 2H), 3.22 (s, 3H), 3.15 (m, 1H), 3.08-3.05 (m, 1H), 1.88-1.81 (m, 2H).

The following compounds were prepared from known starting materials in a manner similar to that used for EXAMPLE 315. For select compounds, the enantiomers were resolved from the racemate using chiral supercritical fluid chromatography (SFC) and are reported with enantiomeric excess (ee) and/or optical rotation values. In some cases, only the more active R-(+) isomer was prepared/isolated.

| Ex. No. | Structure | 400 MHz NMR (δ; CDCl$_3$ unless otherwise noted) | LCMS (ES+; MH+) | Chiral info |
|---|---|---|---|---|
| 316 | 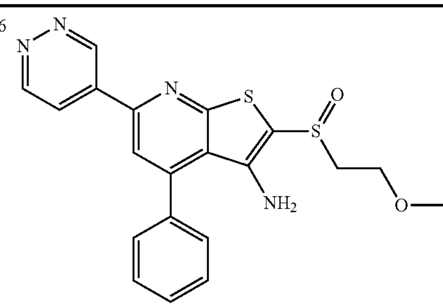 | 9.92 (s, 1H), 9.38-9.36 (m, 1H), 8.22-8.20 (m, 1H), 7.71 (s, 1H), 7.62-7.60 (m, 3H), 7.54-7.52 (m, 2H), 4.66 (s, 2H), 3.89-3.86 (m, 1H), 3.74-3.73 (m, 1H), 3.63-3.62 (m, 1H), 3.42 (s, 3H), 3.31-3.30 (m, 1H). | 411.0 | R-isomer: 99.5% ee; [α] = +98.048°; S-isomer: 99.7% ee; [α] = +90.514° |
| 317 | 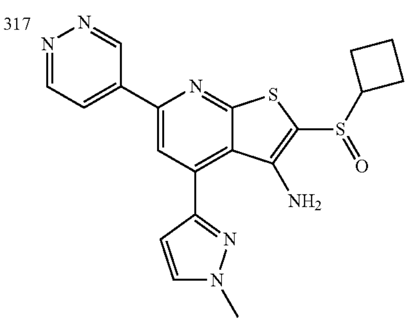 | DMSO-d6 10.06 (dd, J1 = 2.4, J2 = 1.2 Hz, 1H), 9.42 (dd, J1 = 5.6, J2 = 1.2 Hz, 1H), 8.48-8.46 (m, 1H), 8.36 (s, 1H), 8.05 (d, J = 2.4 Hz, 1H), 7.24 (d, J = 2.4 Hz, 1H), 7.06 2H), 4.03 (s, 3H), 3.96-3.88 (m, 1H), 2.69-2.63 (m, 1H), 2.30-2.09 (m, 3H), 2.06-1.99 (m, 1H), 1.97-1.92 (m, 1H). | 429.3 | |

The title compound was prepared by the general procedure starting from Example 315C (300 mg, 0.73 mmol) and H$_2$O$_2$ (167 mg, 1.47 mmol, 30% purity) to give the target compound (300 mg, 96% yield) as a yellow solid.

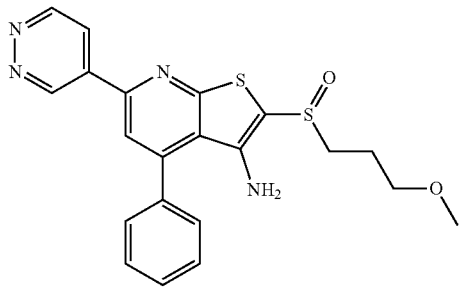 [SMILES: COCCCS(=O)c1sc2nc(-c3ccnnc3)cc(-c3ccccc3)c2c1N]

EXAMPLE 315: 2-((3-methoxypropyl)sulfinyl)-4-phenyl-6-(pyridazin-4-yl)thieno[2,3-b]pyridin-3-amine. The title compound was prepared by the general procedure

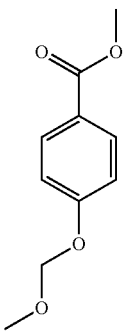

EXAMPLE 318A: methyl 4-(methoxymethoxy)benzoate. To a solution of methyl 4-hydroxybenzoate (20 g, 131.45 mmol) and potassium carbonate (54.50 g, 394.36 mmol) in acetone (200 mL) was stirred at 25° C. for 1 hour. Chloro(methoxy)methane (21.17 g, 262.90 mmol) was then added dropwise at 0° C. The mixture was stirred at 25° C. for 3 hours. The reaction mixture was quenched with aqueous ammonium chloride and the aqueous layer was extracted with ethyl acetate 30 mL (10 mL*3). The combined organic extracts were washed with brine 60 mL (30 mL*2), dried over MgSO$_4$ and concentration under vacuum to give the target compound (30 g, crude) as a yellow oil.

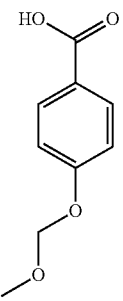

EXAMPLE 318B: 4-(methoxymethoxy)benzoic acid. To a solution of Example 313A (25 g, 127.42 mmol) in water (200 mL) was added sodium hydroxide (6.63 g, 165.65 mmol). The mixture was stirred at 100° C. for 2 hours. The reaction mixture was cooled and poured into acetic acid at 0° C. The crude white product was precipitated, filtered and washed with water. The filter cake was concentrated under high vacuum to give the target compound (22 g, 95% yield) as a white solid. $^1$H NMR (400 MHz, CDCl$_3$) δ 8.01-7.99 (m, 2H), 7.03-7.01 (m, 2H), 5.18 (s, 2H), 3.42 (s, 3H).

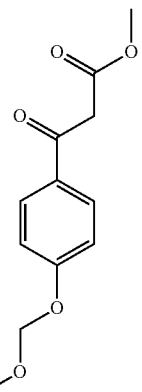

EXAMPLE 318C: ethyl-3-(4-(methoxymethoxy)phenyl)-3-oxopropanoate. To a solution of di(imidazol-1-yl)methanone (20.56 g, 126.80 mmol) and Example 313B (22 g, 120.76 mmol) in THF (200 mL) was stirred at 60° C. for 1 hour, After cooled to 20° C., the mixture was added with potassium 3-ethoxy-3-oxo-propanoate (20.55 g, 120.76 mmol) and magnesium chloride (13.80 g, 144.92 mmol). The mixture was stirred at 60° C. for 1 hour. The mixture was concentrated in vacuum. The residue was partitioned between water (30 mL) and dichloromethane (60 mL). The organic layer was separated, and the aqueous layer was further extracted with dichloromethane 90 mL (3×30 mL). The combined organic layers were washed with water, brine, dried over sodium sulfate, filtered, and concentrated in vacuum to give a residue. The residue was purified by reversed-phase flash (TFA condition) to give the target compound (16 g, 52% yield) as a yellow oil.

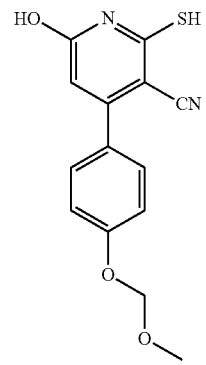

+

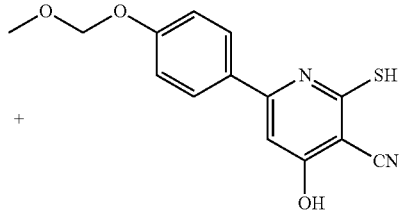

EXAMPLE 318D and EXAMPLE 319A: ethyl-3-(4-(methoxymethoxy)phenyl)-3-oxopropanoate and 4-hydroxy-2-mercapto-6-(4-(methoxymethoxy)phenyl) nicotinonitrile. To a solution of Example 313C (15 g, 59.46 mmol) and 2-cyanothioacetamide (11.91 g, 118.92 mmol) in N,N-Dimethylformamide (30 mL) was added potassium hydroxide (4.34 g, 77.30 mmol). The mixture was stirred at 60° C. for 6 hours. The mixture was purified by Prep-HPLC (basic condition) to give a mixture Example 318D and Example 319A (16 g, 52% yield) as a black oil.

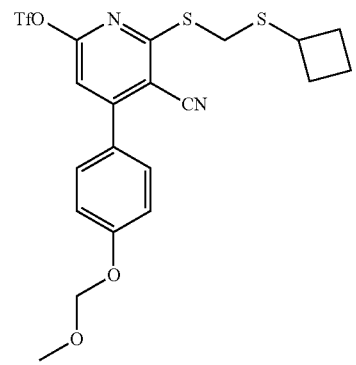

+

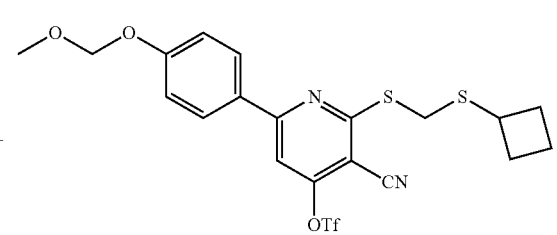

EXAMPLE 318E and EXAMPLE 319B: 5-cyano-6-((((cyclobutylthio)methyl)thio)-4-(4-(methoxymethoxy)phenyl)pyridin-2-yl trifluoromethanesulfonate and 3-cyano-2-((((cyclobutylthio)methyl)thio)-6-(4-(methoxymethoxy) phenyl)pyridin-4-yl trifluoromethanesulfonate. To a solution of Example 318D and Example 319A (1.7 g, 4.38 mmol) and 1,1,1-trifluoro-N-phenyl-N-(trifluoromethylsulfonyl)methanesulfonamide (2.34 g, 6.56 mmol) in THF (50 mL) was added potassium 2-methylpropan-2-olate (737 mg, 6.56 mmol). The mixture was stirred at 25° C. for 6 hours to give a mixture of Example 318E and Example 319B (2.5 g, crude) as a yellow solid.

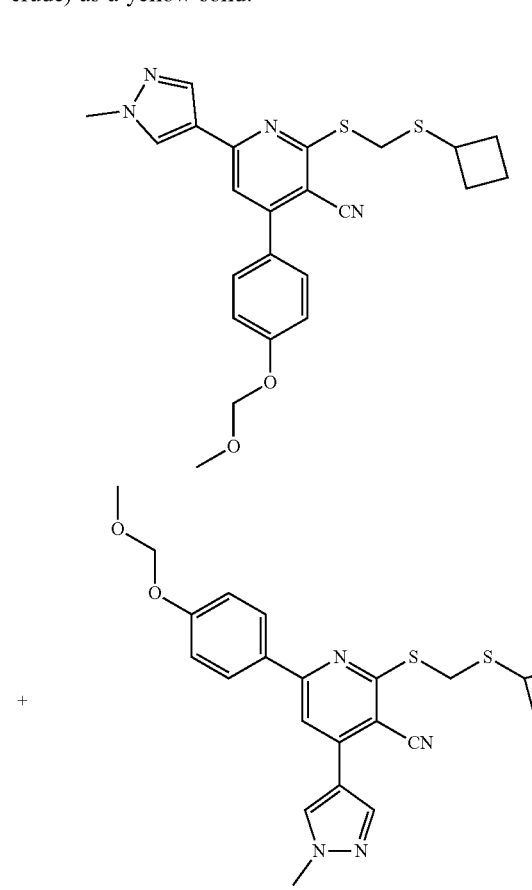

EXAMPLE 318F and EXAMPLE 319C: 2-((((cyclobutylthio)methyl)thio)-4-(4-(methoxymethoxy)phenyl)-6-(1-methyl-1H-pyrazol-4-yl)nicotinonitrile and 2-((((cyclobutylthio)methyl)thio)-6-(4-(methoxymethoxy)phenyl)-4-(1-methyl-1H-pyrazol-4-yl)nicotinonitrile. To a solution of Example 318E and Example 319B (2.5 g, 4.80 mmol) and (1-methylpyrazol-4-yl)boronic acid (907 mg, 7.20 mmol) in tetrahydrofuran (40 mL) and water (20 mL) was added Pd(dppf)Cl$_2$·CH$_2$Cl$_2$ (196 mg, 240 umol) and sodium carbonate (1.02 g, 9.60 mmol). The mixture was stirred at 80° C. for 2 hours. The reaction mixture was concentrated, the residue was purified by column chromatography (SiO$_2$, Petroleum ether: Ethyl acetate=4:1 to 2:1), then the crude product was purified by Prep-HPLC (column: Waters Xbridge 150*255 u; mobile phase: [water (10 mm NH$_4$HCO$_3$)-ACN]; B %: 60%-90%, 14 min) to give Example 318F (400 mg, 37% yield) as a yellow solid and Example 314C (260 mg, 24% yield) as a yellow solid.

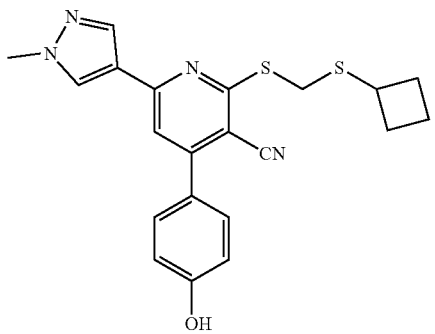 [SMILES: Cn1cc(-c2cc(-c3ccc(O)cc3)c(C#N)c(SCSC3CCC3)n2)cn1]

EXAMPLE 318G: 2-((((cyclobutylthio)methyl)thio)-4-(4-(methoxymethoxy)phenyl)-6-(1-methyl-1H-pyrazol-4-yl) nicotinonitrile. To a solution of Example 313F (260 mg, 574 umol) in CH$_2$Cl$_2$ (10 mL) was added CF$_3$COOH (2.0 g, 17.23 mmol). The mixture was stirred at 25° C. for 2 hours. The pH of the mixture was adjusted to 7 by saturated sodium bicarbonates, and extracted with DCM 60 mL (20 mL*3), the organic phase was concentrated to give compound Example 318G (300 mg, crude) as a white solid.

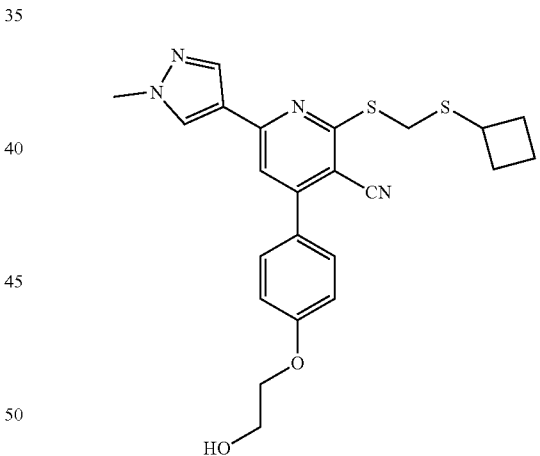

EXAMPLE 318H: 2-((((cyclobutylthio)methyl)thio)-4-(4-(2-hydroxyethoxy) phenyl)-6-(1-methyl-1H-pyrazol-4-yl) nicotinonitrile. To a solution of Example 318G (300 mg, 734 umol) and 2-bromoethanol (459 mg, 3.67 mmol) in DMF (2 mL) was added K$_2$CO$_3$ (203 mg, 1.47 mmol). The mixture was stirred at 50° C. for 6 hours. The mixture was filtered and concentrated, the crude residue was purified by Prep-HPLC (column: Waters Xbridge 150*255 u; mobile phase: [water (10 mM NH$_4$HCO$_3$)-ACN]; B %: 44%-74%, 10 min) to give Example 318H (150 mg, 331 umol, 45% yield) as a white solid.

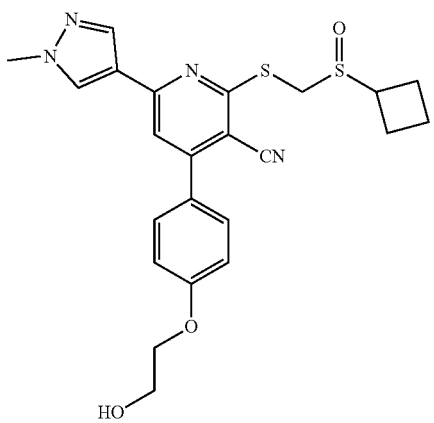 [SMILES: Cn1cc(-c2cc(-c3ccc(OCCO)cc3)c(C#N)c(SCS(=O)C3CCC3)n2)cn1]

EXAMPLE 318I: 2-(((cyclobutylsulfinyl)methyl)thio)-4-(4-(2-hydroxyethoxy)phenyl)-6-(1-methyl-1H-pyrazol-4-yl)nicotinonitrile. The target compound was prepared by the general procedure starting from Example 318H (150 mg, 331 umol) and hydrogen peroxide (537 mg, 8.95 mmol, 512 uL) to give the target compound (155 mg, 99% yield) as white solid.

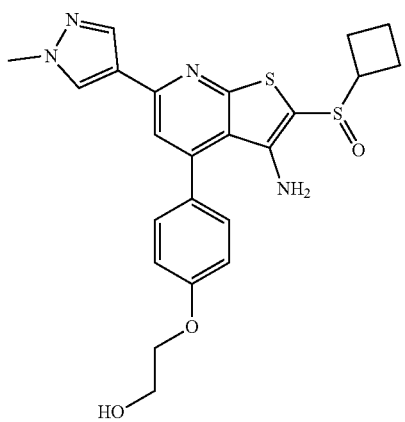 [SMILES: Cn1cc(-c2cc(-c3ccc(OCCO)cc3)c3c(N)c(S(=O)C4CCC4)sc3n2)cn1]

EXAMPLE 318: 2-(4-(3-amino-2-(cyclobutylsulfinyl)-6-(1-methyl-1H-pyrazol-4-yl)thieno[2,3-b]pyridin-4-yl)phenoxy)ethanol. The target compound was prepared by the general procedure starting from Example 313I (150 mg, 320.11 umol) to give Example 313 (96 mg, 63% yield) as a yellow solid. LCMS: (ES⁺) m/z (M+H)⁺=469.2. HPLC: tR=1.903 min. ¹H NMR (400 MHz, CDCl₃) δ 8.02-7.98 (m, 2H), 7.39 (d, J=7.6 Hz, 2H), 7.22 (s, 1H), 7.06 (d, J=8.8 Hz, 2H), 4.56 (s, 2H), 4.19-4.16 (m, 2H), 4.04-4.02 (m, 2H), 3.97 (s, 3H), 3.94-3.90 (m, 1H), 2.83-2.73 (m, 1H), 2.39-2.30 (m, 3H), 2.27-2.18 (m, 1H), 2.11-2.02 (m, 2H).

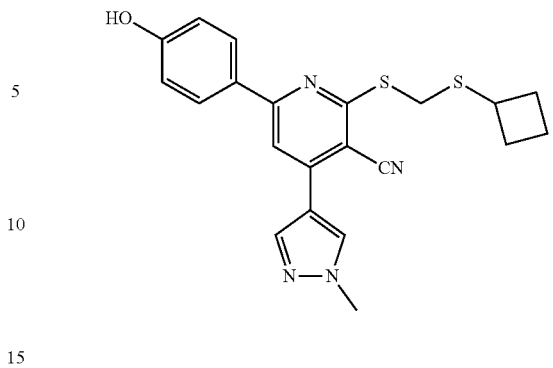

EXAMPLE 319D: 2-(((cyclobutylthio)methyl)thio)-6-(4-hydroxyphenyl)-4-(1-methyl-1H-pyrazol-4-yl)nicotinonitrile. The target compound was prepared by the procedure used for Example 313G starting from Example 314C (2-(cyclobutylsulfanylmethylsulfanyl)-6-[4-(methoxymethoxy)phenyl]-4-(1-methylpyrazol-4-yl)pyridine-3-carbonitrile) (400 mg, 884 umol). The pH of the mixture was adjusted to 7 by saturated sodium bicarbonate, and extracted with DCM 60 mL (20 mL*3), the organic phase was concentrated to give the target compound (300 mg, 83% yield) as a white solid.

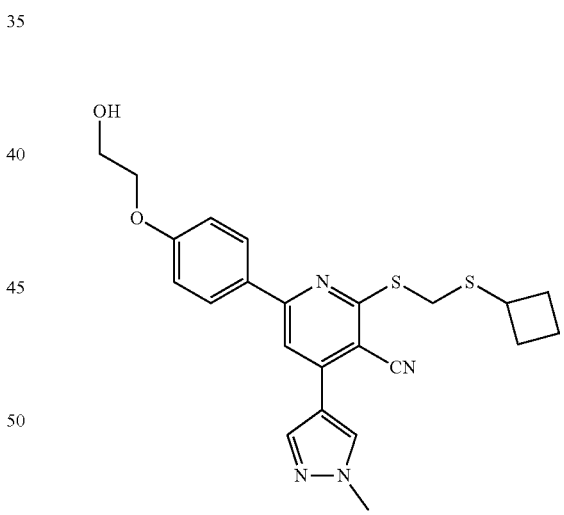

EXAMPLE 319E: 2-(((cyclobutylthio)methyl)thio)-6-(4-(2-hydroxyethoxy)phenyl)-4-(1-methyl-1H-pyrazol-4-yl)nicotinonitrile. The title compound was prepared by the procedure used for Example 318H starting from Example 319D (300 mg, 734 umol) and 2-bromoethanol (275 mg, 2.20 mmol, 156 uL) to give the target compound (1150 mg, 331 umol, 45% yield) as a white solid.

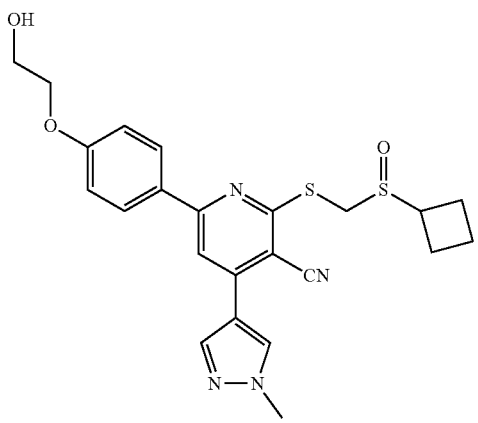 [SMILES: Cn1cc(-c2cc(-c3ccc(OCCO)cc3)nc(SCS(=O)C3CCC3)c2C#N)cn1]

EXAMPLE 319F: 2-(((cyclobutylsulfinyl)methyl)thio)-6-(4-(2-hydroxyethoxy)phenyl)-4-(1-methyl-1H-pyrazol-4-yl)nicotinonitrile. The title compound was prepared by the general procedure starting from Example 319E (150 mg, 331 umol) and hydrogen peroxide (75 mg, 663 umol, 64 uL, 30% purity) to give EXAMPLE 319F (155 mg, 99% yield) as white solid.

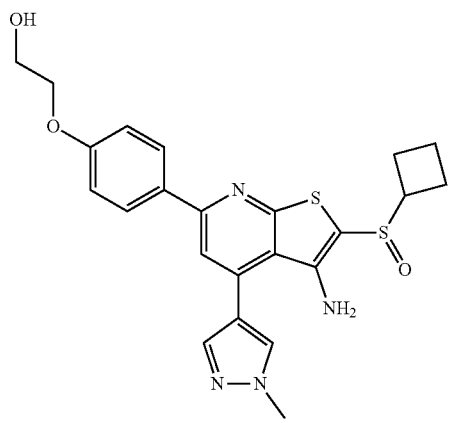 [SMILES: Cn1cc(-c2cc(-c3ccc(OCCO)cc3)nc3sc(S(=O)C4CCC4)c(N)c23)cn1]

EXAMPLE 319: 2-(4-(3-amino-2-(cyclobutylsulfinyl)-6-(1-methyl-1H-pyrazol-4-yl)thieno[2,3-b]pyridin-4-yl)phenoxy)ethanol. The title compound was prepared by the general procedure starting from Example 314F (150 mg, 320 umol) to give compound EXAMPLE 319 (96 mg, 63% yield) as yellow solid. LCMS: (ES+) m/z (M+H)+=469.2. HPLC: tR=1.894 min. $^1$H NMR (400 MHz, CDCl$_3$) δ 8.01 (d, J=8.8 Hz, 2H), 7.73 (s, 1H), 7.67 (s, 1H), 7.43 (s, 1H), 7.00 (d, J=8.8 Hz, 2H), 4.88 (s, 2H), 4.16-4.14 (m, 2H), 4.04 (s, 3H), 4.02-3.99 (m, 2H), 3.97-3.93 (m, 1H), 2.86-2.76 (m, 1H), 2.43-2.33 (m, 2H), 2.28-2.19 (m, 2H), 2.13-2.04 (m, 2H).

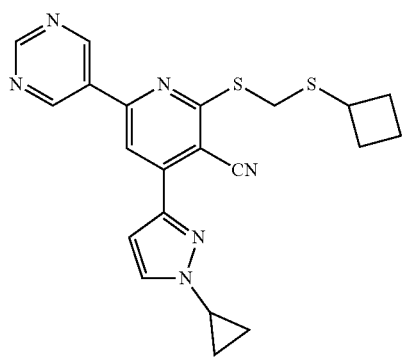 [SMILES: N#Cc1c(-c2ccn(C3CC3)n2)cc(-c2cncnc2)nc1SCSC1CCC1]

EXAMPLE 320A: 2-((((cyclobutylthio)methyl)thio)-4-(1-cyclopropyl-1H-pyrazol-3-yl)-6-(pyrimidin-5-yl)nicotinonitrile. To a solution of 2-(cyclobutylsulfanylmethylsulfanyl)-4-(1H-pyrazol-3-yl)-6-pyrimidin-5-yl-pyridine-3-carbonitrile (500 mg, 1.31 mmol) and potassium cyclopropyl(trifluoro)borate (389 mg, 2.63 mmol) in DCE (5 mL) was added 2-(2-pyridyl)pyridine (205 mg, 1.31 mmol), Na$_2$CO$_3$ (279 mg, 2.63 mmol) and Cu(OAc)$_2$ (238.68 mg, 1.31 mmol, 1 eq). The mixture was stirred at 70° C. for 20 hours. The mixture was concentrated under high vacuum, the residue was purified by Prep-HPLC (column: Phenomenex Luna C18 250*50 mm*10 um; mobile phase: [water (0.075% TFA)-ACN]; B %: 58%-88%, 9 min) to give the target compound (280 mg, 51% yield) as a white solid. $^1$H NMR (400 MHz, CHCl$_3$) δ 9.46 (s, 2H), 9.32 (s, 1H), 8.15 (s, 1H), 7.61 (d, J=2.4 Hz, 1H), 7.17 (d, J=2.4 Hz, 1H), 4.45 (s, 2H), 3.79-3.70 (m, 2H), 2.44-2.37 (m, 2H), 2.15-2.05 (m, 2H), 2.04-1.92 (m, 2H), 1.28-1.24 (m, 2H), 1.16-1.11 (m, 2H).

EXAMPLE 320B: 2-((((cyclobutylsulfinyl)methyl)thio)-4-(1-cyclopropyl-1H-pyrazol-3-yl)-6-(pyrimidin-5-yl)nicotinonitrile. The title compound was prepared by the general procedure starting from Example 315A (270 mg, 642 umol) and hydrogen peroxide (1.04 g, 17.33 mmol, 991 uL) to give the title compound (270 mg, 619 umol, 96% yield) as a white solid.

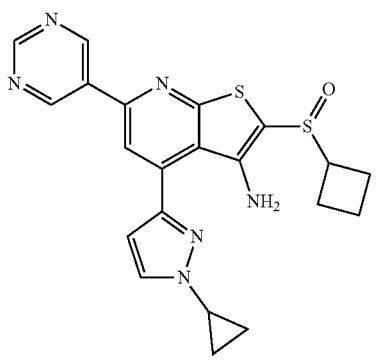 [SMILES: Nc1c(S(=O)C2CCC2)sc2nc(-c3cncnc3)cc(-c3ccn(C4CC4)n3)c12]

EXAMPLE 320: 2-(cyclobutylsulfinyl)-4-(1-cyclopropyl-1H-pyrazol-3-yl)-6-(pyrimidin-5-yl)thieno[2,3-b]pyridin-3-amine. The title compound was prepared by the general procedure starting from Example 315B (270 mg, 619 umol) to give compound EXAMPLE 315 (236 mg, 86% yield) as a yellow solid. LCMS: (ES$^+$) m/z (M+H)$^+$=437.2. HPLC: tR=2.165 min. $^1$H NMR (400 MHz, DMSO-d$_6$) δ 9.58 (s, 2H), 9.30 (s, 1H), 8.26 (s, 1H), 8.15 (d, J=2.4 Hz, 1H), 7.20 (d, J=2.4 Hz, 1H), 7.06 (s, 2H), 3.96-3.86 (m, 2H), 2.69-2.60 (m, 1H), 2.24-2.12 (m, 3H), 2.07-1.98 (m, 1H), 1.97-1.90 (m, 1H), 1.15-1.13 (m, 2H), 1.11-1.08 (m, 2H).

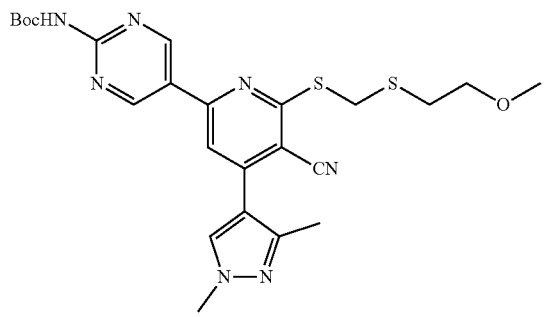 [SMILES: COCCSCSc1nc(-c2cnc(NC(=O)OC(C)(C)C)nc2)cc(-c2cn(C)nc2C)c1C#N]

EXAMPLE 321A: tert-butyl (5-(5-cyano-4-(1,3-dimethyl-1H-pyrazol-4-yl)-6-((((2-methoxyethyl)thio)methyl)thio)pyridin-2-yl)pyrimidin-2-yl)carbamate. The title compound was prepared by the general procedure starting from tert-butyl (5-(5-cyano-4-(1,3-dimethyl-1H-pyrazol-4-yl)-6-mercaptopyridin-2-yl)pyrimidin-2-yl)carbamate (0.5 g, 1.18 mmol) and (bromomethyl)(2-methoxyethyl)sulfane (435 mg, 2.36 mmol) to provide the title compound (410 mg, 778 umol, 50% yield) as a yellow solid.

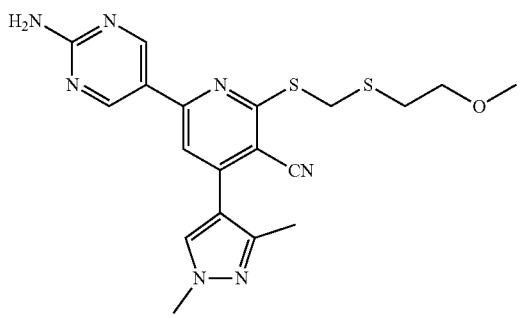 [SMILES: COCCSCSc1nc(-c2cnc(N)nc2)cc(-c2cn(C)nc2C)c1C#N]

EXAMPLE 321B: 6-(2-aminopyrimidin-5-yl)-4-(1,3-dimethyl-1H-pyrazol-4-yl)-2-((((2-methoxyethyl)thio)methyl)thio)nicotinonitrile. To a solution of EXAMPLE 321A (360 mg, 682 umol) in dichloromethane (3 mL) was added trifluoroacetic acid (462 mg, 4.05 mmol, 0.3 mL). The mixture was stirred at 25° C. for 1 hour. The reaction mixture was quenched by addition saturated sodium carbonate (50 mL), and then diluted with water (50 mL) and extracted with dichloromethane (150 mL). The combined organic layers were concentrated and lyophilized to give the title compound (0.3 g, crude) as brown solid.

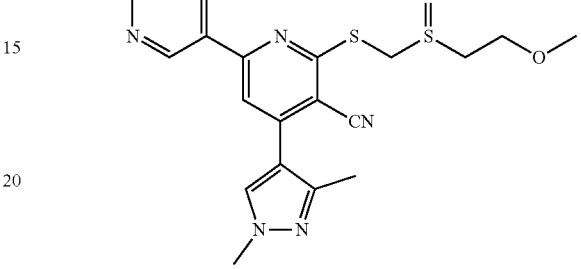

EXAMPLE 321C: 6-(2-aminopyrimidin-5-yl)-4-(1,3-dimethyl-1H-pyrazol-4-yl)-2-((((2-methoxyethyl)sulfinyl)methyl)thio)nicotinonitrile. To a solution of EXAMPLE 321B (280 mg, crude) in chloroform (10 mL) was added 3-chlorobenzoperoxoic acid (113 mg, 655 umol). The mixture was stirred at 25° C. for 1 hour. The reaction mixture was quenched by addition of sodium sulfite 50 ml at 0° C., and then diluted with sodium bicarbonate 50 mL and extracted with ethyl acetate 200 mL. The combined organic layers were washed with saturated sodium chloride 20 mL, dried over sodium sulfate, filtered and concentrated under reduced pressure to give a residue. The residue was purified by reversed-phase HPLC (0.1% NH$_3$·H$_2$O) to give the target compound (150 mg, 338 umol, 52% yield) as brown solid. $^1$H NMR (400 MHz, CDCl$_3$) δ 8.99 (s, 2H), 7.88 (s, 1H), 7.40 (s, 1H), 5.48 (s, 2H), 4.77-4.63 (m, 2H), 4.01-3.95 (m, 1H), 3.94 (s, 3H), 3.87-3.80 (m, 1H), 3.41 (s, 3H), 3.23-3.13 (m, 1H), 3.09-3.01 (m, 1H), 2.43 (s, 3H).

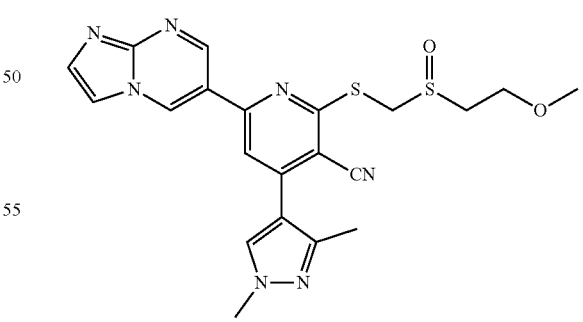

EXAMPLE 321D: To a solution of EXAMPLE 321C (140 mg, 316 umol) in ethyl alcohol was added 2-chloroacetaldehyde (310 mg, 1.58 mmol, 254 uL). The mixture was stirred at 80° C. for 3 hours. The solution was concentrated and purified by Prep-HPLC to give the title compound (110 mg, 235 umol, 75% yield) as a yellow solid.

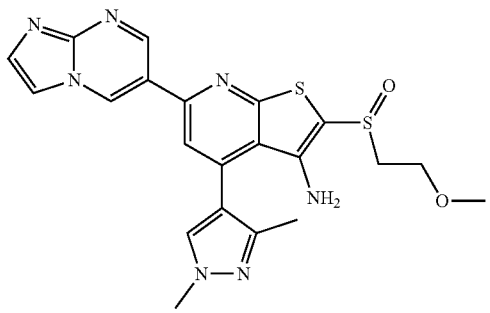 [SMILES: COCCS(=O)c1sc2nc(-c3cnc4nccn4c3)cc(-c3cn(C)nc3C)c2c1N]

EXAMPLE 321: 4-(1,3-dimethyl-1H-pyrazol-4-yl)-6-(imidazo[1,2-a]pyrimidin-6-yl)-2-((2-methoxyethyl)sulfinyl)thieno[2,3-b]pyridin-3-amine. The title compound was prepared by the general procedure starting from EXAMPLE 321D (50 mg, 107 umol) and potassium hydroxide solution (40 mg, 214 umol, 10% purity) to get EXAMPLE 321 (4 mg, 8 umol, 7% yield, 98.08% purity) and a second, less-pure sample of EXAMPLE 321 (6 mg, 11 umol, 10% yield, 94.16% purity), both as yellow solids. LCMS: (ES+) m/z (M+H)+=468.1. HPLC: tR=1.487 min. $^1$HNMR (400 MHz, CDCl$_3$) δ 9.36 (d, J=2.4 Hz, 1H), 9.16 (d, J=2.4 Hz, 1H), 7.90 (d, J=1.2 Hz, 1H), 7.68 (d, J=1.2 Hz, 1H), 7.53 (s, 1H), 7.52 (s, 1H), 4.86 (s, 2H), 3.99 (s, 3H), 3.93-3.86 (m, 1H), 3.75-3.70 (m, 1H), 3.65-3.59 (m, 1H), 3.42 (s, 3H), 3.29 (m, 1H), 2.26 (s, 3H).

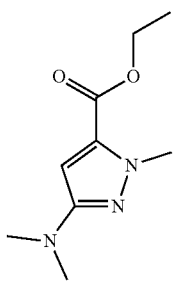

EXAMPLE 322A: ethyl 3-(dimethylamino)-1-methyl-1H-pyrazole-5-carboxylate. To a solution of ethyl 3-amino-1-methyl-1H-pyrazole-5-carboxylate ([89088-57-3], 10.6 g, 62.7 mmol) in MeOH (200 mL) and THF (200 mL) was added NaBH$_3$CN (15.8 g, 251 mmol) and HCHO (9.41 g, 313 mmol) at 25° C. Then the mixture was adjusted to pH=5 by addition of acetic acid and stirred at 25° C. for 12 hours. The reaction mixture was quenched by addition of Na$_2$CO$_3$ to adjust the pH=10. The reaction mixture was concentrated under reduced pressure to give a residue. The residue was diluted with H$_2$O 200 mL and extracted with DCM 900 mL (300 mL*3). The combined organic layers were dried over Na$_2$SO$_4$, filtered and concentrated under reduced pressure to give a residue. The residue was purified by column chromatography (SiO$_2$, Petroleum ether: Ethyl acetate=50:1 to 20:1) and reversed-phase HPLC (0.1% FA condition). The title compound (1.90 g, 15%) was obtained as yellow oil. $^1$H NMR (400 MHz, CDCl$_3$) δ 6.16 (s, 1H), 4.33 (q, J=7.2 Hz, 2H), 4.04 (s, 3H), 2.86 (s, 6H), 1.38 (t, J=7.2 Hz, 3H).

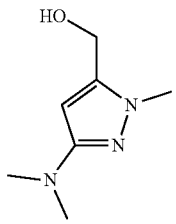

EXAMPLE 322B: (3-(dimethylamino)-1-methyl-1H-pyrazol-5-yl)methanol. To a solution of EXAMPLE 322A (1.40 g, 7.10 mmol) in DCM (30 mL) was added DIBAL-H (1 M, 11.4 mL) at -70° C. Then the mixture was stirred at -70° C. for 1 hour. The reaction mixture was quenched by addition H$_2$O 30 mL at -60° C. The solution was concentrated under reduced pressure to give a residue. The residue was purified by column chromatography (SiO$_2$, Petroleum ether: Ethyl acetate=5:1 to 1:3). The title compound (1.00 g, 91%) was obtained as a yellow oil. $^1$H NMR (400 MHz, CDCl$_3$) δ 5.53 (s, 1H), 4.54 (s, 2H), 3.70 (s, 3H), 2.82 (s, 6H).

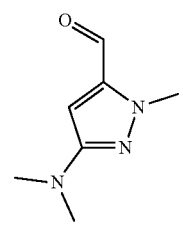

EXAMPLE 322C: 3-(dimethylamino)-1-methyl-1H-pyrazole-5-carbaldehyde. To a solution of EXAMPLE 322B (1.60 g, 10.3 mmol) in DCM (20 mL) was added MnO$_2$ (9.77 g, 112 mmol). The mixture was stirred at 25° C. for 12 hours. The reaction mixture was filtered. The filtrate was concentrated to give a residue. The residue was purified by column chromatography (SiO$_2$, Petroleum ether: Ethyl acetate=10:1 to 1:1) to give the title compound (800 mg, 51%) as yellow oil. $^1$H NMR (400 MHz, CDCl$_3$) δ 9.67 (s, 1H), 6.08 (s, 1H), 3.96 (s, 3H), 2.80 (s, 6H).

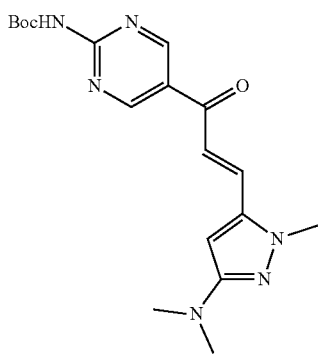 [SMILES: CN(C)c1cc(/C=C/C(=O)c2cnc(NC(=O)OC(C)(C)C)nc2)n(C)n1]

EXAMPLE 322D: (E)-tert-butyl(5-(3-(3-(dimethylamino)-1-methyl-1H-pyrazol-5-yl)acryloyl)pyrimidin-2-yl)carbamate. The title compound was prepared by General Procedure A starting from EXAMPLE 322C (700 mg, 4.57 mmol) and tert-butyl N-(5-acetyl pyrimidin-2-yl)-N-tert-butoxycarbonyl-carbamate (1.85 g, 5.48 mmol) to give the title compound (1.20 g, crude) as a red solid.

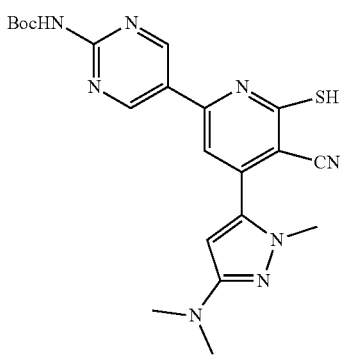 [SMILES: CN(C)c1cc(-c2cc(-c3cnc(NC(=O)OC(C)(C)C)nc3)nc(S)c2C#N)n(C)n1]

EXAMPLE 322E: tert-butyl (5-(5-cyano-4-(3-(dimethylamino)-1-methyl-1H-pyrazol-5-yl)-6-mercaptopyridin-2-yl)pyrimidin-2-yl)carbamate. The title compound was prepared by General Procedure A starting from EXAMPLE 322D (600 mg, 1.61 mmol) and 2-cyanoethanethioamide (242 mg, 2.42 mmol) to give the title compound (700 mg, crude) as yellow solid.

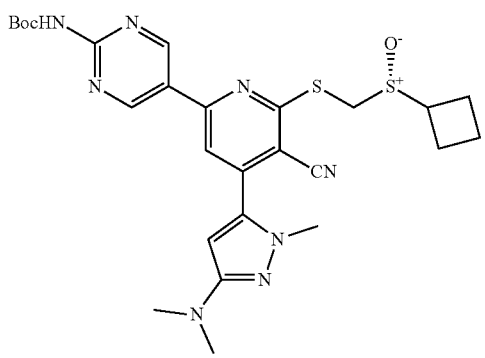 [SMILES: CN(C)c1cc(-c2cc(-c3cnc(NC(=O)OC(C)(C)C)nc3)nc(SC[S@+]([O-])C3CCC3)c2C#N)n(C)n1]

EXAMPLE 322F: (R)-tert-butyl(5-(5-cyano-6-(((cyclobutylsulfinyl)methyl) thio)-4-(3-(dimethylamino)-1-methyl-1H-pyrazol-5-yl)pyridin-2-yl)pyrimidin-2-yl)carbamate. The title compound was prepared by the general procedure starting from EXAMPLE 322E (700 mg, 1.55 mmol) and (R)-((bromo methyl)sulfinyl)cyclobutane (213 mg, 1.08 mmol) to give the title compound (300 mg, 34%) as yellow solid.

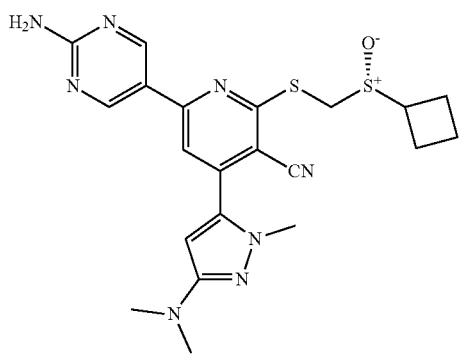 [SMILES: CN(C)c1cc(-c2cc(-c3cnc(N)nc3)nc(SC[S@+]([O-])C3CCC3)c2C#N)n(C)n1]

EXAMPLE 322G: (R)-6-(2-aminopyrimidin-5-yl)-2-(((cyclobutylsulfinyl)meth yl)thio)-4-(3-(dimethylamino)-1-methyl-1H-pyrazol-5-yl)nicotinonitrile. To a solution of EXAMPLE 322F (300 mg, 528 umol) in DCM (3 mL) was added TFA (301 mg, 2.64 mmol, 195 uL). The mixture was stirred at 25° C. for 2 hours. The reaction mixture was concentrated under reduced pressure to give a residue. The crude product was purified by reversed-phase HPLC (0.1% TFA condition). The title compound (220 mg, 72%, TFA) was obtained as a yellow solid. $^1$H NMR (400 MHz, CDCl$_3$) δ 9.01 (s, 2H), 7.33 (s, 1H), 6.40 (s, 2H), 5.87 (s, 1H), 4.50 (d, J=13.2 Hz, 1H), 4.06 (d, J=13.2 Hz, 1H), 3.68 (s, 3H), 2.84 (s, 6H), 2.77-2.65 (m, 1H), 2.46-2.33 (m, 1H), 2.23-2.02 (m, 3H), 2.00-1.89 (m, 2H).

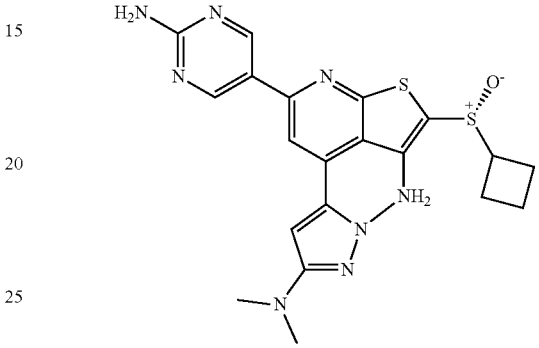

EXAMPLE 322: (R)-6-(2-aminopyrimidin-5-yl)-2-(cyclobutylsulfinyl)-4-(3-(dimethylamino)-1-methyl-1H-pyrazol-5-yl)thieno[2,3-b]pyridin-3-amine. The title compound was prepared by the general procedure starting from EXAMPLE 322G (200 mg, 343 umol) to give EXAMPLE 322 (114.4 mg, 71% yield, 99.2% purity) as a yellow solid. Optical Rotation determination showed the Specific Rotation was +105.454°; LCMS: (ES$^+$) m/z (M+H)$^+$=469.1. HPLC: tR=1.632 min. $^1$H NMR (400 MHz, CDCl$_3$) δ 9.04 (s, 2H), 7.47 (s, 1H), 5.85-5.81 (m, 1H), 5.34 (s, 2H), 4.84-4.67 (m, 2H), 4.02-3.90 (m, 1H), 3.59-3.55 (m, 3H), 2.93 (s, 6H), 2.90-2.78 (m, 1H), 2.45-2.33 (m, 2H), 2.32-2.21 (m, 1H), 2.17-2.03 (m, 2H).

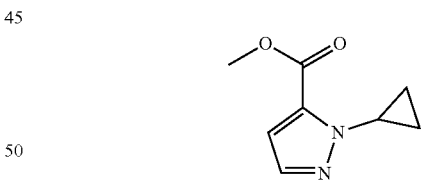

EXAMPLE 323A: methyl 1-cyclopropyl-1H-pyrazole-5-carboxylate. To a solution of methyl 1H-pyrazole-3-carboxylate (24 g, 190 mmol) and cyclopropylboronic acid (32.7 g, 380 mmol) and Na$_2$CO$_3$ (40.3 g, 380 mmol) in DCE (300 mL) was added 2-(2-pyridyl)pyridine (29.7 g, 190 mmol) and Cu(OAc)$_2$ (34.6 g, 190 mmol). The mixture was stirred at 70° C. for 48 hours under O$_2$ (15 psi). The mixture was filtrate and concentrated, the crude product was purified by column chromatography (SiO$_2$, Petroleum ether:Ethyl acetate=10:1 to 2:1) to give the title compound (10 g, 32% yield) as a yellow oil. $^1$H NMR (400 MHz, CDCl$_3$) δ 7.40 (d, J=2.0 Hz, 1H), 6.83 (d, J=2.0 Hz, 1H), 4.33-4.27 (m, 1H), 3.90 (s, 3H), 1.28-1.26 (m, 2H), 1.08-1.03 (m, 2H).

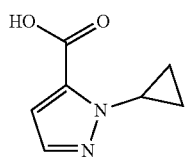

EXAMPLE 323B: 1-cyclopropyl-1H-pyrazole-5-carboxylic acid. To a solution of EXAMPLE 323A (7 g, 42.1 mmol) in H₂O (10 mL) was added NaOH (2.19 g, 54.8 mmol, 1.3 eq). The mixture was stirred at 100° C. for 2 hours. The pH of the mixture was adjust to 7 by acetic acid and then was concentrated, the crude product was purified by Prep-HPLC (TFA condition) to give the title compound (11 g, crude) as a white solid.

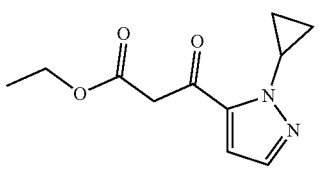 [SMILES: CCOC(=O)CC(=O)c1ccnn1C1CC1]

EXAMPLE 323C: ethyl 3-(1-cyclopropyl-1H-pyrazol-5-yl)-3-oxopropanoate. The title compound was prepared by the procedure used for Example 313C starting from EXAMPLE 323B (10 g, 65.7 mmol) and potassium 3-ethoxy-3-oxo-propanoate (13.4 g, 78.9 mmol) to give EXAMPLE 318C (10 g, 69% yield) as a yellow oil. ¹H NMR (400 MHz, CDCl₃) δ 7.41 (d, J=2.0 Hz, 1H), 6.82 (d, J=2.0 Hz, 1H), 4.32-4.29 (m, 1H), 4.24-4.18 (m, 2H), 3.85 (s, 2H), 1.26 (t, J=7.2 Hz, 3H), 1.23-1.21 (m, 2H), 1.06-1.03 (m, 2H).

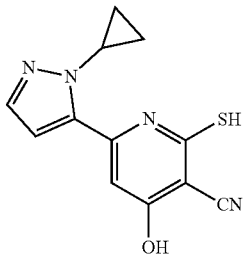 [SMILES: N#Cc1c(O)cc(-c2ccnn2C2CC2)nc1S]

EXAMPLE 323D: 6-(1-cyclopropyl-1H-pyrazol-5-yl)-4-hydroxy-2-mercaptonicotinonitrile. The title compound was prepared by the general procedure starting from EXAMPLE 323C (5 g, 22.5 mmol) and 2-cyanoethanethioamide (4.51 g, 45 mmol) to give the title compound (5 g, 19.4 mmol, 86% yield) as a yellow solid.

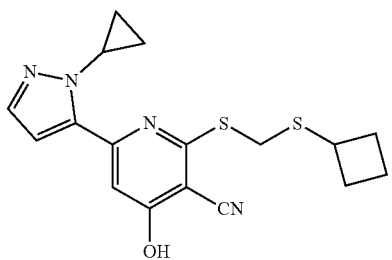 [SMILES: N#Cc1c(O)cc(-c2ccnn2C2CC2)nc1SCSC1CCC1]

EXAMPLE 323E: 2-(((cyclobutylthio)methyl)thio)-6-(1-cyclopropyl-1H-pyrazol-5-yl)-4-hydroxynicotinonitrile.

The title compound was prepared by the general procedure starting from EXAMPLE 323D (4.50 g, 17.4 mmol) and chloromethylsulfanylcyclobutane (2.38 g, 17.4 mmol) to give the crude title compound (2.5 g, 40% yield) as a brown oil.

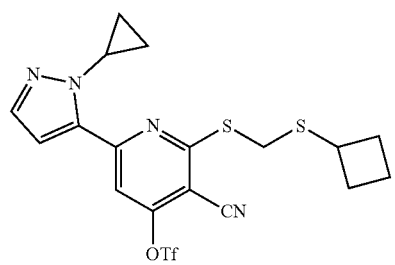 [SMILES: N#Cc1c(OS(=O)(=O)C(F)(F)F)cc(-c2ccnn2C2CC2)nc1SCSC1CCC1]

EXAMPLE 323F: 3-cyano-2-(((cyclobutylthio)methyl)thio)-6-(1-cyclopropyl-1H-pyrazol-5-yl)pyridin-4-yltrifluoromethanesulfonate. The title compound was prepared by the general procedure starting from EXAMPLE 323E (2.50 g, 6.97 mmol) and 1,1,1-trifluoro-N-phenyl-N-((trifluoromethyl)sulfonyl)methanesulfonamide (4.98 g, 13.9 mmol) to give the title compound (1.6 g, 47% yield) as a yellow solid.

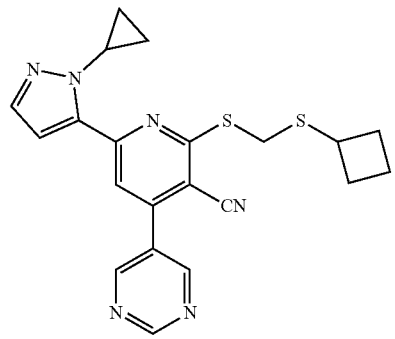 [SMILES: N#Cc1c(-c2cncnc2)cc(-c2ccnn2C2CC2)nc1SCSC1CCC1]

EXAMPLE 323G: 2-((((3-methoxypropyl)thio)methyl)thio)-4-(pyridazin-4-yl)-6-(pyrimidin-5-yl)nicotinonitrile.

The title compound was prepared by the general procedure starting from EXAMPLE 323F (600 mg, 1.22 mmol) and pyrimidin-5-ylboronic acid (181 mg, 1.47 mmol) to give the title compound (320 mg, 761 umol) as a white solid. ¹H NMR (400 MHz, CDCl₃) δ 9.40 (s, 1H), 9.02 (s, 2H), 7.51 (d, J=2.0 Hz, 1H), 7.46 (s, 1H), 6.75 (d, J=2.0 Hz, 1H), 4.46 (s, 2H), 4.29-4.25 (m, 1H), 3.74-3.72 (m, 1H), 2.42-2.39 (m, 2H), 2.08-2.05 (m, 4H), 1.28-1.26 (m, 2H), 1.10-1.08 (m, 2H).

523

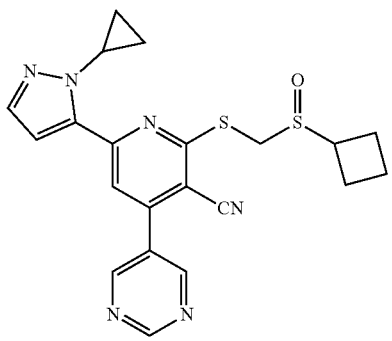 [SMILES: N#Cc1c(-c2cncnc2)cc(-c2ccnn2C2CC2)nc1SCS(=O)C1CCC1]

EXAMPLE 323H: 2-(((cyclobutylsulfinyl)methyl)thio)-6-(1-cyclopropyl-1H-pyrazol-5-yl)-4-(pyrimidin-5-yl)nicotinonitrile. The title compound was prepared by the general procedure starting from EXAMPLE 323G (300 mg, 713 umol), hydrogen peroxide (1.21 g, 10.7 mmol, 1.03 mL, 30% purity) to give the crude title compound (310 mg, 710 umol) as a yellow solid.

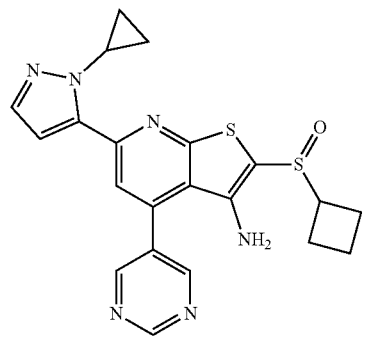 [SMILES: Nc1c(S(=O)C2CCC2)sc2nc(-c3ccnn3C3CC3)cc(-c3cncnc3)c12]

EXAMPLE 323: 2-(cyclobutylsulfinyl)-6-(1-cyclopropyl-1H-pyrazol-5-yl)-4-(pyrimidin-5-yl)thieno[2,3-b]pyridin-3-amine. The title compound was prepared by the general procedure starting from EXAMPLE 323H (300 mg, 687 umol) to give EXAMPLE 323 (125 mg, 279 umol, 40% yield, 97% purity) as a yellow solid. LCMS: (ES+) m/z (M)=437.1. HPLC: tR=1.925 min. $^1$H NMR (400 MHz, CDCl$_3$) δ 9.40 (s, 1H), 8.97 (s, 2H), 7.50 (d, J=2.0 Hz, 1H), 7.45 (s, 1H), 6.69 (d, J=2.0 Hz, 1H), 4.43 (s, 2H), 4.36-4.34 (m, 1H), 3.98-3.94 (m, 1H), 2.84-2.81 (m, 1H), 2.43-2.39 (m, 2H), 2.31-2.27 (m, 1H), 2.17-2.08 (m, 2H), 1.23-1.20 (m, 2H), 1.06-1.04 (m, 2H).

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

524

The following is claimed:
1. A compound of Formula (IA):

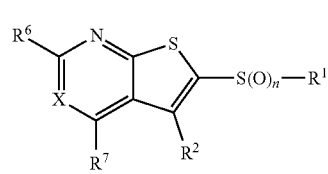

(IA)

or a pharmaceutically acceptable salt, tautomer, or solvate thereof, wherein:

$R^1$ is alkyl, haloalkyl, cycloalkyl, alkylene-cycloalkyl, alkylene-alkoxy, heterocyclyl, or alkylene-heterocyclyl;

$R^2$ is —NH$_2$, CN, or —NHC(O)alkyl;

$R^6$ is a fused bicyclic heterocyclyl or a fused bicyclic heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)NR$^5$-alkyl, each of which is optionally substituted with one or more $R^4$;

$R^3$ is oxo, —OH, —O-alkylene-OH, —O-alkylene-N (R$^5$)$_2$, —N(R$^5$)$_2$, —N(R$^5$) (alkylene-OH), —N(R$^5$)(alkylene-O-alkyl), alkyl, -alkylene-OH, haloalkyl, cycloalkyl, heterocyclyl, -C(O)N(R$^5$)$_2$, —C(O)N(R$^5$)(alkylene-OH), —C(O)-alkyl, —C(O)O-alkyl, or —S(O)$_m$-alkyl, wherein each of the cycloalkyl and the heterocyclyl is optionally substituted with $R^{10}$;

$R^4$ is oxo, halogen, —CN, —N(R$^5$)$_2$, —OH, —O-alkylene-OH, —S(O)$_m$-alkyl, —C(O)-alkyl, —C(O)-cycloalkyl, alkyl, -alkylene-O-alkyl, alkoxy, haloalkyl, cycloalkyl, heterocyclyl, or -alkylene-aryl optionally substituted with $R^8$;

each $R^5$ is independently; H, alkyl, -alkylene-OH optionally substituted with —OH, -alkylene-NH$_2$, -alkylene-N(R$^9$)$_2$, -alkylene-O-alkylene-OH, -alkylene-O-alkylene-NH$_2$, —C(O)-alkyl, —C(O)O-alkyl, -alkylene-COOH, or —S(O)$_m$-alkyl;

or alternatively, two $R^5$ together with the N atom to which they are attached can form a 4- to 7-membered heterocyclyl, optionally containing an additional heteroatom selected from O, S, or N, and wherein the heterocyclyl is optionally substituted with $R^8$;

$R^8$ is halogen, alkyl, or alkoxy;

$R^9$ is H or alkyl, or two $R^9$ together with the N atom to which they are attached can form a 4- to 7-membered heterocyclyl, optionally containing an additional heteroatom selected from O, S(O)$_t$, or N;

$R^{10}$ is —OH, halogen, alkyl, or alkoxy;

X is N or CH;

m is 0, 1, or 2;

n is 0, 1, or 2; and t is 0, 1, or 2.

2. The compound, salt, or solvate of claim 1, wherein $R^1$ is C$_1$-C$_6$ alkyl, C$_1$-C$_6$ haloalkyl, 3- to 6-membered cycloalkyl, —(C$_1$-C$_6$ alkylene)-(3-to 6-membered cycloalkyl), —(C$_1$-C$_6$ alkylene)-(C$_1$-C$_6$ alkoxy), 3- to 6-membered heterocyclyl, or —(C$_1$-C$_6$ alkylene)-(3-to 6-membered heterocyclyl).

3. The compound, salt, or solvate of claim 1, wherein $R^2$ is —NH$_2$.

4. The compound, salt, or solvate of claim 1, wherein $R^6$ is 8- to 10-membered heteroaryl optionally substituted with one or more $R^3$.

5. The compound, salt, or solvate of claim 1, wherein $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)$NR^5$ ($C_1$-$C_6$ alkyl), each of which is optionally substituted with one or more $R^4$.

6. The compound, salt, or solvate of claim 1, wherein $R^3$ is —O—($C_1$-$C_6$ alkylene)-$N(R^5)_2$, —$N(R^5)_2$, —$N(R^5)$($C_1$-$C_6$ alkylene-OH), $C_1$-$C_6$ alkyl, —C(O) $N(R^5)_2$, —C(O) $N(R^5)$($C_1$-$C_6$ alkylene-OH), —C(O)($C_1$-$C_6$ alkyl), —C(O)O ($C_1$-$C_6$ alkyl), —S(O)$_m$ ($C_1$-$C_6$ alkyl), or —($C_1$-$C_3$ alkylene)-OH.

7. The compound, salt, or solvate of claim 1, wherein $R^4$ is halogen, —CN, —$N(R^5)_2$, —OH, —O—($C_1$-$C_6$ alkylene)-OH, —S(O)$_m$ ($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.

8. The compound, salt, or solvate of claim 1, wherein n is 1.

9. The compound, salt, or solvate of claim 1, wherein the compound is:

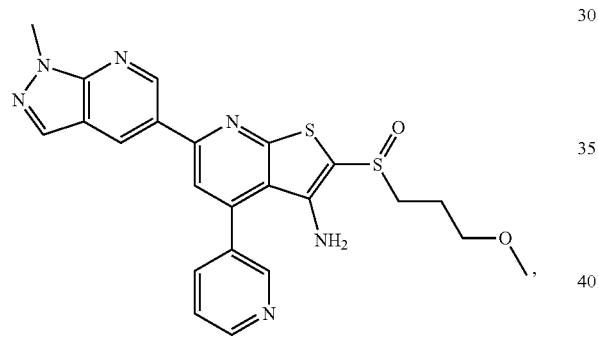

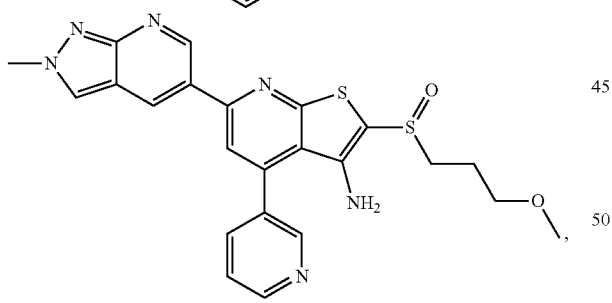

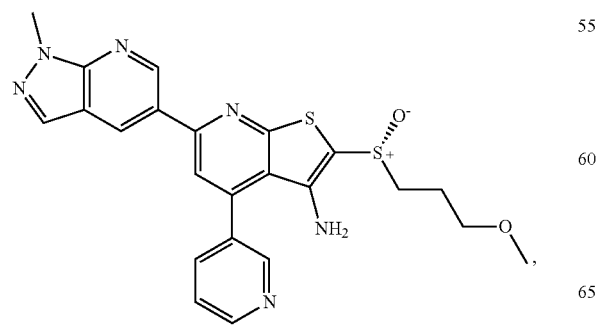

-continued

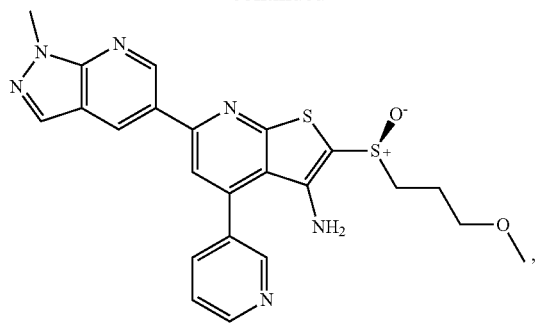

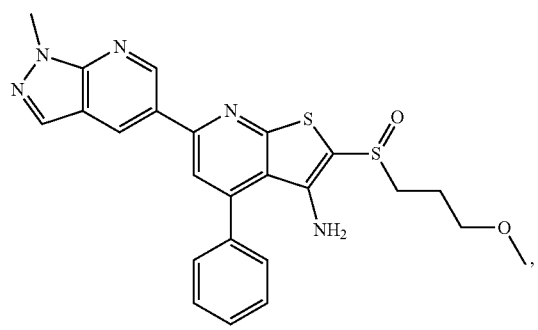

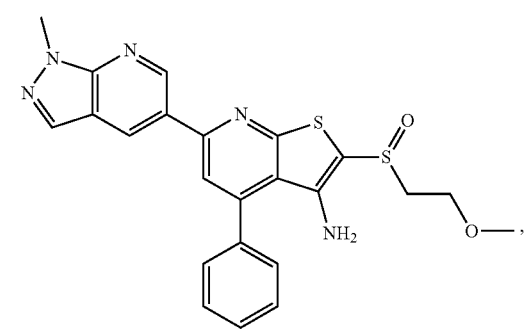

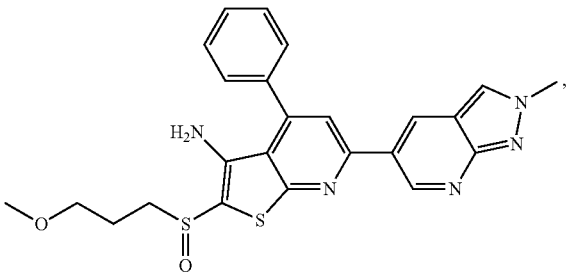

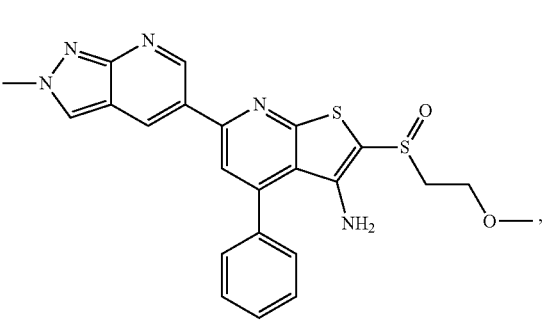

527
-continued
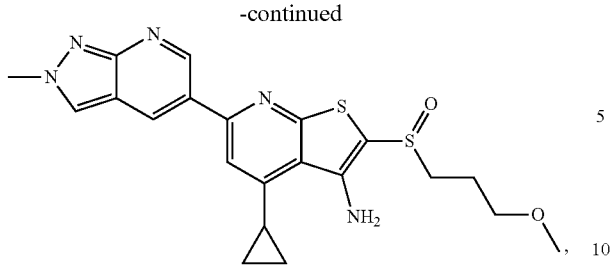
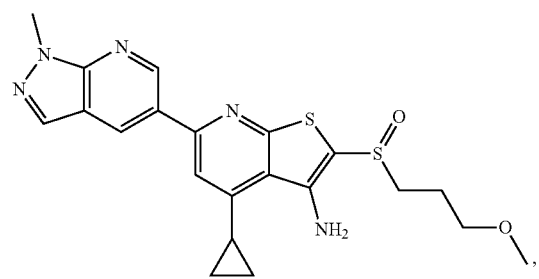
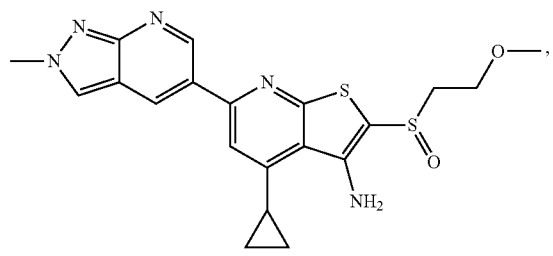
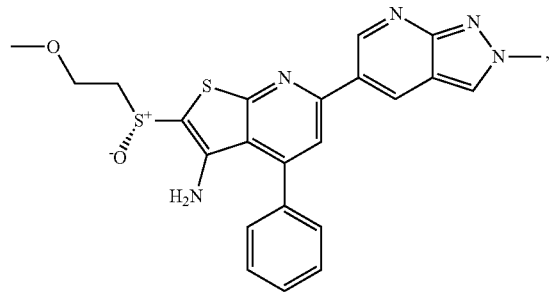
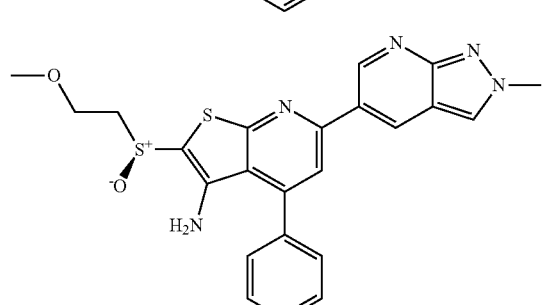
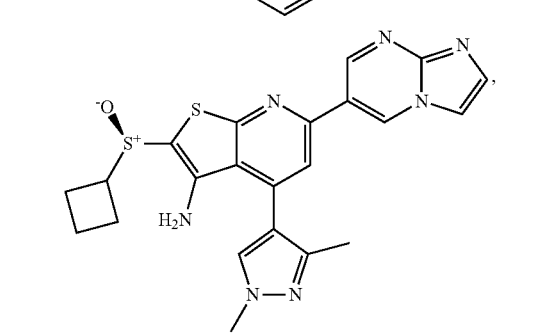
528
-continued
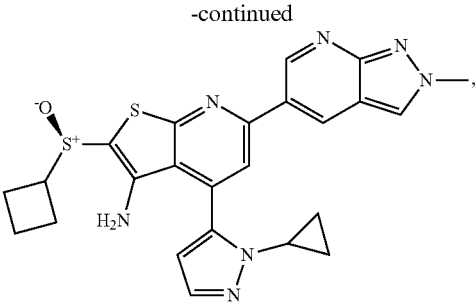
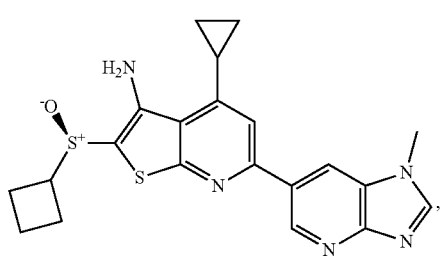
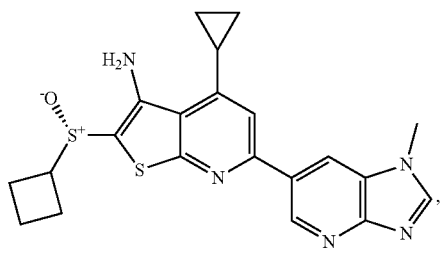
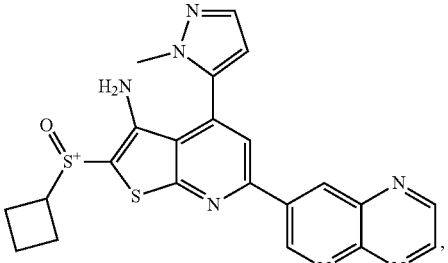
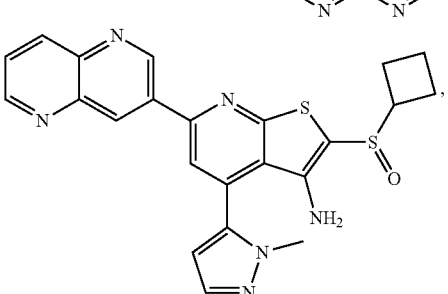
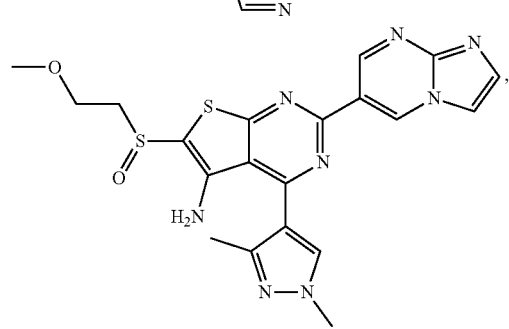

529
-continued
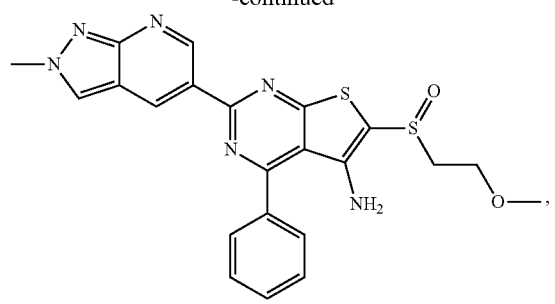
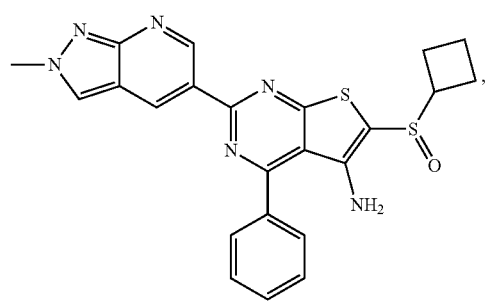
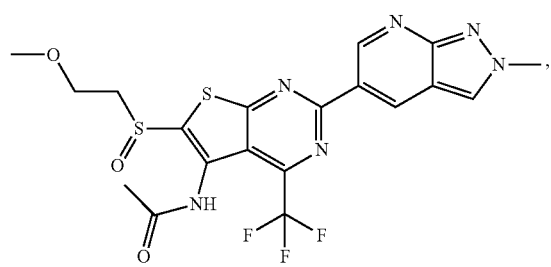
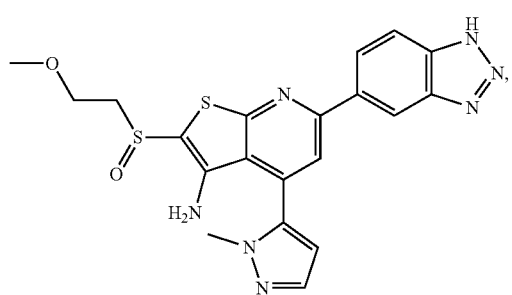
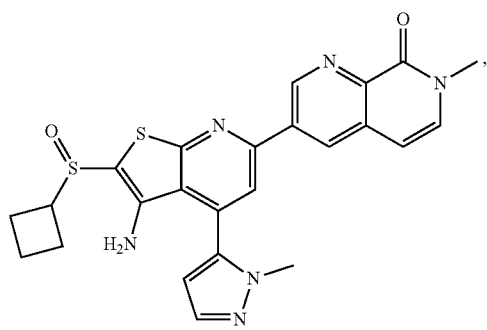
530
-continued
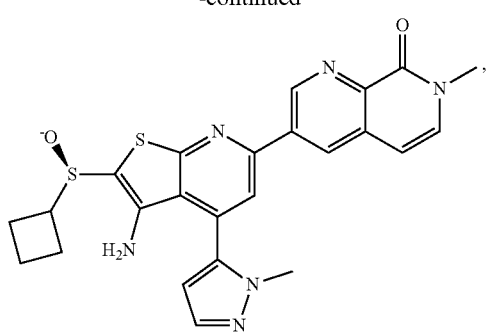
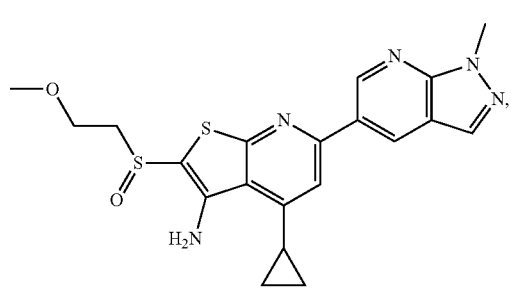
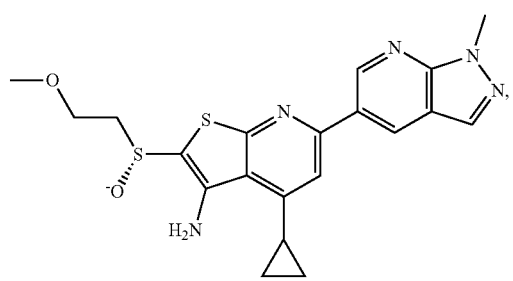
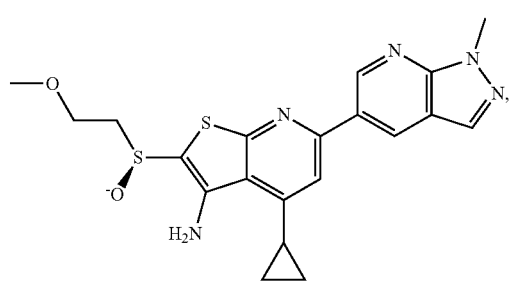
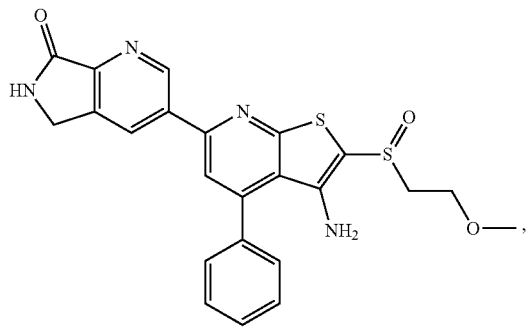

531
-continued
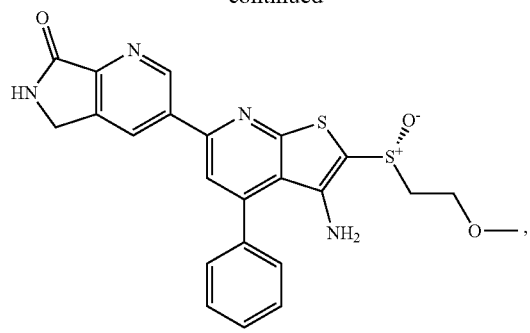
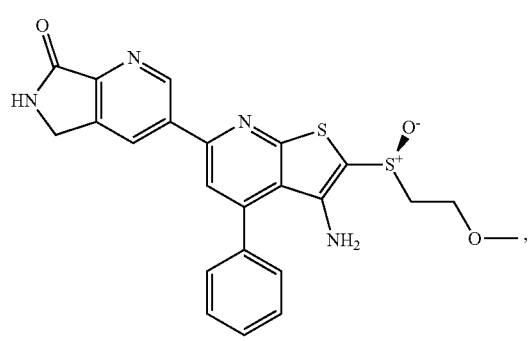
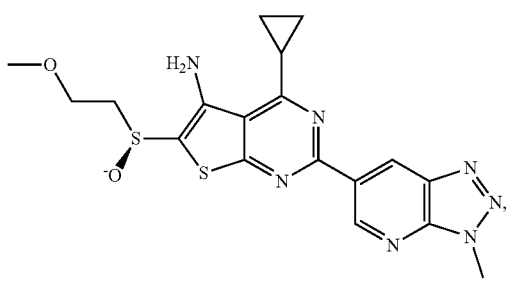
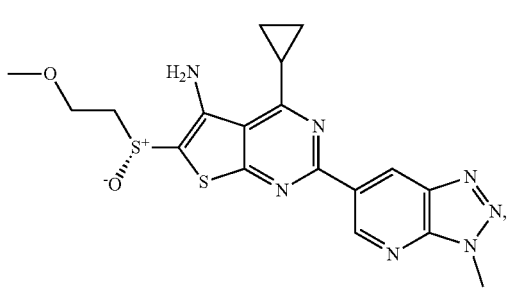
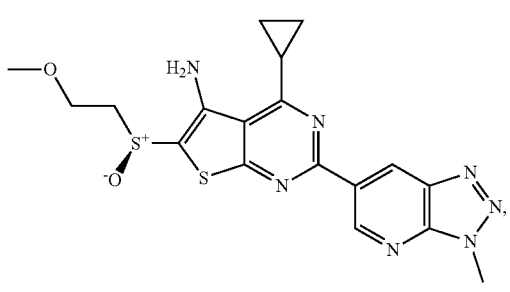
532
-continued
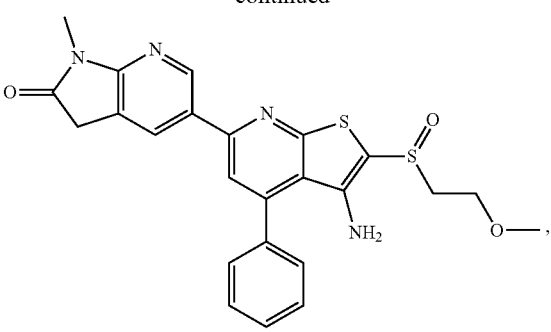
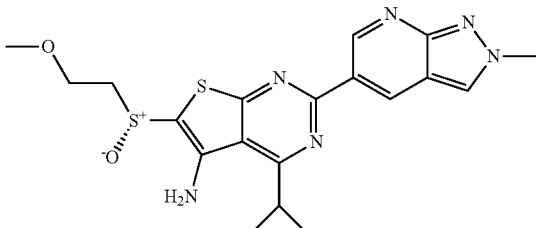

533
-continued
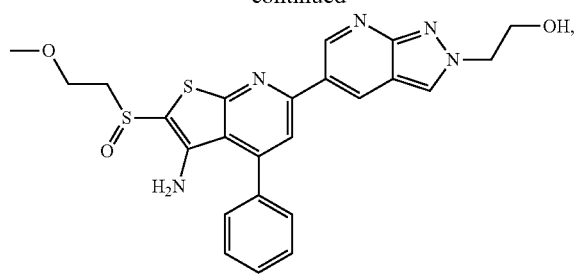
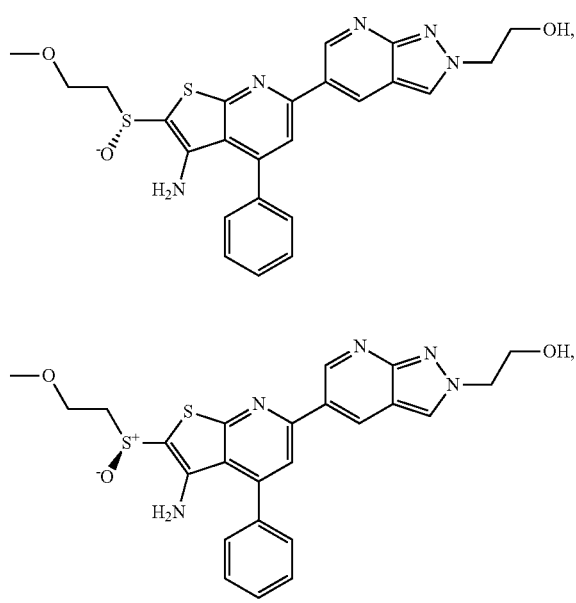
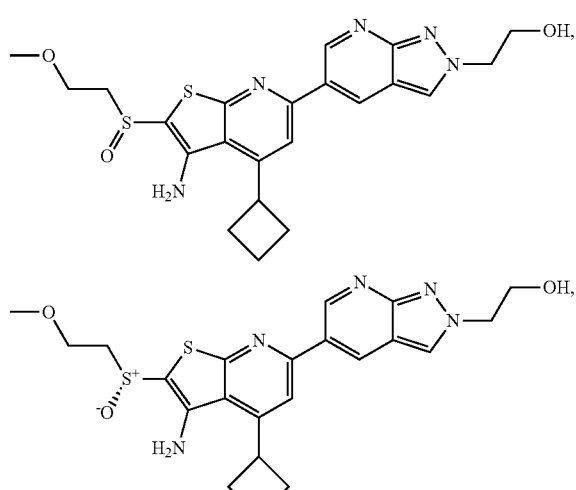
534
-continued
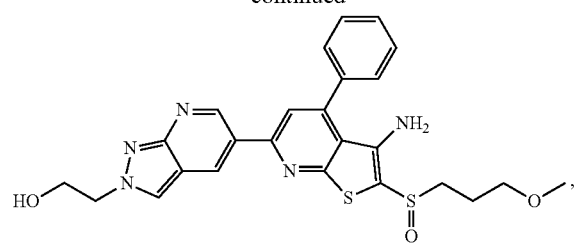
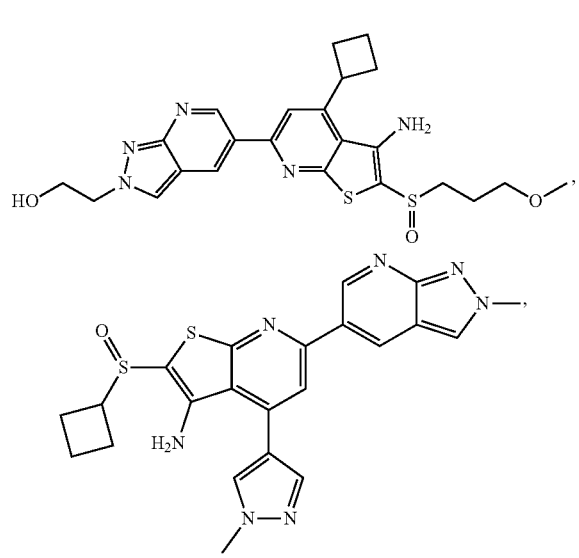
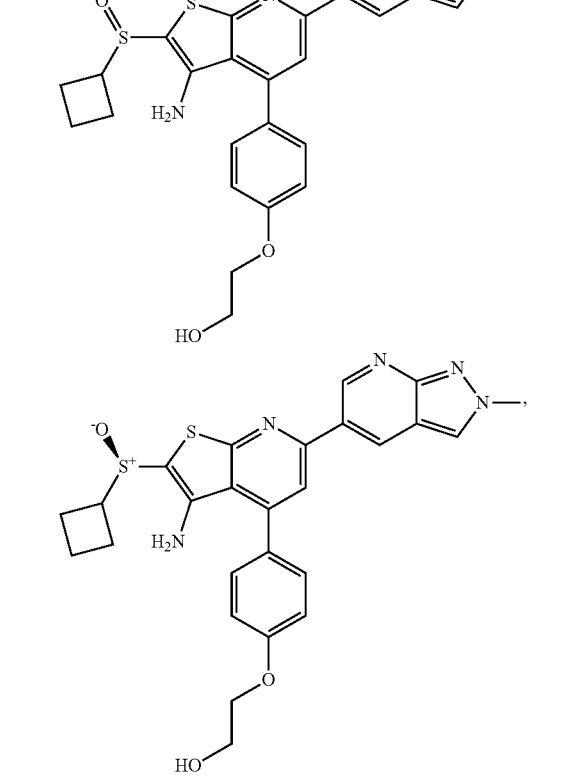

-continued
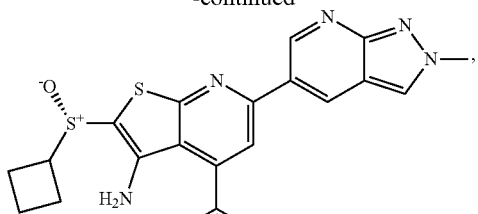
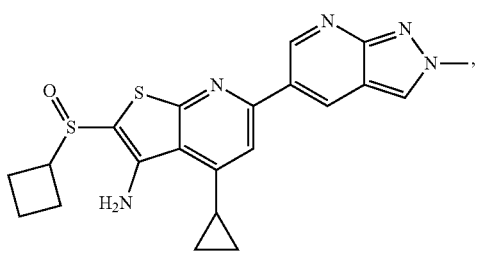
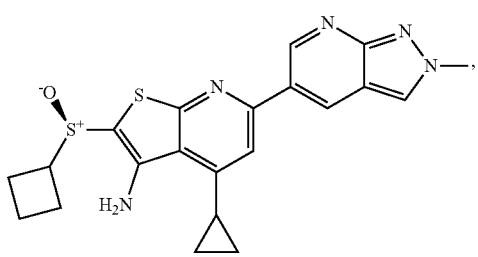
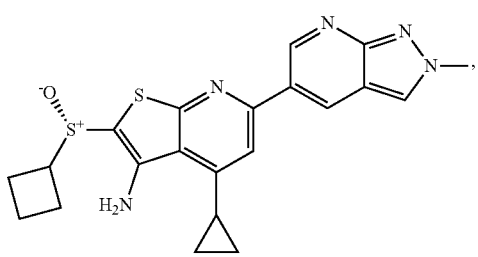
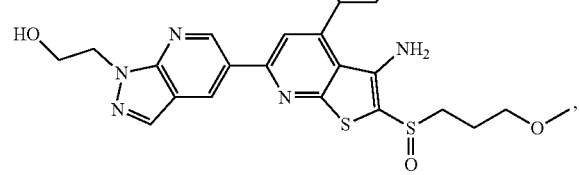
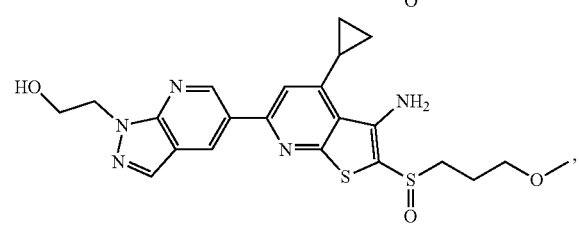
-continued
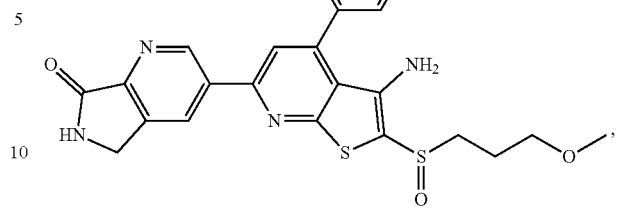
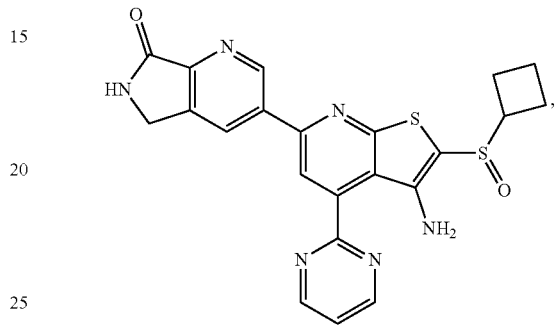
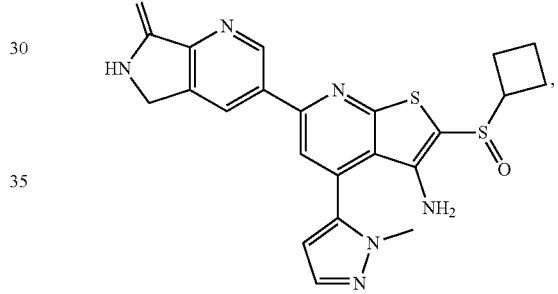
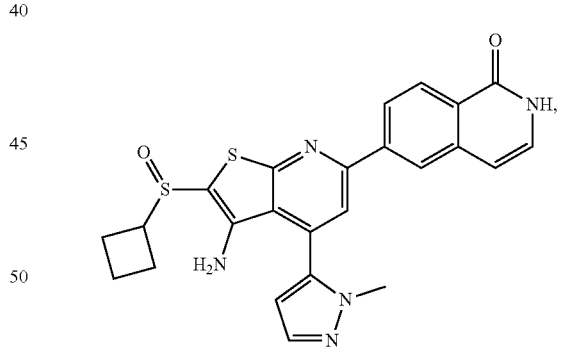
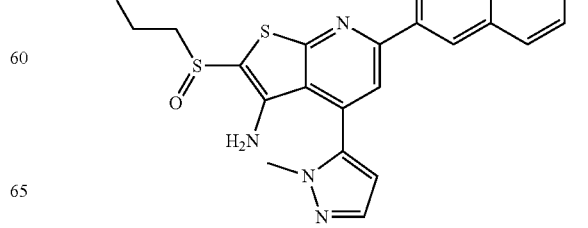

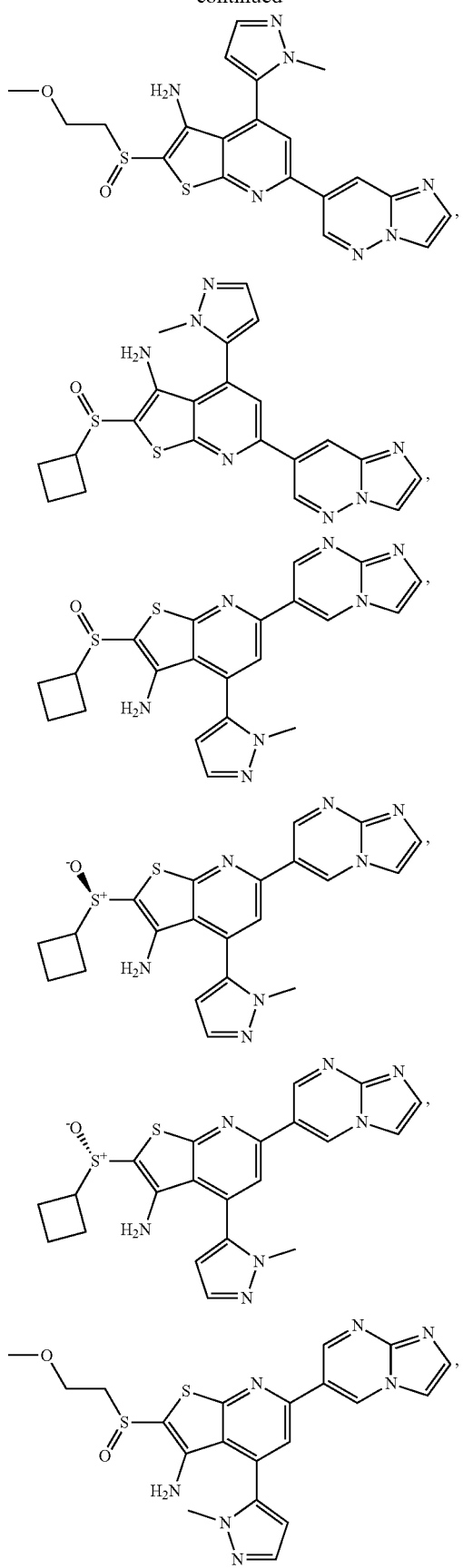
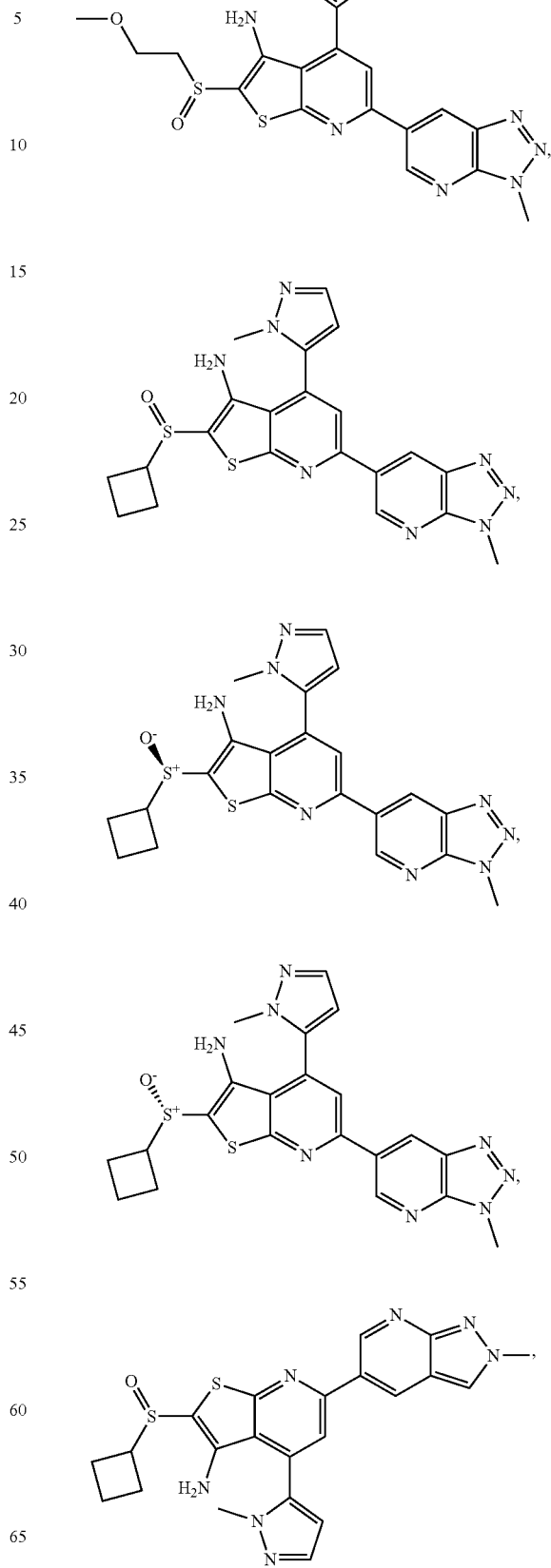

539
-continued
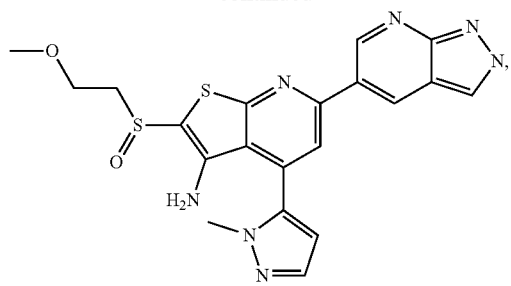
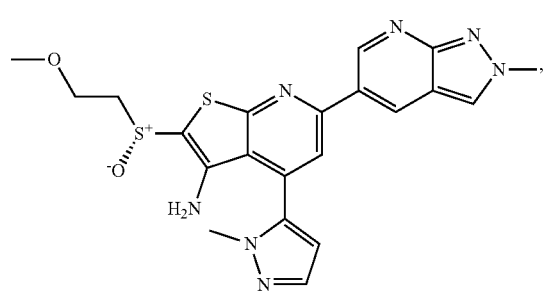
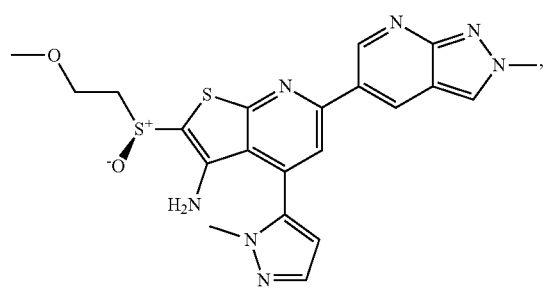
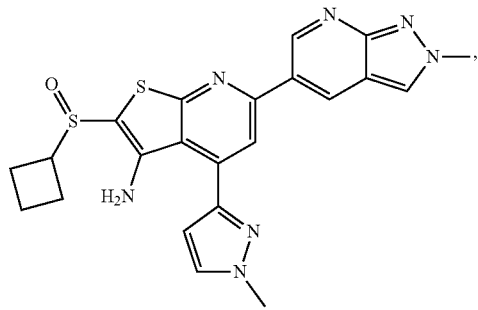
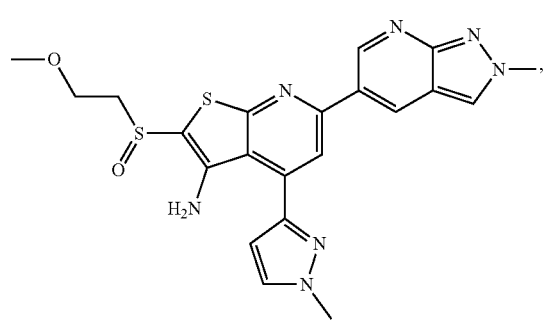
540
-continued
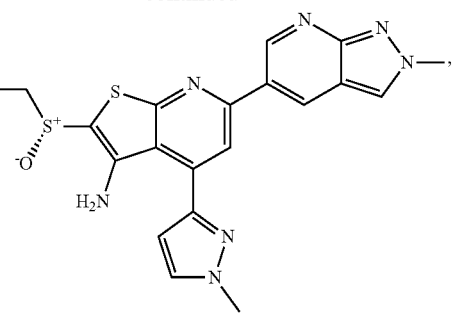
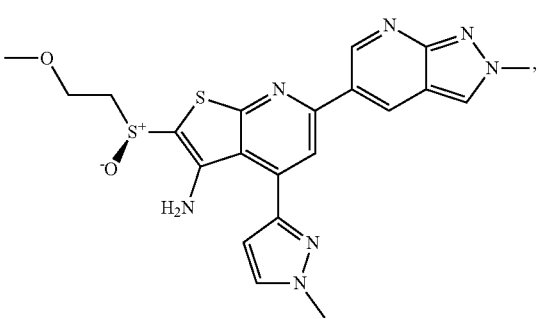
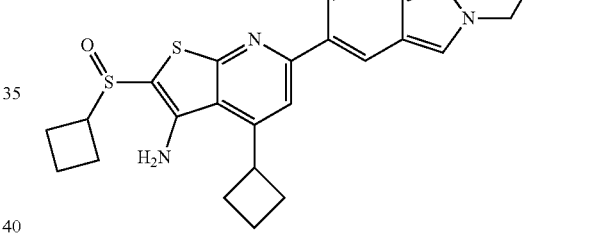
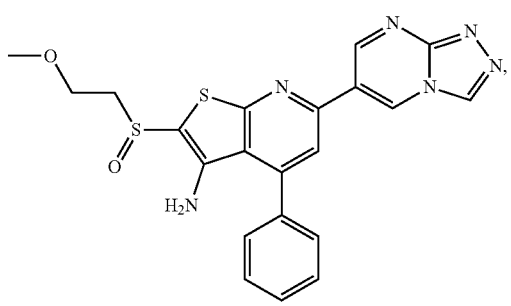
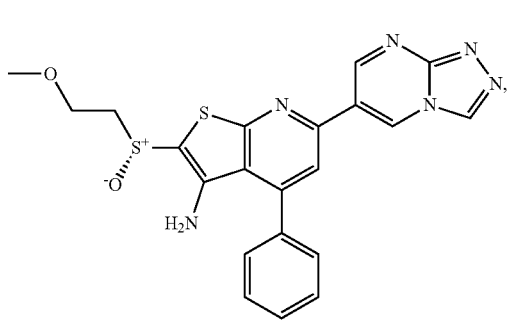

541
-continued
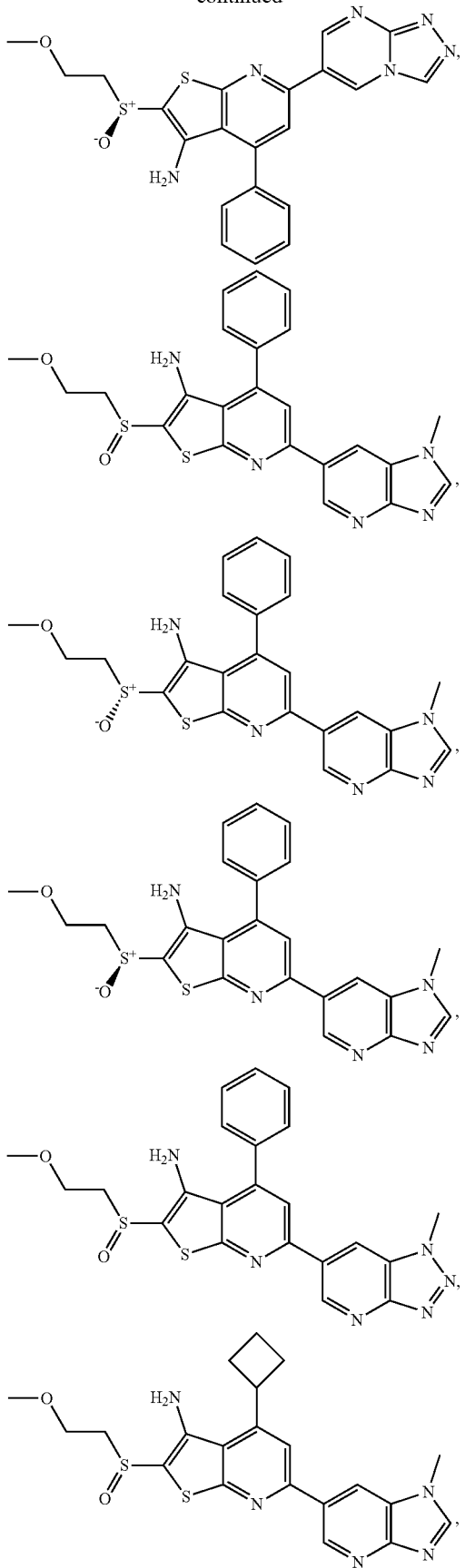
542
-continued
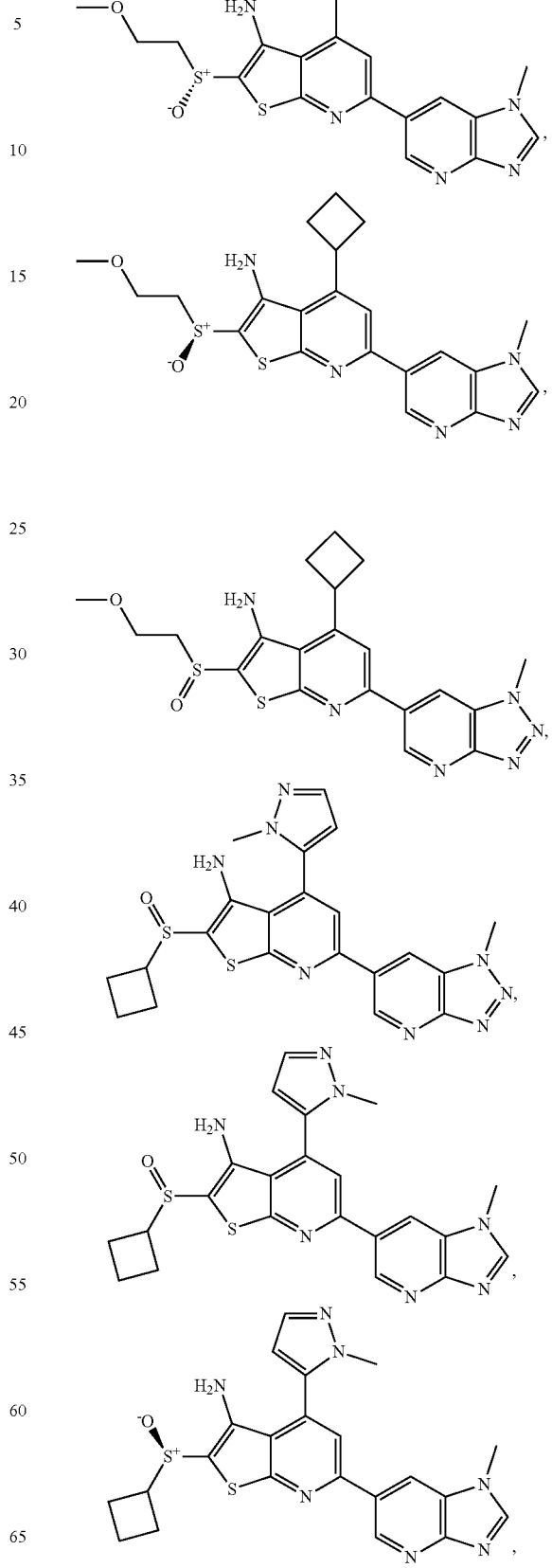

543
-continued
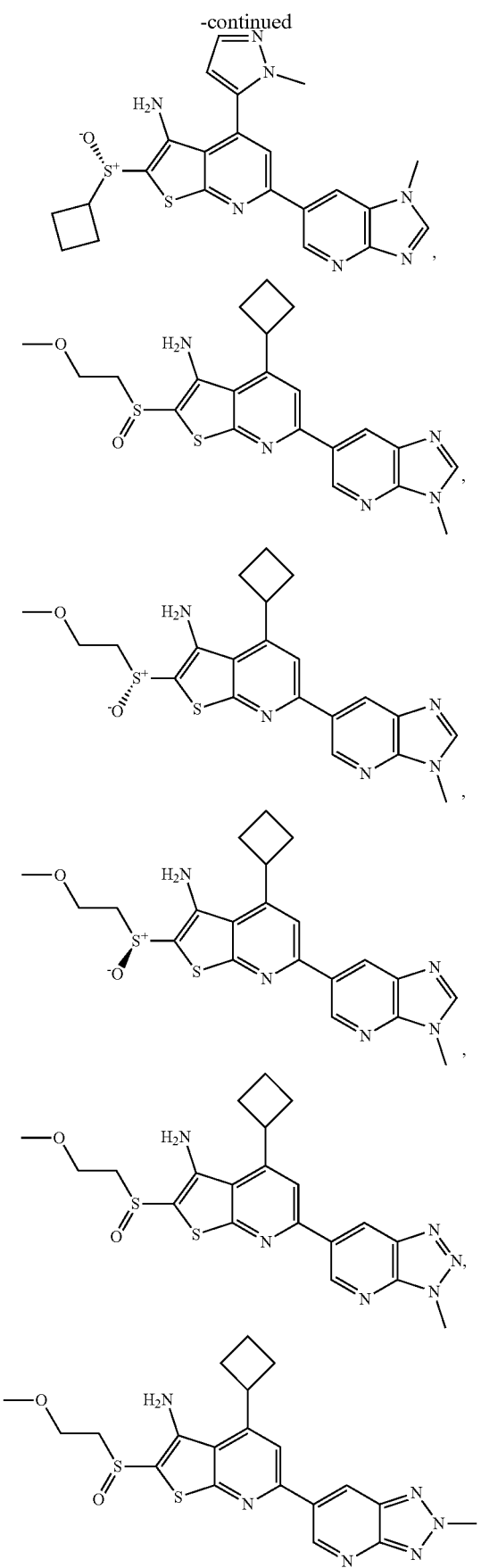
544
-continued
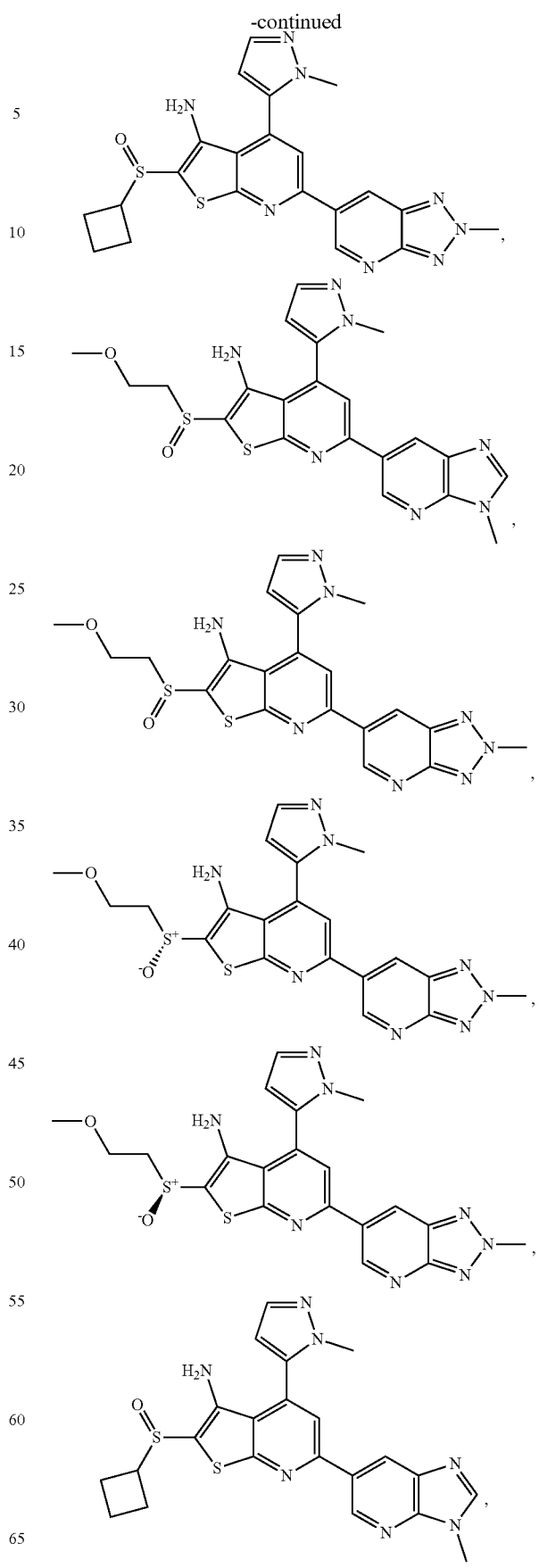

545
-continued
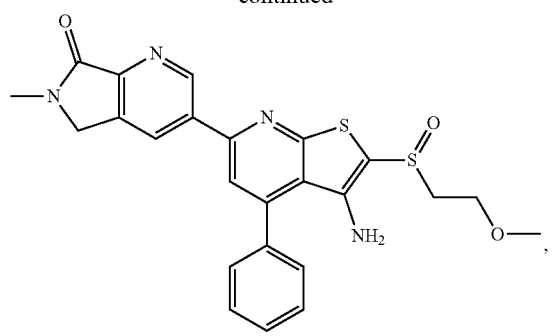
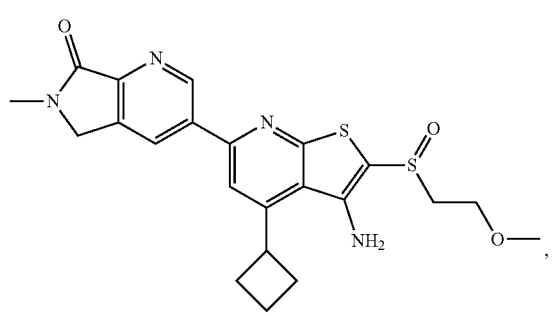
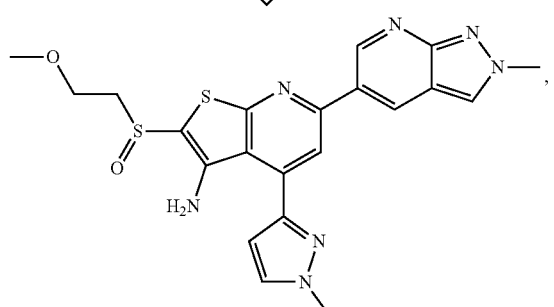
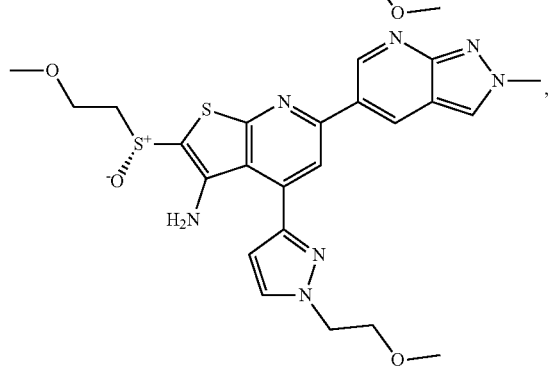
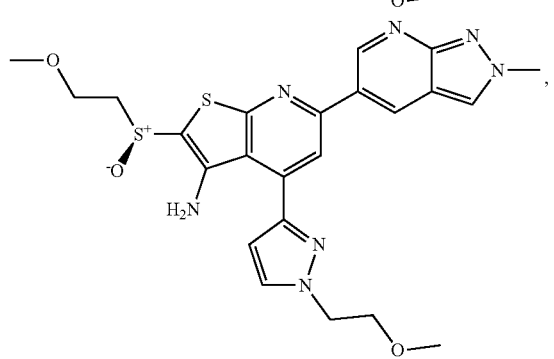
546
-continued
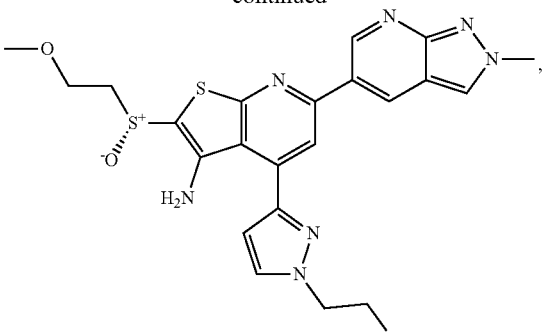
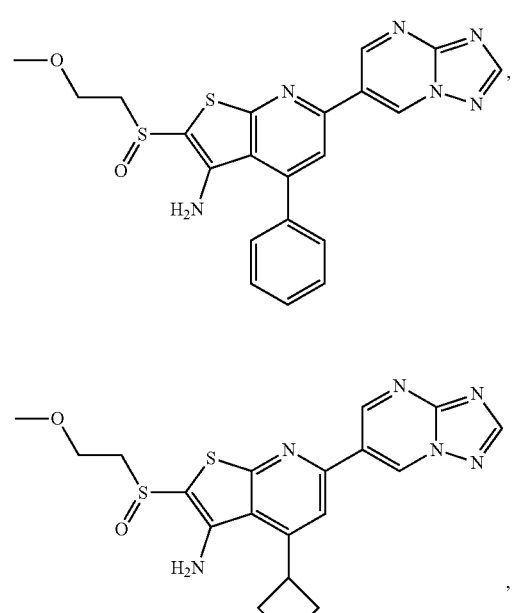
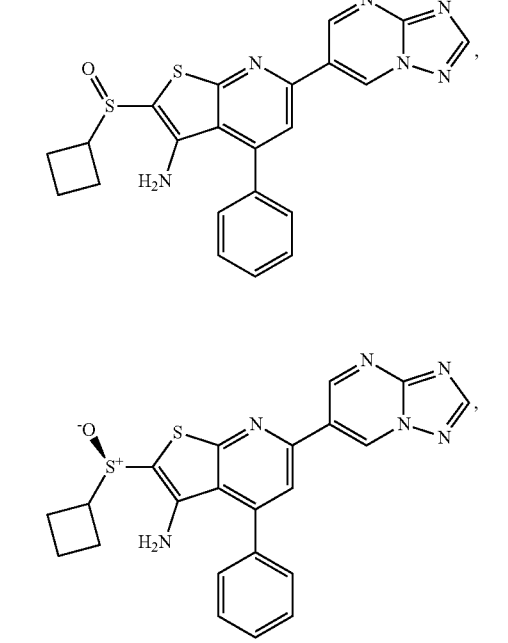

-continued
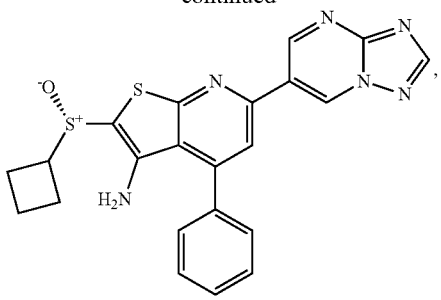
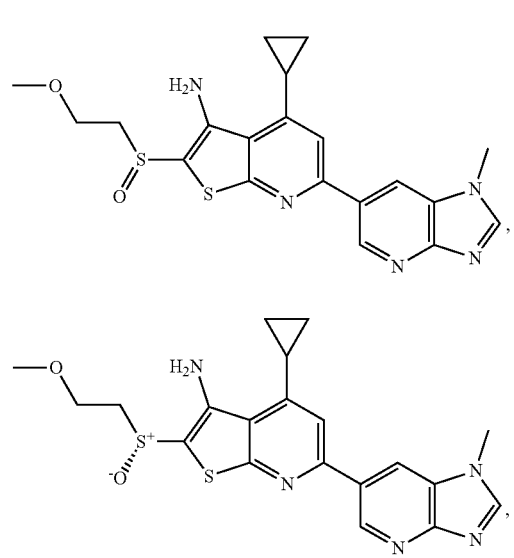
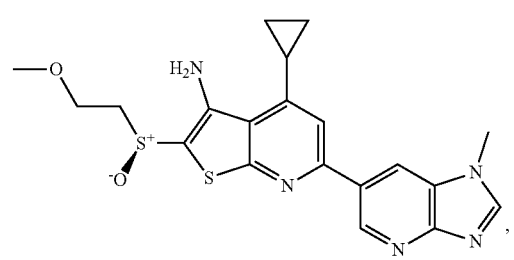
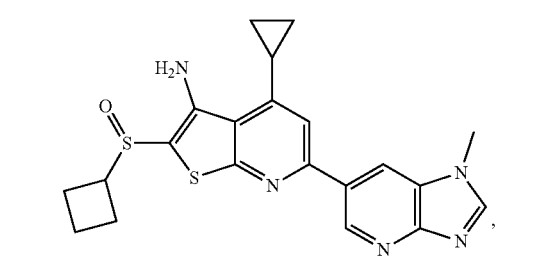
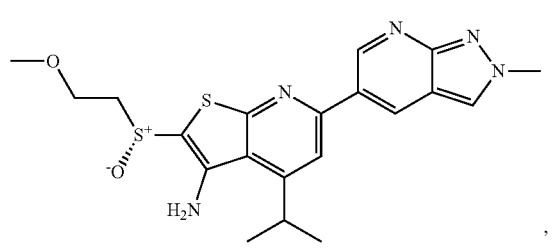
-continued
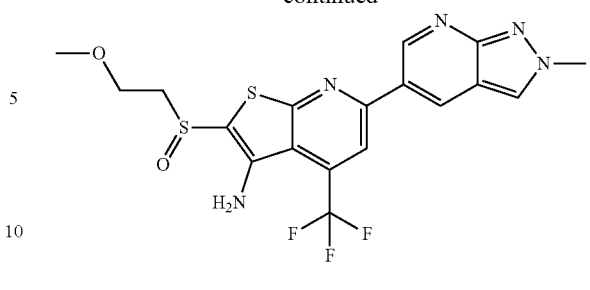
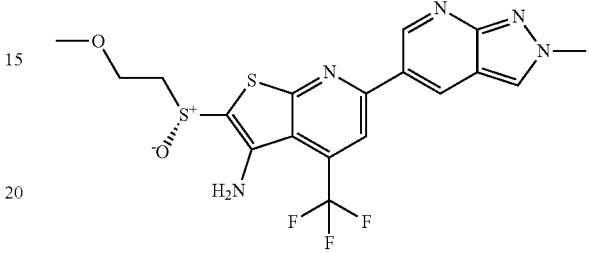
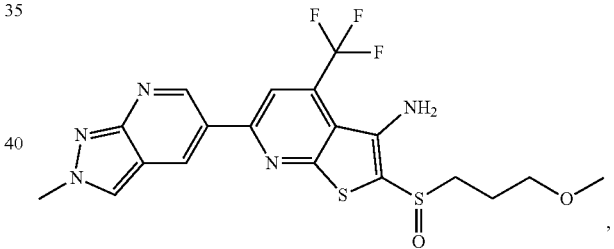
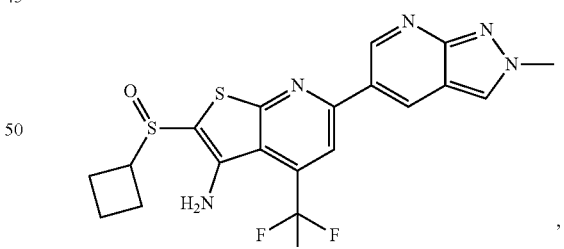
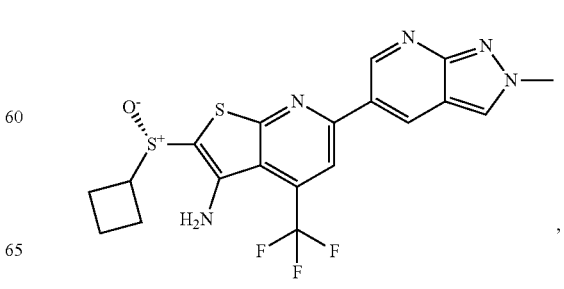

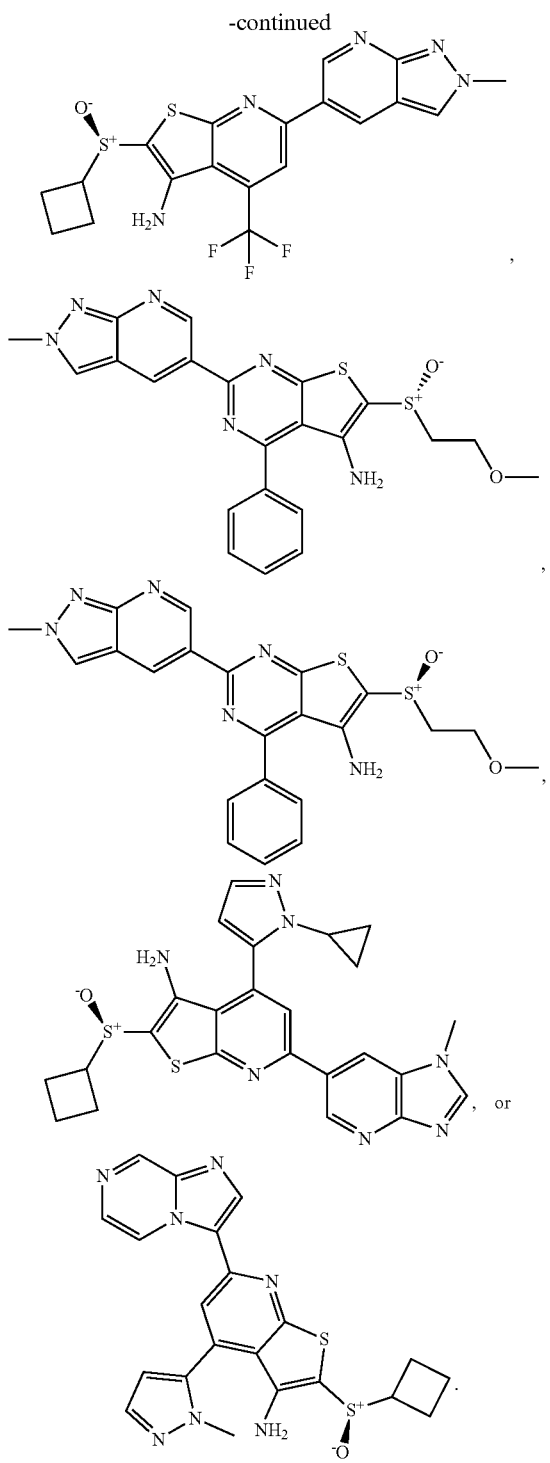

10. A pharmaceutical composition comprising the compound, salt, or solvate of claim 1 and a pharmaceutically acceptable excipient or a carrier.

11. The compound, salt, or solvate of claim 1, wherein $R^1$ is $C_1$-$C_6$ alkyl, $C_1$-$C_6$ haloalkyl, 3- to 10-membered cycloalkyl, —($C_1$-$C_{12}$ alkylene)-(3-to 10-membered cycloalkyl), —($C_1$-$C_{12}$ alkylene)-($C_1$-$C_{12}$ alkoxy), 3- to 20-membered heterocyclyl, or —($C_1$-$C_{12}$ alkylene)-(3-to 20-membered heterocyclyl);

$R^2$ is —$NH_2$, CN, or —NHC(O)($C_1$-$C_6$ alkyl);

$R^6$ is 8- to 10-membered fused bicyclic heteroaryl optionally substituted with one or more $R^3$;

$R^7$ is $C_1$-$C_6$ alkyl, $C_1$-$C_6$ haloalkyl, 3- to 10-membered cycloalkyl, 6- to 18-membered aryl, 3- to 20-membered heterocyclyl, 5- to 20-membered heteroaryl, —C(O)—($C_1$-$C_6$ alkyl), —C(O)O—($C_1$-$C_6$ alkyl), or —C(O)NR$^5$—($C_1$-$C_6$ alkyl), each of which is optionally substituted with one or more $R^4$;

$R^3$ is oxo, —OH, —O—($C_1$-$C_{12}$ alkylene)-OH, —O—($C_1$-$C_{12}$ alkylene)-N($R^5$)$_2$, —N($R^5$)$_2$, —N($R^5$)($C_1$-$C_{12}$ alkylene-OH), —N($R^5$)($C_1$-$C_{12}$ alkylene)-O—($C_1$-$C_6$ alkyl), $C_1$-$C_6$ alkyl, —($C_1$-$C_{12}$ alkylene)-OH, $C_1$-$C_6$ haloalkyl, 3- to 10-membered cycloalkyl, 3- to 20-membered heterocyclyl, —C(O)N($R^5$)$_2$, —C(O)N($R^5$)($C_1$-$C_{12}$ alkylene-OH), —C(O)—($C_1$-$C_6$ alkyl), —C(O)O—($C_1$-$C_6$ alkyl), or —S(O)$_m$—($C_1$-$C_6$ alkyl), wherein each of the 3- to 10-membered cycloalkyl and the 3- to 20-membered heterocyclyl is optionally substituted with $R^{10}$;

$R^4$ is oxo, halogen, —CN, —N($R^5$)$_2$, —OH, —O—($C_1$-$C_{12}$ alkylene)-OH, —S(O)$_m$—($C_1$-$C_6$ alkyl), —C(O)—($C_1$-$C_6$ alkyl), —C(O)-(3-to 10-membered cycloalkyl), $C_1$-$C_6$ alkyl, —($C_1$-$C_{12}$ alkylene)-O—($C_1$-$C_6$ alkyl), $C_1$-$C_6$ alkoxy, $C_1$-$C_6$ haloalkyl, 3- to 10-membered cycloalkyl, 3- to 20-membered heterocyclyl, or —($C_1$-$C_{12}$ alkylene)-($C_6$-$C_{18}$ aryl), wherein the —($C_1$-$C_{12}$ alkylene)-($C_6$-$C_{18}$ aryl) is optionally substituted with $R^8$ each $R^5$ is independently H, $C_1$-$C_6$ alkyl, —($C_1$-$C_{12}$ alkylene)-OH optionally substituted with —OH, —($C_1$-$C_{12}$ alkylene)-NH$_2$, —($C_1$-$C_{12}$ alkylene)-N($R^9$)$_2$, —($C_1$-$C_{12}$ alkylene)-O—($C_1$-$C_{12}$ alkylene)-OH, —($C_1$-$C_{12}$ alkylene)-O—($C_1$-$C_{12}$ alkylene)-NH$_2$, —C(O)—($C_1$-$C_6$ alkyl), —C(O)O—($C_1$-$C_6$ alkyl), —($C_1$-$C_{12}$ alkylene)-COOH, or —S(O)$_m$—($C_1$-$C_6$ alkyl);

or alternatively, two $R^5$ groups together with the N atom to which they are attached can form a 4- to 7-membered heterocyclyl, optionally containing an additional heteroatom selected from O, S, or N, and wherein the heterocycyl is optionally substituted with $R^8$;

$R^8$ is halogen, $C_1$-$C_6$ alkyl, or $C_1$-$C_{12}$ alkoxy;

$R^9$ is H or $C_1$-$C_6$ alkyl, or two $R^9$ together with the N atom to which they are attached can form a 4- to 7-membered heterocyclyl, optionally containing an additional heteroatom selected from O, S(O)$_t$, or N;

$R^{10}$ is —OH, halogen, $C_1$-$C_6$ alkyl, or $C_1$-$C_6$ alkoxy;

X is CH or N;

m is 0, 1, or 2;

n is 0, 1, or 2; and t is 0, 1, or 2.

12. The compound, salt, or solvate of claim 11, wherein $R^1$ is 3- to 10-membered cycloalkyl or —($C_1$-$C_{12}$ alkylene)-($C_1$-$C_{12}$ alkoxy);

$R^2$ is —NH$_2$ or —NHC(O)($C_1$-$C_6$ alkyl);

$R^6$ is 8- to 10-membered fused bicyclic heteroaryl optionally substituted with one or more $R^3$;

$R^7$ is $C_1$-$C_6$ alkyl, $C_1$-$C_6$ haloalkyl, 3- to 10-membered cycloalkyl, 6- to 18-membered aryl, or 5- to 20-membered heteroaryl, each of which is optionally substituted with one or more $R^4$;

$R^3$ is oxo, $C_1$-$C_6$ alkyl, or —($C_1$-$C_{12}$ alkylene)-OH;

$R^4$ is —O—($C_1$-$C_{12}$ alkylene)-OH or $C_1$-$C_6$ alkyl;

X is CH or N; and n is 1.

13. The compound, salt, or solvate of claim 12, wherein $R^2$ is —NH$_2$.

14. The compound, salt, or solvate of claim 12, wherein $R^3$ is $C_1$-$C_6$ alkyl.

15. The compound, salt, or solvate of claim 12, wherein $R^7$ is $C_1$-$C_6$ alkyl, $C_1$-$C_6$ haloalkyl, or 3- to 10-membered cycloalkyl, each of which is unsubstituted.

16. The compound, salt, or solvate of claim 12, wherein $R^4$ is $C_1$-$C_3$ alkyl.

17. The compound, salt, or solvate of claim 12, wherein X is CH.

18. The compound, salt, or solvate of claim 1, where the compound has the structure of Formula (II):

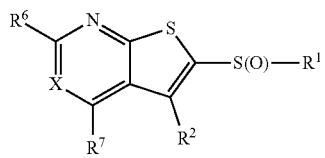

(II)

wherein:
$R^1$ is cyclobutyl or —($C_1$-$C_4$ alkylene)-($C_1$-$C_3$ alkoxy);
$R^2$ is —$NH_2$;
$R^6$ is

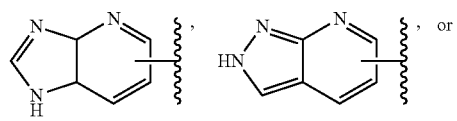, or

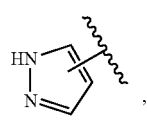, each of which is optionally substituted with one or more $R^3$;
$R^7$ is

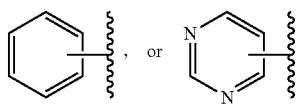,

—$CF_3$, isopropyl, cyclopropyl, cyclobutyl, each of which is optionally substituted with one or more $R^4$;
$R^3$ is —$NH_2$,—$NH(C_1$-$C_3$ alkyl),—$NH(C_1$-$C_4$ alkylene)-OH, or $C_1$-$C_3$ alkyl;
$R^4$ is $C_1$-$C_3$ alkyl; and
X is CH or N.

19. The compound of claim 1, wherein the compound is:

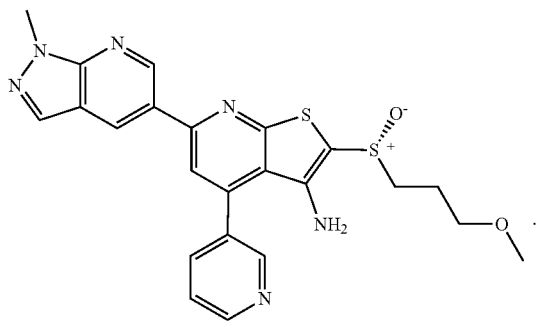

20. The compound of claim 1, wherein the compound is:

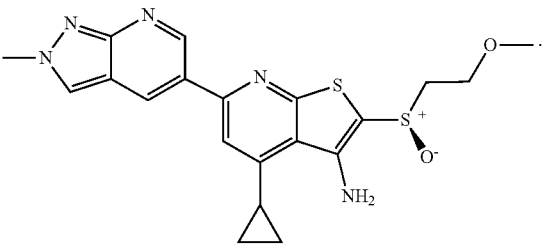

21. The compound of claim 1, wherein the compound is:

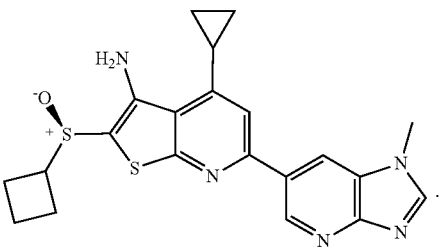

22. The compound of claim 1, wherein the compound is:

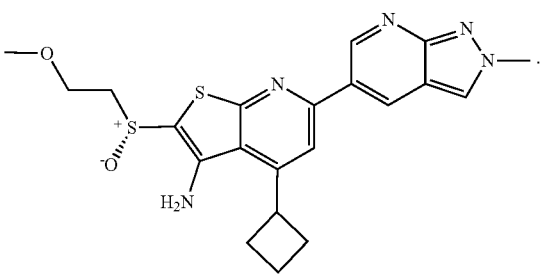

23. The compound of claim 1, wherein the compound is:

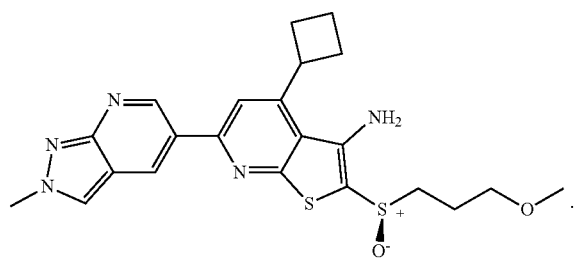

24. The compound of claim 1, wherein the compound is:

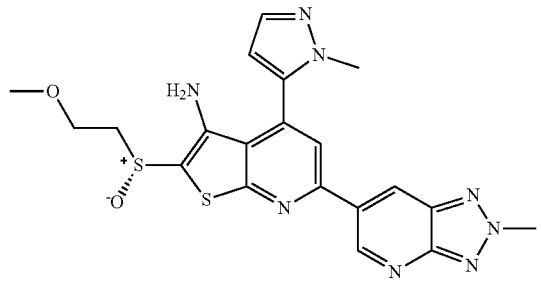

25. The compound of claim 1, wherein the compound is:

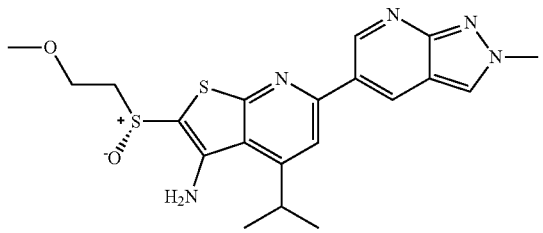

26. The compound of claim 1, wherein the compound is:

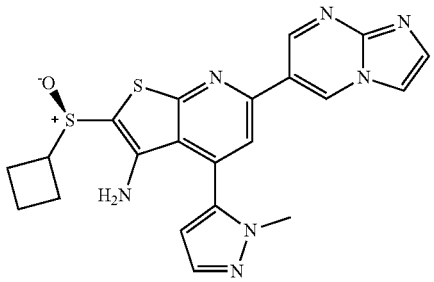

27. The compound of claim 1, wherein the compound is:

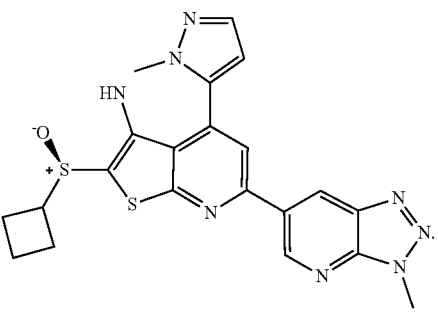

28. The pharmaceutical composition of claim 10, wherein the compound is:

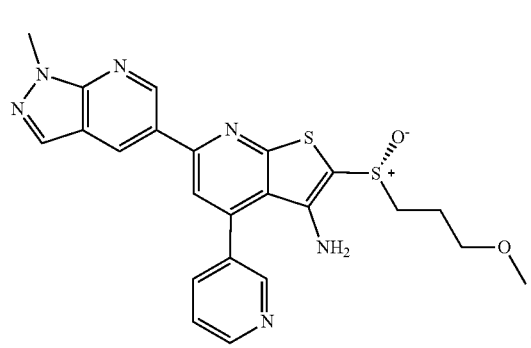

29. The pharmaceutical composition of claim 10, wherein the compound is:

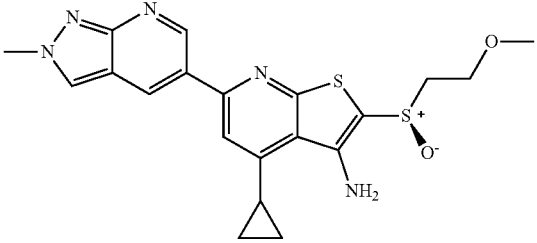

30. The pharmaceutical composition of claim 10, wherein the compound is:

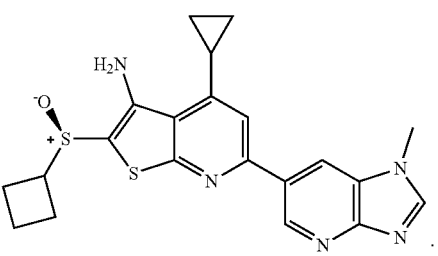

31. The pharmaceutical composition of claim 10, wherein the compound is:

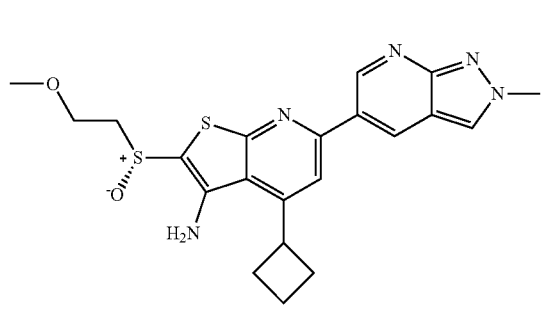

32. The pharmaceutical composition of claim 10, wherein the compound is:

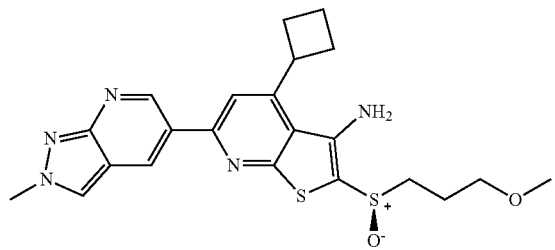

33. The pharmaceutical composition of claim 10, wherein the compound is:

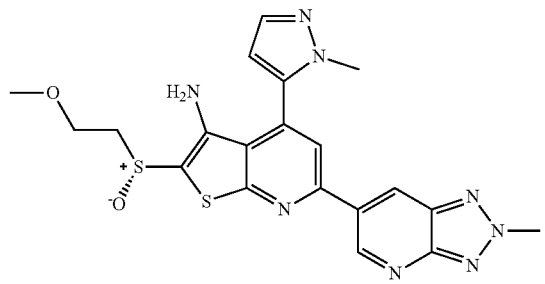

34. The pharmaceutical composition of claim 10, wherein the compound is:

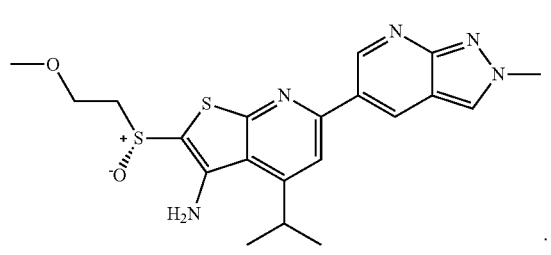

35. The pharmaceutical composition of claim 10, wherein the compound is:

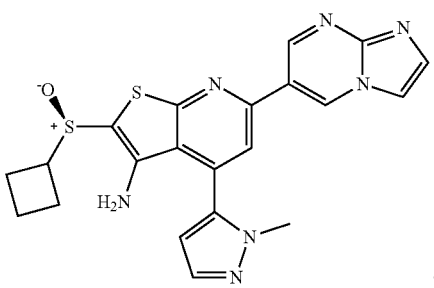

36. The pharmaceutical composition of claim 10, wherein the compound is:

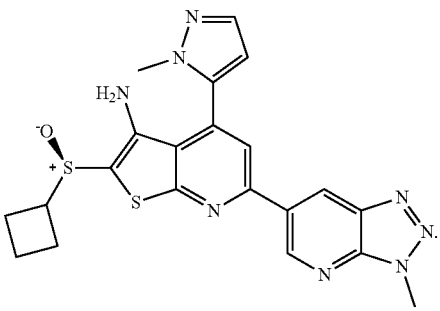

37. The salt of claim 1, wherein the compound is:

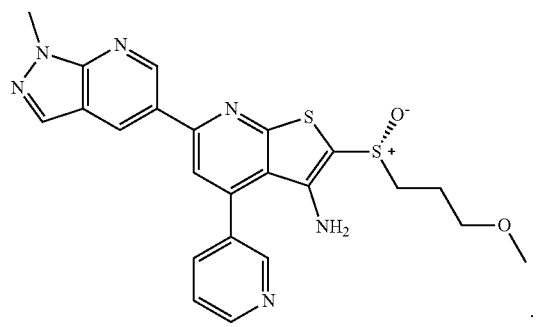

38. The salt of claim 1, wherein the compound is:

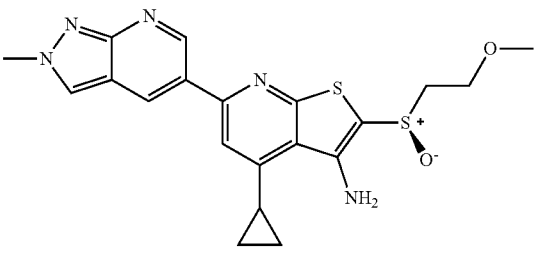

39. The salt of claim 1, wherein the compound is:

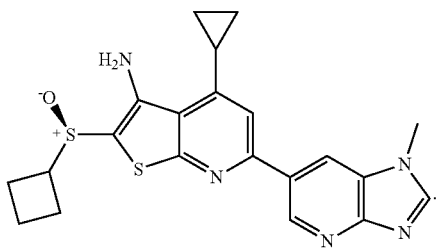

40. The salt of claim 1, wherein the compound is:

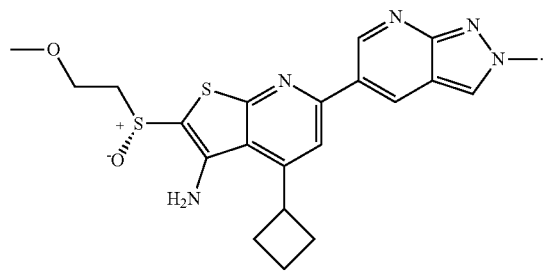

41. The salt of claim 1, wherein the compound is:

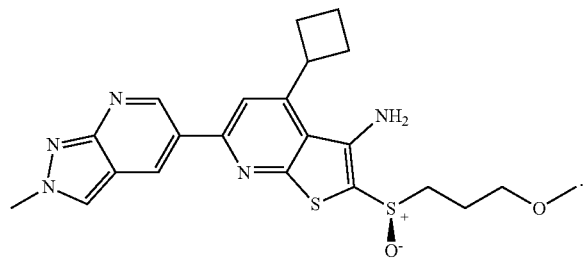

42. The salt of claim 1, wherein the compound is:

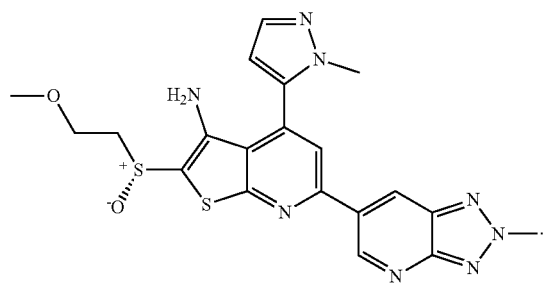

43. The salt of claim 1, wherein the compound is:

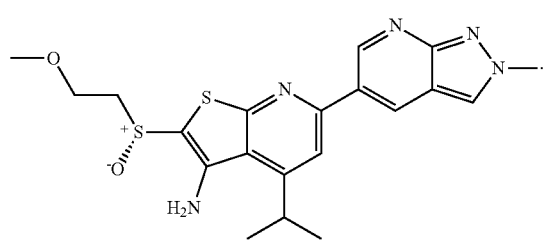

44. The salt of claim 1, wherein the compound is:

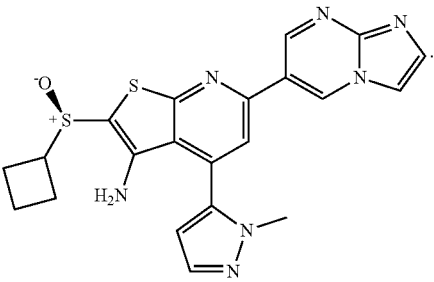

45. The salt of claim 1, wherein the compound is:

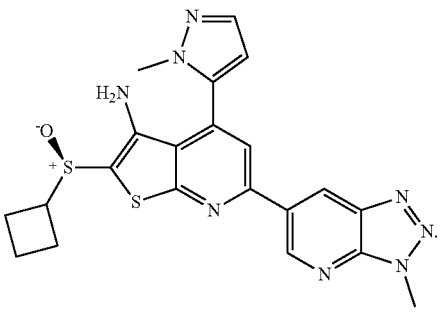

46. The solvate of claim 1, wherein the compound is:

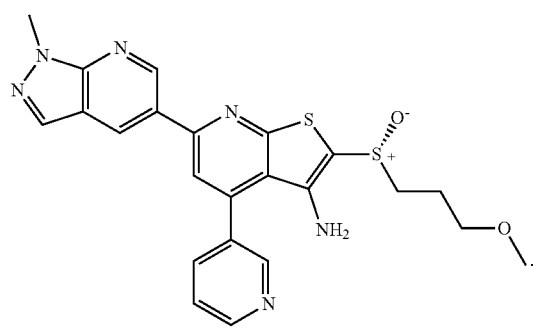

47. The solvate of claim 1, wherein the compound is:

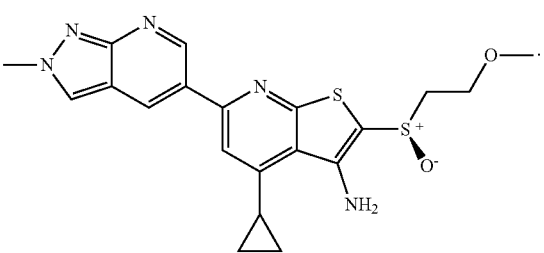

48. The solvate of claim 1, wherein the compound is:

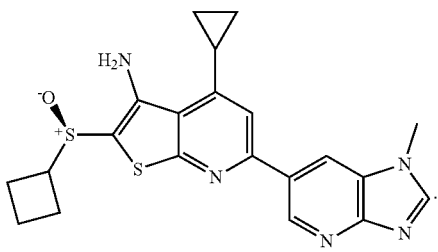

49. The solvate of claim 1, wherein the compound is:

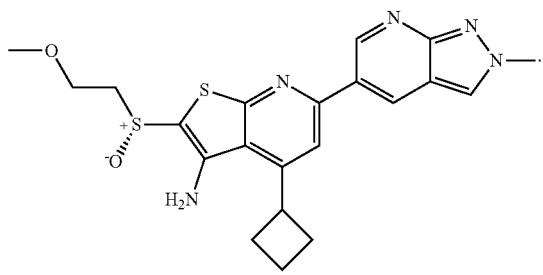

50. The solvate of claim 1, wherein the compound is:

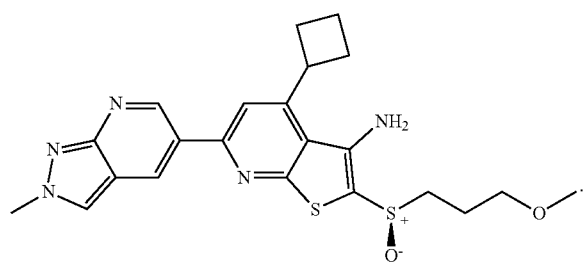

51. The solvate of claim 1, wherein the compound is:

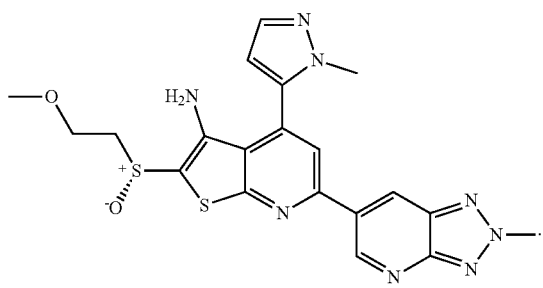

52. The solvate of claim 1, wherein the compound is:

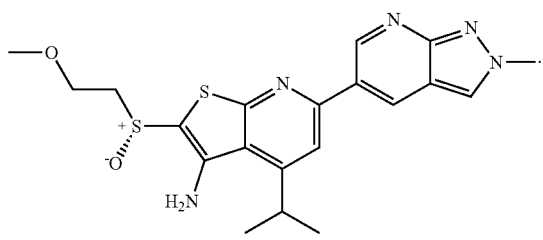

53. The solvate of claim 1, wherein the compound is:

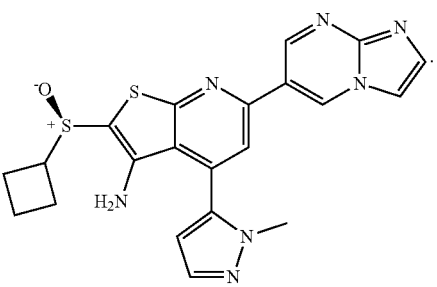

54. The solvate of claim 1, wherein the compound is:

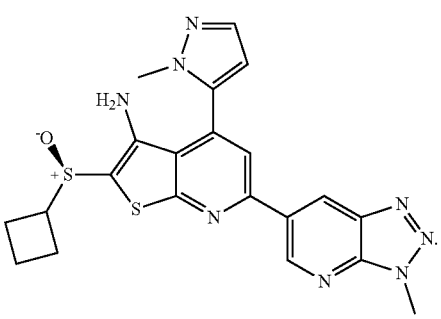

55. A method of treating inflammatory bowel disease, the method comprising administering to a human subject in need of treatment a therapeutic amount of compound of Formula (IA):

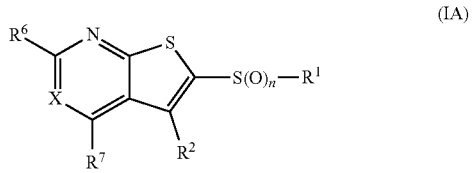

(IA)

or a pharmaceutically acceptable salt or solvate thereof; wherein:
$R^1$ is $C_1$-$C_6$ alkyl, $C_1$-$C_6$ haloalkyl, 3- to 10-membered cycloalkyl, —($C_1$-$C_{12}$ alkylene)-(3-to 10-membered cycloalkyl), —($C_1$-$C_{12}$ alkylene)-($C_1$-$C_{12}$ alkoxy), 3- to 20-membered heterocyclyl, or —($C_1$-$C_{12}$ alkylene)-(3-to 20-membered heterocyclyl);
$R^2$ is —NH$_2$, CN, or —NHC(O)($C_1$-$C_6$ alkyl);
$R^6$ is 8- to 10-membered fused bicyclic heteroaryl optionally substituted with one or more $R^3$;
$R^7$ is $C_1$-$C_6$ alkyl, $C_1$-$C_6$ haloalkyl, 3- to 10-membered cycloalkyl, 6- to 18-membered aryl, 3- to 20-membered heterocyclyl, 5- to 20-membered heteroaryl, —C(O)—($C_1$-$C_6$ alkyl), —C(O)O—($C_1$-$C_6$ alkyl), or —C(O)NR$^5$—($C_1$-$C_6$ alkyl), each of which is optionally substituted with one or more $R^4$;
$R^3$ is oxo, —OH, —O—($C_1$-$C_{12}$ alkylene)-OH, —O—($C_1$-$C_{12}$ alkylene)-N(R$^5$)$_2$, —N(R$^5$)$_2$, —N(R$^5$) ($C_1$-$C_{12}$ alkylene-OH), —N(R$^5$) ($C_1$-$C_{12}$ alkylene)-O—($C_1$-$C_6$ alkyl), $C_1$-$C_6$ alkyl, —($C_1$-$C_{12}$ alkylene)-OH, $C_1$-$C_6$ haloalkyl, 3- to 10-membered cycloalkyl, 3- to 20-membered heterocyclyl, —C(O) N(R$^5$)$_2$, —C(O)

N(R⁵) (C₁-C₁₂ alkylene-OH), —C(O)—(C₁-C₆ alkyl), —C(O)O—(C₁-C₆ alkyl), or —S(O)ₘ—(C₁-C₆ alkyl), wherein each of the 3- to 10-membered cycloalkyl and the 3- to 20-membered heterocyclyl is optionally substituted with R¹⁰;

R⁴ is oxo, halogen, —CN, —N(R⁵)₂, —OH, —O—(C₁-C₁₂ alkylene)-OH, —S(O)ₘ—(C₁-C₆ alkyl), —C(O)—(C₁-C₆ alkyl), —C(O)-(3-to 10-membered cycloalkyl), C₁-C₆ alkyl, —(C₁-C₁₂ alkylene)-O—(C₁-C₆ alkyl), C₁-C₆ alkoxy, C₁-C₆ haloalkyl, 3- to 10-membered cycloalkyl, 3- to 20-membered heterocyclyl, or —(C₁-C₁₂ alkylene)-(C₆-C₁₈ aryl), wherein the —(C₁-C₁₂ alkylene)-(C₆-C₁₈ aryl) is optionally substituted with R⁸;

each R⁵ is independently H, C₁-C₆ alkyl, —(C₁-C₁₂ alkylene)-OH optionally substituted with —OH, —(C₁-C₁₂ alkylene)-NH₂, —(C₁-C₁₂ alkylene)-N(R⁹)₂, —(C₁-C₁₂ alkylene)-O—(C₁-C₁₂ alkylene)-OH, —(C₁-C₁₂ alkylene)-O—(C₁-C₁₂ alkylene)-NH₂, —C(O)—(C₁-C₆ alkyl), —C(O)O—(C₁-C₆ alkyl), —(C₁-C₁₂ alkylene)-COOH, or —S(O)ₘ—(C₁-C₆ alkyl);

or alternatively, two R⁵ groups together with the N atom to which they are attached can form a 4- to 7-membered heterocyclyl, optionally containing an additional heteroatom selected from O, S, or N, and wherein the heterocyclyl is optionally substituted with R⁸;

R⁸ is halogen, C₁-C₆ alkyl, or C₁-C₁₂ alkoxy;

R⁹ is H or C₁-C₆ alkyl, or two R⁹ together with the N atom to which they are attached can form a 4- to 7-membered heterocyclyl, optionally containing an additional heteroatom selected from O, S(O)ₜ, or N;

R¹⁰ is —OH, halogen, C₁-C₆ alkyl, or C₁-C₆ alkoxy;

X is CH or N;

m is 0, 1, or 2;

n is 0, 1, or 2; and t is 0, 1, or 2.

56. The method of claim 55, wherein the compound has the structure of Formula (II):

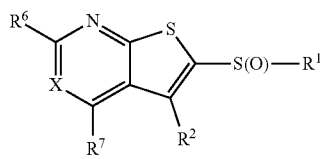

(II)

wherein:

R¹ is cyclobutyl or —(C₁-C₄ alkylene)-(C₁-C₃ alkoxy);

R² is —NH₂;

R⁶ is

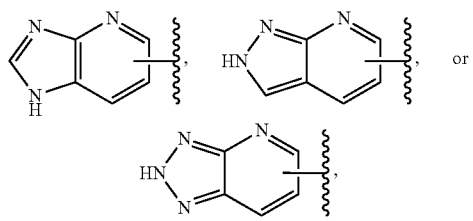

each of which is optionally substituted with one or more R³;

R⁷ is

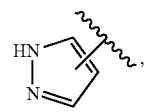

—CF₃, isopropyl, cyclopropyl, cyclobutyl,

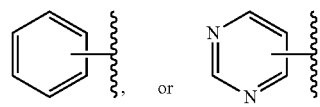

each of which is optionally substituted with one or more R⁴;

R³ is —NH₂, —NH(C₁-C₃ alkyl), —NH(C₁-C₄ alkylene)-OH, or C₁-C₃ alkyl;

R⁴ is C₁-C₃ alkyl; and

X is CH or N.

57. The method of claim 55, wherein the compound is:

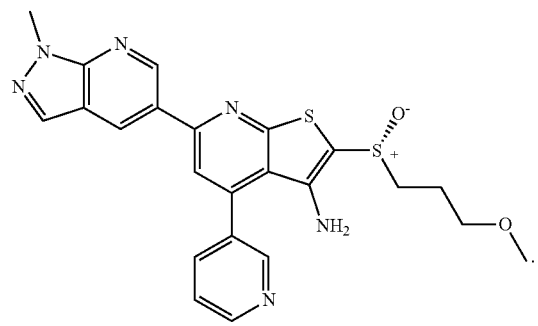

58. The method of claim 55, wherein the compound is:

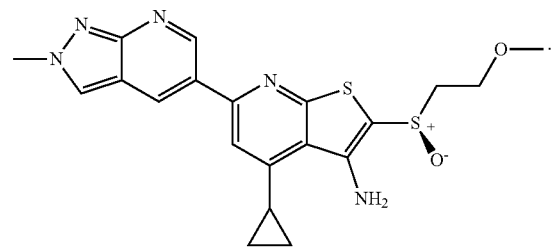

59. The method of claim 55, wherein the compound is:

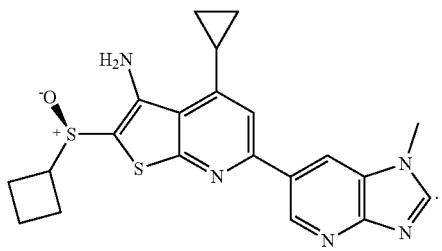

60. The method of claim 55, wherein the compound is:

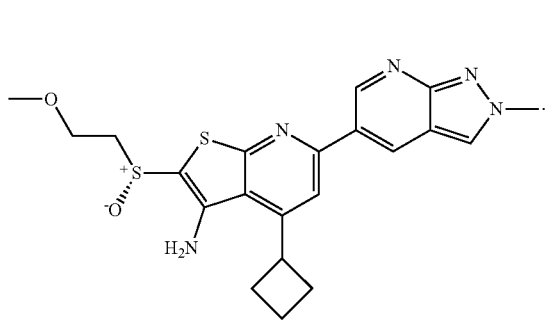

61. The method of claim 55, wherein the compound is:

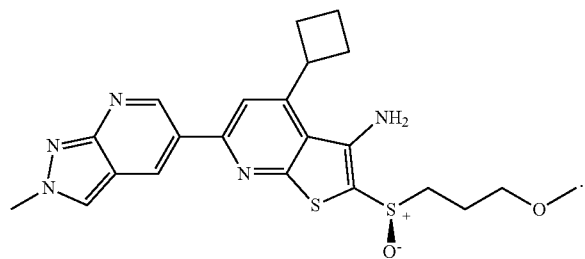

62. The method of claim 55, wherein the compound is:

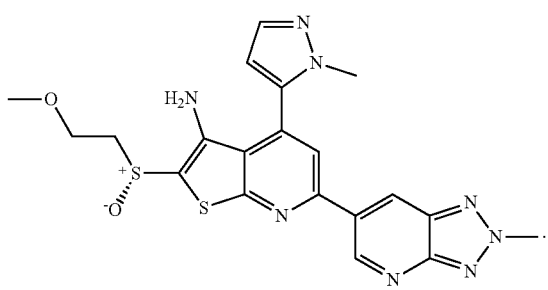

63. The method of claim 55, wherein the compound is:

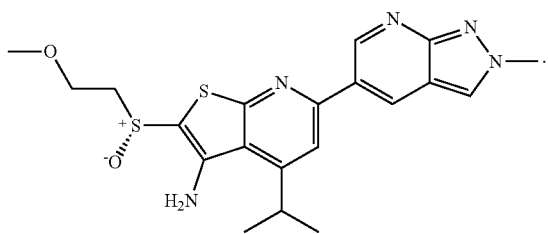

64. The method of claim 55, wherein the compound is:

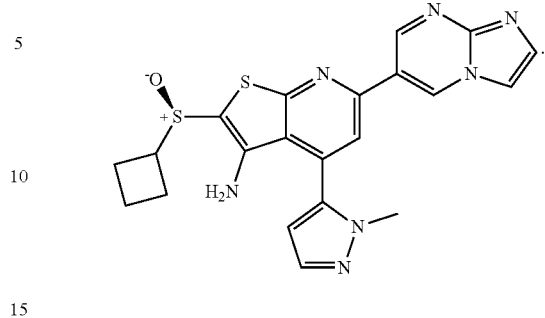

65. The method of claim 55, wherein the compound is:

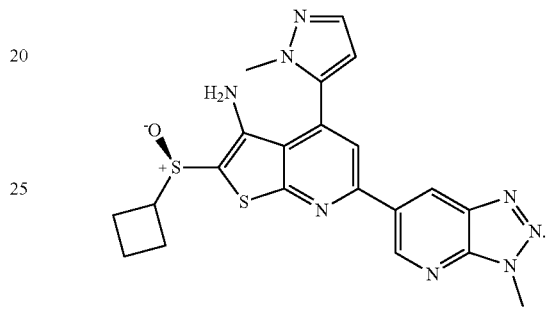

66. A method of treating a human subject in need of cell therapy comprising administering to the subject a therapeutically effective amount of a preparation comprising human hematopoietic stem cells and the compound, salt, or solvate of claim 11.

67. A method of treating a human subject having at least one symptom associated with an ischemic tissue or a tissue damaged by ischemia comprising administering to the subject a therapeutically effective amount of the compound, salt, or solvate of claim 11.

68. A method of increasing neutrophils in a human subject in need thereof, the method comprising administering to the subject a therapeutically effective amount of the compound, salt, or solvate of claim 11.

69. A method of increasing numbers of or mobilizing peripheral blood hematopoietic stem cells in a human subject in need thereof, the method comprising administering to the subject a therapeutically effective amount of the compound, salt, or solvate of claim 11.

70. A method of increasing numbers of hematopoietic stem cells in blood or bone marrow of a human subject, the method comprising administering to blood or bone marrow of the subject a therapeutically effective amount of the compound, salt, or solvate of claim 11.

71. A method of treating or preventing a fibrotic disease, disorder or condition in a human subject in need thereof, the method comprising administering to the subject a therapeutically effective amount of the compound, salt, or solvate of claim 11.

72. A method of treating inflammation or reducing the activity of the immune system in a human subject in need thereof, the method comprising administering to the subject a therapeutically effective amount of the compound, salt, or solvate of claim 11 and a corticosteroid.

73. A method of treatment of glucocorticoid insensitivity, restoring corticosteroid sensitivity, enhancing glucocorticoid sensitivity or reversing the glucocorticoid insensitivity in a human subject experiencing corticosteroid dependence or corticoid resistance or unresponsiveness or intolerance to corticosteroids, comprising administering a pharmaceutical composition comprising the compound, salt, or solvate of claim 11 in combination with a corticosteroid to the subject exhibiting one or more glucocorticoid insensitivity related conditions, wherein the glucocorticoid insensitivity related conditions comprise a range of immune-inflammatory disorders treated with steroids when the therapy fails to achieve disease control or is not effective or intolerant or dependent to corticosteroids, and combinations thereof.

74. The compound, salt, or solvate of claim 1, wherein $R^3$ is —$NH_2$, —$N(C_1\text{-}C_3 \text{ alkyl})_2$, —$NHCH_2CH_2OH$, —$N(C_1\text{-}C_3 \text{ alkyl}) CH_2CH_2OH$, —$N(CH_2CH_2OH)_2$, —$NHCH_2CH_2OCH_2CH_2OH$, —$NHCH_2CH_2OCH_2CH_2NH_2$, —$NHCH_2CH_2NH_2$, —$N(C_1\text{-}C_3 \text{ alkyl}) CH_2CH_2NH_2$, —$NHCH_2CH_2NH(C_1\text{-}C_3 \text{ alkyl})$, —$NHCH_2CH_2N(C_1\text{-}C_3 \text{ alkyl})_2$, —$N(C_1\text{-}C_3 \text{ alkyl}) CH_2CH_2NH(C_1\text{-}C_3 \text{ alkyl})$, —$N(C_1\text{-}C_3 \text{ alkyl}) CH_2CH_2N(C_1\text{-}C_3 \text{ alkyl})_2$, —$NHSO_2CH_3$, —$N(C_1\text{-}C_3 \text{ alkyl}) SO_2CH_3$, —$OCH_2CH_2OH$, —$OCH_2CH_2NH_2$, —$OCH_2CH_2NH(C_1\text{-}C_3 \text{ alkyl})$, or —$OCH_2CH_2N(C_1\text{-}C_3 \text{ alkyl})_2$.

75. The method of claim 57, wherein the inflammatory bowel disease is Crohn's Disease.

76. The method of claim 58, wherein the inflammatory bowel disease is Crohn's Disease.

77. The method of claim 59, wherein the inflammatory bowel disease is Crohn's Disease.

78. The method of claim 60, wherein the inflammatory bowel disease is Crohn's Disease.

79. The method of claim 61, wherein the inflammatory bowel disease is Crohn's Disease.

80. The method of claim 62, wherein the inflammatory bowel disease is Crohn's Disease.

81. The method of claim 63, wherein the inflammatory bowel disease is Crohn's Disease.

82. The method of claim 64, wherein the inflammatory bowel disease is Crohn's Disease.

83. The method of claim 65, wherein the inflammatory bowel disease is Crohn's Disease.

* * * * *